(12) United States Patent
Kuroda et al.

(10) Patent No.: US 8,362,252 B2
(45) Date of Patent: *Jan. 29, 2013

(54) CARBOSTYRIL COMPOUND

(75) Inventors: Takeshi Kuroda, Tokushima (JP);
Takahito Yamauchi, Tokushima (JP);
Tomoichi Shinohara, Tokushima (JP);
Kunio Oshima, Tokushima (JP);
Chiharu Kitajima, Tokushima (JP);
Hitoshi Nagao, Tokushima (JP); Tae Fukushima, Tokushima (JP); Takahiro Tomoyasu, Tokushima (JP); Hironobu Ishiyama, Tokushima (JP); Kazuhide Ohta, Tokushima (JP); Masaaki Takano, Tokushima (JP); Takumi Sumida, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 354 days.

This patent is subject to a terminal disclaimer.

(21) Appl. No.: 12/611,921

(22) Filed: Nov. 3, 2009

(65) Prior Publication Data

US 2010/0261705 A1    Oct. 14, 2010

Related U.S. Application Data

(63) Continuation of application No. 10/582,014, filed as application No. PCT/JP2005/018217 on Sep. 26, 2005, now Pat. No. 7,777,038.

(30) Foreign Application Priority Data

Sep. 28, 2004 (JP) .................. 2004-282814

(51) Int. Cl.
*C07D 215/38* (2006.01)
(52) U.S. Cl. ............................................... 546/157
(58) Field of Classification Search ................. 546/157; 514/312

See application file for complete search history.

(56) References Cited

U.S. PATENT DOCUMENTS

| 3,152,905 A | 10/1964 | Gaspar |
| 3,427,310 A | 2/1969 | Gaspar |
| 4,824,833 A | 4/1989 | Iijima et al. |
| 7,777,038 B2 * | 8/2010 | Kuroda et al. .............. 546/157 |
| 2003/0229120 A1 | 12/2003 | Olsen et al. |

FOREIGN PATENT DOCUMENTS

| WO | WO 92/14837 A1 | 9/1992 |
| WO | WO 01/02377 A1 | 1/2001 |
| WO | WO 02/46226 A2 | 6/2002 |
| WO | WO 02/051409 A1 | 7/2002 |
| WO | WO 02/102403 A1 | 12/2002 |
| WO | WO 2004/028535 A1 | 4/2004 |
| WO | WO 2004/064860 A1 | 8/2004 |

OTHER PUBLICATIONS

Supplementary European Search Report mailed Aug. 24, 2009, in European Application No. 05788152.6.
International Search Report from the Japanese Patent Office mailed Jan. 17, 2006, in International Application No. PCT/JP2005/018217.
Douglas Taupin et al., "Trefoil Factors: Initiators of Mucosal Healing," *Nature Reviews/Molecular Cell Biology*, (2003), vol. 4, pp. 721-732.
Raymond J. Playford et al., "Human Spasmolytic Polypeptide Is a Cytoprotective Agent That Stimulates Cell Migration," *Gastroenterology*, (1995), vol. 108, pp. 108-116.
Mark W. Babyatsky et al., "Oral Trefoil Peptides Protect Against Ethanol- and Indomethacin-Induced Gastric Injury in Rats," *Gastroenterology*, (1996), vol. 110, pp. 489-497.
C. McKenzie et al., "Topical and intravenous administration of trefoil factors protect the gastric mucosa from ethanol-induced injury in the rat," *Alim. Pharmacol. Ther.*, (2000), vol. 14, pp. 1033-1040.
S. S. Poulsen et al, "Metabolism of oral trefoil factor 2 (TFF2) and the effect of oral and parenteral TFF2 on gastric and duodenal ulcer heating in the rat," *Gut*, (1999), vol. 45, pp. 516-522.
C. P. Tran et al., "Trefoil peptide TFF2 (spasmolytic polypeptide) potently accelerates heating and reduces inflammation in a rat model of colitis," *Gut*, (1999), vol. 44, pp. 636-642.
Antonio Soriano-Izquierdo et al.,"Trefoil peptide TFF2 treatment reduces VCAM-1 expression and leukocyte recruitment in experimental intestinal inflammation," *J. Leukoc, Biol.*, (2004), vol. 75, pp. 214-223.

(Continued)

*Primary Examiner* — D M Seaman
(74) *Attorney, Agent, or Firm* — Finnegan, Henderson, Farabow, Garrett & Dunner, L.L.P.

(57) ABSTRACT

The present invention provides a carbostyril compound represented by General Formula (1)

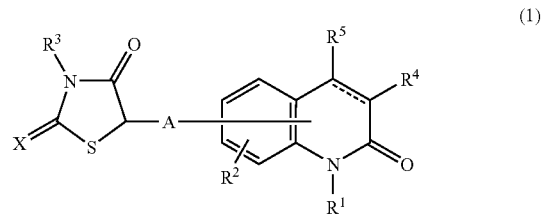

or a salt thereof, wherein A is a direct bond, a lower alkylene group, or a lower alkylidene group; X is an oxygen atom or a sulfur atom; $R^4$ and $R^5$ each represent a hydrogen atom; the bond between the 3 and 4 positions of the carbostyril skeleton is a single bond or a double bond; $R^1$ is a hydrogen atom, etc; $R^2$ is a hydrogen atom, etc; and $R^3$ is a hydrogen atom, etc. The carbostyril compound or salt thereof of the present invention induces the production of TFF, and thus is usable for the treatment and/or prevention of disorders such as alimentary tract diseases, oral diseases, upper respiratory tract diseases, respiratory tract diseases, eye diseases, cancers, and wounds.

7 Claims, 1 Drawing Sheet

OTHER PUBLICATIONS

James J. Farrell, "TFFS/SP-deficient mice show decreased gastric proliferation, increased acid secretion, and increased susceptibility to NSAID injury," *J. Clin. Invest.*, (2002), vol. 109, pp. 193-204.

L. Thim et al., "Effect of trefoil factors on the viscoelastic properties of mucus gels," *Eur. J. Clin. Invest.*, (2002), vol. 32, pp. 519-527.

Nikolaos M. Nikolaidis et al., "Trefoil factor-2 Is an Allergen-Induced Gene Regulated by Th2 Cytokines and STAT6 in the Lung," *Am. J. Respir. Cell Mol. Biol.*, (2003), vol. 29, pp. 458-464.

P.L. Beck et al., "Chemotherapy- and Radiotherapy-Induced Intestinal Damage Is Regulated by Intestinal Trefoil Factor," *Gastroenterology*, (2004), vol. 126, pp. 796-808.

Olivier Lefebvre et al., "Gastric Mucosa Abnormalities and Tumorigenesis in Mice Lacking the pS2 Trefoil Protein," *Science*, (1996), vol. 274, pp. 259-262.

Won Sang Park et al., "Somatic Mutations of the Trefoil Factor Family 1 Gene in Gastric Cancer," *Gastroenterology*, (2000), vol. 119, pp. 691-698.

Masaru Katoh, "Trefoil factors and human gastric cancer (Review)," *Int. J. Mol. Med.*, (2003), vol. 12, pp. 3-9.

T. Shimada et al., "Up-regulation of TFF expression by PPARγ ligands in gastric epithelial cells," *Alim. Pharmacol. Ther.*, (2003), vol. 18 (suppl. 1), pp. 119-125.

Tadahito Shimada, "PPARγ mediates NSAIDs-induced upregulation of TFF2 expression in gastric epithelial cells," *FEBS Lett.*, (2004), vol. 558, pp. 33-38.

Takuji Tanaka et al., "Ligands for Peroxisome Proliferator-activated Receptors α and γ Inhibit Chemically Induced Colitis and Formation of Aberrant Crypt Foci in Rats[1]," *Can. Res.*, (2001), vol. 61, pp. 2424-2428.

Concepción Fernández-Estívariz, "Trefoil peptide expression and goblet cell number in rat intestine: effects of KGF and fasting-refeeding," *Am. J. Physiol. Regul. Integr. Comp. Physiol.*, (2003), vol. 84, pp. R564-R573.

Pia Azarschab et al., "Aspirin promotes TFF2 gene activation in human gastric cancer cell lines," *FEBS Letters*, (2001), vol. 488, No. 3, pp. 206-210.

A. Koitabashi et al., "Indometacin up-regulates TFF2 expression in gastric epithelial cells," (Jul. 2004), vol. 20, Suppl. 1, pp. 171-176.

\* cited by examiner

```
15631  GCTCAACCAT CAGAAACAGA CTGGCAACCC CCTGTCATTT CCCTGGCGTG
                  ACGCGTCAGA CTGGCAACCC CCTGTCATTT CCCTGGCGTG
15681  GGGAACTTCG GGTCCCCTCT GTCCTTCCCA CCACACTTTT CCCTCTTTCT
       GGGAACTTCG GGTCCCCTCT GTCCTTCCCA CCACACTTTT CCCTCTTTCT
15731  TTCCGGGTGT CTACTCTCTG GCTTCTGTCT TCTCTGTCAG GTCCACAGAA
       TTCCGGGTGT CTACTCTCTG GCTTCTGTCT TCTCTGTCAG GTCCACAGAA
15781  TCCTTCTCCA GCACATCCTA CCCCAGGAAG GCCATGGGCT GGGTCCCAGG
       TCCTTCTCCA GCACATCCTA CCCCAGGAAG GCCATGGGCT GGGTCCCAGG
15831  TGCCATCTTT CAGAAGATGT AGAGCATTCC CATGGAACAA AAATAACCCA
       TGCCATCTTT CAGAAGATGT AGAGCATTCC CATGGAACAA AAATAACCCA
15881  TTTCAGGGGT TGGCTGAAAA TGAACTTATT AAAACCTGCC TGTCACAGGC
       TTTCAGGGGT TGGCTGAAAA TGAACTTATT AAAACCTGCC TGTCACAGGC
15931  TACTCCGCTG ACCCTGTCAG CCTCATCTCC ATGGAGAGCA GCCCCTCCTG
       TACTCCGCTG ACCCTGTCAG CCTCATCTCC ATGGAGAGCA GCCCCTCCTG
15981  CTGAAGATGG GACAAAGGGC ATCGTGCTGC GGTTGGGGAG GCTCTAACCA
       CTGAAGATGG GACAAAGGGC ATCGTGCTGC GGTTGGGGAG GCTCTAACCA
16031  CAGCCCTGGG AGCAGTCTCT TACCTCCTCT GAGATGCTTC CCTTCCTCAG
       CAGCCCTGGG AGCAGTCTCT TACCTCCTCT GAGATGCTTC CCTTCCTCAG
16081  GGAGGGGACT TTTCCATGCT ATCTGCTGGC CTGTACATTT TCCCCAGTAA
       GGAGGGGACT TTTCCATGCT ATCTGCTGGC CTGTACATTT TCCCCAGTAA
16131  ACTTGGCCCT AATATTTTCT AAATTCCTGT GGTCCCTGCC CACTCTATCA
       ACTTGGCCCT AATATTTTCT AAATTCCTGT GGTCCCTGCC CACTCTATCA
16181  ATAGAAATGC ATAGCTTATC CCTTCCTGGG TGTGACCCTG TGTGTGCCCA
       ATAGAAATGC ATAGCTTATC CCTTCCTGGG TGTGACCCTG TGTGTGCCCA
16231  GCCCCAGACC TGCACGTGGC CGGTTTTCCA CGCTGGCAGC CTGGCATGAC
       GCCCCAGACC TGCACGTGGC CGGTTTTCCA CGCTGGCAGC CTGGCATGAC
16281  CCAACTCTCT GTCCAGGGCA GGAAGAGGTA TCACCGAGCA GGGAGAGAGT
       CCAACTCTCT GTCCAGGGCA GGAAGAGGTA TCACCGAGCA GGGAGAGAGT
16331  CACCCTGGCC CGGAAGCCTC GCCTGCACAG GGCACAGCTG CCTCTTGCCT
       CACCCTGGCC CGGAAGCCTC GCCTGCACAG GGCACAGCTG CCTCTTGCCT
16381  CCTCTTCGCC TCCACGGTGG AAGGGCTGGG GCCACGGGGC AGAGAAGAAA
       CCTCTTCGCC TCCACGGTGG AAGGGCTGGG GCCACGGGGC AGAGAAGAAA
16431  GGTTATCTCT GCTTGTTGGA CAAACAGAGG GGAGATTATA AAACATACCC
       GGTTATCTCT GCTTGTTGGA CAAACAGAGG GGAGATTATA AAACATACCC
16481  GGCAGTGGAC ACCATGCATT CTGCAAGCCA CCCTGGGGTG CAGCTGAGCT
       GGCAGTGGAC ACCATGCATT CTGCAAGCCA CCCTGGGGTG CAGCTGAGCT
16531  AGACATGGGA CGGCGAGACG CCCAGCTCCT
       AGAAGCTT
```

CARBOSTYRIL COMPOUND

This is a continuation of application Ser. No. 10/582,014, filed Jun. 7, 2006, now U.S. Pat. No. 7,777,038 which is a national stage application of PCT/JP2005/018217, filed Sep. 26, 2005, which claims priority to Japanese Application No. 2004-282814, filed on Sep. 28, 2004, all of which are incorporated herein by reference.

TECHNICAL FIELD

The present invention relates to a carbostyril compound.

BACKGROUND OF THE INVENTION

The trefoil factor family (TFF) is a group of highly stable peptides, having a three-leaved clover-like structure formed from six cysteine residues. Three TFF peptides (TFF1, TFF2 and TFF3) have been identified so far in humans. TFFs are present in mucus-related tissues such as the alimentary tract, and are secreted mainly by mucus-secreting cells. The expression of TTF peptides is up-regulated in the vicinity of damaged mucosa and in regenerating glands. It is reported that the main functions of TFF peptides lie in the augmentation of cell migration processes (motogenic effects), protection of cells, and suppression of apoptosis [Nature Reviews, Molecular Cell Biology, Vol. 4: 721-732(2003)].

TFF2 is a peptide of 106 amino acid residues, initially isolated from porcine pancreas. The TFF2 peptide is abundant in the gastric mucous neck cells, the pyloric region of the stomach, the mucosa surrounding ulcers, the regenerative mucosa, the overlying mucus layer, Brunner's glands, and so forth.

It has been confirmed with experiments using rats that TFF2 prevents the development of colitis and gastric ulceration and also accelerates the healing thereof [Gastroenterology 108: 108-116(1995); Gastroenterology 110: 489-497 (1996); Alim. Pharmacol. Ther., 14: 1033-1040(2000); Gut, 45: 516-522(1999); Gut, 44: 636-642, 1999; and J. Leukoc. Biol., Vol. 75: 214-223(2004)].

Other experiments show that indomethacin-induced gastric ulcers are exacerbated in TFF2 knockout mice [J. Clin. Invest., Vol. 109: 193-204(2002)].

Eur. J. Clin. Invest., 32: 519-527(2002) discloses the ability of TFF2 to stabilize mucus.

Am. J. Respir. Cell Mol. Biol., Vol. 29: 458-464(2003) teaches that TFF2 might be involved in regulating the proliferation of damaged airway epithelia.

It can be understood from the above that TFF2 plays key roles in protection against and repair of mucosal injury. With regard to diseases which are likely to be cured with TFF2, improved therapeutic effects are expected by a promotion of endogenous TFF2 production.

Gastroenterology, 126: 796-808(2004) discloses that TFF3 is effective for curing alimentary tract mucositis such as stomatitis induced by the administration of carcinostatics. Science, Vol. 274: 259-262(1996) and Gastroenterology, 119: 691-698(2000) conclude, from the fact that stomach cancer was developed in TFF1 knockout mice, that the TFF1 gene may function as a tumor suppressor gene. Nature Reviews, Molecular Cell Biology, Vol. 4: 721-732(2003) and Int. J. Mol. Med., 12: 3-9(2003) suggest that TFF2 may act in a similar way as TFF1 and TFF3.

As compounds for up-regulating TFF2 expression, ligands for peroxisome proliferator-activated receptor-γ (PPARγ) (e.g., indomethacin, aspirin, prostaglandin $J_2$ and troglitazone) are known [FEBS Lett., 488: 206-210(2001); Alim. Pharmacol. Ther., 18 (suppl. 1): 119-125(2003); FEBS Lett., 558: 33-38(2004); and Can. Res., 61: 2424-2428(2001)].

Among various proteins, keratinocyte growth factor (KGF) is reported to enhance TFF2 and TFF3 expressions in rat lower gastrointestinal tracts [Am. J. Physiol. Regul. Integr. Comp. Physiol., 284: R564-R573(2003)].

Some studies teach pharmacological actions of the TFF peptides themselves, and suggest the possibility of their application in clinical medicine (WO92/14837, WO02/102403, and WO02/46226).

WO01/002377 and WO02/051419 disclose various compounds having a substituent containing a 2,4-dioxo-thazolidinyl or 4-oxo-2-thioxo-thiazolidinyl moiety on a heteroaryl skeleton such as a quinoline. These documents also disclose that such compounds exhibit telomerase inhibitory activity.

DISCLOSURE OF THE INVENTION

An object of the present invention is to provide a novel compound capable of up-regulating TFF; and to provide a pharmaceutical composition for preventing and/or treating alimentary tract diseases, oral diseases, upper respiratory tract diseases, respiratory tract diseases, eye diseases, cancers, and/or wounds, by up-regulating TFF.

The present inventors carried out extensive research to develop a novel compound capable of up-regulating endogenous TFF, and as a result, they found that carbostyril compounds of the following formula (1) can up-regulate endogenous TFF, particularly TFF2. The present invention has been accomplished based on these findings.

The present invention provides a carbostyril compound, an agent comprising said compound, a use of said compound, a method for treating a disorder, and a process for producing said compound, as described in Items 1 to 35 below.

Item 1. A carbostyril compound represented by General Formula (1)

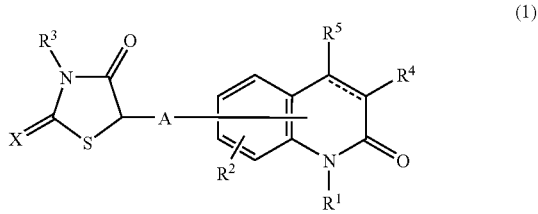

or a salt thereof, wherein A is a direct bond, a lower alkylene group, or a lower alkylidene group;

X is an oxygen atom or a sulfur atom;

the bond between the 3 and 4 positions of the carbostyril skeleton is a single bond or a double bond;

$R^4$ and $R^5$ each represent a hydrogen atom, with the proviso that when the bond between the 3 and 4 positions of the carbostyril skeleton is a double bond, $R^4$ and $R^5$ instead may be linked together in the form of a —CH=CH—CH=CH— group;

$R^1$ is one of the following (1-1) to (1-29):

(1-1) a hydrogen atom, (1-2) a lower alkyl group, (1-3) a phenyl lower alkyl group optionally substituted on the phenyl ring with one or more members selected from the group consisting of a phenyl group, lower alkyl groups, lower alkoxy groups, halogen atoms, —(B)$_i$NR$^6$R$^7$ groups, a nitro group, a carboxy group, lower alkoxycarbonyl groups, a cyano group, phenyl lower alkoxy groups, a phenoxy group, a piperidinyl lower alkoxycarbonyl groups, amino lower alkoxycarbonyl groups optionally substituted with one or more cycloalkyl groups, 2-imidazolinylcarbonyl groups optionally substituted on the 2-imidazoline ring with one or more lower alkylthio groups, 3-pyrrolinylcarbonyl groups optionally substituted on the 3-pyrroline ring with one or more lower alkyl groups, thiazolidinylcarbonyl groups optionally substituted on the thiazolidine ring with a phenyl group, 3-azabicyclo[3.2.2]
nonylcarbonyl groups, piperidinyl lower alkyl groups,
anilino lower aklyl groups optionally substituted on the
amino group with one or more lower alkyl groups, phe-
nylthio lower alkyl groups, indolinyl lower alkyl groups,
and piperidinylcarbonyl groups optionally substituted on
the piperidine ring with one or more lower alkyl groups,
(1-4) a cycloalkyl lower alkyl group,
(1-5) a phenoxy lower alkyl group,
(1-6) a naphthyl lower alkyl group,
(1-7) a lower alkoxy lower alkyl group,
(1-8) a carboxy lower alkyl group,
(1-9) a lower alkoxycarbonyl lower alkyl group,
(1-10) a pyridyl lower alkyl group optionally substituted on
the pyridine ring with one or more members selected from
the group consisting of halogen atoms; piperidinyl groups;
a morpholino group; piperazinyl groups optionally substi-
tuted on the piperazine ring with one or more members
selected from the group consisting of a phenyl group and
lower alkyl group; thienyl groups; a phenyl group; pyridyl
groups; piperidinyl lower alkyl groups; phenylthio lower
alkyl groups; biphenyl groups; lower alkyl groups option-
ally substituted with one or more halogen atoms; pyridy-
lamino groups; pyridylcarbonylamino groups; lower
alkoxy groups; anilino lower alkyl groups optionally sub-
stituted on the amino group with one or more lower alkyl
groups; and anilino groups optionally substituted on the
amino group with one or more lower alkyl groups,
(1-11) a cyano lower alkyl group,
(1-12) an -A$_1$-CONR$^8$R$^9$ group,
(1-13) a group of the following formula

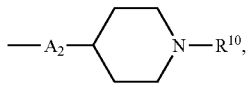

(1-14) a phenyl group,
(1-15) a quinolyl lower alkyl group,
(1-16) a lower alkoxy lower alkoxy-substituted lower alkyl
group,
(1-17) a hydroxy-substituted lower alkyl group,
(1-18) a thiazolyl lower alkyl group optionally substituted on
the thiazole ring with one or more members selected from
the group consisting of halogen atoms, a phenyl group,
thienyl groups, and pyridyl groups,
(1-19) a lower alkyl group optionally substituted with one or
more halogen atoms,
(1-20) a lower alkylsilyloxy lower alkyl group,
(1-21) a phenoxy lower alkyl group optionally substituted on
the phenyl ring with one or more members selected from
the group consisting of lower alkyl groups optionally sub-
stituted with one or more halogen atoms; lower alkoxy
groups; halogen atoms; lower alkenyl groups; cycloalkyl
groups; a nitro group; and a phenyl group,
(1-22) a phenylthio lower alkyl group optionally substituted
on the phenyl ring with one or more halogen atoms,
(1-23) a piperidinyl lower alkyl groups optionally substituted
on the piperidine ring with one or more members selected
from the group consisting of phenyl lower alkyl groups and
a phenyl group,
(1-24) a piperazinyl lower alkyl group optionally substituted
on the piperazine ring with one or more phenyl groups,
(1-25) a 1,2,3,4-tetrahydroisoquinolyl lower alkyl group,
(1-26) a naphthyloxy lower alkyl group,
(1-27) a benzothiazolyloxy lower alkyl group optionally sub-
stituted on the benzothiazole ring with one or more alkyl
groups,
(1-28) a lower alkyl group substituted with one or more mem-
bers selected from the group consisting of quinolyloxy
groups and isoquinolyloxy groups,
(1-29) a pyridyloxy lower alkyl group optionally substituted
on the pyridine ring with one or more lower alkyl groups;
R$^2$ is one of the following (2-1) to (2-33):
(2-1) a hydrogen atom,
(2-2) a lower alkoxy group,
(2-3) a lower alkyl group,
(2-4) a carboxy lower alkoxy group,
(2-5) a lower alkoxycarbonyl lower alkoxy group,
(2-6) a hydroxy group,
(2-7) a phenyl lower alkoxy group optionally substituted on
the phenyl ring with one or more members selected from
the group consisting of halogen atoms; lower alkyl groups
optionally substituted with one or more halogen atoms;
lower alkylthio groups optionally substituted with one or
more halogen atoms; lower alkoxy groups; a nitro group;
lower alkylsulfonyl groups; lower alkoxycarbonyl groups;
phenyl lower alkenyl groups; lower alkanoyloxy groups;
and 1,2,3-thiadiazolyl groups,
(2-8) a piperidinyl lower alkoxy group optionally substituted
on the piperidine ring with one or more lower alkyl groups,
(2-9) an amino-substituted lower alkoxy group optionally
substituted with one or more lower alkyl groups,
(2-10) a lower alkenyloxy group,
(2-11) a pyridyl lower alkoxy group optionally substituted on
the pyridine ring with one or more lower alkyl groups, each
lower alkyl substituent optionally being substituted with
one or more halogen atoms,
(2-12) a lower alkynyloxy group,
(2-13) a phenyl lower alkynyloxy group,
(2-14) a phenyl lower alkenyloxy group,
(2-15) a furyl lower alkoxy group optionally substituted on
the furan ring with one or more lower alkoxycarbonyl
groups,
(2-16) a tetrazolyl lower alkoxy group optionally substituted
on the tetrazole ring with one member selected from the
group consisting of a phenyl group, phenyl lower alkyl
groups, and cycloalkyl lower alkyl groups,
(2-17) a 1,2,4-oxadiazolyl lower alkoxy group optionally
substituted on the 1,2,4-oxadiazole ring with a phenyl
group, the phenyl substituent optionally being substituted
on the phenyl ring with one or more lower alkyl groups,
(2-18) an isoxazolyl lower alkoxy group optionally substi-
tuted on the isoxazole ring with one or more lower alkyl
groups,
(2-19) a 1,3,4-oxadiazolyl lower alkoxy group optionally
substituted on the 1,3,4-oxadiazole ring with a phenyl
group, the phenyl substituent optionally being substituted
on the phenyl ring with one or more lower alkyl groups,
(2-20) a lower alkanoyl lower alkoxy group,
(2-21) a thiazolyl lower alkoxy group optionally substituted
on the thiazole ring with one or more members selected
from the group consisting of lower alkyl groups and a
phenyl group, each phenyl substituent optionally being
substituted on the phenyl ring with one or more halogen
atoms,
(2-22) a piperidinyloxy group optionally substituted on the
piperidine ring with one or more benzoyl groups, each
benzoyl substituent optionally being substituted on the
phenyl ring with one or more halogen atoms,
(2-23) a thienyl lower alkoxy group,
(2-24) a phenylthio lower alkoxy group,
(2-25) a carbamoyl-substituted lower alkoxy group option-
ally substituted with one or more lower alkyl groups,
(2-26) a benzoyl lower alkoxy group,
(2-27) a pyridylcarbonyl lower alkoxy group,
(2-28) an imidazolyl lower alkoxy group optionally substi-
tuted on the imidazole ring with one or more phenyl lower
alkyl groups,
(2-29) a phenoxy lower alkoxy group,
(2-30) a phenyl lower alkoxy-substituted lower alkoxy group,
(2-31) a 2,3-dihydro-1H-indenyloxy group, (2-32) an isoindolinyl lower alkoxy group optionally substituted on the isoindoline ring with one or more oxo groups,
(2-33) a phenyl group;
R³ is one of the following (3-1) to (3-19):
(3-1) a hydrogen atom,
(3-2) a lower alkyl group,
(3-3) a hydroxy-substituted lower alkyl group,
(3-4) a cycloalkyl lower alkyl group,
(3-5) a carboxy lower alkyl group,
(3-6) a lower alkoxycarbonyl lower alkyl group,
(3-7) a phenyl lower alkyl group optionally substituted on the phenyl ring with one or more members selected from the group consisting of halogen atoms; lower alkyl groups optionally substituted with one or more halogen atoms; lower alkoxy groups optionally substituted with one or more halogen atoms; a phenyl group; lower alkoxycarbonyl groups; a phenoxy group; lower alkylthio groups; lower alkylsulfonyl groups; phenyl lower alkoxy groups; and amino groups optionally substituted with one or more lower alkanoyl groups,
(3-8) a naphthyl lower alkyl group,
(3-9) a furyl lower alkyl group optionally substituted on the furan ring with one or more lower alkoxycarbonyl groups,
(3-10) a thiazolyl lower alkyl group optionally substituted on the thiazole ring with one or more members selected from the group consisting of lower alkyl groups and a phenyl group, each phenyl substituent optionally being substituted on the phenyl ring with one or more optionally halogen-substituted lower alkyl groups,
(3-11) a tetrazolyl lower alkyl group optionally substituted on the tetrazole ring with one or more lower alkyl groups,
(3-12) a benzothienyl lower alkyl group optionally substituted on the benzothiophene ring with one or more halogen atoms,
(3-13) a lower alkynyl group,
(3-14) a lower alkenyl group,
(3-15) a phenyl lower alkenyl group,
(3-16) a benzoimidazolyl lower alkyl group,
(3-17) a pyridyl lower alkyl group,
(3-18) an imidazolyl lower alkyl group optionally substituted on the imidazole ring with one or more phenyl lower alkyl groups,
(3-19) a quinolyl lower alkyl group;
B is a carbonyl group or an —NHCO— group;
l is 0 or 1;
R⁶ and R⁷ each independently represent one of the following (4-1) to (4-79):
(4-1) a hydrogen atom,
(4-2) a lower alkyl group,
(4-3) a lower alkanoyl group,
(4-4) a lower alkylsulfonyl group optionally substituted with one or more halogen atoms,
(4-5) an alkoxycarbonyl group optionally substituted with one or more halogen atoms,
(4-6) a hydroxy-substituted lower alkyl group,
(4-7) a pyridylcarbonyl group optionally substituted on the pyridine ring with one or more members selected from the group consisting of pyrrolyl groups and halogen atoms,
(4-8) a pyridyl group optionally substituted on the pyridine ring with one or more members selected from the group consisting of lower alkyl groups and lower alkoxy groups,
(4-9) a pyridyl lower alkyl group,
(4-10) a phenyl group optionally substituted on the phenyl ring with one or more members selected from the group consisting of halogen atoms; lower alkyl groups optionally substituted with one or more halogen atoms; a phenoxy group; lower alkoxy groups optionally substituted with one or more halogen atoms; lower alkylthio groups; lower alkylsulfonyl groups; amino groups optionally substituted with one or more members selected from the group consisting of lower alkyl groups and lower alkanoyl groups; pyrrolidinyl groups optionally substituted on the pyrrolidine ring with one or more-oxo groups; piperidinyl groups optionally substituted on the piperidine ring with one or more lower alkyl groups; lower alkenyl groups; an aminosulfonyl group; a hydroxy group; carbamoyl groups optionally substituted with one or more lower alkyl groups; phenyl lower alkoxy groups; and a cyano group,
(4-11) a cycloalkyl group optionally substituted on the cycloalkyl ring with one or more lower alkyl groups,
(4-12) a benzoyl group optionally substituted on the phenyl ring with one or more members selected from the group consisting of halogen atoms; a phenoxy group; a phenyl group; lower alkyl groups optionally substituted with one or more halogen atoms; lower alkoxy groups; lower alkanoyl groups; a nitro group; a cyano group; amino groups optionally substituted with one or more members selected from the group consisting of a phenyl group and lower alkyl groups; pyrrolidinyl groups optionally substituted on the pyrrolidine ring with one or more oxo groups; pyrrolyl groups; pyrazolyl groups; 1,2,4-triazolyl groups; and imidazolyl groups,
(4-13) a benzoyl group substituted on the phenyl ring with one or more lower alkylenedioxy groups,
(4-14) a cycloalkylcarbonyl group,
(4-15) a furylcarbonyl group,
(4-16) a naphthylcarbonyl group,
(4-17) a phenoxycarbonyl group optionally substituted on the phenyl ring with one or more members selected from the group consisting of lower alkoxy groups, lower alkyl groups, halogen atoms, and a nitro group,
(4-18) a phenyl lower alkoxycarbonyl group optionally substituted on the phenyl ring with one or more members selected from the group consisting of halogen atoms and a nitro group,
(4-19) a piperidinyl group optionally substituted on the piperidine ring with one or more members selected from the group consisting of lower alkyl groups; lower alkanoyl groups; benzoyl groups optionally substituted on the phenyl ring with one or more halogen atoms; and phenyl groups optionally substituted on the phenyl ring with one or more halogen atoms,
(4-20) a tetrahydropyranyl lower alkyl group,
(4-21) a cycloalkyl lower alkyl group,
(4-22) a lower alkenyl group,
(4-23) a phenyl lower alkyl group optionally substituted on the alkyl group with one or more lower alkoxycarbonyl groups; and optionally substituted on the phenyl ring with one or more members selected from the group consisting of halogen atoms, lower alkyl groups optionally substituted with one or more halogen atoms, lower alkoxy groups optionally substituted with one or more halogen atoms, and a hydroxy group,
(4-24) a lower alkylenedioxy-substituted phenyl lower alkyl group,
(4-25) a furyl lower alkyl group,
(4-26) a carbamoyl lower alkyl group optionally substituted with one or more members selected from lower alkyl groups and a phenyl group, each phenyl substituent optionally being substituted on the phenyl ring with one or more lower alkyl groups,
(4-27) a lower alkoxy lower alkyl group,
(4-28) an imidazolyl lower alkyl group optionally substituted on the lower alkyl group with one or more members selected from the group consisting of a carbamoyl group and lower alkoxycarbonyl groups,
(4-29) an amino-substituted lower alkyl group optionally substituted with one or more lower alkyl groups,
(4-30) a 2,3,4,5-tetrahydrofuryl group optionally substituted on the 2,3,4,5-tetrahydrofuran ring with one or more oxo groups,
(4-31) a lower alkoxycarbonyl lower alkyl group, (4-32) a pyrrolidinyl lower alkyl group optionally substituted on the pyrrolidine ring with one or more lower alkyl groups,
(4-33) a phenoxy lower alkanoyl group,
(4-34) a morpholino lower alkyl group,
(4-35) a indolyl group,
(4-36) a thiazolyl group,
(4-37) a 1,2,4-triazolyl group,
(4-38) a pyridyl lower alkanoyl group,
(4-39) a thienylcarbonyl group,
(4-40) a thienyl lower alkanoyl group,
(4-41) a cycloalkyl lower alkanoyl group,
(4-42) an isoxazolylcarbonyl group optionally substituted on the isoxazole ring with one or more lower alkyl groups,
(4-43) a pyrazylcarbonyl group,
(4-44) a piperidinylcarbonyl group optionally substituted on the piperidine ring with one or more members selected from a benzoyl group and lower alkanoyl groups,
(4-45) a chromanylcarbonyl group,
(4-46) an isoindolinyl lower alkanoyl group optionally substituted on the isoindoline ring with one or more oxo groups,
(4-47) a thiazolidinyl lower alkanoyl group optionally substituted on the thiazolidine ring with one or more members selected from an oxo group and a thioxo group,
(4-48) a piperidinyl lower alkanoyl group,
(4-49) a phenyl lower alkenylcarbonyl group optionally substituted on the phenyl ring with one or more halogen atoms,
(4-50) a phenyl lower alkenylcarbonyl group substituted on the phenyl ring with one or more alkylenedioxy groups,
(4-51) a pyridyl lower alkenyl carbonyl group,
(4-52) a pyridylthio lower alkanoyl group,
(4-53) an indolylcarbonyl group,
(4-54) a pyrrolylcarbonyl group,
(4-55) a pyrrolidinylcarbonyl group optionally substituted on the pyrrolidine ring with one or more oxo groups,
(4-56) a benzofurylcarbonyl group,
(4-57) an indolyl lower alkanoyl group,
(4-58) a benzothienylcarbonyl group,
(4-59) a phenyl lower alkanoyl group optionally substituted on the phenyl ring with one or more halogen atoms,
(4-60) a phenylsulfonyl group optionally substituted on the phenyl ring with one or more members selected from the group consisting of lower alkoxycarbonyl groups; a cyano group; a nitro group; amino groups optionally substituted with one or more alkanoyl groups; a hydroxy group; a carboxyl group; lower alkoxycarbonyl lower alkyl groups; halogen atoms; lower alkyl groups optionally substituted with one or more halogen atoms; and lower alkoxy groups optionally substituted with one or more halogen atoms,
(4-61) a thienylsulfonyl group optionally substituted on the thiophene ring with one or more members selected from the group consisting of halogen atoms and lower alkoxycarbonyl groups,
(4-62) a quinolylsulfonyl group,
(4-63) an imidazolylsulfonyl group optionally substituted on the imidazole ring with one or more lower alkyl groups,
(4-64) a phenylsulfonyl group optionally substituted on the phenyl ring with one or more lower alkylenedioxy groups,
(4-65) a lower alkenylsulfonyl group,
(4-66) a cycloalkyl lower alkylsulfonyl group,
(4-67) a 3,4-dihydro-2H-1,4-benzoxazinylsulfonyl group optionally substituted on the 3,4-dihydro-2H-1,4-benzoxazine ring with one or more lower alkyl groups,
(4-68) a pyrazolylsulfonyl group optionally substituted on the pyrazole ring with one or more members selected from halogen atoms and lower alkyl groups,
(4-69) an isoxazolylsulfonyl group optionally substituted on the isoxazole ring with one or more lower alkyl groups,
(4-70) a thiazolylsulfonyl group optionally substituted on the thiazole ring with one or more members selected from the group consisting of lower alkyl groups and an amino group, each amino substituent optionally being substituted with one or more alkanoyl groups,
(4-71) a phenyl lower alkylsulfonyl group,
(4-72) a phenyl lower alkenylsulfonyl group,
(4-73) a naphthyloxycarbonyl group,
(4-74) a lower alkynyloxycarbonyl group,
(4-75) a lower alkenyloxycarbonyl group,
(4-76) a phenyl lower alkoxy-substituted lower alkoxycarbonyl group,
(4-77) a cycloalkyloxycarbonyl group optionally substituted on the cycloalkyl ring with one or more lower alkyl groups,
(4-78) a tetrazolyl group,
(4-79) an isoxazolyl group optionally substituted on the isoxazole ring with one or more lower alkyl groups; or instead, $R^6$ and $R^7$ may be linked together to form, together with the nitrogen atom to which they are bound, a 1,2,3,4-tetrahydroisoquinolyl group, an isoindolinyl group, or a 5- to 7-membered saturated heterocyclic group, the heterocyclic group optionally containing one or more additional heteroatoms and optionally being substituted with one to three members from the following (5-1) to (5-28):
(5-1) lower alkyl groups,
(5-2) lower alkoxy groups,
(5-3) an oxo group,
(5-4) a hydroxy group,
(5-5) pyridyl lower alkyl groups,
(5-6) phenyl groups optionally substituted on the phenyl ring with one or more members selected from the group consisting of halogen atoms; lower alkoxy groups optionally substituted with one or more halogen atoms; lower alkyl groups optionally substituted with one or more halogen atoms; a cyano group; and a hydroxy group,
(5-7) lower alkylenedioxy-substituted phenyl lower alkyl groups,
(5-8) phenyl lower alkyl groups optionally substituted on the phenyl ring with one or more halogen atoms,
(5-9) pyrimidyl groups,
(5-10) pyrazyl groups,
(5-11) cycloalkyl groups,
(5-12) phenyl lower alkoxy groups optionally substituted on the phenyl ring with one or more halogen atoms,
(5-13) benzoyl groups optionally substituted on the phenyl ring with one or more halogen atoms,
(5-14) benzoyl groups substituted on the phenyl ring with one or more lower alkylenedioxy groups,
(5-15) carbamoyl lower alkyl groups optionally substituted with one or more members selected from the group consisting of a phenyl group and lower alkyl groups,
(5-16) benzoxazolyl groups,
(5-17) lower alkoxycarbonyl groups,
(5-18) a carbamoyl group,
(5-19) phenyl lower alkylidene groups optionally substituted on the phenyl ring with one or more halogen atoms,
(5-20) phenyl lower alkoxycarbonyl groups,
(5-21) pyridyl groups optionally substituted on the pyridine ring with one or more members selected from the group consisting of a cyano group and lower alkyl groups,
(5-22) furyl lower alkyl groups,
(5-23) tetrahydropyranyl groups,
(5-24) imidazolyl lower alkyl groups,
(5-25) naphthyl groups,
(5-26) 2,3-dihydro-1H-indenyl groups,
(5-27) 1,3-dioxolanyl lower alkyl groups,
(5-28) -$(A_3)_m NR^{11}R^{12}$ groups;
  $A_1$ is a lower alkylene group;
  $R^8$ and $R^9$ each independently represent one of the following (6-1) to (6-25):
(6-1) a hydrogen atom,
(6-2) a lower alkyl group,
(6-3) a phenyl group optionally substituted on the phenyl ring with one or more members selected from the group consisting of lower alkyl groups optionally substituted with one or more halogen atoms; lower alkylthio groups; lower alkoxy groups optionally substituted with one or more halogen atoms; halogen atoms; a phenyl group; lower alkylamino groups; a cyano group; a phenoxy group; cycloalkyl groups; pyrrolidinyl groups optionally substituted with one or more oxo groups; 1,2,3,4-tetrahydroisoquinolylcarbonyl groups; 1,2,3,4-tetrahydroquinolylcarbonyl groups optionally substituted with one or more lower alkyl groups; 1,2,3,4-tetrahydroquinoxalinylcarbonyl groups optionally substituted with one or more lower alkyl groups; thiazolyl groups optionally substituted with one or more phenyl groups; a carbamoyl group; phenyl lower alkoxy groups; lower alkylsulfonylamino groups; anilino groups optionally substituted with one or more halogen atoms; phenyl lower alkyl groups; and hydroxy-substituted lower alkyl groups,
(6-4) a cycloalkyl group,
(6-5) a cycloakyl lower alkyl group,
(6-6) a carbamoyl lower alkyl group,
(6-7) a phenyl lower alkyl group optionally substituted on the phenyl ring with one or more members selected from the group consisting of lower alkyl groups optionally substituted with one or more halogen atoms; lower alkoxy groups optionally substituted with one or more halogen atoms; halogen atoms; and a phenyl group,
(6-8) lower alkyl-substituted amino lower alkyl group,
(6-9) a naphthyl group,
(6-10) a naphthyl lower alkyl group,
(6-11) a tetrahydronaphthyl lower alkyl group,
(6-12) a fluorenyl group,
(6-13) a pyridyl group,
(6-14) a pyridyl lower alkyl group,
(6-15) a pyrimidinyl group,
(6-16) a pyrazinyl lower alkyl group optionally substituted on the pyrazine ring with one or more lower alkyl groups,
(6-17) a thiazolyl group,
(6-18) a pyrazolyl lower alkyl group optionally substituted on the pyrazole ring with one or more lower alkyl groups,
(6-19) a thienyl lower alkyl group
(6-20) a piperidinyl group optionally substituted on the piperidine ring with one or more members selected from the group consisting of lower alkyl groups; a benzoyl group; and phenyl lower alkyl groups optionally substituted on the phenyl ring with one or more members selected from the group consisting of halogen atoms and lower alkyl groups,
(6-21) an indolyl group,
(6-22) an indazolyl group,
(6-23) a 3,4-dihydrocarbostyril optionally substituted with one or more lower alkyl groups,
(6-24) a quinolyl group optionally substituted with one or more lower alkyl groups,
(6-25) a carbazolyl group optionally substituted with one or more lower alkyl groups; or
$R^8$ and $R^9$ may be linked together to form, together with the nitrogen atom to which they are bound, a 5- to 8-membered saturated heterocyclic group optionally containing one or more additional heteroatoms and optionally substituted on the heterocyclic ring with one or more members selected from the group consisting of the following (6-28-1) to (6-28-24):
(6-28-1) lower alkyl groups,
(6-28-2) phenyl lower alkyl groups optionally substituted on the phenyl ring with one or more members selected from halogen atoms and lower alkoxy groups optionally substituted with one or more halogen atoms,
(6-28-3) naphthyl lower alkyl groups,
(6-28-4) phenyl lower alkylcarbamoyl lower alkyl groups,
(6-28-5) phenylcarbamoyl lower alkyl groups,
(6-28-6) phenyl lower alkoxycarbonyl groups,
(6-28-7) phenoxy lower alkyl groups optionally substituted on the phenyl ring with one or more members selected from the group consisting of halogen atoms and lower alkyl groups optionally substituted with one or more halogen atoms,
(6-28-8) biphenyl groups,
(6-28-9) phenyl groups optionally substituted on the phenyl ring with one or more halogen atoms,
(6-28-10) 2,3-dihydroindenyl groups optionally substituted with one or more halogen atoms,
(6-28-11) benzothiazolyl groups optionally substituted with one or more halogen atoms,
(6-28-12) pyridyl groups optionally substituted with one or more halogen atoms,
(6-28-13) benzothienyl groups,
(6-28-14) benzoisothiazolyl groups,
(6-28-15) thienopyridyl groups,
(6-28-16) a carbamoyl group,
(6-28-17) phenyl lower alkoxy groups optionally substituted on the phenyl ring with one or more halogen atoms,
(6-28-18) phenoxy groups optionally substituted with one or more halogen atoms,
(6-28-19) benzoyl groups optionally substituted on the phenyl ring with one or more members selected from halogen atoms and lower alkoxy groups,
(6-28-20) anilino groups optionally substituted on the phenyl ring with one or more lower alkyl groups, each lower alkyl substituent optionally being substituted with one or more halogen atoms,
(6-28-21) anilino groups substituted on the amino group with one or more lower alkyl groups, and optionally further substituted on the phenyl ring with one or more halogen atoms,
(6-28-22) benzofuryl groups,
(6-28-23) naphthyl groups,
(6-28-24) an oxo group; or
$R^8$ and $R^9$ may be linked together to form, together with the nitrogen atom to which they are bound, a 5- or 6-membered unsaturated heterocyclic group, the unsaturated heterocyclic group optionally being substituted on the heterocyclic ring with one or more members selected from the group consisting of the following (6-29-1) to (6-29-3):
(6-29-1) phenyl groups optionally substituted with one or more halogen atoms,
(6-29-2) 2,3-dihydroindenyl groups,
(6-29-3) benzothienyl groups; or instead,
$R^8$ and $R^9$ may be linked together to form, together with the nitrogen atom to which they are bound, a 1,2,3,4-tetrahydroquinolyl group; a 1,2,3,4-tetrahydroisoquinolyl group, a 1,3-dihydroisoindolyl group; an octahydropyrrolo[1,2-a]pyrazinyl group optionally substituted on the pyrazine ring with one or more lower alkyl groups; or an 8-azabicyclo[3.2.1]octyl group optionally substituted on the 8-azabicyclo[3.2.1]octyl group with one or more phenoxy groups, each phenoxy substituent optionally being substituted on the phenyl ring with one or more halogen atoms;
$A_2$ is a lower alkylene group;
$R^{10}$ is one of the following (7-1) to (7-44):
(7-1) a hydrogen atom,
(7-2) a lower alkyl group,
(7-3) an alkoxycarbonyl group optionally substituted with one or more halogen atoms,
(7-4) a benzoyl group optionally substituted on the phenyl ring with one or more members selected from the group consisting of lower alkyl groups optionally substituted with one or more halogen atoms; a phenyl group; halogen atoms; a cyano group; a phenoxy group; lower alkoxycarbonyl groups; pyrazolyl groups; and lower alkoxy groups optionally substituted with one or more halogen atoms,
(7-5) an alkanoyl group,
(7-6) a phenyl lower alkanoyl group optionally substituted on the phenyl ring with one or more members selected from the group consisting of halogen atoms and lower alkyl groups, (7-7) a cycloalkyl lower alkanoyl group,
(7-8) a phenyl group optionally substituted on the phenyl ring with one or more lower alkyl groups,
(7-9) a phenoxy lower alkanoyl group optionally substituted on the phenyl ring with one or more halogen atoms,
(7-10) a phenyl lower alkenylcarbonyl group,
(7-11) a pyridylcarbonyl group optionally substituted on the pyridine ring with one or more members selected from the group consisting of halogen atoms and lower alkyl groups, each lower alkyl substituent optionally being substituted with one or more halogen atoms,
(7-12) a furylcarbonyl group,
(7-13) a thienylcarbonyl group,
(7-14) a piperidinylcarbonyl group optionally substituted on the piperidine ring with one or more lower alkanoyl groups,
(7-15) a pyrrolidinylcarbonyl group optionally substituted on the pyrrolidine ring with one or more oxo groups,
(7-16) a tetrahydropyranylcarbonyl group,
(7-17) a naphthylcarbonyl group,
(7-18) an indolylcarbonyl group,
(7-19) a benzofurylcarbonyl group,
(7-20) a benzothienylcarbonyl group optionally substituted on the benzothiophene ring with one or more halogen atoms,
(7-21) a furyl lower alkyl group,
(7-22) a pyridyl lower alkyl group optionally substituted on the pyridine ring with one or more members selected from the group consisting of halogen atoms and lower alkyl groups, each lower alkyl substituent optionally being substituted with one or more halogen atoms,
(7-23) a thienyl lower alkyl group optionally substituted on the thiophene ring with one or more halogen atoms,
(7-24) a phenyl lower alkyl group optionally substituted on the phenyl ring with one or more members selected from the group consisting of lower alkoxy groups optionally substituted with one or more halogen atoms; a cyano group; lower alkyl groups optionally substituted with one or more halogen atoms; amino groups optionally substituted with one or more members selected from the group consisting of lower alkyl groups and lower alkanoyl groups; halogen atoms; lower alkoxycarbonyl groups; lower alkanoyloxy groups; lower alkylsulfonyl groups; lower alkylthio groups; and pyrrolidinyl groups,
(7-25) a thiazolyl lower alkyl group,
(7-26) an imidazolyl lower alkyl group optionally substituted on the imidazole ring with one or more lower alkyl groups,
(7-27) a pyrrolyl lower alkyl group optionally substituted on the pyrrole ring with one or more lower alkyl groups,
(7-28) a cycloalkyl lower alkyl group,
(7-29) a lower alkylthio lower alkyl group,
(7-30) a phenoxycarbonyl group optionally substituted on the phenyl ring with one or more members selected from the group consisting of halogen atoms, lower alkyl groups, and lower alkoxy groups,
(7-31) a phenyl lower alkoxycarbonyl group optionally substituted on the phenyl ring with one or more halogen atoms,
(7-32) a naphthyloxycarbonyl group,
(7-33) a lower alkynyloxycarbonyl group,
(7-34) a cycloalkylcarbonyl group,
(7-35) a quinoxalinylcarbonyl group,
(7-36) a —CO—NR$^{13}$R$^{14}$ group,
(7-37) a piperidinyl group optionally substituted on the piperidine ring with one or more lower alkyl groups,
(7-38) a cycloalkyl group,
(7-39) a tetrahydropyranyl group,
(7-40) a lower alkoxy lower alkyl group,
(7-41) a tetrahydro-2H-thiopyranyl group,
(7-42) a naphthyl group,
(7-43) a biphenyl group,
(7-44) a lower alkylsilyl lower alkoxycarbonyl group;
A$^3$ is a lower alkylene group;
m is 0 or 1;

R$^{11}$ and R$^{12}$ each independently represent one of the following (8-1) to (8-5):
(8-1) a hydrogen atom,
(8-2) a lower alkyl group,
(8-3) a lower alkanoyl group,
(8-4) a phenyl lower alkanoyl group,
(8-5) a phenyl group optionally substituted on the phenyl ring with one or more halogen atoms; or instead,
R$^{11}$ and R$^{12}$ may be linked together to form, together with the nitrogen atom to which they are bound, a 5- or 6-membered saturated heterocyclic group which optionally contains one or more additional heteroatoms, the heterocyclic group optionally being substituted with one to three members selected from the group consisting of the following (9-1) and (9-2):
(9-1) lower alkyl groups,
(9-2) a phenyl group; and
R$^{13}$ and R$^{14}$ each independently represent one of the following (10-1) to (10-3):
(10-1) a hydrogen atom,
(10-2) a lower alkyl group,
(10-3) a phenyl group, or instead
R$^{13}$ and R$^{14}$ may be linked together to form, together with the nitrogen atom to which they are bound, a 5- or 6-membered saturated heterocyclic group which optionally contains one or more additional heteroatoms.

Item 2. A carbostyril compound or a salt thereof according to Item 1, wherein the bond between the 3 and 4 positions of the carbostyril skeleton is a single bond or a double bond, and R$^4$ and R$^5$ each represent a hydrogen atom.

Item 3. A carbostyril compound or a salt thereof according to Item 2, wherein a group of the formula

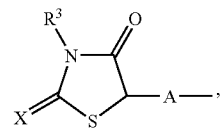

in which R$^3$, A and X are as defined in Item 1 above, is bound to the 3, 4, 5, 6, 7 or 8 position of the carbostyril skeleton.

Item 4. A carbostyril compound or a salt thereof according to Item 3, wherein the bond between the 3 and 4 positions of the carbostyril skeleton is a single bond, and the group of the formula,

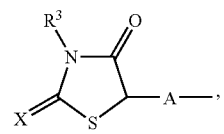

in which R$^3$, A and X are as defined in Item 1 above, is bound to the 5 or 6 position of the carbostyril skeleton.

Item 5. A carbostyril compound or a salt thereof according to Item 3 or 4, wherein A is a lower alkylene group or a lower alkylidene group.

Item 6. A carbostyril compound or a salt thereof according to Item 5, wherein R$^1$ is one of (1-2), (1-3), (1-4), (1-6), (1-10), (1-12), (1-13), (1-18) and (1-21) as defined in Item 1 above.

Item 7. A carbostyril compound or a salt thereof according to Item 6, wherein the group of the formula

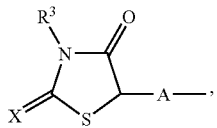

in which $R^3$, A and X are as defined in Item 1 above, is bound to the 5 position of the carbostyril skeleton.

Item 8. A carbostyril compound or a salt thereof according to Item 7, wherein $R^1$ is a phenyl lower alkyl group optionally substituted on the phenyl ring with one or more members selected from the group consisting of a phenyl ring, halogen atoms, —(B)$_l$NR$^6$R$^7$ groups wherein B, l, $R^6$ and $R^7$ are as defined in Item 1, lower alkoxycarbonyl groups, and phenyl lower alkoxy groups.

Item 9. A carbostyril compound or a salt thereof according to Item 8, wherein A is a lower alkylene group, $R^2$ is a hydrogen atom or a lower alkoxy group, $R^3$ is a hydrogen atom, and X is an oxygen atom or a sulfur atom.

Item 10. A carbostyril compound or a salt thereof according to Item 7, wherein A is a lower alkylene group, $R^1$ is a lower alkyl group, $R^2$ is a hydrogen atom or a lower alkoxy group, $R^3$ is a hydrogen atom, and X is an oxygen atom or a sulfur atom.

Item 11. A carbostyril compound or a salt thereof according to Item 7, wherein A is a lower alkylene group, $R^1$ is a naphthyl lower alkyl group, $R^2$ is a hydrogen atom or a lower alkoxy group, $R^3$ is a hydrogen atom, and X is an oxygen atom or a sulfur atom.

Item 12. A carbostyril compound or a salt thereof according to Item 7, wherein A is a lower alkylene group, $R^1$ is a group of the formula

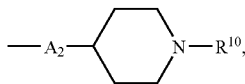

in which $R^{10}$ and $A_2$ are as defined in Item 1 above, $R^2$ is a hydrogen atom or a lower alkoxy group, $R^3$ is a hydrogen atom, and X is an oxygen atom or a sulfur atom.

Item 13. A carbostyril compound or a salt thereof according to Item 3, wherein the bond between the 3 and 4 positions of the carbostyril skeleton is a double bond, and a group of the formula

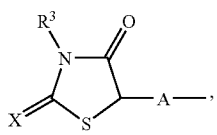

in which $R^3$, A and X are as defined in Item 1 above, is bound to the 3, 4 or 5 position of the carbostyril skeleton.

Item 14. A carbostyril compound or a salt thereof according to Item 13, wherein $R^1$ is one of (1-2) and (1-3) as defined in Item 1.

Item 15. A carbostyril compound or a salt thereof according to Item 14, wherein A is a lower alkylene group or a lower alkylidene group, and $R^2$ is a hydrogen atom or a lower alkoxy group.

Item 16. A carbostyril compound or a salt thereof according to Item 1, wherein the bond between the 3 and 4 positions of the carbostyril skeleton is a double bond, and $R^4$ and $R^5$ are linked together in the form of a —CH=CH—CH=CH— group.

Item 17. A carbostyril compound or a salt thereof according to Item 16, wherein a group of the formula

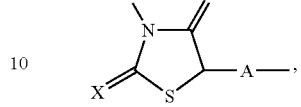

in which $R^3$, A and X are as defined in Item 1 above, is bound to the 7 position of the carbostyril skeleton.

Item 18. A carbostyril compound or a salt thereof according to Item 17, wherein $R^1$ is one of (1-2) and (1-3) as defined in Item 1 above.

Item 19. A carbostyril compound or a salt thereof according to Item 18, wherein A is a lower alkylene group or a lower alkylidene group, $R^2$ and $R^3$ are both hydrogen atoms, and X is an oxygen atom or a sulfur atom.

Item 20. A carbostyril compound or a salt thereof according to Item 1, wherein A is a direct bond.

Item 21. A carbostyril compound or a salt thereof according to Item 1, wherein A is a lower alkylene group.

Item 22. A carbostyril compound or a salt thereof according to Item 1, wherein A is a lower alkylidene group.

Item 23. A carbostyril compound or a salt thereof according to any one of Items 20 to 22, wherein the bond between the 3 and 4 positions of the carbostyril skeleton is a single bond or a double bond, and $R^4$ and $R^5$ each represent a hydrogen atom.

Item 24. A carbostyril compound or a salt thereof according to any one of Items 20 to 22, wherein the bond between the 3 and 4 positions of the carbostyril skeleton is a double bond, and $R^4$ and $R^5$ are linked together in the form of a —CH=CH—CH=CH— group.

Item 25. A carbostyril compound selected from the group consisting of the following compounds:
5-[1-(biphenyl-4-ylmethyl)-8-methoxy-2-oxo-1,2,3,4-tetrahydroquinolin-5-ylmethyl]thiazolidine-2,4-dione,
5-[1-(4-chlorobenzyl)-8-methoxy-2-oxo-1,2,3,4-tetrahydroquinolin-5-ylmethyl]thiazolidine-2,4-dione,
5-[1-(4-bromobenzyl)-8-methoxy-2-oxo-1,2,3,4-tetrahydroquinolin-5-ylmethyl]thiazolidine-2,4-dione,
5-[1-(2-naphthylmethyl)-8-methoxy-2-oxo-1,2,3,4-tetrahydroquinolin-5-ylmethyl]thiazolidine-2,4-dione,
5-{1-[4-(heptyloxycarbonylamino)benzyl]-8-methoxy-2-oxo-1,2,3,4-tetrahydroquinolin-5-ylmethyl}thiazolidine-2,4-dione,
5-[1-(1-biphenyl-4-ylpiperidin-4-ylmethyl)-2-oxo-1,2,3,4-tetrahydroquinolin-5-ylmethyl]thiazolidine-2,4-dione,
5-{1-[1-(4-methylphenyl)piperidin-4-ylmethyl]-2-oxo-1,2,3,4-tetrahydroquinolin-5-ylmethyl}thiazolidine-2,4-dione,
5-{1-[4-(2-chlorobenzyloxycarbonylamino)benzyl]-8-methoxy-2-oxo-1,2,3,4-tetrahydroquinolin-5-ylmethyl}thiazolidine-2,4-dione,
1-(biphenyl-4-ylmethyl)-8-methoxy-5-(4-oxo-2-thioxothiazolidin-5-ylmethyl)-3,4-dihydro-1H-quinolin-2-one,
8-methoxy-1-methyl-5-(4-oxo-2-thioxothiazolidin-5-ylmethyl)-3,4-dihydro-1H-quinolin-2-one,
8-methoxy-1-(3-methylbutyl)-5-(4-oxo-2-thioxothiazolidin-5-ylmethyl)-3,4-dihydro-1H-quinolin-2-one,
1-propyl-8-methoxy-5-(4-oxo-2-thioxothiazolidin-5-ylmethyl)-3,4-dihydro-1H-quinolin-2-one,
1-isobutyl-8-methoxy-5-(4-oxo-2-thioxothiazolidin-5-ylmethyl)-3,4-dihydro-1H-quinolin-2-one,
8-methoxy-1-phenethyl-5-(4-oxo-2-thioxothiazolidin-5-ylmethyl)-3,4-dihydro-1H-quinolin-2-one, and
1-(4-phenylthiomethyl)benzyl-5-(4-oxo-2-thioxothiazolidin-5-ylmethyl)-3,4-dihydro-1H-quinolin-2-one; or a salt thereof.

Item 26. A pharmaceutical composition comprising as an active ingredient a carbostyril compound or salt thereof according to Item 1.

Item 27. A prophylactic and/or therapeutic agent for a disorder on which TFF up-regulation has a prophylactic and/or therapeutic effect, comprising as an active ingredient a carbostyril compound or salt thereof according to Item 1.

Item 28. A prophylactic and/or therapeutic agent according to claim 27, wherein the disorder on which TFF up-regulation has a prophylactic and/or therapeutic effect is an alimentary tract disease, oral disease, upper respiratory tract disease, respiratory tract disease, eye disease, cancer, or wound.

Item 29. A prophylactic and/or therapeutic agent according to claim 27, wherein the disorder on which TFF up-regulation has a prophylactic and/or therapeutic effect is a drug-induced ulcer, peptic gastric ulcer, ulcerative colitis, Crohn's disease, drug-induced enteritis, ischemic colitis, irritable bowel syndrome, ulcer developed after endoscopic demucosation, acute gastritis, chronic gastritis, reflux esophagitis, esophageal ulcer, Barrett esophagus, gastrointestinal mucositis, hemorrhoidal diseases, stomatitis, Sjögren syndrome, xerostomia, rhinitis, pharyngitis, bronchial asthma, chronic obstructive lung disease, dry eye, or keratoconjunctivitis.

Item 30. A prophylactic and/or therapeutic agent according to Item 27, wherein the TFF is TFF2.

Item 31. A use of a carbostyril compound or salt thereof according to Item 1 for manufacturing a prophylactic and/or therapeutic agent for a disorder on which TFF up-regulation has a prophylactic and/or therapeutic effect.

Item 32. A method for preventing and/or treating a disorder on which TFF up-regulation has a prophylactic and/or therapeutic effect, comprising administering to a patient an effective amount of a carbostyril compound or salt thereof according to Item 1.

Item 33. A prophylactic and/or therapeutic agent for alimentary tract diseases, oral diseases, upper respiratory tract diseases, respiratory tract diseases, eye diseases, cancers, or wounds, the agent comprising a compound that induces the production of TFF.

Item 34. A prophylactic and/or therapeutic agent according to Item 33, wherein the TFF is TFF2.

Item 35. A process for the production of a carbostyril compound (1) of the following formula:

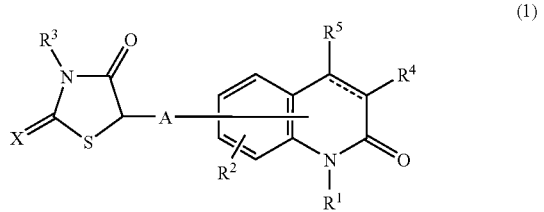

(1)

or a salt thereof, wherein $R^1$, $R^2$, $R^3$, $R^4$, $R^5$, A, X, and the bond between the 3 and 4 positions of the carbostyril skeleton are as defined in Item 1,
which comprises
(i) reacting a compound (2) of the formula:

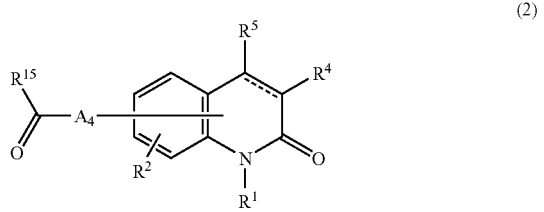

(2)

or a salt thereof, wherein $R^1$, $R^2$, $R^4$, $R^5$, and the bond between the 3 and 4 positions of the carbostyril skeleton are as defined above, and $R^{15}$ is a hydrogen atom or lower alkyl group, and $A_4$ represents a direct bond or lower alkylene group,
with a compound (3) of the formula:

(3)

or a salt thereof, wherein $R^3$ and X are as defined above, to give a compound (1a) of the formula:

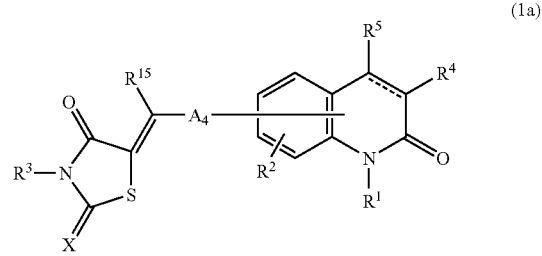

(1a)

or a salt thereof, wherein $R^1$, $R^2$, $R^3$, $R^4$, $R^5$, $R^{15}$, $A_4$ and the bond between the 3 and 4 positions of the carbostyril skeleton are as defined above, and
(ii) reducing the compound (1a) defined above or a salt thereof, to give a compound (1b) of the formula:

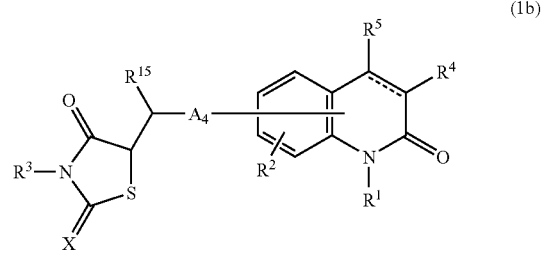

(1b)

or a salt thereof, wherein $R^1$, $R^2$, $R^3$, $R^4$, $R^5$, $R^{15}$, $A_4$ and the bond between the 3 and 4 positions of the carbostyril skeleton are as defined above.

Among carbostyril compounds represented by General Formula (1), compounds wherein the bond between the 3 and 4 positions of the carbostyril skeleton is a single bond and a double bond, and $R^4$ and $R^5$ each represent a hydrogen atom are preferable.

Among carbostyril compounds represented by General Formula (1), compounds wherein a group of the formula

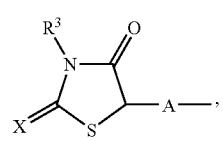

in which $R^3$, A and X are as defined in Item 1 above, is bound to the 3, 4, 5, 6, 7 or 8 position of the carbostyril skeleton are preferable.

Among carbostyril compounds represented by General Formula (1), compounds wherein the bond between the 3 and 4 positions of the carbostyril skeleton is a single bond, and the group of the formula

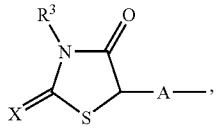

in which $R^3$, A and X are as defined in Item 1 above, is bound to the 5 or 6 position of the carbostyril skeleton are preferable.

Among carbostyril compounds represented by General Formula (1), compounds wherein A is a lower alkylene group or a lower alkylidene group are preferable.

Among carbostyril compounds represented by General Formula (1), compounds wherein $R^1$ is one of (1-2), (1-3), (1-4), (1-6), (1-10), (1-12), (1-13), (1-18) and (1-21) as defined in Item 1 above are preferable.

Among these preferable carbostyril compounds, compounds wherein the group of the formula

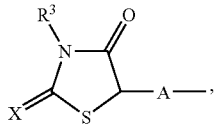

in which $R^3$, A and X are as defined in Item 1 above, is bound to the 5 position of the carbostyril skeleton are more preferable.

Compounds wherein $R^1$ is a phenyl lower alkyl group optionally substituted on the phenyl ring with one or more members selected from a phenyl group, halogen atoms, —(B)$_l$NR$^6$R$^7$ groups wherein B, l, R$^6$ and R$^7$ are as defined in Item 1 above, lower alkoxycarbonyl groups, and phenyl lower alkoxy groups are also more preferable;

of such carbostyril compounds, those wherein A is a lower alkylene group, $R^2$ is a hydrogen atom or a lower alkoxy group, $R^3$ is a hydrogen atom, and X is an oxygen atom or a sulfur atom are particularly preferable.

Among carbostyril compounds represented by General Formula (1), compounds wherein $R^1$ is a lower alkyl group are preferable, and further, those wherein A is a lower alkylene group, $R^2$ is a hydrogen atom or a lower alkoxy group, $R^3$ is a hydrogen atom, and X is an oxygen atom or a sulfur atom are more preferable.

Among carbostyril compounds represented by General Formula (1), compounds wherein $R^1$ is a naphthyl lower alkyl group are preferable, and further, those wherein A is a lower alkylene group, $R^2$ is a hydrogen atom or a lower alkoxy group, $R^3$ is a hydrogen atom, and X is an oxygen atom or a sulfur atom are more preferable.

Among carbostyril compounds represented by General Formula (1), compounds wherein $R^1$ is a group

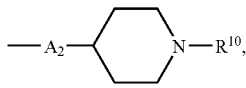

in which $R^{10}$ and $A_2$ are as defined in Item 1 above, are preferable, and further, those wherein A is a lower alkylene group, $R^2$ is a hydrogen atom or a lower alkoxy group, $R^3$ is a hydrogen atom, and X is an oxygen atom or a sulfur atom are preferable.

Among carbostyril compounds represented by General Formula (1), compounds wherein the bond between the 3 and 4 positions of the carbostyril skeleton is a double bond, and a group of the formula

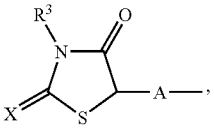

in which $R^3$, A and X are as defined in Item 1 above, is bound to the 3, 4 or 5 position of the carbostyril skeleton are preferable, and further, those wherein $R^1$ is (1-2) or (1-3) as defined in Item 1 are more preferable; of such carbostyril compounds, compounds wherein A is a lower alkylene group or a lower alkylidene group, and $R^2$ is a hydrogen atom or a lower alkoxy group are particularly preferable.

Among carbostyril compounds represented by General Formula (1), compounds wherein the bond between the 3 and 4 positions of the carbostyril skeleton is a double bond and $R^4$ and $R^5$ are linked together in the form of a —CH=CH—CH=CH— group are preferable;

of such carbostyril compounds, compounds wherein a group of the formula

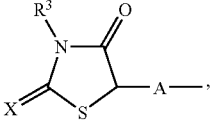

in which $R^3$, A and X are as defined in Item 1 above, is bound to the 7 position of the carbostyril skeleton are more preferable; those wherein $R^1$ is (1-2) or (1-3) as defined in Item 1 above are still more preferable; and those wherein A is a lower alkylene group or a lower alkylidene group, $R^2$ and $R^3$ are both hydrogen atoms, and X is an oxygen atom or a sulfur atom are particularly preferable.

Examples of particularly preferable carbostyril compounds of the present invention are as follows:

5-[1-(biphenyl-4-ylmethyl)-8-methoxy-2-oxo-1,2,3,4-tetrahydroquinolin-5-ylmethyl]thiazolidine-2,4-dione, 5-[1-(4-chlorobenzyl)-8-methoxy-2-oxo-1,2,3,4-tetrahydroquinolin-5-ylmethyl]thiazolidine-2,4-dione, 5-[1-(4-bromobenzyl)-8-methoxy-2-oxo-1,2,3,4-tetrahydroquinolin-5-ylmethyl]thiazolidine-2,4-dione, 5-[1-(2-naphthylmethyl)-8-methoxy-2-oxo-1,2,3,4-tetrahydroquinolin-5-ylmethyl]thiazolidine-2,4-dione, 5-{1-[4-(heptyloxycarbonylamino)benzyl]-8-methoxy-2-oxo-1,2,3,4-tetrahydroquinolin-5-ylmethyl}thiazolidine-2,4-dione, 5-[1-(1-biphenyl-4-ylpiperidin-4-ylmethyl)-2-oxo-1,2,3,4-tetrahydroquinolin-5-ylmethyl]thiazolidine-2,4-dione, 5-{1-[1-(4-methylphenyl)piperidin-4-ylmethyl]-2-oxo-1,2,3,4-tetrahydroquinolin-5-ylmethyl}thiazolidine-2,4-dione, 5-{1-[4-(2-chlorobenzyloxycarbonylamino)benzyl]-8-methoxy-2-oxo-1,2,3,4-tetrahydroquinolin-5-ylmethyl}thiazolidine-2,4-dione, 1-(biphenyl-4-ylmethyl)-8-methoxy-5-(4-oxo-2-thioxothiazolidin-5-ylmethyl)-3,4-dihydro-1H-quinolin-2-one, 8-methoxy-1-methyl-5-(4-oxo-2-thioxothiazolidin-5-ylmethyl)-3,4-dihydro-1H-quinolin-2-one, 8-methoxy-1-(3-methylbutyl)-5-(4-oxo-2-thioxothiazolidin-5-ylmethyl)-3,4-dihydro-1H-quinolin-2-one, 1-propyl-8-methoxy-5-(4-oxo-2-thioxothiazolidin-5-ylmethyl)-3,4-dihydro-1H-quinolin-2-one, 1-isobutyl-8-methoxy-5-(4-oxo-2-thioxothiazolidin-5-ylmethyl)-3,4-dihydro-1H-quinolin-2-one,
8-methoxy-1-phenethyl-5-(4-oxo-2-thioxothiazolidin-5-ylmethyl)-3,4-dihydro-1H-quinolin-2-one, and
1-(4-phenylthiomethyl)benzyl-5-(4-oxo-2-thioxothiazolidin-5-ylmethyl)-3,4-dihydro-1H-quinolin-2-one.

Specific examples of groups in the above formula (1) are as follows.

Examples of lower alkylene groups include straight and branched $C_{1-6}$ alkylene groups, such as methylene, ethylene, trimethylene, 2-methyltrimethylene, 2,2-dimethylethylene, 2,2-dimethyltrimethylene, 1-methyltrimethylene, methylmethylene, ethylmethylene, tetramethylene, pentamethylene, and hexamethylene.

Examples of lower alkylidene groups include straight and branched $C_{1-6}$ alkylidene groups, such as methylidene, ethylidene, propylidene, butylidene, pentylidene, and hexylidene.

Examples of lower alkyl groups include straight and branched $C_{1-6}$ alkyl groups, such as methyl, ethyl, n-propyl, isopropyl, n-butyl, isobutyl, tert-butyl, sec-butyl, n-pentyl, isopentyl, neopentyl, n-hexyl, isohexyl, and 3-methylpentyl.

Examples of lower alkoxy groups include straight and branched $C_{1-6}$ alkoxy groups, such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, and 3-methylpentyloxy.

Examples halogen atoms include fluorine, chlorine, bromine, and iodine.

Examples of lower alkoxycarbonyl groups include alkoxycarbonyl groups wherein the alkoxy moiety is a straight or branched $C_{1-6}$ alkoxy group, such as methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxycarbonyl, n-hexyloxycarbonyl, isohexyloxycarbonyl, and 3-methylpentyloxycarbonyl.

Examples of phenyl lower alkoxy groups include phenylalkoxy groups wherein the alkoxy moiety is a straight or branched $C_{1-6}$ alkoxy group, such as benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, and 2-methyl-3-phenylpropoxy.

Examples of piperidinyl lower alkoxycarbonyl groups include piperidinylalkoxycarbonyl groups wherein the alkoxy moiety is a straight or branched $C_{1-6}$ alkoxy group, such as [(1-, 2-, 3-, or 4-)piperidinyl]methoxycarbonyl, 2-[(1-, 2-, 3-, or 4-)piperidinyl]ethoxycarbonyl, 1-[(1-, 2-, 3-, or 4-)piperidinyl]ethoxycarbonyl, 3-[(1-, 2-, 3-, or 4-)piperidinyl]propoxycarbonyl, 4-[(1-, 2-, 3-, or 4-)piperidinyl]butoxycarbonyl, 5-[(1-, 2-, 3-, or 4-)piperidinyl]pentyloxycarbonyl, 6-[(1-, 2-, 3-, or 4-)piperidinyl]hexyloxycarbonyl, 1,1-dimethyl-2-[(1-, 2-, 3-, or 4-)piperidinyl]ethoxycarbonyl, and 2-methyl-3-[(1-, 2-, 3-, or 4-)piperidinyl]propoxy carbonyl.

Examples of cycloalkyl groups include $C_{3-8}$ cycloalkyl groups, such as cyclopropyl, cyclobutyl, cyclopentyl, cyclohexyl, cycloheptyl, and cyclooctyl.

Examples of amino lower alkoxycarbonyl groups optionally substituted with one or more cycloalkyl groups include:
amino-substituted alkoxycarbonyl groups wherein the alkoxy moiety is a straight or branched $C_{1-6}$ alkoxy group, optionally substituted with one or two $C_{3-8}$ cycloalkyl groups;
such as aminomethoxycarbonyl, 2-aminoethoxycarbonyl, cyclopropylaminomethoxycarbonyl, 2-cyclohexylaminoethoxycarbonyl, 1-cyclobutylaminoethoxycarbonyl, 3-cyclopentylaminopropoxycarbonyl, 4-cycloheptylaminobutoxycarbonyl, 5-cyclooctylaminopentyloxycarbonyl, 6-cyclohexylaminohexyloxycarbonyl, 1,1-dimethyl-2-cyclohexylaminoethoxycarbonyl, 2-methyl-3-cyclopropylaminopropoxycarbonyl, and 2-(N-cyclopropyl-N-cyclohexylamino)ethoxycarbonyl.

Examples of lower alkylthio groups include straight and branched $C_{1-6}$ alkylthio groups such as methylthio, ethylthio, n-propylthio, isopropylthio, n-butylthio, tert-butylthio, n-pentylthio, and n-hexylthio.

Examples of 2-imidazolinylcarbonyl groups optionally substituted on the 2-imidazoline ring with one or more alkylthio groups include 2-imidazolinylcarbonyl groups optionally substituted on the 2-imidazoline ring with one to three lower alkylthio groups, such as (1-, 2-, 4-, or 5-)2-imidazolinylcarbonyl, 2-methylthio-(1-, 4-, or 5-)2-imidazolinylcarbonyl, 2-ethylthio-(1-, 4-, or 5-)2-imidazolinylcarbonyl, 4-propylthio-(1-, 2-, or 5-)2-imidazolinylcarbonyl, 5-isopropylthio-(1-, 2-, or 4-)2-imidazolinylcarbonyl, 2-n-butylthio-(1-, 4-, or 5-)2-imidazolinylcarbonyl, 2-n-pentylthio-(1-, 4-, or 5-)2-imidazolinylcarbonyl, 2-n-hexylthio-(1-, 4-, or 5-)2-imidazolinylcarbonyl, 2,4-dimethylthio-(1- or 5-)2-imidazolinylcarbonyl, and 2,4,5-trimethylthio-(1-)2-imidazolinylcarbonyl.

Examples of 3-pyrrolinylcarbonyl groups optionally substituted on the 3-pyrroline ring with one or more lower alkyl groups include 3-pyrrolinylcarbonyl groups optionally substituted on the 3-pyrroline ring with one to three lower alkyl groups, such as (1-, 2-, or 3-)3-pyrrolinylcarbonyl, 2-methyl-(1-, 2-, 3-, 4-, or 5-)3-pyrrolinylcarbonyl, 2-ethyl-(1-, 2-, 3-, 4-, or 5-)3-pyrrolinylcarbonyl, 3-propyl-(1-, 2-, 4-, or 5-)3-pyrrolinylcarbonyl, 4-isopropyl-(1-, 2-, 3-, or 5-)3-pyrrolinylcarbonyl, 5-n-butyl-(1-, 2-, 3-, 4-, or 5-)3-pyrrolinylcarbonyl, 2-n-pentyl-(1-, 2-, 3-, 4-, or 5-)3-pyrrolinylcarbonyl, 2-n-hexyl-(1-, 2-, 3-, 4-, or 5-)3-pyrrolinylcarbonyl, 2,5-dimethyl-(1-, 2-, 3-, 4-, or 5-)3-pyrrolinylcarbonyl, 2,4-dimethyl-(1-, 2-, 3-, or 5-)3-pyrrolinylcarbonyl, 2,3-dimethyl-(1-, 2-, 4-, or 5-)3-pyrrolinylcarbonyl, and 2,4,5-trimethylthio-(1-, 2-, 3-, or 5-)3-pyrrolinylcarbonyl.

Examples of thiazolidinylcarbonyl groups optionally substituted on the thiazolidine ring with a phenyl group includes (2-, 3-, 4-, or 5-)thiazolidinylcarbonyl, 2-phenyl-(3-, 4-, or 5-)thiazolidinylcarbonyl, 3-phenyl-(2-, 4-, or 5-)thiazolidinylcarbonyl, 4-phenyl-(2-, 3-, or 5-)thiazolidinylcarbonyl, and 5-phenyl-(2-, 3-, or 4-)thiazolidinylcarbonyl.

Examples of piperidinyl lower alkyl groups include piperidinylalkyl groups wherein the alkyl moiety is a straight or branched $C_{1-6}$ alkyl group, such as [(1-, 2-, 3-, or 4-)piperidinyl]methyl, 2-[(1-, 2-, 3-, or 4-)piperidinyl]ethyl, 1-[(1-, 2-, 3-, or 4-)piperidinyl]ethyl, 3-[(1-, 2-, 3-, or 4-)piperidinyl]propyl, 4-[(1-, 2-, 3-, or 4-)piperidinyl]butyl, 5-[(1-, 2-, 3-, or 4-)piperidinyl]pentyl, 6-[(1-, 2-, 3-, or 4-)piperidinyl]hexyl, 1,1-dimethyl-2-[(1-, 2-, 3-, or 4-)piperidinyl]ethyl, and 2-methyl-3-[(1-, 2-, 3-, or 4-)piperidinyl]propyl.

Examples of anilino lower alkyl groups optionally substituted on the amino group with one or more lower alkyl groups include anilinoalkyl groups optionally substituted on the amino group with one or more straight and/or branched $C_{1-6}$ alkyl groups, such as anilinomethyl, N-methylanilinomethyl, N-ethylanilinomethyl, N-n-propylanilinomethyl, N-isopropylanilinomethyl, N-n-butylanilinomethyl, N-sec-butylanilinomethyl, N-tert-butylanilinomethyl, N-n-pentylanilinomethyl, N-n-hexylanilinomethyl, 2-anilinoethyl, 2-(N-methylanilino)ethyl, 2-(N-ethylanilino)ethyl, 2-(N-n-propylanilino)ethyl, 2-(N-isopropylanilino)ethyl, 2-(N-n-butylanilino)ethyl, 2-(N-sec-butylanilino)ethyl, 2-(N-tert-butylanilino)ethyl, 2-(N-n-pentylanilino)ethyl, 2-(N-n-hexylanilino)ethyl, 3-anilinopropyl, 3-(N-methylanilino)propyl, 4-(N-ethylanilino)butyl, 4-(N-n-propylanilino)butyl, 5-(N-isopropylanilino)pentyl, 5-(N-n-butylanilino)pentyl, 6-(N-sec-butylanilino)hexyl, 6-(N-tert-butylanilino)hexyl, 6-(N-n-pentylanilino)hexyl, and 6-(N-n-hexylanilino)hexyl.

Examples of phenylthio lower alkyl groups include phenylthioalkyl groups wherein the alkyl moiety is a straight or branched $C_{1-6}$ alkyl group, such as phenylthiomethyl, 2-phenylthioethyl, 1-phenylthioethyl, 3-phenylthiopropyl, 4-phenylthiobutyl, 5-phenylthiopentyl, 6-phenylthiohexyl, 1,1-dimethyl-2-phenylthioethyl, and 2-methyl-3-phenylthiopropyl.

Examples of indolinyl lower alkyl groups include indolinylalkyl groups wherein the alkyl moiety is a straight or branched $C_{1-6}$ alkyl group, such as [(1-, 2-, 3-, 4-, 5-, 6-, or 7-)indolinyl]methyl, 2-[(1-, 2-, 3-, 4-, or 5-)indolinyl]ethyl, 1-[(1-, 2-, 3-, 4-, 5-, 6-, or 7)indolinyl]ethyl, 3-[(1-, 2-, 3-, 4-, 5-, 6-, or 7)indolinyl]propyl, 4-[(1-, 2-, 3-, 4-, 5-, 6-, or 7)indolinyl]butyl, 5-[(1-, 2-, 3-, 4-, 5-, 6-, or 7)indolinyl]pentyl, 6-[(1-, 2-, 3-, 4-, 5-, 6-, or 7)indolinyl]hexyl, 1,1-dimethyl-2-[(1-, 2-, 3-, 4-, 5-, 6-, or 7)indolinyl]ethyl, and 2-methyl-3-[(1-, 2-, 3-, 4-, 5-, 6-, or 7)indolinyl]propyl.

Examples of piperidinylcarbonyl groups optionally substituted on the piperidine ring with one or more lower alkyl groups include piperidinylcarbonyl groups optionally substituted on the piperidine ring with one to three straight and/or branched $C_{1-6}$ alkyl groups, such as (1-, 2-, 3-, or 4-)piperidinylcarbonyl, 1-methyl-(2-, 3-, or 4-)piperidinylcarbonyl, 1-ethyl-(2-, 3-, or 4-)piperidinylcarbonyl, 1-n-propyl-(2-, 3-, or 4-)piperidinylcarbonyl, 1-n-butyl-(2-, 3-, or 4-)piperidinylcarbonyl, 1-n-pentyl-(2-, 3-, or 4-)piperidinylcarbonyl, 1-n-hexyl-(2-, 3-, or 4-)piperidinylcarbonyl, 1,2-dimethyl-(3-, 4-, 5-, or 6-)piperidinylcarbonyl, 1,2,3-trimethyl-(4-, 5-, or 6-)piperidinylcarbonyl, 2-n-propyl-(1-, 3-, 4-, 5-, or 6-)piperidinylcarbonyl, 3-ethyl-(1-, 2-, 4-, 5-, or 6-)piperidinylcarbonyl, and 2-methyl-4-isopropyl-(1-, 3-, 5-, or 6-)piperidinylcarbonyl.

Examples of phenyl lower alkyl groups optionally substituted on the phenyl ring with one or more members selected from the group consisting of a phenyl group; lower alkyl groups; lower alkoxy groups; halogen atoms; —(B)$_l$NR$^6$R$^7$ groups; a nitro group; a carboxy group; lower alkoxycarbonyl groups; a cyano group; phenyl lower alkoxy groups; a phenoxy group; piperidinyl lower alkoxycarbonyl groups; amino lower alkoxycarbonyl groups optionally substituted with one or more cycloalkyl groups; 2-imidazolinylcarbonyl groups optionally substituted on the 2-imidazoline ring with one or more lower alkylthio groups; 3-pyrrolinylcarbonyl groups optionally substituted on the pyrroline ring with one or more lower alkyl groups; a thiazolidinylcarbonyl groups optionally substituted on the thiazolidine ring with a phenyl group; 3-azabicyclo[3.2.2]nonylcarbonyl groups; piperidinyl lower alkyl groups; anilino lower alkyl groups optionally substituted on the amino group with one or more lower alkyl groups; phenylthio lower alkyl groups; indolinyl lower alkyl groups; and piperidinylcarbonyl groups optionally substituted on the piperidine ring with one or more lower alkyl groups include:

mono- and di-phenylalkyl groups wherein the alkyl moiety is a straight or branched $C_{1-6}$ aklyl group, optionally substituted on the phenyl ring with one to three members selected from the group consisting of a phenyl group; the above-described straight and branched $C_{1-6}$ alkyl groups; the above-described straight and branched $C_{1-6}$ alkoxy groups; halogen atoms; the below-described —(B)$_l$NR$^6$R$^7$ groups; a nitro group; a carboxyl group; the above-described straight and branched $C_{1-6}$ alkoxycarbonyl groups; a cyano group; the above-described phenylalkoxy groups wherein the alkoxy moiety is a straight or branched $C_{1-6}$ alkoxy group; a phenoxy group; the above-described piperidinylalkoxycarbonyl groups wherein the alkoxy moiety is a straight or branched $C_{1-6}$ alkoxy group; the above-described aminoalkoxycarbonyl groups wherein the alkoxy moiety is a straight or branched $C_{1-6}$ alkoxy group, optionally substituted with one or two $C_{3-8}$ cycloalkyl groups; the above-described 2-imidazolinylcarbonyl groups optionally substituted on the 2-imidazoline ring with one to three straight and/or branched $C_{1-6}$ alkylthio groups; the above-described 3-pyrrolinylcarbonyl groups optionally substituted on the 3-pyrroline ring with one to three straight and/or branched $C_{1-6}$ alkyl groups; thiazolidinylcarbonyl groups optionally substituted on the thiazolidine ring with a phenyl group; 3-azabicyclo[3.2.2]nonylcarbonyl groups; piperidinylalkyl groups wherein the alkyl moiety is a straight or branched $C_{1-6}$ alkyl group; anilinoalkyl groups wherein the alkyl moiety is a straight or branched $C_{1-6}$ alkyl group, optionally substituted on the amino group with one or two straight and/or branched $C_{1-6}$ alkyl groups; phenylthioalkyl groups wherein the alkyl moiety is a straight or branched $C_{1-6}$ alkyl group; indolinylalkyl groups wherein the alkyl moiety is a straight or branched $C_{1-6}$ alkyl group; and the above-described piperidinylcarbonyl groups optionally substituted on the piperidine ring with one to three straight and/or branched $C_{1-6}$ alkyl groups;

such as benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl, 1,1-diphenylmethyl, 2,2-diphenylethyl, 3,3-diphenylpropyl, 1,2-diphenylethyl, 4-[N-(3-pyridyl)aminocarbonyl]benzyl, 4-[N-(2-methoxyphenyl)aminocarbonyl-]benzyl, 4-[2-(2-piperidinyl)ethoxycarbonyl]benzyl, 4-[2-(cyclohexylamino)ethoxycarbonyl]benzyl, 4-[4-(3-pyridylmethyl)-1-piperazinylcarbonyl]benzyl, 4-[4-(4-pyridylmethyl)-1-piperazinylcarbonyl]benzyl, 4-[4-(2-pyridylmethyl)-1-piperazinylcarbonyl]benzyl, 4-[4-(2-pyridyl)-1-piperazinylcarbonyl]benzyl, 4-[4-(3-chlorophenyl)-1-piperazinylcarbonyl]benzyl, 4-[4-(2-fluorophenyl)-1-piperazinylcarbonyl]benzyl, 4-[4-(2-pyrimidyl)-1-piperazinylcarbonyl]benzyl, 4-(4-cyclopentyl-1-piperazinylcarbonyl)benzyl, 4-[4-(2-methoxyphenyl)-1-piperazinylcarbonyl]benzyl, 4-[4-(4-fluorophenyl)-1-piperazinylcarbonyl]benzyl, 4-[4-(3,4-methylenedioxybenzyl)-1-piperazinylcarbonyl]benzyl, 4-(N-cyclohexyl-N-methylaminocarbonyl)benzyl, 4-(N,N-di-n-butylaminocarbonyl)benzyl, 4-[4-(1-piperidinyl)-1-piperidinylcarbonyl]benzyl, 4-(1-homopiperidinylcarbonyl)benzyl, 4-[2-methylthio-1-(2-imidazolinyl)carbonyl]benzyl, 4-{N-[2-(2-pyridyl)ethyl]-N-methylaminocarbonyl}benzyl, 4-[N-(1-methyl-4-piperidinyl)-N-methylaminocarbonyl]benzyl, 4-(N,N-diisobutylaminocarbonyl)benzyl, 4-[N-(2-tetrahydropyranyl)methyl-N-ethylaminocarbonyl]benzyl, 4-(4-thiomorpholinocarbonyl)benzyl, 4-[2,5-dimethyl-1-(3-pyronyl)carbonyl]benzyl, 4-(3-thiazolidinylcarbonyl)benzyl, 4-(N-cyclopropylmethyl-N-n-propylaminocarbonyl)benzyl, 4-[1-(3-azabicyclo[3.2.2]nonylcarbonyl)benzyl, 4-(N-cyclopentyl-N-alkylaminocarbonyl)benzyl, 4-[4-(4-pyridyl)-1-piperazinylcarbonyl]benzyl, 4-[4-(4-trifluoromethylphenyl)-1-piperazinylcarbonyl]benzyl, 4-[4-(2-phenylethyl)-1-piperazinylcarbonyl]benzyl, 4-[4-(2-pyrazyl)-1-piperazinylcarbonyl]benzyl, 4-(N-n-butylaminocarbonyl)benzyl, 4-(N-cyclopropylaminocarbonyl)benzyl, 4-[N-(1-methyl-1-phenylethyl)aminocarbonyl]benzyl, 4-(N-benzylaminocarbonyl)benzyl, 4-[N-(2-chlorobenzyl)aminocarbonyl]benzyl, 4-[N-(3-chlorobenzyl)aminocarbonyl]benzyl, 4-[N-(4-chlorobenzyl)aminocarbonyl]benzyl, 4-[N-(2-pyridyl)methylaminocarbonyl]benzyl, 4-[N-(3-pyridyl)methylaminocarbonyl]benzyl, 4-[(4-pyridyl)methylaminocarbonyl]benzyl, 4-[3,5-dimethyl-1-piperidinylcarbonyl]benzyl, 4-[N-(2-furyl)methylaminocarbonyl]benzyl, 4-[4-(2-fluorobenzyloxy)-1-piperidinylcarbonyl]benzyl, 4-{4-[N-(2-phenylacetyl)-N-methylamino]-1-piperidinylcarbonyl}benzyl, 4-[(4-methoxy-1-piperidinyl)carbonyl]benzyl, 4-{[4-(3,4-dimethyl-1-piperazinyl)-1-piperidinyl]carbonyl}benzyl, 4-{[4-(4-chlorobenzoyl)-1-piperidinyl]carbonyl}benzyl, 4-{[4-(4-chlorobenzyl)-1-piperidinyl]carbonyl}benzyl, 4-[(4-ethylcarbamoylmethyl-1-piperidinyl)carbonyl]benzyl, 4-[(4-cyclohexyl-1-piperidinyl)carbonyl]benzyl, 4-{[4-(4-methoxyphenyl)-1-piperidinyl]carbonyl}benzyl, 4-{[4-(2-benzoxazolyl)-1-piperazinyl]carbonyl}benzyl, 4-[(4-anilinocarbonylmethyl-1-piperazinyl)carbonyl]benzyl, 4-[(4-methyl-2-benzyl-1-piperazinyl)carbonyl]benzyl, 4-[(4-phenyl-3-oxo-1-piperazinyl)carbonyl]benzyl, 4-[(4-tertbutyl-3-oxo-1-piperazinyl)carbonyl]benzyl, 4-[N-(1-benzoyl-4-piperidinyl)-N-methylaminocarbonyl]benzyl, 4-[N-(1-acetyl-4-piperidinyl)-N-methylaminocarbonyl]benzyl, 4-{[4-(4-cyanophenyl)-1-piperazinyl]carbonyl}benzyl, 4-[N-methylcarbamoylmethyl-N-benzylaminocarbonyl]benzyl, 4-[N-benzyl-N-cyclohexylaminocarbonyl]benzyl, 4-[2-(N-methyl-N-phenylcarbamoyl)ethyl-N-methylaminocarbonyl]benzyl, 4-{[4-(3-phenyl-1-pyrrolidinyl)-1-piperidinyl]carbonyl}benzyl, 4-[(1,2,3,4-tetrahydroisoquinoline-2-yl)carbonyl]benzyl, 4-[(4-benzyl-1-piperidinyl)carbonyl]benzyl, 4-{[4-(3,4-methylenedioxybenzoyl)-1-piperazinyl]carbonyl}benzyl, 4-[N-methyl-N-(4-methylbenzyl)aminocarbonyl]benzyl, 4-[N-methyl-N-(3,4-methylenedioxybenzyl)aminocarbonyl]benzyl, 4-[(N-methyl-N-(2-methoxybenzyl)aminocarbonyl]benzyl, 4-[(4-phenyl-1-piperazinyl)carbonyl]benzyl, 4-[(4-phenyl-4-hydroxy-1-piperidinyl)carbonyl]benzyl, 4-(N-isopropyl-N-benzylaminocarbonyl)benzyl, 4-(N-ethyl-N-cyclohexylaminocarbonyl)benzyl, 4-[N-ethyl-N-(4-pyridyl)methylaminocarbonyl]benzyl, 4-(N-n-propylaminocarbonyl)benzyl, 4-[N-ethyl-N-(4-ethoxybenzyl)aminocarbonyl]benzyl, 4-(N-ethyl-N-cyclohexylmethylaminocarbonyl)benzyl, 4-[N-(2-ethoxyethyl)aminocarbonyl]benzyl, 4-[N-(1,1-dimethyl-2-phenylethyl)aminocarbonyl]benzyl, 4-[{4-[N-methyl-N-(4-chlorophenyl)amino]-1-piperidinyl}carbonyl]benzyl, 4-[N-(1-methyl-1-cyclopentyl)aminocarbonyl]benzyl, 4-[N-(1-methyl-1-cyclohexyl)aminocarbonyl]benzyl, 4-{N-[2-(3-methoxyphenyl)ethyl]aminocarbonyl}benzyl, 4-[N-(4-trifluoromethoxybenzyl)aminocarbonyl]benzyl, 4-{N-[2-(4-chlorophenyl)ethyl]aminocarbonyl}benzyl, 4-[N-(3,4-methylenedioxybenzyl)aminocarbonyl]benzyl, 4-(N-cyclohexylmethylaminocarbonyl)benzyl, 4-[N-(4-fluorobenzyl)aminocarbonyl]benzyl, 4-[N-(1-phenylethyl)aminocarbonyl]benzyl, 4-[N-(3-phenylpropyl)aminocarbonyl]benzyl, 4-(N-[3-(1-imidazolyl)propyl]aminocarbonyl)benzyl, 4-[N-(2-phenylethyl)aminocarbonyl]benzyl, 4-[2-(N,N-diisopropylamino)ethylaminocarbonyl]benzyl, 4-{N-[1-methoxycarbonyl-2-(4-hydroxyphenyl)ethyl]aminocarbonyl}benzyl, 4-[N-(carbamoylmethyl)aminocarbonyl]benzyl, 4-{N-[1-carbamoyl-2-(5-imidazolyl)ethyl]aminocarbonyl}benzyl, 4-{N-[1-methoxycarbonyl-2-(5-imidazolyl)ethyl]aminocarbonyl}benzyl, 4-[N-(2-oxo-2,3,4,5-tetrahydrofuran-3-yl)aminocarbonyl]benzyl, 4-[(2-ethoxycarbonyl-1-piperidinyl)carbonyl]benzyl, 4-(N-methoxycarbonylmethyl-N-methylaminocarbonyl)benzyl, 4-[(2-carbamoyl-1-pyrrolidinyl)carbonyl]benzyl, 4-{[N-(2,6-dimethylbenzyl)-N-ethyl]aminocarbonyl}benzyl, 4-{N-[(4-methylphenyl)carbamoylmethyl]-N-methylaminocarbonyl}benzyl, 4-[N-(4-chlorobenzyl)-N-ethylaminocarbonyl]benzyl, 4-[N-(4-trifluoromethylbenzyl)-N-ethylaminocarbonyl]benzyl, 4-[N-(3-bromobenzyl)-N-ethylaminocarbonyl]benzyl, 4-{[4-(2-chlorobenzyl)-1-piperidinyl]carbonyl}benzyl, 4-{[4-(3-chlorobenzyl)-1-piperidinyl]carbonyl}benzyl, 4-{[4-(2-chlorobenzylidene)-1-piperidinyl]carbonyl}benzyl, 4-[N-(2-methoxybenzyl)aminocarbonyl]benzyl, 4-{N-[2-(2-fluorophenyl)ethyl]aminocarbonyl}benzyl, 4-{N-[2-(3-fluorophenyl)ethyl]aminocarbonyl}benzyl, 4-[(4-benzyloxycarbonyl-1-piperazinyl)carbonyl]benzyl, 4-{[4-(3-cyano-2-pyridyl)-1-piperazinyl]carbonyl}benzyl, 4-[(4-phenyl-1-piperidinyl)carbonyl]benzyl, 4-[{4-[(3-furyl)methyl]-1-piperazinyl}carbonyl]benzyl, 4-{[4-(3-pyridyl)-1-piperazinyl]carbonyl}benzyl, 4-{[4-(4-tetrahydropyranyl)-1-piperazinyl]carbonyl}benzyl, 4-{[4-(2-fluorobenzyl)-1-piperidinyl]carbonyl}benzyl, 4-{[4-(4-morpholino)-1-piperidinyl]carbonyl}benzyl, 4-{4-[2-(1,3-dioxolane-2-yl)ethyl]-1-piperazinyl}carbonyl]benzyl, 4-phenylbenzyl, 2-phenylbenzyl, 3-phenylbenzyl, 4-tert-butylbenzyl, 4-aminobenzyl, 4-nitrobenzyl, 4-methoxycarbonylbenzyl, 4-carboxybenzyl, 3-methoxy-4-chlorobenzyl, 4-methoxybenzyl, 2,4,6-trimethoxybenzyl, 3,4-dichlorobenzyl, 4-chlorobenzyl, 4-bromobenzyl, 2,4,6-trifluorobenzyl, 4-fluorobenzyl, 4-cyanobenzyl, 4-piperidinylcarbonylbenzyl, 4-anilinocarbonylbenzyl, 4-(N-cyclohexylaminocarbonyl)benzyl, 4-(N-benzoylamino)benzyl, 4-(N-cyclohexylamino)benzyl, 4-phenylcarbamoylaminobenzyl, 4-methylbenzyl, 3,4-dimethylbenzyl, 3,4,5-trimethylbenzyl, 4-benzyloxybenzyl, 4-ethylcarbamoylaminobenzyl, 4-ethylaminocarbonylbenzyl, 4-isopropylaminocarbonylbenzyl, 4-[N-(2-hydroxyethyl)aminocarbonyl]benzyl, 4-[N-(3-pyridyl)aminocarbonyl]benzyl, 4-[N-(4-chlorophenyl)aminocarbonyl]benzyl, 4-[N-(4-isopropylphenyl)aminocarbonyl]benzyl, 4-[N-(4-phenoxyphenyl)aminocarbonyl]benzyl, 4-[N-(3-phenoxyphenyl)aminocarbonyl]benzyl, 4-[N-(3-phenoxybenzoyl)amino]benzyl, 4-[N-(4-phenoxybenzoyl)amino]benzyl, 4-[N-(4-chlorobenzoyl)amino]benzyl, 4-[N-(2-chlorobenzoyl)amino]benzyl, 4-[N-(2,6-dichlorobenzoyl)amino]benzyl, 4-[N-(4-methoxyphenyl)aminocarbonyl]benzyl, 4-[N-(2-furylcarbonyl)amino]benzyl, 4-[N-(4-methoxybenzoyl)amino]benzyl, 4-[N-(3-methoxybenzoyl)amino]benzyl, 4-[N-(2-methoxybenzoyl)amino]benzyl, 4-phenoxybenzyl, 4-n-pentyloxycarbonylaminobenzyl, 4-[N-(4-methoxyphenoxycarbonyl)amino]benzyl, 4-[N-(4-methylphenoxycarbonyl)amino]benzyl, 4-benzyloxycarbonylaminobenzyl, 4-ethanoylaminobenzyl, 4-(N-acetylamino)benzyl, 4-methylsulfonylaminobenzyl, methoxycarbonylaminobenzyl, 4-[N-(4-isopropylphenyl)aminocarbonyl]benzyl, 4-[4-{2-[(1-, 2-, or 3-)imidazolyl]ethyl}-1-piperazinylcarbonyl]benzyl, 4-{4-[3-methyl-(2-, 3-, or 4-)pyridyl]-1-piperazinyl carbonyl}benzyl, 4-{4-[4-methyl-(2-, 3-, or 4-)pyridyl]-1-piperazinylcarbonyl}benzyl, 4-[4-{2-[(2-, 3-, or 4-)pyridyl]ethyl}-1-piperazinylcarbonyl]benzyl, 4-{4-4-[(1- or 2-)naphthyl]-(1-, 2-, or 3-)piperazinylcarbonyl}benzyl, 4-[(1-, 2-, 3-, or 4-piperazinylcarbonyl)]benzyl, 4-[2-methyl-(1-, 3-, 4-, 5-, or 6-)piperidinylcarbonyl]benzyl, 4-[3-ethoxycarbonyl-(1-, 2-, 4-, 5-, or 6-)piperidinyl]benzyl, 4-[4-(3-hydroxyphenyl)-(1-, 2-, 4-, 5-, or 6-)piperidinyl]benzyl, 4-[4-hydroxy-4-benzyl-(1-, 2-, or 3-)piperidinylcarbonyl]benzyl, 4-[3-acetylamino-(1-, 2-, 4-, or 5-)pyrrolidinylcarbonyl]benzyl, 4-[N-{2-[1-ethyl-(2- or 3-)pyrrolidinyl]ethyl}aminocarbonyl]benzyl, 4-[N-{2-[(2- or 3-)pyrrolidinyl]ethyl}aminocarbonyl]benzyl, 4-[N-{2-([2-, 3-, or 4-]morpholino)ethyl}aminocarbonyl]benzyl, 4-[N-{3-([2-, 3-, or 4-]morpholino)propyl}aminocarbonyl]benzyl, 4-[2,6-dimethyl-(3-, 4-, or 5-)morpholinocarbonyl]benzyl, 4-[4-(4-trifluoromethylanilino)-(1-, 2-, or 3-)piperazinylcarbonyl]benzyl, 4-{2-[(1-, 2-, 3-, or 4-)piperidinylmethyl]-(3-, 4-, 5- or 6-)morpholinocarbonyl}benzyl, 4-(N-methyl-N-n-pentylaminocarbonyl)benzyl, 4-{4-[(1-, 2-, 4-, or 5-)2,3-dihydro-1H-indenyl]-(1-, 2-, or 3-)piperidinylcarbonyl}benzyl, 4-[N-(2-methylcyclohexyl)aminocarbonyl]benzyl, 4-isoindolinylcarbonylbenzyl, 4-[2-phenyl-(1-, 3-, 4- or 5-)pyrrolidinylcarbonyl]benzyl, 4-{2-[(1-, 2-, 3-, or 4-morpholinomethyl)-(1-, 3-, 4-, or 5-)pyrrolidinylcarbonyl]benzyl, 4-[2-dimethylaminomethyl-(1-, 3-, 4-, or 5-)pyrrolidinylcarbonyl]benzyl, 4-{N-[1-(4-fluorobenzoyl)-(2-, 3-, or 4-)piperidinyl]-N-methylaminocarbonyl}benzyl, 4-[2-phenyl-(3-, 4-, or 5-)thiazolidinylcarbonyl]benzyl, 4-[N-methyl-(2-methoxyanilino)carbonyl]benzyl, 4-(3-methylthioanilinocarbonyl)benzyl, 4-(2-methylthioanilinocarbonyl)benzyl, 4-(3,4-dichloroanilinocarbonyl)benzyl, 4-(4-trifluoromethoxy-4-anilinocarbonyl)benzyl, 4-anilinocarbonylbenzyl, 4-(4-chloroanilinocarbonyl)benzyl, 4-(4-methoxyanilinocarbonyl)benzyl, 4-(3-methoxyanilinocarbonyl)benzyl, 4-(2-chloroanilinocarbonyl)benzyl, 4-(4-methylanilinocarbonyl)benzyl, 4-(2,4-diiethoxyanilinocarbonyl)benzyl, 4-(4-methoxy-5-chloroanilinocarbonyl)benzyl, 4-(2-methoxy-5-acetylaminoanilinocarbonyl)benzyl, 4-(3,4-dimethoxyanilinocarbonyl)benzyl, 4-[2-(1-methylallyl)

anilinocarbonyl]benzyl, 4-(3-trifluoromethoxyanilinocarbonyl)benzyl, 4-(2-methylanilinocarbonyl)benzyl, 4-(2-fluoroanilinocarbonyl)benzyl, 4-(3-fluoroanilinocarbonyl)benzyl, 4-(4-fluoroanilinocarbonyl)benzyl, 4-(3-dimethylaminoanilinocarbonyl)benzyl, 4-(4-ethoxyanilinocarbonyl)benzyl, 4-(3-trifluoromethylanilinocarbonyl)benzyl, 4-(4-trifluoromethylanilinocarbonyl)benzyl, 4-(3-acetylaminoanilinocarbonyl)benzyl, 4-(4-acetylaminoanilinocarbonyl)benzyl, 4-[(2-, 3-, or 4-pyridylaminocarbonyl)benzyl, 4-[N-methyl-(3-methylanilino)carbonyl]benzyl, 4-[3-methoxy-(2-, 4-, 5-, or 6-)pyridylaminocarbonyl]benzyl, 4-(2-phenoxyanilinocarbonyl)benzyl, 4-(3-phenoxyanilinocarbonyl)benzyl, 4-(4-phenoxyanilinocarbonyl)benzyl, 4-(3,5-dichloroanilinocarbonyl)benzyl, 4-(2,3-dimethylanilinocarbonyl)benzyl, 4-(2,4-dimethylanilinocarbonyl)benzyl, 4-(3,5-dimethylanilinocarbonyl)benzyl, 4-(3,5-difluoroanilinocarbonyl)benzyl, 4-[(1-, 2-, 3-, 4-, 5-, 6-, or 7-)indolylaminocarbonyl]benzyl, 4-(3-fluoro-4-methoxyanilinocarbonyl)benzyl, 4-(4-aminosulfonylanilinocarbonyl)benzyl, 4-(4-methyl-3-methoxyanilinocarbonyl)benzyl, 4-(3-chloro-4-methoxyanilinocarbonyl)benzyl, 4-(3-chloro-4-methylanilinocarbonyl)benzyl, 4-(3-methoxy-5-trifluoromethylanilinocarbonyl)benzyl, 4-(3-chloro-4-fluoroanilinocarbonyl)benzyl, 4-[3-methyl-(2-, 4-, 5- or 6-)pyridylaminocarbonyl]benzyl, 4-[(2-, 4- or 5-thiazolylaminocarbonyl)benzyl, 4-(3-chloro-4-hydroxyanilinocarbonyl)benzyl, 4-(2-chloro-5-acetylaminoanilinocarbonyl)benzyl, 4-(4-methylthioanilinocarbonyl)benzyl, 4-(4-isopropylanilinocarbonyl)benzyl, 4-(4-tert-butylanilinocarbonyl)benzyl, 4-[(2- or 4-)1,2,4-triazolylaminocarbonyl]benzyl, 4-{4-[2-oxo-(1-, 3-, 4-, or 5-)pyrrolidinyl]anilinocarbonyl}benzyl, 4-(4-methylsulfonylamino)benzyl, 4-(4-methylcarbamoylanilinocarbonyl)benzyl, anilinocarbonylbenzyl, 4-(2-benzyloxyanilinocarbonyl)benzyl, 4-(4-vinylanilinocarbonyl)benzyl, 4-(4-acetylaminoanilinocarbonyl)benzyl, 4-(3-acetylaminoanilinocarbonyl)benzyl, 4-(4-trifluoromethylanilinocarbonyl)benzyl, 4-(3-[(2-, 3-, or 4-)pyridyl]propionylamino)benzyl, 4-(3-phenoxypropionylamino)benzyl, 4-[(2-, 3- or 4-)pyridylcarbonylamino]benzyl, 4-{2-[(2-, 3-, or 4-)pyridyl]acetylamino}benzyl, 4-[(2- or 3-)furylcarbonylamino]benzyl, 4-[(2- or 3-)thienylcarbonylamino]benzyl, 4-{2-[(2- or 3-)thienyl]acetylamino}benzyl, 4-{2-[(1-, 2-, or 3-)pyrrolyl]-(3-, 4-, 5-, or 6-)pyridyl carbonylamino}benzyl, 4-cyclopentylcarbonylaminobenzyl, 4-cyclohexylcarbonylaminobenzyl, 4-(2-cyclopentylacetylamino)benzyl, 4-(2-cyclohexylcarbonylamino)benzyl, 4-[1-benzoyl-(2-, 3-, or 4-)piperidinylcarbonylamino]benzyl, 4-[1-acetyl-(2-, 3-, or 4-)piperidinylcarbonylamino]benzyl, 4-[(2-, 3-, 4-, 5-, 6-, 7-, or 8-)chromanyl]benzyl, 4-(2-nitrobenzoylamino)benzyl, 4-(3-nitrobenzoylamino)benzyl, 4-(4-nitrobenzoylamino)benzyl, 4-(2-phenylbenzoylamino)benzyl, 4-(2-dimethylaminobenzoylamino)benzyl, 4-(2-anilinobenzoylamino)benzyl, 4-(2,6-dichlorobenzoylamino)benzyl, 4-(2-cyanobenzoylamino)benzyl, 4-(3-phenoxybenzoylamino)benzyl, 4-(2-phenoxybenzoylamino)benzyl, 4-(4-phenoxybenzoylamino)benzyl, 4-[(1- or 2-)naphthylcarbonylamino]benzyl, 4-(2-methyl-3-fluorobenzoylamino)benzyl, 4-(3,4-methylenedioxybenzoylamino)benzyl, 4-{2-[1,3-dioxo-(2-, 4-, or 5-)isoindolinyl]acetylamino}benzyl, 4-{2-[2-thioxo-4-oxothiazolidinyl]acetylamino}benzyl, 4-{3-[(1-, 2-, 3-, or 4-)piperidinyl]propionylamino}benzyl, 4-(4-acetylbenzoylamino)benzyl, 4-(2-trifluoromethylbenzoylamino)benzyl, 4-(3-trifluoromethylbenzoylamino)benzyl, 4-(4-trifluoromethylbenzoylamino)benzyl, 4-[2-(2-chlorophenyl)acetylamino]benzyl, 4-(2-chloro-4-fluorobenzoylamino)benzyl, 4-(2-chlorocinnamoylamino)benzyl, 4-(3,4-methylenedioxycinnamoylamino)benzyl, 4-[3-(2-, 3-, or 4-)pyridylvinylcarbonylamino]benzyl, 4-[2-chloro-(3-, 4-, 5-, or 6-)pyridylcarbonylamino]benzyl, 4-{2-[(2-, 3-, or 4-)pyridylthio]acetylamino}benzyl, 4-[(2-, 3-, 4-, 5-, 6-, or 7-)indolylcarbonylamino]benzyl, 4-[(1-, 2-, or 3-)pyrrolylcarbonylamino]benzyl, 4-[2-oxo-(1-, 3-, 4-, or 5-)pyrrolidinylcarbonylamino]benzyl, 4-[(2-, 3-, 4-, 5-, 6-, or 7-)benzofurylcarbonylamino]benzyl, 4-[2,6-dichloro-(3-, 4-, or 5-)pyridylcarbonylamino]benzyl, 4-(2-[(1-, 2-, 3-, 4-, 5-, 6-, or 7-)indolyl]acetylamino)benzyl, 4-[(2-, 3-, 4-, 5-, 6-, or 7-)benzothienylcarbonylamino]benzyl, 4-{4-[2-oxo-(1-, 3-, 4-, or 5-)pyrrolidinyl]benzoylamino}benzyl, 4-{4-[(1-, 2-, or 3-)pyrrolyl]benzoylamino}benzyl, 4-{4-[(1-, 3-, 4-, or 5-)pyrazolyl]benzoylamino}benzyl, 4-{4-[(1-, 3-, or 5-)1,2,4-triazolyl]benzoylamino}benzyl, 4-{4-[(1-, 2-, 4-, or 5-)imidazolyl]benzoylamino}benzyl, 4-[4-(3,5-dimethyl-4-isoxazolyl)benzoylamino]benzyl, 4-[(2- or 3-)pyrazylcarbonylamino]benzyl, 4-(2-methoxybenzoylamino)benzyl, 4-(2-methoxy-5-chlorobenzoylamino)benzyl, 4-(4-chlorobenzoylamino)benzyl, 4-(2-phenoxyacetylamino)benzyl, 4-(3-phenylpropionyl)benzyl, 4-[(2-, 3-, or 4-)pyridylcarbonylamino]benzyl, 4-benzoylaminobenzyl, 4-cinnamoylaminobenzyl, 4-(4-methoxyphenylsulfonylamino)benzyl, 4-(3-methoxyphenylsulfonylamino)benzyl, 4-(2-methoxyphenylsulfonylamino)benzyl, 4-(4-chlorophenylsulfonylamino)benzyl, 4-(3-chlorophenylsulfonylamino)benzyl, 4-(2-chlorophenylsulfonylamino)benzyl, 4-(2-methylphenylsulfonylamino)benzyl, 4-(3-methylphenylsulfonylamino)benzyl, 4-(4-methylphenylsulfonylamino)benzyl, 4-(4-fluorophenylsulfonylamino)benzyl, 4-(3-fluorophenylsulfonylamino)benzyl, 4-(2-fluorophenylsulfonylamino)benzyl, 4-(2-methoxy-5-chlorophenylsulfonylamino)benzyl, 4-(2-trifluoromethylphenylsulfonylamino)benzyl, 4-(3-trifluoromethylphenylsulfonylamino)benzyl, 4-(4-trifluoromethylphenylsulfonylamino)benzyl, 4-[(2- or 3-)thienylsulfonylamino]benzyl, 4-(2-chlorophenylsulfonylamino)benzyl, 4-(2-trifluoromethoxyphenylsulfonylamino)benzyl, 4-(3-trifluoromethoxyphenylsulfonylamino)benzyl, 4-(4-trifluoromethoxyphenylsulfonylamino)benzyl, 4-(2-methoxycarbonylphenylsulfonylamino)benzyl, 4-(2-cyanophenylsulfonylamino)benzyl, 4-(3-cyanophenylsulfonylamino)benzyl, 4-(4-cyanophenylsulfonylamino)benzyl, 4-(3,4-dimethoxyphenylsulfonylamino)benzyl, 4-(2,5-dimethoxyphenylsulfonylamino)benzyl, 4-(2-nitrophenylsulfonylamino)benzyl, 4-(3-nitrophenylsulfonylamino)benzyl, 4-(4-nitrophenylsulfonylamino)benzyl, 4-(4-bromophenylsulfonylamino)benzyl, 4-(3-bromophenylsulfonylamino)benzyl, 4-(2-bromophenylsulfonylamino)benzyl, 4-(4-n-butylphenylsulfonylamino)benzyl, 4-(2-methoxy-5-chlorophenylsulfonylamino)benzyl, 4-(2,6-dichlorophenylsulfonylamino)benzyl, 4-[(1-, 2-, 3-, 4-, 5-, 6-, 7-, or 8-)quinolylsulfonylamino]benzyl, 4-[1-methyl-(2-, 4-, or 5-)imidazolylsulfonylamino]benzyl, 4-(2,3-dichlorophenylsulfonylamino)benzyl, 4-(2,5-dichlorophenylsulfonylamino)benzyl, 4-(2,4-dichlorophenylsulfonylamino)benzyl, 4-(3-nitro-4-methylphenylsulfonylamino)benzyl, 4-(2-chloro-4-fluorophenylsulfonylamino)benzyl, 4-(2,4-dichloro-5-methylphenylsulfonylamino)benzyl, 4-(2-methyl-5-nitrophenylsulfonylamino)benzyl, 4-(2-chloro-5-nitrophenylsulfonylamino)benzyl, 4-(2-chloro-4-cyanophenylsulfonylamino)benzyl, 4-(2,4,6-trimethylphenylsulfonylamino)benzyl, 4-(4-acetylaminophenylsulfonylamino)benzyl, 4-(3,5-dichloro-2-hydroxyphenylsulfonylamino)benzyl, 4-(4-methoxy-2-nitrophenylsulfonylamino)benzyl, 4-(3,4-dichlorophenylsulfonylamino)benzyl, 4-(4-tert-butylphenylsulfonylamino)benzyl, 4-(4-carboxyphenylsulfonylamino)benzyl, 4-(2-bromo-5- chlorophenylsulfonylamino)benzyl, 4-(4-ethylphenylsulfonylamino)benzyl, 4-(2,5-dimethylsulfonylamino)benzyl, 4-(4-n-butoxyphenylsulfonylamino)benzyl, 4-(2,5-difluorophenylsulfonylamino)benzyl, 4-(2-chloro-4-acetylaminophenylsulfonylamino)benzyl, 4-(2,4-difluorophenylsulfonylamino)benzyl, 4-(2-methoxy-4-methylphenylsulfonylamino)benzyl, 4-(2-methyl-3-chlorophenylsulfonylamino)benzyl, 4-(2,6-difluorophenylsulfonylamino)benzyl, 4-(3,4-difluorophenylsulfonylamino)benzyl, 4-(2-methyl-5-fluorophenylsulfonylamino)benzyl, 4-(3-methyl-4-chlorophenylsulfonylamino)benzyl, 4-(2-methyl-6-chlorophenylsulfonylamino)benzyl, 4-(4-isopropylphenylsulfonylamino)benzyl, 4-(3,4-dichlorophenylsulfonylamino)benzyl, 4-(2-fluoro-4-bromophenylsulfonylamino)benzyl, 4-(4-methyl-3-chlorophenylsulfonylamino)benzyl, 4-vinylsulfonylaminobenzyl, 4-(3-chloropropylphenylsulfonylamino)benzyl, 4-cyclohexylmethylsulfonylaminobenzyl, 4-[2-chloro-(3-, 4-, or 5-)thienylsulfonylamino]benzyl, 4-(3,5-dichlorophenylsulfonylamino)benzyl, 4-{4-[2-(4-methoxycarbonyl)ethyl]phenylsulfonylamino}benzyl, 4-[4-methyl-(2-, 3-, 4-, 5-, 6-, 7-, or 8-)3,4-dihydro-2H-1,4-dihydro-2H-1,4-benzoxazinylsulfonylamino]benzyl, 4-(2,2,2-trifluoroethylsulfonylamino)benzyl, 4-(2,3,5-trimethyl-4-methoxyphenylsulfonylamino)benzyl, 4-[(1,3-dimethyl-5-chloro-4-pyrazolyl)sulfonylamino]benzyl, 4-[(3,5-dimethyl-4-isoxazolyl)sulfonylamino]benzyl, 4-(3-carboxy-4-hydroxyphenylsulfonylamino)benzyl, 4-{[2,3-dichloro-(4- or 5-)thienyl]sulfonylamino}benzyl, 4-{[2,5-dichloro-(3- or 4-)thienyl]sulfonylamino}benzyl, 4-{[2-bromo-(3-, 4-, or 5-)thienyl]sulfonylamino}benzyl, 4-(4-carboxyphenylsulfonylamino)benzyl, 4-(2-acetylamino-4-methyl-5-thiazolylsulfonylamino)benzyl, 4-{[2-methoxycarbonyl-(3-, 4-, or 5-)thienyl]sulfonylamino}benzyl, 4-benzylsulfonylaminobenzyl, 4-styrylsulfonylaminobenzyl, 4-(2,4,5-trifluorophenylsulfonylamino)benzyl, 4-phenylsulfonylaminobenzyl, 4-phenoxycarbonylaminobenzyl, 4-[(4-chlorophenoxy)carbonylamino]benzyl, 4-[(4-bromophenoxy)carbonylamino]benzyl, 4-benzyloxycarbonylaminobenzyl, 4-methoxycarbonylaminobenzyl, 4-n-butoxycarbonylaminobenzyl, 4-[(4-methoxyphenoxy)carbonylamino]benzyl, 4-[(3-methoxyphenoxy)carbonylamino]benzyl, 4-[(2-methoxyphenoxy)carbonylamino]benzyl, 4-[(1- or 2-)naphthyloxycarbonylamino]benzyl, 4-[(4-fluorophenoxy)carbonylamino]benzyl, 4-[(4-methylphenoxy)carbonylamino]benzyl, 4-[(2-chlorobenzyloxy)carbonylamino]benzyl, 4-[2-propynyloxycarbonylamino]benzyl, 4-[(4-nitrophenoxy)carbonylamino]benzyl, 4-(2-fluoroethoxycarbonylamino)benzyl, 4-(3-butenyloxycarbonylamino)benzyl, 4-(4-chlorobutoxycarbonylamino)benzyl, 4-(2-chloroethoxycarbonylamino)benzyl, 4-[2-(benzyloxy)ethoxycarbonylamino]benzyl, 4-propoxycarbonylaminobenzyl, 4-n-butoxycarbonylaminobenzyl, 4-(2-isopropyl-5-methylcyclohexyloxycarbonylamino)benzyl, 4-[(4-nitrobenzyloxy)carbonylamino]benzyl, 4-(2-ethylhexyloxycarbonylamino)benzyl, 4-[N-methyl-(4-chloroanilino)carbonyl]benzyl, 4-[(2-chloroanilino)carbonyl]benzyl, 4-[(3-cyanoanilino)carbonyl]benzyl, 4-[(4-cyanoanilino)carbonyl]benzyl, 4-[(2-cyanoanilino)carbonyl]benzyl, 4-[(2-chloro-4-fluoroanilino)carbonyl]benzyl, 4-[(1- or 5-)tetrazolylaminocarbonyl]benzyl, 4-[5-methyl-(3- or 4-)isoxazolylaminocarbonyl]benzyl, 4-{4-[4-methyl-(1-, 2-, 3-, or 4-)piperazinyl]anilinocarbonyl}benzyl, (2-, 3-, or 4-)(1-piperidinylmethyl)benzyl, (2-, 3-, or 4-)(N-methylanilinomethyl)benzyl, (2-, 3-, or 4-)(phenylthiomethyl)benzyl, and (2-, 3-, or 4-)(1-indolylmethyl)benzyl.

Examples of cycloalkyl lower alkyl groups include $C_{3-8}$ cycloalkylalkyl groups wherein the alkyl moiety is a straight or branched $C_{1-6}$ alkyl group, such as cyclopropylmethyl, cyclohexylmethyl, 2-cyclopropylethyl, 1-cyclobutylethyl, cyclopentylmethyl, 3-cyclopentylpropyl, 4-cyclohexylbutyl, 5-cycloheptylpentyl, 6-cyclooctylhexyl, 1,1-dimethyl-2-cyclohexylethyl, and 2-methyl-3-cyclopropylpropyl.

Examples of phenoxy lower alkyl groups include phenoxy alkyl groups wherein the alkyl moiety is a straight or branched $C_{1-6}$ alkyl group, such as phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl, 1-phenoxyisopropyl, and 2-methyl-3-phenoxypropyl.

Examples of naphthyl lower alkyl groups include naphthylalkyl groups wherein the alkyl moiety is a straight or branched $C_{1-6}$ alkyl group, such as (1- or 2-)naphthylmethyl, 2-[(1- or 2-)naphthyl]ethyl, 1-[(1- or 2-)naphthyl]ethyl, 3-[(1- or 2-)naphthyl]propyl, 4-[(1- or 2-)naphthyl]butyl, 5-[(1- or 2-)naphthyl]pentyl, 6-[(1- or 2-)naphthyl]hexyl, 1,1-dimethyl-2-[(1- or 2-)naphthyl]ethyl, and 2-methyl-3-[(1- or 2-)naphthyl]propyl.

Examples of lower alkoxy lower alkyl groups include alkoxyalkyl groups wherein the alkyl moiety is a straight or branched $C_{1-6}$ alkyl group and the alkoxy moiety is a straight or branched $C_{1-6}$ alkoxy group, such as methoxymethyl, 2-methoxyethyl, 1-ethoxyethyl, 2-ethoxyethyl, 3-n-butoxypropyl, 4-n-propoxybutyl, 1-methyl-3-isobutoxypropyl, 1,1-dimethyl-2-n-pentyloxyethyl, 5-n-hexyloxypentyl, 6-methoxyhexyl, 1-ethoxyisopropyl, and 2-methyl-3-methoxypropyl.

Examples of carboxy lower alkyl groups include carboxyalkyl groups wherein the alkyl moiety is a straight or branched $C_{1-6}$ alkyl group, such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, and 2-methyl-3-carboxypropyl.

Examples of lower alkoxycarbonyl lower alkyl groups include alkoxycarbonylalkyl groups wherein the alkoxy moiety is a straight or branched $C_{1-6}$ alkoxy group and the alkyl moiety is a straight or branched $C_{1-6}$ alkyl group, such as methoxycarbonylmethyl, ethoxycarbonylmethyl, 2-methoxycarbonylethyl, 2-ethoxycarbonylethyl, 1-ethoxycarbonylethyl, 3-methoxycarbonylpropyl, 3-ethoxycarbonylpropyl, 4-ethoxycarbonylbutyl, 5-isopropoxycarbonylpentyl, 6-n-propoxycarbonylhexyl, 1,1-dimethyl-2-n-butoxycarbonylethyl, 2-methyl-3-tert-butoxycarbonylpropyl, 2-n-pentyloxycarbonylethyl, and n-hexyloxycarbonyl methyl.

Examples of piperazinyl groups optionally substituted on the piperazine ring with one or more members selected from the group consisting of a phenyl group and lower alkyl groups include:

piperazinyl groups optionally substituted on the piperazine ring with one to three members selected from the group consisting of a phenyl group and straight and branched $C_{1-6}$ alkyl groups;

such as (1- or 2-)piperazinyl, 4-methyl-(1-, 2-, or 3-)piperazinyl, 4-ethyl-(1-, 2-, or 3-)piperazinyl, 4-n-propyl-1-, 2-, or 3-)piperazinyl, 4-tert-butyl-(1-, 2-, or 3-)piperazinyl, 4-sec-butyl-(1-, 2-, or 3-)piperazinyl, 4-n-butyl-(1-, 2-, or 3-)piperazinyl, 4-n-pentyl-(1-, 2-, or 3-)piperazinyl, 4-n-hexyl-(1-, 2-, or 3-)piperazinyl, 3,4-dimethyl-(1-, 2-, 5-, or 6-)piperazinyl, 3,4,5-trimethyl-(1- or 2-)piperazinyl, 4-phenyl-(1-, 2-, or 3-)piperazinyl, 2,4-diphenyl-(1-, 3-, 5-, or 6-)piperazinyl, 2,3,4-triphenyl-(1-, 5-, or 6-)piperazinyl, and 4-phenyl-2-methyl-(1-, 3-, 5-, or 6-)piperazinyl.

Examples of pyridylamino groups include (2-, 3-, or 4-)pyridylamino.

Examples of pyridylcarbonylamino groups include (2-, 3-, or 4-)pyridylcarbonylamino.

Examples of anilino groups optionally substituted on the amino group with one or more lower alkyl groups include anilino groups optionally substituted on the amino group with one or more straight and/or branched $C_{1-6}$ alkyl groups, such as anilino, N-methylanilino, N-ethylanilino, N-n-propylanilino, N-isopropylanilino, N-n-butylanilino, N-sec-butylanilino, N-tert-butylanilino, N-n-pentylanilino, and N-n-hexylanilino.

Examples of pyridyl lower alkyl groups optionally substituted on the pyridine ring with one or more members selected from the group consisting of halogen atoms; piperidinyl groups; a morpholino group; piperazinyl groups optionally substituted on the piperizine ring with one or more members selected from the group consisting of a phenyl group and lower alkyl groups; thienyl groups; a phenyl group; pyridyl groups; piperidinyl lower alkyl groups; phenylthio lower alkyl groups; biphenyl groups; lower alkyl groups optionally substituted with one or more halogen atoms; pyridylamino groups; pyridylcarbonylamino groups; lower alkoxy groups; anilino lower alkyl groups optionally substituted on the amino group with one or more lower alkyl groups; and anilino groups optionally substituted on the amino group with one or more lower alkyl groups include:

pyridyl alkyl groups wherein the alkyl moiety is a $C_{1-6}$ straight or branched alkyl group, optionally substituted on the pyridine ring with one to three members selected from the group consisting of the above-described halogen atoms; piperidinyl groups; a morpholino group; the above-described piperazinyl groups optionally substituted on the piperazine ring with one to three members selected from the group consisting of a phenyl group and straight and branched $C_{1-6}$ alkyl groups; thienyl groups; a phenyl group; pyridyl groups; piperidinylalkyl groups wherein the alkyl moiety is a straight or branched $C_{1-6}$ alkyl group; phenylthioalkyl groups wherein the alkyl moiety is a straight or branched $C_{1-6}$ alkyl group; biphenyl groups; lower alkyl groups wherein the alkyl moiety is a straight or branched $C_{1-6}$ alkyl group, optionally substituted with one to three halogen atoms; pyridylamino groups; pyridylcarbonylamino groups; straight and branched $C_{1-6}$ alkoxy groups; anilinoalkyl groups wherein the alkyl moiety is a straight or branched $C_{1-6}$ alkyl group, optionally substituted on the amino group with one or two straight and/or branched $C_{1-6}$ alkyl groups; and the above-described anilino groups optionally substituted on the amino group with one or more straight and/or branched $C_{1-6}$ alkyl groups;

such as (2-, 3-, or 4-)pyridylmethyl, 2-[(2-, 3-, or 4-)pyridyl]ethyl, 1-[(2-, 3-, or 4-)pyridyl]ethyl, 3-[(2-, 3-, or 4-)pyridyl]propyl, 4-[(2-, 3-, or 4-)pyridyl]butyl, 1,1-dimethyl-2-[(2-, 3-, or 4-)pyridyl]ethyl, 5-[(2-, 3-, or 4-)pyridyl]pentyl, 6-[(2-, 3-, or 4-)pyridyl]hexyl, 1-[(2-, 3-, or 4-)pyridyl]isopropyl, 2-methyl-3-[(2-, 3-, or 4-)pyridyl]propyl, (2-chloro-3-pyridyl)methyl, [2-chloro-(3-, 4-, 5-, or 6-)pyridyl]methyl, [2,3-dichloro-(4-, 5-, or 6-)pyridyl]methyl, [2-bromo-(3-, 4-, 5-, or 6-)pyridyl]methyl, [2,4,6-trifluoro-(3-, 5-, or 6-)pyridyl]methyl, [2-(1-piperidinyl)-(3-, 4-, 5-, or 6-)pyridyl]methyl, [2-(4-morpholino)-(3-, 4-, 5-, or 6-)pyridyl]methyl, [2-(4-methyl-1-piperazinyl)-(3-, 4-, 5-, or 6-)pyridyl]methyl, 2-[2-(4-ethyl-1-piperazinyl)-(3-, 4-, 5-, or 6-)pyridyl]ethyl, 3-[2-(4-isopropyl-1-piperazinyl)-(3-, 4-, 5-, or 6-)pyridyl]propyl, 4-[2-(4-sec-butyl-1-piperazinyl)-(3-, 4-, 5-, or 6-)pyridyl]butyl, 5-[2-(4-n-pentyl-1-piperazinyl)-(3-, 4-, 5-, or 6-)pyridyl]pentyl, 6-[2-(4-n-hexyl-1-piperazinyl)-(3-, 4-, 5-, or 6-)pyridyl]hexyl, [2-(4-phenyl-2-methyl-1-piperazinyl)-(3-, 4-, 5-, or 6-)pyridyl]methyl, [2-(4-phenyl-1-piperazinyl)-(3-, 4-, 5-, or 6-)pyridyl]methyl, [2-(3-thienyl)-(3-, 4-, 5-, or 6-)pyridyl]methyl, [2-phenyl-(3-, 4-, 5-, or 6-)pyridyl]methyl, 2-[2,4-diphenyl-(3-, 5-, or 6-)pyridyl]ethyl, 3-[2-(2-pyridyl)-6-(3-thienyl)-(3-, 4-, or 5-)pyridyl]propyl, 4-(3-anilino-(2-, 4-, 5-, or 6-) pyridylbutyl, 5-[2-(4-morpholino)-(3-, 4-, 5-, or 6-)pyridyl]pentyl, 6-[2-(1-piperidinyl)-(3-, 4-, 5-, or 6-)pyridyl]hexyl, [2-(2-pyridyl)-(3-, 4-, 5-, or 6-)pyridyl]methyl, (3-, 4-, 5-, or 6-)(1-piperidinylmethyl)-2-pyridylmethyl, (3-, 4-, 5-, or 6-)phenylthiomethyl-2-pyridylmethyl, (4-, 5-, or 6-)biphenyl-3-pyridylmethyl, (4-, 5-, or 6-)trifluoromethyl-3-pyridylmethyl, (4-, 5-, or 6-)(2-pyridylamino)-3-pyridylmethyl, (4-, 5-, or 6-)[(2- or 3-)pyridylcarbonylamino]-3-pyridylmethyl, 3,5-dimethyl-4-methoxy-2-pyridylmethyl, (3-, 4-, 5-, or 6-)(N-methylanilinomethyl)-2-pyridylmethyl, [2-(N-methylanilino)-(3-, 4-, 5-, or 6-)pyridyl]methyl, 2-[2-(N-ethylanilino)-(3-, 4-, 5-, or 6-)pyridyl]ethyl, 3-[2-(N-n-propylanilino)-(3-, 4-, 5-, or 6-)pyridyl]propyl, 4-[2-(N-n-butylanilino)-(3-, 4-, 5-, or 6-)pyridyl]ethyl, 5-[2-(N-n-pentylanilino)-(3-, 4-, 5-, or 6-)pyridyl]pentyl, and 6-[2-(N-n-hexylanilino)-(3-, 4-, 5-, or 6-)pyridyl]hexyl.

Examples of cyano lower alkyl groups include cyanoalkyl groups wherein the alkyl moiety is a straight or branched $C_{1-6}$ alkyl group, such as cyanomethyl, 2-cyanoethyl, 1-cyanoethyl, 3-cyanopropyl, 4-cyanobutyl, 1,1-dimethyl-2-cyanoethyl, 5-cyanopentyl, 6-cyanohexyl, 1-cyanoisopropyl, and 2-methyl-3-cyanopropyl.

Examples of quinolyl lower alkyl groups include quinolylalkyl groups wherein the alkyl moiety is a straight or branched $C_{1-6}$ alkyl group, such as [(2-, 3-, 4-, 5-, 6-, 7-, or 8-)quinolyl]methyl, 2-[(2-, 3-, 4-, 5-, 6-, 7-, or 8-)quinolyl]ethyl, 1-[(2-, 3-, 4-, 5-, 6-, 7-, or 8-)quinolyl]ethyl, 3-[(2-, 3-, 4-, 5-, 6-, 7-, or 8-)quinolyl]propyl, 4-[(2-, 3-, 4-, 5-, 6-, 7-, or 8-)quinolyl]butyl, 1,1-dimethyl-2-[(2-, 3-, 4-, 5-, 6-, 7-, or 8-)quinolyl]ethyl, 5-[(2-, 3-, 4-, 5-, 6-, 7-, or 8-)quinolyl]pentyl, 6-[(2-, 3-, 4-, 5-, 6-, 7-, or 8-)quinolyl]hexyl, 1-[(2-, 3-, 4-, 5-, 6-, 7-, or 8-)quinolyl]isopropyl, and 2-methyl-3-[(2-, 3-, 4-, 5-, 6-, 7-, or -8)quinolyl]propyl.

Examples of lower alkoxy lower alkoxy-substituted lower alkyl groups include alkoxyalkoxy-substituted alkyl groups wherein each of the two alkoxy moieties is a straight or branched $C_{1-6}$ alkoxy group and the alkyl moiety is a straight or branched $C_{1-6}$ alkyl group, such as methoxymethoxymethyl, 2-(methoxymethoxy)ethyl, 1-(ethoxymethoxy)ethyl, 3-(2-n-butoxyethoxy)propyl, 4-(3-n-propoxypropoxy)butyl, 1,1-dimethyl-2-(4-n-pentyloxybutoxy)ethyl, 5-(5-n-hexyloxypentyloxy)pentyl, 6-(6-methoxyhexyloxy)hexyl, 1-ethoxymethoxyisopropyl, 2-methyl-3-(2-methoxyethoxy)propyl, and 3,3-dimethyl-3-(methoxymethoxy)propyl.

Examples of hydroxy-substituted lower alkyl groups include straight and branched $C_{1-6}$ alkyl groups substituted with one to three hydroxy groups, such as hydroxymethyl, 2-hydroxyethyl, 1-hydroxyethyl, 3-hydroxypropyl, 2,3-dihydroxypropyl, 4-hydroxybutyl, 3,4-dihydroxybutyl, 1,1-dimethyl-2-hydroxyethyl, 5-hydroxypentyl, 6-hydroxyhexyl, 3,3-dimethyl-3-hydroxypropyl, 2-methyl-3-hydroxypropyl, and 2,3,4-trihydroxybutyl.

Examples of thiazolyl lower alkyl groups optionally substituted on the thiazole ring with one or more members selected from the group consisting of halogen atoms, a phenyl group, thienyl groups, and pyridyl groups include:

thiazolylalkyl groups wherein the alkyl moiety is a straight or branched $C_{1-6}$ alkyl group, optionally substituted on the thiazole ring with one to three members selected from the group consisting of halogen atoms, a phenyl group, thienyl groups, and pyridyl groups;

such as [(2-, 4-, or 5-)thiazolyl]methyl, 2-[(2-, 4-, or 5-)thiazolyl]ethyl, 1-[(2-, 4-, or 5-)thiazolyl]ethyl, 3-[(2-, 4-, or 5-)thiazolyl]propyl, 4-[(2-, 4-, or 5-)thiazolyl]butyl, 5-[(2-, 4-, or 5-)thiazolyl]pentyl, 6-[(2-, 4-, or 5-)thiazolyl]hexyl, 1,1-dimethyl-2-[(2-, 4-, or 5-)thiazolyl]ethyl, [2-methyl-3-[(2-, 4-, or 5-)thiazolyl]propyl, [2-chloro-(4- or 5-)thiazolyl]methyl, 2-[2-chloro-(4- or 5-)thiazolyl]ethyl, 1-[2-fluoro-(4- or 5-)thiazolyl]ethyl, 3-[2-bromo-(4- or 5-)thiazolyl]propyl, 4-[2-iodo-(4- or 5-)thiazolyl]butyl, [2-phenyl-(4- or 5-)thiazolyl]methyl, 2-[2-phenyl-(4- or 5-)thiazolyl]ethyl, 1-[2-phenyl-(4- or 5-)thiazolyl]ethyl, 3-[2-phenyl-(4- or 5-)thiazolyl]propyl, 4-[2-phenyl-(4- or 5-)thiazolyl]butyl, 5-[2-phenyl-(4- or 5-)thiazolyl]pentyl, 6-[2-phenyl-(4- or 5-)thiazolyl]hexyl, 1,1-dimethyl-2-[2-phenyl-(4- or 5-)thiazolyl]ethyl, [2-methyl-3-[2-phenyl-(4- or 5-)thiazolyl]propyl, [2-(2- or 3-)thienyl-(4- or 5-)thiazolyl]methyl, 2-[2-(2- or 3-)thienyl-(4- or 5-)thiazolyl]ethyl, 1-[2-(2- or 3-)thienyl-(4- or 5-)thiazolyl]ethyl, 3-[2-(2- or 3-)thienyl-(4- or 5-)thiazolyl]propyl, 4-[2-(2- or 3-)thienyl-(4- or 5-)thiazolyl]butyl, 5-[2-(2- or 3-)thienyl-(4- or 5-)thiazolyl]pentyl, 6-[2-(2- or 3-)thienyl-(4- or 5-)thiazolyl]hexyl, 1,1-dimethyl-2-[2-(2- or 3-)thienyl-(4- or 5-)thiazolyl]ethyl, [2-methyl-3-[2-(2- or 3-)thienyl-(4- or 5-)thiazolyl]propyl, [2-(2-, 3-, or 4-)pyridyl-(4- or 5-)thiazolyl]methyl, 2-[2-(2-, 3-, or 4-)pyridyl-(4- or 5-)thiazolyl]ethyl, 1-[2-(2-, 3-, or 4-)pyridyl-(4- or 5-)thiazolyl]ethyl, 3-[2-(2-, 3-, or 4-)pyridyl-(4- or 5-)thiazolyl]propyl, 4-[2-(2-, 3-, or 4-)pyridyl-(4- or 5-)thiazolyl]butyl, 5-[2-(2-, 3-, or 4-)pyridyl-(4- or 5-)thiazolyl]pentyl, 6-[2-(2-, 3-, or 4-)pyridyl-(4- or 5-)thiazolyl]hexyl, 1,1-dimethyl-2-[2-(2-, 3-, or 4-)pyridyl-(4- or 5-)thiazolyl]ethyl, and [2-methyl-3-[2-(2-, 3-, or 4-)pyridyl-(4- or 5-)thiazolyl]propyl.

Examples of lower alkylsilyloxy lower alkyl groups include alkylsilyloxyalkyl groups wherein each of the two alkyl moieties is a straight or branched $C_{1-6}$ alkyl group, such as trimethylsilyloxymethyl, (1- or 2-)(triethylsilyloxy)ethyl, 3-(trimethylsilyloxy)propyl, dimethyl-tert-butylsilyloxymethyl, 2-(dimethyl-tert-butylsilyloxy)ethyl, 3-(dimethyl-tert-butylsilyloxy)propyl, 4-(dimethyl-tert-butylsilyloxy)butyl, 5-(dimethyl-tert-butylsilyloxy)pentyl, and 6-(dimethyl-tert-butylsilyloxy)hexyl.

Examples of phenoxy lower alkyl groups optionally substituted on the phenyl ring with one or more members selected from the group consisting of lower alkyl groups optionally substituted with one or more halogen atoms; lower alkoxy groups; halogen atoms; lower alkenyl groups, cycloalkyl groups, a nitro group; and a phenyl group include:

phenoxy alkyl groups wherein the alkyl moiety is a straight or branched $C_{1-6}$ alkyl group, optionally substituted on the phenyl ring with one to three members selected from the group consisting of straight and branched $C_{1-6}$ alkyl groups optionally substituted with one to three halogen atoms; straight and branched $C_{1-6}$ alkoxy groups; halogen atoms; straight and branched $C_{2-6}$ alkenyl groups; $C_{3-8}$ cycloalkyl groups; a nitro group; and a phenyl group;

such as 3-[(2-, 3-, or 4-)methylphenoxy]propyl, 3-[(2-, 3-, or 4-)propylphenoxy]propyl, 3-[(2-, 3-, or 4-)methoxyphenoxy]propyl, 3-[(2,3- or 3,4-)dichlorophenoxy]propyl, 3-[(2,3- or 3,4-)difluorophenoxy]propyl, 3-[3-fluoro-4-chlorophenoxy]propyl, 3-[(2-, 3-, or 4-)trifluoromethylphenoxy]propyl, 3-[2-methoxy-4-propenylphenoxy]propyl, 3-[2-chloro-4-methoxyphenoxy]propyl, (2-, 3-, or 4-)cyclopentylphenoxypropyl, 3-[(2-, 3-, or 4-)nitrophenoxy]propyl, 3-[(2,3- or 3,4-)dimethylphenoxy]propyl, and 3-[(2-, 3-, or 4-)phenylphenoxy]propyl.

Examples of phenylthio lower alkyl groups optionally substituted on the phenyl ring with one or more halogen atoms include:

phenylthioalkyl groups wherein the alkyl moiety is a straight or branched $C_{1-6}$ alkyl group, optionally substituted on the phenyl ring with one to three halogen atoms;

such as phenylthiomethyl, 2-phenylthioethyl, 1-phenylthioethyl, 3-phenylthiopropyl, 4-phenylthiobutyl, 5-phenylthiopentyl, 6-phenylthiohexyl, 1,1-dimethyl-2-phenylthioethyl, 2-methyl-3-phenylthiopropyl, (2-, 3-, or 4-)chlorophenylthiomethyl, 2-[(2-, 3-, or 4-)chlorophenylthio]ethyl, 3-[(2-, 3-, or 4-)chlorophenylthio]propyl, 4-[(2-, 3-, or 4-)fluorophenylthio]butyl, 5-[(2-, 3-, or 4-)bromophenylthio]pentyl, and 6-[(2-, 3-, or 4-)iodophenylthio]hexyl.

Examples of piperidinyl lower alkyl groups optionally substituted on the piperidine ring with one or more members selected from the group consisting of a phenyl group and phenyl lower alkyl groups include:

piperidinylalkyl groups wherein the alkyl moiety is a straight or branched $C_{1-6}$ alkyl group, optionally substituted on the piperidine ring with one to three members selected from the group consisting of a phenyl group and phenylalkyl groups wherein the alkyl moiety is a straight or branched $C_{1-6}$ alkyl group;

such as [(1-, 2-, 3-, or 4-)piperidinyl]methyl, 2-[(1-, 2-, 3-, or 4-)piperidinyl]ethyl, 1-[(1-, 2-, 3-, or 4-)piperidinyl]ethyl, 3-[(1-, 2-, 3-, or 4-)piperidinyl]propyl, 4-[(1-, 2-, 3-, or 4-)piperidinyl]butyl, 5-[(1-, 2-, 3-, or 4-)piperidinyl]pentyl, 6-[(1-, 2-, 3-, or 4-)piperidinyl]hexyl, 1,1-dimethyl-2-[(1-, 2-, 3-, or 4-)piperidinyl]ethyl, 2-methyl-3-[(1-, 2-, 3-, or 4-)piperidinyl]propyl, [4-phenyl-1-piperidinyl]methyl, 3-[4-phenyl-1-piperidinyl]propyl, [4-phenylmethyl-1-piperidinyl]methyl, 3-[4-phenylmethyl-1-piperidinyl]propyl, 2-[4-phenyl-(1-, 2-, or 3-)piperidinyl]ethyl, 3-[4-phenylmethyl-(1-, 2-, or 3-)piperidinyl]propyl, 4-[4-phenylethyl-(1-, 2-, or 3-)piperidinyl]butyl, 5-[4-phenyl-(1-, 2-, or 3-)piperidinyl]pentyl, and 6-[4-phenyl-(1-, 2-, or 3-)piperidinyl]hexyl.

Examples of piperazinyl lower alkyl groups optionally substituted on the piperazine ring with one or more phenyl groups include:

piperazinylalkyl groups wherein the alkyl moiety is a straight or branched $C_{1-6}$ alkyl group, optionally substituted on the piperazine ring with one to three phenyl groups;

such as (1- or 2-)piperazinylmethyl, 2-[(1- or 2-)piperazinyl]ethyl, [4-phenyl-(1-, 2-, or 3-)piperazinyl]methyl, 2-[4-phenyl-(1-, 2-, or 3-)piperazinyl]ethyl, 3-[4-phenyl-(1-, 2-, or 3-)piperazinyl]propyl, 4-[4-phenyl-(1-, 2-, or 3-)piperazinyl]butyl, 5-[4-phenyl-(1-, 2-, or 3-)piperazinyl]pentyl, and 6-[4-phenyl-(1-, 2-, or 3-)piperazinyl]hexyl.

Examples of 1,2,3,4-tetrahydroisoquinolyl lower alkyl groups include 1,2,3,4-tetrahydroisoquinolylalkyl groups wherein the alkyl moiety is a straight or branched $C_{1-6}$ alkyl group, such as (1,2,3,4-tetrahydroisoquinolin-2-yl)methyl, 2-(1,2,3,4-tetrahydroisoquinolin-2-yl)ethyl, 3-(1,2,3,4-tetrahydroisoquinolin-2-yl)propyl, 4-(1,2,3,4-tetrahydroisoquinolin-2-yl)butyl, 5-(1,2,3,4-tetrahydroisoquinolin-2-yl)pentyl, and 6-(1,2,3,4-tetrahydroisoquinolin-2-yl)hexyl.

Examples of naphthyloxy lower alkyl groups include naphthyloxyalkyl groups wherein the alkyl moiety is a straight or branched $C_{1-6}$ alkyl group, such as 1-naphthyloxymethyl, 2-(2-naphthyloxy)ethyl, 3-(1-naphthyloxy)propyl, 3-(2-naphthyloxy)propyl, 4-(1-naphthyloxy)butyl, 5-(2-naphthyloxy)pentyl and 6-(1-naphthyloxy)hexyl.

Examples of benzothiazolyloxy lower alkyl group optionally substituted on the benzothiazole ring with one or more alkyl groups include:

benzothiazolyloxyalkyl groups wherein the alkyl moiety is a straight or branched $C_{1-6}$ alkyl group, optionally substituted on the benzothiazoline ring with one to three straight and/or branched $C_{1-6}$ alkyl groups;

such as 1-[benzothiazol-(2-, 4-, 5-, 6- or 7-)yloxy]methyl, 2-[benzothiazol-(2-, 4-, 5-, 6- or 7-)yloxy]ethyl, 3-[benzothiazol-(2-, 4-, 5-, 6- or 7-)yloxy]propyl, 3-[benzothiazol-(2-, 4-, 5-, 6- or 7-)yloxy]propyl, 4-[benzothiazol-(2-, 4-, 5-, 6- or 7-)yloxy]butyl, 5-[benzothiazol-(2-, 4-, 5-, 6- or 7-)yloxy]pentyl, 6-[benzothiazol-(2-, 4-, 5-, 6- or 7-)yloxy]hexyl, 2-methylbenzothiazol-5-yloxymethyl, 2-(2-methylbenzothiazol-5-yloxy)ethyl, 3-(2-methylbenzothiazol-5-yloxy)propyl, 4-(2-ethylbenzothiazol-5-yloxy)butyl, 5-(2-ethylbenzothiazol-5-yloxy)pentyl, and 6-(2-ethylbenzothiazol-5-yloxy)hexyl.

Examples of lower alkyl groups substituted with one or more members selected from the group consisting of quinolyloxy groups and isoquinolyloxy groups include:

alkyl groups wherein the alkyl moiety is a straight or branched $C_{1-6}$ alkyl group, substituted with one to three members selected from the group consisting of quinolyloxy groups and isoquinolyloxy groups;

such as (5-quinolyloxy)methyl, 2-(5-quinolyloxy)ethyl, 3-(5-quinolyloxy)propyl, 4-(5-quinolyloxy)butyl, 5-(5-quinolyloxy)pentyl, 6-(5-quinolyloxy)hexyl, (5-isoquinolyloxy)methyl, 2-(5-isoquinolyloxy)ethyl, 3-(5-isoquinolyloxy)propyl, 4-(5-isoquinolyloxy)butyl, 5-(5-isoquinolyloxy)pentyl, and 6-(5-isoquinolyloxy)hexyl.

Examples of pyridyloxy lower alkyl groups optionally substituted on the pyridine ring with one or more lower alkyl groups include:

pyridyloxyalkyl groups wherein the alkyl moiety is a straight or branched $C_{1-6}$ alkyl group, optionally substituted on the pyridine ring with one to three straight and/or branched $C_{1-6}$ alkyl groups;

such as (2-, 3-, or 4-)pyridyloxymethyl, 2-[(2-, 3-, or 4-)pyridyloxy]ethyl, 1-[(2-, 3-, or 4-)pyridyloxy]ethyl, 3-[(2-, 3-, or 4-)pyridyloxy]propyl, 4-[(2-, 3-, or 4-)pyridyloxy]butyl, 1,1-dimethyl-2-[(2-, 3-, or 4-)pyridyloxy]ethyl, 5-[(2-, 3-, or 4-)pyridyloxy]pentyl, 6-[(2-, 3-, or 4-)pyridyloxy]hexyl, [6-methyl-(2-, 3-, 4-, or 5-)pyridyloxy]methyl, 2-[6-ethyl-(2-, 3-, 4-, or 5-)pyridyloxy]ethyl, 3-[6-methyl-(2-, 3-, 4-, or 5-)pyridyloxy]propyl, 4-[6-methyl-(2-, 3-, 4-, or 5-)pyridyloxy]butyl, 5-[6-methyl-(2-, 3-, 4-, or 5-)pyridyloxy]pentyl, and 6-[6-methyl-(2-, 3-, 4-, or 5-)pyridyloxy]hexyl.

Examples of carboxy lower alkoxy groups include carboxyalkoxy groups wherein the alkoxy moiety is a straight or branched $C_{1-6}$ alkoxy group, such as carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, and 2-methyl-3-carboxypropoxy.

Examples of lower alkoxycarbonyl lower alkoxy groups include alkoxycarbonylalkoxy groups wherein each of the two alkoxy moieties is a straight or branched $C_{1-6}$ alkoxy group, such as methoxycarbonylmethoxy, ethoxycarbonylmethoxy, 2-methoxycarbonylethoxy, 2-ethoxycarbonylethoxy, 1-ethoxycarbonylethoxy, 3-methoxycarbonylpropoxy, 3-ethoxycarbonylpropoxy, 4-ethoxycarbonylbutoxy, 5-isopropoxycarbonylpentyloxy, 6-n-propoxycarbonylhexyloxy, 1,1-dimethyl-2-n-butoxycarbonylethoxy, 2-methyl-3-tert-butoxycarbonylpropoxy, 2-n-pentyloxycarbonylethoxy, and n-hexyloxycarbonylmethoxy.

Examples of lower alkyl groups optionally substituted with one or more halogen atoms include straight and branched $C_{1-6}$ alkyl groups optionally substituted with one to three halogen atoms, such as, in addition to the above-described lower alkyl groups, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 4,4,4-trifluorobutyl, 5-chloropentyl, 3-chloro-2-methylpropyl, 5-bromohexyl, and 5,6-dibromhexyl.

Examples of lower alkylthio groups optionally substituted with one or more halogen atoms include straight and branched $C_{1-6}$ alkylthio groups optionally substituted with one to three halogen atoms, such as, in addition to the above-described lower alkylthio groups, trifluoromethylthio, trichloromethylthio, chloromethylthio, bromomethylthio, fluoromethylthio, iodomethylthio, difluoromethylthio, dibromomethylthio, 2-chloroethylthio, 2,2,2-trifluoroethylthio, 2,2,2-trichloroethylthio, 3-chloropropylthio, 2,3-dichloropropylthio, 4,4,4-trichlorobutylthio, 4-fluorobutylthio, 4,4,4-trifluorobutylthio, 5-chloropentylthio, 3-chloro-2-methylpropylthio, 5-bromohexylthio, and 5,6-dibromhexylthio.

Examples of lower alkylsulfonyl groups include straight and branched $C_{1-6}$ alkyl sulfonyl groups optionally substituted with one to three halogen atoms, such as methylsulfonyl, ethylsulfonyl, n-propylsulfonyl, isopropylsulfonyl, n-butylsulfonyl, isobutylsulfonyl, tert-butylsulfonyl, sec-butylsulfonyl, n-pentylsulfonyl, isopentylsulfonyl, neopentylsulfonyl, n-hexylsulfonyl, isohexylsulfonyl, and 3-methylpentylsulfonyl.

Examples of phenyl lower alkenyl groups include phenylalkenyl groups containing one to three double bonds wherein the alkenyl moiety is a straight or branched $C_{2-6}$ alkenyl group, such as styryl, 3-phenyl-2-propenyl (trivial name: cinnamyl), 4-phenyl-2-butenyl, 4-phenyl-3-butenyl, 5-phenyl-4-pentenyl, 5-phenyl-3-pentenyl, 6-phenyl-5-hexenyl, 6-phenyl-4-hexenyl, 6-phenyl-3-hexenyl, 4-phenyl-1,3-butadienyl, and 6-phenyl-1,3,5-hexatrienyl.

Examples of lower alkanoyloxy groups include straight and branched $C_{2-6}$ alkanoyloxy groups such as acetyloxy, propionyloxy, butyryloxy, isobutyryloxy, pentanoyloxy, tert-butylcarbonyloxy, and hexanoyloxy.

Examples of phenyl lower alkoxy groups optionally substituted on the phenyl ring with one or more members selected from the group consisting of halogen atoms; lower alkyl groups optionally substituted with one or more halogen atoms; lower alkylthio groups optionally substituted with one or more halogen atoms; lower alkoxy groups; a nitro group; lower alkylsulfonyl groups; lower alkoxycarbonyl groups; phenyl lower alkenyl groups; lower alkanoyloxy groups; and 1,2,3-thiadiazolyl groups include:

phenylalkoxy groups wherein the alkoxy moiety is a straight or branched $C_{1-6}$ alkoxy group, optionally substituted on the phenyl ring with one to three members selected from the group consisting of the above-described halogen atoms; the above-described straight and branched $C_{1-6}$ alkyl groups optionally substituted with one to three halogen atoms; the above-described straight and branched $C_{1-6}$ alkylthio groups optionally substituted with one to three halogen atoms; the above-described straight and branched $C_{1-6}$ alkoxy groups; a nitro group; the above-described straight and branched $C_{1-6}$ alkylsulfonyl groups; the above-described straight and branched $C_{1-6}$ alkoxycarbonyl groups; the above-described phenylalkenyl groups containing one to three double bonds wherein the alkenyl moiety is a straight or branched $C_{2-6}$ alkenyl group; the above-described straight and branched $C_{1-6}$ alkanoyloxy groups; and 1,2,3-thiadiazolyl groups;

such as benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, 4-chlorobenzyloxy, 2-chlorobenzyloxy, 3-chlorobenzyloxy, 3-fluorobenzyloxy, 4-fluorobenzyloxy, 2,4-dibromobenzyloxy, 2,4,6-trifluorobenzyloxy, 3-trifluoromethylbenzyloxy, 4-trifluoromethylbenzyloxy, 4-methylbenzyloxy, 3-methylbenzyloxy, 2,4-dimethylbenzyloxy, 2,4,6-trimethylbenzyloxy, 4-methoxycarbonylbenzyloxy, 3-methoxybenzyloxy, 2-methoxybenzyloxy, 3-methoxycarbonylbenzyloxy, 2,3-dimethoxybenzyloxy, 2,4,5-trimethoxybenzyloxy, 3-nitrobenzyloxy, 2-(2,3-dinitrophenyl)ethoxy, 3-(2,4,6-trinitrophenyl)ethoxy, 2-nitro-4-methylbenzyloxy, 4-methylsulfonylbenzyloxy, 4-(4-ethylsulfonylphenyl)butoxy, 5-(4-propylsulfonylphenyl)pentyloxy, 4-acetyloxybenzyloxy, 6-(4-propionyloxyphenyl)hexyloxy, 4-styrylbenzyloxy, 4-(1,2,3-thiadiazol-4-yl)benzyloxy, 4-trifluoromethylthiobenzyloxy, 3-methylthiobenzyloxy, 2,4-dimethylthiobenzyloxy, and 2,4,6-trimethylthiobenzyloxy.

Examples of piperidinyl lower alkoxy groups optionally substituted on the piperidine ring with one or more lower alkyl groups include:

piperidinylalkoxy groups wherein the alkoxy moiety is a straight or branched $C_{1-6}$ alkoxy group, optionally substituted on the piperidine ring with one to three straight and/or branched $C_{1-6}$ alkyl groups;

such as [(1-, 2-, 3-, or 4-)piperidinyl]methoxy, 2-[(1-, 2-, 3-, or 4-)piperidinyl]ethoxy, 1-[(1-, 2-, 3-, or 4-)piperidinyl]ethoxy, 3-[(1-, 2-, 3-, or 4-)piperidinyl]propoxy, 4-[(1-, 2-, 3-, or 4-)piperidinyl]butoxy, 5-[(1-, 2-, 3-, or 4-)piperidinyl]pentyloxy, 6-[(1-, 2-, 3-, or 4-)piperidinyl]hexyloxy, 1,1-dimethyl-2-[(1-, 2-, 3-, or 4-)piperidinyl]ethoxy, 2-methyl-3-[(1-, 2-, 3-, or 4-)piperidinyl]propoxy, [1-methyl-(2-, 3-, or 4-)piperidinyl]methoxy, 2-[1-ethyl-(2-, 3-, or 4-)piperidinyl]ethoxy, 3-[1-n-propyl-(2-, 3-, or 4-)piperidinyl]propoxy, 4-[1-n-butyl-(2-, 3-, or 4-)piperidinyl]butoxy, 5-[1-n-pentyl-(2-, 3-, or 4-)piperidinyl]pentyloxy, 6-[1-n-hexyl-(2-, 3-, or 4-)piperidinyl]hexyloxy, [1,2-dimethyl-(3-, 4-, 5-, or 6-)piperidinyl]methoxy, [1,2,3-trimethyl-(4-, 5-, or 6-)piperidinyl]methoxy, 2-[2-n-propyl-(3-, 4-, 5-, or 6-)piperidinyl]ethoxy, 2-[3-ethyl-(2-, 4-, 5-, or 6-)piperidinyl]ethoxy, and (2-methyl-4-isopropyl-(3-, 5-, or 6-piperidinyl)methoxy.

Examples of amino-substituted lower alkoxy groups optionally substituted on each amino group with one or more lower alkyl groups include amino-substituted straight and branched $C_{1-6}$ alkoxy groups optionally substituted on the amino group with one or two straight and/or branched $C_{1-6}$ alkyl groups, such as aminomethoxy, 2-aminomethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-n-propylaminoethoxy, 3-isopropylaminopropoxy, 4-n-butylaminobutoxy, 5-n-pentylaminopentyloxy, 6-n-hexylaminohexyloxy, dimethylaminomethoxy, 3-dimethylaminopropoxy, 2-diisopropylaminoethoxy, (N-ethyl-N-n-propylamino)methoxy, and 2-(N-methyl-N-n-hexylamino) ethoxy.

Examples of lower alkenyloxy groups include straight and branched $C_{2-6}$ alkenyloxy groups containing one to three double bonds, such as vinyloxy, 1-propenyloxy, 1-methyl-1-propenyloxy, 2-methyl-1-propenyloxy, 2-propenyloxy, 2-butenyloxy, 1-butenyloxy, 3-butenyloxy, 2-pentenyloxy, 1-pentenyloxy, 3-pentenyloxy, 4-pentenyloxy, 1,3-butadienyloxy, 1,3-pentadienyloxy, 2-penten-4-yloxy, 2-hexenyloxy, 1-hexenyloxy, 5-hexenyloxy, 3-hexenyloxy, 4-hexenyloxy, 3,3-dimethyl-1-propenyloxy, 2-ethyl-1-propenyloxy, 1,3,5-hexatrienyloxy, 1,3-hexadienyloxy, and 1,4-hexadienyloxy.

Examples of pyridyl lower alkoxy groups optionally substituted on the pyridine ring with one or more lower alkyl groups, each lower alkyl substituent optionally being substituted with one or more halogen atoms include:

pyridylalkoxy groups wherein the alkoxy moiety is a straight or branched $C_{1-6}$ alkoxy group, optionally substituted on the pyridine ring with one to three above-described straight and/or branched $C_{1-6}$ alkyl groups, each alkyl substituent optionally being substituted with one to three halogen atoms;

such as [(2-, 3-, or 4-)pyridyl]methoxy, 2-[(2-, 3-, or 4-)pyridyl]ethoxy, 1-[(2-, 3-, or 4-)pyridyl]ethoxy, 3-[(2-, 3-, or 4-)pyridyl]propoxy, 4-[(2-, 3-, or 4-)pyridyl]butoxy, 5-[(2-, 3-, or 4-)pyridyl]pentyloxy, 6-[(2-, 3-, or 4-)pyridyl]hexyloxy, 1,1-dimethyl-2-[(2-, 3-, or 4-)pyridyl]ethoxy, 2-methyl-3-[(2-, 3-, or 4-)pyridyl]propoxy, [2-trifluoromethyl-(3-, 4-, 5-, or 6-)pyridyl]methoxy, [2-methyl-(3-, 4-, 5-, or 6-)pyridyl]methoxy, [2,4-dimethyl-(3-, 5-, or 6-)pyridyl]methoxy, [2,4,6-trimethyl-(3- or 5-)pyridyl]methoxy), [2-trifluoromethyl-4-methyl-(3-, 5-, or 6-)pyridyl]methoxy, 2-[3-ethyl-(2-, 4-, 5-, or 6-)pyridyl]ethoxy, 3-[4-n-propyl-(2- or 3-)pyridyl]propoxy, 4-[3-n-butyl-(2-, 4-, 5-, or 6-)pyridyl]butyl, 5-[3-trifluoromethyl-(2-, 4-, 5-, or 6-)pyridyl]pentyloxy, 6-[2-n-pentyl-(3-, 4-, 5-, or 6-)pyridyl]hexyloxy, and [2-n-hexyl-(3-, 4-, 5-, or 6-)pyridyl]methoxy.

Examples of lower alkynyloxy groups include straight and branched $C_{2-6}$ alkynyloxy groups, such as ethynyloxy, 2-propynyloxy, 2-butynyloxy, 3-butynyloxy, 1-methyl-2-propynyloxy, 2-pentynyloxy, and 2-hexynyloxy.

Examples of phenyl lower alkynyloxy groups include phenylalkynyloxy groups wherein the alkynyloxy moiety is a straight or branched $C_{2-6}$ alkynyloxy group, such as 2-phenylethynyloxy, 3-phenyl-2-propynyloxy, 4-phenyl-2-butynyloxy, 4-phenyl-3-butynyloxy, 3-phenyl-1-methyl-2-propynyloxy, 5-phenyl-2-pentynyloxy, and 6-phenyl-2-hexynyloxy.

Examples of phenyl lower alkenyloxy groups include phenylalkenyloxy groups containing one to three double bonds wherein the alkenyloxy moiety is a straight or branched $C_{2-6}$ alkenyloxy group, such as styryloxy, 3-phenyl-1-propenyloxy, 3-phenyl-1-methyl-1-propenyloxy, 3-phenyl-2-methyl-1-propenyloxy, 3-phenyl-2-propenyloxy, 4-phenyl-2-butenyloxy, 4-phenyl-1-butenyloxy, 4-phenyl-3-butenyloxy, 4-phenyl-2-pentenyloxy, 5-phenyl-1-pentenyloxy, 5-phenyl-3-pentenyloxy, 5-phenyl-4-pentenyloxy, 4-phenyl-1,3-butadienyloxy, 5-phenyl-1,3-pentadienyloxy, 5-phenyl-2-penten-4-yloxy, 6-phenyl-2-hexenyloxy, 6-phenyl-1-hexenyloxy, 6-phenyl-5-hexenyloxy, 6-phenyl-3-hexenyloxy, 6-phenyl-4-hexenyloxy, 3-phenyl-3,3-dimethyl-1-propenyloxy, 3-phenyl-2-ethyl-1-propenyloxy, 6-phenyl-1,3,5-hexatrienyloxy, 6-phenyl-1,3-hexadienyloxy, and 6-phenyl-1,4-hexadienyloxy.

Examples of furyl lower alkoxy groups optionally substituted on the furan ring with one or more lower alkoxycarbonyl groups include:

furylalkoxy groups wherein the alkoxy moiety is a straight or branched $C_{1-6}$ alkoxy group, optionally substituted on the furan ring with one to three above-described alkoxycarbonyl groups wherein the alkoxy moiety is a straight or branched $C_{1-6}$ alkoxy group;

such as [(2- or 3-)furyl]methoxy, 2-[(2- or 3-)furyl]ethoxy, 1-[(2- or 3-)furyl]ethoxy, 3-[(2- or 3-)furyl]propoxy, 4-[(2- or 3-)furyl]butoxy, 5-[(2- or 3-)furyl]pentyloxy, 6-[(2- or 3-)furyl]hexyloxy, 1,1-dimethyl-2-[(2- or 3-)furyl]ethoxy, 2-methyl-3-[(2- or 3-)furyl]propoxy, [2-ethoxycarbonyl-(3-, 4-, or 5-)furyl]methoxy, [2-methoxycarbonyl-(3-, 4-, or 5-)furyl]methoxy, [3-n-propoxycarbonyl-(2-, 4-, or 5-)furyl]methoxy, [2-n-butoxycarbonyl-(3-, 4-, or 5-)furyl]methoxy, [3-n-pentyloxycarbonyl-(2-, 4-, or 5-)furyl]methoxy, [2-n-hexyloxycarbonyl-(3-, 4-, or 5-)furyl]methoxy, [2,3-diethoxycarbonyl-(4- or 5-)furyl]methoxy, 2,3,4-trimethoxycarbonyl-5-furyl)methoxy, 2-[3-n-propoxycarbonyl-(2-, 4-, or 5-)furyl] ethoxy, 3-[2-n-butoxycarbonyl-(3-, 4-, or 5-)furyl]propoxy, 4-[3-n-pentyloxycarbonyl-(2-, 4-, or 5-)furyl]butoxy, 5-[2-n-hexyloxycarbonyl-(3-, 4-, or 5-)furyl]pentyloxy, and 6-[2-n-hexyloxycarbonyl-(3-, 4-, or 5-)furyl]hexyloxy.

Examples of tetrazolyl lower alkoxy groups optionally substituted on the tetrazole ring with one member selected from the group consisting of a phenyl group, phenyl lower alkyl groups, and cycloalkyl lower alkyl groups include:

tetrazolylalkoxy groups wherein the alkoxy moiety is a straight or branched $C_{1-6}$ alkoxy group, optionally substituted on the tetrazole ring with one member selected from the group consisting of a phenyl group, the above-described phenylalkyl groups wherein the alkyl moiety is a straight or branched $C_{1-6}$ alkyl group, and the above-described $C_{3-8}$ cycloalkyl alkyl groups wherein the alkyl moiety is a straight or branched $C_{1-6}$ alkyl group;

such as [(1- or 5-)tetrazolyl]methoxy, 2-[(1- or 5-)tetrazolyl]ethoxy, 1-[(1- or 5-)tetrazolyl]ethoxy, 3-[(1- or 5-)tetrazolyl]propoxy, 4-[(1- or 5-)tetrazolyl]butoxy, 5-[(1- or 5-)tetrazolyl]pentyloxy, 6-[(1- or 5-)tetrazolyl]hexyloxy, 1,1-dimethyl-2-[(1- or 5-)tetrazolyl]ethoxy, 2-methyl-3-[(1- or 5-)tetrazolyl]propoxy, (1-benzyl-5-tetrazolyl)methoxy, (1-phenyl-5-tetrazolyl)methoxy, (1-cyclohexylmethyl-5-tetrazolyl)methoxy, [5-(2-phenylethyl)-1-tetrazolyl]methoxy, [1-(1-phenylethyl)-5-tetrazolyl]methoxy, [1-(3-phenylpropyl)-5-tetrazolyl]methoxy, [5-(4-phenylbutyl)-1-tetrazolyl]methoxy, [1-(5-phenylpentyl)-5-tetrazolyl]methoxy, [1-(6-phenylhexyl)-5-tetrazolyl]methoxy, [5-(2-cyclohexylethyl)-1-tetrazolyl]methoxy, [1-(1-cyclopropylethyl)-5-tetrazolyl]methoxy, [1-(3-cyclobutylpropyl)-5-tetrazolyl]methoxy, [5-(4-cyclopentylbutyl)-1-tetrazolyl]methoxy, [1-(5-cycloheptylpentyl)-5-tetrazolyl]methoxy, [1-(6-cyclooctylhexyl)-5-tetrazolyl]methoxy, 2-(1-phenyl-5-tetrazolyl)ethoxy, 3-(1-cyclohexylmethyl-5-tetrazolyl) propoxy, 4-[5-(2-phenylethyl)-1-tetrazolyl]butoxy, 5-(1-benzyl-5-tetrazolyl)pentyloxy, 6-(1-phenyl-5-tetrazolyl) hexyloxy, and 1-(1-cyclohexylmethyl-5-tetrazolyl)ethoxy.

Examples of phenyl groups optionally substituted on the phenyl ring with one or more lower alkyl groups include phenyl groups optionally substituted on the phenyl ring with one to three straight and/or branched $C_{1-6}$ alkyl groups, such as phenyl, 2-methylphenyl, 3-methylphenyl, 4-methylphenyl, 2-ethylphenyl, 3-ethylphenyl, 4-ethylphenyl, 4-isopropylphenyl, 3-n-butylphenyl, 4-n-pentylphenyl, 4-n-hexylphenyl, 3,4-dimethylphenyl, 3,4-diethylphenyl, 2,4-dimethylphenyl, 2,5-dimethylphenyl, 2,6-dimethylphenyl, and 3,4,5-trimethylphenyl.

Examples of 1,2,4-oxadiazolyl lower alkoxy groups optionally substituted on the 1,2,4-oxadiazole ring with a phenyl group, the phenyl substituent optionally being substituted on the phenyl ring with one or more lower alkyl groups, include:

1,2,4-oxadiazolylalkoxy groups wherein the alkoxy moiety is a straight or branched $C_{1-6}$ alkoxy group, optionally substituted on the 1,2,4-oxadiazole ring with one of the above-described phenyl groups optionally substituted on the phenyl ring with one to three straight and/or branched $C_{1-6}$ alkyl groups;

such as [(3- or 5-)1,2,4-oxadiazolyl]methoxy, 2-[(3- or 5-)1,2,4-oxadiazolyl]ethoxy, 1-[(3- or 5-)1,2,4-oxadiazolyl]ethoxy, 3-[(3- or 5-)1,2,4-oxadiazolyl]propoxy, 4-[(3- or 5-)1,2,4-oxadiazolyl]butoxy, 5-[(3- or 5-)1,2,4-oxadiazolyl]pentyloxy, 6-[(3- or 5-)1,2,4-oxadiazolyl]hexyloxy, 1,1-dimethyl-2-[(3- or 5-)1,2,4-oxadiazolyl]ethoxy, 2-methyl-3-[(3- or 5-)1,2,4-oxadiazolyl]propoxy, [3-(4-tert-butylphenyl)-5-1,2,4-oxadiazolyl]methoxy, [3-(3-methylphenyl)-5-1,2,4-oxadiazolyl]methoxy, [5-(2-ethylphenyl)-3-1,2,4-oxadiazolyl]methoxy, [3-(4-n-propylphenyl)-5-1,2,4-oxadiazolyl]methoxy, [5-(3-n-pentylphenyl)-3-1,2,4-oxadiazolyl]methoxy, [3-(2-n-hexylphenyl)-5-1,2,4-oxadiazolyl]methoxy, [3-(2,4-dimethylphenyl)-5-1,2,4-oxadiazolyl]methoxy, [3-(2,3,5-trimethylphenyl)-5-1,2,4-oxadiazolyl]methoxy, 2-[3-(4-tert-butylphenyl)-5-1,2,4-oxadiazolyl]ethoxy, 1-[3-(3-methylphenyl)-5-1,2,4-oxadiazolyl]ethoxy, 3-[5-(2-ethylphenyl)-3-1,2,4-oxadiazolyl]propoxy, 4-[3-(4-n-propylphenyl)-5-1,2,4-oxadiazolyl]butoxy, 5-[5-(3-n-pentylphenyl)-3-1,2,4-oxadiazolyl]pentyloxy, 6-[3-(2-n-hexylphenyl)-5-1,2,4-oxadiazolyl]hexyloxy, 2-[3-(2,4-dimethylphenyl)-5-1,2,4-oxadiazolyl]ethoxy and 1-[3-(2,3,5-trimethylphenyl)-5-1,2,4-oxadiazolyl]ethoxy.

Examples of isoxazolyl lower alkoxy groups optionally substituted on the isoxazole ring with one or more lower alkyl groups include:

isoxazolylalkoxy groups wherein the alkoxy moiety is a straight or branched $C_{1-6}$ alkoxy group, optionally substituted on the isoxazole ring with one or two above-described straight and/or branched $C_{1-6}$ alkyl groups;

such as [(3-, 4-, or 5-)isoxazolyl]methoxy, 2-[(3-, 4-, or 5-)isoxazolyl]ethoxy, 1-[(3-, 4-, or 5-)isoxazolyl]ethoxy, 3-[(3-, 4-, or 5-)isoxazolyl]propoxy, 4-[(3-, 4-, or 5-)isoxazolyl]butoxy, 5-[(3-, 4-, or 5-)isoxazolyl]pentyloxy, 6-[(3-, 4-, or 5-)isoxazolyl]hexyloxy, 1,1-dimethyl-2-[(3-, 4-, or 5-)isoxazolyl]ethoxy, 2-methyl-3-[(3-, 4-, or 5-)isoxazolyl]propoxy, (3,5-dimethyl-4-isoxazolyl)methoxy, [3-methyl-(4- or 5-)isoxazolyl]methoxy, [3-ethyl-(4- or 5-)isoxazolyl]methoxy, [4-n-propyl-(3- or 5-)isoxazolyl]methoxy, [5-n-butyl-(3- or 4-)isoxazolyl]methoxy, [3-n-pentyl-(4- or 5-)isoxazolyl]methoxy, [4-n-hexyl-(3- or 5-)isoxazolyl]methoxy, 2-[3-methyl-(4- or 5-)isoxazolyl]ethoxy, 1-[3-ethyl-(4- or 5-)isoxazolyl]ethoxy, 3-[4-n-propyl-(3- or 5-)isoxazolyl]propoxy, 4-[5-n-butyl-(3- or 4-)isoxazolyl]butoxy, 5-[3-n-pentyl-(4- or 5-)isoxazolyl]pentyloxy, and 6-[4-n-hexyl-(3- or 5-)isoxazolyl]hexyloxy.

Examples of 1,3,4-oxadiazolyl lower alkoxy groups optionally substituted on the 1,3,4-oxadiazole ring with a phenyl group, the phenyl substituent optionally being substituted on the phenyl ring with one or more lower alkyl groups include:

1,3,4-oxadiazolylalkoxy groups wherein the alkoxy moiety is a straight or branched $C_{1-6}$ alkoxy group, optionally substituted on the 1,3,4-oxadiazole ring with one of the above-described phenyl groups optionally substituted on the phenyl ring with one to three straight and/or branched $C_{1-6}$ alkyl groups;

such as [(2- or 5-)1,3,4-oxadiazolyl]methoxy, 2-[(2- or 5-)1,3,4-oxadiazolyl]ethoxy, 1-[(2- or 5-)1,3,4-oxadiazolyl]ethoxy, 3-[(2- or 5-)1,3,4-oxadiazolyl]propoxy, 4-[(2- or 5-)1,3,4-oxadiazolyl]butoxy, 5-[(2- or 5-)1,3,4-oxadiazolyl]pentyloxy, 6-[(2- or 5-)1,3,4-oxadiazolyl]hexyloxy, 1,1-dimethyl-2-[(2- or 5-)1,3,4-oxadiazolyl]ethoxy, 2-methyl-3-[(2- or 5-)1,3,4-oxadiazolyl]propoxy, [2-(4-tert-butylphenyl)-5-1,3,4-oxadiazolyl]methoxy, [2-(4-methylphenyl)-5-1,3,4-oxadiazolyl]methoxy, [5-(2-ethylphenyl)-2-1,3,4-oxadiazolyl]methoxy, [2-(4-n-propylphenyl)-5-1,3,4-oxadiazolyl]methoxy, [5-(3-n-pentylphenyl)-2-1,3,4-oxadiazolyl]methoxy, [2-(2-n-hexylphenyl)-5-1,3,4-oxadiazolyl]methoxy, [2-(2,4-dimethylphenyl)-5-1,3,4-oxadiazolyl]methoxy, [2-(2,3,5-trimethylphenyl)-5-1,3,4-oxadiazolyl]methoxy, 2-[2-(4-tert-butylphenyl)-5-1,3,4-oxadiazolyl]ethoxy, 1-[2-(3-methylphenyl)-5-1,3,4-oxadiazolyl]ethoxy, 3-[5-(2-ethylphenyl)-2-1,3,4-oxadiazolyl]propoxy, 4-[2-(4-n-propylphenyl)-5-1,3,4-oxadiazolyl]butoxy, 5-[5-(3-n-pentylphenyl)-2-1,3,4-oxadiazolyl]pentyloxy, 6-[2-(2-n-hexylphenyl)-5-1,3,4-oxadiazolyl]hexyloxy, 2-[2-(2,4-dimethylphenyl)-5-1,3,4-oxadiazolyl]ethoxy, and 1-[2-(2,3,5-trimethylphenyl)-5-1,3,4-oxadiazolyl]ethoxy.

Examples of lower alkanoyl lower alkoxy groups include alkanoylalkoxy groups wherein the alkanoyl moiety is a straight or branched $C_{2-6}$ alkanoyl group and the alkoxy moiety is a straight or branched $C_{1-6}$ alkoxy group, such as acetylmethoxy, propionylmethoxy, 2-acetylethoxy, 2-propionylethoxy, 1-acetylethoxy, 3-acetylpropoxy, 3-propionylpropoxy, 4-acetylbutoxy, 5-butyrylpentyloxy, 6-pentanoylhexyloxy, 1,1-dimethyl-2-hexanoylethoxy, 2-methyl-3-acetylpropoxy, 2-pentanoylethoxy, and hexanoylmethoxy.

Examples of phenyl groups optionally substituted on the phenyl ring with one or more halogen atoms include phenyl groups optionally substituted on the phenyl ring with one to three halogen atoms, such as phenyl, 4-fluorophenyl, 2,5-difluorophenyl, 2,4-difluorophenyl, 3,4-difluorophenyl, 3,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3-fluorophenyl, 2-fluorophenyl, 3-bromophenyl, 4-iodophenyl, 2-bromophenyl, 4-bromophenyl, 3,5-dichlorophenyl, 2,4,6-trifluorophenyl, 3,4-difluorophenyl, 2-iodophenyl, 3-iodophenyl, 4-iodophenyl, 2,3-dibromophenyl, 2,4-diiodophenyl, and 2,4,6-trichlorophenyl.

Examples of thiazolyl lower alkoxy groups optionally substituted on the thiazole ring with one or more members selected from the group consisting of lower alkyl groups and a phenyl group, each phenyl substituent optionally being substituted on the phenyl ring with one or more halogen atoms, include:

thiazolylalkoxy groups wherein the alkoxy moiety is a straight or branched $C_{1-6}$ alkoxy group, optionally substituted on the thiazole ring with one or two members selected from the group consisting of the above-described straight and branched $C_{1-6}$ alkyl groups and phenyl groups optionally substituted on the phenyl ring with one to three halogen atoms;

such as [(2-, 4-, or 5-)thiazolyl]methoxy, 2-[(2-, 4-, or 5-)thiazolyl]ethoxy, 1-[(2-, 4-, or 5-)thiazolyl]ethoxy, 3-[(2-, 4-, or 5-)thiazolyl]propoxy, 4-[(2-, 4-, or 5-)thiazolyl]butoxy, 5-[(2-, 4-, or 5-)thiazolyl]pentyloxy, 6-[(2-, 4-, or 5-)thiazolyl]hexyloxy, 1,1-dimethyl-2-[(2-, 4-, or 5-)thiazolyl]ethoxy, 2-methyl-3-[(2-, 4-, or 5-)thiazolyl]propoxy, [2-phenyl-(4- or 5-)thiazolyl]methoxy, [2-(4-chlorophenyl)-4-methyl-5-thiazolyl]methoxy, [2-(3-bromophenyl)-(4- or 5-)thiazolyl]methoxy, [2-(2-fluorophenyl)-(4- or 5-)thiazolyl]methoxy, [2-(3,4-dichlorophenyl)-(4- or 5-)thiazolyl]methoxy, [2-(2,4,6-trifluorophenyl)-(4- or 5-)thiazolyl]methoxy, [2-methyl-(4- or 5-)thiazolyl]methoxy, 2-[2-ethyl-(4- or 5-)thiazolyl]methoxy, 2-[4-phenyl-(2- or 5-)thiazolyl]ethoxy, 3-[5-n-propyl-(2- or 4-)thiazolyl]propoxy, 4-[4-n-butyl-(2- or 5-)thiazolyl]butoxy, 5-[2-n-pentyl-(4- or 5-)thiazolyl]pentyloxy, 6-[5-n-hexyl-(2- or 4-)thiazolyl]hexyloxy, [2,4-dimethyl-5-thiazolyl]methoxy, and [2,4-diphenyl-5-thiazolyl]methoxy.

Examples of benzoyl groups optionally substituted on the phenyl ring with one or more halogen atoms include benzoyl groups optionally substituted on the phenyl ring with one to three halogen atoms, such as benzoyl, 4-fluorobenzoyl, 2,5-difluorobenzoyl, 2,4-difluorobenzoyl, 3,4-difluorobenzoyl, 3,5-difluorobenzoyl, 2,6-difluorobenzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 3,4-dichlorobenzoyl, 2,6-dichlorobenzoyl, 3-fluorobenzoyl, 2-fluorobenzoyl, 3-bromobenzoyl, 4-iodobenzoyl, 2-bromobenzoyl, 4-bromobenzoyl, 3,5-dichlorobenzoyl, 2,4,6-trifluorobenzoyl, 2-iodobenzoyl, 3-iodobenzoyl, 4-iodobenzoyl, 2,3-dibromobenzoyl, 2,4-diiodobenzoyl, and 2,4,6-trichlorobenzoyl.

Examples of piperidinyloxy groups optionally substituted on the piperidine ring with one or more benzoyl groups, each benzoyl substituent optionally being substituted on the phenyl ring with one or more halogen atoms, include:

piperidinyloxy groups optionally substituted on the piperidine ring with one to three above-described benzoyl groups, each benzoyl substituent optionally being substituted on the phenyl ring with one to three halogen atoms;

such as (1-, 2-, 3-, or 4-)piperidinyloxy, 1-(4-chlorobenzoyl)-(2-, 3-, or 4-piperidinyloxy, 1-(3-bromobenzoyl)-(2-, 3-, or 4-)piperidinyloxy, 1-benzoyl-(2-, 3-, or 4-)piperidinyloxy, 1-(2-fluorobenzoyl)-(2-, 3-, or 4-)piperidinyloxy, 1-(2,4-dichlorobenzoyl)-(2-, 3-, or 4-)piperidinyloxy, 1-(2,4,6-trifluorobenzoyl)-(2-, 3-, or 4-)piperidinyloxy, 2-(3-chlorobenzoyl)-(1-, 3-, or 4-)piperidinyloxy, 3-(2-chlorobenzoyl)-(1-, 2-, or 4-)piperidinyloxy, 4-(2,3-dibromobenzoyl)-(1-, 2-, or 3-)piperidinyloxy, 1,2-dibenzyl-(3- or 4-)piperidinyloxy, and 1,2,4-tribenzoyl-3-piperidinyloxy.

Examples of thienyl lower alkoxy groups include thienylalkoxy groups wherein the alkoxy moiety is a straight or branched $C_{1-6}$ alkoxy group, such as [(2- or 3-)thienyl]methoxy, 2-[(2- or 3-)thienyl]ethoxy, 1-[(2- or 3-)thienyl]ethoxy, 3-[(2- or 3-)thienyl]propoxy, 4-[(2- or 3-)thienyl]butoxy, 5-[(2- or 3-)thienyl]pentyloxy, 6-[(2- or 3-)thienyl]hexyloxy, 1,1-dimethyl-2-[(2- or 3-)thienyl]ethoxy, and 2-methyl-3-[(2- or 3-)thienyl]propoxy.

Examples of phenylthio lower alkoxy groups include phenylthioalkoxy groups wherein the alkoxy moiety is a straight or branched $C_{1-6}$ alkoxy group, such as phenylthiomethoxy, 2-phenylthioethoxy, 1-phenylthioethoxy, 3-phenylthiopropoxy, 4-phenylthiobutoxy, 5-phenylthiopentyloxy, 6-phenylthiohexyloxy, 1,1-dimethyl-2-phenylthioethoxy, and 2-methyl-3-phenylthiopropoxy.

Examples of carbamoyl-substituted lower alkoxy groups optionally substituted with one or more lower alkyl groups include:

carbamoyl-substituted straight and branched $C_{1-6}$ alkoxy groups optionally substituted on the carbamoyl group with one or two straight and/or branched $C_{1-6}$ alkyl groups;

such as carbamoylmethoxy, 2-carbamoylethoxy, 1-carbamoylethoxy, 3-carbamoylpropoxy, 4-carbamoylbutoxy, 5-carbamoylpentyloxy, 6-carbamoylhexyloxy, 1,1-dimethyl-2-carbamoylethoxy, 2-methyl-3-carbamoylpropoxy, methylcarbamoylmethoxy, 1-ethylcarbamoylethoxy, 2-n-propylcarbamoylethoxy, 3-isopropylcarbamoylpropoxy, 4-n-butylcarbamoylbutoxy, 5-n-pentylcarbamoylpentyloxy, 6-n-hexylcarbamoylhexyloxy, dimethylcarbamoylmethoxy, 3-dimethylcarbamoylpropoxy, 2-diisopropylcarbamoylethoxy, (N-ethyl-N-n-propylcarbamoyl)methoxy, and 2-(N-methyl-N-n-hexylcarbamoyl)ethoxy.

Examples of benzoyl lower alkoxy groups include benzoylalkoxy groups wherein the alkoxy moiety is a straight or branched $C_{1-6}$ alkoxy group, such as benzoylmethoxy, 2-benzoylethoxy, 1-benzoylethoxy, 3-benzoylpropoxy, 4-benzoylbutoxy, 5-benzoylpentyloxy, 6-benzoylhexyloxy, 1,1-dimethyl-2-benzoylethoxy, and 2-methyl-3-benzoylpropoxy.

Examples of pyridylcarbonyl lower alkoxy groups include pyridylcarbonylalkoxy groups wherein the alkoxy moiety is a straight or branched $C_{1-6}$ alkoxy group, such as [(2-, 3-, or 4-)pyridylcarbonyl]methoxy, 2-[(2-, 3-, or 4-)pyridylcarbonyl]ethoxy, 1-[(2-, 3-, or 4-)pyridylcarbonyl]ethoxy, 3-[(2-, 3-, or 4-)pyridylcarbonyl]propoxy, 4-[(2-, 3-, or 4-)pyridylcarbonyl]butoxy, 5-[(2-, 3-, or 4-)pyridylcarbonyl]pentyloxy, 6-[(2-, 3-, or 4-)pyridylcarbonyl]hexyloxy, 1,1-dimethyl-2-[(2-, 3-, or 4-)pyridylcarbonyl]ethoxy, and 2-methyl-3-[(2-, 3-, or 4-)pyridylcarbonyl]propoxy.

Examples of imidazolyl lower alkoxy groups optionally substituted on the imidazole ring with one or more phenyl lower alkyl groups include:

imidazolylalkoxy groups wherein the alkoxy moiety is a straight or branched $C_{1-6}$ alkoxy group, optionally substituted on the imidazole ring with one to three phenylalkyl groups wherein the alkyl moiety is a straight or branched $C_{1-6}$ alkyl group;

such as [(1-, 2-, 4-, or 5-)imidazolyl]methoxy, 2-[(1-, 2-, 4-, or 5-)imidazolyl]ethoxy, 1-[(1-, 2-, 4-, or 5-)imidazolyl]ethoxy, 3-[(1-, 2-, 4-, or 5-)imidazolyl]propoxy, 4-[(1-, 2-, 4-, or 5-)imidazolyl]butoxy, 5-[(1-, 2-, 4-, or 5-)imidazolyl]pentyloxy, 6-[(1-, 2-, 4-, or 5-)imidazolyl]hexyloxy, 1,1-dimethyl-2-[(1-, 2-, 4-, or 5-)imidazolyl]ethoxy, 2-methyl-3-[(1-, 2-, 4-, or 5-)imidazolyl]propoxy, [1-benzyl-(2-, 4-, or 5-)imidazolyl]methoxy, [1-(2-phenylethyl)-(2-, 4-, or 5-)imidazolyl]methoxy, 2-[2-(3-phenylpropyl)-(1-, 4-, or 5-)imidazolyl]ethoxy, 3-[4-(4-phenylbutyl)-(1-, 2-, or 5-)imidazolyl]propoxy, 5-[4-(5-phenylpentyl)-(1-, 2-, or 4-)imidazolyl]pentyloxy, 6-[1-(6-phenylhexyloxy)-(2-, 4-, or 5-)imidazolyl]hexyloxy, [1,2-dibenzyl-(4- or 5-)imidazolyl]methoxy, and [1,2,4-tribenzyl-5-imidazolyl]methoxy.

Examples of phenoxy lower alkoxy groups include phenoxyalkoxy groups wherein the alkoxy moiety is a straight or branched $C_{1-6}$ alkoxy group, such as phenoxymethoxy, 2-phenoxyethoxy, 1-phenoxyethoxy, 3-phenoxypropoxy, 4-phenoxybutoxy, 5-phenoxypentyloxy, 6-phenoxyhexyloxy, 1,1-dimethyl-2-phenoxyethoxy, and 2-methyl-3-phenoxypropoxy.

Examples of phenyl lower alkoxy-substituted lower alkoxy groups include phenylalkoxy-substituted alkoxy groups wherein each of the two alkoxy moieties is a straight or branched $C_{1-6}$ alkoxy group, such as phenylmethoxymethoxy, 2-(phenylmethoxy)ethoxy, 1-(phenylmethoxy)ethoxy, 3-(phenylmethoxy)propoxy, 4-(phenylmethoxy)butoxy, 5-(phenylmethoxy)pentyloxy, 6-(phenylmethoxy)hexyloxy, 1,1-dimethyl-2-(phenylmethoxy)ethoxy, 2-methyl-3-(phenylmethoxy)propoxy, 1-(2-phenylethoxy)ethoxy, 2-(1-phenylethoxy)ethoxy, 3-(3-phenylpropoxy)propoxy, 4-(4-phenylbutoxy)butoxy, 5-(5-phenylpentyloxy)pentyloxy, 6-(6-phenylhexyloxy)hexyloxy, (1,1-dimethyl-2-phenylethoxy)methoxy, and 3-(2-methyl-3-phenylpropoxy)propoxy.

Examples of isoindolinyl lower alkoxy groups optionally substituted on the isoindoline ring with one or more oxo groups include:

isoindolinylalkoxy groups wherein the alkoxy moiety is a straight or branched $C_{1-6}$ alkoxy group, optionally substituted on the isoindoline ring with one or two oxo groups;

such as [(1-, 2-, 4-, or 5-)isoindolinyl]methoxy, 2-[(1-, 2-, 4-, or 5-)isoindolinyl]ethoxy, 1-[(1-, 2-, 4-, or 5-)isoindolinyl]ethoxy, 3-[(1-, 2-, 4-, or 5-)isoindolinyl]propoxy, 4-[(1-, 2-, 4-, or 5-)isoindolinyl]butoxy, 5-[(1-, 2-, 4-, or 5-)isoindolinyl]pentyloxy, 6-[(1-, 2-, 4-, or 5-)isoindolinyl]hexyloxy, 1,1-dimethyl-2-[(1-, 2-, 4-, or 5-)isoindolinyl]ethoxy, 2-methyl-3-[(1-, 2-, 4-, or 5-)isoindolinyl]propoxy, 3-[1,3-dioxo-(2-, 4-, or 5-)isoindolinyl]propoxy, [1-oxo-(2-, 3-, 4-, 5-, 6-, or 7-)isoindolinyl]methoxy, 2-[1,3-dioxo-(1-, 4-, or 5-)isoindolinyl]ethoxy, 4-[1-oxo-(2-, 3-, 4-, 5-, 6-, or 7-)isoindolinyl]butoxy, 5-[1,3-dioxo-(1-, 4-, or 5-)isoindolinyl]pentyloxy, and 6-[1-oxo-(2-, 3-, 4-, 5-, 6-, or 7-)isoindolinyl]hexyloxy.

Examples of lower alkoxy groups optionally substituted with one or more halogen atoms include straight and branched $C_{1-6}$ alkoxy groups optionally substituted with one to three halogen atoms, such as, in addition to the above-described lower alkoxy groups, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, and 5,6-dibromohexyloxy.

Examples of lower alkanoyl groups include straight and branched $C_{1-6}$ alkanoyl groups, such as formyl, acetyl, propionyl, butyryl, isobutyryl, pentanoyl, tert-butylcarbonyl, and hexanoyl.

Examples of amino groups optionally substituted with one or more lower alkanoyl groups include amino groups optionally substituted with one or two straight and/or branched $C_{1-6}$ alkanoyl groups, such as amino, formylamino, acetylamino, propionylamino, butyrylamino, isobutyrylamino, pentanoylamino, tert-butylcarbonylamino, hexanoylamino, N,N-diacetylamino, and N-acetyl-N-propionylamino.

Examples of phenyl lower alkyl groups optionally substituted on the phenyl ring with one or more members selected from the group consisting of halogen atoms; lower alkyl groups optionally substituted with one or more halogen atoms; lower alkoxy groups optionally substituted with one or more halogen atoms; a phenyl group; lower alkoxycarbonyl groups; a phenoxy group; lower alkylthio groups; lower alkylsulfonyl groups; phenyl lower alkoxy groups; and amino groups optionally substituted with one or more lower alkanoyl groups include:

mono- and di-phenylalkyl groups wherein the alkyl moiety is a straight or branched $C_{1-6}$ alkyl group, optionally substituted on the phenyl ring with one to three members selected from the group consisting of the above-described halogen atoms; the above-described straight and branched $C_{1-6}$ alkyl groups optionally substituted with one to three halogen atoms; the above-described straight and branched $C_{1-6}$ alkoxy groups optionally substituted with one to three halogen atoms; a phenyl group; the above-described alkoxycarbonyl groups wherein the alkoxy moiety is a straight or branched $C_{1-6}$ alkoxy group; a phenoxy group, the above-described straight and branched $C_{1-6}$ alylthio groups; the above-described straight and branched $C_{1-6}$ alkylsulfonyl groups; the above-described phenylalkoxy groups wherein the alkoxy moiety is a straight or branched $C_{1-6}$ alkoxy group; and the above-described amino groups optionally substituted with one or two straight and/or branched $C_{1-6}$ alkanoyl groups;

such as benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl, 1,1-diphenylmethyl, 2,2-diphenylethyl, 3,3-diphenylpropyl, 1,2-diphenylethyl, 4-chlorobenzyl, 2-chlorobenzyl, 3-chlorobenzyl, 3-fluorobenzyl, 4-fluorobenzyl, 2,3-dichlorobenzyl, 2,4,6-trifluorobenzyl, 3-trifluoromethylbenzyl, 4-trifluoromethylbenzyl, 2-methylbenzyl, 3-methylbenzyl, 4-methylbenzyl, 4-tert-butylbenzyl, 2,4-dimethylbenzyl, 2,4,6-trimethylbenzyl, 2-phenylbenzyl, 4-phenylbenzyl, 2,4-diphenylbenzyl, 2,4,6-triphenylbenzyl, 2-trifluoromethoxybenzyl, 3-trifluoromethoxybenzyl, 4-trifluoromethoxybenzyl, 2-methoxybenzyl, 3-methoxybenzyl, 4-methoxybenzyl, 3,4-dimethoxybenzyl, 3,4,5-trimethoxybenzyl, 4-methoxycarbonylbenzyl, 3-ethoxycarbonylbenzyl, 2-n-propoxycarbonylbenzyl, 2,4-dimethoxycarbonylbenzyl, 2,4,6-trimethoxycarbonylbenzyl, 4-tert-butoxycarbonylbenzyl, 3-phenoxybenzyl, 2-phenoxybenzyl, 4-phenoxybenzyl, 3,4-diphenoxybenzyl, 3,4,5-triphenoxybenzyl, 4-methylthiobenzyl, 3-methylthiobenzyl, 2-methylthiobenzyl, 2,4-dimethylthiobenzyl, 2,4,6-trimethylthiobenzyl, 4-methylsulfonylbenzyl, 3-methylsulfonylbenzyl, 2-methylsulfonylbenzyl, 3,4-dimethylsulfonylbenzyl, 3,4,5-trimethylsulfonylbenzyl, 4-benzyloxybenzyl, 3-benzyloxybenzyl, 2-benzyloxybenzyl, 2,4-dibenzyloxybenzyl, 2,4,6-tribenzyloxybenzyl, 4-methoxy-3-chlorobenzyl, 4-(N-acetylamino)benzyl, 3-aminobenzyl, 2-aminobenzyl, 4-aminobenzyl, 2,3-diaminobenzyl, 3,4,5-triaminobenzyl, and 4-methyl-3-fluorobenzyl.

Examples of naphthyl lower alkyl groups include naphthylalkyl groups wherein the alkyl moiety is a straight or branched $C_{1-6}$ alkyl group, such as [(1- or 2-)naphthyl]methyl, 1-[(1- or 2-)naphthyl]ethyl, 2-[(1- or 2-)naphthyl]ethyl, 3-[(1- or 2-)naphthyl]propyl, 2-[(1- or 2-)naphthyl]propyl, 4-[(1- or 2-)naphthyl]butyl, 5-[(1- or 2-)naphthyl]pentyl, 4-[(1- or 2-)naphthyl]pentyl, 6-[(1- or 2-)naphthyl]hexyl, 2-methyl-3-[(1- or 2-)naphthyl]propyl, and 1,1-dimethyl-2-[(1- or 2-)naphthyl]ethyl.

Examples of furyl lower alkyl groups optionally substituted on the furan ring with one or more lower alkoxycarbonyl groups include:

furylalkyl groups wherein the alkyl moiety is a straight or branched $C_{1-6}$ alkyl group, optionally substituted on the furan ring with one to three alkoxycarbonyl groups wherein the alkoxy moiety is a straight or branched $C_{1-6}$ alkoxy group;

such as [(2- or 3-)furyl]methyl, 2-[(2- or 3-)furyl]ethyl, 1-[(2- or 3-)furyl]ethyl, 3-[(2- or 3-)furyl]propyl, 4-[(2- or 3-)furyl]butyl, 5-[(2- or 3-)furyl]pentyl, 6-[(2- or 3-)furyl]hexyl, 1,1-dimethyl-2-[(2- or 3-)furyl]ethyl, 2-methyl-3-[(2- or 3-)furyl]propyl, [5-ethoxycarbonyl-(2-, 3-, or 4-)furyl]methyl, [5-methoxycarbonyl-(2-, 3-, or 4-)furyl]methyl, [2-n-propoxycarbonyl-(3-, 4-, or 5-)furyl]methyl, [3-tert-butoxycarbonyl-(2-, 4-, or 5-)furyl]methyl, [4-n-pentyloxycarbonyl-(2-, 3-, or 5-)furyl]methyl, [2-n-hexyloxycarbonyl-(3-, 4-, or 5-)furyl]methyl, [2,5-diethoxycarbonyl-(3- or 4-)furyl]methyl, and [2,4,5-triethoxycarbonyl-3-furyl]methyl.

Examples of phenyl groups optionally substituted on the phenyl ring with one or more lower alkyl groups, each lower alkyl substituent optionally being substituted with one or more halogen atoms, include:

phenyl groups optionally substituted on the phenyl ring with one to three straight and/or branched $C_{1-6}$ alkyl groups, each alkyl substituent optionally being substituted with one to three above-described halogen atoms;

such as phenyl, 2-methylphenyl, 3-methylphenyl, 4-methylphenyl, 2-ethylphenyl, 3-ethylphenyl, 4-ethylphenyl, 4-isopropylphenyl, 3-n-butylphenyl, 4-n-pentylphenyl, 4-n-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-trifluoromethylphenyl, 3-trifluoromethylphenyl, 4-trifluoromethylphenyl, 3,5-difluoromethylphenyl, 2,4,6-tri(trifluoromethyl)phenyl, and 2-methyl-4-trifluoromethylphenyl.

Examples of thiazolyl lower alkyl groups optionally substituted on the thiazole ring with one or more members selected from the group consisting of lower alkyl groups and a phenyl group, each phenyl substituent optionally being substituted with one or more optionally halogen-substituted lower alkyl groups, include thiazolylalkyl groups wherein the alkyl moiety is a straight or branched $C_{1-6}$ alkyl group. Such thiazoylalkyl groups include those optionally substituted on the thiazole ring with one or two members selected from the above-described straight and branched $C_{1-6}$ alkyl groups and the above-described phenyl groups optionally substituted on the phenyl ring with one to three straight and/or branched $C_{1-6}$ alkyl groups, each alkyl substituent on the phenyl substituent optionally further being substituted with one to three halogen atoms. More specific examples of the thiazolyl lower alkyl groups are [(2-, 4-, or 5-)thiazolyl]methyl, 2-[(2-, 4-, or 5-)thiazolyl]ethyl, 1-[(2-, 4-, or 5-)thiazolyl]ethyl, 3-[(2-, 4-, or 5-)thiazolyl]propyl, 4-[(2-, 4-, or 5-)thiazolyl]butyl, 5-[(2-, 4-, or 5-)thiazolyl]pentyl, 6-[(2-, 4-, or 5-)thiazolyl]hexyl, 1,1-dimethyl-2-[(2-, 4-, or 5-)thiazolyl]ethyl, [2-methyl-(4- or 5-)thiazolyl]methyl, [2-(4-trifluoromethylphenyl)-[(4- or 5-)thiazolyl]methyl, 2-[4-ethyl-(2- or 5-)thiazolyl]ethyl, 1-[5-(3-methylphenyl)-(2- or 4-)thiazolyl]ethyl, 3-[5-isopropyl-(2- or 4-)thiazolyl]propyl, 4-[2-(2,4-dimethylphenyl)-(4- or 5-)thiazolyl]butyl, 5-[2-n-butyl-(4- or 5-)thiazolyl]pentyl, 6-[4-(2,4,6-trimethylphenyl)-(2- or 5-)thiazolyl]hexyl, (2,4-dimethyl-5-thiazolyl)methyl, [2-(4-trifluoromethylphenyl)-4-phenyl-5-thiazolyl]methyl, and (2-phenyl-4-thiazolyl)methyl.

Examples of tetrazolyl lower alkyl groups optionally substituted on the tetrazole ring with one or more lower alkyl groups include:

tetrazolylalkyl groups wherein the alkyl moiety is a straight or branched $C_{1-6}$ alkyl group, optionally substituted on the tetrazole ring with one or more straight and/or branched $C_{1-6}$ alkyl groups, such as [(1- or 5-)tetrazolyl]methyl, 2-[(1- or 5-)tetrazolyl]ethyl, 1-[(1- or 5-)tetrazolyl]ethyl, 3-[(1- or 5-)tetrazolyl]propyl, 4-[(1- or 5-)tetrazolyl]butyl, 5-[(1- or 5-)tetrazolyl]pentyl, 6-[(1- or 5-)tetrazolyl]butyl, 5-(1-methyl-5-tetrazolyl)pentyl, 6-(1-methyl-5-tetrazolyl)hexyl, (5-methyl-1-tetrazolyl)methyl, 2-(5-ethyl-1-tetrazolyl)hexyl, 1,1-dimethyl-2-[(1- or 5-)tetrazolyl]ethyl, 2-methyl-3-[(1- or 5-)tetrazolyl]propyl, (1-methyl-5-tetrazolyl)methyl, (1-ethyl-5-tetrazolyl)methyl, 2-(1-n-propyl-5-tetrazolyl)ethyl, 1-(1-n-butyl-5-tetrazolyl)ethyl, 3-(1-n-pentyl-5-tetrazolyl)propyl, 4-(1-n-hexyl-4-tetrazolyl)butyl, 3-(5-isopropyl-1-tetrazolyl)propyl, 4-(5-sec-butyl-1-tetrazolyl)butyl, 5-(5-isopentyl-1-tetrazolyl)pentyl, and 6-(5-n-hexyl-1-tetrazolyl)hexyl.

Examples of benzothienyl lower alkyl groups optionally substituted on the benzothiophene ring with one or more halogen atoms include:

benzothienylalkyl groups wherein the alkyl moiety is a straight and branched $C_{1-6}$ alkyl group, optionally substituted on the benzothiophene ring with one to three halogen atoms;

such as [(2-, 3-, 4-, 5-, 6-, or 7-)benzothienyl]methyl, 2-[(2-, 3-, 4-, 5-, 6-, or 7-)benzothienyl]ethyl, 1-[(2-, 3-, 4-, 5-, 6-, or 7-)benzothienyl]ethyl, 3-[(2-, 3-, 4-, 5-, 6-, or 7-)benzothienyl]propyl, 4-[(2-, 3-, 4-, 5-, 6-, or 7-)benzothienyl]butyl, 5-[(2-, 3-, 4-, 5-, 6-, or 7-)benzothienyl]pentyl, 6-[(2-, 3-, 4-, 5-, 6-, or 7-)benzothienyl]hexyl, 1,1-dimethyl-2-[(2-, 3-, 4-, 5-, 6-, or 7-)benzothienyl]ethyl, 2-methyl-3-[(2-, 3-, 4-, 5-, 6-, or 7-)benzothienyl]propyl, [5-chloro-(2-, 3-, 4-, 6-, or 7-)benzothienyl]methyl, [4-bromo-(2-, 3-, 5-, 6-, or 7-)benzothienyl]methyl, [6-fluoro-(2-, 3-, 4-, 5-, or 7-)benzothienyl]methyl, [7-iodo-(2-, 3-, 4-, 5-, or 6-)benzothienyl]methyl, [2-chloro-(3-, 4-, 5-, 6-, or 7-)benzothienyl]methyl, [4,5-dichloro-(2-, 3-, 6-, or 7-)benzothienyl]methyl, [2,4,5-chloro-(3-, 6- or 7-)benzothienyl]methyl, 2-[6-fluoro-(2-, 3-, 4-, 5-, or 7-)benzothienyl]ethyl, 1-[7-iodo-(2-, 3-, 4-, 5-, or 6-)benzothienyl]ethyl, 3-[2-chloro-(3-, 4-, 5-, 6-, or 7-)benzothienyl]propyl, 4-[4,5-dichloro-(2-, 3-, 6-, or 7-)benzothienyl]butyl, 5-[2,4,5-trichloro-(3-, 6- or 7-)benzothienyl]pentyl, and 6-[5-chloro-(2-, 3-, 4-, 6-, or 7-)benzothienyl]hexyl.

Examples of lower alkynyl groups include $C_{2-6}$ straight and branched alkynyl groups, such as ethynyl, 2-propynyl, 2-butynyl, 3-butynyl, 1-methyl-2-propynyl, 2-pentynyl, and 2-hexynyl.

Examples of lower alkenyl groups include straight and branched $C_{2-6}$ alkenyl groups containing one to three double bonds, such as vinyl, 1-propenyl, 1-methyl-1-propenyl, 2-methyl-1-propenyl, 2-propenyl, 2-butenyl, 1-butenyl, 3-butenyl, 2-penthenyl, 1-penthenyl, 3-penthenyl, 4-penthenyl, 1,3-butadienyl, 1,3-pentadienyl, 2-penten-4-yl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl.

Examples of benzoimidazolyl lower alkyl groups include benzoimidazolylalkyl groups wherein the alkyl moiety is a straight or branched $C_{1-6}$ alkyl group, such as [(1-, 2-, 4-, or 5-)benzoimidazolyl]methyl, 2-[(1-, 2-, 4-, or 5-)benzoimidazolyl]ethyl, 1-[(1-, 2-, 4-, or 5-)benzoimidazolyl]ethyl, 3-[(1-, 2-, 4-, or 5-)benzoimidazolyl]propyl, 4-[(1-, 2-, 4-, or 5-)benzoimidazolyl]butyl, 5-[(1-, 2-, 4-, or 5-)benzoimidazolyl]pentyl, 6-[(1-, 2-, 4-, or 5-)benzoimidazolyl]hexyl, 1,1-dimethyl-2-[(1-, 2-, 4-, or 5-)benzoimidazolyl]ethyl, and 2-methyl-3-[(1-, 2-, 4-, or 5-)benzoimidazolyl]propyl.

Examples of pyridyl lower alkyl groups include pyridylalkyl groups wherein the alkyl moiety is a straight or branched $C_{1-6}$ alkyl group, such as [(2-, 3-, or 4-)pyridyl]methyl, 2-[(2-, 3-, or 4-)pyridyl]ethyl, 1-[(2-, 3-, or 4-)pyridyl]ethyl, 3-[(2-, 3-, or 4-)pyridyl]propyl, 4-[(2-, 3-, or 4-)pyridyl]butyl, 1,1-dimethyl-2-[(2-, 3-, or 4-)pyridyl]ethyl, 5-[(2-, 3-, or 4-)pyridyl]pentyl, 6-[(2-, 3-, or 4-)pyridyl]hexyl, 1-[(2-, 3-, or 4-)pyridyl]isopropyl, and 2-methyl-3-[(2-, 3-, or 4-)pyridyl]propyl.

Examples of imidazolyl lower alkyl groups optionally substituted on the imidazole ring with one or more phenyl lower alkyl groups include:

imidazolylalkyl groups wherein the alkyl moiety is a straight or branched $C_{1-6}$ alkyl group, optionally substituted on the imidazole ring with one to three above-described phenylalkyl groups wherein the alkyl moiety is a straight or branched $C_{1-6}$ alkyl group;

such as [(1-, 2-, 4-, or 5-)imidazolyl]methyl, 2-[(1-, 2-, 4-, or 5-)imidazolyl]ethyl, 1-[(1-, 2-, 4-, or 5-)imidazolyl]ethyl, 3-[(1-, 2-, 4-, or 5-)imidazolyl]propyl, 4-[(1-, 2-, 4-, or 5-)imidazolyl]butyl, 1,1-dimethyl-2-[(1-, 2-, 4-, or 5-)imidazolyl]ethyl, 5-[(1-, 2-, 4-, or 5-)imidazolyl]pentyl, 6-[(1-, 2-, 4-, or 5-)imidazolyl]hexyl, 1-[(1-, 2-, 4-, or 5-)imidazolyl]isopropyl, 2-methyl-3-[(1-, 2-, 4-, or 5-)imidazolyl]propyl, [1-benzyl-(2-, 4-, or 5-)imidazolyl]methyl, [1-(2-phenylethyl)-(2-, 4-, or 5-)imidazolyl]methyl, [1-(1-phenylethyl)-(2-, 4-, or 5-)imidazolyl]methyl, [1-(3-phenylpropyl)-(2-, 4-, or 5-)imidazolyl]methyl, [1-(4-phenylbutyl)-(2-, 4-, or 5-)imidazolyl]methyl, [1-(5-phenylpentyl)-(2-, 4-, or 5-)imidazolyl]methyl, [1-(6-phenylhexyl)-(2-, 4-, or 5-)imidazolyl]methyl, 2-[2-benzyl-(1-, 4-, or 5-)imidazolyl]ethyl, 1-[4-(4-phenylethyl)-(1- or 2-)imidazolyl]ethyl, 3-[2-(2-phenylethyl)-(1-, 4-, or 5-)imidazolyl]methyl, 4-[1-(3-phenylpropyl)-(2-, 4-, or 5-)imidazolyl]butyl, 5-[1-(4-phenylbutyl)-(2-, 4-, or 5-)imidazolyl]pentyl, 6-[1-(5-phenylpentyl)-(2-, 4-, or 5-)imidazolyl]hexyl, [1,2-dibenzyl-(4- or 5-)imidazolyl]methyl, and (1,2,4-tribenzyl-5-imidazolyl)methyl.

Examples of lower alkylsulfonyl groups optionally substituted with one or more halogen atoms include straight and branched $C_{1-6}$ alkylsulfonyl groups optionally substituted with one to three halogen atoms, such as, in addition to the above-described lower alkylsulfonyl groups, trifluoromethylsulfonyl, trichloromethylsulfonyl, chloromethylsulfonyl, bromomethylsulfonyl, fluoromethylsulfonyl, iodomethylsulfonyl, difluoromethylsulfonyl, dibromomethylsulfonyl, 2-chloroethylsulfonyl, 2,2,2-trifluoroethylsulfonyl, 2,2,2-trichloroethylsulfonyl, 3-chloropropylsulfonyl, 2,3-dichloropropylsulfonyl, 4,4,4-trichlorobutylsulfonyl, 4-fluorobutylsulfonyl, 5-chloropentylsulfonyl, 3-chloro-2-methylpropylsulfonyl, 5-bromohexylsulfonyl, and 5,6-dibromohexylsulfonyl.

Examples of alkoxycarbonyl groups optionally substituted with one or more halogen atoms include:

alkoxycarbonyl groups wherein the alkoxy moiety is a straight or branched $C_{1-10}$ alkoxy group, optionally substituted with one to three halogen atoms;

such as, in addition to the above-described lower alkoxycarbonyl groups, n-heptyloxycarbonyl, n-octyloxycarbonyl, n-nonyloxycarbonyl, n-decyloxycarbonyl, 2-ethylhexyloxycarbonyl, trifluoromethoxycarbonyl, trichloromethoxycarbonyl, chloromethoxycarbonyl, bromomethoxycarbonyl, fluoromethoxycarbonyl, iodomethoxycarbonyl, difluoromethoxycarbonyl, dibromomethoxycarbonyl, 2-chloroethoxycarbonyl, 2-fluoroethoxycarbonyl, 2,2,2-trifluoroethoxycarbonyl, 2,2,2-trichloroethoxycarbonyl, 3-chloropropoxycarbonyl, 2,3-dichloropropoxycarbonyl, 4,4,4-trichlorobutoxycarbonyl, 4-fluorobutoxycarbonyl, 4-chlorobutoxycarbonyl, 5-chloropentyloxycarbonyl, 3-chloro-2-methylpropoxycarbonyl, 5-bromohexyloxycarbonyl, 5,6-dibromohexyloxycarbonyl, 7,7,6-trichloroheptyloxycarbonyl, 8-bromooctyloxycarbonyl, 9,9,9-trifluorononyloxycarbonyl, and 10,10,10-trichlorodecyloxycarbonyl.

Examples of pyridylcarbonyl groups optionally substituted on the pyridine ring with one or more members selected from the group consisting of pyrrolyl groups and halogen atoms include:

pyridylcarbonyl groups optionally substituted on the pyridine ring with one to three members selected from the group consisting of pyrrolyl groups and halogen atoms;

such as (2-, 3-, or 4-)pyridylcarbonyl, 2-chloro-(3-, 4-, 5-, or 6-)pyridylcarbonyl, 2,6-dichloro-(3-, 4-, or 5-)pyridylcarbonyl, 2-(1-pyrrolyl)-(3-, 4-, 5-, or 6-)pyridylcarbonyl, 2-bromo-(3-, 4-, 5-, or 6-)pyridylcarbonyl, 2,6-difluoro-(3-, 4-, or 5-)pyridylcarbonyl, 4-(1-pyrrolyl)-(2- or 3-)pyridylcarbonyl, 3-chloro-(2-, 4-, 5-, or 6-)pyridylcarbonyl, 2,5-dibromo-(3-, 4-, or 6-)pyridylcarbonyl, 2-(1-pyrrolyl)-4-chloro-(3-, 5-, or 6-)pyridylcarbonyl, 2,4,6-trifluoro-(3- or 5-)pyridylcarbonyl, and 2,4-di(1-pyrrolyl)-(3-, 5-, or 6-)pyridylcarbonyl.

Examples of pyridyl groups optionally substituted on the pyridine ring with one or more members selected from the group consisting of lower alkyl groups and lower alkoxy groups include:

pyridyl groups optionally substituted on the pyridine ring with one to three members selected from the group consisting of the above-described straight and branched $C_{1-6}$ alkyl groups and the above-described straight and branched $C_{1-6}$ alkoxy groups;

such as (2-, 3-, or 4-)pyridyl, 2-methyl-(3-, 4-, 5-, or 6-)pyridyl, 3-methyl-(2-, 4-, 5-, or 6-)pyridyl, 2-methoxy-(3-, 4-, 5-, or 6-)pyridyl, 4-ethyl-(2- or 3-)pyridyl, 3-n-propyl-(2-, 4-, 5-, or 6-)pyridyl, 2-tert-butyl-(3-, 4-, 5-, or 6-)pyridyl, 2-n-pentyl-(3-, 4-, 5-, or 6-)pyridyl, 3-n-hexyl-(2-, 4-, 5-, or 6-)pyridyl, 2,4-dimethyl-(3-, 5-, or 6-)pyridyl, 2,4,6-trimethyl-(3- or 5-)pyridyl, 3-ethoxy-(2-, 4-, 5-, or 6-)pyridyl, 2-isopropoxy-(3-, 4-, 5-, or 6-)pyridyl, 2-n-butoxy-(3-, 4-, 5-, or 6-)pyridyl, 4-n-pentyloxy-(2- or 3-)pyridyl, 2-n-hexyloxy-(3-, 4-, 5-, or 6-)pyridyl, 2,3-dimethoxy-(4-, 5-, or 6-)pyridyl, 3-methyl-(2-, 4-, 5-, or 6-)pyridyl, 3,4,5-trimethoxy-(2- or 6-)pyridyl, and 2-methyl-3-methoxy-(4-, 5-, or 6-)pyridyl.

Examples of amino groups optionally substituted with one or more members selected from the group consisting of lower alkyl groups and lower alkanoyl groups:

include amino groups optionally substituted with one or two members selected from the group consisting of straight and branched $C_{1-6}$ alkyl groups and straight and branched $C_{1-6}$ alkanoyl groups;

such as amino, methylamino, ethylamino, n-propylamino, isopropylamino, n-butylamino, tert-butylamino, n-pentylamino, n-hexylamino, dimethylamino, diethylamino, di-n-propylamino, di-n-butylamino, di-n-pentylamino, di-n-hexylamino, N-methyl-N-ethylamino, N-ethyl-N-n-propylamino, N-methyl-N-n-butylamino, N-methyl-N-n-hexylamino, formylamino, acetylamino, propionylamino, butyrylamino, isobutyrylamino, pentanoylamino, tert-butylcarbonylamino, hexanoylamino, N,N-diacetylamino, N-acetyl-N-propionylamino, N-methyl-N-acetylamino, and N-ethyl-N-propionylamino.

Examples of pyrrolidinyl groups optionally substituted on the pyrrolidine ring with one or more oxo groups include pyrrolidinyl groups optionally substituted with one or two oxo groups, such as (1-, 2-, or 3-)pyrrolidinyl, 2-oxo-(1-, 3-, 4-, or 5-)pyrrolidinyl, and 2,5-dioxo-(1- or 3-)pyrrolidinyl.

Examples of piperidinyl groups optionally substituted on the piperidine ring with one or more lower alkyl groups include piperidinyl groups optionally substituted on the piperidine ring with one to three straight and/or branched $C_{1-6}$ alkyl groups, such as (1-, 2-, 3-, or 4-)piperidinyl, 1-methyl-(2-, 3-, or 4-)piperidinyl, 1-ethyl-(2-, 3-, or 4-)piperidinyl, 1-n-propyl-(2-, 3-, or 4-)piperidinyl, 1-isopropyl-(2-, 3-, or 4-)piperidinyl, 1-n-butyl-(2-, 3-, or 4-)piperidinyl, 1-n-pentyl-(2-, 3-, or 4-)piperidinyl, 1-n-hexyl-(2-, 3-, or 4-)piperidinyl, 1,2-dimethyl-(3-, 4-, 5-, or 6-)piperidinyl, 1,2,3-trimethyl-(4-, 5-, or 6-)piperidinyl, 2-n-propyl-(1-, 3-, 4-, 5- or 6-)piperidinyl, 3-ethyl-(1-, 2-, 4-, 5-, or 6-)piperidinyl, and 2-methyl-4-isopropyl-(1-, 3-, 5-, or 6-)piperidinyl.

Examples of carbamoyl groups optionally substituted with one or more lower alkyl groups include carbamoyl groups optionally substituted with one or two straight and/or branched $C_{1-6}$ alkyl groups, such as carbamoyl, methylcarbamoyl, ethylcarbamoyl, n-propylcarbamoyl, isopropylcarbamoyl, n-butylcarbamoyl, tert-butylcarbamoyl, n-pentylcarbamoyl, n-hexylcarbamoyl, dimethylcarbamoyl, diethylcarbamoyl, di-n-propyl carbamoyl, di-n-butylcarbamoyl, di-n-pentylcarbamoyl, di-n-hexylcarbamoyl, N-methyl-N-ethylcarbamoyl, N-ethyl-N-n-propylcarbamoyl, N-methyl-N-n-butylcarbamoyl, and N-methyl-N-n-hexylcarbamoyl.

Examples of phenyl groups optionally substituted with on the phenyl ring one or more members selected from the group consisting of halogen atoms; lower alkyl groups optionally substituted with one or more halogen atoms; a phenoxy group; lower alkoxy groups optionally substituted with one or more halogen atoms; lower alkylthio groups; lower alkylsulfonyl groups; amino groups optionally substituted with one or more members selected from the group consisting of lower alkyl groups and lower alkanoyl groups; pyrrolidinyl groups optionally substituted on the pyrrolidine ring with one or more oxo groups; piperidinyl groups optionally substituted on the piperidine ring with one or more lower alkyl groups; lower alkenyl groups; an aminosulfonyl group; a hydroxy group; carbamoyl groups optionally substituted with one or more lower alkyl groups; phenyl lower alkoxy groups; and a cyano group include:

phenyl groups optionally substituted on the phenyl ring with one to three members selected from the group consisting of the above-described halogen atoms; the above-described straight and branched $C_{1-6}$ alkyl groups optionally substituted with one to three halogen atoms; a phenoxy group; the above-described straight and branched $C_{1-6}$ alkoxy groups optionally substituted with one to three halogen atoms; the above-described straight and branched $C_{1-6}$ alkylthio groups; the above-described straight and branched $C_{1-6}$ alkylsulfonyl groups; the above-described amino groups optionally substituted with one or two members selected from the group consisting of straight and branched $C_{1-6}$ alkyl groups and straight and branched $C_{1-6}$ alkanoyl groups; the above-described pyrrolidinyl groups optionally substituted on the pyrrolidine ring with one or two oxo groups; the above-described piperidinyl groups optionally substituted on the piperidine ring with one to three straight and/or branched $C_{1-6}$ alkyl groups; the above-described straight and branched $C_{2-6}$ alkenyl groups containing one to three double bonds; an aminosulfonyl group; a hydroxy group; the above-described carbamoyl groups optionally substituted with one or two straight and/or branched $C_{1-6}$ alkyl groups; the above-described phenylalkoxy groups wherein the alkoxy moiety is a straight or branched $C_{1-6}$ alkoxy group; and a cyano group;

such as phenyl, 4-phenoxyphenyl, 3-phenoxyphenyl, 2-phenoxyphenyl, 4-isopropylphenyl, 3-isopropylphenyl, 2-isopropylphenyl, 4-tert-butylphenyl, 4-methylphenyl, 3-methylphenyl, 2-methylphenyl, 2,3-dimethylphenyl, 2,4-dimethylphenyl, 3,5-dimethylphenyl, 2,4,6-trimethylphenyl, 4-methyl-3-methoxyphenyl, 4-trifluoromethylphenyl, 3-trifluoromethylphenyl, 2-trifluoromethylphenyl, 4-methyl-3-chlorophenyl, 4-chlorophenyl, 3-chlorophenyl, 2-chlorophenyl, 2-fluorophenyl, 3-fluorophenyl, 4-fluorophenyl, 3-bromophenyl, 3,4-dichlorophenyl, 3,5-dichlorophenyl, 3,4,5-trichlorophenyl, 2,4,6-trifluorophenyl, 3,5-difluorophenyl, 3-chloro-4-fluorophenyl, 2-chloro-5-fluorophenyl, 3-fluoro-4-methoxyphenyl, 3-chloro-4-methoxyphenyl, 3-chloro-4-hydroxyphenyl, 4-methoxyphenyl, 3-methoxyphenyl, 2-methoxyphenyl, 2,4-dimethoxyphenyl, 3,4- dimethoxyphenyl, 2,4,6-trimethoxyphenyl, 2-methoxy-5-chlorophenyl, 2-methoxy-5-acetylaminophenyl, 2-chloro-5-acetylaminophenyl, 4-ethoxyphenyl, 4-trifluoromethoxyphenyl, 3-trifluoromethoxyphenyl, 2-trifluoromethoxyphenyl, 3-methoxy-5-trifluoromethylphenyl, 4-methylthiophenyl, 3-methylthiophenyl, 2-methylthiophenyl, 2-(1-methyl-1-vinyl)phenyl, 4-vinylphenyl, 3-dimethylaminophenyl, 4-methylaminophenyl, 2-(N-methyl-N-acetylamino)phenyl, 3-acetylaminophenyl, 4-propionylaminophenyl, 4-acetylaminophenyl, 2-acetylaminophenyl, 4-aminosulfonylphenyl, 3-aminosulfonylphenyl, 2-aminosulfonylphenyl, 4-methylthiophenyl, 3-methylthiophenyl, 2-methylthiophenyl, 4-methylsulfonylphenyl, 3-methylsulfonylphenyl, 2-methylsulfonylphenyl, 4-methylcarbamoylphenyl, 3-carbamoylphenyl, 2-ethylcarbamoylphenyl, 2-benzyloxyphenyl, 3-benzyloxyphenyl, 4-benzyloxyphenyl, 2-phenylphenyl, 3-phenylphenyl, 4-phenylphenyl, 2-cyanophenyl, 3-cyanophenyl, 4-cyanophenyl, 4-[2-oxo-(1-, 3-, 4-, or 5-)pyrrolidinyl]phenyl, 3-[2,5-dioxo-(1- or 3-)pyrrolidinyl]phenyl, 4-[4-methyl-(1-, 2-, or 3-)piperazinyl]phenyl, 3-[4-ethyl-(1-, 2-, or 3-)piperazinyl]phenyl, and 2-[4-isopropyl-(1-, 2-, or 3-)piperazinyl]phenyl.

Examples of cycloalkyl groups optionally substituted on the cycloalkyl ring with one or more lower alkyl groups include $C_{3-8}$ cycloalkyl groups optionally substituted on the cycloalkyl ring with one to three straight and/or branched $C_{1-6}$ alkyl groups, such as, in addition to the above-described cycloalkyl groups, 1-methylcyclopropyl, 1-methylcyclopentyl, 1-methylcyclohexyl, 2-methylcyclohexyl, 1-methylcyclobutyl, 1-ethylcyclooctyl, 1-n-propylcycloheptyl, 1,2-dimethylcyclohexyl, 1,4,5-trimethylcyclooctyl, 1-n-butylcyclopropyl, 1-n-pentylcyclopentyl, and 1-n-hexylcyclohexyl.

Examples of amino groups optionally substituted with one or more members selected from the group consisting of a phenyl group and lower alkyl groups include:

amino groups optionally substituted with one or two members selected from the group consisting of a phenyl group and straight and branched $C_{1-6}$ alkyl groups;

such as amino, methylamino, ethylamino, n-propylamino, isopropylamino, n-butylamino, tert-butylamino, n-pentylamino, n-hexylamino, dimethylamino, diethylamino, di-n-propylamino, di-n-butylamino, di-n-pentylamino, di-n-hexylamino, N-methyl-N-ethylamino, N-ethyl-N-n-propylamino, N-methyl-N-n-butylamino, N-methyl-N-n-hexylamino, phenylamino, N,N-diphenylamino, N-methyl-N-phenylamino, N-ethyl-N-phenylamino, and N-n-propyl-N-phenylamino.

Examples of benzoyl groups optionally substituted on the phenyl ring with one or more members selected from the group consisting of halogen atoms; a phenoxy group; a phenyl group; lower alkyl groups optionally substituted with one or more halogen atoms; lower alkoxy groups; lower alkanoyl groups; a nitro group; a cyano group; amino groups optionally substituted with one or more members selected from the group consisting of a phenyl group and lower alkyl groups; pyrrolidinyl groups optionally substituted on the pyrrolidine ring with one or more oxo groups; pyrrolyl groups; pyrazolyl groups; 1,2,4-triazolyl groups; and imidazolyl groups include:

benzoyl groups optionally substituted on the phenyl ring with one to three members selected from the group consisting of halogen atoms; a phenoxy group; a phenyl group; the above-described straight and branched $C_{1-6}$ alkyl groups optionally substituted with one to three halogen atoms; the above-described straight and branched $C_{1-6}$ alkoxy groups; the above-described straight and branched $C_{1-6}$ alkanoyl groups; a nitro group; a cyano group; the above-described amino groups optionally substituted with one or two members selected from the group consisting of a phenyl group and straight and branched $C_{1-6}$ alkyl groups; the above-described pyrrolidinyl groups optionally substituted on the pyrrolidine ring with one or two oxo groups; pyrrolyl groups; pyrazolyl groups; 1,2,4-triazolyl groups; and imidazolyl groups;

such as benzoyl, 4-methoxybenzoyl, 3-methoxybenzoyl, 2-methoxybenzoyl, 2,4-dimethoxybenzoyl, 3,4,5-trimethoxybenzoyl, 2-methoxy-5-chlorobenzoyl, 4-phenoxybenzoyl, 2-phenoxybenzoyl, 3-phenoxybenzoyl, 4-chlorobenzoyl, 3-chlorobenzoyl, 2-chlorobenzoyl, 2,6-dichlorobenzoyl, 2-chloro-4-fluorobenzoyl, 2,4,6-trifluorobenzoyl, 4-bromobenzoyl, 3-fluorobenzoyl, 4-trifluoromethylbenzoyl, 3-trifluoromethylbenzoyl, 2-trifluoromethylbenzoyl, 3-fluoro-2-methylbenzoyl, 4-methylbenzoyl, 3-methylbenzoyl, 2-methylbenzoyl, 3,4-dimethylbenzoyl, 2,4,5-trimethylbenzoyl, 2-phenylbenzoyl, 3-phenylbenzoyl, 4-phenylbenzoyl, 4-nitrobenzoyl, 3-nitrobenzoyl, 2-nitrobenzoyl, 2-dimethylaminobenzoyl, 3-methylaminobenzoyl, 4-(N-methylanilino)benzoyl, 2-anilinobenzoyl, 3-cyanobenzoyl, 4-cyanobenzoyl, 2-cyanobenzoyl, 4-acetylbenzoyl, 2-propionylbenzoyl, 3-butyrylbenzoyl, 4-[(1-, 2-, or 3-)pyrrolyl]benzoyl, 4-[(1-, 3-, 4-, or 5-)pyrazolyl]benzoyl, 4-[(1-, 3- or 5-)1,2,4-triazolyl]benzoyl, 4-[(1-, 2-, 4-, or 5-)imidazolyl]benzoyl, and 4-[2-oxo-(1-, 3-, 4-, or 5-)pyrrolidinyl]benzoyl.

Examples of lower alkylenedioxy groups include straight and branched $C_{1-4}$ alkylene groups, such as methylenedioxy, ethylenedioxy, trimethylenedioxy, and tetramethylenedioxy.

Examples of benzoyl groups substituted on the phenyl ring with one or more lower alkylenedioxy groups include:

benzoyl groups substituted on the phenyl ring with one or more of the above-described straight and branched $C_{1-4}$ alkylenedioxy groups;

such as 3,4-methylenedioxybenzoyl, 2,3-ethylenedioxybenzoyl, 3,4-trimethylenedioxybenzoyl, and 2,3-tetramethylenedioxybenzoyl.

Examples of cycloalkylcarbonyl groups include cycloalkylcarbonyl groups wherein the cycloalkyl moiety is a $C_{3-8}$ cycloalkyl group, such as cyclopropylcarbonyl, cyclobutylcarbonyl, cyclopentylcarbonyl, cyclohexylcarbonyl, cycloheptylcarbonyl, and cyclooctylcarbonyl.

Examples of furylcarbonyl groups include (2- or 3-)furylcarbonyl.

Examples of naphthylcarbonyl groups include (1- or 2-)naphthylcarbonyl.

Examples of phenoxycarbonyl groups optionally substituted on the phenyl ring with one or more members selected from the group consisting of lower alkoxy groups, lower alkyl groups, halogen atoms, and a nitro group include:

phenoxycarbonyl groups optionally substituted on the phenyl ring with one to three members selected from the group consisting of the above-described straight and branched $C_{1-6}$ alkoxy groups, the above-described straight and branched $C_{1-6}$ alkyl groups, halogen atoms, and a nitro group;

such as phenoxycarbonyl, 4-chlorophenoxycarbonyl, 3-chlorophenoxycarbonyl, 2-chlorophenoxycarbonyl, 3,4-dichlorophenoxycarbonyl, 2,4,6-trichlorophenoxycarbonyl, 4-fluorophenoxycarbonyl, 3-fluorophenoxycarbonyl, 2-fluorophenoxycarbonyl, 2,4-difluorophenoxycarbonyl, 3,4,5-trifluorophenoxycarbonyl, 4-bromophenoxycarbonyl, 2-chloro-4-methoxyphenoxycarbonyl, 3-fluoro-5-methylphenoxycarbonyl, 4-methoxyphenoxycarbonyl, 3-methoxyphenoxycarbonyl, 2-methoxyphenoxycarbonyl, 3,4-dimethoxyphenoxycarbonyl, 2,4,5-trimethoxyphenoxycarbonyl, 4-methylphenoxycarbonyl, 3-methylphenoxycarbonyl, 2-methylphenoxycarbonyl, 2,5-dimethylphenoxycarbonyl, 2,3,4-trimethylphenoxycarbonyl, 4-nitrophenoxycarbonyl, 3-nitrophenoxycarbonyl, 2-nitrophenoxycarbonyl, 2,4-dinitrophenoxycarbonyl, and 2,4,6-trinitrophenoxycarbonyl.

Examples of phenyl lower alkoxycarbonyl groups optionally substituted on the phenyl ring with one or more members selected from the group consisting of halogen atoms and a nitro group include:

phenylalkoxycarbonyl groups wherein the alkoxy moiety is a straight or branched $C_{1-6}$ alkoxy group, optionally substituted on the phenyl ring with one to three members selected from the group consisting of halogen atoms and a nitro group;

such as benzyloxycarbonyl, 2-phenylethoxycarbonyl, 1-phenylethoxycarbonyl, 3-phenylpropoxycarbonyl, 4-phenylbutoxycarbonyl, 5-phenylpentyloxycarbonyl, 6-phenylhexyloxycarbonyl, 1,1-dimethyl-2-phenylethoxycarbonyl, 2-methyl-3-phenylpropoxycarbonyl, 4-chlorobenzyloxycarbonyl, 3-chlorobenzyloxycarbonyl, 2-chlorobenzyloxycarbonyl, 3,4-dichlorobenzyloxycarbonyl, 2,4,6-trichlorobenzyloxycarbonyl, 4-fluorobenzyloxycarbonyl, 3-fluorobenzyloxycarbonyl, 2-fluorobenzyloxycarbonyl, 2,4-difluorobenzyloxycarbonyl, 3,4,5-trifluorobenzyloxycarbonyl, 4-bromobenzyloxycarbonyl, 4-nitrobenzyloxycarbonyl, 3-nitrobenzyloxycarbonyl, 2-nitrobenzyloxycarbonyl, 2,4-dinitrobenzyloxycarbonyl, 2,4,6-trinitrobenzyloxycarbonyl, and 2-nitro-4-chlorobenzyloxycarbonyl.

Examples of piperidinyl groups optionally substituted on the piperidine ring with one or more members selected from the group consisting of lower alkyl groups; lower alkanoyl groups; benzoyl groups optionally substituted on the phenyl ring with one or more halogen atoms; and phenyl groups optionally substituted on the phenyl ring with one or more halogen atoms include:

piperidinyl groups optionally substituted on the piperidine ring with one to three members selected from the group consisting of the above-described straight and branched $C_{1-6}$ alkyl groups; the above-described straight and branched $C_{1-6}$ alkanoyl groups; the above-described benzoyl groups optionally substituted on the phenyl ring with one to three halogen atoms; and the above-described phenyl groups optionally substituted on the phenyl ring with one to three halogen atoms;

such as (1-, 2-, 3-, or 4-)piperidinyl, 1-methyl-(2-, 3-, or 4-)piperidinyl, 1-acetyl-(2-, 3-, or 4-)piperidinyl, 1-benzoyl-(2-, 3-, or 4-)piperidinyl, 1-(4-chlorobenzoyl)-(2-, 3-, or 4-)piperidinyl, 1-(3-bromobenzoyl)-(2-, 3-, or 4-)piperidinyl, 1-benzoyl-(2-, 3-, or 4-)piperidinyl, 1-(4-fluorobenzoyl)-(2-, 3-, or 4-)piperidinyl, 1-(2,4-dichloro benzoyl)-(2-, 3-, or 4-)piperidinyl, 1-(2,4,6-trifluorobenzoyl)-(2-, 3-, or 4-)piperidinyl, 2-(3-chlorobenzoyl)-(1-, 3-, or 4-)piperidinyl, 3-(2-chlorobenzoyl)-(1-, 2-, or 4-)piperidinyl, 4-(2,3-dibromobenzoyl)-(1-, 2-, or 3-)piperidinyl, 1,2-dibenzoyl-(3- or 4-)piperidinyl, 1,2,4-tribenzoyl-3-piperidinyl, 1,4-dimethyl-(2-, 3-, 5-, or 6-)piperidinyl, 1,2,4-trimethyl-(3-, 5-, or 6-)piperidinyl, 1-benzoyl-2-methyl-(3-, 4-, 5-, or 6-)piperidinyl, 1-phenyl-2-methyl-(3-, 4-, 5-, or 6-)piperidinyl, 1-acetyl-3-methyl-(2-, 4-, 5-, or 6-)piperidinyl, 1-phenyl-(2-, 3-, or 4-)piperidinyl, 1-(4-chlorophenyl)-(2-, 3-, or 4-)piperidinyl, 1-(3-bromophenyl)-(2-, 3-, or 4-)piperidinyl, 1-(4-iodophenyl)-(2-, 3-, or 4-)piperidinyl, 1-(4-fluorophenyl)-(2-, 3-, or 4-)piperidinyl, 1-(2,4-dichlorophenyl)-(2-, 3-, or 4-)piperidinyl, 1-(2,4,6-trifluorophenyl)-(2-, 3-, or 4-)piperidinyl, 2-(3-chlorophenyl)-(1-, 3-, 4-, 5-, or 6-)piperidinyl, 3-(2-chlorophenyl)-(1-, 2-, 4-, 5-, or 6-)piperidinyl, 4-(2,3-dibromophenyl)-(1-, 2-, or 3-)piperidinyl, 1,2-diphenyl-(3-, 4-, 5- or 6-)piperidinyl, and 1,2,4-triphenyl-(3-, 5-, or 6-)piperidinyl.

Examples of tetrahydropyranyl lower alkyl groups include tetrahydropyranylalkyl groups wherein the alkyl moiety is a straight or branched $C_{1-6}$ alkyl group, such as [(2-, 3-, or 4-)tetrahydropyranyl]methyl, 2-[(2-, 3-, or 4-)tetrahydropyranyl]ethyl, 1-[(2-, 3-, or 4-)tetrahydropyranyl]ethyl, 3-[(2-, 3-, or 4-)tetrahydropyranyl]propyl, 4-[(2-, 3-, or 4-)tetrahydropyranyl]butyl, 1,1-dimethyl-2-[(2-, 3-, or 4-)tetrahydropyranyl]ethyl, 5-[(2-, 3-, or 4-)tetrahydropyranyl]pentyl, 6-[(2-, 3-, or 4-)tetrahydropyranyl]hexyl, 1-[(2-, 3- or 4-)tetrahydropyranyl]isopropyl, and 2-methyl-3-[(2-, 3-, or 4-)tetrahydropyranyl]propyl.

Examples of phenyl lower alkyl groups optionally substituted on the alkyl group with one or more lower alkoxycarbonyl groups; and optionally further substituted on the phenyl ring with one or more members selected from the group consisting of halogen atoms, lower alkyl groups optionally substituted with one or more halogen atoms, lower alkoxy groups optionally substituted with one or more halogen atoms, and a hydroxy group include:

mono- and di-phenylalkyl groups wherein the alkyl moiety is a straight or branched $C_{1-6}$ alkyl group, optionally substituted on the alkyl group with one or more lower alkoxycarbonyl groups wherein the alkoxy moiety is a straight or branched $C_{1-6}$ alkoxy group; and optionally further substituted on the phenyl group with one to three members selected from the group consisting of halogen atoms, the above-described straight and branched $C_{1-6}$ alkyl groups optionally substituted with one to three halogen atoms, the above-described straight and branched $C_{1-6}$ alkoxy groups optionally substituted with one to three halogen atoms, and a hydroxy group;

such as benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl, 1,1-dimethyl-1-phenylmethyl, 1,1-diphenylmethyl, 2,2-diphenylethyl, 3,3-diphenylpropyl, 1,2-diphenylethyl, 4-chlorobenzyl, 2-chlorobenzyl, 3-chlorobenzyl, 3-fluorobenzyl, 4-fluorobenzyl, 3-bromobenzyl, 2,3-dichlorobenzyl, 2,6-dichlorobenzyl, 2,4,6-trifluorobenzyl, 2-(4-chlorophenyl)ethyl, 2-(2-fluorophenyl)ethyl, 2-(3-fluorophenyl)ethyl, 3-trifluoromethylbenzyl, 4-trifluoromethylbenzyl, 2-methylbenzyl, 3-methylbenzyl, 4-methylbenzyl, 4-tert-butylbenzyl, 2,4-dimethylbenzyl, 2,4,6-trimethylbenzyl, 2-trifluoromethoxybenzyl, 3-trifluoromethoxybenzyl, 4-trifluoromethoxybenzyl, 2-methoxybenzyl, 3-methoxybenzyl, 4-methoxybenzyl, 4-ethoxybenzy, 2-(3-methoxyphenyl)ethyl, 3,4-dimethoxybenzyl, 3,4,5-trimethoxybenzyl, 4-hydroxybenzyl, 3-hydroxybenzyl, 2-hydroxybenzyl, 2,4-dihydroxybenzyl, 3,4,5-trihydroxybenzyl, 2-methoxy-4-chlorobenzyl, 3-methyl-5-fluorobenzyl, 2-(4-hydroxyphenyl)-1-methoxycarbonylethyl, and 2-(4-chlorophenyl)-1-ethoxycarbonylethyl.

Examples of lower alkylenedioxy-substituted phenyl lower alkyl groups include:

alkylenedioxy-substituted phenylalkyl groups wherein the alkyl moiety is a straight or branched $C_{1-6}$ alkyl group, substituted on the phenyl ring with one or more of the above-described straight and branched $C_{1-4}$ alkylenedioxy groups;

such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyl)ethyl, and 2-methyl-3-(3,4-ethylenedioxyphenyl)propyl.

Examples of furyl lower alkyl groups include furylalkyl groups wherein the alkyl moiety is a straight or branched $C_{1-6}$ alkyl group, such as [(2- or 3-)furyl]methyl, 2-[(2- or 3-)furyl]ethyl, 1-[(2- or 3-)furyl]ethyl, 3-[(2- or 3-)furyl]propyl, 4-[(2- or 3-)furyl]butyl, 5-[(2- or 3-)furyl]pentyl, 6-[(2- or 3-)furyl]hexyl, 1,1-dimethyl-2-[(2- or 3-)furyl]ethyl, and 2-methyl-3-[(2- or 3-)furyl]propyl.

Examples of carbamoyl lower alkyl groups optionally substituted with one or more members selected from the group consisting of lower alkyl groups and a phenyl group, each phenyl substituent optionally being substituted on the phenyl ring with one or more lower alkyl groups, include:

carbamoylalkyl groups wherein the alkyl moiety is a straight or branched $C_{1-6}$ alkyl group, optionally substituted with one or two members selected from the group consisting of the above-described straight and branched $C_{1-6}$ alkyl groups and the above-described phenyl groups optionally substituted on the phenyl ring with one to three straight and/or branched $C_{1-6}$ alkyl groups;

such as carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl, 2-methyl-3-carbamoylpropyl, 2-(N-methyl-N-phenylcarbamoyl)ethyl, N-(4-methylphenyl)carbamoylmethyl, 2-[N-methyl-N-(3-methylphenyl)carbamoyl]ethyl, N-(2-methylphenyl)carbamoylmethyl, 2-[N-ethyl-N-(3,4-dimethylphenyl)carbamoyl]ethyl, N-(2,4,6-trimethylphenyl)carbamoylmethyl, N,N-dimethylcarbamoylmethyl, N,N-diphenylcarbamoylmethyl, N-methyl-N-ethylcarbamoylmethyl, N-methylcarbamoylmethyl, and 2-(N-methylcarbamoyl)ethyl.

Examples of imidazolyl lower alkyl groups optionally substituted on the lower alkyl group with one or more members selected from the group consisting of a carbamoyl group and lower alkoxycarbonyl groups include:

imidazolylalkyl groups wherein the alkyl moiety is a straight or branched $C_{1-6}$ alkyl group, optionally substituted on the lower alkyl group with one or more members selected from the group consisting of a carbamoyl group and alkoxycarbonyl groups wherein the alkoxy moiety is a straight or branched $C_{1-6}$ alkoxy group;

such as, in addition to the above-described imidazolyl lower alkyl groups, 1-carbamoyl-2-[(1-, 2-, 4-, or 5-)imidazolyl]ethyl, 1-methoxycarbonyl-2-[(1-, 2-, 4-, or 5-)imidazolyl]ethyl, 1-carbamoyl-1-[(1-, 2-, 4-, or 5-)imidazolyl]methyl, 1-ethoxycarbonyl-1-[(1-, 2-, 4-, or 5-)imidazolyl]methyl, 1-carbamoyl-3-[(1-, 2-, 4-, or 5-)imidazolyl]propyl, 1-n-propoxycarbonyl-4-[(1-, 2-, 4-, or 5-)imidazolyl]butyl, 1-carbamoyl-5-[(1-, 2-, 4-, or 5-)imidazolyl]pentyl, and 1-tert-butoxycarbonyl-6-[(1-, 2-, 4-, or 5-)imidazolyl]hexyl.

Examples of amino-substituted lower alkyl groups optionally substituted on each amino group with one or more lower alkyl groups include:

amino-substituted straight and branched $C_{1-6}$ alkyl groups optionally substituted on the amino group with one or two straight and/or branched $C_{1-6}$ alkyl groups;

such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 2-ethylaminoethyl, 3-n-propylaminopropyl, 3-isopropylaminopropyl, 4-n-butylaminobutyl, 5-n-pentylaminopentyl, 6-n-hexylaminohexyl, dimethylaminoethyl, 2-diisopropylaminopropyl, 3-diisopropylaminopropyl, (N-ethyl-N-n-propylamino)methyl, and 2-(N-methyl-N-n-hexylamino)methyl.

Examples of 2,3,4,5-tetrahydrofuryl groups optionally substituted on the 2,3,4,5-tetrahydrofuran ring with one or more oxo groups include:

2,3,4,5-tetrahydrofuryl groups optionally substituted on the 2,3,4,5-tetrahydrofuran ring with one or two oxo groups;

such as (2- or 3-)2,3,4,5-tetrahydrofuryl, 2-oxo-(3-, 4-, or 5-)2,3,4,5-tetrahydrofuryl, 3-oxo-(2-, 4-, or 5-)2,3,4,5-tetrahydrofuryl, and 2,5-dioxo-(3- or 4-)2,3,4,5-tetrahydrofuryl.

Examples of pyrrolidinyl lower alkyl groups optionally substituted on the pyrrolidine ring with one or more lower alkyl groups include:

pyrrolidinylalkyl groups wherein the alkyl moiety is a straight or branched $C_{1-6}$ alkyl group, optionally substituted on the pyrrolidine ring with one to three above-described straight and/or branched $C_{1-6}$ alkyl groups;

such as [(1-, 2-, or 3-)pyrrolidinyl]methyl, 2-[(1-, 2-, or 3-)pyrrolidinyl]ethyl, 1-[(1-, 2-, or 3-)pyrrolidinyl]ethyl, 3-[(1-, 2-, or 3-)pyrrolidinyl]propyl, 4-[(1-, 2-, or 3-)pyrrolidinyl]butyl, 5-[(1-, 2-, or 3-)pyrrolidinyl]pentyl, 6-[(1-, 2-, or 3-)pyrrolidinyl]hexyl, 1,1-dimethyl-2-[(1-, 2-, or 3-)pyrrolidinyl]ethyl, 2-methyl-3-[(1-, 2-, or 3-)pyrrolidinyl]propyl, 1-ethyl-[(2- or 3-)pyrrolidinyl]methyl, 1-ethyl-[(2- or 3-)pyrrolidinyl]methyl, 2-methyl-[(1-, 3-, 4-, or 5-)pyrrolidinyl]methyl, 3-n-propyl-[(1-, 2-, 4-, or 5-)pyrrolidinyl]methyl, 1-n-butyl-[(2- or 3-)pyrrolidinyl]methyl, 2-n-pentyl-[(1-, 3-, 4-, or 5-)pyrrolidinyl]methyl, 1-n-hexyl-[(2- or 3-)pyrrolidinyl]methyl, 1,2-dimethyl-[(3-, 4-, or 5-)pyrrolidinyl]methyl, and 1,2,3-trimethyl-[(4- or 5-)pyrrolidinyl]methyl.

Examples of phenoxy lower alkanoyl groups include phenoxyalkanoyl groups wherein the alkanoyl moiety is a straight or branched $C_{2-6}$ alkanoyl group, such as 2-phenoxyacetyl, 3-phenoxypropionyl, 2-phenoxypropionyl, 4-phenoxybutyryl, 5-phenoxypentanoyl, 6-phenoxyhexanoyl, 2,2-dimethyl-3-phenoxypropionyl, and 2-methyl-3-phenoxypropionyl.

Examples of morpholino lower alkyl groups include morpholinoalkyl groups wherein the alkyl moiety is a straight or branched $C_{1-6}$ alkyl group, such as [(2-, 3-, or 4-)morpholino]methyl, 2-[(2-, 3-, or 4-)morpholino]ethyl, 1-[(2-, 3-, or 4-)morpholino]ethyl, 3-[(2-, 3-, or 4-)morpholino]propyl, 4-[(2-, 3-, or 4-)morpholino]butyl, 5-[(2-, 3-, or 4-)morpholino]pentyl, 6-[(2-, 3-, or 4-)morpholino]hexyl, 1,1-dimethyl-2-[(2-, 3-, or 4-)morpholino]ethyl, and 2-methyl-3-[(2-, 3-, or 4-)morpholino]propyl.

Examples of pyridyl lower alkanoyl groups include pyridylalkanoyl groups wherein the alkanoyl moiety is a straight or branched $C_{2-6}$ alkanoyl group, such as 2-[(2-, 3-, or 4-)pyridyl]acetyl, 3-[(2-, 3-, or 4-)pyridyl]propionyl, 2-[(2-, 3-, or 4-)pyridyl]propionyl, 4-[(2-, 3-, or 4-)pyridyl]butyryl, 5-[(2-, 3-, or 4-)pyridyl]pentanoyl, 6-[(2-, 3-, or 4-)pyridyl]hexanoyl, 2,2-dimethyl-3-[(2-, 3-, or 4-)pyridyl]propionyl, and 2-methyl-3-[(2-, 3-, or 4-)pyridyl]propionyl.

Examples of thienylcarbonyl groups include 2-thienylcarbonyl and 3-thienylcarbonyl.

Examples of thienyl lower alkanoyl groups include thienylalkanoyl groups wherein the alkanoyl moiety is a straight or branched $C_{2-6}$ alkanoyl group, such as 2-[(2- or 3-)thienyl]acetyl, 3-[(2- or 3-)thienyl]propionyl, 2-[(2- or 3-)thienyl]propionyl, 4-[(2- or 3-)thienyl]butyryl, 5-[(2- or 3-)thienyl]pentanoyl, 6-[(2- or 3-)thienyl]hexanoyl, 2,2-dimethyl-3-[(2- or 3-)thienyl]propionyl, and 2-methyl-3-[(2- or 3-)thienyl]propionyl.

Examples of cycloalkyl lower alkanoyl groups include $C_{3-8}$ cycloalkylalkanoyl groups wherein the alkanoyl moiety is a straight or branched $C_{2-6}$ alkanoyl group, such as 2-cyclopropylacetyl, 2-cyclohexylacetyl, 3-cyclopropylpropionyl, 2-cyclobutylpropionyl, 2-cyclopentylacetyl, 3-cyclopentylpropionyl, 4-cyclohexylbutyryl, 5-cycloheptylpentanoyl, 6-cyclooctylhexanoyl, 2,2-dimethyl-3-cyclohexylpropionyl, and 2-methyl-3-cyclopropylpropionyl.

Examples of isoxazolylcarbonyl groups optionally substituted on the isoxazole ring with one or more lower alkyl groups include isoxazoylcarbonyl groups optionally substituted on the isoxazole ring with one or two straight and/or branched $C_{1-6}$ alkyl groups, such as (3-, 4-, or 5-)isoxazolylcarbonyl, [3,5-dimethyl-4-isoxazolyl]carbonyl, [3-ethyl-(4- or 5-)isoxazolyl]carbonyl, [4-n-propyl-(3- or 5-)isoxazolyl]carbonyl, [5-n-butyl-(3- or 4-)isoxazolyl]carbonyl, [3-n-pentyl-(4- or 5-)isoxazolyl]carbonyl, and [4-n-hexyl-(3- or 5-)isoxazolyl]carbonyl.

Examples of pyrazylcarbonyl groups include 2-pyrazylcarbonyl.

Examples of piperidinylcarbonyl groups optionally substituted on the piperidine ring with one or more members selected from the group consisting of a benzoyl group and lower alkanoyl groups include:

piperidinylcarbonyl groups optionally substituted on the piperidine ring with one to three members selected from the group consisting of a benzoyl group and the above-described straight and branched $C_{1-6}$ alkanoyl groups;

such as (1-, 2-, 3-, or 4-)piperidinylcarbonyl, [1-acetyl-(2-, 3-, or 4-)piperidinyl]carbonyl, [1-benzoyl-(2-, 3-, or 4-)piperidinyl]carbonyl, [2-propionyl-(1-, 3-, 5-, or 6-)piperidinyl]carbonyl, [3-butyryl-(1-, 2-, 5-, or 6-)piperidinyl]carbonyl,

[4-pentanoyl-(1-, 2-, or 3-)piperidinyl]carbonyl, [1-hexanoyl-(2-, 3-, or 4-)piperidinyl]carbonyl, [1-acetyl-4-benzoyl-(2-, 3-, 5-, or 6-)piperidinyl]carbonyl, and [1,2,4-triacetyl-(3-, 5-, or 6-)piperidinyl]carbonyl.

Examples of chromanylcarbonyl groups include 2-chromanylcarbonyl, 3-chromanylcarbonyl, 4-chromanylcarbonyl, 5-chromanylcarbonyl, 6-chromanylcarbonyl, 7-chromanylcarbonyl, and 8-chromanylcarbonyl.

Examples of isoindolinyl lower alkanoyl groups optionally substituted on the isoindoline ring with one or more oxo groups include:

isoindolinyl lower alkanoyl groups wherein the alkanoyl moiety is a straight or branched $C_{2-6}$ alkanoyl group, optionally substituted on the isoindoline ring with one or two oxo groups;

such as 2-[(1-, 2-, 4-, or 5-)isoindolinyl]acetyl, 3-[(1-, 2-, 4-, or 5-)isoindolinyl]propionyl, 2-[(1-, 2-, 4-, or 5-)isoindolinyl]propionyl, 4-[(1-, 2-, 4-, or 5-)isoindolinyl]butyryl, 5-[(1-, 2-, 4-, or 5-)isoindolinyl]pentanoyl, 6-[(1-, 2-, 4-, or 5-)isoindolinyl]hexanoyl, 2,2-dimethyl-3-[(1-, 2-, 4-, or 5-)isoindolinyl]propionyl, 2-methyl-3-[(1-, 2-, 4-, or 5-)isoindolinyl]propionyl, [1,3-dioxo-2-(2-, 4-, or 5-)isoindolinyl]acetyl, and [1-oxo-2-(2-, 3-, 4-, 5-, 6-, or 7-)isoindolinyl]acetyl.

Examples of thiazolidinyl lower alkanoyl groups optionally substituted on the thiazolidine ring with one or more members selected from the group consisting of an oxo group and a thioxo group include:

thiazolidinylalkanoyl groups wherein the alkanoyl moiety is a straight or branched $C_{2-6}$ alkanoyl group, optionally substituted on the thiazolidine ring with one or two members selected from the group consisting of an oxo group and a thioxo group;

such as 2-[(2-, 3-, 4-, or 5-)thiazolidinyl]acetyl, 3-[(2-, 3-, 4-, or 5-)thiazolidinyl]propionyl, 2-[(2-, 3-, 4-, or 5-)thiazolidinyl]propionyl, 4-[(2-, 3-, 4-, or 5-)thiazolidinyl]butyryl, 5-[(2-, 3-, 4-, or 5-)thiazolidinyl]pentanoyl, 6-[(2-, 3-, 4-, or 5-)thiazolidinyl]hexanoyl, 2,2-dimethyl-3-[(2-, 3-, 4-, or 5-)thiazolidinyl]propionyl, 2-methyl-3-[(2-, 3-, 4-, or 5-)thiazolidinyl]propionyl, [2-thioxo-4-oxo-2-(3- or 5-)thiazolidinyl]acetyl, [2-thioxo-2-(3-, 4-, or 5-)thiazolidinyl]acetyl, [2-oxo-2-(3-, 4-, or 5-)thiazolidinyl]acetyl, [2,4-dithioxo-2-(3- or 5-)thiazolidinyl]acetyl, and [2,4-dioxo-2-(3- or 5-)thiazolidinyl]acetyl.

Examples of piperidinyl lower alkanoyl groups include piperidinylalkanoyl groups wherein the alkanoyl moiety is a straight or branched $C_{2-6}$ alkanoyl group, such as 2-[(1-, 2-, 3-, or 4-)piperidinyl]acetyl, 3-[(1-, 2-, 3-, or 4-)piperidinyl]propionyl, 2-[(1-, 2-, 3-, or 4-)piperidinyl]propionyl, 4-[(1-, 2-, 3-, or 4-)piperidinyl]butyryl, 5-[(1-, 2-, 3- or 4-)piperidinyl]pentanoyl, 6-[(1-, 2-, 3-, or 4-)piperidinyl]hexanoyl, 2,2-dimethyl-3-[(1-, 2-, 3-, or 4-)piperidinyl]propionyl, and 2-methyl-3-[(1-, 2-, 3-, or 4-)piperidinyl]propionyl.

Examples of phenyl lower alkenylcarbonyl groups optionally substituted on the phenyl ring with one or more halogen atoms include:

phenylalkenylcarbonyl groups containing one to three double bonds wherein the alkenyl moiety is a straight or branched $C_{2-6}$ alkenyl group, optionally substituted on the phenyl ring with one to three halogen atoms;

such as styrylcarbonyl (trivial name: cinnamoyl group), 3-phenyl-2-propenylcarbonyl, 4-phenyl-2-butenylcarbonyl, 4-phenyl-3-butenylcarbonyl, 5-phenyl-4-pentenylcarbonyl, 5-phenyl-3-pentenylcarbonyl, 6-phenyl-5-hexenylcarbonyl, 6-phenyl-4-hexenylcarbonyl, 6-phenyl-3-hexenylcarbonyl, 4-phenyl-1,3-butadienylcarbonyl, 6-phenyl-1,3,5-hexatrienylcarbonyl, 2-chlorostyrylcarbonyl, 3-(4-bromophenyl)-2-propenylcarbonyl, 4-(3-fluorophenyl)-2-butenylcarbonyl, 4-(2,4-dichlorophenyl)-3-butenylcarbonyl, 5-(2,4,6-trifluorophenyl)-4-pentenylcarbonyl, 5-(4-iodophenyl)-3-pentenylcarbonyl, 6-(3-chlorophenyl)-5-hexenylcarbonyl, 6-(4-chlorophenyl)-4-hexenylcarbonyl, 6-(3,4-dichlorophenyl)-3-hexenylcarbonyl, 4-(3-chloro-4-fluorophenyl)-1,3-butadienylcarbonyl, and 6-(2,6-difluorophenyl)-1,3,5-hexatrienylcarbonyl.

Examples of phenyl lower alkenylcarbonyl groups optionally substituted on the phenyl ring with one or more lower alkylenedioxy groups include:

phenylalkenylcarbonyl groups containing one to three double bonds wherein the alkenyl moiety is a straight or branched $C_{2-6}$ alkenyl group, optionally substituted on the phenyl ring with one or more of the above-described straight and branched $C_{1-4}$ alkylenedioxy groups;

such as 3,4-methylenedioxystyrylcarbonyl, 3-(2,3-ethylenedioxyphenyl)-2-propenylcarbonyl, 4-(3,4-trimethylenedioxyphenyl)-2-butenylcarbonyl, 4-(2,3-tetramethylenedioxyphenyl)-3-butenylcarbonyl, 5-(2,3-methylenedioxyphenyl)-4-pentenylcarbonyl, 5-(3,4-ethylenedioxyphenyl)-3-pentenylcarbonyl, 6-(2,3-trimethylenedioxyphenyl)-5-hexenylcarbonyl, 6-(3,4-tetramethylenedioxyphenyl)-4-hexenylcarbonyl, 6-(2,3-methylenedioxyphenyl)-3-hexenylcarbonyl, 4-(3,4-methylenedioxyphenyl)-1,3-butadienylcarbonyl, and 6-(2,3-methylenedioxyphenyl)-1,3,5-hexatrienylcarbonyl.

Examples of pyridyl lower alkenylcarbonyl groups include pyridylalkenylcarbonyl groups containing one to three double bonds wherein the alkenyl moiety is a straight or branched $C_{2-6}$ alkenyl group, such as 2-[(2-, 3-, or 4-)pyridyl]vinylcarbonyl, 3-[(2-, 3-, or 4-)pyridyl]-2-propenylcarbonyl, 4-[(2-, 3-, or 4-)pyridyl]-2-butenylcarbonyl, 4-[(2-, 3-, or 4-)pyridyl]-3-butenylcarbonyl, 5-[(2-, 3- or 4-)pyridyl]-4-pentenyl carbonyl, 5-[(2-, 3-, or 4-)pyridyl]-3-pentenylcarbonyl, 6-[(2-, 3-, or 4-)pyridyl]-5-hexenylcarbonyl, 6-[(2-, 3-, or 4-)pyridyl]-4-hexenylcarbonyl, 6-[(2-, 3-, or 4-)pyridyl]-3-hexenylcarbonyl, 4-phenyl-1,3-butadienylcarbonyl, and 6-[(2-, 3-, or 4-)pyridyl]-1,3,5-hexatrienylcarbonyl.

Examples of pyridylthio lower alkanoyl groups include pyridylthioalkanoyl groups wherein the alkanoyl moiety is a straight or branched $C_{2-6}$ alkanoyl group, such as 2-[(2-, 3-, or 4-)pyridylthio]acetyl, 3-[(2-, 3-, or 4-)pyridylthio]propionyl, 2-[(2-, 3-, or 4-)pyridylthio]propionyl, 4-[(2-, 3-, or 4-)pyridylthio]butyryl, 5-[(2-, 3-, or 4-)pyridylthio]pentanoyl, 6-[(2-, 3-, or 4-)pyridylthio]hexanoyl, 2,2-dimethyl-3-[(2-, 3-, or 4-)pyridylthio]propionyl, and 2-methyl-3-[(2-, 3-, or 4-)pyridylthio]propionyl.

Examples of indolylcarbonyl groups include 1-indolylcarbonyl, 2-indolylcarbonyl, 3-indolylcarbonyl, 4-indolylcarbonyl, 5-indolylcarbonyl, 6-indolylcarbonyl, and 7-indolylcarbonyl.

Examples of pyrrolylcarbonyl groups include 2-pyrrolylcarbonyl and 3-pyrrolylcarbonyl.

Examples of pyrrolidinylcarbonyl groups optionally substituted on the pyrrolidine ring with one or more oxo groups include pyrrolidinylcarbonyl groups optionally substituted on the pyrrolidine ring with one or two oxo groups, such as (1-, 2-, or 3-)pyrrolidinylcarbonyl, 2-oxo-(1-, 3-, 4-, or 5-)pyrrolidinylcarbonyl, 3-oxo-(1-, 2-, 4-, or 5-)pyrrolidinyl carbonyl, 2,5-dioxo-(1- or 3-)pyrrolidinylcarbonyl, and 2,3-dioxo-(1-, 4-, or 5-)pyrrolidinyl carbonyl.

Examples of benzofurylcarbonyl groups include 2-benzofurylcarbonyl, 3-benzofurylcarbonyl, 4-benzofurylcarbonyl, 5-benzofurylcarbonyl, 6-benzofurylcarbonyl, and 7-benzofurylcarbonyl.

Examples of indolyl lower alkanoyl groups include indolylalkanoyl groups wherein the alkanoyl moiety is a straight or branched $C_{2-6}$ alkanoyl group, such as 2-[(1-, 2-, 3-, 4-, 5-, 6-, or 7-)indolyl]acetyl, 3-[(1-, 2-, 3-, 4-, 5-, 6-, or 7-)indolyl]propionyl, 2-[(1-, 2-, 3-, 4-, 5-, 6-, or 7-)indolyl]propionyl, 4-[(1-, 2-, 3-, 4-, 5-, 6-, or 7-)indolyl]butyryl, 5-[(1-, 2-, 3-, 4-, 5-, 6-, or 7-)indolyl]pentanoyl, 6-[(1-, 2-, 3-, 4-, 5-, 6-, or 7-)indolyl]hexanoyl, 2,2-dimethyl-3-[(1-, 2-, 3-, 4-, 5-, 6-, or 7-)indolyl]propionyl, and 2-methyl-3-[(1-, 2-, 3-, 4-, 5-, 6-, or 7-)indolyl]propionyl.

Examples of benzothienylcarbonyl groups include 2-benzothienylcarbonyl, 3-benzothienylcarbonyl, 4-benzothienylcarbonyl, 5-benzothienylcarbonyl, 6-benzothienylcarbonyl, and 7-benzothienylcarbonyl.

Examples of phenyl lower alkanoyl groups optionally substituted on the phenyl ring with one or more halogen atoms include:

phenylalkanoyl groups wherein the alkanoyl moiety is a straight or branched $C_{2-6}$ alkanoyl group, optionally substituted on the phenyl ring with one to three halogen atoms;

such as 2-phenylacetyl, 3-phenylpropionyl, 2-phenylpropionyl, 4-phenylbutyryl, 5-phenylpentanoyl, 6-phenylhexanoyl, 2,2-dimethyl-3-phenylpropionyl, 2-methyl-3-phenylpropionyl, 2-(4-fluorophenyl)acetyl, 3-(2,5-difluorophenyl)propionyl, 2-(2,4-difluorophenyl)propionyl, 4-(3,4-difluorophenyl)butyryl, 5-(3,5-difluorophenyl)pentanoyl, 6-(2,6-difluorophenyl)hexanoyl, 2-(2-chlorophenyl)acetyl, 3-(3-chlorophenyl)propionyl, 2-(4-chlorophenyl)propionyl, 4-(2,3-dichlorophenyl)propionyl, 5-(2,4-dichlorophenyl)pentanoyl, 6-(2,5-dichlorophenyl)hexanoyl, 2-(3,4-dichlorophenyl)acetyl, 3-(2,6-dichlorophenyl)propionyl, 2-(3-fluorophenyl)propionyl, 4-(2-fluorophenyl)butyryl, 5-(3-bromophenyl)pentanoyl, 6-(4-iodophenyl)hexanoyl, 2-(2-bromophenyl)acetyl, 3-(4-bromophenyl)propionyl, 2-(3,5-dichlorophenyl)propionyl, 4-(2,4,6-trifluoro phenyl)butyryl, 5-(3,4-difluorophenyl)pentanoyl, 6-(2-iodophenyl)hexanoyl, 2-(3-iodophenyl)acetyl, 3-(4-iodophenyl)propionyl, 2-(2,3-dibromophenyl)propionyl, 4-(2,4-diiodophenyl)butyryl, and 2-(2,4,6-trichlorophenyl)acetyl.

Examples of phenylsulfonyl groups optionally substituted on the phenyl ring with one or more members selected from the group consisting of lower alkoxycarbonyl groups; a cyano group; a nitro group; amino groups optionally substituted with one or more lower alkanoyl groups; a hydroxy group; a carboxyl group; lower alkoxycarbonyl lower alkyl groups; halogen atoms; lower alkyl groups optionally substituted with one or more halogen atoms; and lower alkoxy groups optionally substituted with one or more halogen atoms include:

phenylsulfonyl groups optionally substituted on the phenyl ring with one to five members selected from the group consisting of the above-described lower alkoxycarbonyl groups wherein the alkoxy moiety is a straight or branched $C_{1-6}$ alkoxy group; a cyano group; a nitro group; the above-described amino groups optionally substituted with one or two straight and/or branched $C_{1-6}$ alkanoyl groups; a hydroxy group; a carboxyl group; the above-described alkoxycarbonylalkyl groups wherein the alkoxy moiety is a straight or branched $C_{1-6}$ alkoxy group and the alkyl moiety is a straight or branched $C_{1-6}$ alkyl group; halogen atoms; the above-described straight and branched $C_{1-6}$ alkyl groups optionally substituted with one to three halogen atoms; and the above-described straight and branched $C_{1-6}$ alkoxy groups optionally substituted with one to three halogen atoms;

such as phenylsulfonyl, 4-methoxyphenylsulfonyl, 3-methoxyphenylsulfonyl, 2-methoxyphenylsulfonyl, 2-trifluoromethoxyphenylsulfonyl, 3-trifluoromethoxyphenylsulfonyl, 4-trifluoromethoxyphenylsulfonyl, 3,4-dimethoxyphenylsulfonyl, 2,5-dimethoxyphenylsulfonyl, 2,4,6-trimethoxyphenylsulfonyl, 4-n-butoxyphenylsulfonyl, 2-methoxy-5-chlorophenylsulfonyl, 2-methoxy-5-methylphenylsulfonyl, 2-methoxy-4-methylphenylsulfonyl, 4-chlorophenylsulfonyl, 3-chlorophenylsulfonyl, 2-chlorophenylsulfonyl, 4-fluorophenylsulfonyl, 3-fluorophenylsulfonyl, 2-fluorophenylsulfonyl, 4-bromophenylsulfonyl, 3-bromophenylsulfonyl, 2-bromophenylsulfonyl, 2,6-dichlorophenylsulfonyl, 2,3-dichlorophenylsulfonyl, 2,5-dichlorophenylsulfonyl, 2,4-dichlorophenylsulfonyl, 3,4-dichlorophenylsulfonyl, 3,5-dichlorophenylsulfonyl, 2-chloro-4-fluorophenylsulfonyl, 2-bromo-5-chlorophenylsulfonyl, 2,5-difluorophenylsulfonyl, 2,4-difluorophenylsulfonyl, 2,6-difluorophenylsulfonyl, 3,4-difluorophenylsulfonyl, 2,4-dichloro-5-methylphenylsulfonyl, 2,4,5-trifluorophenylsulfonyl, 2,3,4,5,6-pentafluorophenylsulfonyl, 3-chloro-4-fluorophenylsulfonyl, 2-chloro-6-methylphenylsulfonyl, 2,4-dichloro-6-methylphenylsulfonyl, 2-methyl-3-chlorophenylsulfonyl, 2-methyl-3-chlorophenylsulfonyl, 4-methyl-3-chlorophenylsulfonyl, 2-methyl-5-fluorophenylsulfonyl, 2-methyl-4-bromophenylsulfonyl, 2-fluoro-4-bromophenylsulfonyl, 2,5-dimethyl-4-chlorophenylsulfonyl, 2-methylphenylsulfonyl, 3-methylphenylsulfonyl, 4-methylphenylsulfonyl, 2,5-dimethylphenylsulfonyl, 2,4,6-trimethylphenylsulfonyl, 2,3,6-trimethyl-4-methoxyphenylsulfonyl, 4-tert-butylphenylsulfonyl, 4-ethylphenylsulfonyl, 4-isopropylphenylsulfonyl, 2-trifluoromethylphenylsulfonyl, 3-trifluoromethylphenylsulfonyl, 4-trifluoromethylphenylsulfonyl, 2-methoxycarbonylphenylsulfonyl, 2-cyanophenylsulfonyl, 3-cyanophenylsulfonyl, 4-cyanophenylsulfonyl, 3-nitrophenylsulfonyl, 2-nitrophenylsulfonyl, 4-nitrophenylsulfonyl, 3-nitro-4-methylphenylsulfonyl, 3-nitro-6-methylphenylsulfonyl, 3-nitro-6-chlorophenylsulfonyl, 2-chloro-4-cyanophenylsulfonyl, 4-acetylaminophenylsulfonyl, 3-chloro-4-acetylaminophenylsulfonyl, 2-hydroxy-3,5-dichlorophenylsulfonyl, 2-hydroxyphenylsulfonyl, 3-hydroxyphenylsulfonyl, 4-hydroxyphenylsulfonyl, 2-nitro-4-methoxyphenylsulfonyl, 3-carboxyphenylsulfonyl, 4-carboxyphenylsulfonyl, 2-carboxyphenylsulfonyl, 4-(2-methoxycarbonylethyl)phenylsulfonyl, 3-carboxy-4-hydroxyphenylsulfonyl, 3-aminophenylsulfonyl, 2-aminophenylsulfonyl, and 4-aminophenylsulfonyl.

Examples of thienylsulfonyl groups optionally substituted on the thiophene ring with one or more members selected from the group consisting of halogen atoms and lower alkoxycarbonyl groups include:

thienylsulfonyl groups optionally substituted on the thiophene ring with one to three members selected from halogen atoms and the above-described alkoxycarbonyl groups wherein the alkoxy moiety is a straight or branched $C_{1-6}$ alkoxy group;

such as (2- or 3-)thienylsulfonyl, [2-chloro-(3-, 4-, or 5-)thienyl]sulfonyl, [2,3-dichloro-(4- or 5-)thienyl]sulfonyl, [2,5-dichloro-(3- or 4-)thienyl]sulfonyl, [2-bromo-(3-, 4-, or 5-)thienyl]sulfonyl, [2-fluoro-(3-, 4-, or 5-)thienyl]sulfonyl, (2,3,4-trichloro-5-thienyl)sulfonyl, [2-methoxycarbonyl-(3-, 4-, or 5-)thienyl]sulfonyl, [3-ethoxycarbonyl-(2-, 4-, or 5-)thienyl]sulfonyl, [3-n-propoxycarbonyl-(2-, 4-, or 5-)thienyl]sulfonyl, [2-tert-butoxycarbonyl-(3-, 4-, or 5-)thienyl] sulfonyl, [2-n-pentyloxycarbonyl-(3-, 4-, or 5-)thienyl]sulfonyl, [3-n-hexyloxycarbonyl-(2-, 4-, or 5-)thienyl]sulfonyl, [2,3-dimethoxycarbonyl-(4- or 5-)thienyl]sulfonyl, and [2-chloro-3-methoxycarbonyl-(4- or 5-)thienyl]sulfonyl.

Examples of quinolylsulfonyl groups include 2-quinolylsulfonyl, 3-quinolylsulfonyl, 4-quinolylsulfonyl, 5-quinolylsulfonyl, 6-quinolylsulfonyl, 7-quinolylsulfonyl, and 8-quinolylsulfonyl.

Examples of imidazolylsulfonyl groups optionally substituted on the imidazole ring with one or more lower alkyl groups include imidazolylsulfonyl groups optionally substituted on the imidazole ring with one to three above-described straight and branched $C_{1-6}$ alkyl groups, such as (1-, 2-, 4-, or 5-)imidazolylsulfonyl, [1-methyl-(2-, 4-, or 5-)imidazolyl]sulfonyl, [2-ethyl-(1-, 4-, or 5-)imidazolyl]sulfonyl, [1-isopropyl-(2-, 4-, or 5-)imidazolyl]sulfonyl, [4-n-butyl-(1-, 2-, or 5-)imidazolyl]sulfonyl, [5-n-pentyl-(1-, 2-, or 4-)imidazolyl]sulfonyl, [1-n-hexyl-(2-, 4-, or 5-)imidazolyl]sulfonyl, [1,2-dimethyl-(4- or 5-)imidazolyl]sulfonyl, and (1,2,4-trimethyl-5-imidazolyl)sulfonyl.

Examples of phenylsulfonyl groups optionally substituted on the phenyl ring with one or more lower alkylenedioxy groups include phenylsulfonyl groups optionally substituted on the phenyl ring with one or more one to three the above-described straight and branched $C_{1-4}$ alkylenedioxy groups, such as (3,4-ethylenedioxyphenyl)sulfonyl, (2,3-methylenedioxyphenyl)sulfonyl, (3,4-trimethylenedioxyphenyl)sulfonyl, and (2,3-tetramethylenedioxyphenyl)sulfonyl.

Examples of lower alkenylsulfonyl groups include straight and branched $C_{2-6}$ alkenylsulfonyl groups containing one to three double bonds, such as vinylsulfonyl, 1-propenylsulfonyl, 1-methyl-1-propenylsulfonyl, 2-methyl-1-propenylsulfonyl, 2-propenylsulfonyl, 2-butenylsulfonyl, 1-butenylsulfonyl, 3-butenylsulfonyl, 2-pentenylsulfonyl, 1-pentenylsulfonyl, 3-pentenylsulfonyl, 4-pentenylsulfonyl, 1,3-butadienylsulfonyl, 1,3-pentadienylsulfonyl, 2-pentene-4-ynylsulfonyl, 2-hexenylsulfonyl, 1-hexenylsulfonyl, 5-hexenylsulfonyl, 3-hexenylsulfonyl, 4-hexenylsulfonyl, 3,3-dimethyl-1-propenylsulfonyl, 2-ethyl-1-propenylsulfonyl, 1,3,5-hexatrienylsulfonyl, 1,3-hexadienylsulfonyl, and 1,4-hexadienylsulfonyl.

Examples of cycloalkyl-substituted lower alkylsulfonyl groups include $C_{3-8}$ cycloalkyl-substituted alkylsulfonyl groups wherein the alkyl moiety is a straight or branched $C_{1-6}$ alkyl group, such as cyclopropylmethylsulfonyl, cyclohexylmethylsulfonyl, 2-cyclopropylethylsulfonyl, 1-cyclobutylethylsulfonyl, cyclopentylmethylsulfonyl, 3-cyclopentylpropylsulfonyl, 4-cyclohexylbutylsulfonyl, 5-cycloheptylpentylsulfonyl, 6-cyclooctylhexylsulfonyl, 1,1-dimethyl-2-cyclohexylethylsulfonyl, and 2-methyl-3-cyclopropylpropylsulfonyl.

Examples of 3,4-dihydro-2H-1,4-benzoxazinylsulfonyl groups optionally substituted on the 3,4-dihydro-2H-1,4-benzoxazine ring with one or more lower alkyl groups include 3,4-dihydro-2H-1,4-benzoxazinylsulfonyl groups optionally substituted on the 3,4-dihydro-2H-1,4-benzoxazine ring with one to three above-described straight and/or branched $C_{1-6}$ alkyl groups, such as (2-, 3-, 4-, 5-, 6-, 7- or 8-)3,4-dihydro-2H-1,4-benzoxazinylsulfonyl, [4-methyl-(2-, 3-, 5-, 6-, 7- or 8-)3,4-dihydro-2H-1,4-benzoxazinyl]sulfonyl, [5-ethyl-(2-, 3-, 4-, 6-, 7- or 8-)3,4-dihydro-2H-1,4-benzoxazinyl]sulfonyl, [6-n-propyl-(2-, 3-, 4-, 5-, 7- or 8-)3,4-dihydro-2H-1,4-benzoxazinyl]sulfonyl, [7-n-butyl-(2-, 3-, 5-, 6-, 7- or 8-)3,4-dihydro-2H-1,4-benzoxazinyl]sulfonyl, [8-n-pentyl-(2-, 3-, 5-, 6-, 7- or 8-)3,4-dihydro-2H-1,4-benzoxazinyl]sulfonyl, [2-n-hexyl-(3-, 4-, 5-, 6-, 7- or 8-)3,4-dihydro-2H-1,4-benzoxazinyl]sulfonyl, [3-methyl-(2-, 4-, 5-, 6-, 7- or 8-)3,4-dihydro-2H-1,4-benzoxazinyl]sulfonyl, [4,6-dimethyl-(2-, 3-, 5-, 7- or 8-)3,4-dihydro-2H-1,4-benzoxazinyl]sulfonyl, and [4,5,6-trimethyl-(2-, 3-, 7- or 8-)3,4-dihydro-2H-1,4-benzoxazinyl]sulfonyl.

Examples of pyrazolylsulfonyl groups optionally substituted on the pyrazole ring with one or more members selected from the group consisting of halogen atoms and lower alkyl groups include:

pyrazolylsulfonyl groups optionally substituted on the pyrazole ring with one to three members selected from the group consisting of halogen atoms and the above-described straight and branched $C_{1-6}$ alkyl groups;

such as (1-, 3-, 4-, or 5-)pyrazolylsulfonyl, (1,3-dimethyl-5-chloro-4-pyrazolyl)sulfonyl, [1-ethyl-(3-, 4-, or 5-)pyrazolyl]sulfonyl, [3-n-propyl-(1-, 4-, or 5-)pyrazolyl]sulfonyl, [4-n-butyl-(3-, 4-, or 5-)pyrazolyl]sulfonyl, [5-n-pentyl-(1-, 3-, or 4-)pyrazolyl]sulfonyl, [1-n-hexyl-(3-, 4-, or 5-)pyrazolyl]sulfonyl, [1,3-dimethyl-(4- or 5-)pyrazolyl]sulfonyl, (1,3,5-trimethyl-4-pyrazolyl)sulfonyl, [3-bromo-(1-, 4-, or 5-)pyrazolyl]sulfonyl, [4-fluoro-(1-, 3-, or 5-)pyrazolyl]sulfonyl, [5-iodo-(1-, 3-, or 4-)pyrazolyl]sulfonyl, [3,4-dichloro-(1- or 5-)pyrazolyl]sulfonyl, and (3,4,5-trichloro-4-pyrazolyl)sulfonyl.

Examples of isoxazolylsulfonyl groups optionally substituted on the isoxazole ring with one or more lower alkyl groups include isoxazolylsulfonyl groups optionally substituted on the isoxazole ring with one or two above-described straight and/or branched $C_{1-6}$ alkyl groups, such as (3-, 4-, or 5-)isoxazolylsulfonyl, (3,5-dimethyl-4-isoxazolyl)sulfonyl, [3-methyl-(4- or 5-)isoxazolyl]sulfonyl, [3-ethyl-(4- or 5-)isoxazolyl]sulfonyl, [4-n-propyl-(3- or 5-)isoxazolyl]sulfonyl, [5-n-butyl-(3- or 4-)isoxazolyl]sulfonyl, [3-n-pentyl-(4- or 5-)isoxazolyl]sulfonyl, and [4-n-hexyl-(3- or 5-)isoxazolyl]sulfonyl.

Examples of thiazolylsulfonyl groups optionally substituted on the thiazole ring with one or more members selected from the group consisting of lower alkyl groups and an amino group, each amino substituent optionally being substituted with one or more lower alkanoyl groups, include:

thiazolylsulfonyl groups optionally substituted on the thiazole ring with one or two members selected from the group consisting of the above-described straight or branched $C_{1-6}$ alkyl groups and the above-described amino groups optionally substituted with one or two straight and/or branched $C_{1-6}$ alkanoyl groups;

such as (2-, 4-, or 5-)thiazolylsulfonyl, (2-acetylamino-4-methyl-5-thiazolyl)sulfonyl, [2-ethyl-(4- or 5-)thiazolyl]sulfonyl, [4-n-propyl-(2- or 5-)thiazolyl]sulfonyl, [5-n-butyl-(2- or 4-)thiazolyl]sulfonyl, [2-n-pentyl-(4- or 5-)thiazolyl]sulfonyl, [4-n-hexyl-(2- or 5-)thiazolyl]sulfonyl, (2,4-dimethyl-5-thiazolyl)sulfonyl, [2-amino-(4- or 5-)thiazolyl]sulfonyl, [2-formylamino-(4- or 5-)thiazolyl]sulfonyl, [4-n-propionylamino-(2- or 5-)thiazolyl]sulfonyl, [5-n-butyryl amino-(2- or 4-)thiazolyl]sulfonyl, [2-n-pentanoylamino-(4- or 5-)thiazolyl]sulfonyl, [4-n-hexanoylamino-(2- or 5-)thiazolyl]sulfonyl, (2,4-diacetyl-5-thiazolyl)sulfonyl, and [2-(N,N-diacetylamino)-(4- or 5-)thiazolyl]sulfonyl.

Examples of phenyl lower alkylsulfonyl groups include mono- and di-phenylalkyl groups wherein the alkyl moiety is a straight or branched $C_{1-6}$ alkyl group, such as benzylsulfonyl, 1-phenethylsulfonyl, 2-phenethylsulfonyl, 3-phenylpropylsulfonyl, 2-phenylpropylsulfonyl, 4-phenylbutylsulfonyl, 5-phenylpentylsulfonyl, 4-phenylpentylsulfonyl, 6-phenylhexylsulfonyl, 2-methyl-3-phenylpropylsulfonyl, 1,1-dimethyl-2-phenylethylsulfonyl, 1,1-dimethyl-1-phenylmethylsulfonyl, 1,1-diphenylmethylsulfonyl, 2,2-diphenylethylsulfonyl, 3,3-diphenylpropylsulfonyl, and 1,2-diphenylethylsulfonyl.

Examples of phenyl lower alkenylsulfonyl groups include:

phenylalkenylsulfonyl groups containing one to three double bonds wherein the alkenyl moiety is a straight or branched $C_{2-6}$ alkenyl group, optionally substituted on the phenyl ring with one to three halogen atoms;

such as styrylsulfonyl, 3-phenyl-2-propenylsulfonyl, 4-phenyl-2-butenylsulfonyl, 4-phenyl-3-butenylsulfonyl, 5-phenyl-4-pentenylsulfonyl, 5-phenyl-3-pentenylsulfonyl, 6-phenyl-5-hexenylsulfonyl, 6-phenyl-4-hexenylsulfonyl, 6-phenyl-3-hexenylsulfonyl, 4-phenyl-1,3-butadienylsulfonyl, 6-phenyl-1,3,5-hexatrienylsulfonyl, 2-chlorostyrylsulfonyl, 3-(4-bromophenyl)-2-propenylsulfonyl, 4-(3-fluorophenyl)-2-butenylsulfonyl, 4-(2,4-dichlorophenyl)-3-butenylsulfonyl, 5-(2,4,6-trifluorophenyl)-4-pentenylsulfonyl, 5-(4-iodophenyl)-3-pentenylsulfonyl, 6-(3-chlorophenyl)-5-hexenylsulfonyl, 6-(4-chlorophenyl)-4-hexenylsulfonyl, 6-(3,4-dichlorophenyl)-3-hexenylsulfonyl, 4-(3-chloro-4-fluorophenyl)-1,3-butadienylsulfonyl, and 6-(2,6-difluorophenyl)-1,3,5-hexatrienylsulfonyl.

Examples of naphthyloxycarbonyl groups include 1-naphthyloxycarbonyl and 2-naphthyloxycarbonyl.

Examples of lower alkynyloxycarbonyl groups include alkynyloxycarbonyl groups wherein the alkynyl moiety is a straight or branched $C_{2-6}$ alkynyl group, such as ethynyloxycarbonyl, 2-propynyloxycarbonyl, 2-butynyloxycarbonyl, 3-butynyloxycarbonyl, 1-methyl-2-propynyloxycarbonyl, 2-pentynyloxycarbonyl, and 2-hexynyloxycarbonyl.

Examples of lower alkenyloxycarbonyl groups include alkenyloxycarbonyl groups containing one to three double bonds wherein the alkenyl moiety is a straight or branched $C_{2-6}$ alkenyl group, such as vinyloxycarbonyl, 1-propenyloxycarbonyl, 1-methyl-1-propenyloxycarbonyl, 2-methyl-1-propenyloxycarbonyl, 2-propenyloxycarbonyl, 2-butenyloxycarbonyl, 1-butenyloxycarbonyl, 3-butenyloxycarbonyl, 2-pentenyloxycarbonyl, 1-pentenyloxycarbonyl, 3-pentenyloxycarbonyl, 4-pentenyloxycarbonyl, 1,3-butadienyloxycarbonyl, 1,3-pentadienyloxycarbonyl, 2-pentene-4-ynyloxycarbonyl, 2-hexenyloxycarbonyl, 1-hexenyloxycarbonyl, 5-hexenyloxycarbonyl, 3-hexenyloxycarbonyl, 4-hexenyloxycarbonyl, 3,3-dimethyl-1-propenyloxycarbonyl, 2-ethyl-1-propenyloxycarbonyl, 1,3,5-hexatrienyloxycarbonyl, 1,3-hexadienyloxycarbonyl, and 1,4-hexadienyloxycarbonyl.

Examples of phenyl lower alkoxy-substituted lower alkoxycarbonyl groups include phenylalkoxy-substituted alkoxycarbonyl groups wherein each of the two alkoxy moieties is a straight or branched $C_{1-6}$ alkoxy group, such as phenylmethoxymethoxycarbonyl, 2-(phenylmethoxy)ethoxycarbonyl, 1-(phenylmethoxy)ethoxycarbonyl, 3-(phenylmethoxy)propoxycarbonyl, 4-(phenylmethoxy)butoxycarbonyl, 5-(phenylmethoxy)pentyloxycarbonyl, 6-(phenylmethoxy)hexyloxycarbonyl, 1,1-dimethyl-2-(phenylmethoxy)ethoxycarbonyl, 2-methyl-3-(phenylmethoxy)propoxycarbonyl, 1-(2-phenylethoxy)ethoxycarbonyl, 2-(1-phenylethoxy)ethoxycarbonyl, 3-(3-phenylpropoxy) propoxy carbonyl, 4-(4-phenylbutoxy)butoxycarbonyl, 5-(5-phenylpentyloxy)pentyloxycarbonyl, 6-(6-phenylhexyloxy)hexyloxycarbonyl, (1,1-dimethyl-2-phenylethoxy)methoxycarbonyl, and 3-(2-methyl-3-phenylpropoxy)propoxycarbonyl.

Examples of cycloalkyloxycarbonyl groups optionally substituted on the cycloalkyl ring with one or more lower alkyl groups include:
cycloalkyloxycarbonyl groups wherein the cycloalkoxy moiety is a $C_{3-8}$ cycloalkoxy group, optionally substituted on the cycloalkyl ring with one to three above-described straight and branched $C_{1-6}$ alkyl groups;
such as cyclopropyloxycarbonyl, cyclobutyloxycarbonyl, cyclopentyloxycarbonyl, cyclohexyloxycarbonyl, cycloheptyloxycarbonyl, cyclooctyloxycarbonyl, 3-methyl-6-isopropylcyclohexyloxycarbonyl, 2-ethylcyclopropyloxycarbonyl, 2-n-propylcyclobutyloxycarbonyl, 3-n-butylcycloheptyloxycarbonyl, 3-n-pentylcyclooctyloxydarbonyl, 2-methylcyclopentyloxycarbonyl, and 2,3,6-trimethylcyclohexyloxycarbonyl.

Examples of isoxazolyl groups optionally substituted on the isoxazole ring with one or more lower alkyl groups include isoxazolyl groups optionally substituted on the isoxazole ring with one or two straight and/or branched $C_{1-6}$ alkyl groups, such as (3-, 4-, or 5-)isoxazolyl, 5-methyl-(3- or 4-)isoxazolyl, 3,5-dimethyl-4-isoxazolyl, 3-ethyl-(4- or 5-)isoxazolyl, 4-n-propyl-(3- or 5-)isoxazolyl, 5-n-butyl-(3- or 4-)isoxazolyl, 3-n-pentyl-(4- or 5-)isoxazolyl and 4-n-hexyl-(3- or 5-)isoxazolyl.

Examples of 5- to 7-membered saturated heterocyclic rings formed from $R^6$ and $R^7$ being linked together, together with the nitrogen atom to which they are bound, the heterocyclic ring optionally containing one or more additional heteroatoms, include:
5- to 7-membered saturated heterocyclic rings formed from $R^6$ and $R^7$ being linked together, together with the nitrogen atom to which they are bound, the heterocyclic group optionally containing one or more additional heteroatoms selected from oxygen, sulfur atom, and nitrogen atom;
such as pyrrolidine, piperazine, piperidine, morpholine, thiomorpholine, homopiperazine, homopiperidine, imidazolidine, thiazolidine, isothiazolidine, oxazolidine, isoxazolidine, isothiazolidine, and pyrazolidine.

Examples of phenyl groups optionally substituted on the phenyl ring with one or more members selected from the group consisting of halogen atoms; lower alkoxy groups optionally substituted with one or more halogen atoms; lower alkyl groups optionally substituted with one or more halogen atoms; a cyano group; and a hydroxy group include:
phenyl groups optionally substituted on the phenyl ring with one to three members selected from the group consisting of halogen atoms; the above-described straight and branched $C_{1-6}$ alkoxy groups optionally substituted with one to three halogen atoms; the above-described straight and branched $C_{1-6}$ alkyl groups optionally substituted with one to three halogen atoms; a cyano group; and a hydroxy group;
such as phenyl, 4-isopropylphenyl, 3-isopropylphenyl, 2-isopropylphenyl, 4-tert-butylphenyl, 4-methylphenyl, 3-methylphenyl, 2-methylphenyl, 2,3-dimethylphenyl, 2,4-dimethylphenyl, 3,5-dimethylphenyl, 2,4,6-trimethylphenyl, 4-methyl-3-methoxyphenyl, 4-trifluoromethylphenyl, 3-trifluoromethylphenyl, 2-trifluoromethylphenyl, 4-methyl-3-chlorophenyl, 4-chlorophenyl, 3-chlorophenyl, 2-chlorophenyl, 2-fluorophenyl, 3-fluorophenyl, 4-fluorophenyl, 3-bromophenyl, 3,4-dichlorophenyl, 3,5-dichlorophenyl, 3,4,5-trichlorophenyl, 2,4,6-trifluorophenyl, 3,5-difluorophenyl, 3-chloro-4-fluorophenyl, 2-chloro-5-fluorophenyl, 3-fluoro-4-methoxyphenyl, 3-chloro-4-methoxyphenyl, 3-chloro-4-hydroxyphenyl, 4-methoxyphenyl, 3-methoxyphenyl, 2-methoxyphenyl, 2,4-dimethoxyphenyl, 3,4-dimethoxyphenyl, 2,4,6-trimethoxyphenyl, 2-methoxy-5-chlorophenyl, 4-ethoxyphenyl, 4-trifluoromethoxyphenyl, 3-trifluoromethoxyphenyl, 2-trifluoromethoxyphenyl, 3-methoxy-5-trifluoromethyl phenyl, 2-cyanophenyl, 3-cyanophenyl, 4-cyanophenyl, 3-hydroxyphenyl, 2-hydroxyphenyl, and 4-hydroxyphenyl.

Examples of phenyl lower alkyl groups optionally substituted on the phenyl ring with one or more halogen atoms include:
mono- and di-phenylalkyl groups wherein the alyl moiety is a straight or branched $C_{1-6}$ alkyl group, optionally substituted on each phenyl ring with one to three halogen atoms;
such as benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl, 1,1-diphenylmethyl, 2,2-diphenylethyl, 3,3-diphenylpropyl, 1,2-diphenylethyl, 4-chlorobenzyl, 2-chlorobenzyl, 3-chlorobenzyl, 2-fluorobenzyl, 3-fluorobenzyl, 4-fluorobenzyl, 2,3-dichlorobenzyl, and 2,4,6-trifluorobenzyl.

Examples of phenyl lower alkoxy groups optionally substituted on the phenyl ring with one or more halogen atoms include:
phenylalkoxy groups wherein the alkoxy moiety is a straight or branched $C_{1-6}$ alkoxy group, optionally substituted on the phenyl ring with one to three halogen atoms;
such as benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, 4-chlorobenzyloxy, 2-chlorobenzyloxy, 3-chlorobenzyloxy, 2-fluorobenzyloxy, 3-fluorobenzyloxy, 4-fluorobenzyloxy, 2,4-dibromobenzyloxy, and 2,4,6-trifluorobenzyloxy.

Examples of carbamoyl lower alkyl groups optionally substituted with one or more members selected from the group consisting of phenyl group and lower alkyl groups include:
carbamoylalkyl groups wherein the alkyl moiety is a straight or branched $C_{1-6}$ alkyl group, optionally substituted with one or two members selected from the group consisting of a phenyl group and the above-described straight and branched $C_{1-6}$ alkyl groups;
such as carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl, 2-methyl-3-carbamoylpropyl, 2-(N-methyl-N-phenylcarbamoyl)ethyl, N-phenylcarbamoylmethyl, 2-(N,N-dimethylcarbamoyl)ethyl, 3-(N-phenylcarbamoyl)propyl, 2-(N-ethyl-N-phenylcarbamoyl)ethyl, N,N-dimethylcarbamoylmethyl, N-methyl-N-ethylcarbamoylmethyl, N-methylcarbamoylmethyl, and 2-(N-methylcarbamoyl)ethyl.

Examples of phenyl lower alkylidene groups optionally substituted on the phenyl ring with one or more halogen atoms include:

phenylalkylidene groups wherein the alkylidene moiety is a straight or branched $C_{1-6}$ alkylidene group, optionally substituted on the phenyl ring with one to three halogen atoms;

such as phenylmethylidene, phenylethylidene, phenylpropylidene, phenylisopropylidene, phenylbutylidene, phenylpentylidene, phenylhexylidene, 2-chlorophenylmethylidene, 3-chlorophenylmethylidene, 4-chlorophenylmethylidene, 2-fluorophenylmethylidene, 3-fluorophenylmethylidene, 4-fluorophenylmethylidene, 2-bromophenylmethylidene, 3-bromophenylmethylidene, 4-bromophenylmethylidene, 2-iodophenylmethylidene, 2,3-dichlorophenylmethylidene, 2,4-difluorophenylmethylidene, 2,4,6-trichlorophenylmethylidene, 2,3,5-trifluorophenylmethylidene, and 2-fluoro-4-chlorophenylmethylidene.

Examples of phenyl lower alkoxycarbonyl groups include phenylalkoxycarbonyl groups wherein the alkoxy moiety is a straight or branched $C_{1-6}$ alkoxy group, such as benzyloxycarbonyl, 2-phenylethoxycarbonyl, 1-phenylethoxycarbonyl, 3-phenylpropoxy carbonyl, 4-phenylbutoxycarbonyl, 5-phenylpentyloxycarbonyl, 6-phenylhexyloxycarbonyl, 1,1-dimethyl-2-phenylethoxycarbonyl, and 2-methyl-3-phenylpropoxycarbonyl.

Examples of pyridyl groups optionally substituted on the pyridine ring with one or more members selected from the group consisting of a cyano group and lower alkyl groups include;

pyridyl groups optionally substituted on the pyridine ring with one to three members selected from the group consisting of a cyano group and the above-described straight and branched $C_{1-6}$ alkyl groups;

such as (2-, 3-, or 4-)pyridyl, 2-methyl-(3-, 4-, 5-, or 6-)pyridyl, 3-methyl-(2-, 4-, 5-, or 6-)pyridyl, 4-methyl-(2- or 3-)pyridyl, 2-cyano-(3-, 4-, 5-, or 6-)pyridyl, 3-cyano-(2-, 4-, 5-, or 6-)pyridyl, 4-cyano-(2- or 3-)pyridyl, 2,3-dimethyl-(4-, 5-, or 6-)pyridyl, 3,4,5-trimethyl-(2- or 6-)pyridyl, 2,4-dicyano-(3-, 5-, or 6-)pyridyl, 2,4,5-tricyano-(3- or 6-)pyridyl, and 2-methyl-4-cyano-(3-, 5-, or 6-)pyridyl.

Examples of 1,3-dioxolanyl lower alkyl groups include 1,3-dioxolanylalkyl groups wherein the alkyl moiety is a straight or branched $C_{1-6}$ alkyl group, such as [(2- or 4-)1,3-dioxolanyl]methyl, 2-[(2- or 4-)1,3-dioxolanyl]ethyl, 1-[(2- or 4-)1,3-dioxolanyl]ethyl, 3-[(2- or 4-)1,3-dioxolanyl]propyl, 4-[(2- or 4-)1,3-dioxolanyl]butyl, 1,1-dimethyl-2-[(2- or 4-)1,3-dioxolanyl]ethyl, 5-[(2- or 4-)1,3-dioxolanyl]pentyl, 6-[(2- or 4-)1,3-dioxolanyl]hexyl, 1-[(2- or 4-)1,3-dioxolanyl]isopropyl, and 2-methyl-3-[(1-, 2-, or 4-)1,3-dioxolanyl]propyl.

Examples of 5- to 8-membered saturated heterocyclic rings formed from $R^8$ and $R^9$ being linked together, together with the nitrogen atom to which they are bound, the heterocyclic ring optionally containing one or more additional heteroatoms, include:

5- to 8-membered saturated heterocyclic rings formed from $R^8$ and $R^9$ being linked together, together with the nitrogen atom to which they are bound, the heterocyclic ring optionally containing one or more additional heteroatoms selected from oxygen, nitrogen, and sulfur atom;

such as pyrrolidine, piperazine, piperidine, morpholine, thiomorpholine, imidazolidine, thiazolidine, isothiazolidine, oxazolidine, isoxazolidine, isothiazolidine, pyrazolidine, perhydroazepine, and perhydroazocine.

Examples of octahydropyrrolo[1,2-a]pyrazinyl groups optionally substituted on the pyrazine ring with one or more lower alkyl groups include octahydropyrrolo[1,2-a]pyrazinyl groups optionally substituted on the pyrazine ring with one to three straight and/or branched $C_{1-6}$ alkyl groups.

Examples of 8-azabicyclo[3.2.1]octyl groups optionally substituted on the 8-azabicyclo[3.2.1]octyl group with one or more phenoxy groups, each phenoxy substituent optionally being substituted on the phenyl ring with one or more halogen atoms, include 8-azabicyclo[3.2.1]octyl groups optionally substituted on the 8-azabicyclo[3.2.1]octyl group with one to three phenoxy groups, each phenoxy substituent optionally being substituted on the phenyl ring with one to three halogen atoms.

Examples of 5- or 6-membered saturated heterocyclic rings formed from $R^{11}$ and $R^{12}$, or $R^{13}$ and $R^{14}$ being linked together, together with the nitrogen atom to which they are bound, the heterocyclic ring optionally containing one or more additional heteroatoms, include:

5- or 6-membered saturated heterocyclic rings formed from $R^{11}$ and $R^{12}$, or $R^{13}$ and $R^{14}$ being linked together, together with the nitrogen atom to which they are bound, the heterocyclic ring optionally containing one or more additional heteroatoms selected from oxygen, nitrogen, and sulfur atom;

such as pyrrolidine, piperazine, piperidine, morpholine, thiomorpholine, imidazolidine, thiazolidine, isothiazolidine, oxazolidine, isoxazolidine, isothiazolidine, and pyrazolidine.

Examples of phenyl groups optionally substituted on the phenyl ring with one or more members selected from the group consisting of lower alkyl groups optionally substituted with one or more halogen atoms; lower alkylthio groups; lower alkoxy groups optionally substituted with one or more halogen atoms; halogen atoms; a phenyl group; lower alkylamino groups; a cyano group; a phenoxy group; cycloalkyl groups; pyrrolidinyl groups optionally substituted with one or more oxo groups; 1,2,3,4-tetrahydroisoquinolylcarbonyl groups; 1,2,3,4-tetrahydroquinolylcarbonyl groups optionally substituted with one or more lower alkyl groups; 1,2,3,4-tetrahydroquinoxalinylcarbonyl groups optionally substituted with one or more lower alkyl groups; thiazolyl groups optionally substituted with one or more phenyl groups; a carbamoyl group; phenyl lower alkoxy groups; lower alkylsulfonylamino groups; anilino groups optionally substituted with one or more halogen atoms; phenyl lower alkyl groups; and hydroxy-substituted lower alkyl groups include:

phenyl groups optionally substituted on the phenyl ring with one to three members selected from the group consisting of straight and branched $C_{1-6}$ alkyl groups optionally substituted with one to three halogen atoms; straight and branched $C_{1-6}$ alkylthio groups; straight and branched $C_{1-6}$ alkoxy groups optionally substituted with one to three halogen atoms; halogen atoms; a phenyl group; amino groups optionally substituted with one or two straight and/or branched $C_{1-6}$ alkyl groups; a cyano group; a phenoxy group; $C_{3-8}$ cycloalkyl groups; pyrrolidinyl groups optionally substituted with one or two oxo groups; 1,2,3,4-tetrahydroisoquinolylcarbonyl groups; 1,2,3,4-tetrahydroquinolylcarbonyl groups optionally substituted with one to three straight and/or branched $C_{1-6}$ alkyl groups; 1,2,3,4-tetrahydroquinoxalinylcarbonyl groups optionally substituted with one to three straight and/or branched $C_{1-6}$ alkyl groups; thiazolyl groups optionally substituted with one to three phenyl groups; a carbamoyl group; phenyl alkoxy groups wherein the alkoxy moiety is a straight or branched $C_{1-6}$ alkoxy group; straight and branched $C_{1-6}$ alkylsulfonylamino groups; anilino groups optionally substituted with one to three halogen atoms; phenyl alkyl groups wherein the alkyl moiety is a straight or branched $C_{1-6}$ alkyl group; and hydroxy-substituted alkyl groups wherein the alkyl moiety is a straight or branched $C_{1-6}$ alkyl group, substituted with one to three hydroxy groups;

such as (2-, 3-, or 4-)trifluoromethylphenyl, (2-, 3-, or 4-)methylthiophenyl, (2-, 3-, or 4-)trifluoromethoxyphenyl, (2-, 3-, or 4-)ethylphenyl, (2-, 3-, or 4-)propylphenyl, (2-, 3-, or 4-)butylphenyl, (2-, 3-, or 4-)pentylphenyl, (2-, 3-, or 4-)hexylphenyl, (2-, 3-, or 4-)isopropylphenyl, (2-, 3-, or 4-)chlorophenyl, (2-, 3-, or 4-)fluorophenyl, (2-, 3-, or 4-)phenylphenyl, (2-, 3-, or 4-)dimethylaminophenyl, (2-, 3-, or 4-)cyanophenyl, (2-, 3-, or 4-)phenyloxyphenyl, (3,4-, 2,3-, 2,6-, or 3,5-)dimethylphenyl, (3,4-, 2,3-, 2,6-, or 3,5-)difluorophenyl, 2-chloro-4-methylphenyl, (2-, 3-, or 4-)cyclohexylphenyl, (2-, 3-, or 4-)benzyloxyphenyl, (2-, 3-, or 4-)methylsulfonylaminophenyl, (2-, 3- or 4-)anilinophenyl, (3,4-, 2,3-, 2,6- or 3,5-)dimethoxyphenyl, 3-chloro-4-methoxyphenyl, 3-chloro-4-methylphenyl, 3-methoxy-5-trifluoromethylphenyl, 2-chloro-5-trifluoromethylphenyl, 2-chloro-6-cyanophenyl, 2-chloro-5-carbamoylphenyl, (2-, 3-, or 4-)phenylmethylphenyl, (2-, 3-, or 4-)pyrrolidinylphenyl, (2-, 3-, or 4-)[(1-, 2-, 3-, or 4-)(1,2,3,4-tetrahydroisoquinolylcarbonyl)phenyl, (2-, 3-, or 4-)[(1-, 2-, 3-, or 4-)(6-methyl-1,2,3,4-tetrahydroquinolyl carbonyl)]phenyl, (2-, 3-, or 4-)(4-fluoroanilino)phenyl, (2-, 3- or 4-)[4-methyl-1-(1,2,3,4-tetrahydroquinoxalinyl)carbonyl]phenyl, and (2-, 3-, or 4-)[(4- or 5-)phenylthiazolyl-2-yl]phenyl.

Examples of phenyl lower alkyl groups optionally substituted on the phenyl ring with one or more members selected from the group consisting of lower alkyl groups optionally substituted with one or more halogen atoms; lower alkoxy groups optionally substituted with one or more halogen atoms; halogen atoms; and a phenyl group include:

phenyl alkyl groups wherein the alkyl moiety is a straight or branched $C_{1-6}$ alkyl group, optionally substituted on the phenyl ring with one to three members selected from the group consisting of straight and branched $C_{1-6}$ alkyl groups optionally substituted with one to three halogen atoms; straight and branched $C_{1-6}$ alkoxy groups optionally substituted with one to three halogen atoms; halogen atoms; and a phenyl group;

such as benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl, 1,1-diphenylmethyl, 2,2-diphenylethyl, 3,3-diphenylpropyl, 1,2-diphenylethyl, 4-chlorobenzyl, 2-chlorobenzyl, 3-chlorobenzyl, 3-fluorobenzyl, 4-fluorobenzyl, (2- or 4-)bromobenzyl, 2,3-dichlorobenzyl, 2,4-dichlorobenzyl, 3-chloro-4-fluorobenzyl, 2,4,6-trifluorobenzyl, 3-trifluoromethylbenzyl, 4-trifluoromethylbenzyl, 2-methylbenzyl, 3-methylbenzyl, 4-methylbenzyl, 4-tert-butylbenzyl, 2,4-dimethylbenzyl, 2,4,6-trimethylbenzyl, 2-phenylbenzyl, 3-phenylbenzyl, 4-phenylbenzyl, 2,4-diphenylbenzyl, 2,4,6-triphenylbenzyl, 2-trifluoromethoxybenzyl, 3-trifluoromethoxybenzyl, 4-trifluoromethoxybenzyl, 3-chloro-4-difluoromethoxybenzyl, 4-chloro-3-trifluoromethylbenzyl, 2-methoxybenzyl, 3-methoxybenzyl, 4-methoxybenzyl, 3,4-dimethoxybenzyl, 3,4,5-trimethoxybenzyl, 2-(4-methoxyphenyl)ethyl, 2-(2-methoxyphenyl)ethyl, and 2-(4-chlorophenyl)ethyl.

Examples of lower alkyl-substituted amino lower alkyl groups include:

aminoalkyl groups wherein the alkyl moiety is a straight or branched $C_{1-6}$ alkyl group, having on the amino group one or two straight and/or branched $C_{1-6}$ alkyl groups;

such as N-methylaminomethyl, N,N-diethylaminomethyl, N,N-di-n-propylaminoethyl, N,N-diisopropylaminoethyl, 3-(N,N-dimethylamino)propyl, 4-(N,N-dimethylamino)butyl, 5-(N,N-dimethylamino)pentyl, and 6-(N,N-dimethylamino)hexyl.

Examples of pyrazinyl lower alkyl groups optionally substituted on the pyrazine ring with one or more lower alkyl groups include:

pyrazinylalkyl groups wherein the alkyl moiety is a straight or branched $C_{1-6}$ alkyl group, optionally substituted on the pyrazine ring with one to three straight and/or branched $C_{1-6}$ alkyl groups;

such as (2- or 3-)pyrazinylmethyl, (1- or 2-)(2- or 3-pyrazinyl)ethyl, 3-(2- or 3-)pyrazinylpropyl, 4-(2- or 3-)pyrazinylbutyl, 5-(2- or 3-)pyrazinylpentyl, 6-(2- or 3-)pyrazinylhexyl, 2-methyl-5-pyrazinylmethyl, (1- or 2-)(2-methyl-5-pyrazinyl)ethyl, 3-(2-methyl-5-pyrazinyl)propyl, 4-(2-ethyl-5-pyrazinyl)butyl, 5-(2-ethyl-5-pyrazinyl)pentyl, and 6-(2-methyl-5-pyrazinyl)hexyl.

Examples of pyrazolyl lower alkyl groups optionally substituted on the pyrazoline ring with one or more lower alkyl groups include:

pyrazolylalkyl groups wherein the alkyl moiety is a straight or branched $C_{1-6}$ alkyl group, optionally substituted on the pyrazoline ring with one to three straight and/or branched $C_{1-6}$ alkyl groups;

such as (3-, 4-, or 5-)pyrazolylmethyl, (1- or 2-)(3-, 4-, or 5-)pyrazolylethyl, 3-(3-, 4-, or 5-)pyrazolylpropyl, 4-(3-, 4-, or 5-)pyrazolylbutyl, 5-(3-, 4-, or 5-)pyrazolylpentyl, 6-(3-, 4-, or 5-)pyrazolylhexyl, [1-methyl-(3-, 4-, or 5-)pyrazolyl]methyl, [1,5-dimethyl-(3- or 4-)pyrazolyl]methyl, and [1,5-dimethyl-(3- or 4-)pyrazolyl]ethyl.

Examples of piperidinyl groups optionally substituted on the piperidine ring with one or more members selected from the group consisting of lower alkyl groups; a benzoyl group; and phenyl lower alkyl groups optionally substituted on the phenyl ring with one or more members selected from halogen atoms and lower alkyl groups include:

piperidinyl groups optionally substituted on the piperidine ring with one to three members selected from the group consisting of straight and branched $C_{1-6}$ alkyl groups; a benzoyl group; and phenyl lower alkyl groups wherein the alkyl moiety is a straight or branched $C_{1-6}$ alkyl group, optionally substituted on the phenyl ring with one to three members selected from the group consisting of halogen atoms and straight and branched $C_{1-6}$ alkyl groups;

such as, N-methyl-(2-, 3-, or 4-)piperidinyl, N-ethyl-(2-, 3-, or 4-)piperidinyl, N-n-propyl-(2-, 3-, or 4-)piperidinyl, N-benzoyl-(2-, 3-, or 4-)piperidinyl, 1-benzyl-4-piperidinyl, 1-phenylethyl-4-piperidinyl, 1-(2-, 3-, or 4-)chlorophenylmethyl-4-piperidinyl, and 1-(2-, 3-, or 4-)methylphenylmethyl-4-piperidinyl, 1,2,3-trimethyl-(4-, 5-, or 6-)piperidinyl, 1-benzyl-3-methyl-(2-, 4-, 5-, or 6-)piperidinyl, and 1-benzoyl-2-benzyl-(3-, 4-, 5-, or 6-)piperidinyl.

Examples of 3,4-dihydrocarbostyril groups optionally substituted with one or more lower alkyl groups include 3,4-dihydrocarbostyril groups optionally substituted with one to three straight and/or branched $C_{1-6}$ alkyl groups, such as 3,4-dihydro-(5-, 6-, 7-, or 8-)carbostyril and (6-, 7-, or 8-)methyl-3,4-dihydro-5-carbostyril.

Examples of quinolyl groups optionally substituted with one or more lower alkyl groups include quinolyl groups optionally substituted with one to three straight and/or branched $C_{1-6}$ alkyl groups, such as (2-, 3-, 4-, 5-, 6-, 7- or 8-)quinolyl and 2-methyl-4-quinolyl.

Examples of carbazolyl groups optionally substituted with one or more lower alkyl groups include carbazolyl groups optionally substituted with one to three straight and branched $C_{1-6}$ alkyl groups, such as N-methyl-(2-, 3-, 4-, or 5-)carbazolyl and N-ethyl-(2-, 3-, 4-, or 5-)carbazolyl.

Examples of phenyl lower alkylcarbamoyl lower alkyl groups include phenylalkylcarbamoylalkyl groups wherein each of the two alkyl moieties is a straight or branched $C_{1-6}$ alkyl group, such as phenylmethylcarbamoylmethyl, (1- or 2-)phenylethyl carbamoylmethyl, (1- or 2-)phenylethylcarbamoylethyl, 3-(2-phenylethylcarbamoyl)propyl, 4-(2-phenylethylcarbamoyl)butyl, 5-(2-phenylethylcarbamoyl)pentyl, and 6-(2-phenylethylcarbamoyl)hexyl.

Examples of phenylcarbamoyl lower alkyl groups include phenylcarbamoylalkyl groups wherein the alkyl moiety is a straight or branched $C_{1-6}$ alkyl group, such as phenylcarbamoylmethyl, (1- or 2-)phenylcarbamoylethyl, 3-(phenylcarbamoyl)propyl, 4-(phenylcarbamoyl)butyl, 5-(phenylcarbamoyl)pentyl, and 6-(phenylcarbamoyl)hexyl.

Examples of anilino groups optionally substituted on the phenyl ring with one or more lower alkoxy groups, each lower alkoxy substituent optionally being substituted with one or more halogen atoms, include:

anilino groups optionally substituted on the phenyl ring with one to three straight and/or branched $C_{1-6}$ alkoxy groups, each alkoxy substituent optionally being substituted with one to three halogen atoms;

such as (2-, 3-, or 4-)chloromethoxyanilino, and (2-, 3-, or 4-)trifluoromethoxyanilino.

Examples of anilino groups substituted on the amino group with one or more lower alkyl groups and further substituted on the phenyl ring with one or more halogen atoms include:

anilino groups substituted on the amino group with one to three straight and/or branched $C_{1-6}$ alkyl groups and further substituted on the phenyl ring with one to three halogen atoms;

such as N-methyl-(2-, 3-, or 4-)chloroanilino, N-ethyl-(2-, 3-, or 4-)chloroanilino, N-methyl-(2-, 3-, or 4-)bromoanilino, N-methyl-(2-, 3-, or 4-)fluoroanilino, N-ethyl-(2-, 3-, or 4-)iodoanilino, and N-n-propyl-(2-, 3-, or 4-)chloroanilino.

Examples of 5- and 6-membered unsaturated heterocyclic rings formed from $R^8$ and $R^9$ being linked together, together with the nitrogen atom to which they are bound, include (2- or 3-)pyrroline, 1,2-dihydropyridine, 2,3-dihydropyridine, 1,2,3,4-tetrahydropyridine, and 1,2,5,6-tetrahydropyridine.

Examples of benzoyl groups optionally substituted on the phenyl ring with one or more members selected from the group consisting of lower alkyl groups optionally substituted with one or more halogen atoms; a phenyl group; halogen atoms; a cyano group; a phenoxy group; lower alkoxycarbonyl groups; pyrazolyl groups; and lower alkoxy groups optionally substituted with one or more halogen atoms include:

benzoyl groups optionally substituted on the phenyl ring with one to three members selected from the group consisting of the above-described straight and branched $C_{1-6}$ alkyl groups optionally substituted with one to three halogen atoms; a phenyl group; halogen atoms; a cyano group; a phenoxy group; the above-described straight and branched $C_{1-6}$ alkoxycarbonyl groups; pyrazolyl groups; and the above-described straight and branched $C_{1-6}$ alkoxy groups optionally substituted with one to three halogen atoms;

such as benzoyl, 4-methylbenzoyl, 3-methylbenzoyl, 2-methylbenzoyl, 4-tert-butylbenzoyl, 2,4-dimethylbenzoyl, 2,4,6-trimethylbenzoyl, 3-trifluoromethylbenzoyl, 4-trifluoromethylbenzoyl, 2-trifluoromethylbenzoyl, 4-phenylbenzoyl, 4-chlorobenzoyl, 3-chlorobenzoyl, 2-chlorobenzoyl, 4-fluorobenzoyl, 3-fluorobenzoyl, 2-fluorobenzoyl, 3-bromobenzoyl, 2-bromobenzoyl, 4-bromobenzoyl, 3,4-dichlorobenzoyl, 2,3-dichlorobenzoyl, 2-chloro-4-fluorobenzoyl, 2-methoxy-5-chlorobenzoyl, 4-methoxybenzoyl, 3-methoxybenzoyl, 2-methoxybenzoyl, 3,4-dimethoxybenzoyl, 3,4,5-trimethoxybenzoyl, 3-trifluoromethoxybenzoyl, 4-trifluoromethoxybenzoyl, 2-trifluoromethoxybenzoyl, 3-cyanobenzoyl, 4-cyanobenzoyl, 2-cyanobenzoyl, 3-phenoxybenzoyl, 2-phenoxybenzoyl, 4-phenoxybenzoyl, 4-methoxycarbonylbenzoyl, 3-ethoxycarbonylbenzoyl, 2-tert-butoxycarbonylbenzoyl, and 4-(1-pyrazolyl)benzoyl.

Examples of alkanoyl groups include straight and branched $C_{1-10}$ alkanoyl groups, such as, in addition to the above-described lower alkanoyl groups, heptanoyl, octanoyl, nonanoyl, decanoyl, and 2-ethyl-hexanoyl.

Examples of phenyl lower alkanoyl groups optionally substituted on the phenyl ring with one or more members selected from the group consisting of halogen atoms and lower alkyl groups include:

phenylalkanoyl groups wherein the alkanoyl moiety is a straight or branched $C_{2-6}$ alkanoyl group, optionally substituted on the phenyl ring with one to three members selected from the group consisting of halogen atoms and straight and branched $C_{1-6}$ alkyl groups;

such as 2-phenylacetyl, 3-phenylpropionyl, 2-phenylpropionyl, 4-phenylbutyryl, 5-phenylpentanoyl, 6-phenylhexanoyl, 2,2-dimethyl-3-phenylpropionyl, 2-methyl-3-phenylpropionyl, 2-(4-fluorophenyl)acetyl, 3-(2,5-difluorophenyl)propionyl, 2-(2,4-difluorophenyl)propionyl, 4-(3,4-difluorophenyl)butyryl, 5-(3,5-difluorophenyl)pentanoyl, 6-(2,6-difluorophenyl)hexanoyl, 2-(2-chlorophenyl)acetyl, 3-(3-chlorophenyl)propionyl, 2-(4-chlorophenyl)propionyl, 4-(2,3-dichlorophenyl)propionyl, 5-(2,4-dichlorophenyl)pentanoyl, 6-(2,5-dichlorophenyl)hexanoyl, 2-(3,4-dichlorophenyl)acetyl, 3-(2,6-dichlorophenyl)propionyl, 2-(3-fluorophenyl)propionyl, 4-(2-fluorophenyl)butyryl, 5-(3-bromophenyl)pentanoyl, 6-(4-iodophenyl)hexanoyl, 2-(2-bromophenyl)acetyl, 3-(4-bromophenyl)propionyl, 2-(3,5-dichlorophenyl)propionyl, 4-(2,4,6-trifluorophenyl)butyryl, 5-(3,4-difluorophenyl)pentanoyl, 6-(2-iodophenyl)hexanoyl, 2-(3-iodophenyl)acetyl, 3-(4-iodophenyl)propionyl, 2-(2,3-dibromophenyl)propionyl, 4-(2,4-diiodophenyl)butyryl, 2-(2,4,6-trichlorophenyl)acetyl, 2-(4-methylphenyl)acetyl, 3-(2,5-dimethylphenyl)propionyl, 2-(2,4-diethylphenyl)propionyl, 4-(3,4-di-n-propylphenyl)butyryl, 2-(2-ethylphenyl)acetyl, 3-(3-n-propylphenyl)propionyl, 2-(4-tert-butylphenyl)propionyl, 2-(2,4,6-trimethylphenyl)acetyl, 2-(2,5-dichloro-4-methylphenyl)acetyl, 2-(3-methyl-4-chlorophenyl)acetyl, 4-(2-n-butylphenyl)butyryl, 5-(3-n-pentylphenyl)pentanoyl, and 6-(4-n-hexylphenyl)hexanoyl.

Examples of phenoxy lower alkanoyl groups optionally substituted on the phenyl ring with one or more halogen atoms include:

phenoxyalkanoyl groups wherein the alkanoyl moiety is a straight or branched $C_{2-6}$ alkanoyl group, optionally substituted on the phenyl ring with one to three halogen atoms;

such as, in addition to the above-described phenoxy lower alkanoyl groups, 2-(4-chlorophenoxy)acetyl, 2-(4-fluorophenoxy)acetyl, 3-(2,5-difluorophenoxy)propionyl, 2-(2,4-difluorophenoxy)propionyl, 4-(3,4-difluorophenoxy)butyryl, 5-(3,5-difluorophenoxy)pentanoyl, 6-(2,6-difluorophenoxy)hexanoyl, 2-(2-chlorophenoxy)acetyl, 3-(3-chlorophenoxy)propionyl, 2-(4-chlorophenoxy)propionyl, 4-(2,3-dichlorophenoxy)propionyl, 5-(2,4-dichlorophenoxy)pentanoyl, 6-(2,5-dichlorophenoxy)hexanoyl, 2-(3,4-dichlorophenoxy)acetyl, 3-(2,6-dichlorophenoxy)propionyl, 2-(3-fluorophenoxy)propionyl, 4-(2-fluorophenoxy)butyryl, 5-(3-bromophenoxy)pentanoyl, 6-(4-iodophenoxy)hexanoyl, 2-(2-bromophenoxy)acetyl, 3-(4-bromophenoxy)propionyl, 2-(3,5-dichlorophenoxy)propionyl, 4-(2,4,6-trifluorophenoxy)butyryl, 5-(3,4-difluorophenoxy)pentanoyl, 6-(2-iodophenoxy)hexanoyl, 2-(3-iodophenoxy)acetyl, 3-(4-iodophenoxy)propionyl, 2-(2,3-dibromophenoxy)propionyl, 4-(2,4-diiodophenoxy)butyryl, and 2-(2,4,6-trichlorophenoxy)acetyl.

Examples of phenyl lower alkenylcarbonyl groups include phenylalkenylcarbonyl groups containing one to three double bonds wherein the alkenyl moiety is a straight or branched $C_{2-6}$ alkenyl group, such as styrylcarbonyl (trivial name: cinnamoyl), 3-phenyl-2-propenylcarbonyl, 4-phenyl-2-butenylcarbonyl, 4-phenyl-3-butenylcarbonyl, 5-phenyl-4-pentenylcarbonyl, 5-phenyl-3-pentenylcarbonyl, 6-phenyl-5-hexenylcarbonyl, 6-phenyl-4-hexenylcarbonyl, 6-phenyl-3-hexenylcarbonyl, 4-phenyl-1,3-butadienylcarbonyl, and 6-phenyl-1,3,5-hexatrienylcarbonyl.

Examples of pyridylcarbonyl groups optionally substituted on the pyridine ring with one or more members selected from the group consisting of halogen atoms and lower alkyl groups, each lower alkyl substituent optionally being substituted with one or more halogen atoms, include:

pyridylcarbonyl groups optionally substituted on the pyridine ring with one to three members selected from the group consisting of halogen atoms and the above-described straight and branched $C_{1-6}$ alkyl groups optionally substituted with one to three halogen atoms;

such as (2-, 3-, or 4-)pyridylcarbonyl, 2-chloro-(3-, 4-, 5-, or 6-)pyridylcarbonyl, 2,6-dichloro-(3-, 4-, or 5-)pyridylcarbonyl, 2,3-dichloro-(4-, 5-, or 6-)pyridylcarbonyl, 2-trifluoromethyl-(3-, 4-, 5-, or 6-)pyridylcarbonyl, 2-bromo-(3-, 4-, 5-, or 6-)pyridylcarbonyl, 2,6-difluoro-(3-, 4-, or 5-)pyridylcarbonyl, 4-methyl-(2-, 3-, 5-, or 6-)pyridylcarbonyl, 3-chloro-(2-, 4-, 5-, or 6-)pyridylcarbonyl, 2,5-dibromo-(3-, 4-, or 5-)pyridylcarbonyl, 2-ethyl-4-chloro-(3-, 5-, or 6-)pyridylcarbonyl, 2,4,6-trifluoro-(3- or 5-)pyridylcarbonyl, 2,4- dimethyl-(3-, 5-, or 6-)pyridylcarbonyl, 2,4,6-trimethyl-(3- or 5-)pyridylcarbonyl, and 2-methyl-4-chloro-(3-, 5-, or 6-)pyridylcarbonyl.

Examples of piperidinylcarbonyl groups optionally substituted on the piperidine ring with one or more lower alkanoyl groups include piperidinylcarbonyl groups optionally substituted on the piperidine ring with one to three straight and/or branched $C_{1-6}$ alkanoyl groups, such as (2-, 3-, or 4-)piperidinylcarbonyl, 1-acetyl-(2-, 3-, or 4-)piperidinylcarbonyl, 1-n-propanoyl-(2-, 3-, or 4-)piperidinylcarbonyl, 1-isopropanoyl-(2-, 3-, or 4-)piperidinylcarbonyl, 1-n-butyryl-(2-, 3-, or 4-)piperidinylcarbonyl, 1-n-pentanoyl-(2-, 3-, or 4-)piperidinylcarbonyl, 1-n-hexanoyl-(2-, 3-, or 4-)piperidinylcarbonyl, 1,2-diacetyl-(3-, 4-, 5-, or 6-)piperidinylcarbonyl, 1,2,3-triacetyl-(4-, 5-, or 6-)piperidinylcarbonyl, 2-acetyl-(1-, 3-, 4-, 5-, or 6-)piperidinylcarbonyl, 3-propanoyl-(1-, 2-, 4-, 5-, or 6-)piperidinylcarbonyl, and 2-formyl-4-propanoyl-(1-, 3-, 5-, or 6-)piperidinylcarbonyl.

Examples of tetrahydropyranylcarbonyl groups include 2-tetrahydropyranylcarbonyl, 3-tetrahydropyranylcarbonyl, and 4-tetrahydropyranylcarbonyl.

Examples of benzothienylcarbonyl groups optionally substituted on the benzothiophene ring with one or more halogen atoms include benzothienylcarbonyl groups optionally substituted on the benzothiophene ring with one to three halogen atoms, such as (2-, 3-, 4-, 5-, 6-, or 7-)benzothienylcarbonyl, [3-chloro-(2-, 4-, 5-, 6-, or 7-)benzothienyl]carbonyl, [4-bromo-(2-, 3-, 5-, 6-, or 7-)benzothienyl]carbonyl, [5-fluoro-(2-, 3-, 4-, 6-, or 7-)benzothienyl]carbonyl, [6-iodo-(2-, 3-, 4-, 5-, or 7-)benzothienyl]carbonyl, [7-chloro-(2-, 3-, 4-, 5-, or 6-)benzothienyl]carbonyl, [2-chloro-(3-, 4-, 5-, 6-, or 7-)benzothienyl]carbonyl, [2,3-dichloro-(4-, 5-, 6-, or 7-)benzothienyl]carbonyl, and [3,4,6-trichloro-(2-, 5- or 7-)benzothienyl]carbonyl.

Examples of pyridyl lower alkyl groups optionally substituted on the pyridine ring with one or more members selected from the group consisting of halogen atoms and lower alkyl groups, each lower alkyl substituent optionally being substituted with one or more halogen atoms, include:

pyridylalkyl groups wherein the alkyl moiety is a straight or branched $C_{1-6}$ alkyl group, optionally substituted on the pyridine ring with one to three members selected from the group consisting of halogen atoms and the above-described straight and branched $C_{1-6}$ alkyl groups optionally substituted with one to three halogen atoms;

such as (2-, 3-, or 4-)pyridylmethyl, 2-[(2-, 3-, or 4-)pyridyl]ethyl, 1-[(2-, 3-, or 4-)pyridyl]ethyl, 3-[(2-, 3-, or 4-)pyridyl]propyl, 4-[(2-, 3-, or 4-)pyridyl]butyl, 1,1-dimethyl-2-[(2-, 3-, or 4-)pyridyl]ethyl, 5-[(2-, 3-, or 4-)pyridyl]pentyl, 6-[(2-, 3-, or 4-)pyridyl]hexyl-1-[(2-, 3-, or 4-)pyridyl]isopropyl, 2-methyl-3-[(2-, 3-, or 4-)pyridyl]propyl, [2-chloro-(3-, 4-, 5-, or 6-)pyridyl]methyl, [2,3-dichloro-(4-, 5-, or 6-)pyridyl]methyl, [2-bromo-(3-, 4-, 5-, or 6-)pyridyl]methyl, [2,4,6-trifluoro-(3-, 5-, or 6-)pyridyl]methyl, [2-trifluoromethyl-(3-, 4-, 5-, or 6-)pyridyl]methyl, [2-methyl-(3-, 4-, 5-, or 6-)pyridyl]methyl, [2-ethyl-(3-, 4-, 5-, or 6-)pyridyl]methyl, 2-[2-n-propyl-(3-, 4-, 5-, or 6-)pyridyl]ethyl, 3-[2-n-butyl-(3-, 4-, 5-, or 6-)pyridyl]propyl, 4-[2-n-pentyl-(3-, 4-, 5-, or 6-)pyridyl]butyl, 5-[2-n-hexyl-(3-, 4-, 5-, or 6-)pyridyl]pentyl, 6-[2-isopropyl-(3-, 4-, 5-, or 6-)pyridyl]hexyl, [2-tert-butyl-(3-, 4-, 5-, or 6-)pyridyl]methyl, [2,4-dimethyl-(3-, 5-, or 6-)pyridyl]methyl, [2,4,6-trimethyl-(3- or 5-)pyridyl]methyl, [2,4-ditrifluoromethyl-(3-, 5-, or 6-)pyridyl]methyl, 2-(2,4-bistrifluoromethyl)-(3-, 5-, or 6-)pyridyl)ethyl, and 3-[2-methyl-6-chloro-(3-, 4-, or 5-)pyridyl]propyl.

Examples of thienyl lower alkyl groups optionally substituted on the thiophene ring with one or more halogen atoms include:

thienylalkyl groups wherein the alkyl moiety is a straight or branched $C_{1-6}$ alkyl group, optionally substituted on the thiophene ring with one to three halogen atoms;

such as [(2- or 3-)thienyl]methyl, 2-[(2- or 3-)thienyl]ethyl, 1-[(2- or 3-)thienyl]ethyl, 3-[(2- or 3-)thienyl]propyl, 4-[(2- or 3-)thienyl]butyl, 5-[(2- or 3-)thienyl]pentyl, 6-[(2- or 3-)thienyl]hexyl, 1,1-dimethyl-2-[(2- or 3-)thienyl]ethyl, 2-methyl-3-[(2- or 3-)thienyl]propyl, [2-chloro-(3-, 4-, or 5-)thienyl]methyl, [4-bromo-(2-, 3-, or 5-)thienyl]methyl, [5-fluoro-(2-, 3-, or 4-)thienyl]methyl, [3-iodo-(2-, 4-, or 5-)thienyl]methyl, [2,3-dichloro-(4- or 5-)thienyl]methyl, (2,4,5-trichloro-3-thienyl)methyl, 2-[2-fluoro-(3-, 4-, or 5-)thienyl]ethyl, 1-[4-iodo-(2-, 3-, or 5-)thienyl]ethyl, 3-[3-chloro-(2-, 4-, or 5-)thienyl]propyl, 4-[4,5-dichloro-(2- or 3-)thienyl]butyl, 5-(2,4,5-trichloro-3-thienyl)pentyl, and 6-[2-chloro-(3-, 4-, or 5-)thienyl]hexyl.

Examples of amino groups optionally substituted with one or more members selected from the group consisting of lower alkyl groups and lower alkanoyl groups include:

amino groups optionally substituted with one or two members selected from the group consisting of straight and branched $C_{1-6}$ alkyl groups and straight and branched $C_{1-6}$ alkanoyl groups;

such as amino, formylamino, acetylamino, propionylamino, butyrylamino, isobutyrylamino, pentanoylamino, tert-butylcarbonylamino, hexanoylamino, N,N-diacetylamino, N-acetyl-N-propionylamino, methylamino, ethylamino, n-propylamino, isopropylamino, n-butylamino, n-pentylamino, n-hexylamino, dimethylamino, 3-diethylamino, diisopropylamino, N-ethyl-N-n-propylamino, N-methyl-N-n-hexylamino, N-methyl-N-acetylamino, and N-ethyl-N-acetylamino.

Examples of phenyl lower alkyl groups optionally substituted on the phenyl ring with one or more members selected from the group consisting of lower alkoxy groups optionally substituted with one or more halogen atoms; a cyano group; lower alkyl groups optionally substituted with one or more halogen atoms; amino groups optionally substituted with one or more members selected from the group consisting of lower alkyl groups and lower alkanoyl groups; halogen atoms; lower alkoxycarbonyl groups; lower alkanoyloxy groups; lower alkylsulfonyl groups; lower alkylthio groups; and pyrrolidinyl groups include:

mono- and di-phenylalkyl groups wherein the alkyl moiety is a straight or branched $C_{1-6}$ alkyl group, optionally substituted on the phenyl ring with one to three members selected from the group consisting of the above-described straight and branched $C_{1-6}$ alkoxy groups optionally substituted with one to three halogen atoms; a cyano group; the above-described straight and branched $C_{1-6}$ alkyl groups optionally substituted with one to three halogen atoms; the above-described amino groups optionally substituted with one or two members selected from the group consisting of straight and branched $C_{1-6}$ alkyl groups and straight and branched $C_{1-6}$ alkanoyl groups; halogen atoms; the above-described straight and branched $C_{1-6}$ alkoxycarbonyl groups; the above-described straight and branched $C_{2-6}$ alkanoyloxy groups; the above-described straight and branched $C_{1-6}$ alkylsulfonyl groups; the above-described straight and branched $C_{1-6}$ alkylthio groups; and pyrrolidinyl groups;

such as benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl, 1,1-diphenylmethyl, 2,2-diphenylethyl, 3,3-diphenylpropyl, 1,2-diphenylethyl, 4-chlorobenzyl, 2-chlorobenzyl, 3-chlorobenzyl, 3-fluorobenzyl, 4-fluorobenzyl, 2-fluorobenzyl, 4-bromobenzyl, 3-bromobenzyl, 2-bromobenzyl, 1-(2-chlorophenyl)ethyl, 2,3-dichlorobenzyl, 2,4,6-trifluorobenzyl, 2-trifluoromethylbenzyl, 3-trifluoromethylbenzyl, 4-trifluoromethylbenzyl, 2-methylbenzyl, 3-methylbenzyl, 4-methylbenzyl, 4-tert-butylbenzyl, 4-n-butylbenzyl, 2,4-dimethylbenzyl, 2,4,6-trimethylbenzyl, 2-phenylbenzyl, 4-phenylbenzyl, 2,4-diphenylbenzyl, 2,4,6-triphenylbenzyl, 2-trifluoromethoxybenzyl, 3-trifluoromethoxybenzyl, 4-trifluoromethoxybenzyl, 4-difluoromethoxybenzyl, 2-methoxybenzyl, 3-methoxybenzyl, 4-methoxybenzyl, 4-n-butoxybenzyl, 4-tert-butoxybenzyl, 1-(3-methoxyphenyl)ethyl, 1-(4-methoxyphenyl)ethyl, 1-(2-methoxyphenyl)ethyl, 3,4-dimethoxybenzyl, 3,4,5-trimethoxybenzyl, 4-methoxycarbonylbenzyl, 3-ethoxycarbonylbenzyl, 2-n-propoxycarbonylbenzyl, 2,4-dimethoxycarbonylbenzyl, 2,4,6-trimethoxycarbonylbenzyl, 1-(4-n-butoxyphenyl)ethyl, 4-tert-butoxycarbonylbenzyl, 4-methylthiobenzyl, 3-methylthiobenzyl, 2-methylthiobenzyl, 4-ethylthiobenzyl, 2,4-dimethylthiobenzyl, 2,4,6-trimethylthiobenzyl, 4-methylsulfonylbenzyl, 3-methylsulfonylbenzyl, 2-methylsulfonylbenzyl, 3,4-dimethylsulfonylbenzyl, 3,4,5-trimethylsulfonylbenzyl, 4-methoxy-3-chlorobenzyl, 4-(N-acetylamino)benzyl, 4-(N,N-diethylamino)benzyl, 4-(N,N-dimethylamino)benzyl, 4-(N-methylamino)benzyl, 3-aminobenzyl, 2-aminobenzyl, 4-aminobenzyl, 4-acetyloxybenzyl, 2,3-diaminobenzyl, 3,4,5-triaminobenzyl, 4-methyl-3-fluorobenzyl, 4-cyanobenzyl, 3-cyanobenzyl, 2-cyanobenzyl, 4-(1-pyrrolidinyl)benzyl, 4-methoxy-2-chlorobenzyl, and 3-chloro-5-methylbenzyl.

Examples of thiazolyl lower alkyl groups include thiazolylalkyl groups wherein the alkyl moiety is a straight or branched $C_{1-6}$ alkyl group, such as [(2-, 4-, or 5-)thiazolyl]methyl, 2-[(2-, 4-, or 5-)thiazolyl]ethyl, 1-[(2-, 4-, or 5-)thiazolyl]ethyl, 3-[(2-, 4-, or 5-)thiazolyl]propyl, 4-[(2-, 4-, or 5-)thiazolyl]butyl, 5-[(2-, 4-, or 5-)thiazolyl]pentyl, 6-[(2-, 4-, or 5-)thiazolyl]hexyl, 1,1-dimethyl-2-[(2-, 4-, or 5-)thiazolyl]ethyl, and [2-methyl-3-[(2-, 4-, or 5-)thiazolyl]propyl.

Examples of imidazolyl lower alkyl groups optionally substituted on the imidazole ring with one or more lower alkyl groups include:

imidazolylalkyl groups wherein the alkyl moiety is a straight or branched $C_{1-6}$ alkyl group, optionally substituted on the imidazole ring with one to three above-described straight and branched $C_{1-6}$ alkyl groups;

such as [(1-, 2-, 4-, or 5-)imidazolyl]methyl, 2-[(1-, 2-, 4-, or 5-)imidazolyl]ethyl, 1-[(1-, 2-, 4-, or 5-)imidazolyl]ethyl, 3-[(1-, 2-, 4-, or 5-)imidazolyl]propyl, 4-[(1-, 2-, 4-, or 5-)imidazolyl]butyl, 1,1-dimethyl-2-[(1-, 2-, 4-, or 5-)imidazolyl]ethyl, 5-[(1-, 2-, 4-, or 5-)imidazolyl]pentyl, 6-[(1-, 2-, 4-, or 5-)imidazolyl]hexyl, 1-[(1-, 2-, 4-, or 5-)imidazolyl]isopropyl, 2-methyl-3-[(1-, 2-, 4-, or 5-)imidazolyl]propyl, [1-methyl-(2-, 4-, or 5-)imidazolyl]methyl, [1-ethyl-(2-, 4-, or 5-)imidazolyl]methyl, [1-n-propyl-(2-, 4-, or 5-)imidazolyl]methyl, [1-n-butyl-(2-, 4-, or 5-)imidazolyl]methyl, [1-n-pentyl-(2-, 4-, or 5-)imidazolyl]methyl, [1-n-hexyl-(2-, 4-, or 5-)imidazolyl]methyl, 2-[2-methyl-(1-, 4-, or 5-)imidazolyl]ethyl, 1-[1-ethyl-(2-, 4-, or 5-)imidazolyl]ethyl, 3-[1-ethyl-(2-, 4-, or 5-)imidazolyl]methyl, 4-[1-n-propyl-(2-, 4-, or 5-)imidazolyl]butyl, 5-[1-n-butyl-(2-, 4-, or 5-)imidazolyl]pentyl, 6-[1-n-pentyl-(2-, 4-, or 5-)imidazolyl]hexyl, [1,2-dimethyl-(4- or 5-)imidazolyl]methyl, and (1,2,4-trimethyl-5-imidazolyl)methyl.

Examples of pyrrolyl lower alkyl groups optionally substituted on the pyrrole ring with one or more lower alkyl groups include:

pyrrolylalkyl groups wherein the alkyl moiety is a straight or branched $C_{1-6}$ alkyl group, optionally substituted on the pyrrole ring with one to three above-described straight and branched $C_{1-6}$ alkyl groups;

such as [(1-, 2-, or 3-)pyrrolyl]methyl, 2-[(1-, 2-, or 3-)pyrrolyl]ethyl, 1-[(1-, 2-, or 3-)pyrrolyl]ethyl, 3-[(1-, 2-, or 3-)pyrrolyl]propyl, 4-[(1-, 2-, or 3-)pyrrolyl]butyl, 1,1-dimethyl-2-[(1-, 2-, or 3-)pyrrolyl]ethyl, 5-[(1-, 2-, or 3-)pyrrolyl]pentyl, 6-[(1-, 2-, or 3-)pyrrolyl]hexyl, 1-[(1-, 2-, or 3-)pyrrolyl]isopropyl, 2-methyl-3-[(1-, 2-, or 3-)pyrrolyl]propyl, [1-methyl-(2- or 3-)pyrrolyl]methyl, [1-ethyl-(2- or 3-)pyrrolyl]methyl, [1-n-propyl-(2- or 3-)pyrrolyl]methyl, [1-n-butyl-(2- or 3-)pyrrolyl]methyl, [1-n-pentyl-(2- or 3-)pyrrolyl]methyl, [1-n-hexyl-(2- or 3-)pyrrolyl]methyl, 2-[2-methyl-(1-, 3-, 4-, or 5-)pyrrolyl]ethyl, 1-[1-ethyl-(2- or 3-)pyrrolyl]ethyl, 3-[1-ethyl-(2- or 3-)pyrrolyl]methyl, 4-[1-n-propyl-(2- or 3-)pyrrolyl]butyl, 5-[1-n-butyl-(2- or 3-)pyrrolyl]pentyl, 6-[1-n-pentyl-(2- or 3-)pyrrolyl]hexyl, [1,2-dimethyl-(3-, 4-, or 5-)pyrrolyl]methyl, and [1,2,4-trimethyl-(3- or 5-)pyrrolyl]methyl.

Examples of lower alkylthio lower alkyl groups include alkylthioalkyl groups wherein each of the two alkyl moieties is a straight or branched $C_{1-6}$ alkyl group, such as methylthiomethyl, 2-methylthioethyl, 1-ethylthioethyl, 2-ethylthioethyl, 3-n-butylthiopropyl, 4-n-propylthiobutyl, 1,1-dimethyl-2-n-pentylthioethyl, 5-n-hexylthiopentyl, 6-methylthiohexyl, 1-ethylthioisopropyl, and 2-methyl-3-methylthiopropyl.

Examples of phenoxycarbonyl groups optionally substituted on the phenyl ring with one or more members selected from the group consisting of halogen atoms, lower alkyl groups, and lower alkoxy groups include:

phenoxycarbonyl groups optionally substituted on the phenyl ring with one to three members selected from the group consisting of halogen atoms, the above-described straight and branched $C_{1-6}$ aklyl groups, and the above-described straight and branched $C_{1-6}$ alkoxy groups;

such as phenoxycarbonyl, 4-chlorophenoxycarbonyl, 3-chlorophenoxycarbonyl, 2-chlorophenoxycarbonyl, 3,4-dichlorophenoxycarbonyl, 2,4,6-trichlorophenoxycarbonyl, 4-fluorophenoxycarbonyl, 3-fluorophenoxycarbonyl, 2-fluorophenoxycarbonyl, 2,4-difluorophenoxycarbonyl, 3,4,5-trifluorophenoxycarbonyl, 4-bromophenoxycarbonyl, 2-chloro-4-methoxyphenoxycarbonyl, 3-fluoro-5-methylphenoxycarbonyl, 4-methoxyphenoxycarbonyl, 3-methoxyphenoxycarbonyl, 2-methoxyphenoxycarbonyl, 3,4-dimethoxyphenoxycarbonyl, 2,4,5-trimethoxyphenoxycarbonyl, 4-methylphenoxycarbonyl, 3-methylphenoxycarbonyl, 2-methylphenoxycarbonyl, 2,5-dimethylphenoxycarbonyl, and 2,3,4-trimethylphenoxycarbonyl.

Examples of phenyl lower alkoxycarbonyl groups optionally substituted on the phenyl ring with one or more halogen atoms include:

phenylalkoxycarbonyl groups wherein the alkoxy moiety is a straight or branched $C_{1-6}$ alkoxy group, optionally substituted on the phenyl ring with one to three halogen atoms;

such as benzyloxycarbonyl, 2-phenylethoxycarbonyl, 1-phenylethoxycarbonyl, 3-phenylpropoxycarbonyl, 4-phenylbutoxycarbonyl, 5-phenylpentyloxycarbonyl, 6-phenylhexyloxycarbonyl, 1,1-dimethyl-2-phenylethoxycarbonyl, 2-methyl-3-phenylpropoxycarbonyl, 2-chlorobenzyloxycarbonyl, 3-chlorobenzyloxycarbonyl, 2-chlorobenzyloxycarbonyl, 3,4-dichlorobenzyloxycarbonyl, 2,4,6-trichlorobenzyloxycarbonyl, 4-fluorobenzyloxycarbonyl, 3-fluorobenzyloxycarbonyl, 2-fluorobenzyloxycarbonyl, 2,4-difluorobenzyloxycarbonyl, 3,4,5-trifluorobenzyloxycarbonyl, 4-bromobenzyloxycarbonyl, 4-nitrobenzyloxycarbonyl, and 3-nitrobenzyloxycarbonyl.

Examples of quinoxalinylcarbonyl groups include 2-quinoxalinylcarbonyl, 5-quinoxalinylcarbonyl, and 6-quinoxalinylcarbonyl.

Examples of phenyl lower alkanoyl groups include phenylalkanoyl groups wherein the alkanoyl moiety is a straight or branched $C_{2-6}$ alkanoyl group, such as 2-phenylacetyl, 3-phenylpropionyl, 2-phenylpropionyl, 4-phenylbutyryl, 5-phenylpentanoyl, 6-phenylhexanoyl, 2,2-dimethyl-2-phenylpropionyl, and 2-methyl-3-phenylpropionyl.

The compounds of the present invention can be produced according to, for example, Reaction Schemes 1 to 16. All the starting materials and target compounds shown in Reaction Schemes 1 to 16 may be in the form of suitable salts. Examples of such salts are as described for carbostyril compound of Formula (1) below.

Reaction Scheme 1

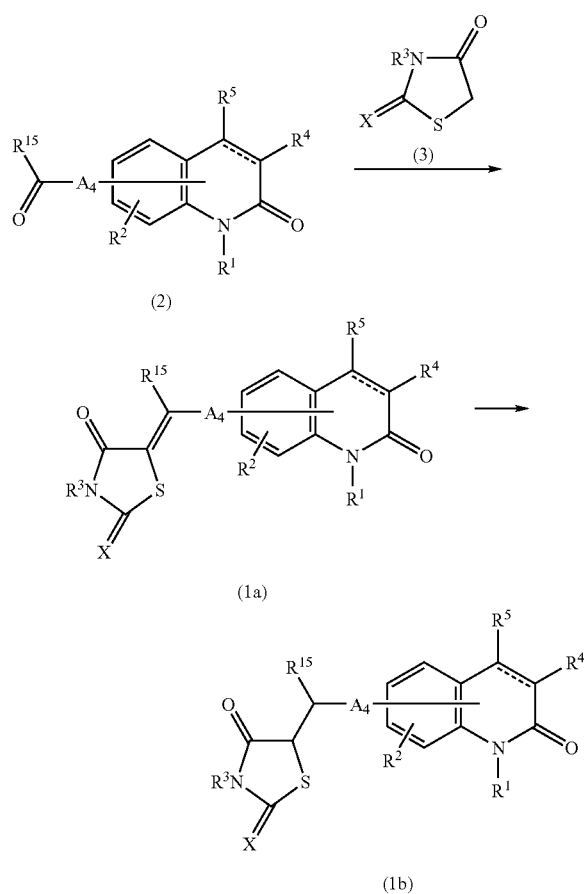

wherein $R^1$, $R^2$, $R^3$, $R^4$, $R^5$, X, and the bond between the 3- and 4-positions of the carbostyril skeleton are as defined above, $R^{15}$ is a hydrogen atom or lower alkyl group, and $A_4$ represents a direct bond or lower alkylene group, provided that the total number of carbon atoms of the group substituting the carbostyril skeleton, i.e., —$CH(R^{15})$-$A_4$-, is no greater than 6.

The reaction of Compound (2) with Compound (3) is carried out in a suitable solvent in the presence of a basic compound or acid.

Examples of solvents usable herein are aromatic hydrocarbons such as benzene, toluene and xylene, ethers such as diethyl ether, tetrahydrofuran, dioxane, monoglyme and diglyme, halogenated hydrocarbons such as dichloromethane, dichloroethane, chloroform and carbon tetrachloride, lower alcohols such as methanol, ethanol, isopropanol, butanol, tert-butanol and ethylene glycol, aliphatic acids such as acetic acid, esters such as ethyl acetate and methyl acetate, ketones such as acetone and methyl ethyl ketone, acetonitrile, pyridine, dimethyl sulfoxide, N,N-dimethylformamide, hexamethylphosphoric triamide, mixed solvents of such solvents, etc.

Examples of basic compounds are carbonates such as sodium carbonate, potassium carbonate, sodium hydrogencarbonate, potassium hydrogencarbonate and cesium carbonate, metal hydroxides such as sodium hydroxide, potassium hydroxide and calcium hydroxide, sodium hydride, potassium hydride, potassium, sodium, sodium amide, metal alcoholates such as sodium methylate, sodium ethylate and sodium n-butoxide, piperidine, pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), and like organic bases and mixtures thereof.

Examples of acids are organic acids such as p-toluenesulfonic acid and like sulfonic acids, and acetic acid, trifluoroacetic acid, trichloroacetic acid and like aliphatic acids; inorganic acids such as hydrochloric acid, sulfuric acid, hydrobromic acid, and phosphoric acid; and mixtures thereof.

In the present invention, a basic compound and an acid may be used in combination.

Basic compound or acid is usually used in a catalytic amount, and preferably about 0.01 to about 1 mol, per mol of Compound (2).

Compound (3) is usually used in an amount of at least 1 mol, and preferably about 1 to about 2 mol, per mol of Compound (2).

The reaction is usually carried out at about room temperature to about 200° C., and preferably about room temperature to about 150° C. The reaction is usually finished in about 0.5 to about 20 hours.

The reaction for producing Compound (1b) from Compound (1a) is carried out, for example, either without a solvent or in a suitable solvent, in the presence of a reducing agent.

Examples of solvents usable herein are water, lower alcohols such as methanol, ethanol, isopropanol, butanol, tert-butanol and ethylene glycol, acetonitrile, aliphatic acids such as formic acid and acetic acid, ethers such as diethyl ether, tetrahydrofuran, dioxane, monoglyme and diglyme, aromatic hydrocarbons such as benzene, toluene and xylene, halogenated hydrocarbons such as dichloromethane, dichloroethane, chloroform and carbon tetrachloride, N,N-dimethylformamide, mixtures of such solvents, etc.

Examples of reducing agents are mixtures of silicon dioxide and pyridine compounds such as diethyl 1,4-dihydro-2,6-dimethyl-3,5-pyridinedicarboxylate; sodium borohydride, lithium borohydride, sodium cyanoborohydride, sodium triacetoxy borohydride, aluminium lithium hydride, and like hydride reducing agents; mixtures of such hydride reducing agents; palladium black, palladium carbon, platinum oxide, platinum black, Raney nickel, and like catalytic hydrogenation reducing agent; etc.

When a mixture of a pyridine compound and silicon dioxide is used as a reducing agent, a suitable reaction temperature is usually about room temperature to about 200° C., and preferably about room temperature to about 150° C. The reaction is usually finished in about 0.5 to about 50 hours. The pyridine compound is usually used in an amount of at least 1 mol, and preferably 1 to 3 mol, per mol of Compound (1a). Silicon dioxide is usually used in an amount of at least 1 mol, and preferably 1 to 10 mol, per mol of Compound (1a).

When a hydride reducing agent is used, a suitable reaction temperature is usually about −80 to about 100° C. and preferably about −80 to about 70° C. The reaction is usually finished in about 30 minutes to about 60 hours. The hydride reducing agent is usually used in an amount of about 0.1 to about 20 mol, and preferably about 0.1 to about 6 mol, per mol of Compound (1b). In particular, when lithium aluminium hydride is used as a hydride reducing agent, it is preferable to use diethyl ether, tetrahydrofuran, dioxane, monoglyme, diglyme, and like ethers, and benzene, toluene, xylene, and like aromatic hydrocarbons as solvents. Cobalt(II) chloride, cobalt(III) chloride, cobalt(II) acetate, or like cobalt compound may be added to the reaction system of the reaction in the presence of pyridine, trimethylamine, triethylamine, N-ethyldiisopropylamine, or like amine; sodium hydroxide or like inorganic base; and/or dimethylglyoxime, 2,2'-bipyridyl, 1,10-phenanthroline, or like ligand.

When a catalytic hydrogenation reducing agent is used, the reaction is usually carried out at about −30 to about 100° C., and preferably about 0 to about 100° C., in a hydrogen atmosphere of about atmospheric pressure to about 20 atm, and preferably about atmospheric pressure to about 10 atm, or in the presence of formic acid, ammonium formate, cyclohexene, hydrazine hydrate, or like hydrogen donor. The reaction is usually finished in about 1 to about 12 hours. The catalytic hydrogenation reducing agent is usually used in an amount of about 0.01 to about 5 times, and preferably about 1 to about 3 times, the weight of Compound (1a).

ric acid, hydrobromic acid, and the like. Such acids are usually used in a large excess relative to the reaction product to be treated.

Examples of solvents usable in the acid treatment include those that are usable in the reaction of Compound (4) with Compound (5) above.

Reaction Scheme 2

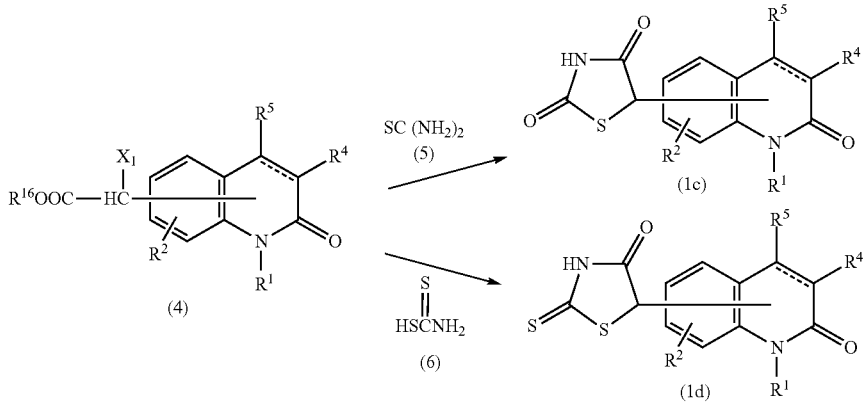

wherein $R^1$, $R^2$, $R^4$, $R^5$, and the bond between the 3- and 4-positions of the carbostyril skeleton are as defined above; and $R^{16}$ is a lower alkyl group.

Compound (1c) is produced by reacting Compound (4) and Compound (5) in a suitable solvent in the presence of a basic compound followed by acid treatment. This acid treatment is hereinafter referred to as "Acid Treatment A".

Examples of solvents usable herein are water, aromatic hydrocarbons such as benzene, toluene and xylene, ethers such as diethyl ether, tetrahydrofuran, dioxane, 2-methoxyethanol, monoglyme and diglyme, halogenated hydrocarbons such as dichloromethane, dichloroethane, chloroform and carbon tetrachloride, lower alcohols such as methanol, ethanol, isopropanol, butanol, tert-butanol and ethylene glycol, aliphatic acids such as acetic acid, esters such as ethyl acetate and methyl acetate, ketones such as acetone and methyl ethyl ketone, acetonitrile, pyridine, dimethyl sulfoxide, N,N-dimethylformamide, hexamethylphosphoric triamide, mixed solvents of such solvents, etc.

Examples of basic compounds are carbonates such as sodium carbonate, potassium carbonate, sodium hydrogencarbonate, potassium hydrogencarbonate and cesium carbonate, metal hydroxides such as sodium hydroxide, potassium hydroxide and calcium hydroxide, sodium hydride, potassium hydride, potassium, sodium, sodium amide, metal alcoholates such as sodium methylate, sodium ethylate and sodium n-butoxide, sodium acetate, piperidine, pyridine, imidazole, N-ethyldiisopropylamine, dimethylaminopyridine, triethylamine, trimethylamine, dimethylaniline, N-methylmorpholine, DBN, DBU, DABCO, other organic bases, and mixtures thereof.

Basic compound is usually used in an amount of at least about 1 mol, and preferably about 1 to about 3 mol, per mol of Compound (4).

Compound (5) is usually used in an amount of at least about 1 mol, and preferably about 1 to about 2 mol, per mol of Compound (4).

The reaction is usually carried out at about room temperature to about 200° C., and preferably about room temperature to about 150° C. The reaction is usually finished in about 0.5 to about 10 hours.

Examples of acids usable in acid-treating the reaction product are inorganic acids such as hydrochloric acid, sulfu- The acid treatment is usually carried out at about room temperature to about 200° C., and preferably about room temperature to about 150° C. The acid treatment is usually finished in about 0.5 to about 30 hours.

The reaction of Compound (4) with Compound (6) is carried out under the same conditions selected for the reaction of Compound (4) with Compound (5).

Reaction Scheme 3

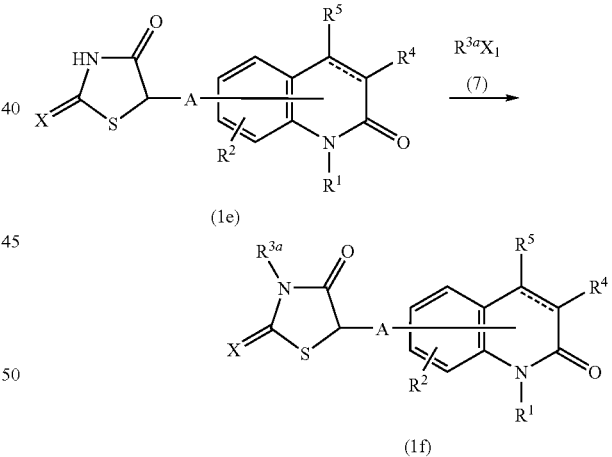

wherein $R^1$, $R^2$, $R^4$, $R^5$, X, A, and the bond between the 3- and 4-positions of the carbostyril skeleton are as defined above; $X_1$ is a halogen atom; and $R^{3a}$ is a group other than a hydrogen atom as defined in connection with $R^3$ above.

The reaction of Compound (1e) and Compound (7) is carried out in a suitable inert solvent in the presence of a basic compound.

Examples of inert solvents usable herein are aromatic hydrocarbons such as benzene, toluene and xylene, ethers such as diethyl ether, tetrahydrofuran, dioxane, 2-methoxyethanol, monoglyme and diglyme, halogenated hydrocarbons such as dichloromethane, dichloroethane, chloroform and carbon tetrachloride, lower alcohols such as methanol, ethanol, isopropanol, butanol, tert-butanol and ethylene glycol, aliphatic acids such as acetic acid, esters such as ethyl acetate and methyl acetate, ketones such as acetone and methyl ethyl ketone, acetonitrile, pyridine, dimethyl sulfoxide, N,N-dimethylformamide, hexamethylphosphoric triamide, mixed solvents of such solvents, etc.

Examples of basic compounds are carbonates such as sodium carbonate, potassium carbonate, sodium hydrogencarbonate, potassium hydrogencarbonate and cesium carbonate, metal hydroxides such as sodium hydroxide, potassium hydroxide and calcium hydroxide, sodium hydride, potassium hydride, potassium, sodium, sodium amide, metal alcoholates such as sodium methylate, sodium ethylate, sodium n-butoxide, sodium tert-butoxide and potassium tert-butoxide, pyridine, imidazole, N-ethyldiisopropylamine, dimethylaminopyridine, triethylamine, trimethylamine, dimethylaniline, N-methylmorpholine, DBN, DBU, DABCO, other organic bases, and mixtures thereof.

Basic compound is usually used in an amount of at least 1 mol, and preferably 1 to 10 mol, per mol of Compound (1e).

Compound (7) is usually used in an amount of at least 1 mol, and preferably 1 to 10 mol, per mol of Compound (1e).

The reaction is usually carried out at about 0 to about 200° C., and preferably 0 to about 150° C. The reaction is usually finished in about 5 minutes to about 80 hours.

Sodium iodide, potassium iodide, or like alkali metal halide compound may be introduced into the reaction system of the reaction.

When a Compound (1e) in which X is sulfur is used in the reaction of Compound (1e) with Compound (7), a compound represented by the formula:

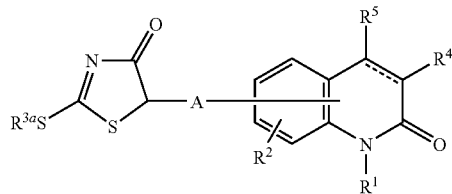

wherein $R^1$, $R^2$, $R^4$, $R^5$, $R^{3a}$, A, and the bond between the 3- and 4-positions of the carbostyril skeleton are as defined above, is sometimes generated. This compound can be easily separated from the reaction mixture.

wherein $R^1$, $R^2$, $R^4$, $R^5$, $A_4$, $R^{15}$, $R^{16}$, $X_1$, and the bond between the 3- and 4-positions of the carbostyril skeleton are as defined above, and $R^{17}$ is a lower alkyl group.

The reaction to produce Compound (9) from Compound (8) is carried out by hydrolyzing Compound (8).

This hydrolysis reaction is performed, for example, either in a suitable solvent or without a solvent, in the presence of an acid or basic compound.

Examples of usable solvents are water, lower alcohols such as methanol, ethanol, isopropanol and tert-butanol, ketones such as acetone and methyl ethyl ketone, ethers such as diethyl ether, dioxane, tetrahydrofuran, monoglyme and diglyme, aliphatic acids such as acetic acid and formic acid, esters such as methyl acetate and ethyl acetate, halogenated hydrocarbons such as chloroform, dichloroethane, dichloromethane, carbon tetrachloride, dimethyl sulfoxide, N,N-dimethylformamide, hexamethylphosphoric triamide, mixed solvents of such solvents, etc.

Examples of acids are mineral acids such as hydrochloric acid, sulfuric acid and hydrobromic acid; and organic acids such as formic acid, acetic acid, trifluoroacetic acid, p-toluenesulfonic acid and like sulfonic acids. Such acids may be used singly or as a combination of two or more such acids.

Examples of basic compounds are carbonates such as sodium carbonate, potassium carbonate, sodium hydrogencarbonate and potassium hydrogencarbonate; metal hydroxides such as sodium hydroxide, potassium hydroxide, calcium hydroxide and lithium hydroxide; etc. Such basic compounds may be used singly or as a combination of two or more such compounds.

The hydrolysis reaction advantageously proceeds usually at about 0 to about 200° C., and preferably about 0 to about 150° C. The reaction is usually finished in about 10 minutes to about 30 hours.

Compound (1g) can be produced by reacting Compound (8) with Compound (5) in a suitable solvent in the presence or absence of basic compound, and then acid-treating the reaction product. Alternatively, Compound (1g) can be produced by reacting Compound (9) with Compound (5) in a suitable solvent in the presence or absence of basic compound, and then acid-treating the reaction product.

Reaction Scheme 4

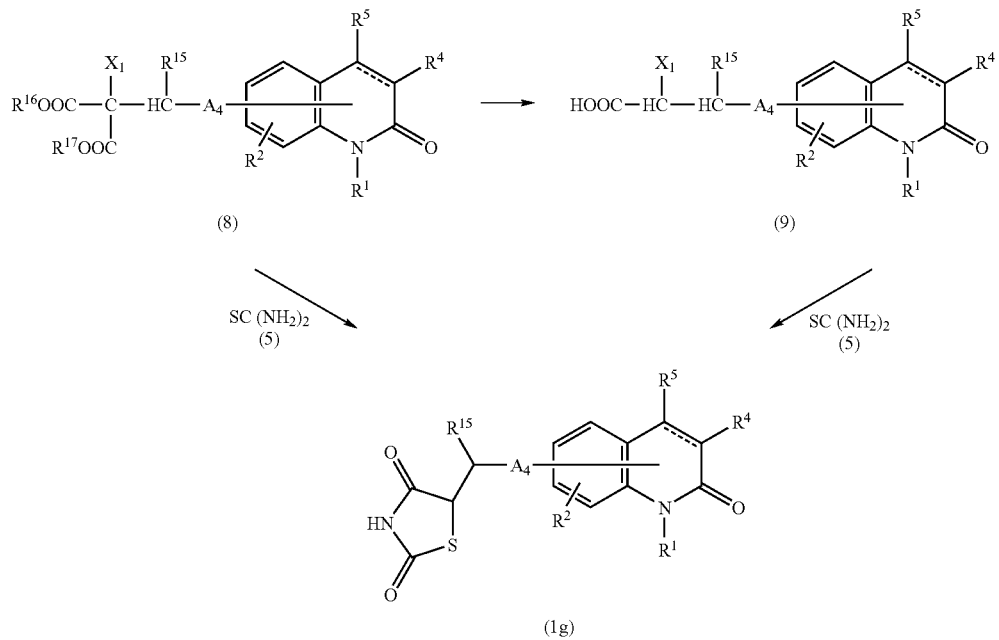

Examples of solvents for use in the reaction of Compound (8) with Compound (5) and the reaction of Compound (9) with Compound (5) include, in addition to sulfolane, those that are usable in the reaction of Compound (4) with Compound (5) shown in Reaction Scheme 2 presented above.

Examples of usable basic compounds include those that are usable in the reaction of Compound (4) with Compound (5) shown in Reaction Scheme 2 presented above.

Basic compound is usually used in an amount of at least 1 mol, and preferably 1 to 2 mol, per mol of Compound (5). Compound (8) and Compound (9) are usually used in amounts of at least 1 mol, and preferably 1 to 5 mol, per mol of Compound (5).

The reaction is usually carried out at about room temperature to about 200° C., and preferably about room temperature to about 150° C. The reaction is usually finished in about 0.5 to about 10 hours.

The subsequent acid treatment is carried out under the same conditions as described with respect to "Acid Treatment A" in Reaction Scheme 2 above.

Reaction Scheme 5

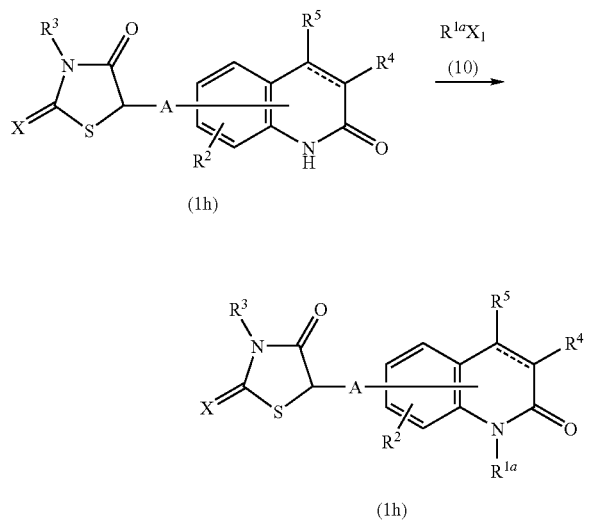

(1h)

(1h)

wherein $R^1$, $R^2$, $R^3$, $R^4$, $R^5$, X, A, $X_1$, and the bond between the 3- and 4-positions of the carbostyril skeleton are as defined above, and $R^{1a}$ is a group other than a hydrogen atom as defined in connection with $R^1$.

The reaction of Compound (1h) with Compound (10) is carried out under the same conditions as described in connection with the reaction of Compound (1e) with Compound (7) shown in Reaction Scheme 3 above.

Reaction Scheme 6

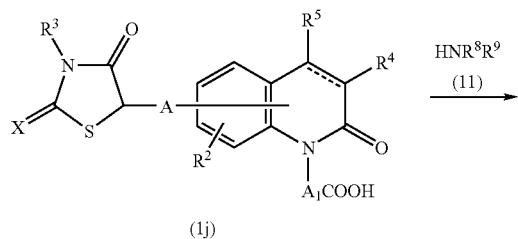

(1j)

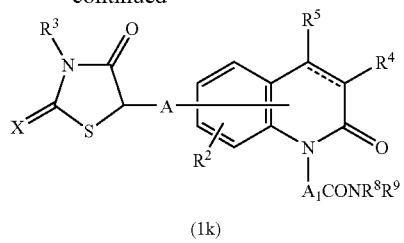

(1k)

wherein $R^2$, $R^3$, $R^4$, $R^5$, X, A, $R^8$, $R^9$, $A_1$, and the bond between the 3- and 4-positions of the carbostyril skeleton are as defined above.

A wide variety of reaction conditions selected for an ordinary amide bond formation reaction are applicable to the reaction of Compound (1j) with Compound (11), such as, in particular, (a) a mixed acid anhydride process in which Carboxylic Acid (1j) is reacted with an alkyl halocarboxylate to form a mixed acid anhydride and reacting this anhydride with Amine (11), (b) an activated ester process in which Carboxylic Acid (1j) is activated into an activated ester such as phenyl ester, p-nitrophenyl ester, N-hydroxysuccinimide ester, 1-hydroxybenzotriazole ester, etc., or into an activated amide with benzoxazoline-2-thione, and then reacted with Amine (11), (c) a carbodiimide process in which Carboxylic Acid (1j) and Amine (11) are subjected to a condensation reaction in the presence of an activating agent such as dicyclohexylcarbodiimide, 1-(3-dimethylaminopropyl)-3-ethylcarbodiimide (WSC), carbonyldiimidazole, or the like, (d) other processes, for example, in which Carboxylic Acid (1j) is converted into a carboxylic anhydride using a dehydration agent such as acetic anhydride, and reacting this carboxylic anhydride with Amine (11); an ester of Carboxylic Acid (1j) formed with a lower alcohol is reacted with Amine (11) at a high temperature and high pressure; an acid halide of Carboxylic Acid (1j), i.e., a carboxylic acid halide, is reacted with Amine (11), and like processes.

A mixed acid anhydride for use in the mixed acid anhydride process described above can be obtained by an ordinary Schotten-Baumann reaction, and the reaction product is usually used for the reaction with Amine (11) to give the desired compound of Formula (1k) without isolation from the reaction mixture.

The above-described Schotten-Baumann reaction is usually carried out in the presence of a basic compound.

Such basic compounds include any conventional basic compounds for use in Schotten-Baumann reactions, for example, triethylamine, trimethylamine, pyridine, dimethylaniline, N-ethyldiisopropylamine, dimethylaminopyridine, N-methylmorpholine, DBN, DBU, DABCO, and like organic bases; and carbonates such as sodium carbonate, potassium carbonate, sodium hydrogencarbonate and potassium hydrogencarbonate, metal hydroxides such as sodium hydroxide, potassium hydroxide and calcium hydroxide, potassium hydride, sodium hydride, potassium, sodium, sodium amide, metal alcoholates such as sodium methylate and sodium ethylate, and like inorganic bases. Such basic compounds are used singly or as a combination of two or more such compounds. The reaction is usually carried out at about −20 to about 100° C., and preferably about 0 to about 50° C. The reaction time is about 5 minutes to about 10 hours, and preferably about 5 minutes to about 2 hours.

The reaction of the resulting mixed acid anhydride with Amine (11) is usually carried out at about −20 to about 150° C., and preferably about 10 to about 50° C. The reaction time is about 5 minutes to about 10 hours, and preferably about 5 minutes to about 5 hours.

The mixed acid anhydride process is usually carried out in a solvent. Examples of solvents are those that are commonly used in connection with mixed acid anhydride processes.

Specific examples are chloroform, dichloromethane, dichloroethane, carbon tetrachloride, and like halogenated hydrocarbons; benzene, toluene, xylene, and like aromatic hydrocarbons; diethyl ether, diisopropyl ether, tetrahydrofuran, dimethoxyethane, and like ethers; methyl acetate, ethyl acetate, isopropyl acetate, and like esters; N,N-dimethylformamide, dimethyl sulfoxide, hexamethylphosphoric triamide, and like aprotic polar solvents; mixtures of such solvents; etc.

Examples of alkyl halocarboxylates usable in the mixed anhydride process are methyl chloroformate, methyl bromoformate, ethyl chloroformate, ethyl bromoformate, isobutyl chloroformate, etc.

nylphosphoramide chloridate, diethyl chlorophosphate, diethyl cyanophosphate, diphenyl azidophosphate, bis(2-oxo-3-oxazolidinyl)phosphinic chloride, etc. Such condensing agents can be used singly or as a combination of two or more such agents.

The reaction is usually carried out at about −20 to about 150° C., and preferably about 0 to about 100° C., using a solvent and basic compound that are also usable in the aforementioned process in which a carboxylic acid halide and Amine (11) are reacted. The reaction is usually finished in about 5 minutes to about 30 hours. Condensing agent and Amine (11) are each used in an amount of at least about 1 mol, and preferably about 1 to about 2 mol, per mol of Carboxylic Acid (1j).

Reaction Scheme 7

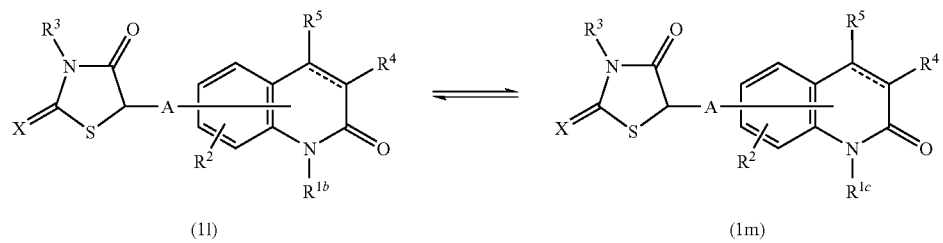

(11)    (1m)

In the mixed acid anhydride process, Carboxylic Acid (1j), an alkyl halocarboxylate, and Amine (11) are preferably used equimolar to each other. However, an alkyl halocarboxylate and Amine (11) are each usable in an amount of about 1 to about 1.5 mol per mol of Carboxylic Acid (1j).

Process (c) in which a condensation reaction carried out in the presence of an activating agent as described above is performed in a suitable solvent either in the presence or absence of a basic compound. Examples of solvents and basic compounds usable herein are those that are usable in the process in which a carboxylic acid halide is reacted with Amine (1b) as described in Processes (d) below. The amount of activating agent is usually used in an amount of at least 1 mol, and preferably 1 to 5 mol, per mol of Compound (1j). When WSC is used as an activating agent, the reaction advantageously progresses by introducing 1-hydroxybenzotriazole into the reaction system. The reaction is usually carried out at about −20 to 180° C., and preferably about 0 to about 150° C. The reaction usually completes in about 5 minutes to about 90 hours.

Among Processes (d), if a process in which a carboxylic acid halide is reacted with Amine (11) is selected, this reaction is carried out in the presence of a basic compound in a suitable solvent. Examples of basic compounds for use include a wide variety of known compounds such as those described above in connection with the Schotten-Baumann reaction. Examples of solvents include, in addition to those usable in the aforementioned mixed acid anhydride process, methanol, ethanol, isopropanol, propanol, butanol, 3-methoxy-1-butanol, ethyl cellosolve, methyl cellosolve, and like alcohols, acetonitrile, pyridine, acetone, water, etc. The ratio of carboxylic acid halide to Amine (11) is not limited and can be suitably selected from a broad range. It is usually such that, per mol of the former, the latter is used in an amount of at least about 1 mol, and preferably about 1 to about 5 mol. The reaction is usually carried out at about −20 to about 180° C., and preferably about 0 to about 150° C. The reaction is usually finished in about 5 minutes to about 30 hours.

Moreover, the amide bond formation reaction shown in Reaction Scheme 6 can be carried out by reacting Carboxylic Acid (1j) and Amine (11) in the presence of a condensing agent composed of a phosphorus compound such as triphenylphosphine, diphenylphosphinyl chloride, phenyl-N-phewherein $R^2$, $R^3$, $R^4$, $R^5$, X, A, and the bond between the 3- and 4-positions of the carbostyril skeleton are as defined above; $R^{1b}$ is a group as defined in (1-9) in connection with $R^1$ above; and $R^{1c}$ is a group as defined in (1-8) in connection with $R^1$ above.

The reaction for producing Compound (1m) from Compound (1l) is carried out under conditions as described in connection with the reaction for producing Compound (9) from Compound (8) shown in Reaction Scheme 4 above.

The reaction for producing Compound (1l) from Compound (1m) can be carried out by reacting Compound (1m) with a compound represented by the formula $$R^{23}OH \qquad (50)$$

wherein $R^{23}$ is a lower alkyl group.

Conditions usually selected for esterification reactions are applicable to the reaction. For example, it may be carried out in the presence of hydrochloric acid, sulfuric acid, or like a mineral acid; or thionyl chloride, phosphorus oxychloride, phosphorus pentachloride, phosphorus trichloride, or like halogenating agent. Compound (50) is used in a large excess relative to Compound (1m). The reaction advantageously progresses usually at about 0 to about 150° C., and preferably about 50 to about 100° C. The reaction is usually finished in about 1 to about 10 hours.

Reaction Scheme 8

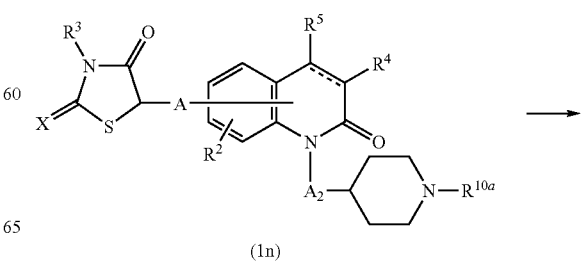

(1n)

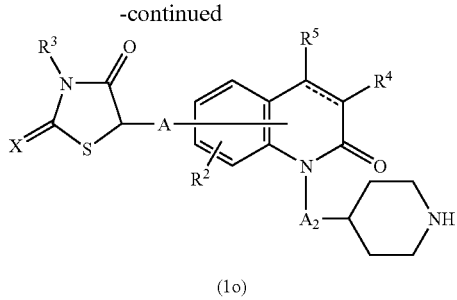

(1o)

wherein $R^2$, $R^3$, $R^4$, $R^5$, X, A, $A_2$, and the bond between the 3- and 4-positions of the carbostyril skeleton are as defined above, and $R^{10a}$ is a group as defined in (7-3) and (7-44) in connection with $R^{10}$ above.

The reaction for producing Compound (1o) from Compound (1n) is carried out under the same conditions as described in connection with the reaction for producing Compound (9) from Compound (8) shown in Reaction Scheme 4 above.

When $R^{10a}$ of Compound (1n) is a group as defined in (7-44), the above-presented reaction may be carried out in the presence of a fluorine compound. Examples of fluorine compounds are ammonium tetrafluoride, tetra-N-butyl ammonium fluoride, pyridine hydrofluoride, etc. Among such examples, tetra-N-butyl ammonium fluoride is preferable. Fluorine compound is usually used in at least 1 mol, and preferably 1 to 2 mol, per mol of Compound (1n).

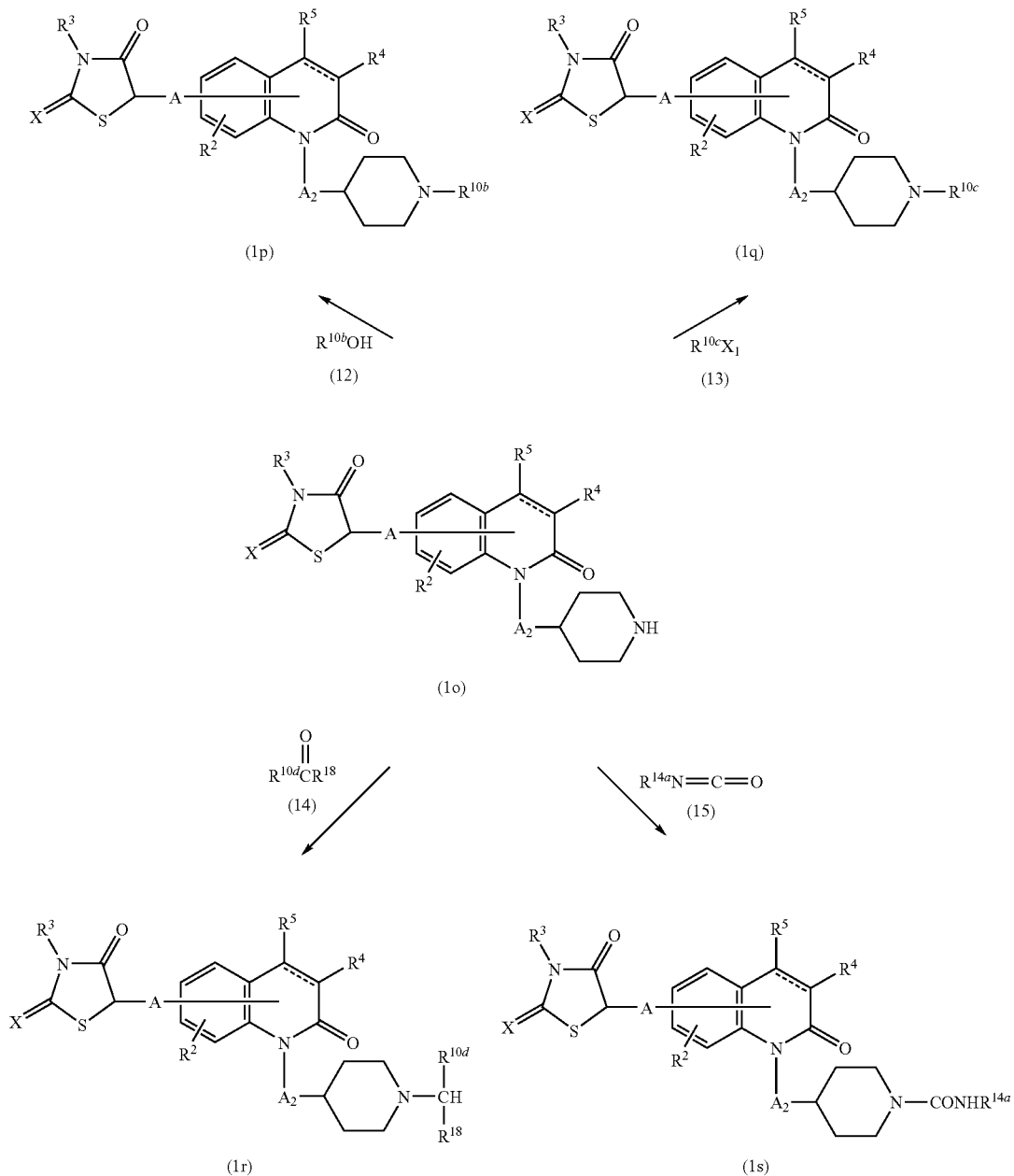

Reaction Scheme 9 wherein $R^2$, $R^3$, $R^4$, $R^5$, X, A, $A_2$, $X_1$, and the bond between the 3- and 4-positions of the carbostyril skeleton are as defined above;

$R^{10b}$ is a group as defined in (7-3) to (7-7), (7-9) to (7-20), (7-30) to (7-35), and (7-44) in connection with $R^{10}$ above;

$R^{10c}$ is a group as defined in (7-2), (7-8), (7-21) to (7-29), and (7-37) to (7-43) in connection with $R^{10}$ above;

$R^{10d}$ is a group as defined in (7-1), (7-2), (7-21) to (7-29), and (7-40) in connection with $R^{10}$ above; furyl group; pyridyl group optionally substituted on the pyridine ring with one or more members selected from the group consisting of halogen atoms and lower alkyl groups, each lower alkyl substituent optionally being substituted with one or more halogen atoms; thienyl group optionally substituted on the thiophene ring with one or more halogen atoms; phenyl group optionally substituted on the phenyl ring with one or more members selected from the group consisting of lower alkoxy groups optionally substituted with one or more halogen atoms, a cyano group, lower alkyl groups optionally substituted with one or more halogen atoms, amino groups optionally substituted with one or more members selected from the group consisting of lower alkyl groups and lower alkanoyl groups, halogen atoms, lower alkoxycarbonyl groups, lower alkanoyloxy groups, lower alkylsulfonyl groups, lower alkylthio groups, and pyrrolidinyl groups; thiazolyl group; imidazolyl group optionally substituted on the imidazole ring with one or more lower alkyl groups; pyrrolyl group optionally substituted on the pyrrole ring with one or more lower alkyl groups; or cycloalkyl group;

$R^{14a}$ is a group as defined in (10-1) to (10-3) in connection with $R^{14}$ above; and $R^{18}$ is a hydrogen atom or lower alkyl group, provided that the total number of carbon atoms of the group CH($R^{10d}$)$R^{18}$ of Compound (1r) is not greater than 6.

The reaction of Compound (1o) with Compound (12) is carried out under the same conditions as described in connection with the reaction of Compound (1j) with Compound (11) shown in Reaction Scheme 6 above, provided that with respect to the reaction of Compound (1o) with Compound (12), the amounts of alkyl halocarboxylate, Carboxylic Acid (12), activating agent, condensing agent, carboxylic acid halide, etc., are relative to Compound (1o).

The reaction of Compound (1o) with Compound (13) is carried out under the same conditions as described in connection with the reaction of Compound (1e) with Compound (7) shown in Reaction Scheme 3 above.

The reaction of Compound (1o) with Compound (14) may be carried out, for example, either in a suitable solvent or without a solvent, in the presence of a reducing agent.

Examples of solvents usable herein are water, lower alcohols such as methanol, ethanol, isopropanol, butanol, tert-butanol and ethylene glycol, acetonitrile, aliphatic acids such as formic acid and acetic acid, ethers such as diethyl ether, tetrahydrofuran, dioxane, monoglyme and diglyme, aromatic hydrocarbons such as benzene, toluene and xylene, halogenated hydrocarbons such as dichloromethane, dichloroethane, chloroform, carbon tetrachloride, mixtures of such solvents, etc.

Examples of reducing agents are aliphatic acids such as formic acid, aliphatic acid alkali metal salts such as sodium formate and sodium acetate, hydride reducing agents such as sodium borohydride, sodium cyanoborohydride, sodium triacetoxyborohydride and aluminium lithium hydride, mixtures of such hydride reducing agents, catalytic hydrogenation reducing agent such as palladium black, palladium carbon, platinum oxide, platinum black, Raney nickel, etc.

When an aliphatic acid such as formic acid or an aliphatic acid alkali metal salt such as sodium formate or sodium acetate is used as a reducing agent, a suitable reaction temperature is usually about room temperature to about 200° C., and preferably about 50 to about 150° C. The reaction is usually finished in about 10 minutes to about 10 hours. Such aliphatic acids and aliphatic acid alkali metal salts are usually used in a large excess relative to Compound (1o).

When a hydride reducing agent is used, a suitable reaction temperature is usually about −80 to about 100° C., and preferably about −80 to about 70° C. The reaction is usually finished in about 30 minutes to about 60 hours. The hydride reducing agent is usually used in an amount of about 1 to about 20 mol, and preferably about 1 to about 6 mol, per mol of Compound (1o). In particular, when aluminium lithium hydride is used as a hydride reducing agent, it is preferable to use diethyl ether, tetrahydrofuran, dioxane, monoglyme, diglyme, or like ether; or benzene, toluene, xylene, or like aromatic hydrocarbon as a solvent. Trimethylamine, triethylamine, N-ethyldiisopropylamine, or like amine; or molecular sieves 3A (MS-3A), molecular sieves 4A (MS-4A), or like molecular sieves may be introduced into the reaction system of the reaction.

When a catalytic hydrogenation reducing agent is used, the reaction is usually carried out at about −30 to about 100° C., and preferably about 0 to about 60° C., in a hydrogen atmosphere usually of about atmospheric pressure to about 20 atm, and preferably about atmospheric pressure to about 10 atm, or in the presence of formic acid, ammonium formate, cyclohexene, hydrazine hydrate, or like hydrogen donor. The reaction is usually finished in about 1 to about 12 hours. The catalytic hydrogenation reducing agent is usually used in an amount of about 0.1 to about 40 wt. %, and preferably about 1 to about 20 wt. %, relative to Compound (1o).

In the reaction of Compound (1o) with Compound (14), Compound (14) is usually used in an amount at least equimolar, and preferably equimolar to a large excess, relative to Compound (1o).

The reaction of Compound (1o) with Compound (15) is carried out in the presence or absence of basic compound, but preferably in the absence of basic compound, in a suitable inert solvent or without a solvent.

Examples of inert solvents and basic compounds include those that are for use in one of the Processes (d) in which a carboxylic acid halide is reacted with Amine (11) for the reaction of Compound (1o) with Compound (12) (amide bond formation reaction).

The amount of Compound (15) is usually about 1 to about 5 mol, and preferably about 1 to about 3 mol, per mol of Compound (1o).

The reaction advantageously proceeds usually at about 0 to about 200° C., and preferably about room temperature to about 150° C. The reaction is usually finished in about 5 minutes to about 30 hours.

Boron trifluoride diethyl ether complex or like boron compound may be introduced into the reaction system of the reaction.

Reaction Scheme 10

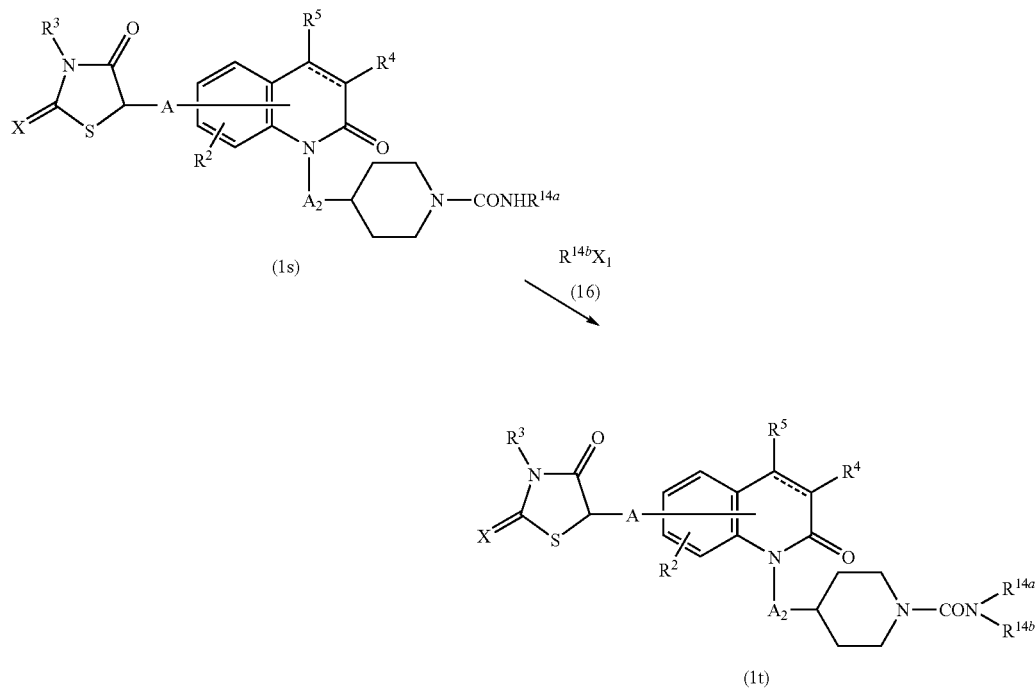

wherein $R^2$, $R^3$, $R^4$, $R^5$, X, A, $A_2$, $X_1$, $R^{14a}$, and the bond between the 3- and 4-positions of the carbostyril skeleton are as defined above, and $R^{14b}$ is a group as defined in (10-2) and (10-3) in connection with $R^{14}$ above.

The reaction of Compound (1s) with Compound (16) is carried out under the same conditions as described in connection with the reaction of Compound (1e) with Compound (7) shown in Reaction Scheme 3 above.

Reaction Scheme 11

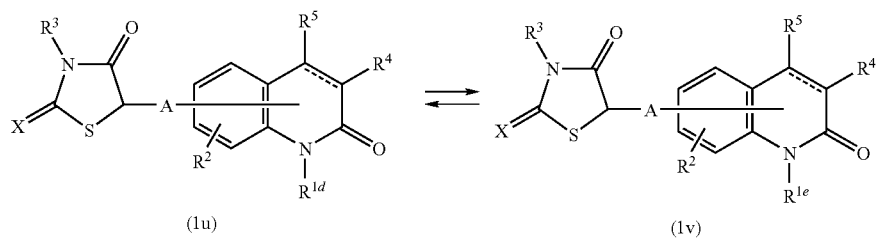

wherein $R^2$, $R^3$, $R^4$, $R^5$, X, A, and the bond between the 3- and 4-positions of the carbostyril skeleton are as defined above; $R^{1d}$ is a group as defined in (1-3) in connection with $R^1$ above except for having at least one lower alkoxycarbonyl group on the phenyl ring; and $R^{1e}$ is a group as defined in (1-3) in connection with $R^1$ above except for having at least one carboxy group on the phenyl ring.

The reaction for producing Compound (1v) from Compound (1u) is carried out under the same conditions as described in connection with the reaction for producing Compound (9) from Compound (8) shown in Reaction Scheme 4 above.

The reaction for producing Compound (1u) from Compound (1v) is carried out under the same conditions as described in connection with the reaction for producing Compound (11) from Compound (1m) shown in Reaction Scheme 7 above.

Reaction Scheme 12

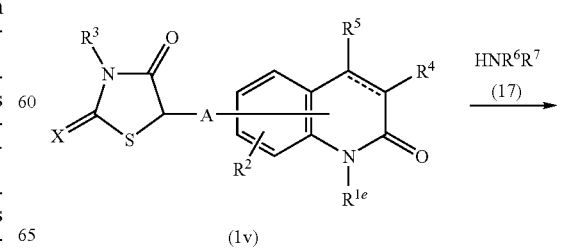

87

-continued

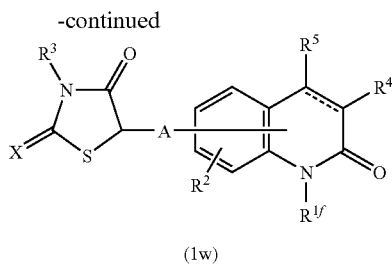

(1w)

wherein $R^2$, $R^3$, $R^4$, $R^5$, X, A, $R^6$, $R^7$, $R^{1e}$, and the bond between the 3- and 4-positions of the carbostyril skeleton are as defined above; and $R^{1f}$ is a group as defined in (1-3) in connection with $R^1$ above except for having at least one —$CONR^6R^7$ group on the phenyl ring.

The reaction of Compound (1v) with Compound (17) is carried out under the same conditions as described in connection with the reaction of Compound (1j) with Compound (11) shown in Reaction Scheme 6 above.

88 l is as defined above;
$R^{7a}$ is a group as defined in (4-1) to (4-79) in connection with $R^7$ above;
$R^{6a}$ is a group as defined in (4-2), (4-4), (4-6), (4-8) to (4-11), (4-19) to (4-32), (4-34) to (4-37), (4-60), (4-62) to (4-72), (4-78), and (4-79) in connection with $R^6$ above;
$R^{6b}$ is a group as defined in (4-3), (4-5), (4-7), (4-12) to (4-18), (4-33), (4-38) to (4-59), (4-61), (4-73) to (4-77) in connection with $R^6$ above; and
$R^{6c}$ is a group as defined in (4-1), (4-2), (4-6), (4-9), (4-20), (4-21), (4-23) to (4-29), (4-31), (4-32), and (4-34); pyridyl group; tetrahydropyranyl group; cycloalkyl group; phenyl group optionally substituted on the phenyl ring with one or more members selected from the group consisting of halogen atoms, lower alkyl groups optionally substituted with one or more halogen atoms, lower alkoxy groups optionally substituted with one or more halogen atoms, and hydroxy groups; lower alkylenedioxy-substituted phenyl group; furyl group; imidazolyl group optionally substituted on the imidazole ring with one or more members selected from the group consisting of a carbamoyl group Reaction Scheme 13

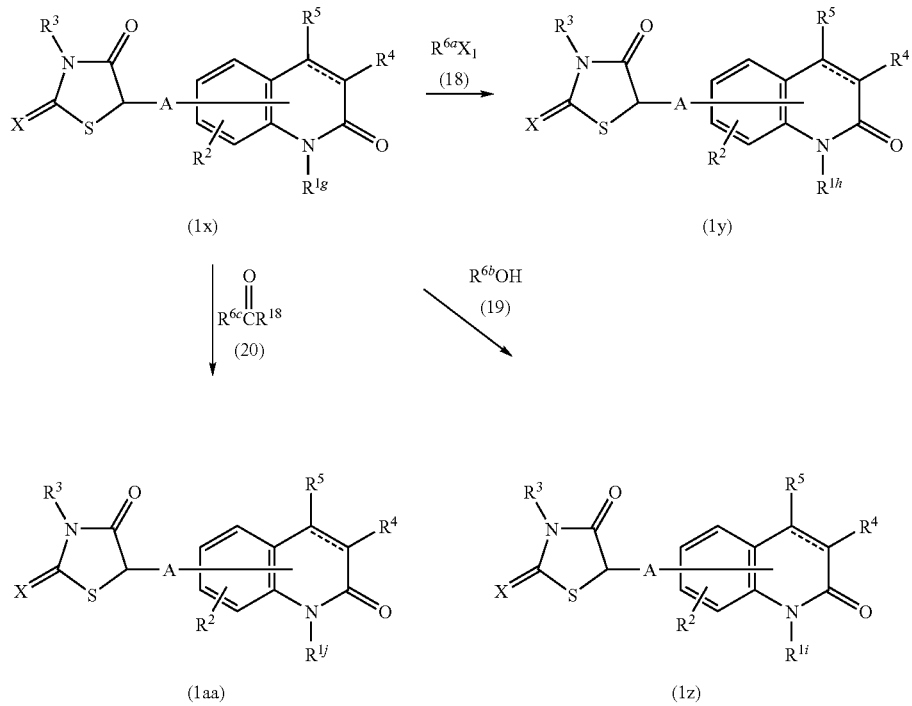

wherein $R^2$, $R^3$, $R^4$, $R^5$, X, A, $X_1$, $R^{18}$, and the bond between the 3- and 4-positions of the carbostyril skeleton are as defined above;
$R^{1g}$ is a group as defined in (1-3) in connection with $R^1$ above except for having at least one —$(B)_lNHR^{7a}$ group on the phenyl ring, provided that l is as defined above;
$R^{1h}$ is a group as defined in (1-3) in connection with $R^1$ above except for having at least one —$(B)_lN(R^{6a})R^{7a}$ group on the phenyl ring;
$R^{1i}$ is a group as defined in (1-3) in connection with $R^1$ above except for having at least one —$(B)_lN(R^{6b})R^{7a}$ group on the phenyl ring;
$R^{1j}$ is a group as defined in (1-3) in connection with $R^1$ above except for having at least one —$(B)_lN[CH(R^{6c})R^{18}]R^{7a}$ group on the phenyl ring, provided that the total number of carbon atoms of $CH(R^{6c})R^{18}$ is no greater than 6;

and lower alkoxycarbonyl groups; pyrrolidinyl group optionally substituted on the pyrrolidine ring with one or more lower alkyl groups; or morpholino group.

The reaction of Compound (1x) with Compound (18) is carried out under the same conditions as described in connection with the reaction of Compound (1o) with Compound (12) shown in Reaction Scheme 9 above.

The reaction of Compound (1x) with Compound (19) is carried out under the same conditions as described in connection with the reaction of Compound (1o) with Compound (13) shown in Reaction Scheme 9 above.

The reaction of Compound (1x) with Compound (20) is carried out under the same conditions as described in connection with the reaction of Compound (1o) with Compound (14) shown in Reaction Scheme 9 above.

Reaction Scheme 14

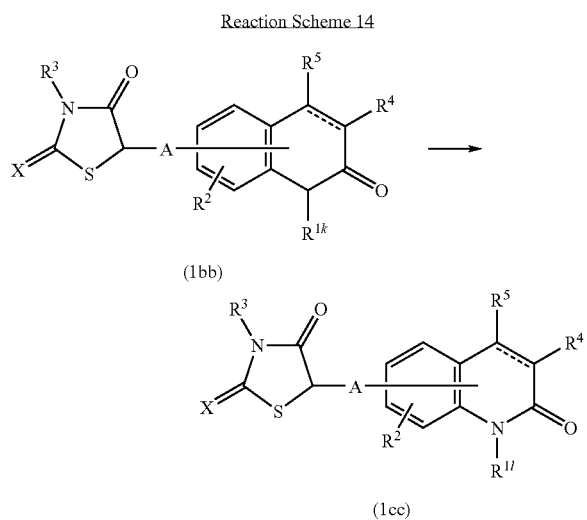

(1bb)

(1cc)

wherein $R^2$, $R^3$, $R^4$, $R^5$, X, A, and the bond between the 3- and 4-positions of the carbostyril skeleton are as defined above; $R^{1k}$ is a group as defined in (1-3) in connection with $R^1$ above except for having at least one nitro group on the phenyl ring; and $R^{1l}$ is a group as defined in (1-3) in connection with $R^1$ above except for having at least one amino group on the phenyl ring.

The reaction for producing Compound (1cc) from Compound (1bb) can be carried out by, for example, (1) reducing Compound (1bb) in a suitable solvent using a catalytic hydrogenation reducing agent, or (2) reducing Compound (1bb) in a suitable inert solvent using as a reducing agent a mixture of an acid with a metal or metal salt, a mixture of a metal or metal salt with an alkali metal hydroxide, sulfide, or ammonium salt, or the like.

When using Method (1) above, examples of usable solvents are water, acetic acid, alcohols such as methanol, ethanol and isopropanol, hydrocarbons such as n-hexane and cyclohexane, ethers such as dioxane, tetrahydrofuran, diethyl ether and diethylene glycol dimethyl ether, esters such as ethyl acetate and methyl acetate, aprotic polar solvents such as N,N-dimethylformamide, mixtures of such solvents, etc. Examples of usable catalytic hydrogenation reducing agent include palladium, palladium black, palladium carbon, platinum carbon, platinum, platinum oxide, copper chromite, Raney nickel, etc. Such reducing agent may be used singly or as a combination of two or more such agents. Reducing agent is usually used in an amount of about 0.02 times to equal to the weight of Compound (1bb). The reaction temperature is usually about −20 to about 150° C., and preferably about 0 to about 100° C. The hydrogen pressure is usually about 1 to 10 atm. The reaction is usually finished in about 0.5 to about 100 hours. An acid such as hydrochloric acid may be introduced into the reaction system of the reaction.

When using Method (2) above, a mixture of iron, zinc, tin, or tin(II) chloride, with a mineral acid such as hydrochloric acid, or sulfuric acid; or a mixture of iron, iron(II) sulfate, zinc, or tin, with an alkali metal hydroxide such as sodium hydroxide, a sulfide such as ammonium sulfide, aqueous ammonia, or an ammonium salt such as ammonium chloride, or the like can be used as a reducing agent. Examples of inert solvents are water, acetic acid, alcohols such as methanol and ethanol, ethers such as dioxane, mixtures of such solvents, etc. Conditions for the reduction reaction can be suitably selected according to the reducing agent to be used. For example, when a mixture of tin(II) chloride and hydrochloric acid is used as a reducing agent, it is advantageous to carry out the reaction at about 0 to about 150° C. for about 0.5 to about 10 hours. Reducing agent is used in an amount of at least 1 mol, and usually about 1 to 5 mol, per mol of Compound (1bb).

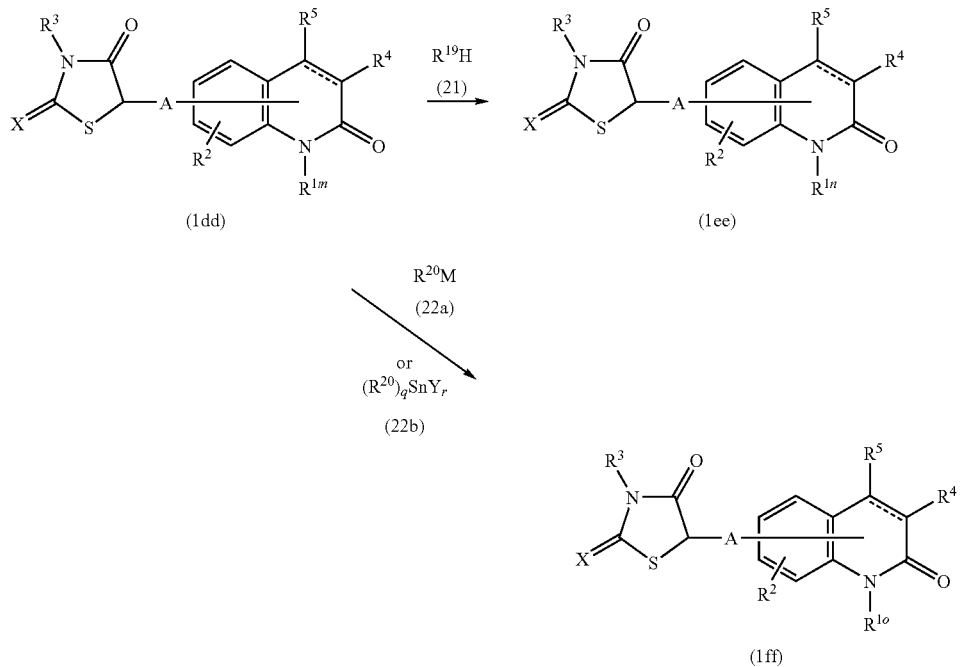

wherein $R^2$, $R^3$, $R^4$, $R^5$, X, A, and the bond between the 3- and 4-positions of the carbostyril skeleton are as defined above;

$R^{1m}$ is a group as defined in (1-10) in connection with $R^1$ above except for having at least one halogen atom on the pyridine ring;

$R^{1n}$ is a group as defined in (1-10) in connection with $R^1$ above except for having on the pyridine ring at least one member selected from piperidinyl groups; morpholino group; piperazinyl group optionally substituted on the piperazine ring with one or more members selected from the group consisting of a phenyl group and lower alkyl groups; anilino group optionally substituted on the amino group with one or more lower alkyl groups; pyridylamino group; or pyridylcarbonylamino group;

$R^{1o}$ is a group as defined in (1-10) in connection with $R^1$ above except for having at least one member selected from thienyl groups, a phenyl group, pyridyl groups and a biphenyl group;

$R^{19}$ is a piperidinyl group; morpholino group; piperazinyl group optionally substituted on the piperazine ring with one or more members selected from the group consisting of a phenyl group and lower alkyl groups; anilino group optionally substituted on the amino group with one or more lower alkyl groups; pyridylamino group; or pyridylcarbonylamino group;

$R^{20}$ is a thienyl group, phenyl group, pyridyl group, or biphenyl group;

M is an alkali metal such as lithium, potassium, sodium or the like, —$MgX_1$ ($X_1$ is as defined above), —$ZnX_1$ ($X_1$ is as defined above), or —$B(OH)_2$;

Y is a lower alkyl group;

q is 1 to 4; and r is 1 to 3, provided that q+r equals 4.

The reaction of Compound (1dd) with Compound (21) is carried out in a suitable solvent in the presence of a basic compound and a catalyst.

Examples of solvents and basic compounds usable herein include those that are usable in the reaction of Compound (1e) with Compound (7) shown in Reaction Scheme 3 above.

Examples of catalysts are bis(tributyltin)/bis(dibenzylideneacetone)palladium, R-tris(dibenzylideneacetone)dipalladium, S-tris(dibenzylideneacetone)dipalladium, palladium (II) acetate, and like palladium compounds; R-2,2'-bis (diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl (RAC-BINAP), 2,2-bis(diphenylimidazolidinylidene), and like compounds; 4,5-bis(diphenylphosphino)-9,9-dimethylxanthene, and like xanthene compounds; tert-butylphosphine, tert-butylphosphine tetrafluoroborate, and like alkylphosphines; salts thereof; mixtures thereof; etc.

Basic compound is usually used in an amount of at least 1 mol, and preferably 1 to 2 mol, per mol of Compound (1dd).

Catalyst is used in a typical catalytic amount relative to Compound (1dd).

Compound (21) is usually used in an amount of at least 1 mol, and preferably 1 to 2 mol, per mol of Compound (1dd).

The reaction is usually carried out at about room temperature to about 200° C., and preferably about room temperature to about 150° C. The reaction is usually finished in about 0.5 to about 20 hours.

The reaction of Compound (1dd) with Compound (22a) or (22b) is carried out in a suitable solvent in the presence of a basic compound and a catalyst.

Solvents usable herein include, in addition to water, those that are usable in the reaction of Compound (1e) with Compound (7) shown in Reaction Scheme 3 above.

Basic compounds usable herein include those that are usable in the reaction of Compound (1e) with Compound (7) shown in Reaction Scheme 3 above.

Examples of catalysts are tetrakis(triphenylphosphine)palladium(0), dichlorobis(triphenylphosphine)palladium(II), and like palladium compounds.

Basic compound is usually used in an amount of at least 1 mol, and preferably 1 to 5 mol, per mol of Compound (1dd).

Catalyst is usually used in an amount of 0.001 to 1 mol per mol of Compound (1dd), and preferably 0.01 to 0.5 mol, per mol of Compound (1dd).

Compound (21) is usually used in an amount of at least 1 mol, and preferably 1 to 5 mol, per mol of Compound (1dd).

The reaction is usually carried out at about −30 to about 200° C., and preferably about 0 to about 150° C. The reaction is usually finished in about 0.5 to about 20 hours.

With respect to the reaction, when M is an alkali metal salt or $MgX_1$, the reaction proceeds in the absence of basic compound and catalyst.

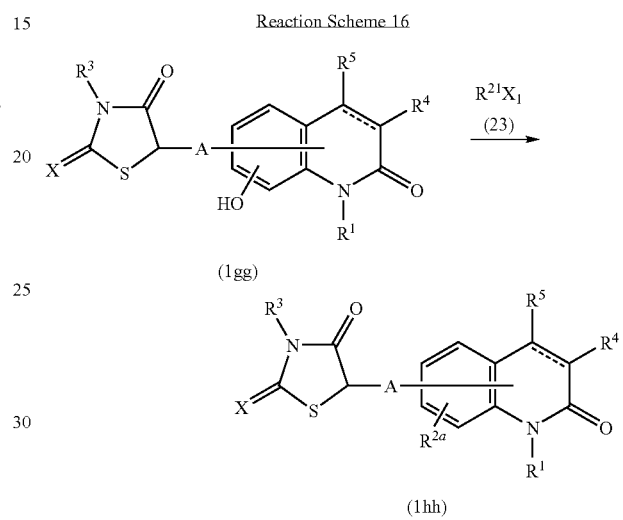

Reaction Scheme 16 wherein $R^1$, $R^3$, $R^4$, $R^5$, X, A, $X_1$, and the bond between the 3- and 4-positions of the carbostyril skeleton are as defined above;

$R^{2a}$ is a group as defined in (2-2), (2-4), (2-5), and (2-7) to (2-32) in connection with $R^2$ above; and $R^{21}$ is a lower alkyl group; carboxy lower alkyl group; lower alkoxycarbonyl lower alkyl; phenyl lower alkyl group optionally substituted on the phenyl ring with one or more members selected from the group consisting of halogen atoms, lower alkyl groups optionally substituted with one or more halogen atoms, lower alkylthio groups optionally substituted with one or more halogen atoms, lower alkoxy groups, a nitro group, lower alkylsulfonyl groups, lower alkoxycarbonyl groups, phenyl lower alkenyl groups, lower alkanoyloxy groups, and 1,2,3-thiodiazolyl groups; piperidinyl lower alkyl group optionally substituted on the piperidine ring with one or more lower alkyl groups; amino-substituted lower alkyl group optionally substituted with one or more lower alkyl groups; lower alkenyl group; pyridyl lower alkyl group optionally substituted on the pyridine ring with one or more lower alkyl groups, each lower alkyl substituent optionally being substituted with one or more halogen atoms; lower alkynyl group; phenyl lower alkynyl group; phenyl lower alkenyl group; furyl lower alkyl group optionally substituted on the furan ring with one or more lower alkoxycarbonyl groups; tetrazolyl lower alkyl group optionally substituted on the tetrazole ring with a substituent selected from the group consisting of a phenyl group, phenyl lower alkyl groups, and cycloalkyl lower alkyl groups; 1,2,4-oxadiazolyl lower alkyl group optionally substituted on the 1,2,4-oxadiazole ring with a phenyl group, the phenyl substituent optionally being substituted on the phenyl ring with one or more lower alkyl groups; isooxazolyl lower alkyl group optionally substituted on the isoxazole ring with one or more lower alkyl groups; 1,3,4-oxadiazolyl lower alkyl group optionally substituted on the 1,3,4-oxadiazole ring with a phenyl group, the phenyl substituent optionally being substituted on the phenyl ring with one or more lower alkyl groups; lower alkanoyl lower alkyl group; thiazolyl lower alkyl group optionally substituted on the thiazole ring with one or more members selected from the group consisting of lower alkyl groups and phenyl groups, each phenyl substituent optionally being substituted on the phenyl ring with one or more halogen atoms; piperidinyl group optionally substituted on the piperidine ring with one or more benzoyl groups, each benzoyl substituent optionally being substituted on the phenyl ring with one or more halogen atoms; thienyl lower alkyl group; phenylthio lower alkyl group; carbamoyl-substituted lower alkyl group optionally substituted with one or more lower alkyl groups; benzoyl lower alkyl group; pyridylcarbonyl lower alkyl group; imidazolyl lower alkyl group optionally substituted on the imidazole ring with one or more phenyl lower alkyl groups; phenoxy lower alkyl group; phenyl lower alkoxy-substituted lower alkyl group; 2,3-dihydro-1H-indenyl group; or isoindolinyl lower alkyl group optionally substituted on the isoindoline ring with one or more oxo groups.

The reaction of Compound (1gg) with Compound (23) is carried out under the same conditions as described in connection with the reaction of Compound (1e) with Compound (7) shown in Reaction Scheme 3 above.

Compounds (2), (4) and (8) used as starting materials as shown in the reaction scheme given above can be produced according to, for example, the reaction scheme below.

Reaction Scheme 17

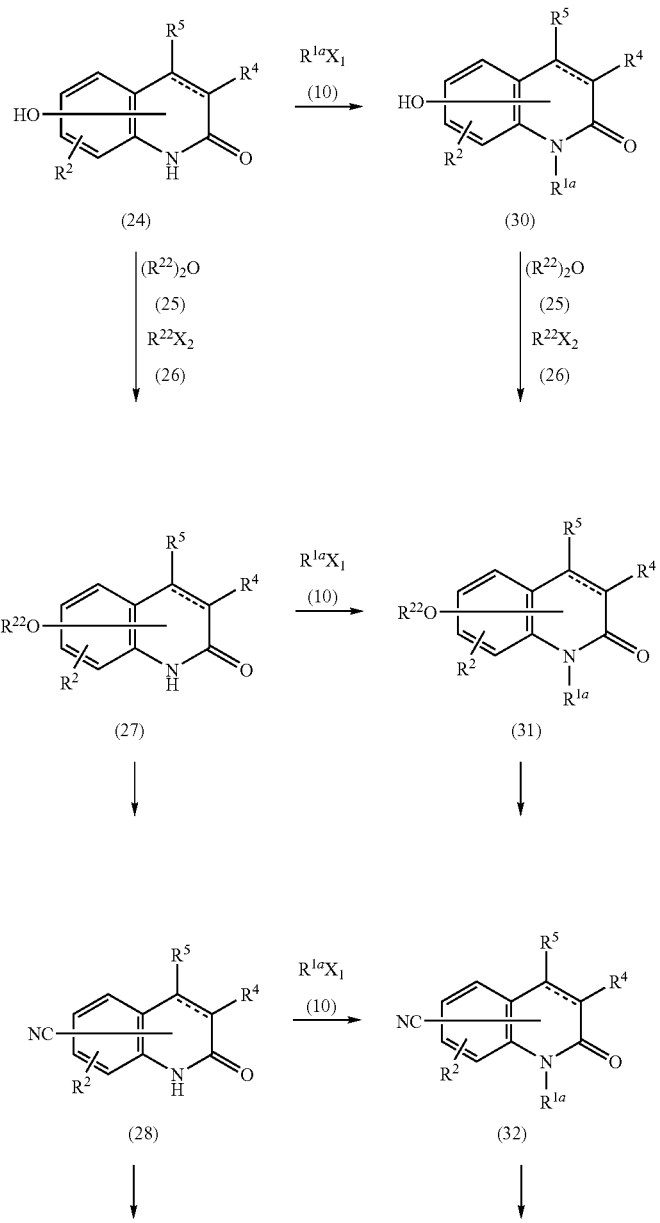

-continued

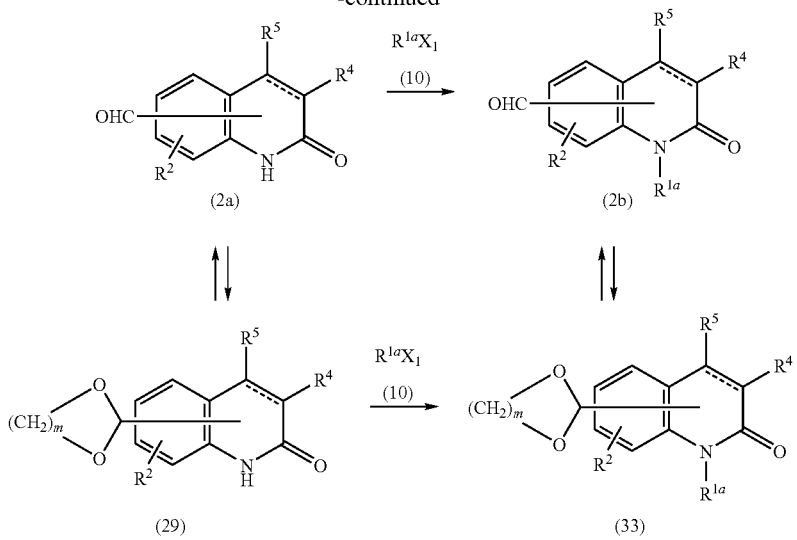

wherein $R^{1a}$, $R^2$, $R^4$, $R^5$, $X_1$, and the bond between the 3- and 4-positions of the carbostyril skeleton are as defined above; $R^{22}$ is a lower alkylsulfonyl group optionally having at least one halogen atom; $X_2$ is a halogen atom; and m is 1 to 4.

The reaction of Compound (24) with Compound (25) or (26) and the reaction of Compound (30) with Compound (25) or (26) can be carried out under the same conditions as described in one of the Processes (d) in which an acid halide of Carboxylic Acid (1j), i.e., a carboxylic acid halide, is reacted with Amine (11) for the reaction of Compound (1j) with Compound (11) shown in Reaction Scheme 6 above.

The reaction for producing Compound (28) from Compound (27) and the reaction for producing Compound (32) from Compound (31) can be achieved by reacting Compound (27) with a metal cyanide, and Compound (31) with a metal cyanide, respectively, in a suitable solvent in the presence of a catalyst.

Examples of metal cyanides are sodium cyanide, potassium cyanide, silver cyanide, zinc cyanide, cuprous cyanide, etc.

Examples of solvents and catalysts usable in these reactions include those that are usable in the reaction of Compound (1dd) with Compound (22) shown in Reaction Scheme 15 above.

Catalyst is usually used in an amount of 0.01 to 1 mol, and preferably 0.01 to 0.5 mol, per mol of Compound (27) or (31).

Metal cyanide is usually used in an amount of at least 1 mol, and preferably 1 to 3 mol, per mol of Compound (27) or (31).

The reactions are usually carried out at about room temperature to 200° C., and preferably about room temperature to about 150° C. The reactions are usually finished in about 1 hour to about 1 week.

The reaction for producing Compound (2a) from Compound (28) and the reaction for producing Compound (2b) from Compound (32) are carried out in a suitable solvent in the presence of a reducing agent.

Examples of solvents usable herein are formic acid and like aliphatic acids; dioxane, tetrahydrofuran, diethyl ether, diethylene glycol dimethyl ether, and like ethers; benzene, toluene, xylene, and like aromatic hydrocarbons, dichloromethane, dichloroethane, chloroform, carbon tetrachloride, and like halogenated hydrocarbons; and mixtures of such solvents.

Examples of reducing agents are diisobutylaluminum hydride and like alkylaluminum hydrides, Raney nickel, etc.

Reducing agent is usually used in an amount at least equal to, and preferably equal to 5 times, the weight of Compound (28) or (32).

The reactions are usually carried out at about room temperature to 200° C., and preferably about room temperature to about 150° C. The reactions are usually finished in about 0.5 to about 20 hours.

Compounds (2a) and (2b) can be produced by reducing compounds (28) and (32), respectively, under the same conditions as described in connection with the reaction, as shown in Reaction scheme 1, for producing Compound (1b) from Compound (1a) when a catalytic hydrogenation reducing agent is used. It is desirable to introduce an inorganic acid such as hydrochloric acid or sulfuric acid into the reaction system usually in an amount of at least 1 mol, and preferably 1 to 2 mol, per mol of compounds (28) or (32).

The reaction for producing Compound (29) from Compound (2a) and the reaction for producing Compound (33) from Compound (2b) are carried out, in a suitable solvent in the presence of an acid, by separately reacting Compound (2a) and Compound (2b) with an alcohol compound represented by

HO—(CH$_2$)$_m$—OH (51)

wherein m is as defined above.

Solvents and acids usable herein include those that are usable in the reaction of Compound (2) with Compound (3) shown in Reaction Scheme 1 above.

It is usually advantageous to use an acid in a catalytic amount. The amount of Compound (51) is usually at least 1 mol, and preferably 1 to 5 mol, per mol of Compound (2a) or (2b).

The reactions are usually carried out at about room temperature to 200° C., and preferably about room temperature to about 150° C. The reactions are usually finished in about 0.5 hours to about 10 hours.

The reaction of Compound (24) with Compound (10), the reaction of Compound (27) with Compound (10), the reaction of Compound (28) with Compound (10), the reaction of Compound (2a) with Compound (10), and the reaction of Compound (29) with Compound (10) are carried out under the same conditions as described in connection with the reaction of Compound (1e) with Compound (7) shown in Reaction scheme 3.

The reaction for producing Compound (2a) from Compound (29) and the reaction for producing Compound (2b) from Compound (33) are carried out under the same conditions as described in connection with the reaction for producing Compound (9) from Compound (8) shown in Reaction scheme 4. In these reactions, pyridinium p-toluenesulfonate and like sulfonates are usable as acids.

Reaction Scheme 18

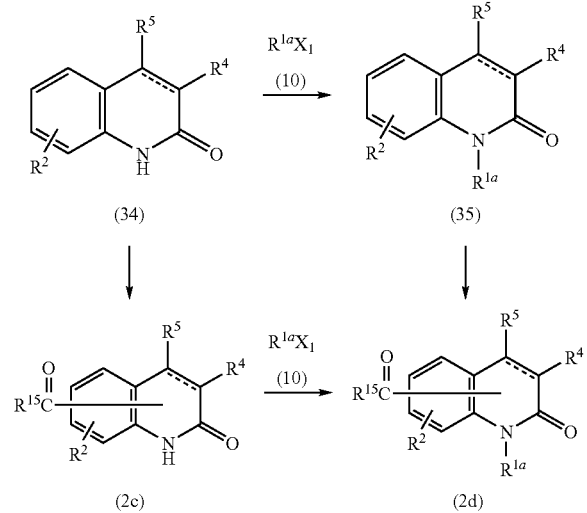

wherein $R^{1a}$, $R^2$, $R^4$, $R^5$, $R^{15}$, $X_1$, and the bond between the 3- and 4-positions of the carbostyril skeleton are as defined above.

The reaction for producing, from Compound (34), Compound (2c) wherein $R^{15}$ is a hydrogen atom, and the reaction for producing, from Compound (35), Compound (2d) wherein $R^{15}$ is a hydrogen atom, are carried out, in a suitable solvent in the presence of a catalyst, by separately reacting Compound (34) and Compound (35) with a compound represented by $$X_1(X_2)CHOR^{24} \tag{52}$$

wherein $X_1$ and $X_2$ are as defined above, and $R^{24}$ is a lower alkyl group.

Solvents usable herein include those that are usable in the reaction of Compound (1dd) with Compound (22) shown in Reaction Scheme 15 above.

Examples of catalysts are titanium tetrachloride and like titanium compounds; tin(IV) chloride and like tin compounds; aluminium chloride and like aluminium compounds; etc. Catalyst is usually used in an amount of at least 1 mol, and preferably 1 to 5 mol, per mol of Compound (34) or (35).

Compound (52) is usually used in an amount of at least 1 mol, and preferably 1 to 5 mol, per mol of Compound (34) or (35).

The reaction is usually carried out at about 0 to about 70° C., and preferably about 0 to about 50° C. The reaction is usually finished in about 1 minute to about 1 hour.

The reaction for producing, from Compound (34), Compound (2c) wherein $R^{15}$ is a hydrogen atom, and the reaction for producing, from Compound (35), Compound (2d) wherein $R^{15}$ is a hydrogen atom, can be carried out, in the presence of a halogenating agent and an acid, by separately reacting Compound (34) and Compound (35) with p-formaldehyde and then hexamethylenetetramine.

Examples of halogenating agents usable herein are hydrochloric acid, hydrobromic acid, etc. Examples of acids are sulfuric acid, phosphoric acid, and like inorganic acids; p-toluenesulfonic acid, formic acid, acetic acid, and like organic acids; and mixtures of such acids. Halogenating agent and acid are usually used in large excess.

p-Formaldehyde is usually used in an amount at least 0.1 times, and preferably 0.1 times to equal to, Compound (34) or (35).

Hexamethylenetetramine is usually used in an amount of at least 1 mol, and preferably 1 to 5 mol, per mol of compound (34) or (35).

The reaction is usually carried out at about room temperature to about 150° C., and preferably about room temperature to about 100° C. The reaction is usually finished in about 0.5 to about 10 hours.

The reaction for producing, from Compound (34), Compound (2c) wherein $R^{15}$ is a hydrogen atom and the reaction for producing, from Compound (35), Compound (2d) wherein $R^{15}$ is a hydrogen atom can be carried out, in a suitable solvent in the presence of an acid, by separately reacting Compound (34) and Compound (35) with hexamethylenetetramine.

These reactions are generally called Duff reactions. Acids usable herein are those that are preferably used in Duff reactions, for example, acetic acid, boric acid/anhydrous glycerol, trifluoroacetic acid, etc. Acid is usually used in an amount at least equimolar, and preferably equimolar to a large excess, per mol of Compound (34) or (35).

Solvents usable herein include those that are usable in the reaction of Compound (1dd) with Compound (22) shown in Reaction Scheme 15 above.

The reactions are usually carried out at about room temperature to about 200° C., and preferably about room temperature to about 150° C. The reactions are usually finished in about 0.5 to about 10 hours.

Compound (2c) wherein $R^{15}$ is a lower alkyl group and Compound (2d) wherein $R^{15}$ is a lower alkyl group are produced by separately reacting, in a suitable solvent in the presence of an acid, reacting Compound (34) and Compound (35) with a compound represented by $$X_1COR^{15a} \tag{53}$$

wherein $X_1$ is as described above and $R^{15a}$ is a lower alkyl group.

These reactions are generally called Friedel-Crafts reactions and performed in a suitable solvent in the presence of a Lewis acid.

Lewis acids usable herein include any Lewis acids typically used in such Friedel-Crafts reactions, and examples are aluminium chloride, zinc chloride, iron chloride, tin(IV) chloride, boron tribromide, boron trifluoride, concentrated sulfuric acid, etc.

Examples of usable solvents are carbon disulfide, nitrobenzene, chlorobenzene, and like aromatic hydrocarbons; dichloromethane, dichloroethane, carbon tetrachloride, tetrachloroethane, and like halogenated hydrocarbons; nitroethane, nitromethane, and like aliphatic nitro compounds; mixed solvents of such solvents; etc.

Lewis acid is usually used in an amount of 1 to 6 mol per mol of compounds (34) or (35).

Compound (53) is usually used in an amount of at least 1 mol, and preferably 1 to 5 mol, per mol of Compound (34) or (35).

The reactions are usually carried out at about 0 to about 150° C., and preferably about 0 to about 100° C. The reactions are usually finished in about 0.5 to about 25 hours.

The reaction of Compound (34) with Compound (10) and the reaction of Compound (2c) with Compound (10) are carried out under the same conditions as described in connection with the reaction of Compound (1e) with Compound (7) shown in Reaction Scheme 3 above.

Reaction Scheme 19

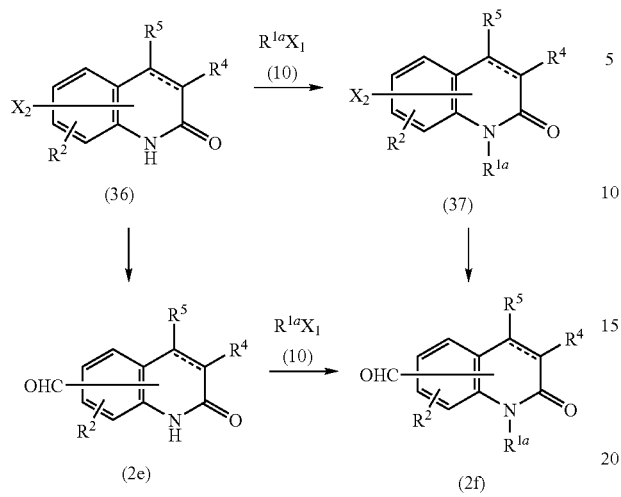

wherein $R^{1a}$, $R^2$, $R^4$, $R^5$, $X_1$, $X_2$, and the bond between the 3- and 4-positions of the carbostyril skeleton are as defined above.

The reaction for producing Compound (2e) from Compound (36) and the reaction for producing Compound (2f) from Compound (37) are carried out by reacting Compound (36) with carbon monoxide gas, and Compound (37) with carbon monoxide gas, respectively, in a suitable solvent in the presence of a catalyst and an acid alkali metal salt.

Examples of solvents and catalysts usable in these reactions include those that are usable in the reaction of Compound (1dd) with Compound (22) shown in Reaction Scheme 15 above.

Examples of acid alkali metal salts are sodium formate, potassium formate, sodium acetate, potassium acetate, etc. Acid alkali metal salt is usually used in an amount of at least 1 mol, and preferably 1 to 5 mol, per mol of Compound (36) or (37).

Catalyst is usually used in an amount of 0.01 to 1 mol per mol of Compound (36) or (37).

Carbon monoxide gas is usually used in a large excess relative to Compound (36) or (37).

The reactions are usually carried out at about room temperature to about 200° C., and preferably about room temperature to about 150° C. The reactions are usually finished in about 0.5 to about 10 hours.

The reaction of Compound (36) with Compound (10) and the reaction of Compound (2e) with Compound (10) are carried out under the same conditions as described in connection with the reaction of Compound (1e) with Compound (7) shown in Reaction Scheme 3 above.

Reaction Scheme 20

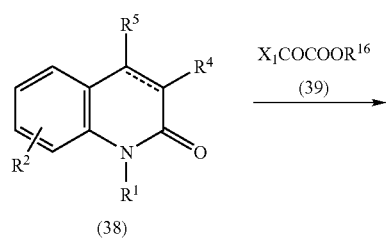

wherein $R^1$, $R^2$, $R^4$, $R^5$, $X_1$, $R^{16}$, $X_2$, and the bond between the 3- and 4-positions of the carbostyril skeleton are as defined above.

The reaction of Compound (38) with Compound (39) is carried out under the same conditions as described in connection with the reaction of Compound (34) with Compound (53) shown in Reaction Scheme 18 above.

The reaction for producing Compound (41) from Compound (40) is carried out by reducing Compound (40) under the same conditions as described in connection with the reaction for producing Compound (1b) from Compound (1a) using a hydride reducing agent, shown in Reaction Scheme 1 above.

The reaction for producing Compound (4a) from Compound (41) is carried out by reacting Compound (41) with a halogenating agent either in a suitable solvent or without a solvent.

Examples of halogenating agents are hydrochloric acid, hydrobromic acid, and like mineral acids, N,N-diethyl-1,2,2-trichlorovinylazide, phosphorus pentachloride, phosphorus pentabromide, phosphorus oxychloride, thionyl chloride, and mixtures of sulfonyl halide compounds (mesyl chloride, tosyl chloride, and the like) with basic compounds, etc.

Basic compounds usable herein are those that are usable in the reaction of Compound (2) with Compound (3) shown in Reaction Scheme 1 above.

Examples of usable solvents are dioxane, tetrahydrofuran, diethyl ether, and like ethers; chloroform, methylene chloride, carbon tetrachloride, and like halogenated hydrocarbons; etc.

When a mixture of sulfonyl halide compound and basic compound is used as a halogenating agent, sulfonyl halide compound is usually used in an amount of at least 1 mol, and preferably 1 to 2 mol, per mol of Compound (41). Basic compound is usually used in a catalytic amount, and preferably a catalytic to equimolar amount, relative to Compound (41). When other halogenating agents are used, the halogenating agent is usually used in an amount of at least 1 mol, and preferably 1 to 10 mol, per mol of Compound (41).

The reaction advantageously proceeds usually at room temperature to 150° C., and preferably room temperature to 100° C. The reaction is usually finished in about 1 to about 10 hours.

Reaction Scheme 21

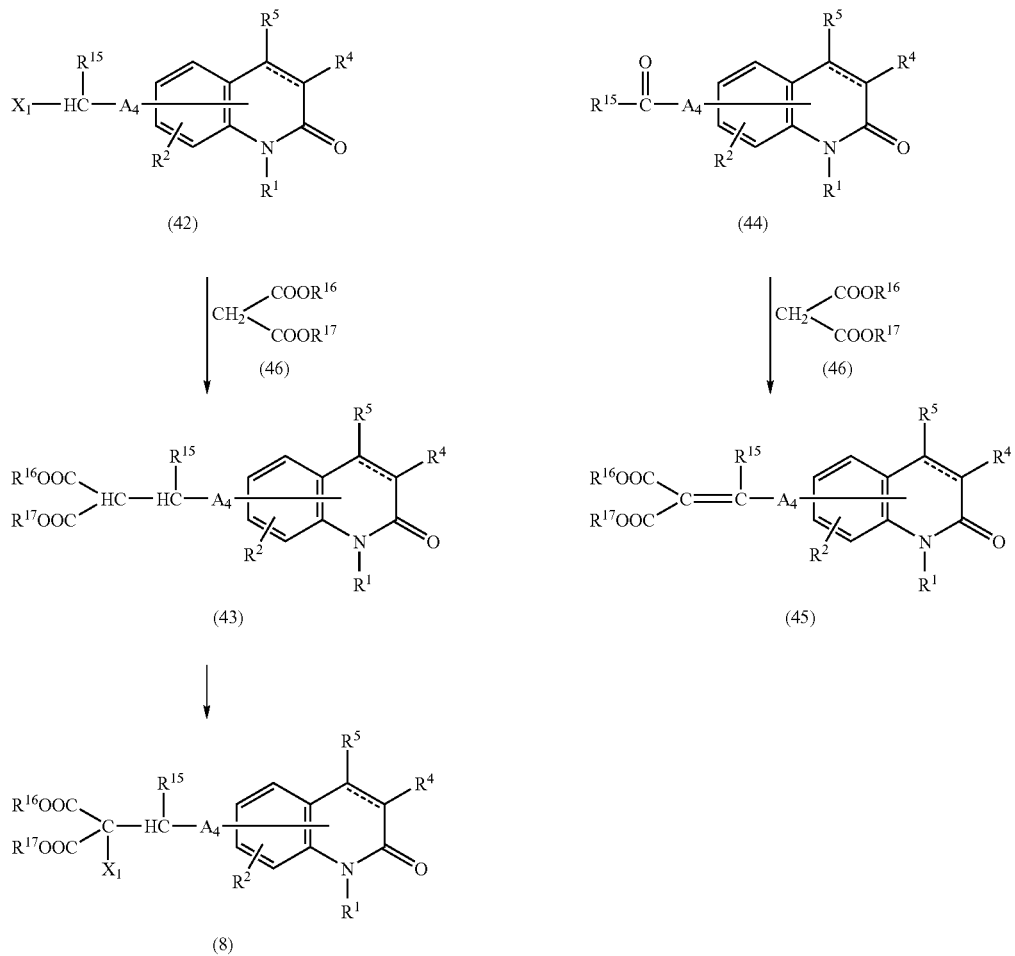

wherein $R_1$, $R_2$, $R_4$, $R_5$, $X_1$, $R^{15}$, $R^{16}$, $R^{17}$, $A_4$, and the bond between the 3- and 4-positions of the carbostyril skeleton are as defined above.

The reaction of Compound (42) with Compound (46) is carried out under the same conditions as described in connection with the reaction of Compound (1e) with Compound (7) shown in Reaction Scheme 3 above.

The reaction for producing Compound (8) from Compound (43) is carried out in a suitable solvent in the presence of a halogenating agent either in the presence or absence of a basic compound.

Examples of halogenating agents usable herein are $Br_2$, $Cl_2$, and like halogen molecules, iodine chloride, sulfuryl chloride, copper compounds such as copper(I) bromide, N-bromosuccinimide and like N-halosuccinimides, etc.

Examples of usable solvents are diethyl ether, tetrahydrofuran, dioxane, 2-methoxyethanol, monoglyme, diglyme, and like ethers; dichloromethane, dichloroethane, chloroform, carbon tetrachloride, and like halogenated hydrocarbons; acetic acid, propionic acid, and like aliphatic acids; carbon disulfide; etc.

Examples of basic compounds include those that are usable in the reaction of Compound (2) with Compound (3) shown in Reaction Scheme 1 presented above.

Halogenating agent is usually used in an amount of 1 to 10 mol, and preferably 1 to 5 mol, per mol of Compound (43).

Basic compound is usually used in an amount of 1 to 10 mol, and preferably 1 to 5 mol, per mol of Compound (43).

The reaction is usually carried out at about 0 to about 200° C., and preferably about 0 to about 100° C. The reaction is usually finished in about 5 minutes to about 20 hours.

The reaction of Compound (44) with Compound (46) is carried out in a suitable solvent in the presence of a basic compound.

Examples of basic compounds usable herein are sodium hydroxide, potassium hydroxide, calcium hydroxide, sodium carbonate, potassium carbonate, and like inorganic basic compounds; sodium acetate and like aliphatic acid alkali metal salts; piperidine, triethylamine, trimethylamine, pyridine, dimethylaniline, N-ethyldiisopropylamine, dimethylaminopyridine, N-methylmorpholine, DBN, DBU, DABCO, and like organic bases; etc. Such basic compounds may be used singly or as a combination of two or more such compounds.

Any inert solvents are usable insofar as they do not adversely affect the reaction, for example, water, aromatic hydrocarbons such as benzene, toluene and xylene, ethers such as diethyl ether, tetrahydrofuran, dioxane, monoglyme and diglyme, halogenated hydrocarbons such as dichloromethane, dichloroethane, chloroform and carbon tetrachloride, lower alcohols such as methanol, ethanol, isopropanol, butanol, tert-butanol and ethylene glycol, aliphatic acids such as acetic acid, esters such as ethyl acetate and methyl acetate, ketones such as acetone and methyl ethyl ketone, acetonitrile, pyridine, dimethyl sulfoxide, N,N-dimethylformamide, hexamethylphosphoric triamide, mixtures of such solvents, etc.

Basic compound is usually used in an amount of about 0.1 to about 5 mol per mol of Compound (45).

Compound (46) is usually used in an amount of at least 1 mol, and preferably about 1 to about 5 mol, per mol of Compound (45).

The reaction temperature is usually about room temperature to about 200° C., and preferably about 50 to about 150° C. The reaction is usually finished in about 5 minutes to about 30 hours.

The reaction for producing Compound (43) from Compound (46) is carried out by reducing Compound (46) under the same conditions as described in connection with the reaction for producing Compound (1b) from Compound (1a) shown in Reaction Scheme 1 in which a catalytic hydrogenation reducing agent is used.

Each of the objective compounds obtained according to the above reaction schemes can be isolated and purified from the reaction mixture by, for example, after cooling the reaction mixture, performing an isolation procedure such as filtration, concentration, extraction, etc., to separate a crude reaction product, and then subjecting the crude reaction product to a usual purification procedure such as column chromatography, recrystallization, etc.

The carbostyril compound of Formula (1) according to the present invention includes stereoisomers and optical isomers, and solvents such as hydrate, etc.

Among the compounds of the present invention, those having a basic group or groups can easily form salts with common pharmaceutically acceptable acids. Examples of such acids include hydrochloric acid, hydrobromic acid,

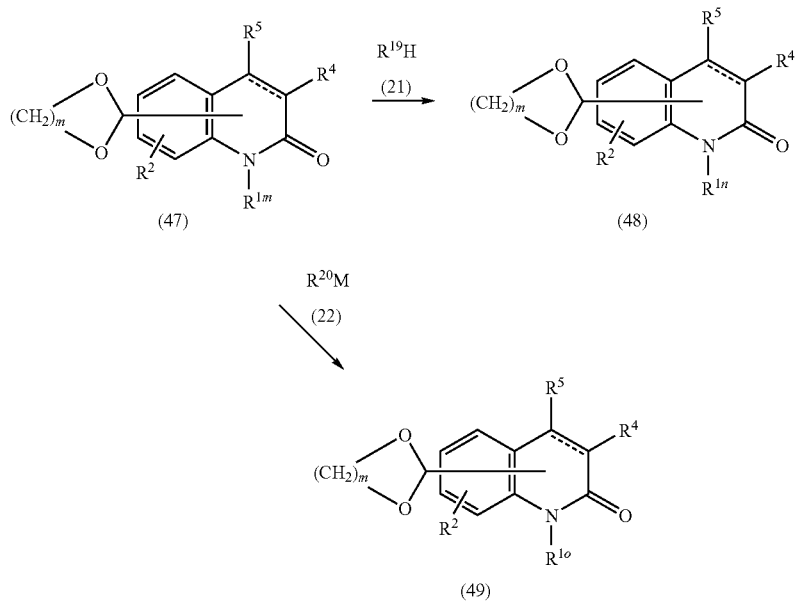

Reaction Scheme 22 wherein $R^{1m}$, $R^{1n}$, $R^{1o}$, $R^2$, $R^4$, $R^5$, M, m, and the bond between the 3- and 4-positions of the carbostyril skeleton are as defined above.

The reaction of Compound (47) with Compound (21) is carried out under the same conditions as described in connection with the reaction of Compound (1dd) with Compound (21) shown in Reaction Scheme 15 above.

The reaction of Compound (47) with Compound (22) is carried out under the same conditions as described in connection with the reaction of Compound (1dd) with Compound (21) shown in Reaction Scheme 15 above.

By reacting Compound (23) with starting Compounds (24), (34), (36), (38), (42) and (47) in which $R^2$ is a hydroxyl group, the corresponding compounds in which $R^2$ is a group as defined in (2-2), (2-4), (2-5), and (2-7) to (2-32) can be produced. These reactions are carried out under the same conditions as described in connection with the reaction of Compound (1gg) with Compound (23) shown in Reaction Scheme 16 above.

By reacting Compound (10) with starting Compounds (38) and (42) in which $R^1$ is a hydrogen atom, the corresponding compounds in which $R^1$ is a group as defined in (1-2) to (1-29) can be produced. These reactions are carried out under the same conditions as described in connection with the reaction of Compound (1h) with Compound (1o) shown in Reaction Scheme 5 above.

nitric acid, sulfuric acid, phosphoric acid and other inorganic acid, methansulfonic acid, p-toluenesulfonic acid, acetic acid, citric acid, tartric acid, maleic acid, fumaric acid, malic acid, lactic acid and other organic acid, etc.

Among the compounds of the present invention, those having an acidic group or groups can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

The following is an explanation of pharmaceutical preparations comprising the compound of the present invention as an active ingredient.

Such pharmaceutical preparations are obtained by formulating the compound of the present invention into usual pharmaceutical preparations, using usually employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, fatty acid esters of polyoxyethylenesorbitan, sodium laurylsulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with usual coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, ethanol and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, ethanol, propylene glycol, ethoxylated isostearyl alcohol, polyoxylated isostearyl alcohol, fatty acid esters of polyoxyethylene sorbitan, etc. In this case, the pharmaceutical preparation may contain sodium chloride, glucose or glycerin in an amount sufficient to prepare an isotonic solution, and may contain usual solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is usually preferable that the pharmaceutical preparation contain the compound of the present invention in a proportion of 1 to 70 wt. %.

The route of administration of the pharmaceutical preparation according to the present invention is not limited, and the preparation is administered by a route suitable for the form of the preparation, patient's age and sex, conditions of the disease, and other conditions. For example, tablets, pills, solutions, suspensions, emulsions, granules and capsules are administered orally. Injections are intravenously administered singly or as mixed with usual injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, patient's age and sex, severity of the disease, and other conditions, and is usually about 0.001 to about 100 mg/kg body weight/day, and preferably 0.001 to 50 mg/kg body weight/day, in single or divided doses.

Since the dosage varies depending on various conditions, a dosage smaller than the above range may be sufficient or a dosage larger than the above range may be required.

The carbostyril derivative of the present invention induces TFF production, such as TFF2 production, and thus is useful as an active ingredient of a TFF inducer (up-regulator), particularly TFF2 inducer.

The compound of the present invention can be used, based on its TFF production inducing activity, as an agent for preventing or treating various diseases, for example, mucosal injury, in human and veterinary medicines. Specific examples of diseases for which preventive or therapeutic effects can be obtained based on TFF production inducing activity, particularly TFF2 production inducing activity, include acute and chronic alimentary tract diseases of various origins (e.g., drug-induced ulcers, peptic gastric ulcers, ulcerative colitis, Crohn's disease, drug-induced enteritis, ischemic colitis, irritable bowel syndrome, ulcers developed after endoscopic demucosation, acute gastritis, chronic gastritis, reflux esophagitis, esophageal ulcer, Barrett esophagus, gastrointestinal mucositis (such as gastrointestinal mucositis caused by chemotherapy, radiotherapy, etc), hemorrhoidal diseases, etc.); oral diseases (e.g., stomatitis (such as stomatitis caused by chemotherapy or radiotherapy, aphthous stomatitis, etc), Sjögren syndrome, xerostomia, etc.); upper respiratory tract diseases (e.g., rhinitis, pharyngitis, etc.); respiratory tract diseases (e.g., bronchial asthma, chronic obstructive lung diseases, etc.); eye diseases (e.g., dry eye, keratoconjunctivitis, etc.); cancers; wounds; etc.

The compound of the present invention has few side effects and is highly safe.

The carbostyril compounds of Formula (1) and salts thereof encompassed by the present invention can be administered in combination with TFF peptides (TFF1, TFF2, TFF3, etc), other type of compounds having an inducing activity of TFF production, and/or other drugs (such as, anti-inflammatory agents, anti-ulcer drugs, etc).

The patents, patent applications and publications cited herein are incorporated by reference.

BRIEF DESCRIPTION OF DRAWINGS

FIG. 1 shows a comparison between the nucleotide sequence of the PCR product cloned to the plasmid pCR-Blunt-TFF2pro (Sequence Number 1 in Sequence Listing) and the counterpart of the hTFF2 promoter region reported in a gene bank (GenBank accession AB038162).

BEST MODE FOR CARRYING OUT THE INVENTION

The following Examples are intended to illustrate the present invention in further detail.

Reference Example 1

Synthesis of 8-methoxy-1-methyl-2-oxo-1,2-dihydroquinoline-5-carboxaldehyde

8-Methoxy-1-methyl-1H-quinolin-2-one (21.14 g, 0.11 mol) and paraformaldehyde (10.6 g) were suspended in concentrated hydrochloric acid (105 ml), and 4 ml of concentrated sulfuric acid was added, followed by stirring at 70 to 80° C. for 2.5 hours. After cooling to room temperature, ice water was added to the reaction mixture, and extraction with dichloromethane was performed. The organic layer was washed with a saturated sodium chloride solution and dried over anhydrous sodium sulfate. The solvent was then distilled off under reduced pressure. The residue was dissolved in 400 ml of chloroform, and hexamethylenetetramine (4.25 g, 0.03 mol) was added, followed by heating under reflux for 2.5 hours. After cooling to room temperature, the solvent was distilled off under reduced pressure. 50% acetic acid (110 ml) was added to the residue, and stirring was carried out at 100° C. for 2 hours. After cooling to room temperature, water was added, and the insoluble matter was collected by filtration and dried to thereby obtain 13.81 g (yield: 57%) of 8-methoxy-1-methyl-2-oxo-1,2-dihydroquinoline-5-carboxaldehyde as a light yellow powder.

$^1$H-NMR(DMSO-d$_6$) dppm: 3.80 (3H, s), 4.01 (3H, s), 6.79 (1H, d, J=9.9 Hz), 7.45 (1H, d, J=8.4 Hz), 7.86 (1H, d, J=8.4 Hz), 9.05 (1H, d, J=9.9 Hz), 10.14 (1H, s)

Reference Example 2

Synthesis of diethyl 2-(8-methoxy-1-methyl-2-oxo-1,2-dihydroquinolin-5-ylmethylene)malonate 8-Methoxy-1-methyl-2-oxo-1,2-dihydroquinoline-5-carboxaldehyde (18.9 g), diethyl malonate (26.5 ml) and piperidine (2.7 ml) were added to pyridine (90 ml), and the resulting mixture was stirred at 90 to 100° C. for 6 hours. After cooling to room temperature, the reaction mixture was added to cold concentrated hydrochloric acid, and the precipitated solid was collected by filtration, washed with water and dried to thereby obtain 16.62 g (yield: 53%) of diethyl 2-(8-methoxy-1-methyl-2-oxo-1,2-dihydroquinolin-5-ylmethylene)malonate as a yellow powder.

$^1$H-NMR(DMSO-d$_6$) dppm: 1.10 (3H, t, J=7.2 Hz), 1.28 (3H, t, J=7.2 Hz), 3.80 (3H, s), 3.92 (3H, s), 4.05-4.3 (4H, m), 6.69 (1H, d, J=9.8 Hz), 7.18 (1H, d, J=8.5 Hz), 7.30 (1H, d, J=8.5 Hz), 7.84 (1H, d, J=9.8 Hz), 8.14 (1H, s)

Reference Example 3

Synthesis of diethyl 2-(8-methoxy-1-methyl-2-oxo-1,2-dihydroquinolin-5-ylmethyl)malonate Diethyl 2-(8-methoxy-1-methyl-2-oxo-1,2-dihydroquinolin-5-ylmethylene)malonate (16.62 g) and 10% palladium carbon (1.6 g) were added to 300 ml of ethanol, followed by catalytic hydrogenation at room temperature and atmospheric pressure for 6 hours. The catalyst was filtered off, and the filtrate was concentrated under reduced pressure. The residue was purified by silica gel column chromatography (ethyl acetate:n-hexane=1:1) to thereby obtain 13.59 g (yield: 81%) of diethyl 2-(8-methoxy-1-methyl-2-oxo-1,2-dihydroquinolin-5-ylmethyl)malonate as a light yellow oil.

$^1$H-NMR(CDCl$_3$) dppm: 1.15-1.3 (6H, m), 3.45 (2H, d, J=7.6 Hz), 3.60 (1H, t, J=7.6 Hz), 3.89 (3H, s), 3.95 (3H, s), 4.1-4.25 (4H, m), 6.75 (1H, d, J=9.8 Hz), 6.96 (1H, d, J=8.3 Hz), 7.04 (1H, d, J=8.3 Hz), 7.86 (1H, d, J=9.8 Hz)

Reference Example 4

Synthesis of diethyl 2-chloro-2-(8-methoxy-1-methyl-2-oxo-1,2-dihydroquinolin-5-ylmethyl)malonate Sodium hydride (60% in oil) (1.0 g) was added under ice cooling to a tetrahydrofuran (THF) solution (140 ml) of 13.59 g of diethyl 2-(8-methoxy-1-methyl-2-oxo-1,2-dihydroquinolin-5-ylmethyl)malonate, and stirring was carried out until the generation of hydrogen stopped. N-chlorosuccinimide (5.6 g) was added, followed by stirring for 1 hour. The reaction mixture was added to cold hydrochloric acid, and extraction with dichloromethane was performed. After drying over anhydrous sodium sulfate, the dry product was concentrated under reduced pressure, diisopropyl ether was added to the residue, and the precipitated solid was collected by filtration and dried to thereby obtain 12.77 g (yield: 86%) of diethyl 2-chloro-2-(8-methoxy-1-methyl-2-oxo-1,2-dihydroquinolin-5-ylmethyl)malonate as a light yellow powder.

$^1$H-NMR(CDCl$_3$) dppm: 1.28 (3H, t, J=7.2 Hz), 3.86 (2H, s), 3.89 (3H, s), 3.92 (3H, s), 4.2-4.3 (4H, m), 6.71 (1H, d, J=9.8 Hz), 6.98 (1H, d, J=8.4 Hz), 7.10 (1H, d, J=8.4 Hz), 7.93 (1H, d, J=9.8 Hz)

Reference Example 5

Synthesis of 2-chloro-3-(8-methoxy-1-methyl-2-oxo-1,2-dihydroquinolin-5-yl)propionic acid Diethyl 2-chloro-2-(8-methoxy-1-methyl-2-oxo-1,2-dihydroquinolin-5-ylmethyl)malonate (5.1 g) was added to a mixture of 20 ml of acetic acid and 15 ml of 6N hydrochloric acid, followed by heating under reflux for 9 hours. After cooling to room temperature, water was added to the reaction mixture, followed by cooling with ice. The precipitated solid was collected by filtration, washed with water and dried to thereby obtain 3.1 g of 2-chloro-3-(8-methoxy-1-methyl-2-oxo-1,2-dihydroquinolin-5-yl)propionic acid as a light yellow powder.

$^1$H-NMR(DMSO-d$_6$) dppm: 3.45-3.65 (2H, m), 3.77 (3H, s), 3.86 (3H, s), 4.5-4.65 (1H, m), 6.62 (1H, d, J=9.8 Hz), 7.14 (1H, d, J=8.3 Hz), 7.21 (1H, d, J=8.3 Hz), 8.03 (1H, d, J=9.8 Hz), 13.4 (1H, brs)

Reference Example 6

Synthesis of diethyl 2-[2-(8-methoxy-1-methyl-2-oxo-1,2-dihydroquinolin-5-yl)ethyl]malonate Sodium hydride (60% in oil) (0.5 g) was added under ice cooling to a tetrahydrofuran (THF) solution (30 ml) of diethyl malonate (2.2 ml), and stirring was carried out until the generation of hydrogen stopped. 5-(2-iodoethyl)-8-methoxy-1-methyl-2-oxo-1,2-dihydroquinoline (1.54 g) was added, followed by stirring at room temperature overnight. The reaction mixture was added to cold hydrochloric acid, and extraction with dichloromethane was performed. After drying over anhydrous sodium sulfate, the dry product was concentrated under reduced pressure, and the residue was purified by silica gel column chromatography (dichloromethane:methanol=50:1→40:1). The purified product was under reduced pressure to thereby obtain 1.73 g (yield: quantitative) of diethyl 2-[2-(8-methoxy-1-methyl-2-oxo-1,2-dihydroquinolin-5-yl)ethyl]malonate as a yellow oil.

$^1$H-NMR(CDCl$_3$) dppm: 1.2-1.4 (6H, m), 2.1-2.25 (2H, m), 2.8-3.0 (2H, m), 3.3-3.5 (1H, m), 3.88 (3H, s), 3.93 (3H, s), 4.1-4.4 (4H, m), 6.75 (1H, d, J=9.7 Hz), 6.9-7.1 (2H, m), 7.92 (1H, d, J=9.7 Hz)

Reference Example 7

Synthesis of diethyl of 2-chloro-2-[2-(8-methoxy-1-methyl-2-oxo-1,2-dihydroquinolin-5-yl)ethyl]malonate Sodium hydride (60% in oil) (0.21 g) was added under ice cooling to a THF solution (30 ml) of 1.79 g of diethyl 2-[2-(8-methoxy-1-methyl-2-oxo-1,2-dihydroquinolin-5-yl)ethyl]malonate, and stirring was carried out until the generation of hydrogen stopped. N-chlorosuccinimide (0.7 g) was added, followed by stirring for 1.5 hours. The reaction mixture was added to cold hydrochloric acid, and extraction with dichloromethane was performed. The extract was dried over anhydrous sodium sulfate, and concentrated under reduced pressure to thereby obtain 2.38 g (yield: quantitative) of diethyl 2-chloro-2-[2-(8-methoxy-1-methyl-2-oxo-1,2-dihydroquinolin-5-yl)ethyl]malonate as a yellow oil.

$^1$H-NMR(CDCl$_3$) dppm: 1.31 (6H, t, J=7.1 Hz), 2.47 (2H, t, J=8.7 Hz), 2.98 (2H, t, J=8.7 Hz), 3.88 (3H, s), 3.93 (3H, s), 6.75 (1H, d, J=9.7 Hz), 6.9-7.1 (2H, m), 7.87 (1H, d, J=9.7 Hz)

Reference Example 8

Synthesis of 2-chloro-4-(8-methoxy-1-methyl-2-oxo-1,2-dihydroquinolin-5-yl)butyric acid Diethyl 2-chloro-2-[2-(8-methoxy-1-methyl-2-oxo-1,2-dihydroquinolin-5-yl)ethyl]malonate (2.38 g) was added to a mixture of acetic acid (10 ml) and 6N hydrochloric acid (15 ml), and the resulting mixture was heated under reflux overnight. After cooling to room temperature, water and a small quantity of ethanol was added to the reaction mixture, followed by ice cooling. The precipitated solid was collected by filtration, washed with water and dried to thereby obtain 0.99 g (yield: 55%) of 2-chloro-4-(8-methoxy-1-methyl-2-oxo-1,2-dihydroquinolin-5-yl)butyric acid as a gray powder.

$^1$H-NMR(DMSO-$d_6$) dppm: 1.9-2.3 (2H, m), 2.8-3.1 (2H, m), 3.77 (3H, s), 3.85 (3H, s), 4.4-4.6 (1H, m), 6.61 (1H, d, J=9.7 Hz), 7.05 (1H, d, J=7.1 Hz), 7.18 (1H, d, J=7.1 Hz), 7.98 (1H, d, J=9.7 Hz), 13.4 (1H, brs)

Reference Example 9

Synthesis of diethyl 2-[3-(8-methoxy-1-methyl-2-oxo-1,2-dihydroquinolin-5-yl)propyl]malonate Sodium hydride (60% in oil) (0.39 g) was added under ice cooling to a THF solution (30 ml) of diethyl malonate (1.85 ml), and stirring was carried out until the generation of hydrogen stopped. 5-(3-Iodopropyl)-8-methoxy-1-methyl-2-oxo-1,2-dihydroquinoline (2.89 g) was added, followed by stirring at room temperature for 4.5 hours. The reaction mixture was added to cold hydrochloric acid, and extraction with dichloromethane was performed. After drying over anhydrous sodium sulfate, the dry product was concentrated under reduced pressure, and the residue was purified by silica gel column chromatography (dichloromethane:methanol=20:1). The purified product was concentrated under reduced pressure to thereby obtain 2.94 g (yield: 93%) of diethyl 2-[3-(8-methoxy-1-methyl-2-oxo-1,2-dihydroquinolin-5-yl)propyl] malonate as a yellow oil.

$^1$H-NMR(CDCl$_3$) dppm: 1.27 (6H, t, J=7.1 Hz), 1.6-1.8 (2H, m), 1.95-2.1 (2H, m), 2.87 (2H, t, J=7.7 Hz), 3.56 (1H, t, J=7.5 Hz), 3.89 (3H, s), 3.95 (3H, s), 4.1-4.4 (4H, m), 6.73 (1H, d, J=9.8 Hz), 7.00 (2H, s), 7.84 (1H, d, J=9.8 Hz)

Reference Example 10

Synthesis of diethyl 2-chloro-2-[3-(8-methoxy-1-methyl-2-oxo-1,2-dihydroquinolin-5-yl)propyl]malonate Sodium hydride (60% in oil) (0.33 g) was added under ice cooling to a THF solution (30 ml) of diethyl 2-[3-(8-methoxy-1-methyl-2-oxo-1,2-dihydroquinolin-5-yl)propyl]malonate (2.94 g), and stirring was carried out until the generation of hydrogen stopped. N-chlorosuccinimide (1.2 g) was added, followed by stirring for 2 hours. The reaction mixture was added to cold hydrochloric acid, and extraction with dichloromethane was performed. The extract was dried over anhydrous sodium sulfate, and concentrated under reduced pressure to thereby obtain 4.02 g (yield: quantitative) of diethyl 2-chloro-2-[3-(8-methoxy-1-methyl-2-oxo-1,2-dihydroquinolin-5-yl)propyl]malonate as a yellow oil.

$^1$H-NMR(CDCl$_3$) dppm: 1.26 (6H, t, J=7.1 Hz), 1.6-1.9 (2H, m), 2.31 (2H, t, J=8.0 Hz), 2.88 (2H, t, J=7.7 Hz), 3.88 (3H, s), 3.94 (3H, s), 6.72 (1H, d, J=9.8 Hz), 6.99 (2H, s), 7.79 (1H, d, J=9.8 Hz)

Reference Example 11

Synthesis of 2-chloro-5-(8-methoxy-1-methyl-2-oxo-1,2-dihydroquinolin-5-yl)valeric acid Diethyl 2-chloro-2-[3-(8-methoxy-1-methyl-2-oxo-1,2-dihydroquinolin-5-yl)propyl]malonate (4.02 g) was added to a mixture of acetic acid (15 ml) and 6N hydrochloric acid (20 ml), followed by heating under reflux for 24 hours. After cooling to room temperature, water was added to the reaction mixture, followed by cooling with ice. The precipitated solid was collected by filtration, washed with water and dried to thereby obtain 2.30 g (yield: 75%) of 2-chloro-5-(8-methoxy-1-methyl-2-oxo-1,2-dihydroquinolin-5-yl)valeric acid as a light yellow powder.

$^1$H-NMR(DMSO-$d_6$) dppm: 1.6-2.2 (4H, m), 2.7-3.1 (2H, m), 3.77 (3H, s), 3.84 (3H, s), 4.5-4.65 (1H, m), 6.59 (1H, d, J=9.7 Hz), 7.05 (1H, d, J=8.1 Hz), 7.17 (1H, d, J=8.1 Hz), 7.99 (1H, d, J=9.7 Hz), 13.2 (1H, brs)

Reference Example 12

Synthesis of 8-methoxy-2-oxo-1,2,3,4-tetrahydroquinoline-5-carboxaldehyde

8-Methoxy-3,4-dihydro-1H-quinolin-2-one (5 g) was dissolved in dichloromethane (100 ml), and dichloromethyl methyl ether (6.4 ml) was added at room temperature, followed by cooling in an ice water bath. Titanium tetrachloride (85 ml) was added dropwise at a temperature not higher than 10° C., and the resulting mixture was stirred at room temperature overnight. The reaction mixture was poured into ice water, and the aqueous layer was subjected to extraction with dichloromethane. The organic layer was dried over sodium sulfate, filtered, and concentrated under reduced pressure. Diethyl ether was added to the residue and the produced solid was collected by filtration and dried to thereby obtain 5.2 g (yield: 90%) of 8-methoxy-2-oxo-1,2,3,4-tetrahydroquinoline-5-carboxaldehyde.

$^1$H-NMR(CDCl$_3$) dppm: 2.63 (2H, t, J=7.4 Hz), 3.54 (2H, t, J=7.4 Hz), 3.97 (3H, s), 6.92 (1H, d, J=8.5 Hz), 7.50 (1H, d, J=8.5 Hz), 7.84 (1H, brs), 10.02 (1H, s)

Reference Example 13

Synthesis of 8-methoxy-1-ethyl-2-oxo-1,2,3,4-tetrahydroquinoline-5-carboxaldehyde 8-Methoxy-2-oxo-1,2,3,4-tetrahydroquinoline-5-carboxaldehyde (2.0 g) was dissolved in DMF (20 ml), and 0.43 g of sodium hydride (60% in oil) was added under ice cooling. After the addition, stirring was carried out at room temperature until the generation of hydrogen stopped. The resulting mixture was cooled in an ice water bath again, 1.2 ml of ethyl iodide was added dropwise, and stirring was carried out at room temperature for 8 hours. The reaction mixture was poured into iced aqueous hydrochloric acid, extraction with methylene chloride was performed, and the organic layer was dried over sodium sulfate, filtered, and concentrated under reduced pressure. The residue was purified by silica gel column chromatography to thereby obtain 2.1 g (yield: 91%) of 8-methoxy-1-ethyl-2-oxo-1,2,3,4-tetrahydroquinoline-5-carboxaldehyde.

$^1$H-NMR(CDCl$_3$) dppm: 1.15 (3H, t, J=7.1 Hz), 2.51 (2H, t, J=7.0 Hz), 3.36 (2H, t, J=7.0 Hz), 3.97 (3H, s), 4.01 (2H, t, J=7.4 Hz), 6.98 (1H, d, J=8.6 Hz), 7.60 (1H, d, J=8.6 Hz), 10.06 (1H, s)

Reference Example 14

Synthesis of
8-methoxy-1-methyl-3,4-dihydro-1H-quinolin-2-one

8-Methoxy-3,4-dihydro-1H-quinolin-2-one (15 g) was dissolved in DMF (150 ml), and 3.6 g of sodium hydride (60% in oil) was added under ice cooling. After the addition, stirring was carried out at room temperature until the generation of hydrogen stopped. The resulting mixture was cooled with ice water again, and 5.8 ml of methyl iodide was added dropwise, followed by stirring at room temperature overnight. The solvent was distilled off under reduced pressure, and the residue was purified by silica gel column chromatography to thereby obtain 16.7 g (yield: 96%) of 8-methoxy-1-methyl-3,4-dihydro-1H-quinolin-2-one.
$^1$H-NMR(CDCl$_3$) dppm: 2.5-2.6 (2H, m), 2.8-2.9 (2H, m), 3.39 (3H, s), 3.85 (3H, s), 6.75-6.9 (2H, m), 7.0-7.05 (1H, m)

Reference Example 15

Synthesis of 8-methoxy-1-methyl-2-oxo-1,2,3,4-tetrahydroquinoline-5-carboxaldehyde 8-Methoxy-1-methyl-3,4-dihydro-1H-quinolin-2-one (1.5 g) was dissolved in dichloromethane (15 ml), and dichloromethyl methyl ether (0.86 ml) was added at room temperature, followed by cooling with ice water. Titanium tetrachloride (10.5 ml) was added dropwise, and the resulting mixture was stirred at room temperature overnight. Further, dichloromethyl methyl ether (1.29 ml) and titanium tetrachloride (15.8 ml) were added, and stirring was carried out at room temperature for 5 hours. The reaction mixture was poured into ice water, and the aqueous layer was subjected to extraction with dichloromethane. The organic layer was dried over sodium sulfate, filtered, and concentrated under reduced pressure. Hexane was added to the residue, and the produced insoluble matter was collected by filtration and dried to thereby obtain 1.37 g (yield: 80%) of 8-methoxy-1-methyl-2-oxo-1,2,3,4-tetrahydroquinoline-5-carboxaldehyde.
$^1$H-NMR(CDCl$_3$) dppm: 2.5-2.55 (2H, m), 3.3-3.45 (2H, m), 3.96 (3H, s), 6.99 (1H, d, J=8.6 Hz), 7.60 (1H, d, J=8.6 Hz), 10.06 (1H, s)

Reference Example 16

Synthesis of 1-(4-biphenylmethyl)-6-bromo-3,4-dihydro-1H-quinolin-2-one

Sodium hydride (60% in oil) (0.49 g) was added at 0° C. to a DMF solution (20 ml) of 6-bromo-3,4-dihydro-1H-quinolin-2-one (2.54 g), followed by stirring for 30 minutes. 4-Bromomethylbiphenyl (3.05 g) was added, and the resulting mixture was stirred at room temperature overnight. Water was added to the reaction mixture, extraction with ethyl acetate was performed, and the extract was dried over anhydrous sodium sulfate, and concentrated under reduced pressure. The residue was purified by silica gel column chromatography (ethyl acetate:n-hexane=1:6→1:2). The purified product was recrystallized from a chloroform-diisopropyl ether mixed solvent to thereby obtain 4.06 g (yield: 92%) of 1-(4-biphenylmethyl)-6-bromo-3,4-dihydro-1H-quinolin-2-one as a white powder.
$^1$H-NMR(DMSO-d$_6$) dppm: 2.65-2.78 (2H, m), 2.89-3.03 (2H, m), 5.17 (2H, s), 6.90 (1H, d, J=8.7 Hz), 7.23-7.39 (4H, m), 7.39-7.50 (3H, m), 7.50-7.71 (4H, m)

Reference Example 17

Synthesis of 1-(4-biphenylmethyl)-2-oxo-1,2,3,4-tetrahydroquinoline-6-carboxaldehyde A DMF solution (30 ml) of 1-(4-biphenylmethyl)-6-bromo-3,4-dihydro-1H-quinolin-2-one (2.80 g), sodium formate (0.171 g) and bistriphenylphosphine palladium chloride (0.25 g) was stirred under a carbon monoxide atmosphere at 100° C. for 4 hours. Water was added to the reaction mixture, extraction with ethyl acetate was performed, and the extract was dried over anhydrous sodium sulfate, and concentrated under reduced pressure. The residue was purified by silica gel column chromatography (ethyl acetate:n-hexane=1:4→1:2). The purified product was recrystallized from a chloroform-diethyl ether mixed solvent to thereby obtain 1.95 g (yield: 78%) of 1-(4-biphenylmethyl)-2-oxo-1,2,3,4-tetrahydroquinoline-6-carboxaldehyde as a white powder.
$^1$H-NMR(DMSO-d$_6$) dppm: 2.78 (2H, t, J=8.0 Hz), 3.07 (2H, t, J=8.0 Hz), 5.24 (2H, s), 7.15 (1H, d, J=8.4 Hz), 7.25-7.49 (5H, m), 7.55-7.82 (6H, m), 9.84 (1H, s)

Reference Example 18

Synthesis of 1-(4-chlorobenzyl)-2-oxo-1,2-dihydro-quinoline-4-carboxaldehyde

Sodium hydride (60% in oil) (1.3 g) was added at 0° C. to a DMF solution (50 ml) of 2-oxo-1,2-dihydroquinoline-4-carboxaldehyde (5.13 g), followed by stirring for 30 minutes. 4-chlorobenzylbromide (7.0 g) was added, and the resulting mixture was stirred at room temperature overnight. Water was added to the reaction mixture, extraction with ethyl acetate was performed, and the extract was dried over anhydrous sodium sulfate, and concentrated under reduced pressure. The residue was purified by silica gel column chromatography (ethyl acetate:n-hexane=1:10→1:4). The purified product was recrystallized from a chloroform-diisopropyl ether-n-hexane mixed solvent to thereby obtain 4.13 g (yield: 47%) of 1-(4-chlorobenzyl)-2-oxo-1,2-dihydroquinoline-4-carboxaldehyde as a white powder.
$^1$H-NMR(DMSO-d$_6$) dppm: 5.55 (2H, s), 7.24 (2H, d, J=8.5 Hz), 7.28-7.39 (4H, m), 7.45 (1H, d, J=8.4 Hz), 7.50-7.64 (1H, m), 8.68 (1H, dd, J=1.3, 8.1 Hz), 10.24 (1H, s)

Reference Example 19

Synthesis of 1-(4-chlorobenzyl)-2-oxo-1,2-dihydro-quinoline-3-carboxaldehyde

Sodium hydride (60% in oil) (1.3 g) was added at 0° C. to a DMF solution (50 ml) of 2-oxo-1,2-dihydroquinoline-3-carboxaldehyde (5.13 g), followed by stirring for 30 minutes. 4-chlorobenzyl bromide (7.0 g) was added, and the resulting mixture was stirred at room temperature overnight. Water was added to the reaction mixture, extraction with ethyl acetate was performed, and the extract was dried over anhydrous sodium sulfate, and concentrated under reduced pressure. The residue was purified by silica gel column chromatography (ethyl acetate:n-hexane=1:10→1:4). The purified product was recrystallized from a chloroform-diisopropyl ether mixed solvent to thereby obtain 6.57 g (yield: 72%) of 1-(4-chlorobenzyl)-2-oxo-1,2-dihydroquinoline-3-carboxaldehyde as a white powder.
$^1$H-NMR(DMSO-d$_6$) dppm: 5.56 (2H, s), 7.21-7.39 (5H, m), 7.44 (1H, d, J=8.6 Hz), 7.61-7.72 (1H, m), 8.02 (1H, dd, J=1.4, 7.8 Hz), 8.59 (1H, s), 10.31 (1H, s)

Reference Example 20

Synthesis of 5-trifluoromethanesulfonyloxy-3,4-dihydro-1H-quinolin-2-one

Pyridine (30 ml) and trifluoromethanesulfonic anhydride (25 g) were added with stirring at 0° C. to an anhydrous dichloromethane solution (200 ml) of 5-hydroxy-3,4-dihydro-1H-quinolin-2-one (15.9 g), followed by stirring for 2 hours. The resulting mixture was concentrated under reduced pressure, water was added to the residue, and extraction with dichloromethane was performed. The extract was washed with water, an aqueous potassium hydrogensulfate solution and water in this order, and dried over anhydrous sodium sulfate. After concentration under reduced pressure, the residue was recrystallized from an ethyl acetate-diisopropyl ether mixed solvent to thereby obtain 28 g (yield: 97%) of 5-trifluoromethanesulfonyloxy-3,4-dihydro-1H-quinolin-2-one as a light brown powder.

$^1$H-NMR(CDCl$_3$) dppm: 2.67 (2H, dd, J=6.3 Hz, J=8.8 Hz), 3.07 (2H, t, J=7.2 Hz), 6.80-6.90 (1H, m), 6.90-7.02 (1H, m), 7.16-7.32 (1H, m), 8.95 (1H, brs)

Reference Example 21

Synthesis of 5-cyano-3,4-dihydro-1H-quinolin-2-one

5-Trifluoromethanesulfonyloxy-3,4-dihydro-1H-quinolin-2-one (1.5 g), zinc cyanide (1.3 g) and tetrakis(triphenylphosphine)palladium (0.59 g) were suspended in DMF (20 ml), and the suspension was stirred at 100° C. for 2 hours. The insoluble matter was filtered off, and ethyl acetate was added to the filtrate, followed by washing with water. The resulting mixture was dried over anhydrous magnesium sulfate, and concentrated under reduced pressure, and the residue was recrystallized from an ethyl acetate-diethyl ether mixed solvent to thereby obtain 0.71 g (yield: 81%) of 5-cyano-3,4-dihydro-1H-quinolin-2-one as a light brown powder.

$^1$H-NMR(DMSO-d$_6$) dppm: 2.45-2.60 (2H, m), 3.05 (2H, t, J=7.2 Hz), 7.08-7.18 (1H, m), 7.28-7.40 (2H, m), 10.37 (1H, brs)

Reference Example 22

Synthesis of 2-oxo-1,2,3,4-tetrahydroquinoline-5-carboxaldehyde

5-Cyano-3,4-dihydro-1H-quinolin-2-one (100 mg) and Raney nickel (100 mg) were suspended in formic acid (10 ml), and the suspension was heated under reflux for 2 hours. An additional 100 mg of Raney nickel was added, followed by heating under reflux for 1 hour. The reaction mixture was filtered to remove the insoluble matter, and the filtrate was concentrated. Ethyl acetate and water were added to the residue, and after stirring, the mixture was filtered through Celite. The filtrate was separated into layers, and the organic layer was washed with water and dried over anhydrous sodium sulfate. After concentration under reduced pressure, the residue was recrystallized from an ethyl acetate-n-hexane mixed solvent to thereby obtain 77 mg (yield: 76%) of 2-oxo-1,2,3,4-tetrahydroquinoline-5-carboxaldehyde as a light brown powder.

$^1$H-NMR(DMSO-d$_6$) dppm: 2.39-2.51 (2H, m), 3.35 (2H, t, J=7.4 Hz), 7.10-7.17 (1H, m), 7.31-7.41 (1H, m), 7.44-7.50 (1H, m), 10.18 (1H, s), 10.26 (1H, brs)

Reference Example 23

Synthesis of 1-(4-biphenylmethyl)-2-oxo-1,2,3,4-tetrahydroquinoline-5-carboxaldehyde Sodium hydride (60% in oil) (0.25 g) was added at 0° C. to a DMF solution (10 ml) of 2-oxo-1,2,3,4-tetrahydroquinoline-5-carboxaldehyde (1.0 g), followed by stirring for 30 minutes. 4-bromomethylbiphenyl (1.69 g) was added, and the resulting mixture was stirred at room temperature for 1 hour. Water was added to the reaction mixture, and extraction with ethyl acetate was performed. The extract was washed with a saturated sodium chloride solution, dried over anhydrous magnesium sulfate, and concentrated under reduced pressure. The residue was purified by silica gel column chromatography (ethyl acetate:n-hexane=1:4→1:2). The purified product was recrystallized from a chloroform-diisopropyl ether mixed solvent to thereby obtain 1.11 g (yield: 56%) of 1-(4-biphenylmethyl)-2-oxo-1,2,3,4-tetrahydroquinoline-5-carboxaldehyde as a colorless plate crystals.

$^1$H-NMR(DMSO-d$_6$) dppm: 2.65-2.78 (2H, m), 3.45 (2H, t, J=7.6 Hz), 5.24 (2H, s), 7.21-7.49 (7H, m), 7.49-7.57 (1H, m), 7.57-7.70 (4H, m), 10.24 (1H, s)

Reference Example 24

Synthesis of 5-(1,3-dioxolan-2-yl)-8-methoxy-3,4-dihydro-1H-quinolin-2-one

8-Methoxy-2-oxo-1,2,3,4-tetrahydroquinoline-5-carboxaldehyde (42 g) was suspended in toluene (400 ml), and ethylene glycol (33.7 ml) and p-toluenesulfonic acid monohydrate (0.78 g) were added, and the resulting mixture was heated under reflux in a Dean-Stark apparatus for 4.5 hours. The reaction mixture was cooled, and 10 ml of an aqueous solution containing 1.72 g of sodium bicarbonate was added. Stirring was carried out for some time, and the produced solid was collected by filtration. The solid was washed with water and toluene and dried at 60° C. to thereby obtain 35.5 g (yield: 70%) of 5-(1,3-dioxolan-2-yl)-8-methoxy-3,4-dihydro-1H-quinolin-2-one as white crystals.

$^1$H-NMR(DMSO-d$_6$) dppm: 2.33-2.44 (2H, m), 2.85-2.98 (2H, m), 3.79 (3H, s), 3.86-4.08 (4H, m), 5.78 (1H, s), 6.86 (1H, d, J=8.5 Hz), 7.07 (1H, d, J=8.5 Hz), 8.97 (1H, s)

Reference Example 25

Synthesis of 1-(6-chloropyridin-3-ylmethyl)-5-(1,3-dioxolan-2-yl)-8-methoxy-3,4-dihydro-1H-quinolin-2-one Sodium hydride (55% in oil) (2.1 g) was added in small portions under ice cooling to a DMF solution (70 ml) of 5-(1,3-dioxolan-2-yl)-8-methoxy-3,4-dihydro-1H-quinolin-2-one (10 g), and stirring was carried out at room temperature until the generation of hydrogen stopped. The resulting mixture was cooled with ice again, and a DMF solution (30 ml) of 2-chloro-5-chloromethyl pyridine (9.74 g) was added dropwise. After stirring at room temperature for 4 hours, the reaction mixture was poured into ice water, and the produced insoluble matter was collected by filtration. The solid was washed with water and diethyl ether and dried to thereby obtain 11.84 g (yield: 79%) of 1-(6-chloropyridin-3-ylmethyl)-5-(1,3-dioxolan-2-yl)-8-methoxy-3,4-dihydro-1H-quinolin-2-one as a light yellow solid.

$^1$H-NMR(DMSO-d$_6$) dppm: 2.47-2.53 (2H, m), 2.88-2.94 (2H, m), 3.63 (3H, s), 3.91-4.04 (4H, m), 5.08 (2H, s), 5.80 (1H, s), 6.88 (1H, d, J=8.6 Hz), 7.19 (1H, d, J=8.6 Hz), 7.38 (1H, d, J=8.3 Hz), 7.60 (1H, dd, J$_1$=2.3 Hz, J$_2$=8.3 Hz), 8.19 (1H, d, J=2.3 Hz)

Reference Example 26

Synthesis of 5-(1,3-dioxolan-2-yl)-8-methoxy-1-[6-(N-methyl-N-phenylamino)pyridin-3-ylmethyl]-3,4-dihydro-1H-quinolin-2-one 1-(6-Chloropyridin-3-ylmethyl)-5-[1,3]dioxolan-2-yl-8-methoxy-3,4-dihydro-1H-quinolin-2-one (0.4 g), tris(dibenzylideneacetone)dipalladium (48.8 mg), 4,5-bis(diphenylphosphino)-9,9-dimethylxanthene (92.6 mg) and sodium tert-butoxide (0.15 g) were suspended in toluene (10.6 ml). N-methylaniline (0.17 g) was added, and the resulting mixture was heated under reflux in an argon atmosphere for 13 hours. After concentration under reduced pressure, the residue was purified by silica gel column chromatography (ethyl acetate:n-hexane=1:1→dichloromethane:methanol=20:1). The purified product was concentrated under reduced pressure to thereby obtain 0.45 g (yield: 95%) of 5-(1,3-dioxolan-2-yl)-8-methoxy-1-[6-(N-methyl-N-phenylamino)pyridin-3-ylmethyl]-3,4-dihydro-1H-quinolin-2-one as an amorphous solid.

$^1$H-NMR(CDCl$_3$) dppm: 2.52-2.58 (2H, m), 2.74-2.80 (2H, m), 3.40 (3H, s), 3.83 (3H, s), 3.98-4.12 (4H, m), 5.22 (2H, s), 5.81 (1H, s), 6.39 (1H, d, J=8.7 Hz), 6.76 (1H, d, J=8.7 Hz), 7.13-7.26 (4H, m), 7.33-7.39 (3H, m), 7.99 (1H, d, J=2.0 Hz)

Reference Example 27

Synthesis of 8-methoxy-1-[6-(N-methyl-N-phenylamino)pyridin-3-ylmethyl]-2-oxo-1,2,3,4-tetrahydroquinoline-5-carboxaldehyde Pyridinium p-toluene sulfonate (PPTS) (0.54 g) was added to a mixed solution of 5-(1,3-dioxolan-2-yl)-8-methoxy-1-[6-(N-methyl-N-phenylamino)pyridin-3-ylmethyl]-3,4-dihydro-1H-quinolin-2-one (0.95 g) in acetone (19 ml) and water (9.5 ml), followed by heating under reflux for 2 hours. An aqueous sodium hydrogencarbonate solution was added to the reaction mixture, and extraction with ethyl acetate was performed. The extract was washed twice with water, washed with a saturated sodium chloride solution, dried over sodium sulfate, filtered, and concentrated under reduced pressure. The residue was purified by silica gel column chromatography (ethyl acetate:n-hexane=1:1). The purified product was concentrated under reduced pressure to thereby obtain 0.69 g (yield: 81%) of 8-methoxy-1-[6-(N-methyl-N-phenylamino)pyridin-3-ylmethyl]-2-oxo-1,2,3,4-tetrahydroquinoline-5-carboxaldehyde as a light yellow amorphous solid.

$^1$H-NMR(CDCl$_3$) dppm: 2.53-2.59 (2H, m), 3.28-3.34 (2H, m), 3.39 (3H, s), 3.95 (3H, s), 5.23 (2H, s), 6.37 (1H, d, J=8.8 Hz), 6.90 (1H, d, J=8.6 Hz), 7.09 (1H, dd, J$_1$=2.4 Hz, J$_2$=8.8 Hz), 7.16-7.21 (3H, m), 7.33-7.39 (2H, m), 7.54 (1H, d, J=8.6 Hz), 7.94 (1H, d, J=2.4 Hz), 10.00 (1H, s)

Reference Example 28

Synthesis of 5-(1,3-dioxolan-2-yl)-8-methoxy-1-(6-thiophen-3-ylpyridin-3-ylmethyl)-3,4-dihydro-1H-quinolin-2-one 1-(6-Chloropyridin-3-ylmethyl)-5-(1,3-dioxolan-2-yl)-8-methoxy-3,4-dihydro-1H-quinolin-2-one (0.4 g), tetrakis(triphenylphosphine)palladium (0.12 g) and a 2N aqueous solution of sodium carbonate (2.5 ml) were suspended in 8 ml of 1,2-dimethoxyethane, and 0.20 g of 3-thiopheneboronic acid was added, followed by heating under reflux in an argon atmosphere for 4 hours. Water was added to the reaction mixture, and extraction with ethyl acetate was performed. The extract was washed twice with water, washed with a saturated sodium chloride solution, dried over sodium sulfate, filtered, and concentrated under reduced pressure. The residue was purified by silica gel column chromatography (ethyl acetate:n-hexane=1:1). The purified product was concentrated under reduced pressure to thereby obtain 0.45 g (yield: 95%) of 5-(1,3-dioxolan-2-yl)-8-methoxy-1-(6-thiophen-3-ylpyridin-3-ylmethyl)-3,4-dihydro-1H-quinolin-2-one as a light brown amorphous solid.

$^1$H-NMR(DMSO-d$_6$) dppm: 2.49-2.51 (2H, m), 2.89-2.91 (2H, m), 3.71 (3H, s), 3.91-4.04 (4H, m), 5.19 (2H, s), 5.79 (1H, s), 6.87 (1H, d, J=8.8 Hz), 7.16 (1H, d, J=8.8 Hz), 7.51-7.74 (4H, m), 8.09-8.10 (1H, m), 8.32 (1H, d, J=2.0 Hz)

Reference Example 29

Synthesis of 8-methoxy-1-(6-thiophen-3-ylpyridin-3-ylmethyl)-2-oxo-1,2,3,4-tetrahydroquinoline-5-carboxaldehyde Pyridinium p-toluenesulfonate (PPTS) (0.24 g) was added to a mixed solution of 5-(1,3-dioxolan-2-yl)-8-methoxy-1-(6-thiophen-3-ylpyridin-3-ylmethyl)-3,4-dihydro-1H-quinolin-2-one (0.4 g) in acetone (8 ml) and water (4 ml), followed by heating under reflux 1.5 hours. The resulting mixture was concentrated under reduced pressure, subjected to extraction with dichloromethane, washed with water, washed with a saturated sodium chloride solution, dried over sodium sulfate, filtrated, and concentrated under reduced pressure to thereby obtain 0.4 g (yield: quantitative) of 8-methoxy-1-(6-thiophen-3-ylpyridin-3-ylmethyl)-2-oxo-1,2,3,4-tetrahydroquinoline-5-carboxaldehyde as a light brown amorphous solid.

$^1$H-NMR(DMSO-d$_6$) dppm: 2.51-2.58 (2H, m), 3.34-3.41 (2H, m), 3.81 (3H, s), 5.19 (2H, s), 7.09 (1H, d, J=8.8 Hz), 7.54-7.74 (5H, m), 8.09-8.10 (1H, m), 8.35 (1H, d, J=1.8 Hz), 10.03 (1H, s)

Reference Example 30

Synthesis of 5-(1,3-dioxolan-2-yl)-1-phenyl-3,4-dihydro-1H-quinolin-2-one 5-(1,3-Dioxolan-2-yl)-3,4-dihydro-1H-quinolin-2-one (2.30 g, 10.5 mmol), iodobenzene (3.5 ml, 31.5 mmol), copper(I) iodide (400 mg, 2.10 mmol), trans-1,2-diaminocyclohexane (0.129 ml, 1.05 mmol) and cesium carbonate (6.84 g, 21.0 mmol) were stirred in 30 ml of 1,4-dioxane under reflux for three days. After cooling, the insoluble matter was filtered off through a Celite pad. Ethyl acetate and water were added to the filtrate, and the resulting mixture was washed (twice with water and once with a saturated sodium chloride solution), dried (MgSO$_4$), and concentrated under reduced pressure. The residue was purified by silica gel column chromatography (ethyl acetate:n-hexane=1:3→1:1) to thereby obtain 2.91 g (yield: 92%) of 5-(1,3-dioxolan-2-yl)-1-phenyl-3,4-dihydro-1H-quinolin-2-one as a white solid.

$^1$H-NMR(CDCl$_3$) dppm: 2.75-2.90 (2H, m), 3.11-3.27 (2H, m), 3.98-4.25 (4H, m), 5.99 (1H, s), 6.39 (1H, d, J=7.6 Hz), 7.05 (1H, t, J=8.0 Hz), 7.16-7.30 (3H, m), 7.35-7.56 (3H, m)

Reference Example 31

Synthesis of 1-phenyl-2-oxo-1,2,3,4-tetrahydroquinoline-5-carboxaldehyde

2N Hydrochloric acid (5 ml) was added to a solution of 5-(1,3-dioxolan-2-yl)-1-phenyl-3,4-dihydro-1H-quinolin-2-one (2.60 g) in THF (30 ml), followed by stirring at room temperature overnight. After distilling off THF under reduced pressure, ethyl acetate-water was added, and the resulting mixture was washed (twice with water and once with a saturated sodium chloride solution), dried (MgSO$_4$), and concentrated under reduced pressure. The obtained solid was recrystallized from chloroform-diethyl ether to thereby obtain 1.93 g (yield: 87%) of 1-phenyl-2-oxo-1,2,3,4-tetrahydroquinoline-5-carboxaldehyde as a beige powder.

$^1$H-NMR(CDCl$_3$) dppm: 2.75-2.89 (2H, m), 3.53-3.68 (2H, m), 6.65 (1H, dd, J=0.9 Hz, J=8.2 Hz), 7.15-7.20 (3H, m), 7.39-7.61 (4H, m), 10.24 (1H, s)

Reference Example 32

Synthesis of 5-methoxy-2-oxo-1,2,3,4-tetrahydroquinoline-8-carboxaldehyde

5-Methoxy-3,4-dihydro-1H-quinolin-2-one (5.00 g, 26 mmol) was dissolved in dichloromethane (100 ml), and dichloromethyl methyl ether (7.65 ml, 85 mmol) was added at 0° C. Titanium tetrachloride (12.4 ml, 113 mmol) was added dropwise at a temperature not higher than 10° C. Stirring was carried out at room temperature for 2 hours, and the reaction mixture was poured into ice water and separated into layers. The aqueous layer was subjected to extraction with dichloromethane. The organic layers were combined and washed twice with water, washed with a saturated sodium chloride solution, dried over sodium sulfate, filtered, and concentrated under reduced pressure. The residue was dissolved in dichloromethane, diethyl ether was added, and the produced insoluble matter was collected by filtration and dried to thereby obtain 5.32 g (yield: 92%) of 5-methoxy-2-oxo-1,2,3,4-tetrahydroquinoline-8-carboxaldehyde as a light brown powder.

$^1$H-NMR(CDCl$_3$) dppm: 2.55-2.67 (2H, m), 2.90-3.04 (2H, m), 3.94 (3H, s), 6.69 (1H, d, J=8.6 Hz), 7.53 (1H, d, J=8.6 Hz), 9.79 (1H, s), 10.60 (1H, brs)

Reference Example 33

Synthesis of 5-methoxy-8-methyl-3,4-dihydro-1H-quinolin-2-one

5-Methoxy-2-oxo-1,2,3,4-tetrahydroquinoline-8-carboxaldehyde (1.00 g) and 10% palladium carbon (100 mg) were added to a mixed solvent of acetic acid (10 ml) and ethanol (10 ml), followed by catalytic reduction at 50° C. for 1 hour. The catalyst was filtered off, and the filtrate was concentrated under reduced pressure. The residue was subjected to extraction with ethyl acetate, and the extract was washed twice with water, washed with a saturated sodium chloride solution, dried over sodium sulfate, filtered, and concentrated under reduced pressure. The residue was recrystallized from an ethyl acetate-diethyl ether mixed solvent to thereby obtain 826 mg (yield: 89%) of 5-methoxy-8-methyl-3,4-dihydro-1H-quinolin-2-one as a white powder.

$^1$H-NMR(CDCl$_3$) dppm: 2.04 (3H, s), 2.54-2.65 (2H, m), 2.89-3.02 (2H, m), 3.81 (3H, s), 6.51 (1H, d, J=8.4 Hz), 6.97 (1H, d, J=8.4 Hz), 7.37 (1H, brs)

Reference Example 34

Synthesis of 5-hydroxy-8-methyl-3,4-dihydro-1H-quinolin-2-one

A 2N dichloromethane solution (52 ml) of boron tribromide was added dropwise at −20° C. to a dichloromethane solution (100 ml) of 5-methoxy-8-methyl-3,4-dihydro-1H-quinolin-2-one (10.0 g). After stirring for 1 hour, the reaction mixture was poured into ice water and separated into layers. The organic layer was washed twice with water, washed with a saturated sodium chloride solution, dried over sodium sulfate, filtered, and concentrated under reduced pressure. The residue was recrystallized from an ethyl acetate-diethyl ether mixed solvent to thereby obtain 9.4 g (yield: quantitative) of 5-hydroxy-8-methyl-3,4-dihydro-1H-quinolin-2-one as a white powder.

$^1$H-NMR(CDCl$_3$) dppm: 2.14 (3H, s), 2.60-2.65 (2H, m), 2.94-2.99 (2H, m), 5.50 (1H, brs), 6.45 (1H, d, J=8.2 Hz), 6.88 (1H, d, J=8.2 Hz), 7.40 (1H, brs)

Reference Example 35

Synthesis of 8-methyl-5-trifluoromethanesulfonyloxy-3,4-dihydro-1H-quinolin-2-one Pyridine (6.2 ml) and trifluoromethanesulfonic anhydride (10.3 ml) were added with stirring at 0° C. to an anhydrous dichloromethane solution (30 ml) of 5-hydroxy-8-methyl-3,4-dihydro-1H-quinolin-2-one (9.0 g), followed by stirring for 1 hour. The resulting mixture was concentrated under reduced pressure, water was added to the residue, and extraction with dichloromethane was performed. The extract was washed with water, an aqueous potassium hydrogensulfate solution and water in this order, and dried over anhydrous sodium sulfate. After concentration under reduced pressure, the residue was recrystallized from an ethyl acetate-diisopropyl ether mixed solvent to thereby obtain 28 g (yield: 97%) of 8-methyl-5-trifluoromethanesulfonyloxy-3,4-dihydro-1H-quinolin-2-one as a light brown powder.

$^1$H-NMR(CDCl$_3$) dppm: 2.26 (3H, s), 2.60-2.73 (2H, m), 2.99-3.12 (2H, m), 6.89 (1H, d, J=8.5 Hz), 7.11 (1H, d, J=8.5 Hz), 7.67 (1H, brs)

Reference Example 36

Synthesis of 5-cyano-8-methyl-3,4-dihydro-1H-quinolin-2-one

8-Methyl-5-trifluoromethanesulfonyloxy-3,4-dihydro-1H-quinolin-2-one (4.0 g), zinc cyanide (3.34 g) and tetrakis(triphenylphosphine)palladium (0.299 g) were suspended in DMF (40 ml), and the suspension was stirred at 100° C. for 4 hours. The insoluble matter was filtered off, and ethyl acetate was added to the filtrate, followed by washing with water. After drying over anhydrous magnesium sulfate, the dry product was concentrated, and the residue was recrystallized from a DMF-ethanol mixed solvent to thereby obtain 2.1 g (yield: 87%) of 5-cyano-8-methyl-3,4-dihydro-1H-quinolin-2-one as a light brown powder.

$^1$H-NMR(CDCl$_3$) dppm: 2.31 (3H, s), 2.64-2.75 (2H, m), 3.15-3.27 (2H, m), 7.14 (1H, d, J=7.9 Hz), 7.24 (1H, d, J=7.9 Hz), 7.67 (1H, brs)

Reference Example 37

Synthesis of 8-methyl-2-oxo-1,2,3,4-tetrahydroquinoline-5-carboxaldehyde

5-Cyano-8-methyl-3,4-dihydro-1H-quinolin-2-one (2.0 g) and Raney nickel (10 g) were suspended in formic acid (40 ml), and the suspension was heated under reflux for 6 hours. The reaction mixture was filtered to remove the insoluble matter, and the filtrate was concentrated. Ethyl acetate and water were added to the residue, and after stirring, the mixture was filtered through Celite. The filtrate was separated into layers, and the organic layer was washed with water and dried over anhydrous sodium sulfate. After concentration under reduced pressure, the residue was recrystallized from an ethyl acetate-diethyl ether mixed solvent to thereby obtain 1.29 g (yield: 62%) of 8-methyl-2-oxo-1,2,3,4-tetrahydroquinoline-5-carboxaldehyde as a light brown powder.

$^1$H-NMR(DMSO-d$_6$) dppm: 2.30 (3H, s), 2.37-2.50 (2H, m), 3.28-3.43 (2H, m), 7.26 (1H, d, J=7.8 Hz), 7.44 (1H, d, J=7.8 Hz), 9.56 (1H, s), 10.15 (1H, s)

Reference Example 38

Synthesis of 5-methoxy-8-phenyl-3,4-dihydro-1H-quinolin-2-one

8-Bromo-5-methoxy-3,4-dihydro-1H-quinolin-2-one (10.0 g), tetrakis(triphenylphosphine)palladium (0.45 g) and potassium carbonate (5.4 g) were suspended in dioxane (100 ml), and phenylboronic acid (5.24 g) was added, followed by heating under reflux in an argon atmosphere for 2 hours. The reaction mixture was concentrated under reduced pressure, water was added to the residue, and the resulting mixture was subjected to extraction with ethyl acetate. The extract was washed twice with water, washed with a saturated sodium chloride solution, dried over magnesium sulfate, filtered, and concentrated under reduced pressure. The residue was recrystallized from an ethyl acetate-n-hexane mixed solvent to thereby obtain 8.3 g (yield: 84%) of 5-methoxy-8-phenyl-3,4-dihydro-1H-quinolin-2-one as a light yellow powder.

$^1$H-NMR(CDCl$_3$) dppm: 2.57-2.64 (2H, m), 2.97-3.04 (3H, m), 3.88 (2H, s), 6.66 (1H, d, J=8.5 Hz), 7.09 (1H, d, J=8.5 Hz), 7.27-7.52 (6H, m)

Reference Example 39

Synthesis of 1-(biphenyl-4-ylmethyl)-5-methoxy-8-phenyl-3,4-dihydro-1H-quinolin-2-one Sodium hydride (60% in oil) (0.87 g) was added at 0° C. to a DMF solution (50 ml) of 5-methoxy-8-phenyl-3,4-dihydro-1H-quinolin-2-one (5.0 g), followed by stirring for 30 minutes. 4-Bromomethylbiphenyl (5.37 g) was added, and the resulting mixture was stirred at room temperature for 1 hour. Water was added to the reaction mixture, and extraction with ethyl acetate was performed. The extract was washed with a saturated sodium chloride solution, dried over anhydrous magnesium sulfate, and concentrated under reduced pressure. The residue was purified by silica gel column chromatography (ethyl acetate:n-hexane=1:10→1:5). The purified product was recrystallized from an ethyl acetate-n-hexane-diethyl ether mixed solvent to thereby obtain 6.8 g (yield: 82%) of 1-(biphenyl-4-ylmethyl)-5-methoxy-8-phenyl-3,4-dihydro-1H-quinolin-2-one as a white powder.

$^1$H-NMR(CDCl$_3$) dppm: 2.64-2.70 (2H, m), 2.84-2.96 (2H, m), 3.86 (3H, s), 4.49 (2H, s), 6.73 (1H, d, J=8.6 Hz), 6.91 (2H, d, J=8.1 Hz), 7.13 (1H, d, J=8.6 Hz), 7.24-7.55 (12H, m)

Reference Example 40

Synthesis of 1-(biphenyl-4-ylmethyl)-5-hydroxy-8-phenyl-3,4-dihydro-1H-quinolin-2-one A dichloromethane solution (12 ml) of 2N boron tribromide was added dropwise at −20° C. to a dichloromethane solution (50 ml) of 1-(biphenyl-4-ylmethyl)-5-methoxy-8-phenyl-3,4-dihydro-1H-quinolin-2-one (5.00 g). After stirring for 4 hours, the reaction mixture was poured into ice water and separated into layers. The organic layer was washed twice with water, washed with a saturated sodium chloride solution, dried over sodium sulfate, filtered, and concentrated under reduced pressure. The residue was recrystallized from a dichloromethane-diisopropyl ether mixed solvent to thereby obtain 5.01 g (yield: quantitative) of 1-(biphenyl-4-ylmethyl)-5-hydroxy-8-phenyl-3,4-dihydro-1H-quinolin-2-one as a white powder.

$^1$H-NMR(CDCl$_3$) dppm: 2.66-2.74 (2H, m), 2.84-2.90 (2H, m), 4.48 (2H, s), 5.84 (1H, brs), 6.61 (1H, d, J=8.4 Hz), 6.92 (2H, d, J=8.2 Hz), 7.01 (1H, d, J=8.4 Hz), 7.22-7.54 (12H, m)

Reference Example 41

Synthesis of 1-(biphenyl-4-ylmethyl)-8-phenyl-5-trifluoromethanesulfonyloxy-3,4-dihydro-1H-quinolin-2-one Pyridine (1.12 ml) and trifluoromethanesulfonic anhydride (1.99 ml) were added with stirring at 0° C. to an anhydrous dichloromethane solution (40 ml) of 1-(biphenyl-4-ylmethyl)-5-hydroxy-8-phenyl-3,4-dihydro-1H-quinolin-2-one (4.0 g), followed by stirring for 1 hour. The resulting mixture was concentrated under reduced pressure, water was added to the residue, and extraction with dichloromethane was performed. The extract was washed with water, an aqueous potassium hydrogensulfate solution and water in this order, dried over anhydrous sodium sulfate, and concentrated under reduced pressure to thereby obtain 5.45 g (yield: quantitative) of 1-(biphenyl-4-ylmethyl)-8-phenyl-5-trifluoromethanesulfonyloxy-3,4-dihydro-1H-quinolin-2-one as a white amorphous solid.

$^1$H-NMR(CDCl$_3$) dppm: 2.67-2.81 (2H, m), 2.90-3.03 (2H, m), 4.48 (2H, s), 6.85 (2H, d, J=8.2 Hz), 7.05-7.15 (1H, m), 7.20-7.58 (13H, m)

Reference Example 42

Synthesis of 1-(biphenyl-4-ylmethyl)-5-cyano-8-phenyl-3,4-dihydro-1H-quinolin-2-one 1-(Biphenyl-4-ylmethyl)-8-phenyl-5-trifluoromethanesulfonyloxy-3,4-dihydro-1H-quinolin-2-one (5.2 g), zinc cyanide (2.50 g) and tetrakis(triphenylphosphine)palladium (0.224 g) were suspended in DMF (50 ml), followed by stirring at 100° C. for 4 hours. The insoluble matter was filtered off, and ethyl acetate was added to the filtrate, and the resulting mixture was washed with water. After drying over anhydrous magnesium sulfate, the dry product was concentrated to thereby obtain 2.1 g (yield: 90%) of 1-(biphenyl-4-ylmethyl)-5-cyano-8-phenyl-3,4-dihydro-1H-quinolin-2-one as a white amorphous solid.

$^1$H-NMR(CDCl$_3$) dppm: 2.75-2.82 (2H, m), 3.09-3.15 (2H, m), 4.48 (2H, s), 6.85 (2H, d, J=8.3 Hz), 7.20-7.57 (14H, m)

Reference Example 43

Synthesis of 1-(biphenyl-4-ylmethyl)-8-phenyl-2-oxo-1,2,3,4-tetrahydroquinoline-5-carboxaldehyde 1-(Biphenyl-4-ylmethyl)-5-cyano-8-phenyl-3,4-dihydro-1H-quinolin-2-one (3.0 g) and Raney nickel (15 g) were suspended in formic acid (60 ml), and the suspension was heated under reflux for 11 hours. The reaction mixture was filtered to remove the insoluble matter, and the filtrate was concentrated. Ethyl acetate and water were added to the residue, and after stirring, the mixture was filtered through Celite. The filtrate was separated into layers, and the organic layer was washed with water, dried over anhydrous sodium sulfate, and concentrated under reduced pressure. The residue was purified by silica gel column chromatography (ethyl acetate:n-hexane=1:10→1:3). The purified product was concentrated to thereby obtain 0.44 g (yield: 15%) of 1-(biphenyl-4-ylmethyl)-8-phenyl-2-oxo-1,2,3,4-tetrahydroquinoline-5-carboxaldehyde as a white amorphous solid.

$^1$H-NMR(CDCl$_3$) dppm: 2.69-2.75 (2H, m), 2.37-2.43 (2H, m), 4.48 (2H, s), 6.87 (2H, d, J=8.3 Hz), 7.25-7.55 (13H, m), 7.61 (1H, d, J=8.0 Hz), 10.20 (1H, s)

Reference Example 44

Synthesis of 1-benzyl-8-methoxy-2-oxo-1,2,3,4-tetrahydroquinoline-5-carboxaldehyde Sodium hydride (60% in oil) (1.07 g) was added at 0° C. to a DMF solution (50 ml) of 8-methoxy-2-oxo-1,2,3,4-tetrahydroquinoline-5-carboxaldehyde (5.0 g), followed by stirring for 30 minutes. Benzyl bromide (3.47 ml) was added, and the resulting mixture was stirred at room temperature for 1 hour. Water was added to the reaction mixture, and extraction with ethyl acetate was performed. The extract was washed with a saturated sodium chloride solution, dried over anhydrous magnesium sulfate, and concentrated under reduced pressure. The residue was recrystallized from an ethyl acetate-n-hexane mixed solvent to thereby obtain 6.6 g (yield: 92%) of 1-benzyl-8-methoxy-2-oxo-1,2,3,4-tetrahydroquinoline-5-carboxaldehyde as a white powder.

$^1$H-NMR(CDCl$_3$) dppm: 2.60 (2H, t, J=7.0 Hz), 3.38 (2H, t, J=7.0 Hz), 3.82 (3H, s), 5.29 (2H, s), 6.82 (1H, d, J=8.6 Hz), 7.0-7.3 (5H, m), 7.5 (1H, d, J=8.6 Hz), 10.00 (1H, s)

Reference Example 45

Synthesis of 1-benzyl-8-hydroxy-2-oxo-1,2,3,4-tetrahydroquinoline-5-carboxaldehyde 1-Benzyl-8-methoxy-2-oxo-1,2,3,4-tetrahydroquinoline-5-carboxaldehyde (3.0 g) and sodium 4-methylbenzenethiolate (3.27 g) were added to DMSO (30 ml), followed by stirring at 100° C. for 40 minutes. Water and an aqueous solution of potassium hydrogensulfate were added to the reaction mixture, and extraction with ethyl acetate was performed. The extract was washed with a saturated sodium chloride solution, dried over anhydrous magnesium sulfate, and concentrated under reduced pressure. The residue was recrystallized from an ethyl acetate-n-hexane mixed solvent to thereby obtain 6.6 g (yield: 92%) of 1-benzyl-8-methoxy-2-oxo-1,2,3,4-tetrahydroquinoline-5-carboxaldehyde as a light brown powder.

$^1$H-NMR(DMSO-d$_6$) dppm: 2.42-2.59 (2H, m), 3.19-3.40 (2H, m), 5.31 (2H, s), 6.85 (1H, d, J=8.5 Hz), 7.05-7.27 (5H, m), 7.43 (1H, d, J=8.5 Hz), 9.94 (1H, s), 11.12 (1H, s)

Reference Example 46

Synthesis of 1-(4-carbomethoxybenzyl)-8-methoxy-2-oxo-1,2,3,4-tetrahydroquinoline-5-carboxaldehyde Sodium hydride (60% in oil) (2.87 g) was added at 0° C. to a DMF solution (100 ml) of 8-methoxy-2-oxo-1,2,3,4-tetrahydroquinoline-5-carboxaldehyde (13.4 g), followed by stirring for 30 minutes. Methyl 4-bromomethyl benzoate (18.0 g) was added, and the resulting mixture was stirred at room temperature overnight. Water was added to the reaction mixture, and extraction with ethyl acetate was performed. The extract was washed with a saturated sodium chloride solution, dried over anhydrous magnesium sulfate, and concentrated under reduced pressure. The residue was purified by silica gel column chromatography (ethyl acetate:n-hexane=1:4→1:2). The purified product was recrystallized from a chloroform-diisopropyl ether mixed solvent to thereby obtain 14.43 g (yield: 62%) of 1-(4-carbomethoxybenzyl)-8-methoxy-2-oxo-1,2,3,4-tetrahydroquinoline-5-carboxaldehyde as a white powder.

$^1$H-NMR(DMSO-d$_6$) dppm: 2.50-2.61 (2H, m), 3.29-3.41 (2H, m), 3.71 (3H, s), 3.79 (3H, s), 5.18 (2H, s), 7.06 (1H, d, J=8.7 Hz), 7.25 (2H, d, J=8.2 Hz), 7.60 (1H, d, J=8.7 Hz), 7.81 (2H, d, J=8.2 Hz), 10.02 (1H, s)

Using appropriate starting materials and following the procedure of Reference Example 41, the compounds of Reference Examples 47 to 50 were synthesized.

Reference Example 47

8-Chloro-5-trifluoromethanesulfonyloxy-3,4-dihydro-1H-quinolin-2-one $^1$H-NMR(CDCl$_3$) dppm: 2.63-2.75 (2H, m), 3.02-3.15 (2H, m), 6.94 (1H, d, J=8.9 Hz), 7.34 (1H, d, J=8.9 Hz), 7.85 (1H, brs)

Reference Example 48

6-Trifluoromethanesulfonyloxy-3,4-dihydro-1H-quinolin-2-one $^1$H-NMR(CDCl$_3$) dppm: 2.60-2.73 (2H, m), 3.01 (2H, t, J=8.0 Hz), 6.81-6.92 (1H, m), 7.00-7.12 (2H, m), 9.09 (1H, brs)

Reference Example 49

7-Trifluoromethanesulfonyloxy-3,4-dihydro-1H-quinolin-2-one $^1$H-NMR(CDCl$_3$) dppm: 2.60-2.71 (2H, m), 3.00 (2H, t, J=8.0 Hz), 6.70-6.77 (1H, m), 6.84-6.95 (1H, m), 7.16-7.30 (1H, m), 8.80 (1H, brs)

Reference Example 50

8-Trifluoromethanesulfonyloxy-3,4-dihydro-1H-quinolin-2-one $^1$H-NMR(CDCl$_3$) dppm: 2.63-2.75 (2H, m), 3.05 (2H, t, J=7.9 Hz), 7.03 (1H, t, J=7.9 Hz), 7.12-7.28 (2H, m), 7.78 (1H, brs)

Reference Example 51

Synthesis of 6-oxo-5,6-dihydrophenanthridine-2-carbonitrile 2-(4,4-Dimethyl-[1,3,2]dioxaboronan-2-yl)-benzoic acid ethyl ester (19.84 g), 2-iodo-4-cyanoaniline (18.47 g), tetrakis(triphenylphosphine)palladium (8.75 g) and potassium phosphate (35.36 g) were added to dioxane (360 ml), and the resulting mixture was heated under reflux overnight. The reaction solvent was cooled, and the produced solid was collected by filtration, washed with water and dried to thereby obtain 17.3 g (yield: quantitative) of the title compound as a yellow solid.

$^1$H-NMR(DMSO-d$_6$) dppm: 7.47 (1H, d, J=8.5 Hz), 7.6-8.0 (3H, m), 8.1-8.2 (1H, m), 8.3-8.4 (1H, m), 8.98 (1H, s), 12.05 (1H, brs)

Reference Example 52

Synthesis of 5-benzyl-6-oxo-5,6-dihydrophenanthridine-2-carbonitrile

6-Oxo-5,6-dihydrophenanthridine-2-carbonitrile (1 g) was suspended in DMF (20 ml), 60% sodium hydride (0.2 g) was added under ice cooling, and stirring was carried out until the generation of hydrogen stopped. Benzyl bromide (0.59 ml) was added, followed by stirring at room temperature for 1 hour. Water was added, and the produced solid was collected by filtration and purified by silica gel chromatography (dichloromethane:n-hexane=1:1) to thereby obtain 0.68 g (yield: 48%) of the title compound as colorless crystals.

$^1$H-NMR(DMSO-d$_6$) dppm: 5.57 (2H, s), 7.1-7.5 (6H, m), 7.6-7.95 (3H, m), 8.27 (1H, d, J=8.3 Hz), 8.58 (1H, d, J=1.8 Hz), 8.63 (1H, dd, J=8.3 Hz, J=1.8 Hz)

Using appropriate starting materials and following the procedure of Reference Example 52, the compounds of Reference Examples 53 to 54 were synthesized.

Reference Example 53

5-Ethyl-6-oxo-5,6-dihydrophenanthridine-2-carbonitrile $^1$H-NMR(DMSO-d$_6$) dppm: 1.43 (3H, t, J=7.1 Hz), 4.47 (2H, t, J=7.1 Hz), 7.35-7.9 (4H, m), 8.27 (1H, d, J=8.3 Hz), 8.5-8.65 (2H, m)

Reference Example 54

5-(1-Biphenyl-4-ylmethyl)-6-oxo-5,6-dihydrophenanthridine-2-carbonitrile $^1$H-NMR(DMSO-d$_6$) dppm: 5.57 (2H, s), 7.1-7.5 (6H, m), 7.6-7.95 (3H, m), 8.27 (1H, d, J=8.3 Hz), 8.58 (1H, d, J=1.8 Hz), 8.63 (1H, dd, J=8.3 Hz, J=1.8 Hz)

Reference Example 55

Synthesis of 5-benzyl-6-oxo-5,6-dihydrophenanthridine-2-carboxaldehyde

5-Benzyl-6-oxo-5,6-dihydrophenanthridine-2-carbonitrile (1.24 g) and Raney nickel (0.8 g) were suspended in 75% formic acid (25 ml). The suspension was heated under reflux for 1 hour and 40 minutes, and filtered while hot. The filtrate was concentrated and purified by silica gel chromatography (methylene chloride:methanol=50:1) to thereby obtain 1.08 g (yield: 80%) of the title compound as a colorless crystals.

$^1$H-NMR(DMSO-d$_6$) dppm: 5.69 (2H, s), 7.15-7.35 (6H, m), 7.5-8.05 (3H, m), 8.47 (1H, d, J=7.9 Hz), 8.70 (1H, d, J=8.1 Hz), 8.63 (1H, d, J=1.4 Hz), 10.08 (1H, s)

Using appropriate starting materials and following the procedure of Reference Example 55, the compound of Reference Example 56 was synthesized.

Reference Example 56

5-Ethyl-6-oxo-5,6-dihydrophenanthridine-2-carboxaldehyde $^1$H-NMR(DMSO-d$_6$) dppm: 1.45 (3H, t, J=7.1 Hz), 4.50 (2H, t, J=7.1 Hz), 7.15-7.35 (6H, m), 7.5-8.15 (4H, m), 8.39 (1H, d, J=8.1 Hz), 8.56 (1H, dd, J=8.1 Hz, J=1.3 Hz), 8.81 (1H, d, J=1.8 Hz), 10.11 (1H, s)

Using appropriate starting materials and following the procedure of Reference Example 13, the compounds of Reference Examples 104 to 130, 133, 134 and 137 to 141 were synthesized.

Using appropriate starting materials and following the procedure of Reference Example 19, the compounds of Reference Examples 147 and 148 were synthesized.

Using appropriate starting materials and following the procedure of Reference Example 21, the compounds of Reference Examples 57 to 63 were synthesized.

Using appropriate starting materials and following the procedure of Reference Example 23, the compounds of Reference Examples 144 to 145 and 152 to 156 were synthesized.

Using appropriate starting materials and following the procedure of Reference Example 24, the compounds of Reference Examples 70, 71 and 81 were synthesized.

Using appropriate starting materials and following the procedure of Reference Example 25, the compounds of Reference Examples 64 to 69, 72, 79, 80, 82 and 83 were synthesized.

Using appropriate starting materials and following the procedure of Reference Example 26, the compounds of Reference Examples 75 to 77 were synthesized.

Using appropriate starting materials and following the procedure of Reference Example 28, the compounds of Reference Examples 74 and 78 were synthesized.

Using appropriate starting materials and following the procedure of Reference Example 29, the compounds of Reference Examples 98, 99, 100 to 103, 131, 135, 136 and 146 were synthesized.

Using appropriate starting materials and following the procedure of Reference Example 31, the compounds of Reference Examples 84 to 97 and 142 were synthesized.

Using appropriate starting materials and following the procedure of Reference Example 37, the compounds of Reference Examples 149 to 151 were synthesized.

TABLE 1

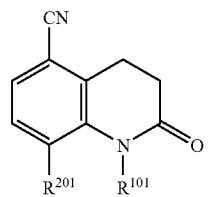

| Ref. Ex. | R$^{101}$ | R$^{201}$ | $^1$HNMR dppm |
|---|---|---|---|
| 57 | —H | —OCH$_3$ | CDCl$_3$: 2.65-2.72 (2H, m), 3.15-3.22 (2H, m), 3.94 (3H, s), 6.86 (1H, d, J = 8.6 Hz), 7.32 (1H, d, J = 8.6 Hz), 7.82 (1H, brs)." |
| 58 | —H | —Cl | CDCl$_3$: 2.82-2.68 (2H, m), 3.20-3.32 (2H, m), 7.27 (1H, d, J = 8.4 Hz), 7.38 (1H, d, J = 8.4 Hz), 7.85 (1H, brs). |

TABLE 2

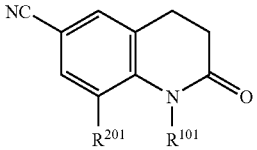

| Ref. Ex. | R$^{101}$ | R$^{201}$ | $^1$HNMR dppm |
|---|---|---|---|
| 59 | —H | —H | DMSO-d$_6$: 2.41-2.55 (2H, m), 2.91 (2H, t, J = 7.9 Hz), 6.96 (1H, d, J = 8.2 Hz), 7.55-7.67 (2H, m), 10.49 (1H, brs). |
| 60 | —H | —CH$_3$ | CDCl$_3$:: 2.67 (3H, s), 2.61-2.72 (2H, m), 2.94-3.08 (2H, m), 7.30-7.39 (2H, m), 7.66 (1H, brs). |
| 61 | —H | —OCH$_3$ | CDCl$_3$: 2.62-2.69 (2H, m), 2.96-3.03 (2H, m), 3.91 (3H, s), 7.01 (1H, s), 7.13 (1H, s), 7.86 (1H, brs). |

TABLE 2-continued

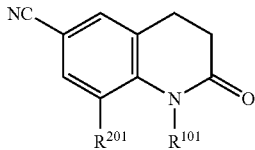

| Ref. Ex. | R¹⁰¹ | R²⁰¹ | ¹HNMR dppm |
|---|---|---|---|
| 62 | 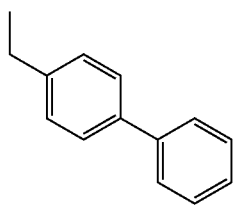 | —OCH₃ | CDCl₃: 2.65-2.71 (2H, m), 2.85-2.92 (2H, m), 3.78 (3H, s), 5.38 (2H, s), 6.98 (1H, d, J = 1.5 Hz), 7.10 (1H, d, J = 1.5 Hz), 7.15 (2H, d, J = 8.1 Hz), 7.30-7.36 (1H, m), 7.36-7.49 (4H, m), 7.49-7.59 (2H, m). |

TABLE 2-continued

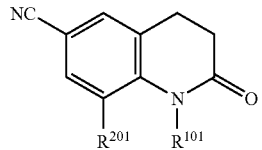

| Ref. Ex. | R¹⁰¹ | R²⁰¹ | ¹HNMR dppm |
|---|---|---|---|
| 63 | 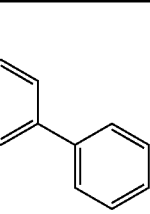 | —CH₃ | CDCl₃: 2.40 (3H, s), 2.57-2.70 (2H, m), 2.77-2.90 (2H, m), 5.17 (2H, s), 7.13 (2H, d, J = 8.3 Hz), 7.29-7.37 (3H, m), 7.37-7.50 (4H, m), 7.50-7.90 (2H, m). |

TABLE 3

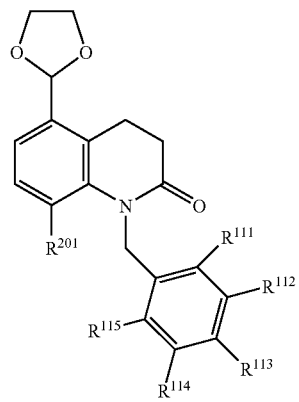

| Ref. Ex. | R¹¹¹ | R¹¹² | R¹¹³ | R¹¹⁴ | R¹¹⁵ | R²⁰¹ | ¹HNMR dppm |
|---|---|---|---|---|---|---|---|
| 64 | —H | —H | —Br | —H | —H | —H | CDCl₃: 2.70-2.83 (2H, m), 3.01-3.16 (2H, m), 3.97-4.22 (4H, m), 5.12 (2H, s), 5.95 (1H, s), 6.85 (1H, dd, J = 0.8, 8.1 Hz), 7.02-7.19 (3H, m), 7.22-7.31 (1H, m), 7.38-7.50 (2H, m). |
| 65 | —H | —H | —Cl | —H | —H | —H | CDCl₃: 2.68-2.82 (2H, m), 3.02-3.17 (2H, m), 3.97-4.20 (4H, m), 5.14 (2H, s), 5.95 (1H, s), 6.84 (1H, dd, J = 0.8, 8.1 Hz), 7.05-7.18 (3H, m), 7.20-7.33 (3H, m). |
| 66 | —H | —H | —CH₃ | —H | —H | —H | CDCl₃: 2.30 (3H, s), 2.68-2.82 (2H, m), 3.01-3.16 (2H, m), 3.97-4.20 (4H, m), 5.14 (2H, s), 5.95 (1H, s), 6.91 (1H, dd, J = 0.8, 8.1 Hz), 7.04-7.17 (5H, m), 7.24 (1H, dd, J = 0.8, 8.1). |
| 67 | —H | —H | —OC₆H₅ | —H | —H | —OCH₃ | CDCl₃: 2.55-2.66 (2H, m), 2.87-2.99 (2H, m), 3.74 (3H, s), 3.96-4.18 (4H, m), 5.25 (2H, s), 5.84 (1H, s), 6.75 (1H, d, J = 8.7 Hz), 6.84 (2H, d, J = 8.6 Hz), 6.94 (2H, dd, J = 1.1, 8.7 Hz), 7.03-7.22 (3H, m), 7.22-7.36 (3H, m). |
| 68 | —H | —H | —CO₂CH₃ | —H | —H | —H | CDCl₃: 2.75-2.81 (2H, m), 3.09-3.15 (2H, m), 3.89 (3H, s), 4.04-4.17 (4H, m), 5.23 (2H, s), 5.96 (1H, s), 6.80 (1H, d, J = 7.9 Hz), 7.11 (1H, t, J = 7.9 Hz), 7.25-7.28 (3H, m), 7.98 (2H, d, J = 8.3 Hz) |
| 69 | —H | —H | —NO₂ | —H | —H | —H | CDCl₃: 2.76-2.82 (2H, m), 3.10-3.16 (2H, m), 4.05-4.15 (4H, m), 5.27 (2H, s), 5.96 (1H, s), 6.76 (1H, d, J = 8.0 Hz), 7.14 (1H, t, J = 8.0 Hz), 7.29 (1H, d, J = 8.0 Hz), 7.37 (2H, d, J = 8.8 Hz), 8.18 (2H, d, J = 8.8 Hz) |

TABLE 4

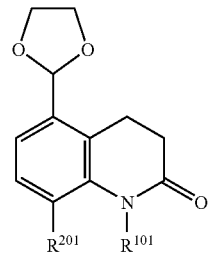

| Ref. Ex. | R^101 | R^201 | $^1$HNMR dppm |
|---|---|---|---|
| 70 | —H | —OCH$_3$ | DMSO-d$_6$: 2.33-2.44 (2H, m), 2.85-2.98 (2H, m), 3.79 (3H, s), 3.86-4.08 (4H, m), 5.78 (1H, s), 6.86 (1H, d, J = 8.5 Hz), 7.07 (1H, d, J = 8.5 Hz), 8.97 (1H, s). |
| 71 | —H | —H | CDCl$_3$: 2.56-2.70 (2H, m), 3.01-3.18 (2H, m), 3.97-4.22 (4H, m), 5.93 (1H, s), 6.80 (1H, dd, J = 1.4, 7.6 Hz), 7.13-7.31 (2H, m), 8.52 (1H, s). |
| 72 | ethyl-2-naphthyl | —H | CDCl$_3$: 2.77-2.89 (2H, m), 3.07-3.21 (2H, m), 3.98-4.19 (4H, m), 5.34 (2H, s), 5.96 (1H, s), 6.89-6.97 (1H, m), 7.02-7.12 (1H, m), 7.19-7.29 (1H, m), 7.31-7.40 (1H, m), 7.40-7.53 (2H, m), 7.61 (1H, s), 7.69-7.88 (3H, m). |
| 73 | —C$_6$H$_5$ | —H | CDCl$_3$: 2.75-2.90 (2H, m), 3.11-3.27 (2H, m), 3.98-4.25 (4H, m), 5.99 (1H, s), 6.39 (1H, d, J = 7.6 Hz), 7.05 (1H, t, J = 8.0 Hz), 7.16-7.30 (3H, m), 7.35-7.56 (3H, m). |
| 74 | ethyl-(6-phenylpyridin-3-yl) | —OCH$_3$ | DMSO-d$_6$: 2.49-2.55 (2H, m), 2.89-2.91 (2H, m), 3.70 (3H, s), 3.91-4.04 (4H, m), 5.20 (2H, s), 5.80 (1H, s), 6.89 (1H, d, J = 8.7 Hz), 7.18 (1H, d, J = 8.7 Hz), 7.42-7.67 (4H, m), 7.84 (1H, d, J = 8.3 Hz), 8.09-8.10 (1H, m), 8.42 (1H, d, J = 1.8 Hz) |
| 75 | ethyl-(6-morpholinopyridin-3-yl) | —OCH$_3$ | DMSO-d$_6$: 2.49-2.52 (2H, m), 2.77-2.80 (2H, m), 3.24-3.26 (4H, m), 3.61-3.63 (4H, m), 3.80 (3H, s), 3.90-4.02 (4H, m), 5.12 (2H, s), 6.65 (1H, d, J = 8.5 Hz), 6.88 (1H, d, J = 8.5 Hz), 7.15 (1H, d, J = 8.5 Hz), 7.25-7.28 (1H, m), 7.85 (1H, d, J = 2.3 Hz) |

TABLE 5
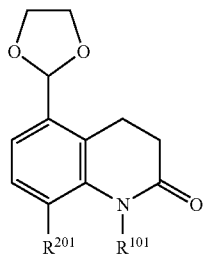
| Ref. Ex. | R¹⁰¹ | R²⁰¹ | ¹H-NMR δppm |
|---|---|---|---|
| 76 | 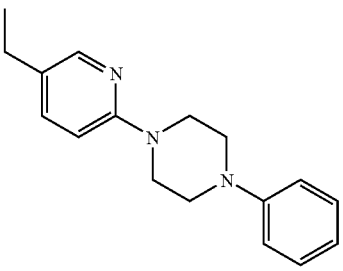 | —OCH₃ | CDCl₃: 2.57-2.60 (2H, m), 2.86-2.89 (2H, m), 3.24-3.28 (4H, m), 3.59-3.63 (4H, m), 3.83 (3H, s), 3.99-4.13 (4H, m), 5.23 (2H, s), 5.81 (1H, s), 6.54 (1H, d, J = 8.7 Hz), 6.76 (1H, d, J = 8.7 Hz), 6.85-6.90 (1H, m), 6.96 (1H, d, J = 8.4 Hz), 7.22-7.34 (4H, m), 7.98 (1H, d, J = 2.2 Hz) |
| 77 | 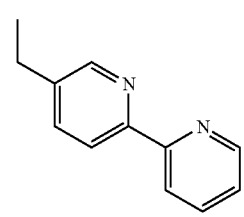 | —OCH₃ | CDCl₃: 2.32 (3H, s), 2.46-2.50 (4H, m), 2.54-2.59 (2H, m), 2.85-2.90 (2H, m), 3.45-3.49 (4H, m), 3.82 (3H, s), 3.99-4.12 (4H, m), 5.22 (2H, s), 5.80 (1H, s), 6.49 (1H, d, J = 8.7 Hz), 6.75 (1H, d, J = 8.7 Hz), 7.24 (1H, d, J = 8.7 Hz), 7.30 (1H, d, J = 2.3 Hz), 7.95 (1H, d, J = 2.3 Hz) |
| 78 | 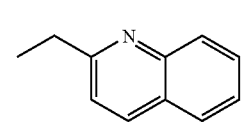 | —OCH₃ | CDCl₃: 2.62-2.66 (2H, m), 2.95-2.99 (2H, m), 3.71 (3H, s), 3.99-4.14 (4H, m), 5.31 (2H, s), 5.84 (1H, s), 6.74 (1H, d, J = 8.7 Hz), 7.23-7.29 (2H, m), 7.46-7.82 (2H, m), 8.22-8.33 (2H, m), 8.47-8.48 (1H, m), 8.63-8.65 (1H, m) |
| 79 | 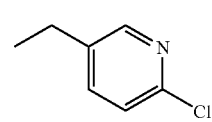 | —OCH₃ | CDCl₃: 2.69-2.74 (2H, m), 3.11-3.16 (2H, m), 3.45 (3H, s), 4.03-4.17 (4H, m), 5.36 (2H, s), 5.91 (1H, s), 6.72 (1H, d, J = 8.6 Hz), 7.25-7.31 (2H, m), 7.44-7.50 (1H, m), 7.64-7.69 (1H, m), 7.76 (1H, d, J = 8.1 Hz), 8.02 (2H, t, J = 9.3 Hz) |
| 80 |  | —H | CDCl₃: 2.72-2.78 (2H, m), 3.06-3.12 (2H, m), 4.02-4.17 (4H, m), 5.17 (2H, s), 5.94 (1H, s), 6.84 (1H, d, J = 8.1 Hz), 7.13-7.31 (2H, m), 7.49 (1H, dd, J1 = 2.5 Hz, J2 = 8.2 Hz), 8.32 (1H, d, J = 2.5 Hz) |

TABLE 6

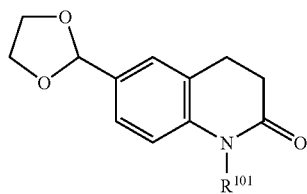

| Ref. Ex. | R¹⁰¹ | ¹HNMR dppm |
|---|---|---|
| 81 | —H | DMSO-d₆: 2.35-2.51 (2H, m), 2.86 (2H, t, J = 7.9 Hz), 3.84-4.08 (4H, m), 5.61 (1H, s), 6.83 (1H, d, J = 8.0 Hz), 7.12-7.25 (2H, m), 10.12 (1H, s). |
| 82 | 4-Br-C₆H₄-CH₂- | CDCl₃: 2.71-2.82 (2H, m), 2.91-3.06 (2H, m), 3.94-4.18 (4H, m), 5.12 (2H, s), 5.71 (1H, s), 6.81 (1H, d, J = 8.3 Hz), 7.07 (2H, d, J = 8.5 Hz), 7.15-7.27 (1H, m), 7.31 (1H, d, J = 1.7 Hz), 7.35-7.46 (2H, m). |
| 83 | 4-NO₂-C₆H₄-CH₂- | CDCl₃: 2.73-2.87 (2H, m), 2.94-3.10 (2H, m), 3.97-4.20 (4H, m), 5.26 (2H, s), 5.71 (1H, s), 6.74 (1H, d, J = 8.4 Hz), 7.22 (1H, dd, J = 1.9, 8.4 Hz), 7.30-7.41 (3H, m), 8.16 (2H, d, J = 8.7 Hz). |

TABLE 7

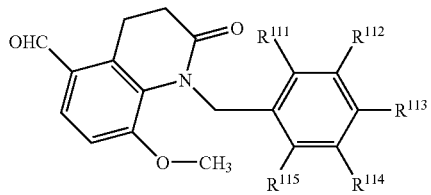

| Ref. Ex. | R¹¹¹ | R¹¹² | R¹¹³ | R¹¹⁴ | R¹¹⁵ | ¹HNMR dppm |
|---|---|---|---|---|---|---|
| 84 | —H | —H | —C₆H₅ | —H | —H | CDCl₃: 2.62 (2H, t, J = 7.0 Hz), 3.41 (2H, t, J = 7.0 Hz), 3.86 (3H, s), 5.33 (2H, s), 6.86 (1H, d, J = 8.6 Hz), 7.15 (1H, d, J = 8.6 Hz), 7.25-7.6 (5H, m), 10.00 (1H, s) |
| 85 | —H | —H | —C(CH₃)₃ | —H | —H | CDCl₃: 1.23 (9H, s), 2.55-2.65 (2H, m), 3.3-3.4 (2H, m), 3.86 (3H, s), 5.27 (2H, s), 6.86 (1H, d, J = 8.6 Hz), 7.00 (2H, d, J = 7.3 Hz), 7.19 (2H, d, J = 7.3 Hz), 7.52 (1H, d, J = 8.6 Hz), 10.02 (1H, s) |
| 86 | —H | —H | —H | —C₆H₅ | —H | CDCl₃: 2.63 (2H, t, J = 7.0 Hz), 3.42 (2H, t, J = 7.0 Hz), 3.84 (3H, s), 5.36 (2H, s), 6.85 (1H, d, J = 8.6 Hz), 7.06 (1H, d, J = 7.4 Hz), 7.2-7.65 (7H, m), 10.02 (1H, s) |
| 87 | —H | —H | —H | —H | —C₆H₅ | CDCl₃: 2.52 (2H, t, J = 7.0 Hz), 3.18 (2H, t, J = 7.0 Hz), 3.45 (3H, s), 5.34 (2H, s), 6.67 (1H, d, J = 8.6 Hz), 7.06 (1H, d, J = 7.4 Hz), 7.1-7.5 (10H, m), 9.98 (1H, s) |
| 88 | —H | —H | —NO₂ | —H | —H | DMSO-d₆: 2.52-2.65 (2H, m), 2.34-2.46 (2H, m), 3.66 (3H, s), 5.16 (2H, s), 7.09 (1H, d, J = 8.7 Hz), 7.41 (2H, d, J = 8.6 Hz), 7.63 (1H, d, J = 8.7 Hz), 8.11 (2H, d, J = 8.6 Hz), 10.04 (1H, s). |
| 89 | —H | —H | —CO₂H | —H | —H | DMSO-d₆: 2.4-2.64 (2H, m), 3.20-3.50 (2H, m), 3.73 (3H, s), 5.19 (2H, s), 7.06 (1H, d, J = 8.7 Hz), 7.22 (2H, d, J = 8.6 Hz), 7.60 (1H, d, J = 8.6 Hz), 7.78 (2H, d, J = 8.0 Hz), 10.01 (1H, s), 12.80 (1H, brs). |

TABLE 8

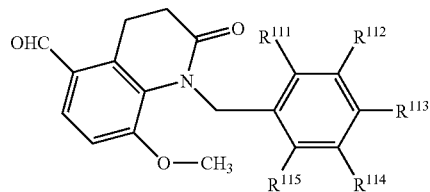

| Ref. Ex. | $R^{111}$ | $R^{112}$ | $R^{113}$ | $R^{114}$ | $R^{115}$ | $^1$HNMR dppm: |
|---|---|---|---|---|---|---|
| 90 | —H | —H | —OCH$_3$ | —H | —H | DMSO-d$_6$: 2.40-2.59 (2H, m), 3.17-3.38 (2H, m), 3.63 (3H, s), 3.87 (3H, s), 5.16 (2H, s), 6.73 (2H, d, J = 8.5 Hz), 6.99 (2H, d, J = 8.5 Hz), 7.06 (1H, d, J = 8.7 Hz), 7.58 (1H, d, J = 8.7 Hz), 9.98 (1H, s). |
| 91 | —H | —H | —Cl | —H | —H | CDCl$_3$: 2.60 (2H, t, J = 7.0 Hz), 3.39 (2H, t, J = 7.0 Hz), 3.82 (3H, s), 5.23 (2H, s), 6.86 (1H, d, J = 8.6 Hz), 6.98-7.06 (2H, m), 7.13-7.21 (2H, m), 7.54 (1H, d, J = 8.6 Hz), 10.02 (1H, s). |
| 92 | —H | —H | —Br | —H | —H | DMSO-d$_6$: 2.42-2.60 (2H, m), 3.22-3.39 (2H, m), 3.77 (3H, s), 5.12 (2H, s), 7.00-7.15 (3H, m), 7.38 (2H, d, J = 8.2 Hz), 7.60 (1H, d, J = 8.7 Hz), 10.00 (1H, s). |
| 93 | —H | —H | —OCH$_2$C$_6$H$_5$ | —H | —H | CDCl$_3$: 2.53-2.63 (2H, m), 3.29-3.40 (2H, m), 3.87 (3H, s), 4.96 (2H, s), 5.25 (2H, s), 6.78 (2H, dd, J = 2.1, 6.7 Hz), 6.85 (1H, d, J = 8.6 Hz), 7.00 (2H, d, J = 8.7 Hz), 7.25-7.42 (5H, m), 7.51 (1H, d, J = 8.6 Hz), 10.00 (1H, s). |
| 94 | —H | —H | —F | —H | —H | DMSO-d$_6$: 2.44-2.58 (2H, m), 3.23-3.38 (2H, m), 3.80 (3H, s), 5.16 (2H, s), 6.94-7.19 (5H, m), 7.59 (1H, d, J = 8.7 Hz), 10.00 (1H, s). |
| 95 | —H | —H | —CN | —H | —H | DMSO-d$_6$: 2.50-2.64 (2H, m), 3.32-3.45 (2H, m), 3.66 (3H, s), 5.13 (2H, s), 7.08 (1H, d, J = 8.7 Hz), 7.32 (2H, d, J = 8.2 Hz), 7.63 (1H, d, J = 8.7 Hz), 7.69 (2H, d, J = 8.2 Hz), 10.04 (1H, s). |
| 96 | —H | —H | —CH$_3$ | —H | —H | CDCl$_3$: 2.23 (3H, s), 2.55-2.62 (2H, m), 3.32-3.39 (2H, m), 3.86 (3H, s), 5.28 (2H, s), 6.84 (1H, d, J = 8.6 Hz), 6.90-7.11 (4H, m), 7.51 (1H, d, J = 8.6 Hz), 10.00 (1H, s). |

TABLE 9

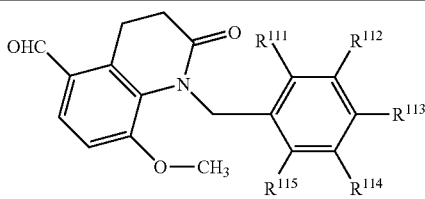

| Ref. Ex. | $R^{111}$ | $R^{112}$ | $R^{113}$ | $R^{114}$ | $R^{115}$ | $^1$H-NMR dppm |
|---|---|---|---|---|---|---|
| 97 | —H | —H | —OC$_6$H$_5$ | —H | —H | CDCl$_3$: 2.60 (2H, t, J = 7.0 Hz), 3.37 (2H, t, J = 7.0 Hz), 3.86 (3H, s), 5.27 (2H, s), 6.75-6.97 (5H,m), 7.00-7.12 (3H, m), 7.22-7.37 (2H, m), 7.54 (1H, d, J = 8.6 Hz), 10.02 (1H, s). |
| 98 | —H | —H | —CO$_2$CH$_3$ | —H | —H | CDCl$_3$: 2.77-2.83 (2H, m), 3.51-3.57 (2H, m), 3.90 (3H, s), 5.26 (2H, s), 7.03 (1H, d, J = 8.2 Hz), 7.26-7.32 (3H, m), 7.50(2H, dd, J1 = 0.9 Hz, J2 = 7.7 Hz), 10.21 (1H, s) |

TABLE 10

| Ref. Ex. | R¹²¹ | ¹HNMR dppm: |
|---|---|---|
| 99 | —C₆H₅ | DMSO-d₆: 2.52-2.59 (2H, m), 3.18-3.25 (2H, m), 3.81 (3H, s), 5.21 (2H, s), 7.11 (1H, d, J = 8.8 Hz), 7.39-7.66 (5H, m), 7.83 (1H, d, J = 8.0 Hz), 8.01-8.03 (1H, m), 8.44-8.45 (1H, m), 10.04 (1H, s) |
| 100 | -2-PYRIDYL | CDCl₃: 2.61-2.67 (2H, m), 3.39-3.45 (2H, m), 3.83 (3H, s), 5.34 (2H, s), 6.85 (1H, d, J = 8.6 Hz), 7.25-7.30 (1H, m), 7.46-7.82 (3H, m), 8.24 (1H, d, J = 8.2 Hz), 8.30 (1H, J = 8.0 Hz), 8.45 (1H, d, J = 1.8 Hz), 8.64 (1H, d, 4.7 Hz), 10.01 (1H, s) |
| 101 | 4-morpholinyl | DMSO-d₆: 2.47-2.52 (2H, m), 3.23-3.33 (6H, m), 3.61-3.65 (4H, m), 3.90 (3H, s), 5.12 (2H, s), 6.67 (1H, d, J = 8.8 Hz), 7.11 (1H, d, J = 8.7 Hz), 7.29 (1H, dd, J1 = 2.2 Hz, J2 = 8.8 Hz), 7.61 (1H, d, 8.7 Hz), 7.87 (1H, d, J = 2.2 Hz), 10.00 (1H, s) |
| 102 | 4-phenylpiperazin-1-yl | CDCl₃: 2.55-2.60 (2H, m), 3.23-3.27 (4H, m), 3.30-3.36 (2H, m), 3.58-3.62 (4H, m), 3.94 (3H, s), 5.24 (2H, s), 6.54 (1H, d, J = 8.8 Hz), 6.85-6.97 (4H, m), 7.24-7.31 (3H, m), 7.53 (1H, d, J = 8.6 Hz), 7.93 (1H, d, J = 2.2 Hz), 9.99 (1H, s) |
| 103 | 4-methylpiperazin-1-yl | CDCl₃: 2.31 (3H, s), 2.45-2.49 (4H, m), 2.54-2.60 (2H, m), 3.29-3.35 (2H, m), 3.44-3.48 (4H, m), 3.94 (3H, s), 3.99-4.12 (4H, m), 5.22 (2H, s), 6.48 (1H, d, J = 8.7 Hz), 6.88 (1H, d, J = 8.6 Hz), 7.23-7.28 (1H, m), 7.52 (1H, d, J = 8.6 Hz), 7.90 (1H, d, J = 2.2 Hz), 9.99 (1H, s) |

TABLE 11

| Ref. Ex. | R¹⁰¹ | ¹HNMR dppm: |
|---|---|---|
| 104 | —(CH₂)₂C(CH₃)₂OCH₂OCH₃ | CDCl₃: 1.20 (6H, s), 1.89 (2H, t, J = 7.1 Hz), 2.45 (3H, s), 3.27 (3H, s), 4.18 (2H, t, J = 7.1 Hz), 4.62 (2H, s), 7.35 (2H, d, J = 8.3 Hz), 7.80 (2H, d, J = 8.3 Hz) |
| 105 | —(CH₂)₃CF₃ | CDCl₃: 1.8-2.2 (4H, m), 2.5-2.6 (2H, m), 3.3-3.45 (2H, m), 3.9-4.05 (2H, m), 3.97 (3H, s), 7.00 (1H, d, J = 8.6 Hz), 7.61 (1H, d, J = 8.6 Hz), 10.06 (1H, s) |
| 106 | —C₄H₉ | CDCl₃: 0.85 (3H, t, J = 7.5 Hz), 1.2-1.35 (2H, m), 1.4-1.5 (2H, m), 2.51 (2H, t, J = 7.0 Hz), 3.35 (2H, t, J = 7.0 Hz), 3.96 (3H, s), 4.04 (2H, t, J = 7.4 Hz), 6.98 (1H, d, J = 8.6 Hz), 7.60 (1H, d, J = 8.6 Hz), 10.06 (1H, s) |
| 107 | —C₂H₅ | CDCl₃: 1.15 (3H, t, J = 7.1 Hz), 2.51 (2H, t, J = 7.0 Hz), 3.36 (2H, t, J = 7.0 Hz), 3.97 (3H, s), 4.01 (2H, t, J = 7.4 Hz), 6.98 (1H, d, J = 8.6 Hz), 7.60 (1H, d, J = 8.6 Hz), 10.06 (1H, s) |

TABLE 11-continued

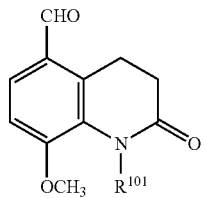

| Ref. Ex. | R101 | 1HNMR dppm: |
|---|---|---|
| 108 | —C3H7 | CDCl3: 0.81 (3H, t, J = 7.4 Hz), 1.4-1.6 (2H, m), 2.52 (2H, t, J = 6.8 Hz), 3.36 (2H, t, J = 6.8 Hz), 3.96 (3H, s), 4.00 (2H, t, J = 7.4 Hz), 6.97 (1H, t, J = 8.6 Hz), 7.59 (1H, t, J = 8.6 Hz), 10.06 (1H, s) |
| 109 | —C5H11 | CDCl3: 0.83 (3H, t, J = 7.2 Hz), 1.1-1.3 (4H, m), 1.4-1.5 (2H, m), 2.52 (2H, t, J = 6.8 Hz), 3.36 (2H, t, J = 6.8 Hz), 3.96 (3H, s), 4.02 (2H, t, J = 7.4 Hz), 6.97 (1H, t, J = 8.6 Hz), 7.59 (1H, t, J = 8.6 Hz), 10.06 (1H, s) |
| 110 | —CH(CH3)2 | CDCl3: 1.53 (6H, d, J = 6.8 Hz), 2.4-2.5 (2H, m), 3.35-3.45 (2H, m), 3.85-4.0 (1H, m), 3.97 (3H, s), 6.97 (1H, t, J = 8.6 Hz), 7.59 (1H, t, J = 8.6 Hz), 10.06 (1H, s) |
| 111 | —CH2CH(CH3)2 | CDCl3: 0.76 (6H, d, J = 6.6 Hz), 1.4-1.7 (1H, m), 2.5-2.6 (2H, m), 3.3-3.45 (2H, m), 3.96 (3H, s), 4.04 (1H, d, J = 7.4 Hz), 6.97 (1H, t, J = 8.6 Hz), 7.60 (1H, t, J = 8.6 Hz), 10.07 (1H, s) |
| 112 | —CH2CO2C(CH3)3 | CDCl3: 1.42 (9H, s), 2.55-2.65 (2H, m), 3.4-3.55 (2H, m), 3.81 (3H, s), 4.60 (2H, s), 6.97 (1H, d, J = 8.6 Hz), 7.59 (1H, d, J = 8.6 Hz), 10.07 (1H, s) |

TABLE 12

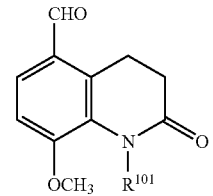

| Ref. Ex. | R101 | 1H-NMR dppm |
|---|---|---|
| 113 | —(CH2)2C6H5 | CDCl3: 2.44 (2H, t, J = 7.0 Hz), 2.82 (2H, t, J = 7.5 Hz), 3.02 (2H, t, J = 7.0 Hz), 4.01 (3H, s), 4.32 (2H, t, J = 7.5 Hz), 6.95-7.1 (3H, m), 7.1-7.25 (3H, m), 7.60 (1H, d, J = 8.6 Hz), 10.03 (1H, s) |
| 114 | —(CH2)3C6H5 | CDCl3: 1.75-1.95 (2H, m), 2.5-2.65 (4H, m), 3.36 (2H, t, J = 7.0 Hz), 3.79 (3H, s), 4.05 (2H, t, J = 7.4 Hz), 6.93 (1H, d, J = 8.6 Hz), 7.05-7.35 (5H, m), 7.58 (1H, d, J = 8.6 Hz), 10.05 (1H, s) |
| 115 | —CH2-cyclo-C3H5 | CDCl3: 0.1-0.4 (4H, m), 0.8-0.9 (1H, m), 2.53 (2H, t, J = 7.0 Hz), 3.39 (2H, t, J = 7.0 Hz), 3.97 (3H, s), 4.01 (2H, t, J = 7.3 Hz), 6.97 (1H, d, J = 8.6 Hz), 7.61 (1H, d, J = 8.6 Hz), 10.08 (1H, s) |
| 116 | —CH2CH2OCH3 | CDCl3: 2.54 (2H, t, J = 7.0 Hz), 3.23 (3H, s), 3.36 (2H, t, J = 7.0 Hz), 3.47 (2H, t, J = 6.0 Hz), 3.96 (3H, s), 4.25 (2H, t, J = 6.0 Hz), 6.96 (1H, d, J = 8.6 Hz), 7.61 (1H, d, J = 8.6 Hz), 10.07 (1H, s) |

TABLE 12-continued

| Ref. Ex. | R101 | 1H-NMR dppm |
|---|---|---|
| 117 | —(CH2)2OC6H5 | CDCl3: 2.54 (2H, t, J = 7.0 Hz), 3.34 (2H, t, J = 7.0 Hz), 3.93 (3H, s), 4.16 (2H, t, J = 6.0 Hz), 4.42 (2H, t, J = 6.0 Hz), 6.72 (1H, dd, J1 = 8.8 Hz, J2 = 0.95 Hz), 6.85-7.05 (2H, m), 7.15-7.3 (2H, m), 7.60 (1H, d, J = 8.6 Hz), 10.05 (1H, s) |
| 118 | —CH2-cyclo-C6H11 | CDCl3: 0.8-1.75 (11H, m), 2.5-2.6 (2H, m), 3.3-3.45 (2H, m), 3.96 (3H, s), 4.06 (2H, t, J = 7.2 Hz), 6.97 (1H, d, J = 8.6 Hz), 7.60 (1H, d, J = 8.6 Hz), 10.07 (1H, s) |
| 119 | —(CH2)4C6H5 | CDCl3: 1.45-1.6 (4H, m), 2.45-2.6 (4H, m), 3.34 (2H, t, J = 7.0 Hz), 3.85 (3H, s), 4.02 (2H, t, J = 6.6 Hz), 6.93 (1H, d, J = 8.6 Hz), 7.05-7.35 (5H, m), 7.58 (1H, d, J = 8.6 Hz), 10.05 (1H, s) |

TABLE 13

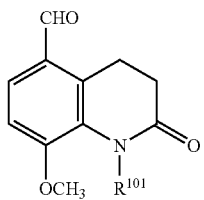

| Ref. Ex. | R¹⁰¹ | ¹H-NMR dppm |
|---|---|---|
| 120 | —(CH₂)₅C₆H₅ | CDCl₃: 1.15-1.3 (2H, m), 1.42-1.61 (4H, m), 2.4-2.6 (4H, m), 3.28 (2H, t, J = 7.0 Hz), 3.92 (3H, s), 4.02 (2H, t, J = 7.4 Hz), 6.96 (1H, d, J = 8.6 Hz), 7.1-7.3 (5H, m), 7.59 (1H, d, J = 8.6 Hz), 10.05 (1H, s) |
| 121 | —CH(C₆H₅)₂ | CDCl₃: 2.52 (2H, t, J = 7.0 Hz), 3.33 (2H, t, J = 7.0 Hz), 3.48 (3H, s), 6.30 (1H, s), 6.81 (1H, d, J = 8.6 Hz), 7.15-7.35 (10H, m), 7.57 (1H, d, J = 8.6 Hz), 10.00 (1H, s) |
| 122 | —(CH₂)₃CO₂C₂H₅ | CDCl₃: 1.24 (3H, t, J = 7.1 Hz), 1.79-1.94 (2H, m), 2.24 (2H, t, J = 7. Hz), 2.45-2.57 (2H, m), 3.36 (2H, t, J = 7.0 Hz), 3.97 (3H, s), 4.00-4.16 (4H, m), 6.99 (1H, d, J = 8.6 Hz), 7.60 (1H, d, J = 8.6 Hz), 10.06 (1H, s). |
| 123 | —CH₂CH₂CN | DMSO-d₆: 2.37-2.49 (2H, m), 2.76 (2H, t, J = 6.8 Hz), 3.21-3.44 (2H, m), 3.96 (3H, s), 4.08 (2H, t, J = 6.8 Hz), 7.24 (1H, d, J = 8.7 Hz), 7.72 (1H, d, J = 8.7 Hz), 10.06 (1H, s). |

TABLE 13-continued

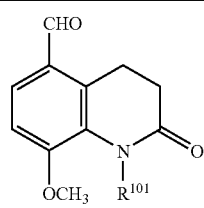

| Ref. Ex. | R¹⁰¹ | ¹H-NMR dppm |
|---|---|---|
| 124 | —C₆H₅ | CDCl₃: 2.65-2.79 (2H, m), 3.41 (3H, s), 3.54 (2H, t, J - 7.0 Hz), 6.86 (1H, d, J = 8.6 Hz), 7.08-7.44 (5H, m), 7.61 (1H, d, J = 8.6 Hz), 10.09 (1H, s). |
| 125 | —CH₂CH=CH₂ | CDCl₃: 2.52-2.57 (2H, m), 3.36-3.41 (2H, m), 3.94 (3H, s), 4.66 (2H, dt, J = 6.0 and 1.3 Hz), 5.02-5.15 (2H, m), 5.64-5.77 (1H, m), 6.96 (1H, d, J = 8.6 Hz), 7.59 (1H, d, J = 8.6 Hz), 10.05 (1H, s) |
| 126 | —C₈H₁₇ | CDCl₃: 0.85 (3H, t, J = 6.7 Hz), 1.20-1.38 (10H, m), 1.38-1.53 (2H, m), 2.49-2.54 (2H, m), 3.33-3.40 (2H, m), 3.96 (3H, s), 5.83 (2H, t, J = 7.5 Hz), 6.98 (1H, d, J = 8.6 Hz), 7.60 (1H, d, J = 8.6 Hz), 10.06 (1H, s) |

TABLE 14

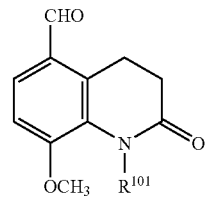

| Ref. Ex. | R¹⁰¹ | ¹H-NMR dppm |
|---|---|---|
| 127 | 4-ethyl-piperidine-N-CO-O-tBu | CDCl₃: 0.9-1.2 (2H, m), 1.42 (9H, s), 1.25-1.85 (3H, m), 2.4-2.7 (4H, m), 3.2-3.6 (2H, m), 3.8-4.2 (4H, m), 3.96 (3H, s), 6.99 (1H, d, J = 6.6 Hz), 7.61 (1H, d, J = 6.6 Hz), 10.06 (1H, s) |
| 128 | 4-ethyl-1-(4-methylphenyl)piperidine | CDCl₃: 1.2-1.75 (5H, m), 2.24 (3H, s), 2.4-2.6 (4H, m), 3.3-3.6 (4H, m), 3.97 (3H, s), 4.0-4.2 (2H, m), 6.78 (2H, d, J = 8.5 Hz), 6.95-7.1 (3H, m), 7.61 (1H, d, J = 7.6 Hz), 10.07 (1H, s) |
| 129 | 1-ethyl-naphthalene | CDCl₃: 2.65 (2H, t, J = 7.0 Hz), 3.30 (2H, t, J = 7.0 Hz), 3.76 (3H, s), 5.78 (2H, s), 6.78 (1H, d, J = 8.6 Hz), 7.2-7.35 (2H, m), 7.4-7.55 (3H, m), 7.66 (1H, d, J = 8.1 Hz), 7.79 (1H, d, J = 7.9 Hz), 8.00 (1H, d, J = 8.5 Hz), 9.93 (1H, s) |
| 130 | 2-ethyl-naphthalene | CDCl₃: 2.64 (2H, t, J = 7.0 Hz), 3.42 (2H, t, J = 7.0 Hz), 3.85 (3H, s), 5.47 (2H, s), 6.81 (1H, d, J = 8.6 Hz), 7.19 (1H, dd, J1 = 8.5 Hz, J2 = 1.6 Hz), 7.35-7.6 (7H, m), 9.98 (1H, s) |

TABLE 14-continued

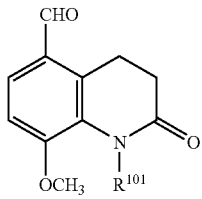

| Ref. Ex. | R¹⁰¹ | ¹H-NMR dppm |
|---|---|---|
| 131 | 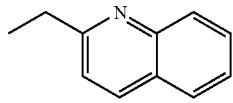 | CDCl₃: 2.68-2.74 (2H, m), 3.57-3.63 (2H, m), 3.62 (3H, s), 5.42 (2H, s), 6.85 (1H, d, J = 8.6 Hz), 7.28 (1H, d, J = 8.5 Hz), 7.47 (1H, ddd, J1 = 1.1 Hz, J2 = 7.5 Hz, J3 = 8.2 Hz), 7.54 (1H, d, J = 8.6 Hz), 7.66 (1H, ddd, J1 = 1.1 Hz, J2 = 7.5 Hz, J3 = 8.5 Hz), 7.76 (1H, dd, J1 = 1.1 Hz, J2 = 8.2 Hz), 7.96 (1H, d, J = 8.5 Hz), 8.04 (1H, d, J = 8.5 Hz) |

TABLE 15

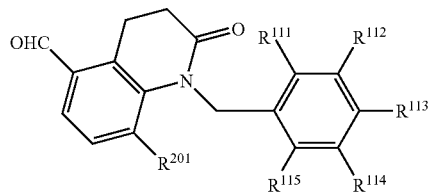

| Ref. Ex. | $R^{111}$ | $R^{112}$ | $R^{113}$ | $R^{114}$ | $R^{115}$ | $R^{201}$ | ¹H-NMR dppm |
|---|---|---|---|---|---|---|---|
| 132 | —H | —H | —C₆H₅ | —H | —H | —OH | CDCl₃: 2.64 (2H, t, J = 7.0 Hz), 3.41 (2H, t, J = 7.0 Hz), 5.37 (2H, s), 6.30 (1H, br s), 6.80 (1H, d, J = 8.6 Hz), 7.2-7.6 (10H, m), 10.00 (1H, s) |
| 133 | —H | —H | —C₆H₅ | —H | —H | —OC₄H₉ | CDCl₃: 0.94 (3H, t, J = 7.4 Hz), 1.35-1.5 (2H, m), 1.65-1.8 (2H, m), 2.62 (2H, t, J = 7.0 Hz), 3.41 (2H, t, J = 7.0 Hz), 4.03 (2H, t, J = 6.6 Hz), 5.35 (2H, s), 6.89 (1H, d, J = 8.6 Hz), 7.1-7.6 (10H, m), 10.02 (1H, s) |
| 134 | —H | —H | —C₆H₅ | —H | —H | —OCH₂CO₂C(CH₃)₃ | CDCl₃: 1.53 (9H, s), 2.64 (2H, t, J = 7.0 Hz), 3.42 (2H, t, J = 7.0 Hz), 4.48 (2H, s), 5.47 (2H, s), 6.71 (1H, d, J = 8.6 Hz), 7.15-7.65 (10H, m), 10.03 (1H, s) |
| 135 | —H | —H | —Br | —H | —H | —H | CDCl₃: 2.77 (2H, t, J = 7.4 Hz), 3.52 (2H, t, J = 7.5 Hz), 5.16 (2H, s), 7.03-7.14 (3H, m), 7.32 (1H, t, J = 8.0 Hz), 7.40-7.48 (2H, m), 7.50 (1H, dd, J = 0.8, 7.7 Hz), 10.20 (1H, s). |
| 136 | —H | —H | —Cl | —H | —H | —H | CDCl₃: 2.70-2.82 (2H, m), 3.2 (2H, t, J = 7.6 Hz), 5.17 (2H, s), 7.07 (1H, dd, J = 1.0, 8.2 Hz), 7.10-7.20 (2H, m), 7.22-7.35 (3H, m), 7.49 (1H, d, J = 1.1, 7.7 Hz), 10.20 (1H, s). |

TABLE 16

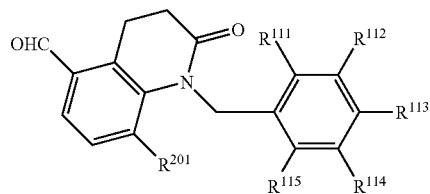

| Ref. Ex. | $R^{111}$ | $R^{112}$ | $R^{113}$ | $R^{114}$ | $R^{115}$ | $R^{201}$ | $^1$H-NMR dppm |
|---|---|---|---|---|---|---|---|
| 137 | —H | —H | —CH$_3$ | —H | —H | —H | CDCl$_3$: 2.31 (3H, s), 2.70-2.85 (2H, m), 3.51 (2H, t, J = 7.7 Hz), 5.17 (2H, s), 7.03-7.19 (5H, m), 7.20-7.36 (1H, m), 7.47 (1H, d, J = 7.6 Hz), 10.20 (1H, s). |
| 138 | —H | —H | —C$_6$H$_5$ | —H | —H | —CH$_3$ | CDCl$_3$: 2.46 (3H, s), 2.54-2.60 (2H, m), 3.27-3.34 (2H, m), 5.13 (2H, s), 7.14 (2H, d, J = 8.3 Hz), 7.20-7.60 (9H, m), 10.13 (1H, s). |
| 139 | —H | —H | —C$_6$H$_5$ | —H | —H | —Cl | CDCl$_3$: 2.58-2.64 (2H, m), 3.30-3.36 (2H, m), 5.44 (2H, s), 7.17 (2H, d, J = 8.2 Hz), 7.22-7.61 (9H, m), 10.12 (1H, s). |
| 140 | —H | —H | —NO$_2$ | —H | —H | —H | CDCl$_3$: 2.78-2.84 (2H, m), 3.53-3.59 (2H, m), 5.30 (2H, s), 6.98 (1H, d, J = 8.2 Hz), 7.26-7.32 (1H, m), 7.38 (2H, d, J = 8.8 Hz), 7.53 (1H, d, J = 6.7 Hz), 8.20 (2H, d, J = 8.8 Hz), 10.22 (1H, s) |

TABLE 17

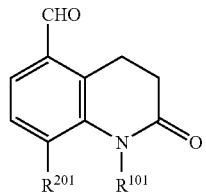

| Ref. Ex. | $R^{101}$ | $R^{201}$ | $^1$H-NMR dppm |
|---|---|---|---|
| 141 | —(CH$_2$)$_4$OSi(CH$_3$)$_2$C(CH$_3$)$_3$ | —H | CDCl$_3$: 0.09 (3H, s), 0.88 (9H, s), 1.6-2.1 (2H, m), 2.62 (2H, t, J = 7.2 Hz), 3.42 (2H, t, J = 7.7 Hz), 3.71 (2H, t, J = 5.7 Hz), 4.06 (2H, t, J = 7.8 Hz), 7.1-7.6 (2H, m), 10.22 (1H, s) |
| 142 | —C$_6$H$_5$ | —H | CDCl$_3$: 2.75-2.89 (2H, m), 3.53-3.68 (2H, m), 6.65 (1H, dd, J = 0.9, 8.2 Hz), 7.15-7.20 (3H, m), 7.39-7.61 (4H, m), 10.24 (1H, s). |
| 143 | —H | —Cl | CDCl$_3$: 2.61-2.72 (2H, m), 3.50-3.64 (2H, m), 7.40-7.51 (2H, m), 7.88 (1H, brs), 10.15 (1H, s). |

TABLE 18

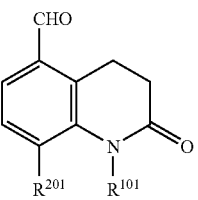

| Ref. Ex. | $R^{101}$ | $R^{201}$ | $^1$H-NMR dppm |
|---|---|---|---|
| 144 | ![piperidine-Boc with propyl] | —H | CDCl$_3$: 1.05-1.9 (9H, m), 1.51 (9H, s), 2.6-2.8 (4H, m), 3.35-3.50 (2H, m), 3.95-4.2 (2H, m), 7.23 (1H, dd, J1 = 8.0 Hz, J2 = 1.0 Hz), 7.46 (1H, t, J = 8 Hz), 7.54 (1H, dd, J1 = 8.0 Hz, J2 = 1.0 Hz), 10.23 (1H, s) |
| 145 | ![naphthyl-ethyl] | —H | CDCl$_3$: 2.84 (2H, t, J = 7.5 Hz), 3.56 (2H, t, J = 7.5 Hz), 5.37 (2H, s), 7.13-7.21 (1H, m), 7.21-7.29 (1H, m), 7.29-7.40 (1H, m), 7.40-7.50 (3H, m), 7.61 (1H, s), 7.70-7.78 (1H, m), 7.78-7.87 (2H, m), 10.19 (1H, s). |
| 146 | ![chloropyridyl-ethyl] | —H | CDCl$_3$: 2.74-2.80 (2H, m), 3.49-3.55 (2H, m), 5.21 (2H, s), 7.07 (1H, d, J = 8.1 Hz), 7.26-7.38 (2H, m), 7.49-7.54 (2H, m), 8.33 (1H, d, J = 2.5 Hz), 10.20 (1H, s) |

TABLE 19

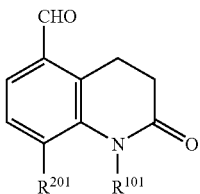

| Ref. Ex. | R<sup>101</sup> | R<sup>201</sup> | $^1$H-NMR dppm |
|---|---|---|---|
| 147 | —(CH$_2$)$_2$CH(CH$_3$)$_2$ | —OCH$_3$ | CDCl$_3$: 0.99 (6H, d, J = 6.2 Hz), 1.5-1.8 (3H, m), 4.03 (3H, s), 4.57 (2H, t, J = 7.0 Hz), 6.84 (1H, d, J = 9.9 Hz), 7.16 (1H, d, J = 8.3 Hz), 7.63 (1H, d, J = 8.3 Hz), 9.18 (1H, d, J = 9.9 Hz), 10.09 (1H, s), |
| 148 | 4-bromophenylethyl | —OCH$_3$ | CDCl$_3$: 3.71 (3H, s), 5.77 (2H, brs), 6.89-7.00 (3H, m), 7.06 (1H, d, J = 8.4 Hz), 7.39 (2H, d, J = 8.4 Hz), 7.63 (1H, d, J = 8.4 Hz), 9.28 (1H, d, J = 9.9 Hz), 10.10 (1H, s). |

TABLE 20

| Ref. Ex. | R<sup>201</sup> | $^1$H-NMR dppm |
|---|---|---|
| 149 | —H | DMSO-d$_6$: 2.44-2.59 (2H, m), 2.96 (2H, t, J = 7.9 Hz), 7.00 (1H, d, J = 8.7 Hz), 7.65-7.78 (2H, m), 9.82 (1H, s), 10.50 (1H, brs). |
| 150 | —CH$_3$ | CDCl$_3$: 2.32 (3H, s), 2.65-2.72 (2H, m), 3.01-3.08 (2H, m), 7.54-7.65 (2H, m), 7.75 (1H, brs), 9.87 (1H, s). |
| 151 | —OCH$_3$ | CDCl$_3$: 2.65-2.72 (2H, m), 3.02-3.09 (2H, m), 3.95 (3H, m), 7.32 (2H, s), 7.94 (1H, brs), 9.86 (1H, s). |

TABLE 21

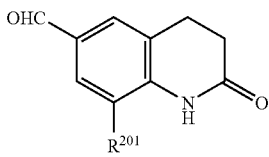

| Ref. Ex. | R<sup>101</sup> | R<sup>201</sup> | $^1$H-NMR dppm |
|---|---|---|---|
| 152 | 4-bromophenylethyl | —H | DMSO-d$_6$: 2.68-2.81 (2H, m), 2.96- 3.10 (2H, m), 5.17 (2H, s), 7.08 (1H, d, J = 8.4 Hz), 7.19 (2H, d, J = 8.4 Hz), 7.43-7.52 (2H, m), 7.68 (1H, dd, J = 1.9, 8.4 Hz), 7.76 (1H, d, J = 1.9 Hz), 9.84 (1H, s). |
| 153 | 4-nitrophenylethyl | —H | CDCl$_3$: 2.82-2.93 (2H, m), 3.05-3.17 (2H, m), 5.31 (2H, s), 6.88 (1H, d, J = 8.4 Hz), 7.37 (2H, d, J = 8.8 Hz), 7.64 (1H, dd, J = 1.9, 8.4 Hz), 7.75 (1H, d, J = 1.9 Hz), 8.20 (2H, d, J = 8.7 Hz), 9.89 (1H, s). |
| 154 | 4-biphenylethyl | —OCH$_3$ | CDCl$_3$: 2.67-2.74 (2H, m), 2.91-2.98 (2H, m), 3.83 (3H, s), 5.41 (2H, s), 7.18 (2H, d, J = 8.1 Hz), 7.23-7.35 (3H, m), 7.35-7.48 (4H, m), 7.48-7.57 (2H, m), 9.85 (1H, s). |
| 155 | 4-biphenylethyl | —CH$_3$ | CDCl$_3$: 2.46 (3H, s), 2.62-2.68 (2H, m), 2.85-2.92 (2H, m), 5.20 (2H, s), 7.15 (2H, d, J = 8.1 Hz), 7.20-7.65 (9H, m), 9.88 (1H, s). |

TABLE 22

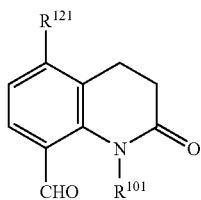

| Ref. Ex. | R[101] | R[121] | $^1$H-NMR dppm |
|---|---|---|---|
| 156 | ![benzyl-phenyl] | —H | DMSO-d$_6$: 2.55-2.68 (2H, m), 2.85-2.98 (2H, m), 5.07 (2H, s), 7.10 (2H, d, J = 8.2 Hz), 7.27-7.70 (10 H, m), 10.05 (1H, s). |
| 157 | —H | —H | DMSO-d$_6$: 7.51-7.62 (2H, m), 2.99 (2H, t, J = 7.9 Hz), 7.17 (1H, t, J = 7.5 Hz), 7.54 (1H, d, J = 7.5 Hz), 7.74 (1H, d, J = 7.5 Hz),10.00 (1H, s), 10.31 (1H, brs). |

In the above Tables, Me represents methyl and tBu represents tert-butyl.

Reference Example 158

Synthesis of 5-(1,3-dioxolan-2-yl)-1-{4-[(N-methyl-N-phenylamino)methyl]benzyl}-3,4-dihydro-1H-quinolin-2-one 1-(4-Chloromethylbenzyl)-5-(1,3-dioxolan-2-yl)-3,4-dihydro-1H-quinolin-2-one (100 mg, 0.28 mmol), N-methylaniline (0.045 ml, 0.42 mmol) and potassium carbonate (57.9 mg, 0.42 mmol) were added to acetonitrile (1 ml), followed by heating under reflux for 4 hours. After cooling to room temperature, water was added to the reaction mixture, and extraction with dichloromethane was performed. The organic layer was washed with water and a saturated sodium chloride solution, and dried over anhydrous sodium sulfate. The dry product was concentrated under reduced pressure, and the residue was purified by preparative silica gel thin layer chromatography (n-hexane:ethyl acetate=1:1). The purified product was concentrated to dryness under reduced pressure to thereby obtain 80 mg (yield: 67%) of 5-(1,3-dioxolan-2-yl)-1-(4-[(N-methyl-N-phenylamino)methyl]benzyl)-3,4-dihydro-1H-quinolin-2-one as a light yellow amorphous solid.

$^1$H-NMR(CDCl$_3$) dppm: 2.72-2.78 (2H, m), 2.98 (3H, s), 3.08-3.12 (2H, m), 4.06-4.16 (4H, m), 4.48 (2H, s), 5.15 (2H, s), 5.94 (1H, s), 6.67-6.74 (3H, m), 6.90 (1H, d, J=8.1 Hz), 7.09-7.26 (8H, m)

Reference Example 159

Synthesis of 5-(1,3-dioxolan-2-yl)-1-(6-piperidinomethylpyridin-2-ylmethyl)-3,4-dihydro-1H-quinolin-2-one 1-(6-Chloromethylpyridin-2-ylmethyl)-5-(1,3-dioxolan-2-yl)-3,4-dihydro-1H-quinolin-2-one (1.0 g, 2.8 mmol) was added to piperidine (2 ml), followed by stirring in an argon atmosphere at 100° C. for 2 hours. After cooling to room temperature, water and a small quantity of acetic acid were added to the reaction mixture, and extraction with ethyl acetate was performed twice. The organic layers were combined, washed twice with water and once with a saturated sodium chloride solution, and dried over anhydrous sodium sulfate. The dry product was concentrated under reduced pressure, and the residue was purified by silica gel column chromatography (dichloromethane:methanol=20:1). The purified product was concentrated to dryness under reduced pressure to thereby obtain 0.73 g (yield: 64%) of 5-(1,3-dioxolan-2-yl)-1-(6-piperidinomethylpyridin-2-ylmethyl)-3,4-dihydro-1H-quinolin-2-one as a light yellow amorphous solid.

$^1$H-NMR(CDCl$_3$) dppm: 1.44-1.49 (2H, m), 1.56-1.65 (4H, m), 2.42-2.46 (4H, m), 2.74-2.80 (2H, m), 3.09-3.15 (2H, m), 3.64 (2H, s), 4.01-4.17 (4H, m), 5.27 (2H, s), 5.95 (1H, s), 6.95-7.02 (2H, m), 7.11 (1H, t, J=7.9 Hz), 7.23-7.31 (2H, m), 7.54 (1H, t, J=7.7 Hz)

Reference Example 160

Synthesis of 5-(1,3-dioxolan-2-yl)-1-(4-phenylsulfanylbenzyl)-3,4-dihydro-1H-quinolin-2-one 1-(4-Chloromethylbenzyl)-5-(1,3-dioxolan-2-yl)-3,4-dihydro-1H-quinolin-2-one (1.0 g, 2.79 mmol), thiophenol (0.37 ml, 3.63 mmol) and 1,8-diazabicyclo[5.4.0]undecene-7 (DBU) (0.84 ml, 5.59 mmol) were added to THF (30 ml), followed by heating under reflux for 7 hours. After cooling to room temperature, the reaction mixture was concentrated under reduced pressure. The residue was purified by silica gel column chromatography (n-hexane:ethyl acetate=1:1). The purified product was concentrated to dryness under reduced pressure to thereby obtain 1.13 g (yield: 94%) of 5-(1,3-dioxolan-2-yl)-1-(4-phenylsulfanylbenzyl)-3,4-dihydro-1H-quinolin-2-one as a white solid.

$^1$H-NMR(CDCl$_3$) dppm: 2.73-2.79 (2H, m), 3.06-3.12 (2H, m), 4.01-4.17 (6H, m), 5.14 (2H, s), 5.95 (1H, s), 6.85-6.88 (1H, m), 7.09-7.17 (4H, m), 7.19-7.32 (7H, m)

Reference Example 161

Synthesis of 1-[2-(1-biphenyl-4-ylpiperidin-4-yl)ethyl]-2-oxo-1,2,3,4-tetrahydroquinoline-5-carboxaldehyde Palladium acetate (34 mg, 0.15 mmol), tri-tert-butylphosphine tetrafluoroborate (66 mg, 0.23 mmol) and sodium tert-butoxide (218 mg, 2.27 mmol) were added to a toluene solution (10 ml) of 5-(1,3-dioxolan-2-yl)-1-(2-piperidin-4-ylethyl)-3,4-dihydro-1H-quinolin-2-one (500 mg, 1.52 mmol) and 4-bromobiphenyl (424 mg, 1.82 mmol), followed by stirring in an argon atmosphere at 100° C. for 7.5 hours. After cooling to room temperature, water was added to the reaction mixture, and extraction with ethyl acetate was performed. The extract was dried over sodium sulfate and concentrated under reduced pressure, and the residue was purified by basic silica gel column chromatography (n-hexane:ethyl acetate=2:1). The purified product was concentrated under reduced pressure, and the residue was dissolved in acetone (10 ml). p-Toluenesulfonic acid monohydrate (104 mg) and water (2 ml) were added, followed by heating under reflux for 15 minutes. The resulting mixture was cooled to room temperature and concentrated under reduced pressure. The residue was rendered basic by adding an aqueous solution of potassium carbonate, and washed for 10 minutes in an ultrasonic washing machine. The produced insoluble matter was collected by filtration, washed with water and dried to thereby obtain 213 mg (yield: 32.1%) of 1-[2-(1-biphenyl-4-ylpiperidin-4-yl)ethyl]-2-oxo-1,2,3,4-tetrahydroquinoline-5-carboxaldehyde as a colorless solid.

$^1$H-NMR (CDCl$_3$) dppm: 1.2-2.3 (7H, m), 2.6-2.7 (2H, m), 3.0-3.25 (2H, m), 3.4-3.55 (2H, m), 3.65-3.8 (2H, m), 3.95-4.1 (2H, m), 7.18 (1H, d, J=8.0 Hz), 7.25-7.7 (10H, m), 7.84 (1H, d, J=8.1 Hz), 10.22 (1H, s)

Reference Example 162

Synthesis of 1-[3-(4-chlorophenylsulfanyl)propyl]-2-oxo-1,2,3,4-tetrahydroquinoline-5-carboxaldehyde 1-(3-Bromopropyl)-5-(1,3-dioxolan-2-yl)-3,4-dihydro-1H-quinolin-2-one (797 mg, 2.34 mmol), 4-chlorothiophenol (407 mg, 2.81 mmol) and potassium carbonate (421 mg, 3.05 mmol) were added to acetonitrile (16 ml), followed by heating under reflux for 5 hours. After cooling to room temperature, water was added to the reaction mixture, and extraction with ethyl acetate was performed. The extract was dried over sodium sulfate and concentrated under reduced pressure, and the residue was purified by silica gel column chromatography (n-hexane:ethyl acetate=3:1→2:1). The purified product was concentrated under reduced pressure, and the residue was dissolved in acetone (16 ml). p-Toluenesulfonic acid monohydrate (53.5 mg) and water (3 ml) were added, followed by stirring at room temperature overnight. An aqueous solution of potassium carbonate was added to the reaction mixture, and extraction with dichloromethane was performed. The organic layer was washed with a saturated sodium chloride solution, dried over anhydrous sodium sulfate, and concentrated under reduced pressure to thereby obtain 700 mg (yield: 83%) of 1-[3-(4-chlorophenylsulfanyl)propyl]-2-oxo-1,2,3,4-tetrahydroquinoline-5-carboxaldehyde as a colorless oil.

$^1$H-NMR(CDCl$_3$) dppm: 1.9-2.05 (2H, m), 2.55-2.65 (2H, m), 2.9-3.05 (4H, m), 4.0-4.2 (6H, m), 5.94 (1H, s), 6.96 (1H, d, J=7.9 Hz), 7.2-7.35 (6H, m)

Reference Example 163

Synthesis of 1-[3-(4-benzylpiperidin-1-yl)propyl]-2-oxo-1,2,3,4-tetrahydroquinoline-5-carboxaldehyde 1-(3-Bromopropyl)-5-(1,3-dioxolan-2-yl)-3,4-dihydro-1H-quinolin-2-one (790 mg, 2.32 mmol), 4-benzylpiperidine (0.49 ml, 2.79 mmol) and potassium carbonate (142 mg, 1.03 mmol) were added to acetonitrile (15 ml), followed by heating under reflux for 1.5 hours. After cooling to room temperature, the reaction mixture was filtered to remove the insoluble matter. The solid was washed with acetonitrile, and the filtrate and washing were combined and concentrated under reduced pressure. The residue was purified by silica gel column chromatography (n-hexane:ethyl acetate=3:1→ethyl acetate: methanol=50:1). The purified product was concentrated under reduced pressure, and the residue was dissolved in acetone (15 ml). p-Toluenesulfonic acid monohydrate (368 mg) was added, and the resulting mixture was heated under reflux for 2 hours. An aqueous solution of potassium carbonate was added to the reaction mixture, followed by concentration under reduced pressure. Water was added to the residue, and extraction with dichloromethane was performed. The organic layer was washed with a saturated sodium chloride solution, dried over anhydrous sodium sulfate, and concentrated under reduced pressure to thereby obtain 672 mg (yield: quantitative) of 1-[3-(4-benzylpiperidin-1-yl)propyl]-2-oxo-1,2,3,4-tetrahydroquinoline-5-carboxaldehyde as a colorless oil.

$^1$H-NMR(CDCl$_3$) dppm: 1.2-1.95 (9H, m), 2.35 (2H, t, J=7.0 Hz), 2.4-2.7 (4H, m), 2.8-3.1 (4H, m), 3.9-4.2 (6H, m), 5.94 (1H, s), 7.1-7.4 (8H, m)

Using appropriate starting materials and following the procedure of Reference Example 24, the compounds of Reference Examples 178 and 185 shown below were synthesized.

Using appropriate starting materials and following the procedure of Reference Example 25, the compounds of Reference Examples 164, 165, 167 to 172, 176, 177, 179, 183 and 184 shown below were synthesized.

Using appropriate starting materials and following the procedure of Reference Example 26, the compounds of Reference Examples 186 to 190, 192, 193, 197, 198, 203 and 206 to 209 shown below were synthesized.

Using appropriate starting materials and following the procedure of Reference Example 27, the compounds of Reference Examples 166 and 180 to 182 shown below were synthesized.

Using appropriate starting materials and following the procedure of Reference Example 30, the compounds of Reference Examples 73, 196, 200, 201 and 210 shown below were synthesized.

Using appropriate starting materials and following the procedure of Reference Example 158, the compound of Reference Example 175 shown below was synthesized.

Using appropriate starting materials and following the procedure of Reference Example 159, the compounds of Reference Examples 173 and 174 shown below were synthesized.

Using appropriate starting materials and following the procedure of Reference Example 161, the compounds of Reference Examples 202, 204, 205 and 214 shown below were synthesized.

Using appropriate starting materials and following the procedure of Reference Example 162, the compounds of Reference Examples 191 and 195 shown below were synthesized.

Using appropriate starting materials and following the procedure of Reference Example 163, the compounds of Reference Examples 194, 199 and 211 to 213 shown below were synthesized.

Using appropriate starting materials and following the procedure of Reference Example 32, the compounds of Reference Example 132 shown below was synthesized.

Using appropriate starting materials and following the procedure of Reference Example 41, the compounds of Reference Example 143 shown below was synthesized.

Using appropriate starting materials and following the procedure of Reference Example 22, the compounds of Reference Example 157 shown below was synthesized.

TABLE 23

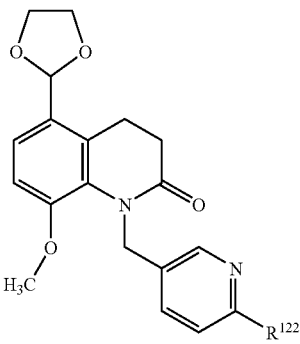

| Ref. Ex. | R[122] | NMR |
|---|---|---|
| 164 | —NHC₆H₅ | ¹H-NMR (CDCl₃) dppm: 2.55-2.61 (2H, m), 2.86-2.94 (2H, m), 3.82 (3H, s), 3.98-4.15 (4H, m), 5.22 (2H, s), 5.82 (1H, s), 6.42 (1H, s), 6.70-6.78 (2H, m), 7.27-7.30 (1H, m), 7.23-7.98 (6H, m), 7.99 (1H, s) |
| 165 | —CF₃ | ¹H-NMR (CDCl₃) dppm: 2.61-2.67 (2H, m), 2.98-3.03 (2H, m), 3.63 (3H, s), 4.00-4.16 (4H, m), 5.21 (2H, s), 5.85 (1H, s), 6.77 (1H, d, J = 8.7 Hz), 7.30 (1H, d, J = 8.7 Hz), 7.57 (1H, d, J = 8.1 Hz), 7.68 (1H, dd, J1 = 2.1 Hz, J2 = 8.1 Hz), 8.55 (1H, d, J = 2.1 Hz) |
| 166 | —C₆H₄C₆H₅(PARA) | ¹H-NMR (CDCl₃) dppm: 2.61-2.66 (2H, m), 2.96-3.01 (2H, m), 3.74 (3H, s), 3.98-4.15 (4H, m), 5.30 (2H, s), 5.84 (1H, s), 6.76 (1H, d, J = 8.7 Hz), 7.27 (1H, d, J = 8.7 Hz), 7.34-7.70 (9H, m), 7.99-8.03 (2H, m), 8.50 (1H, d, J = 1.6 Hz) |
| 167 | ![structure: N-methyl nicotinamide] | ¹H-NMR (CDCl₃) dppm: 2.60-2.65 (2H, m), 2.90-2.97 (2H, m), 3.78 (3H, s), 3.99-4.14 (4H, m), 5.24 (2H, s), 5.83 (1H, s), 6.77 (1H, d, J = 8.7 Hz), 7.40-7.48 (2H, m), 7.55-7.62 (1H, m), 8.13 (1H, d, J = 1.7 Hz), 8.18-8.25 (2H, m), 8.61 (1H, s), 8.78 (1H, dd, J1 = 1.7 Hz, J2 = 4.8 Hz), 9.13 (1H, d, J = 2.1 Hz) |
| 168 | ![structure: 2-(methylamino)pyridine] | ¹H-NMR (CDCl₃) dppm: 2.55-2.62 (2H, m), 2.87-2.94 (2H, m), 3.80 (3H, s), 4.00-4.14 (4H, m), 5.25 (2H, s), 5.82 (1H, s), 6.50 (1H, ddd, J1 = 0.8 Hz, J2 = 8.5 Hz), 6.62-6.67 (1H, m), 6.76 (1H, d, J = 8.7 Hz), 6.78-6.84 (1H, m), 7.23 (1H, s), 7.38-7.48 (2H, m), 7.53-7.60 (1H, m), 8.05-8.08 (1H, m), 8.20-8.23 (1H, m). |

TABLE 24

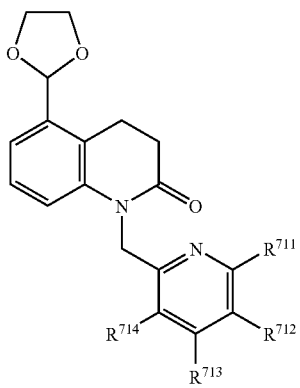

| Ref. Ex. | R[711] | R[712] | R[713] | R[714] | NMR |
|---|---|---|---|---|---|
| 169 | —CH₂Cl | —H | —H | —H | ¹H-NMR (CDCl₃) dppm: 2.74-2.80 (2H, m), 3.09-3.15 (2H, m), 4.02-4.17 (4H, m), 4.67 (2H, s), 5.27 (2H, s), 5.96 (1H, s), 7.00 (1H, d, J = 7.8 Hz), 7.07 (1H, d, J = 7.8 Hz), 7.15 (1H, t, J = 7.8 Hz), 7.27 (1H, d, J = 7.8 Hz), 7.35 (1H, d, J = 7.8 Hz), 7.63 (1H, t, J = 7.8 Hz) |

TABLE 24-continued

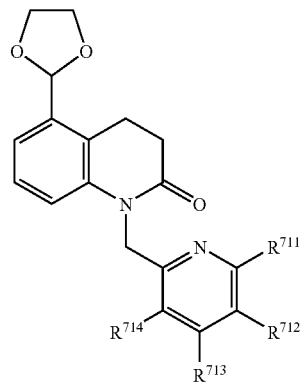

| Ref. Ex. | R711 | R712 | R713 | R714 | NMR |
|---|---|---|---|---|---|
| 170 | —H | —CH$_3$ | —OCH$_3$ | —CH$_3$ | $^1$H-NMR (CDCl$_3$) dppm: 2.19 (3H, s), 2.27 (3H, s), 2.73-2.79 (2H, m), 3.05-3.11 (2H, m), 3.78 (3H, s), 4.01-4.16 (4H, m), 5.19 (2H, s), 5.96 (1H, s), 6.85-6.89 (1H, m), 7.11 (1H, t, J = 7.9 Hz), 7.22-7.26 (1H, m), 8.10 (1H, s) |

TABLE 25

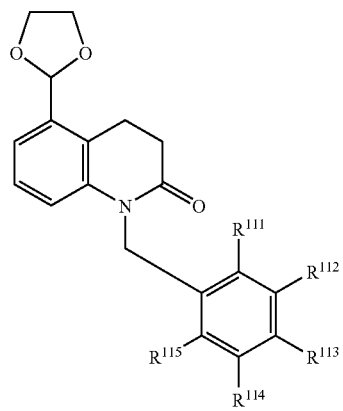

| Ref. Ex. | R111 | R112 | R113 | R114 | R115 | NMR |
|---|---|---|---|---|---|---|
| 171 | —H | —H | —CH$_2$Cl | —H | —H | $^1$H-NMR (CDCl$_3$) dppm: 2.74-2.79 (2H, m), 3.08-3.13 (2H, m), 4.02-4.17 (4H, m), 4.58 (2H, s), 5.17 (2H, s), 5.95 (1H, s), 6.87 (1H, d, J = 8.0 Hz), 7.13 (1H, t, J = 8.0 Hz), 7.19 (2H, d, J = 8.0 Hz), 7.25-7.28 (1H, m), 7.33 (2H, d, J = 8.0 Hz) |
| 172 | —H | —H | —H | —CH$_2$Cl | —H | $^1$H-NMR (CDCl$_3$) dppm: 2.75-2.81 (2H, m), 3.08-3.14 (2H, m), 4.02-4.17 (4H, m), 4.55 (2H, s), 5.17 (2H, s), 5.96 (1H, s), 6.88 (1H, d, J = 8.1 Hz), 7.10-7.16 (2H, m), 7.23-7.33 (4H, m), |
| 173 | —H | —H | —H | 1-ethylpiperidinyl | —H | $^1$H-NMR (CDCl$_3$) dppm: 1.50-1.60 (6H, m), 2.30-2.34 (4H, m), 2.74-2.80 (2H, m), 3.07-3.13 (2H, m), 3.43 (2H, s), 4.01-4.16 (4H, m), 5.17 (2H, s), 5.95 (1H, s), 6.90 (1H, d, J = 8.1 Hz), 7.03-7.27 (6H, m) |
| 174 | —H | —H | 1-ethylpiperidinyl | —H | —H | $^1$H-NMR (CDCl$_3$) dppm: 1.41-1.47 (2H, m), 1.57-1.65 (4H, m), 2.40-2.44 (4H, m), 2.73-2.79 (2H, m), 3.07-3.13 (2H, m), 3.50 (2H, s), 4.00-4.17 (4H, m), 5.16 (2H, s), 5.95 (1H, s), 6.91 (1H, d, J = 8.1 Hz), 7.09-7.17 (3H, m), 7.24-7.29 (3H, m) |

TABLE 25-continued
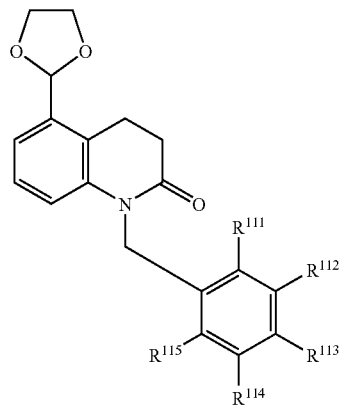
| Ref. Ex. | $R^{111}$ | $R^{112}$ | $R^{113}$ | $R^{114}$ | $R^{115}$ | NMR |
|---|---|---|---|---|---|---|
| 175 | —H | —H | 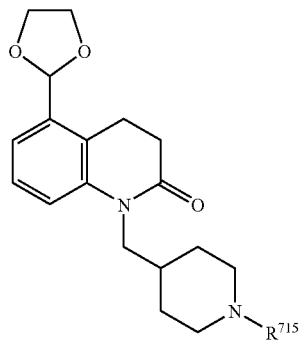 | —H | —H | $^1$H-NMR (CDCl$_3$) dppm: 2.73-2.79 (2H, m), 2.92-2.98 (2H, m), 3.07-3.13 (2H, m), 3.24-3.30 (2H, m), 4.01-4.17 (4H, m), 4.20 (2H, s), 5.17 (2H, s), 5.95 (1H, s), 6.48 (1H, d, J = 7.8 Hz), 6.61-6.68 (1H, m), 6.90-7.18 (6H, m), 7.24-7.31 (3H, m) |
TABLE 26
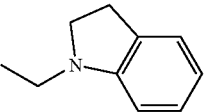
| Ref. Ex. | $R^{715}$ | NMR |
|---|---|---|
| 176 | —CO$_2$CH$_2$CH$_2$Si(CH$_3$)$_3$ | $^1$H-NMR (CDCl$_3$) dppm: 0.04 (9H, s), 0.98 (2H, d, J = 8.3 Hz), 1.2-1.4 (2H, m), 1.5-2.0 (2H, m), 2.5-2.8 (4H, m), 2.95-3.1 (2H, m), 3.75-4.3 (10H, m), 7.02 (1H, dd, J1 = 1.8 Hz, J2 = 7.4 Hz), 7.2-7.4 (2H, m) |
| 177 | —CO$_2$C(CH$_3$)$_3$ | $^1$H-NMR (CDCl$_3$) δ ppm: 1.15-1.95 (5H, m), 1.44 (9H, s), 2.5-2.7 (4H, m), 2.95-3.1 (2H, m), 3.75-4.2 (8H, m), 5.94 (1H, s), 7.0-7.1 (1H, m), 7.2-7.35 (2H, m) |
| 178 | —H | $^1$H-NMR (CDCl$_3$) dppm: 1.25-1.8 (5H, m), 2.45-3.3 (8H, m), 3.92 (2H, d, J = 7.1 Hz), 4.0-4.25 (4H, m), 5.94 (1H, s), 6.9-7.1 (1H, m), 7.2-7.4 (2H, m) |

TABLE 27

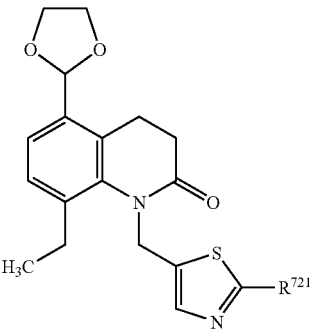

| Ref. Ex. | $R^{721}$ | NMR |
|---|---|---|
| 179 | —Cl | $^1$H-NMR (CDCl$_3$) dppm: 2.54-2.60 (2H, m), 2.89-2.95 (2H, m), 3.88 (3H, s), 3.99-4.16 (4H, m), 5.23 (2H, s), 5.84 (1H, s), 6.86 (1H, d, J = 8.7 Hz), 7.32 (1H, d, J = 8.7 Hz), 7.39 (1H, s) |
| 180 | —C$_6$H$_5$ | $^1$H-NMR (CDCl$_3$) dppm: 2.56-2.62 (2H, m), 2.89-2.95 (2H, m), 3.91 (3H, s), 3.97-4.14 (4H, m), 5.45 (2H, s), 5.82 (1H, s), 6.84 (1H, d, J = 8.7 Hz), 7.30 (1H, d, J = 8.7 Hz), 7.37-7.43 (3H, m), 7.61 (1H, s), 7.84-7.88 (2H, m) |

TABLE 27-continued

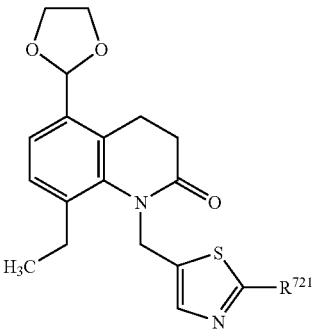

| Ref. Ex. | $R^{721}$ | NMR |
|---|---|---|
| 181 | -3-THIENYL | $^1$H-NMR (CDCl$_3$) dppm: 2.55-2.61 (2H, m), 2.89-2.95 (2H, m), 3.90 (3H, s), 4.00-4.14 (4H, m), 5.42 (2H, s), 5.82 (1H, s), 6.84 (1H, d, J = 8.9 Hz), 7.30 (1H, d, J = 8.9 Hz), 7.33-7.35 (1H, m), 7.47-7.49 (1H, m), 7.55 (1H, s), 7.74 (1H, dd, J1 = 1.0 Hz, J2 = 2.8 Hz) |
| 182 | -3-PYRIDYL | $^1$H-NMR (CDCl$_3$) dppm: 2.57-2.62 (2H, m), 2.91-2.96 (2H, m), 3.91 (3H, s), 4.01-4.20 (4H, m), 5.43 (2H, s), 5.83 (1H, s), 6.86 (1H, d, J = 8.7 Hz), 7.29-7.37 (2H, m), 7.69 (1H, s), 8.13-8.18 (1H, m), 8.60 (1H, dd, J1 = 1.6 Hz, J2 = 4.8 Hz), 9.08 (1H, d, J = 2.0 Hz) |

TABLE 28

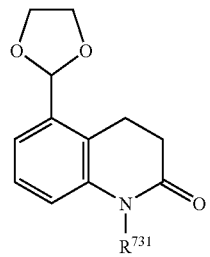

| Ref. Ex. | $R^{731}$ | NMR |
|---|---|---|
| 183 | —(CH$_2$)$_3$Br | $^1$H-NMR (CDCl$_3$) dppm: 2.15-2.3 (2H, m), 2.5-2.7 (2H, m), 2.9-3.1 (2H, m), 3.44 (2H, t, J = 6.5 Hz), 4.0-4.25 (6H, m), 5.94 (1H, s), 7.0-7.1 (1H, m), 7.25-7.35 (2H, m) |
| 184 | 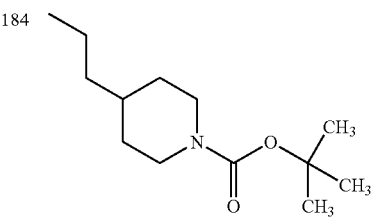 | $^1$H-NMR (CDCl$_3$) dppm: 1.1-1.2 (2H, m), 1.42 (9H, s), 1.4-1.6 (3H, m), 1.7-1.8 (2H, m), 2.55-2.8 (4H, m), 2.95-3.05 (2H, m), 3.9-4.2 (8H, m), 5.94 (1H, s), 6.95-7.05 (1H, m), 7.2-7.35 (2H, m) |

TABLE 28-continued

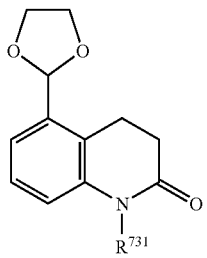

| Ref. Ex. | R⁷³¹ | NMR |
|---|---|---|
| 185 | 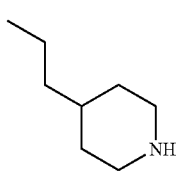 | ¹H-NMR (CDCl₃) dppm: 1.1-1.65 (7H, m), 2.5-2.7 (4H, m), 2.9-3.2 (4H, m), 3.97 (2H, t, J = 8.2 Hz), 4.05-4.2 (4H, m), 5.94 (1H, s), 6.95-7.05 (1H, m), 7.2-7.4 (2H, m) |

TABLE 29

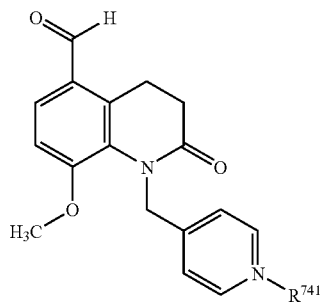

| Ref. Ex. | R⁷⁴¹ | NMR |
|---|---|---|
| 186 | —NHC₆H₅ | ¹H-NMR (CDCl₃) dppm: 2.55-2.62 (2H, m), 3.31-3.38 (2H, m), 3.93 (3H, s), 5.23 (2H, s), 6.42 (1H, s), 6.70 (1H, d, J = 8.6 Hz), 6.89 (1H, d, J = 8.6 Hz), 6.98-7.06 (1H, m), 7.23-7.33 (5H, m), 7.54 (1H, d, J = 8.2 Hz), 7.94 (1H, d, J = 2.1 Hz), 10.00 (1H, s) |
| 187 | —CF₃ | ¹H-NMR (CDCl₃) dppm: 2.61-2.67 (2H, m), 3.41-3.47 (2H, m), 3.75 (3H, s), 5.23 (2H, s), 6.92 (1H, d, J = 8.6 Hz), 7.58 (1H, d, J = 8.0 Hz), 7.59 (1H, d, J = 8.6 Hz), 7.68 (1H, dd, J1 = 2.0 Hz, J2 = 8.0 Hz), 8.54 (1H, d, J = 2.0 Hz), 10.04 (1H, s) |
| 188 | —C₆H₄C₆H₅(PARA) | ¹H-NMR (CDCl₃) dppm: 2.61-2.67 (2H, m), 3.40-3.45 (2H, m), 3.86 (3H, s), 5.32 (2H, s), 6.89 (1H, d, J = 8.7 Hz), 7.33-7.39 (1H, m), 7.42-7.49 (2H, m), 7.52-7.56 (2H, m), 7.62-7.69 (5H, m), 7.99-8.02 (2H, m), 8.46 (1H, d, J = 1.6 Hz), 10.01 (1H, s) |
| 189 | 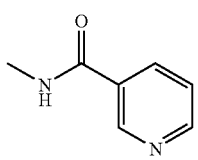 | ¹H-NMR (DMSO-d₆) dppm: 2.59-2.65 (2H, m), 3.37-3.42 (2H, m), 3.87 (3H, s), 5.26 (2H, s), 6.91 (1H, d, J = 8.6 Hz), 7.44 (1H, dd, J1 = 4.9 Hz, J2 = 7.9 Hz), 7.52-7.58 (2H, m), 8.10 (1H, d, J = 1.8 Hz), 8.18-8.24 (2H, m), 8.59 (1H, s), 8.79 (1H, dd, J1 = 1.8 Hz, J2 = 4.9 Hz), 9.12 (1H, d, J = 1.8 Hz), 10.02 (1H, s) |
| 190 | 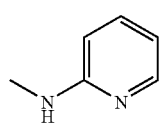 | ¹H-NMR (CDCl₃) dppm: 2.57-2.62 (2H, m), 3.34-3.39 (2H, m), 3.92 (3H, s), 5.26 (2H, s), 6.79-6.85 (1H, m), 6.89 (1H, d, J = 8.7 Hz), 7.34-7.45 (4H, m), 7.51-7.60 (2H, m), 8.01 (1H, d, J = 2.0 Hz), 8.20-8.23 (1H, m), 10.00 (1H, s) |

TABLE 30

| Ref. Ex. | R711 | R712 | R713 | R714 | NMR |
|---|---|---|---|---|---|
| 191 | —CH$_2$SC$_6$H$_5$ | —H | —H | —H | $^1$H-NMR (CDCl$_3$) dppm: 2.72-2.78 (2H, m), 3.49-3.55 (2H, m), 4.24 (2H, s), 5.26 (2H, s), 7.04 (1H, d, J = 7.7 Hz), 7.15-7.33 (8H, m), 7.47-7.55 (2H, m), 10.20 (1H, s) |
| 192 | —H | —CH$_3$ | —OCH$_3$ | —CH$_3$ | $^1$H-NMR (CDCl$_3$) dppm: 2.20 (3H, s), 2.27 (3H, s), 2.74-2.80 (2H, m), 3.47-3.53 (2H, m), 3.75 (3H, s), 5.22 (2H, s), 7.12 (1H, dd, J1 = 1.0 Hz, J2 = 7.9 Hz), 7.29 (1H, t, J = 7.9 Hz), 7.47 (1H, dd, J1 = 1.0 Hz, J2 = 7.9 Hz), 8.12 (1H, s), 10.21 (1H, s) |
| 193 | (1-ethylpiperidinyl) | —H | —H | —H | $^1$H-NMR (CDCl$_3$) dppm: 1.44-1.50 (2H, m), 1.62-1.68 (4H, m), 2.50-2.54 (4H, m), 2.74-2.80 (2H, m), 3.51-3.57 (2H, m), 3.72 (2H, s), 5.30 (2H, s), 7.06 (1H, d, J = 8.5 Hz), 7.30 (2H, d, J = 4.4 Hz), 7.33 (1H, d, J = 8.5 Hz), 7.49 (1H, t, J = 4.4 Hz), 7.59 (1H, t, J = 8.5 Hz), 10.21 (1H, s) |
| 194 | N-ethyl-N-methylanilino | —H | —H | —H | $^1$H-NMR (CDCl$_3$) dppm: 2.72-2.78 (2H, m), 3.09 (3H, s), 3.49-3.55 (2H, m), 4.63 (2H, s), 5.28 (2H, s), 6.67-6.73 (3H, m), 7.03 (1H, d, J = 3.8 Hz), 7.06 (1H, d, J = 3.8 Hz), 7.16-7.23 (2H, m), 7.30-7.33 (2H, m), 7.47-7.55 (2H, m), 10.22 (1H, s) |

TABLE 31

| Ref. Ex. | R111 | R112 | R113 | R114 | R115 | NMR |
|---|---|---|---|---|---|---|
| 195 | —H | —H | —H | —CH$_2$SC$_6$H$_5$ | —H | $^1$H-NMR (CDCl$_3$) dppm: 2.71-2.77 (2H, m), 3.47-3.53 (2H, m), 4.06 (2H, s), 5.15 (2H, s), 7.02-7.12 (3H, m), 7.14-7.32 (8H, m), 7.48 (1H, dd, J1 = 1.1 Hz, J2 = 7.7 Hz), 10.20 (1H, s) |

TABLE 31-continued

[Structure: 1-benzyl-2-oxo-1,2,3,4-tetrahydroquinoline-5-carbaldehyde with R^111, R^112, R^113, R^114, R^115 substituents on the benzyl phenyl ring]

| Ref. Ex. | R^111 | R^112 | R^113 | R^114 | R^115 | NMR |
|---|---|---|---|---|---|---|
| 196 | —H | —H | —CH₂SC₆H₅ | —H | —H | ¹H-NMR (CDCl₃) dppm: 2.74-2.80 (2H, m), 3.49-3.55 (2H, m), 4.08 (2H, s), 5.18 (2H, s), 7.07-7.13 (3H, m), 7.16-7.33 (8H, m), 7.49 (1H, dd, J1 = 1.1 Hz, J2 = 7.6 Hz), 10.21 (1H, s) |
| 197 | —H | —H | —H | 1-ethylpiperidin-yl | —H | ¹H-NMR (CDCl₃) dppm: 1.39-1.45 (2H, m), 1.50-1.58 (4H, m), 2.30-2.34 (4H, m), 2.76-2.82 (2H, m), 3.45 (2H, s), 3.50-3.56 (2H, m), 5.22 (2H, s), 7.03-7.31 (6H, m), 7.47 (1H, d, J = 7.6 Hz), 10.20 (1H, s) |
| 198 | —H | —H | | 1-ethylpiperidin-yl | —H | ¹H-NMR (CDCl₃) dppm: 1.39-1.45 (2H, m), 1.50-1.62 (4H, m), 2.34-2.38 (4H, m), 2.75-2.81 (2H, m), 3.44 (2H, s), 3.49-3.55 (2H, m), 5.19 (2H, s), 7.14 (2H, d, J = 8.1 Hz), 7.25-7.33 (4H, m), 7.48 (1H, dd, J1 = 1.0 Hz, J2 = 7.6 Hz), 10.21 (1H, s) |
| 199 | —H | —H | —H | N-ethyl-N-methylaniline | —H | ¹H-NMR (CDCl₃) dppm: 2.64-2.70 (2H, m), 2.93 (3H, s), 3.37-3.43 (2H, m), 4.48 (2H, s), 5.18 (2H, s), 6.61-6.69 (3H, m), 6.95-7.30 (8H, m), 7.47 (1H, dd, J1 = 0.9 Hz, J2 = 7.7 Hz), 10.20 (1H, s) |
| 200 | —H | —H | N-ethyl-N-methylaniline | —H | —H | ¹H-NMR (CDCl₃) dppm: 2.73-2.79 (2H, m), 2.98 (3H, s), 3.48-3.54 (2H, m), 4.49 (2H, s), 5.18 (2H, s), 6.67-6.73 (3H, m), 7.11-7.33 (8H, m), 7.48 (1H, dd, J1 = 1.0 Hz, J2 = 7.6 Hz), 10.20 (1H, s) |
| 201 | —H | —H | 1-ethylindolin-yl | —H | —H | ¹H-NMR (CDCl₃) dppm: 2.75-2.81 (2H, m), 2.92-2.98 (2H, m), 3.25-3.31 (2H, m), 3.49-3.55 (2H, m), 4.21 (2H, s), 5.20 (2H, s), 6.47 (1H, dd, J = 7.7 Hz), 6.63-6.69 (1H, m), 7.01-7.07 (1H, m), 7.11 (1H, dd, J1 = 1.0 Hz, J2 = 5.6 Hz), 7.17 (2H, d, J = 8.2 Hz), 7.26-7.34 (4H, m), 7.49 (1H, dd, J1 = 1.0 Hz, J2 = 7.7 Hz), 10.21 (1H, s) |

TABLE 32

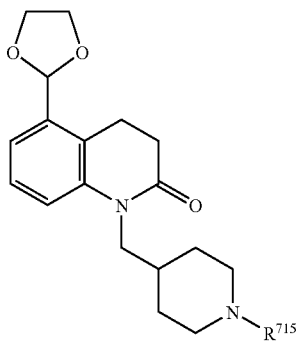

| Ref. Ex. | R715 | NMR |
|---|---|---|
| 202 | —C6H4C6H5(PARA) | 1H-NMR (CDCl3) dppm: 1.4-2.2 (5H, m), 2.5-3.0 (4H, m), 3.4-3.55 (2H, m), 3.65-3.8 (2H, m), 4.03 (1H, br s), 7.2-7.65 (12H, m), 10.23 (1H, s) |
| 203 | —CO2CH2CH2Si(CH3)3 | 1H-NMR (CDCl3) dppm: 0.04 (9H, s), 0.97 (2H, d, J = 8.3 Hz), 1.2-2.0 (5H, m), 2.55-2.8 (4H, m), 3.3-3.6 (2H, m), 3.75-4.3 (6H, m), 7.2-7.6 (3H, m), 10.22 (1H, s) |
| 204 | ![p-tolyl] | 1H-NMR (CDCl3) dppm: 1.35-1.9 (5H, m), 2.56 (3H, s), 2.5-2.7 (4H, m), 2.9-3.1 (2H, m), 3.5-3.7 (2H, m) 3.97 (2H, d, J = 7.1 Hz), 4.0-4.2 (4H, m), 6.82 (1H, d, J = 6.1 Hz), 7.0-7.2 (3H, m), 7.25-7.4 (2H, m) |
| 205 | ![1-methylnaphthyl] | 1H-NMR (DMSO-d6) dppm: 1.45-1.9 (5H, m), 2.6-3.0 (4H, m), 2.56 (3H, s), 2.5-2.7 (4H, m), 3.15-3.4 (2H, m), 3.85-4.15 (6H, m), 5.92 (1H, s), 7.04 (1H, d, J = 7.3 Hz), 7.15-7.6 (8H, m), 7.86 (1H, d, J = 6.8 Hz), 8.06 (1H, d, J = 7.0 Hz), 10.23 (1H, s) |

TABLE 33

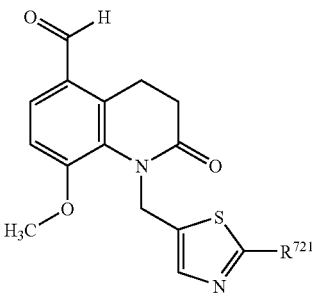

| Ref. Ex. | R721 | NMR |
|---|---|---|
| 206 | —Cl | 1H-NMR (CDCl3) dppm: 2.54-2.60 (2H, m), 3.34-3.40 (2H, m), 3.99 (3H, s), 5.25 (2H, s), 7.01 (1H, d, J = 8.6 Hz), 7.36 (1H, s), 7.62 (1H, d, J = 8.6 Hz), 10.04 (1H, s) |
| 207 | —C6H5 | 1H-NMR (CDCl3) dppm: 2.57-2.62 (2H, m), 3.34-3.40 (2H, m), 4.01 (3H, s), 5.48 (2H, s), 6.98 (1H, d, J = 8.7 Hz), 7.37-7.40 (3H, m), 7.56-7.60 (2H, m), 7.82-7.86 (2H, m), 10.01 (1H, s) |
| 208 | -3-THIENYL | 1H-NMR (CDCl3) dppm: 2.56-2.62 (2H, m), 3.34-3.39 (2H, m), 4.01 (3H, s), 5.46 (2H, s), 6.98 (1H, d, J = 8.7 Hz), 7.34 (1H, dd, J1 = 3.0 Hz, J2 = 5.0 Hz), 7.44-7.47 (1H, m), 7.51 (1H, m), 7.58 (1H, d, J = 8.7 Hz), 7.72-7.75 (1H, m), 10.01 (1H, s) |
| 209 | -3-PYRIDYL | 1H-NMR (CDCl3) dppm: 2.58-2.63 (2H, m), 3.35-3.41 (2H, m), 4.02 (3H, s), 5.46 (2H, s), 7.00 (1H, d, J = 8.6 Hz), 7.34 (1H, dd, J1 = 4.8 Hz, J2 = 8.0 Hz), 7.60 (1H, d, J = 8.6 Hz), 7.66 (1H, d, J = 8.6 Hz), 8.13 (1H, ddd, J1 = 1.9 Hz, J2 = 8.0 Hz), 8.61 (1H, dd, J1 = 1.9 Hz, J2 = 4.8 Hz), 9.07 (1H, d, J = 1.9 Hz), 10.02 (1H, s) |

TABLE 34

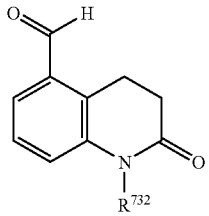

| Ref. Ex. | R732 | NMR |
|---|---|---|
| 210 | —(CH2)4F | 1H-NMR (CDCl3) dppm: 1.5-1.75 (2H, m), 2.45-2.6 (2H, m), 3.3-3.45 (2H, m), 3.69 (3H, s), 4.02 (2H, t, J = 7.2 Hz), 4.25-4.35 (1H, m), 4.45-4.55 (1H, m), 6.98 (1H, d, J = 8.6 Hz), 7.60 (1H, d, J = 8.6 Hz), 10.06 (1H, s) |
| 211 | ![4-(4-phenylpiperazin-1-yl)butyl] | 1H-NMR (CDCl3) dppm: 1.8-1.95 (2H, m), 2.4-2.75 (6H, m), 3.1-3.25 (4H, m), 3.35-3.6 (3H, m), 3.95-4.2 (3H, m), 6.8-7.0 (3H, m), 7.2-7.6 (5H, m), 10.22 (1H, s) |

TABLE 34-continued

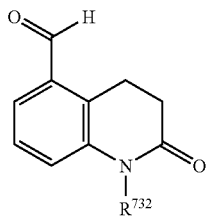

| Ref. Ex. | R<sup>732</sup> | NMR |
|---|---|---|
| 212 | (1,2,3,4-tetrahydroisoquinolin-2-yl)butyl | ¹H-NMR (CDCl₃) dppm: 1.8-2.05 (2H, m), 2.5-3.05 (8H, m), 3.35-3.5 (2H, m), 3.61 (2H, s), 4.0-4.25 (2H, m), 6.9-7.6 (7H, s), 10.2 (1H, s) |
| 213 | (4-phenylpiperidin-1-yl)butyl | ¹H-NMR (CDCl₃) dppm: 1.6-2.3 (8H, m), 2.45-2.8 (4H, m), 3.0-3.25 (2H, m), 3.4-3.65 (2.5H, m), 3.95-4.2 (2.5H, m), 7.1-7.6 (8H, m), 10.21 (1H, s) |
| 214 | [4-(4-methylphenyl)piperidin-1-yl]propyl | ¹H-NMR (CDCl₃) dppm: 1.35-1.95 (7H, m), 2.26 (3H, s), 2.5-2.75 (4H, m), 3.35-3.5 (2H, m), 3.5-3.65 (2H, m), 3.95-4.1 (2H, m), 6.86 (2H, d, J = 8.5 Hz), 7.06 (2H, d, J = 8.5 Hz), 7.15-7.6 (3H, m), 10.22 (1H, s) |

Example 1

Synthesis of 5-(8-methoxy-1-methyl-2-oxo-1,2-dihydroquinolin-5-ylmethyl)thiazolidine-2,4-dione 1.0 g of 2-chloro-3-(8-methoxy-1-methyl-2-oxo-1,2-dihydroquinolin-5-yl)propionic acid, 0.45 g of thiourea, and 0.4 g of sodium acetate were added to 20 ml of methoxy ethanol, and the mixture was stirred at 110° C. for 7.5 hours. The reaction mixture was concentrated under reduced pressure, an aqueous sodium hydrogencarbonate solution was added to the residue to precipitate a solid, and the precipitated solid was collected by filtration. The filtrate was extracted with dichloromethane, and the extract was dried over anhydrous sodium sulfate and concentrated. The concentrated residue and the solid collected by filtration were combined and added to a mixed solvent of 10% hydrochloric acid and ethanol, followed by heating and refluxing overnight. The solvent was distilled off under reduced pressure, and the residue was recrystallized from an aqueous DMF, giving 0.41 g of 5-(8-methoxy-1-methyl-2-oxo-1,2-dihydroquinolin-5-ylmethyl)thiazolidine-2,4-dione as a yellow powder.

Melting point: 254° C.-255° C.

Example 2

Synthesis of 5-[2-(8-methoxy-1-methyl-2-oxo-1,2-dihydroquinolin-5-yl)ethyl]thiazolidine-2,4-dione 912 mg of 2-chloro-4-(8-methoxy-1-methyl-2-oxo-1,2-dihydroquinolin-5-yl)butyric acid, 390 mg of thiourea, and 394 mg of sodium acetate were added to 20 ml of methoxyethanol, followed by stirring at 110° C. for 4 hours. The reaction mixture was concentrated under reduced pressure. Water was added to the residue, and the mixture was extracted with dichloromethane. The extract was dried over anhydrous sodium sulfate and concentrated. The residue was added to a mixed solvent of 10 ml of 10% hydrochloric acid and 10 ml of ethanol, followed by heating and refluxing overnight. The solvent was distilled off under reduced pressure, and the residue was recrystallized from a DMF-ethanol mixed solvent, giving 332 mg (31% yield) of 5-[2-(8-methoxy-1-methyl-2-oxo-1,2-dihydroquinolin-5-yl)ethyl]thiazolidine-2,4-dione as a yellow powder.

Melting point: 222° C. to 224° C.

Example 3

Synthesis of 5-[3-(8-methoxy-1-methyl-2-oxo-1,2-dihydroquinolin-5-yl)propyl]thiazolidine-2,4-dione 1 g of 2-chloro-5-(8-methoxy-1-methyl-2-oxo-1,2-dihydroquinolin-5-yl)valeric acid, 380 mg of thiourea, and 380 mg of sodium acetate were added to 20 ml of methoxyethanol, followed by stirring at 110° C. for 5 hours. The reaction mixture was concentrated under reduced pressure, and water and a small amount of ethanol were added to the residue to precipitate a solid. The precipitated solid was collected by filtration. The solid collected by filtration was added to a mixed solvent of 10 ml of 10% hydrochloric acid and 10 ml of ethanol, followed by heating and refluxing overnight. The solvent was distilled off under reduced pressure, and the residue was extracted with dichloromethane. The extract was dried over anhydrous sodium sulfate and concentrated. The concentrated residue was purified by silica gel column chromatography (dichloromethane:methanol of 100:1→10:1), and recrystallized from an ethanol-ether mixed solvent, giving 332 mg (29% yield) of 5-[3-(8-methoxy-1-methyl-2-oxo-1,2-dihydroquinolin-5-yl)propyl]thiazolidine-2,4-dione as a light yellow powder.

Melting point: 172° C. to 175° C.

Example 4

Synthesis of 5-(8-methoxy-1-methyl-2-oxo-1,2-dihydroquinolin-5-yl)thiazolidine-2,4-dione 3.02 g of ethyl chloro-(8-methoxy-1-methyl-2-oxo-1,2-dihydroquinolin-5-yl)acetate, 1.4 g of thiourea, and 2 g of sodium acetate were added to 50 ml of methoxyethanol, followed by stirring at 110° C. for 2.5 hours. The reaction mixture was concentrated under reduced pressure. Water was added to the residue to precipitate a solid, and the precipitated solid was collected by filtration. The collected solid was added to a mixed solvent of 30 ml of 10% hydrochloric acid and 30 ml of ethanol, followed by heating and refluxing overnight. The resultant was concentrated to half its original volume under reduced pressure. Water was added thereto, and the mixture was cooled with ice to precipitate a solid. The precipitated solid was collected by filtration. The solid was recrystallized from a DMF-ethanol mixed solvent, giving 1.68 g (57% yield) of 5-(8-methoxy-1-methyl-2-oxo-1,2-dihydroquinolin-5-yl)thiazolidine-2,4-dione as a gray powder.

Melting point: 255° C. (decomposition)

Example 5

Synthesis of 5-[1-(4-chlorobenzyl)-2-oxo-1,2-dihydroquinolin-4-ylmethylidene]thiazolidine-2,4-dione 1.50 g of 1-(4-chlorobenzyl)-2-oxo-1,2-dihydroquinolin-4-carboxaldehyde and 0.826 g of 2,4-thiazolidinedione were suspended in 30 ml of toluene. Five drops of piperidine and five drops of acetic acid were added, followed by heating and refluxing for 6 hours. The resultant was allowed to cool to precipitate a solid, and the precipitated solid was collected by filtration and dried, giving 1.01 g (50% yield) of 5-[1-(4-chlorobenzyl)-2-oxo-1,2-dihydroquinolin-4-ylmethylidene]thiazolidine-2,4-dione as a light-brown powder.

$^1$H-NMR(DMSO-$d_6$) dppm: 5.53 (2H, s), 6.76 (1H, s), 7.11-7.49 (6H, m), 7.53-7.64 (1H, m), 7.81 (1H, d, J=8.1 Hz), 8.04 (1H, s), 12.21-13.32 (1H, br)

Example 6

Synthesis of 5-[1-(4-chlorobenzyl)-2-oxo-1,2-dihydroquinolin-3-ylmethylidene]thiazolidine-2,4-dione 1.50 g of 1-(4-chlorobenzyl)-2-oxo-1,2-dihydroquinolin-3-carboxaldehyde and 0.826 g of 2,4-thiazolidinedione were suspended in 30 ml of toluene, and five drops of piperidine and five drops of acetic acid were added, followed by heating and refluxing for 6 hours. The resultant was allowed to cool to precipitate a solid. The precipitated solid was collected by filtration and dried, giving 1.36 g of 5-[1-(4-chlorobenzyl)-2-oxo-1,2-dihydroquinolin-3-ylmethylidene]thiazolidine-2,4-dione as a yellow powder (68% yield).

$^1$H-NMR(DMSO-$d_6$) dppm: 5.55 (2H, s), 7.18-7.45 (6H, m), 7.53-7.65 (1H, m), 7.88-8.00 (2H, m), 8.21 (1H, s), 12.59 (1H, brs)

Using appropriate starting materials, the same procedure as in Example 6 was conducted, giving compounds of the following Examples 7 to 13.

Example 7

5-[1-(1-Biphenyl-4-ylmethyl-2-oxo-1,2-dihydroquinolin-4-yl)methylidene]thiazolidine-2,4-dione $^1$H-NMR(DMSO-$d_6$) dppm: 5.59 (2H, brs), 6.78 (1H, s), 7.18-7.70 (12H, m), 7.82 (1H, d, J=8.0 Hz), 8.05 (1H, s), 12.81 (1H, brs)

Example 8

5-[1-(1-Biphenyl-4-ylmethyl-2-oxo-1,2-dihydroquinolin-3-yl)methylidene]thiazolidine-2,4-dione $^1$H-NMR(DMSO-$d_6$) dppm: 5.61 (2H, brs), 7.21-7.51 (7H, m), 7.51-7.68 (5H, m), 7.87-8.00 (2H, m), 8.22 (1H, s), 12.60 (1H, brs)

Example 9

5-[1-(8-Methoxy-1-methyl-2-oxo-1,2-dihydroquinolin-5-yl)methylidene]thiazolidine-2,4-dione Melting point: 300° C. or higher $^1$H-NMR(DMSO-$d_6$) dppm: 3.80 (3H, s), 3.95 (3H, s), 6.70 (1H, d, J=9.8 Hz), 7.35-7.45 (2H, m), 8.05 (1H, d, J=9.8 Hz), 8.14 (1H, s), 12.63 (1H, brs)

Example 10

5-[1-(8-Methoxy-1-methyl-2-oxo-1,2-dihydroquinolin-5-yl)methylidene]-3-methylthiazolidine-2,4-dione Melting point: 270° C. (decomposition)

Example 11

5-{1-[8-Methoxy-1-(4-bromobenzyl)-2-oxo-1,2-dihydroquinolin-5-yl]methylidene}thiazolidine-2,4-dione $^1$H-NMR(DMSO-$d_6$) dppm: 3.65 (3H, s), 5.67 (2H, s), 6.80 (1H, d, J=9.8 Hz), 7.03 (2H, d, J=8.5 Hz), 7.25-7.40 (2H, m), 7.40-7.52 (2H, m), 8.16 (2H, d, J=10.9 Hz), 12.64 (1H, brs)

Example 12

5-[1-(1-Biphenyl-4-ylmethyl-2-oxo-1,2,3,4-tetrahydroquinolin-7-yl)methylidene]thiazolidine-2,4-dione $^1$H-NMR(DMSO-$d_6$) dppm: 2.70-2.84 (2H, m), 2.97-3.09 (2H, m), 5.22 (2H, brs), 7.12 (1H, s), 7.15-7.25 (1H, m), 7.25-7.49 (6H, m), 7.56-7.71 (5H, m), 12.52 (1H, brs)

Example 13

5-[1-(1-Biphenyl-4-ylmethyl-2-oxo-1,2,3,4-tetrahydroquinolin-8-yl)methylidene]thiazolidine-2,4-dione $^1$H-NMR(DMSO-$d_6$) dppm: 2.55-2.68 (2H, m), 2.80-2.94 (2H, m), 4.98 (2H, s), 6.98-7.16 (3H, m), 7.22-7.63 (9H, m), 7.75 (1H, s), 12.57 (1H, brs)

Example 14

Synthesis of 5-[1-(4-chlorobenzyl)-2-oxo-1,2-dihydroquinolin-4-ylmethyl]thiazolidine-2,4-dione 0.96 g of 5-[1-(4-chlorobenzyl)-2-oxo-1,2-dihydroquinolin-4-ylmethylidene]thiazolidine-2,4-dione, 0.735 g of diethyl 1,4-dihydro-2,6-dimethyl-3,5-pyridinedicarboxylate, and 0.96 g of silica gel were added to 30 ml of toluene, followed by heating and refluxing overnight. The solvent was distilled off, and the residue was purified by silica gel column chromatography (dichloromethane:ethyl acetate of 10:1→3:1), and the purified product was recrystallized from a chloroform-ether mixed solvent, giving 0.87 g (91% yield) of 5-[1-(4-chlorobenzyl)-2-oxo-1,2-dihydroquinolin-4-ylmethyl]thiazolidine-2,4-dione as a white powder.

Melting point: 142.1° C. to 143.7° C.

Example 15

Synthesis of 5-[1-(4-chlorobenzyl)-2-oxo-1,2-dihydroquinolin-3-ylmethyl]thiazolidine-2,4-dione 1.207 g of 5-[1-(4-chlorobenzyl)-2-oxo-1,2-dihydroquinolin-3-ylmethylidene]thiazolidine-2,4-dione, 0.924 g of diethyl 1,4-dihydro-2,6-dimethyl-3,5-pyridinedicarboxylate, and 1.2 g of silica gel were added to 30 ml of toluene, followed by heating and refluxing overnight. 0.77 g of diethyl 1,4-dihydro-2,6-dimethyl-3,5-pyridine dicarboxylate was further added to the reaction liquid, followed by heating and refluxing overnight. The solvent was distilled off, and the residue was purified by silica gel column chromatography (dichloromethane:ethyl acetate of 10:1→3:1). The purified product was recrystallized from a chloroform-ether mixed solvent, giving 0.74 g (61% yield) of 5-[1-(4-chlorobenzyl)-2-oxo-1,2-dihydroquinolin-4-ylmethyl]thiazolidine-2,4-dione as a white powder.

Melting point: 230.7° C. to 231.9° C.

Using appropriate starting materials, the same procedure as in Example 15 was conducted, giving compounds of the following Examples 16 to 19.

Example 16

5-(2-Oxo-1,2-dihydroquinolin-3-ylmethyl)thiazolidine-2,4-dione $^1$H-NMR(DMSO-d$_6$) dppm: 2.45-2.55 (1H, m), 3.35-3.5 (1H, m), 4.9-5.0 (1H, m), 7.15-7.7 (4H, m), 7.84 (1H, s), 11.91 (1H, brs), 12.08 (1H, brs)

Example 17

5-[1-(Biphenyl-4-ylmethyl)-2-oxo-1,2-dihydroquinolin-3-ylmethyl]thiazolidine-2,4-dione Melting point: 220.4° C. to 221.8° C.

Example 18

5-[1-(Biphenyl-4-ylmethyl)-2-oxo-1,2,3,4-tetrahydroquinolin-7-ylmethyl]thiazolidine-2,4-dione Melting point: 213.2° C. to 213.7° C.

Example 19

5-[1-(Biphenyl-4-ylmethyl)-2-oxo-1,2,3,4-tetrahydroquinolin-8-ylmethyl]thiazolidine-2,4-dione $^1$H-NMR(DMSO-d$_6$) dppm: 2.40-2.53 (2H, m), 2.70-2.85 (2H, m), 3.09-3.25 (1H, m), 3.50-3.64 (1H, m), 4.79-4.90 (1H, m), 4.90-5.16 (2H, m), 7.02 (1H, t, J=7.5 Hz), 7.08-7.21 (4H, m), 7.28-7.64 (7H, m), 12.04 (1H, s)

Example 20

Synthesis of 5-[8-methoxy-1-(4-nitrobenzyl)-2-oxo-1,2,3,4-tetrahydroquinolin-5-ylmethyl]thiazolidine-2,4-dione 600 mg of 5-[8-methoxy-1-(4-nitrobenzyl)-2-oxo-1,2,3,4-tetrahydroquinolin-5-ylmethylidene]thiazolidine-2,4-dione, 415 mg of diethyl 1,4-dihydro-2,6-dimethyl-3,5-pyridinedicarboxylate, and 600 mg of silica gel were added to 20 ml of toluene, followed by heating and refluxing for 14 hours. The solvent was distilled off, and the residue was purified by silica gel column chromatography (n-hexane:ethyl acetate=4:1→1:1). The purified product was recrystallized from an ethyl acetate-ether mixed solvent, giving 585 mg (97% yield) of 5-[8-methoxy-1-(4-nitrobenzyl)-2-oxo-1,2,3,4-tetrahydroquinolin-5-ylmethyl]thiazolidine-2,4-dione as a white powder.

Melting point: 246.5° C. to 246.6° C.

Example 21

Synthesis of 5-[1-(4-aminobenzyl)-8-methoxy-2-oxo-1,2,3,4-tetrahydroquinolin-5-ylmethyl]thiazolidine-2,4-dione 10 g of 10% palladium carbon was added to a DMF solution (100 ml) of 10.0 g of 5-[8-methoxy-1-(4-nitrobenzyl)-2-oxo-1,2,3,4-tetrahydroquinolin-5-ylmethyl]thiazolidine-2,4-dione, and the mixture was subjected to a catalytic reduction at 40° C. for 5 hours. The catalyst was removed by filtration, and the filtrate was concentrated. Ethyl acetate and water were added to the residue, and celite filtration was carried out. The filtrate was washed with water and dried over magnesium sulfate, followed by concentration. The residue was purified by silica gel chromatography (n-hexane:ethyl acetate=4:1→1:4), and the purified product was recrystallized from ethyl acetate, giving 7.98 g (86% yield) of 5-[1-(4-aminobenzyl)-8-methoxy-2-oxo-1,2,3,4-tetrahydroquinolin-5-ylmethyl]thiazolidine-2,4-dione as a white powder.

Melting point: 174.1° C. to 174.8° C.

Example 22

Synthesis of 5-{8-methoxy-1-[4-(2-naphthoylamino)benzyl]-2-oxo-1,2,3,4-tetrahydroquinolin-5-ylmethyl}thiazolidine-2,4-dione 0.52 g of triethylamine and 0.42 g of diethylphosphoro cyanidate (DEPC) were added with ice cooling to a DMF solution (14 ml) of 0.7 g of 5-[1-(4-aminobenzyl)-8-methoxy-2-oxo-1,2,3,4-tetrahydroquinolin-5-ylmethyl]thiazolidine-2,4-dione and 0.59 g of 2-naphthoic acid, followed by stirring for 16 hours. Water and ethyl acetate were added to the reaction liquid, and the insoluble matter thus formed was collected by filtration. The collected insoluble matter was dissolved in a dichloromethane-methanol mixed solvent and concentrated. The residue was washed with diethylether and diisopropyl ether. The residue was dried under reduced pressure, giving 0.74 g (77% yield) of 5-{8-methoxy-1-[4-(2-naphthoylamino)benzyl]-2-oxo-1,2,3,4-tetrahydroquinolin-5-ylmethyl}thiazolidin-2,4-dione as a white amorphous solid.

Melting point: 202° C. to 208° C.

$^1$H-NMR(DMSO-d$_6$) dppm: 2.44-2.52 (2H, m), 2.82-2.88 (2H, m), 3.03-3.13 (1H, m), 3.35-3.45 (1H, m), 3.73 (3H, s), 4.79 (1H, dd, J$_1$=4.1 Hz, J$_2$=9.9 Hz), 5.20 (2H, s), 6.83 (1H, d, J=8.6 Hz), 6.91 (1H, d, J=8.6 Hz), 7.05 (2H, d, J=8.4 Hz), 7.58-7.66 (4H, m), 7.95-8.08 (4H, m), 8.52 (1H, s), 10.33 (1H, s), 12.06 (1H, s)

Example 23

Synthesis of 5-[1-(4-pentyloxycarbonylaminobenzyl)-8-methoxy-2-oxo-1,2,3,4-tetrahydroquinolin-5-ylmethyl]thiazolidine-2,4-dione 0.6 g of 5-[1-(4-aminobenzyl)-8-methoxy-2-oxo-1,2,3,4-tetrahydroquinolin-5-ylmethyl]thiazolidine-2,4-dione was suspended in dichloromethane (6 ml), and 4 ml of pyridine was added with ice cooling to form a solution. 0.26 g of amyl chloroformate was added to this solution, followed by stirring for 1 hour. 1 N hydrochloric acid was added to the reaction liquid, and extracted with ethyl acetate. The extract was washed twice with water and once with saturated sodium chloride solution, dried over anhydrous sodium sulfate, and concentrated under reduced pressure. The residue was purified by silica gel column chromatography (n-hexane:ethyl acetate=2:1→1:1), and recrystallized from diisopropyl ether, giving 3.75 g (97% yield) of 5-[1-(4-pentyloxycarbonylaminobenzyl)-8-methoxy-2-oxo-1,2,3,4-tetrahydroquinolin-5-ylmethyl]thiazolidine-2,4-dione as a white powder.

Melting point: 98° C. to 102° C.

Example 24

Synthesis of 5-[8-methoxy-1-(4-methoxycarbonylbenzyl)-2-oxo-1,2,3,4-tetrahydroquinolin-5-ylmethylidene]thiazolidine-2,4-dione 7.0 g of 8-methoxy-1-(4-methoxycarbonylbenzyl)-2-oxo-1,2,3,4-tetrahydroquinoline-5-carboxaldehyde and 3.25 g of 2,4-thiazolidinedione were suspended in 70 ml of toluene. Ten drops of piperidine and ten drops of acetic acid were added, followed by heating and refluxing for 4 hours. The resultant was allowed to cool to precipitate a solid, and the precipitated solid was collected by filtration and dried, giving 8.0 g (90% yield) of 5-[8-methoxy-1-(4-methoxycarbonylbenzyl)-2-oxo-1,2,3,4-tetrahydroquinolin-5-ylmethylidene]thiazolidine-2,4-dione as a light yellow powder.

$^1$H-NMR(DMSO-$d_6$) dppm: 2.52-2.66 (2H, m), 2.91-3.05 (2H, m), 3.65 (3H, s), 3.79 (3H, s), 5.17 (2H, s), 7.02 (1H, d, J=8.7 Hz), 7.16 (1H, d, J=8.7 Hz), 7.25 (2H, d, J=8.3 Hz), 7.74-7.90 (3H, m) 12.55 (1H, brs)

Example 25

Synthesis of 5-[8-methoxy-1-(4-methoxycarbonylbenzyl)-2-oxo-1,2,3,4-tetrahydroquinolin-5-ylmethyl]thiazolidine-2,4-dione 7.0 g of 10% palladium carbon was added to a DMF solution (70 ml) of 7.0 g of 5-[8-methoxy-1-(4-methoxycarbonylbenzyl)-2-oxo-1,2,3,4-tetrahydroquinolin-5-ylmethylidene]thiazolidine-2,4-dione, and a catalytic reduction was carried out at 40° C. for 5 hours. The catalyst was removed by filtration and the filtrate was concentrated. The residue was purified by silica gel column chromatography (n-hexane:ethyl acetate=4:1→1:1). The purified product was recrystallized from an ethyl acetate-diethyl ether mixed solvent, giving 5.23 g (74% yield) of 5-[8-methoxy-1-(4-methoxycarbonylbenzyl)-2-oxo-1,2,3,4-tetrahydroquinolin-5-ylmethyl]thiazolidine-2,4-dione as a white powder.

Melting point: 193.1° C. to 195.5° C.

Example 26

Synthesis of 5-[8-methoxy-1-(4-carboxybenzyl)-2-oxo-1,2,3,4-tetrahydroquinolin-5-ylmethyl]thiazolidine-2,4-dione 35 ml of an aqueous 1 N-lithium hydroxide solution was added to a mixed ethanol (200 ml) and THF (200 ml) solution of 4.0 g of 5-[8-methoxy-1-(4-methoxycarbonylbenzyl)-2-oxo-1,2,3,4-tetrahydroquinolin-5-ylmethyl]thiazolidine-2,4-dione, followed by stirring at room temperature overnight. The solvent was distilled off under reduced pressure, hydrochloric acid was added to the residue, and the insoluble matter thus formed was collected by filtration. The collected insoluble matter was purified by silica gel column chromatography (n-hexane:ethyl acetate=1:1→1:3), and recrystallized from ethyl acetate, giving 3.75 g (97% yield) of 5-[8-methoxy-1-(4-carboxybenzyl)-2-oxo-1,2,3,4-tetrahydroquinolin-5-ylmethyl]thiazolidine-2,4-dione as a white powder.

$^1$H-NMR(DMSO-$d_6$) dppm: 2.42-2.61 (2H, m), 2.70-2.94 (2H, m), 3.01-3.15 (1H, m), 3.34-3.48 (1H, m), 3.56 (3H, s), 4.78 (1H, dd, J=4.4, 9.8 Hz), 5.17 (2H, brs), 6.81 (1H, d, J=8.6 Hz), 6.90 (1H, d, J=8.6 Hz), 7.17 (2H, d, J=8.2 Hz), 7.77 (2H, d, J=8.2 Hz), 12.06 (1H, brs), 12.76 (1H, brs)

Example 27

Synthesis of 5-{1-[4-(4-isopropylphenylamino carbonyl)benzyl]-8-methoxy-2-oxo-1,2,3,4-tetrahydroquinolin-5-ylmethyl}thiazolidine-2,4-dione 0.34 g of triethylamine and 0.28 g of diethyl phosphorocyanidate (DEPC) were added with ice cooling to a DMF solution (10 ml) of 0.5 g of 5-[8-methoxy-1-(4-carboxybenzyl)-2-oxo-1,2,3,4-tetrahydroquinolin-5-ylmethyl]thiazolidine-2,4-dione and 0.23 g of 4-isopropylaniline, followed by stirring for 0.5 hours. Water was added to the reaction liquid and the mixture was extracted with ethyl acetate. The organic layer was washed twice with water and once with saturated sodium chloride solution, and dried over anhydrous sodium sulfate. The solvent was distilled off under a reduced pressure, the residue was purified by silica gel column chromatography (dichloromethane:methanol=100:1→20:1), and recrystallized from a mixed solvent of ethyl acetate and n-hexane, giving 0.57 g (64% yield) of 5-{1-[4-(4-isopropylphenylaminocarbonyl)benzyl]-8-methoxy-2-oxo-1,2,3,4-tetrahydroquinolin-5-ylmethyl}thiazolidine-2,4-dione as a white powder.

Melting point: 243° C. to 244° C.

Using appropriate starting materials, the same procedure as in Example 27 was conducted, giving compounds of the following Examples 28 and 29.

Example 28

5-{8-Methoxy-1-[4-(piperidine-1-carbonyl)benzyl]-2-oxo-1,2,3,4-tetrahydroquinolin-5-ylmethyl}thiazolidine-2,4-dione $^1$H-NMR(DMSO-$d_6$) dppm: 1.25-1.80 (6H, m), 2.39-2.62 (2H, m), 2.72-2.95 (2H, m), 2.95-3.72 (9H, m), 4.77 (1H, dd, J=4.3, 9.6 Hz), 5.16 (2H, s), 6.81 (1H, d, J=8.6 Hz), 6.90 (1H, d, J=8.6 Hz), 7.09 (2H, d, J=8.0 Hz), 7.18 (2H, d, J=8.0 Hz), 12.05 (1H, brs)

Example 29

5-[1-(4-Cyclohexylaminocarbonylbenzyl)-8-methoxy-2-oxo-1,2,3,4-tetrahydroquinolin-5-ylmethyl]thiazolidine-2,4-dione $^1$H-NMR(DMSO-$d_6$) dppm: 0.95-1.85 (10H, m), 2.39-2.60 (2H, m), 2.70-2.94 (2H, m), 3.00-3.19 (1H, m), 3.23-3.50 (1H, m), 3.63 (3H, s), 3.80-3.99 (1H, m), 4.64-4.88 (1H, m), 5.19 (2H, s), 6.80 (1H, d, J=8.6 Hz), 6.89 (1H, d, J=8.6 Hz), 7.11 (2H, d, J=8.0 Hz), 7.65 (2H, d, J=8.0 Hz), 8.03 (1H, d, J=7.8 Hz), 12.06 (1H, brs)

Example 30

Synthesis of 5-(1-benzyl-8-hydroxy-2-oxo-1,2,3,4-tetrahydroquinolin-5-ylmethylidene)thiazolidine-2,4-dione 2.0 g of 1-benzyl-8-hydroxy-2-oxo-1,2,3,4-tetrahydroquinoline-5-carboxaldehyde and 0.874 g of 2,4-thiazolidinedione were suspended in 20 ml of toluene. Ten drops of piperidine and ten drops of acetic acid were added, followed by heating and refluxing for 8 hours. The resultant was allowed to cool to precipitate a solid, and the precipitated solid was collected by filtration and dried, giving 2.7 g (92% yield) of 5-(1-benzyl-8-hydroxy-2-oxo-1,2,3,4-tetrahydroquinolin-5-ylmethylidene)thiazolidine-2,4-dione as a yellow powder.

$^1$H-NMR(DMSO-d$_6$) dppm: 2.41-2.60 (2H, m), 2.75-2.98 (2H, m), 5.31 (2H, s), 6.84 (1H, d, J=8.6 Hz), 7.00-7.30 (6H, m), 7.81 (1H, s), 10.72 (1H, s), 12.48 (1H, brs)

Example 31

Synthesis of 5-(1-benzyl-8-hydroxy-2-oxo-1,2,3,4-tetrahydroquinolin-5-ylmethyl)thiazolidine-2,4-dione 2.2 g of 10% palladium carbon was added to a DMF solution (20 ml) of 2.2 g of 5-(1-benzyl-8-hydroxy-2-oxo-1,2,3,4-tetrahydroquinolin-5-ylmethylidene)thiazolidine-2,4-dione, and the mixture was subjected to catalytic reduction at room temperature for 2 hours. The catalyst was removed by filtration, and the filtrate was concentrated. The residue was dissolved in ethyl acetate, washed with water and saturated sodium chloride solution, and concentrated. The residue was purified by silica gel column chromatography (dichloromethane:methanol=50:1). The purified product was recrystallized from a dichloromethane-ether mixed solvent, giving 1.9 g (88% yield) of 5-(1-benzyl-8-hydroxy-2-oxo-1,2,3,4-tetrahydroquinolin-5-ylmethyl)thiazolidine-2,4-dione as a white powder.

Melting point: 213.2° C. to 213.7° C.

Example 32

Synthesis of 5-(1-benzyl-8-butoxy-2-oxo-1,2,3,4-tetrahydroquinolin-5-ylmethyl)thiazolidine-2,4-dione 55.5 mg of potassium tert-butoxide was added to a DMSO solution (1 ml) of 90 mg of 5-(1-benzyl-8-hydroxy-2-oxo-1,2,3,4-tetrahydroquinolin-5-ylmethyl)thiazolidine-2,4-dione, followed by stirring at room temperature for 1 hour. 29.8 μl of 4-iodobutane was added thereto, followed by stirring at room temperature for 2 hours. Water was added to the reaction liquid, potassium hydrogensulfate was added to the mixture, and the mixture was extracted with ethyl acetate. After washing with water, the extract was dried over anhydrous magnesium sulfate, and concentrated. The residue was purified by preparative silica gel thin layer chromatography (dichloromethane:methanol=20:1), giving 42 mg (41% yield) of 5-(1-benzyl-8-butoxy-2-oxo-1,2,3,4-tetrahydroquinolin-5-ylmethyl)thiazolidine-2,4-dione as a colorless amorphous solid.

$^1$H-NMR(CDCl$_3$) dppm: 0.93 (3H, t, J=7.3 Hz), 1.35-1.50 (2H, m), 1.57-1.73 (2H, m), 2.52-2.67 (2H, m), 2.67-2.95 (2H, m), 3.05 (1H, dd, J=10.1 Hz, J=14.0 Hz), 3.51 (1H, dd, J=4.0 Hz, J=14.0 Hz), 3.89 (2H, t, J=6.6 Hz), 4.39 (1H, dd, J=4.0 Hz, J=10.1 Hz), 5.32 (2H, s), 6.71 (1H, d, J=8.6 Hz), 6.87 (1H, d, J=8.6 Hz), 7.02-7.25 (5H, m), 9.15 (1H, brs)

Example 33

Synthesis of 5-(1-benzyl-8-benzyloxy-2-oxo-1,2,3,4-tetrahydroquinolin-5-ylmethyl)thiazolidine-2,4-dione 55.5 mg of potassium tert-butoxide was added to a DMSO solution (1 ml) of 90 mg of 5-(1-benzyl-8-hydroxy-2-oxo-1,2,3,4-tetrahydroquinolin-5-ylmethyl)thiazolidine-2,4-dione, followed by stirring at room temperature for 1 hour. 30 μl of benzyl bromide was added thereto, followed by stirring at room temperature for 1 hour. Water was added to the reaction liquid, potassium hydrogensulfate was added to the mixture, and the mixture was extracted with ethyl acetate. The extract was washed with water, dried over anhydrous magnesium sulfate, and concentrated. The residue was purified by preparative silica gel thin layer chromatography (dichloromethane:methanol=20:1), giving 84.5 mg (76% yield) of 5-(1-benzyl-8-benzyloxy-2-oxo-1,2,3,4-tetrahydroquinolin-5-ylmethyl)thiazolidine-2,4-dione as a colorless amorphous solid.

$^1$H-NMR(CDCl$_3$) dppm: 2.49-2.65 (2H, m), 2.65-2.94 (2H, m), 3.07 (1H, dd, J=10.0 Hz, J=14.5 Hz), 3.51 (1H, dd, J=4.1 Hz, J=14.5 Hz), 4.39 (1H, dd, J=4.1 Hz, J=10.0 Hz), 4.97 (2H, s), 5.32 (2H, s), 6.76 (1H, d, J=8.6 Hz), 6.86 (1H, d, J=8.6 Hz), 6.93-7.02 (2H, m), 7.03-7.19 (3H, m), 7.29-7.45 (5H, m), 9.07 (1H, brs)

Example 34

Synthesis of 5-(1-carboxymethyl-8-methoxy-2-oxo-1,2,3,4-tetrahydroquinolin-5-ylmethyl)thiazolidine-2,4-dione 4.16 g of 1-tert-butoxycarbonylmethyl-8-methoxy-2-oxo-1,2,3,4-tetrahydroquinolin-5-carboxaldehyde and 1.66 g of 2,4-thiazolidinedione (1.00 eq.) were suspended in 40 ml of toluene, and two drops of acetic acid and two drops of piperidine were added, followed by heating and refluxing for 13 hours using a Dean Stark trap. After cooling, crystals were separated by filtration and washed with toluene. The crystals obtained were suspended in 3.15 g of silica gel, 2.09 g of dihydropyridine, and 60 ml of toluene, followed by heating and refluxing overnight. 3.15 g of silica gel was added, the solvent was distilled off under reduced pressure, and the residue was purified by silica gel column chromatography (n-hexane:ethyl acetate=2:1), and recrystallized from ethyl acetate-hexane, giving 2.13 g (38% yield) of 5-(1-carboxymethyl-8-methoxy-2-oxo-1,2,3,4-tetrahydroquinolin-5-ylmethyl)thiazolidine-2,4-dione as a white powder.

Melting point: 251° C. to 255° C.

Example 35

Synthesis of 5-{1-[N-(3-trifluoromethyl phenyl)amino]carbonylmethyl-8-methoxy-2-oxo-1,2,3,4-tetrahydroquinolin-5-ylmethyl}thiazolidine-2,4-dione potassium salt 500 mg of 5-(1-carboxymethyl-8-methoxy-2-oxo-1,2,3,4-tetrahydroquinolin-5-ylmethyl)thiazolidine-2,4-dione was dissolved in 5 ml of DMF. 0.35 ml of 3-trifluoromethyl aniline, 0.32 g of 1-(3-dimethylaminopropyl)-3-ethylcarbodiimide hydrochloride(WSC), and 0.25 g of 1-hydroxybenzotriazole (HOBT) were added to the solution, followed by stirring at room temperature overnight. Water was added to the reaction liquid, and the solid thus obtained was separated by filtration. The solid was dissolved in methylene chloride, washed with sodium chloride solution, and dried over sodium sulfate. After filtration, the filtrate was concentrated under reduced pressure. The residue was purified by silica gel column chromatography (methylene chloride:methanol=50:1), giving 412 mg of 5-{1-[N-(3-trifluoromethylphenyl)amino]carbonylmethyl-8-methoxy-2-oxo-1,2,3,4-tetrahydroquinolin-5-ylmethyl}thiazolidine-2,4-dione.

The 5-{1-[N-(3-trifluoromethyl phenyl)amino]carbonylmethyl-8-methoxy-2-oxo-1,2,3,4-tetrahydroquinolin-5-ylmethyl}thiazolidine-2,4-dione thus obtained was dissolved in 4 ml of THF. 84.5 mg of potassium t-butoxide was added to dissolve the solid. Diethyl ether was added, and trituration was carried out. The crystals produced were separated by filtration and dried, giving 340 mg (49% yield) of 5-{1-[N-(3-trifluoromethyl phenyl)amino]carbonylmethyl-8-methoxy-2-oxo-1,2,3,4-tetrahydroquinolin-5-ylmethyl}thiazolidine-2,4-dione•potassium salt as a brown powder.

Melting point: 135° C. to 139.5° C.

Example 36

Synthesis of 5-(8-methoxy-1-piperidin-4-ylmethyl-2-oxo-1,2,3,4-tetrahydroquinolin-5-ylmethyl)thiazolidine-2,4-dione 1.7 g of 5-[8-methoxy-1-(1-tert-butoxycarbonyl piperidin-4-ylmethyl)-2-oxo-1,2,3,4-tetrahydroquinolin-5-ylmethyl]thiazolidine-2,4-dione was added to 50 ml of a 4 N-hydrogen chloride ethyl acetate solution, followed by stirring at room temperature for 6 hours. The resultant was concentrated under reduced pressure, and an aqueous sodium hydrogencarbonate solution was added to the residue. The insoluble matter thus formed was collected by filtration and dried, giving 1.5 g (yield: quantitative) of 5-(8-methoxy-1-piperidin-4-ylmethyl-2-oxo-1,2,3,4-tetrahydroquinolin-5-ylmethyl)thiazolidine-2,4-dione as a white powder.

$^1$H-NMR(DMSO-d$_6$) dppm: 1.05-1.3 (2H, m), 1.4-1.7 (3H, m), 2.3-2.9 (6H, m), 3.0-3.25 (3H, m), 3.82 (3H, s), 4.00 (2H, d, J=6.8 Hz), 4.63 (1H, dd, J=8.7 Hz, J=4.2 Hz), 6.9-7.05 (2H, m)

Example 37

Synthesis of 5-(1-{2-[1-(4-methylbenzoyl)piperidin-4-yl]ethyl}-2-oxo-1,2,3,4-tetrahydroquinolin-5-ylmethyl)thiazolidine-2,4-dione 2 ml of DMF was added to 100 mg of 5-{1-[2-(1-piperidin-4-yl)ethyl]-2-oxo-1,2,3,4-tetrahydroquinolin-5-ylmethyl}thiazolidine-2,4-dione, 42.2 mg of p-toluic acid, 59.4 mg of 1-(3-dimethylaminopropyl)-3-ethylcarbodiimide hydrochloride (WSC), and 43.5 mg of 1-hydroxybenzotriazole (HOBt), followed by stirring at room temperature for 2.5 hours. Water was added, the mixture was stirred for a while, and the solid thus produced was collected by filtration. The collected solid was dissolved in methylene chloride, and purified by silica gel chromatography (methylene chloride:methanol=20:1), giving 68.4 mg (97% yield) of the target compound as a white solid.

Melting point: 60° C. to 65° C.

Example 38

Synthesis of 5-[1-(5-benzyl-6-oxo-5,6-dihydrophenanthridin-2-yl)methylidene]thiazolidine-2,4-dione 592 mg of 5-benzyl-6-oxo-5,6-dihydrophenanthridine-2-carboxaldehyde and 221 mg of 2,4-thiazolidinedione were suspended in 10 ml of toluene. Two drops of acetic acid and two drops of piperidine were added to the suspension, followed by heating and refluxing overnight. The reaction liquid was cooled, and the solid thus obtained was collected by filtration. The collected solid was washed with toluene-diethyl ether, and dried, giving 620 mg (80% yield) of 5-[1-(5-benzyl-6-oxo-5,6-dihydrophenanthridin-2-yl)methylidene]thiazolidine-2,4-dione as a yellow solid.

$^1$H-NMR(DMSO-d$_6$) dppm: 5.67 (2H, s), 7.0-8.0 (10H, m), 8.45 (1H, dd, J=8.0 Hz, 1.3 Hz), 8.60 (1H, d, J=8.0 Hz), 8.80 (1H, d, J=1.8 Hz), 12.6 (1H, brs)

Example 39

Synthesis of 5-[1-(5-benzyl-6-oxo-5,6-dihydrophenanthridin-2-yl)methyl]thiazolidine-2,4-dione 620 mg of 5-[1-(5-benzyl-6-oxo-5,6-dihydrophenanthridin-2-yl)methylidene]thiazolidine-2,4-dione was dissolved in 2.31 ml of THF. 2.31 ml of pyridine and 2.31 ml of a THF solution of 2 M lithium borohydride were added to the solution, followed by heating and refluxing for 4 hours. The reaction liquid was cooled, acidified with diluted hydrochloric acid, and extracted with dichloromethane. The organic layer was washed with water, then with saturated sodium chloride solution, and dried over sodium sulfate. After filtration, the solvent was distilled off under reduced pressure, the residue was crystallized using dichloromethane, and the solid thus obtained was separated by filtration. The solid separated by filtration was air-dried, giving 232 mg (36% yield) of 5-[1-(5-benzyl-6-oxo-5,6-dihydrophenanthridin-2-yl)methyl]thiazolidine-2,4-dione as white crystals.

$^1$H-NMR(DMSO-d$_6$) dppm: 3.1-3.7 (2H, m), 5.04 (1H, dd, J=13.8 Hz, J=4.8 Hz), 5.76 (2H, s), 7.1-7.45 (5H, m), 7.6-8.0 (2H, m), 8.3-8.6 (3H, m), 12.0 (1H, brs)

Example 40

Synthesis of 5-{8-methoxy-1-[1-(2-methylbenzyl)piperidin-4-yl]methyl-2-oxo-1,2,3,4-tetrahydroquinolin-5-ylmethyl}thiazolidine-2,4-dione To 5-(8-methoxy-1-piperidin-4-ylmethyl-2-oxo-1,2,3,4-tetrahydroquinolin-5-ylmethyl)thiazolidine-2,4-dione (20 μmol, 1.0 eq.) was added a DMF (200 μl) solution of 2-methylbenzaldehyde (24 μmol, 1.2 eq) and acetic acid (10 μl). Si-sodium cyanoborohydride was added further thereto. The solution was shaken for several minutes, diisopropylethylamine (30 μl) was added, and a reaction was carried out at room temperature overnight. The resin was removed by filtration and washed with dichloromethane. The solvent was distilled off from the filtrate in a nitrogen gas stream, and the residue was purified by HPLC (UV-trigger, column: CAPCELL PAK C18, UG 120 S-5, 20 mm×50 mm, 0.05% trifluoroacetic acid-H$_2$O, 0.05% trifluoroacetic acid-CH$_3$CN). The structure was confirmed by LC-MS, and freeze-drying was conducted, giving 5-{8-methoxy-1-[1-(2-methylbenzyl)piperidin-4-yl]methyl-2-oxo-1,2,3,4-tetrahydroquinolin-5-ylmethyl}thiazolidine-2,4-dione in 50.5% yield.

MS: 508 (M$^{+1}$)

Example 41

Synthesis of 5-{8-methoxy-1-[1-(tetrahydropyran-4-yl)piperidin-4-yl]methyl-2-oxo-1,2,3,4-tetrahydroquinolin-5-ylmethyl}thiazolidine-2,4-dione To 5-(8-methoxy-1-piperidin-4-ylmethyl-2-oxo-1,2,3,4-tetrahydroquinolin-5-ylmethyl)thiazolidine-2,4-dione (20 μmol, 1.0 eq.) was added a DMF (200 μl) solution of tetrahydropyran-4-one (24 μmol, 1.2 eq.) and acetic acid (10 μl). MP-sodium triacetoxy borohydride was added further. After this solution was shaken for several minutes, DIEA (30 μl) was added and a reaction was carried out at 60° C. overnight. The resin was removed by filtration and washed with methylene chloride. The solvent was distilled off with nitrogen gas, and the residue was purified by HPLC (UV-trigger, column:CAPCELL PAK C18, UG 120 S-5, 20 mm×50 mm, 0.05% trifluoroacetic acid-H$_2$O, 0.05% trifluoroacetic acid-CH$_3$CN). The structure was confirmed by LC-MS, and freeze-drying was conducted, giving 5-{8-methoxy-1-[1-(tetrahydropyran-4-yl)piperidin-4-yl]methyl-2-oxo-1,2,3,4-tetrahydroquinolin-5-ylmethyl}thiazolidine-2,4-dione in 30% yield.

MS: 488 (M$^{+1}$)

Example 42

Synthesis of 5-[1-(4-methanesulfonylaminobenzyl)-8-methoxy-2-oxo-1,2,3,4-tetrahydroquinolin-5-ylmethyl]thiazolidine-2,4-dione To a dichloromethane (20 ml) solution of 1.00 g (0.00243 mM) of 5-[1-(4-aminobenzyl)-8-methoxy-2-oxo-1,2,3,4-tetrahydroquinolin-5-ylmethyl]thiazolidine-2,4-dione were successively added pyridine (2.0 ml) and 0.21 ml (0.0027 mM) of methanesulfonyl chloride under ice cooling with stirring. The mixture was stirred at the same temperature for 30 minutes, and water was added to stop the reaction. The resultant was washed (twice with water and once with saturated sodium chloride solution), dried (magnesium sulfate), and concentrated under reduced pressure. The residue was purified by silica gel column chromatography (dichloromethane:ethyl acetate=1:10→1:1), giving 1.1 g (92% yield) of the target compound as a white amorphous solid.

$^1$H-NMR(DMSO-d$_6$) dppm: 2.39-2.54 (2H, m), 2.72-2.87 (2H, m), 2.88 (3H, s), 3.05 (1H, dd, J=10.0 Hz, J=14.4 Hz), 3.39 (1H, dd, J=4.0 Hz, J=14.4 Hz), 3.67 (3H, s), 4.76 (1H, dd, J=4.0 Hz, J=10.0 Hz), 5.13 (2H, s), 6.80 (1H, d, J=8.6 Hz), 6.89 (1H, d, J=8.6 Hz), 6.93-7.06 (4H, m), 9.57 (1H, s), 12.05 (1H, s)

Example 43

Synthesis of 3-methoxycarbonylmethyl-5-(8-methoxy-1-methyl-2-oxo-1,2-dihydroquinolin-5-ylmethyl)thiazolidine-2,4-dione 350 mg of 5-(8-methoxy-1-methyl-2-oxo-1,2-dihydroquinolin-5-ylmethyl)thiazolidine-2,4-dione was dissolved in 5 ml of DMF. 0.156 ml of methyl bromoacetate and 0.25 g of potassium carbonate were added to the solution, followed by stirring at room temperature overnight. Water was added, and the mixture was extracted with methylene chloride. The organic layer was washed with saturated sodium chloride solution, and dried over sodium sulfate. After filtration, the solvent was distilled off under reduced pressure. The residue was purified by silica gel chromatography and recrystallized from methanol-acetone, giving 245 mg (57% yield) of 3-methoxycarbonylmethyl-5-(8-methoxy-1-methyl-2-oxo-1,2-dihydroquinolin-5-ylmethyl)thiazolidine-2,4-dione as white crystals.

Melting point: 182° C. to 184° C.

Example 44

Synthesis of 1-(biphenyl-4-ylmethyl)-5-(4-oxo-2-thioxothiazolidine-5-ylidenemethyl)-3,4-dihydro-1H-quinolin-2-one 1.50 g of 1-(biphenyl-4-ylmethyl)-2-oxo-1,2,3,4-tetrahydroquinoline-5-carboxaldehyde and 0.761 g of 2-thioxo-1,3-thiazolidin-4-one were suspended in 20 ml of toluene. Two drops of piperidine and two drops of acetic acid were added to the suspension, followed by heating and refluxing for 4 hours. After allowing to cool, the solid thus precipitated was collected by filtration, and dried, giving 2.34 g (91% yield) of 1-(biphenyl-4-ylmethyl)-5-(4-oxo-2-thioxothiazolidine-5-ylidenemethyl)-3,4-dihydro-1H-quinolin-2-one as a yellow powder.

$^1$H-NMR(DMSO-d$_6$) dppm: 2.76-2.81 (2H, m), 3.04-3.09 (2H, m), 5.23 (2H, m), 7.10-7.47 (8H, m), 7.54 (1H, s), 7.59-7.65 (4H, m), 13.78 (1H, brs)

Using an appropriate starting material, the same procedure as in Example 44 was performed, giving a compound of the following Example 45.

Example 45

1-(4-Bromobenzyl)-5-(4-oxo-2-thioxothiazolidine-5-ylidenemethyl)-3,4-dihydro-1H-quinolin-2-one $^1$H-NMR(DMSO-d$_6$) dppm: 2.67-2.80 (2H, m), 2.93-3.09 (2H, m), 5.14 (2H, s), 7.04 (1H, d, J=8.6 Hz), 7.10-7.25 (2H, m), 7.32-7.57 (5H, m), 13.77 (1H, brs)

Example 46

Synthesis of 1-(biphenyl-4-ylmethyl)-5-(4-oxo-2-thioxothiazolidin-5-ylmethyl)-3,4-dihydro-1H-quinolin-2-one To 20 ml of toluene were added 1.4 g of 1-(biphenyl-4-ylmethyl)-5-(4-oxo-2-thioxothiazolidine-5-ylidenemethyl)-3,4-dihydro-1H-quinolin-2-one, 1.01 g of diethyl 1,4-dihydro-2,6-dimethyl-3,5-pyridine dicarboxylate, and 1.4 g of silica gel, followed by heating and refluxing overnight. The solvent was distilled off, and the residue was purified by silica gel column chromatography (n-hexane:ethyl acetate=4:1→2:1). The purified product was recrystallized from toluene, giving 0.84 g (60% yield) of 1-(biphenyl-4-ylmethyl)-5-(4-oxo-2-thioxothiazolidin-5-ylmethyl)-3,4-dihydro-1H-quinolin-2-one as a white powder.

Melting point: 186.3° C. to 187.1° C.

Example 47

Synthesis of 1-(4-bromobenzyl)-5-(4-oxo-2-thioxothiazolidin-5-ylmethyl)-3,4-dihydro-1H-quinolin-2-one 50 mg of 1-(4-bromobenzyl)-5-(4-oxo-2-thioxothiazolidine-5-ylidenemethyl)-3,4-dihydro-1H-quinolin-2-one was suspended in a mixed solvent of 0.15 ml of methanol, 0.1 ml of water, 0.08 ml of an aqueous 1 N-sodium hydroxide solution, and 0.1 ml of THF. 0.03 ml of a DMF (5 ml) solution of 42 mg of cobalt chloride 6-hydrate and 250 mg of dimethylglyoxime was further added to the suspension, and the mixture was heated to 30° C. to 40° C. An aqueous solution (0.1 ml) of 15 mg of sodium borohydride was added, followed by stirring for 30 minutes. A saturated aqueous potassium hydrogensulfate solution was added, the mixture was extracted with ethyl acetate, and the extract was washed with water. The extract was dried over anhydrous magnesium sulfate and concentrated. The residue was purified by preparative silica gel thin layer chromatography (ethyl acetate:n-hexane=1:1) to give 44.7 mg (89% yield) of 1-(4-bromobenzyl)-5-(4-oxo-2-thioxothiazolidin-5-ylmethyl)-3,4-dihydro-1H-quinolin-2-one as a colorless amorphous solid, and further recrystallized from ethyl acetate-diethyl ether, giving a white powder.

Melting point: 191.3° C. to 192.1° C.

Using an appropriate starting material, the same procedure as in Example 47 was conducted, giving a compound of the following Example 48.

Example 48

1-(6-Chloropyridin-3-ylmethyl)-5-(4-oxo-2-thioxothiazolidin-5-ylmethyl)-3,4-dihydro-1H-quinolin-2-one hydrochloride Melting point: 70° C. to 80° C.

Using appropriate starting materials, the same procedure as in Example 6 was conducted, giving compounds of the following Examples 49 to 110.

Using appropriate starting materials, the same procedure as in Example 15 was conducted, giving compounds of the following Examples 111 to 119, 121 to 131, 134 to 138, 140 to 144, 148, 150 to 153, 156 to 159, 161 to 165, 173, 177 to 182, 184 to 188, 859 to 860, 965 to 969, 975 to 976, and 986 to 1001.

Using appropriate starting materials, the same procedure as in Example 21 was conducted, giving compounds of the following Examples 120 and 133.

Using appropriate starting materials, the same procedure as in Example 22 was conducted, giving compounds of the following Examples 189 to 225, and 258 to 291.

Using appropriate starting materials, the same procedure as in Example 23 was conducted, giving compounds of the following Examples 228 to 257, 292 to 309, 656 to 658, 664, 666 to 667, 681 to 686, and 690 to 694.

Using appropriate starting materials, the same procedure as in Example 27 was conducted, giving compounds of the following Examples 176, 310 to 545, and 1034.

Using appropriate starting materials, the same procedure as in Example 32 was conducted, giving compounds of the following Examples 546 to 606.

Using appropriate starting materials, the same procedure as in Example 35 was conducted, giving compounds of the following Examples 607 to 613, 614 to 655, 659 to 663, 665, 668 to 680, and 687 to 689.

Using appropriate starting materials, the same procedure as in Example 38 was conducted, giving compounds of the following Examples 695 to 699, and 921 to 959.

Using appropriate starting materials, the same procedure as in Example 39 was conducted, giving compounds of the following Examples 139, 145 to 147, 154 to 155, 166 to 172, 174 to 175, 700 to 704, 913 to 920, 960 to 964, 970 to 972, and 977 to 985.

Using appropriate starting materials, the same procedure as in Example 40 was conducted, giving compounds of the following Examples 705 to 759.

Using appropriate starting materials, the same procedure as in Example 42 was conducted, giving compounds of the following Examples 760 to 855.

Using appropriate starting materials, the same procedure as in Example 43 was conducted, giving compounds of the following Examples 857, and 861 to 912.

Using appropriate starting materials, the same procedure as in Example 6 was conducted, giving compounds of Examples 1002 to 1031.

Using appropriate starting materials, the same procedure as in Example 15 was conducted, giving compounds of Examples 1032 to 1033, 1038, 1041 to 1045, 1047, 1050 to 1055, 1057 to 1058, 1069 to 1070, 1076 to 1079, and 1088.

Using appropriate starting materials, the same procedure as in Example 23 was conducted, giving a compound of Example 1059.

Using appropriate starting materials, the same procedure as in Example 35 was conducted, giving compounds of Examples 1115 to 1314.

Using appropriate starting materials, the same procedure as in Example 36 was conducted, giving compounds of Examples 160 and 1056.

Using appropriate starting materials, the same procedure as in Example 47 was conducted, giving compounds of Examples 974, 1035 to 1037, 1039 to 1040, 1048, 1060 to 1068, 1071 to 1075, 1080 to 1087, and 1089 to 1090.

The same procedure as in Example 1 was conducted, giving compound of Example 856.

Using appropriate starting materials, the same procedure as in Example 1317 was conducted, giving compounds of Examples 1049, and 1091 to 1114.

Using appropriate starting materials, the same procedure as in Example 25 was conducted, giving compounds of the following Examples 226, 227, and 1046.

Using appropriate starting materials, the same procedure as in Example 26 was conducted, giving compounds of the following Examples 149, 858, and 973.

Using an appropriate starting material, the same procedure as in Example 31 was conducted, giving a compound of the following Example 183.

Using an appropriate starting material, the same procedure as in Example 34 was conducted, giving a compound of the following Example 132.

TABLE 35

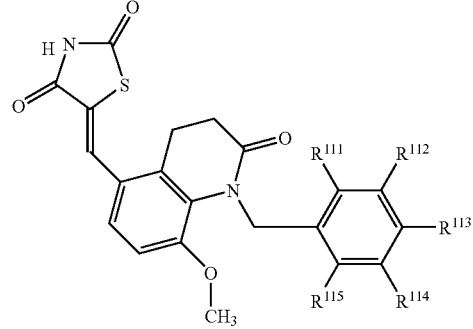

| Ex. | $R^{111}$ | $R^{112}$ | $R^{113}$ | $R^{114}$ | $R^{115}$ | $^1$H NMR (DMSO-$d_6$) dppm |
|---|---|---|---|---|---|---|
| 49 | —H | —H | —H | —H | —H | 2.55 (1H, t, J = 6.9 Hz), 2.93 (2H, t, J = 6.9 Hz), 3.76 (3H, s), 5.21 (2H, s), 7.0-7.25 (7H, m), 7.83 (1H, s), 12.56 (1H, br s) |
| 50 | —H | —H | —$C_6H_5$ | —H | —H | 2.57 (2H, t, J = 6.9 Hz), 2.97 (2H, t, J = 6.9 Hz), 3.80 (3H, s), 5.25 (2H, s), 7.0-7.65 (11H, m), 7.85 (1H, s), 13.1 (1H, br s) |
| 51 | —H | —H | —C(CH$_3$)$_3$ | —H | —H | 1.20 (9H, s), 2.54 (2H, t, J = 6.9 Hz), 2.93 (2H, t, J = 6.9 Hz), 3.81 (3H, s), 5.20 (2H, s), 7.00 (2H, d, J = 8.2 Hz), 7.08 (1H, d, J = 8.8 Hz), 7.17 (1H, d, J = 8.8 Hz), 7.22 (2H, d, J = 8.2 Hz), 7.84 (1H, s), 12.5 (1H, br s) |
| 52 | —H | —H | —H | —$C_6H_5$ | —H | 2.58 (2H, t, J = 6.9 Hz), 2.96 (2H, t, J = 6.9 Hz), 3.77 (3H, s), 5.77 (2H, s), 6.8-7.65 (11H, m), 7.86 (1H, s), 12.7 (1H, br s) |
| 53 | —H | —H | —H | —H | —$C_6H_5$ | 2.50 (2H, t, J = 6.9 Hz), 2.78 (2H, t, J = 6.9 Hz), 3.36 (3H, s), 5.20 (2H, s), 6.90 (1H, d, J = 8.6 Hz), 7.1-7.6 (10H, m), 7.81 (1H, s), 12.6 (1H, br s) |
| 54 | —H | —H | —NO$_2$ | —H | —H | 2.55-2.69 (2H, m), 2.95-3.10 (2H, m), 3.60 (3H, s), 5.15 (2H, s), 7.05 (1H, d, J = 8.8 Hz), 7.19 (1H, d, J = 8.8 Hz), 7.40 (2H, d, J = 8.8 Hz), 7.85 (1H, s), 8.11 (2H, d, J = 8.8 Hz), 12.56 (1H, brs). |

TABLE 35-continued

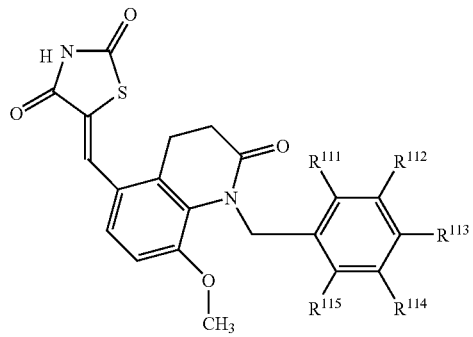

| Ex. | $R^{111}$ | $R^{112}$ | $R^{113}$ | $R^{114}$ | $R^{115}$ | $^1$H NMR (DMSO-$d_6$) δppm |
|---|---|---|---|---|---|---|
| 55 | —H | —H | —CO$_2$CH$_3$ | —H | —H | 2.52-2.66 (2H, m), 2.91-3.05 (2H, m), 3.65 (3H, s), 3.79 (3H, s), 5.17 (2H, s), 7.02 (1H, d, J = 8.7 Hz), 7.16 (1H, d, J = 8.7 Hz), 7.25 (2H, d, J = 8.3 Hz), 7.74-7.90 (3H, m), 12.55 (1H, brs). |

TABLE 36

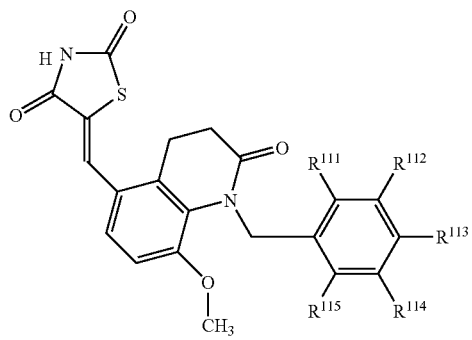

| Ex. | $R^{111}$ | $R^{112}$ | $R^{113}$ | $R^{114}$ | $R^{115}$ | $^1$H NMR (DMSO-$d_6$) δppm |
|---|---|---|---|---|---|---|
| 56 | —H | —H | —OCH$_3$ | —H | —H | 2.40-2.62 (2H, m), 2.80-3.00 (2H, m), 3.64 (3H, s), 3.81 (3H, s), 5.16 (2H, s), 6.69-6.82 (2H, m), 6.95-7.10 (3H, m), 7.10-7.13 (1H, m), 7.81 (1H, s), 12.54 (1H, brs). |
| 57 | —H | —H | —Cl | —H | —H | 7.45-7.65 (2H, m), 2.85-3.04 (2H, m), 3.72 (3H, s), 5.12 (2H, s), 7.03 (1H, d, J = 8.7 Hz), 7.06-7.31 (5H, m), 7.82 (1H, s), 12.53 (1H, brs). |
| 58 | —H | —H | —Br | —H | —H | 2.42-2.65 (2H, m), 2.85-3.04 (2H, m), 3.72 (3H, s), 5.11 (2H, s), 6.96-7.12 (3H, m), 7.16 (1H, d, J = 8.7 Hz), 7.39 (2H, d, J = 8.0 Hz), 7.83 (1H, s), 12.54 (1H, brs). |
| 59 | —H | —H | —OCH$_2$C$_6$H$_5$ | —H | —H | 2.42-2.61 (2H, m), 2.81-2.99 (2H, m), 3.80 (3H, s), 4.97 (2H, s), 5.16 (2H, s), 6.82 (2H, d, J = 8.7 Hz), 6.95-7.10 (3H, m), 7.15 (1H, d, J = 8.8 Hz), 7.22-7.43 (5H, m), 7.81 (1H, s), 12.50 (1H, brs). |
| 60 | —H | —H | —F | —H | —H | 2.85-3.05 (2H, m), 3.28-3.42 (2H, m), 4.19 (3H, s), 5.60 (2H, s), 7.36-7.52 (3H, m), 7.52-7.70 (3H, m), 8.21 (1H, s), 12.40-13.45 (1H, br). |
| 61 | —H | —H | —CN | —H | —H | 2.50-2.66 (2H, m), 2.90-3.06 (2H, m), 3.61 (3H, s), 5.12 (2H, s), 7.04 (1H, d, J = 8.8 Hz), 7.18 (1H, d, J = 8.8 Hz), 7.32 (2H, d, J = 8.2 Hz), 7.70 (2H, d, J = 8.2 Hz), 7.85 (1H, s), 12.56 (1H, s). |

TABLE 37

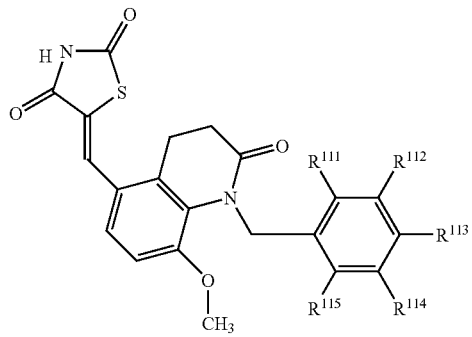

| Ex. | $R^{111}$ | $R^{112}$ | $R^{113}$ | $R^{114}$ | $R^{115}$ | $^1$H NMR (DMSO-$d_6$) dppm |
|---|---|---|---|---|---|---|
| 62 | —H | —H | —CH$_3$ | —H | —H | 2.17 (3H, s), 2.42-2.62 (2H, m), 2.76-3.00 (2H, m), 3.79 (3H, s), 5.18 (2H, s), 6.88-7.08 (5H, m), 7.14 (1H, d, J = 8.7 Hz), 7.8 (1H, s), 12.54 (1H, s). |

TABLE 37-continued

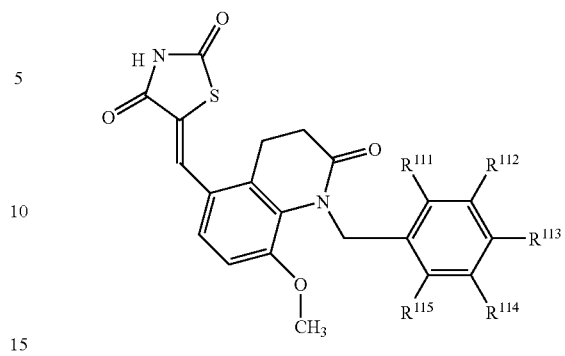

| Ex. | $R^{111}$ | $R^{112}$ | $R^{113}$ | $R^{114}$ | $R^{115}$ | $^1$H NMR (DMSO-$d_6$) dppm |
|---|---|---|---|---|---|---|
| 63 | —H | —H | —OC$_6$H$_5$ | —H | —H | 2.50-2.64 (2H, m), 2.87-3.02 (2H, m), 3.78 (3H, s), 5.18 (2H, s), 6.84 (2H, d, J = 8.6 Hz), 6.90-6.93 (2H, m), 7.03-7.11 (4H, m), 7.18 (1H, d, J = 8.7 Hz), 7.32-7.37 (2H, m), 7.84 (1H, s), 12.59 (1H, brs). |

TABLE 38

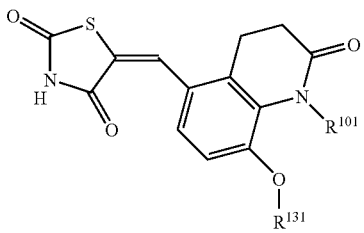

| Ex. | $R^{101}$ | $R^{131}$ | $^1$H NMR (DMSO-$d_6$) dppm |
|---|---|---|---|
| 64 | —CH3 | —CH$_3$ | 2.44 (2H, t, J = 6.9 Hz), 2.90 (2H, t, J = 6.9 Hz), 3.21 (3H, s), 3.89 (3H, s), 7.17 (1H, d, J = 8.6 Hz), 7.23 (1H, d, J = 8.8 Hz), 7.86 (1H, s), 12.59 (1H, br s) |
| 65 | —H | —CH$_3$ | 2.47 (2H, t, J = 6.9 Hz), 2.99 (2H, t, J = 6.9 Hz), 3.89 (3H, s), 7.05-7.2 (2H, m), 7.86 (1H, s) |
| 66 | —C$_4$H$_9$ | —CH$_3$ | 0.81 (3H, t, J = 7.3 Hz), 1.1-1.2 (2H, m), 1.3-1.4 (2H, m), 2.43 (2H, t, J = 6.9 Hz), 2.87 (2H, t, J = 6.9 Hz), 3.89 (3H, s), 3.92 (2H, t, J = 7.3 Hz), 7.17 (1H, d, J = 8.8 Hz), 7.24 (1H, d, J = 8.8 Hz), 7.86 (1H, s), 12.57 (1H, br s) |
| 67 | —(CH$_2$)$_3$C$_6$H$_5$ | —CH$_3$ | 1.65-1.8 (2H, m), 2.35-2.5 (4H, m), 2.89 (2H, t, J = 6.9 Hz), 3.78 (3H, s), 3.92 (2H, t, J = 7.3 Hz), 7.0-7.3 (7H, m), 7.86 (1H, s), 12.25 (1H, br s) |
| 68 | —(CH$_2$)$_2$C$_6$H$_5$ | —CH$_3$ | 2.35 (2H, t, J = 6.9 Hz), 2.55 (2H, t, J = 4.5 Hz), 2.73 (2H, t, J = 6.9 Hz), 3.96 (3H, s), 4.16 (2H, t, J = 4.5 Hz), 6.99 (1H, d, J = 8.8 Hz), 7.1-7.3 (5H, m), 7.79 (1H, s), 12.59 (1H, br s) |
| 69 | —C$_2$H$_5$ | —CH$_3$ | 1.07 (3H, t, J = 7.0 Hz), 2.42 (2H, t, J = 6.9 Hz), 2.87 (2H, t, J = 6.9 Hz), 3.85 (2H, q, J = 7.0 Hz), 3.90 (3H, s), 7.18 (1H, d, J = 8.8 Hz), 7.24 (1H, d, J = 8.8 Hz), 7.86 (1H, s), 12.59 (1H, br s) |
| 70 | —CH$_2$-cyclo-C$_3$H$_5$ | —CH$_3$ | 0.05-0.10 (2H, m), 0.25-0.30 (2H, m), 0.75-0.80 (1H, m), 2.45 (2H, t, J = 6.9 Hz), 2.90 (2H, t, J = 6.9 Hz), 3.85-3.90 (5H, m), 7.17 (1H, d, J = 8.8 Hz), 7.26 (1H, d, J = 8.8 Hz), 7.86 (1H, s), 12.59 (1H, br s) |
| 71 | —(CH$_2$)$_2$OC$_6$H$_5$ | —CH$_3$ | 2.47 (2H, t, J = 6.9 Hz), 2.84 (2H, t, J = 6.9 Hz), 3.86 (3H, s), 4.04 (2H, t, J = 5.9 Hz), 4.29 (2H, t, J = 5.9 Hz), 6.77 (2H, d, J = 8.6 Hz), 6.89 (1H, t, J = 8.6 Hz), 7.1-7.3 (4H, m), 7.82 (1H, s), 13.2 (1H, br s) |

TABLE 39

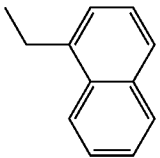

| Ex. | R^101 | R^131 | $^1$H NMR (DMSO-d$_6$) dppm |
|---|---|---|---|
| 72 | —CH$_2$-cyclo- | —CH$_3$ | 0.75-1.57 (11H, m), 2.45 (2H, t, J = 6.9 Hz), 2.88 (2H, t, J = 6.9 Hz), 3.89 (3H, s), 3.90-3.95 (2H, m), 7.17 (1H, d, J = 8.8 Hz), 7.25 (1H, d, J = 8.8 Hz), 7.88 (1H, s), 12.59 (1H, br s) |
| 73 | —CH$_2$CH$_2$OCH$_3$ | —CH$_3$ | 2.46 (2H, t, J = 6.9 Hz), 2.86 (2H, t, J = 6.9 Hz), 3.10 (3H, s), 3.35 (2H, t, J = 6.0 Hz), 3.90 (3H, s), 4.10 (2H, t, J = 6.0 Hz), 7.17 (2H, d, J = 8.6 Hz), 7.24 (1H, t, J = 8.6 Hz), 7.86 (1H, s), 12.6 (1H, br s) |
| 74 | —CH(C$_6$H$_5$)$_2$ | —CH$_3$ | 2.47 (2H, t, J = 6.9 Hz), 285 (2H, t, J = 6.9 Hz), 3.40 (3H, s), 6.29 (2H, s), 7.00 (1H, d, J = 8.8 Hz), 7.15-7.3 (11H, m), 7.87 (1H, s), 12.55 (1H, br s) |
| 75 | —CH$_2$C$_6$H$_5$ | —H | 2.41-2.60 (2H, m), 2.75-2.98 (2H, m), 5.31 (2H, s), 6.84 (1H, d, J = 8.6 Hz), 7.00-7.30 (6H, m), 7.81 (1H, s), 10.72 (1H, s), 12.48 (1H, brs). |

TABLE 39-continued

| Ex. | R^101 | R^131 | $^1$H NMR (DMSO-d$_6$) dppm |
|---|---|---|---|
| 76 | —CH$_2$CH$_2$CN | —CH$_3$ | 2.37-2.55 (2H, m), 2.78 (2H, t, J = 6.8 Hz), 2.83-2.98 (2H, m), 3.92 (3H, s), 4.06 (2H, t, J = 6.8 Hz), 7.19 (1H, d, J = 8.8 Hz), 7.27 (1H, d, J = 8.8 Hz), 7.85 (1H, s), 12.57 (1H, s). |
| 77 | —(CH$_2$)$_4$C$_6$H$_5$ | —CH$_3$ | 1.35-1.55 (4H, m), 2.40-2.70 (4H, m), 2.80 (2H, t, J = 6.9 Hz), 3.83 (3H, s), 3.85-3.95 (2H, m), 7.05-7.3 (7H, m), 7.85 (1H, s), 12.7 (1H, br s) |
| 78 | —(CH$_2$)$_5$C$_6$H$_5$ | —CH$_3$ | 1.05-1.15 (2H, m), 1.35-1.5 (4H, m), 2.35-2.70 (4H, m), 2.77 (2H, t, J = 6.9 Hz), 3.87 (3H, s), 3.91 (2H, t, J = 7.0 Hz), 7.05-7.3 (7H, m), 7.83 (1H, s), 12.6 (1H, br s) |
| 79 | —(CH$_2$)$_2$CO$_2$C$_2$H$_5$ | —CH$_3$ | 1.13 (3H, t, J = 7.1 Hz), 1.60-1.76 (2H, m), 2.17 (2H, t, J = 7.3 Hz), 2.35-2.47 (2H, m), 2.80-2.92 (2H, m), 3.79-3.84 (5H, m), 3.98 (2H, q, J = 7.1 Hz), 7.16 (1H, d, J = 8.8 Hz), 7.24 (1H, d, J = 8.8 Hz), 7.85 (1H, s), 12.54 (1H, s). |

TABLE 40

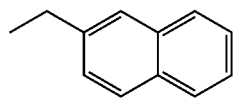

| Ex. | R^101 | R^131 | $^1$H NMR dppm |
|---|---|---|---|
| 80 | 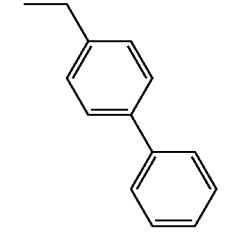 | —CH$_3$ | 2.60 (2H, t, J = 6.9 Hz), 2.84 (2H, t, J = 6.9 Hz), 3.70 (3H, s), 5.64 (2H, s), 6.95-8.0 (9H, m), 12.5 (1H, br s) |
| 81 | 2-naphthylethyl | —CH$_3$ | 2.60 (2H, t, J = 6.9 Hz), 2.99 (2H, t, J = 6.9 Hz), 3.78 (3H, s), 5.37 (2H, s), 6.95-7.85 (9H, m), 12.6 (1H, br s) |
| 82 | 4-biphenylylethyl | —C$_4$H$_9$ | 0.82 (3H, t, J = 7.4 Hz), 1.2-1.35 (2H, m), 1.45-1.6 (2H, m), 2.59 (2H, t, J = 6.9 Hz), 2.97 (2H, t, J = 6.9 Hz), 3.99 (2H, t, J = 6.4 Hz), 5.21 (2H, 2), 7.0-7.65 (11H, m), 7.85 (1H, s), 12.6 (1H, br s) |

TABLE 40-continued
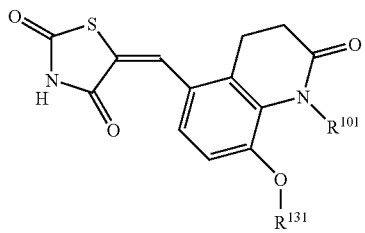
| Ex. | $R^{101}$ | $R^{131}$ | $^1$H NMR dppm |
|---|---|---|---|
| 83 | ![biphenylmethyl] | —CH$_2$CO$_2$C(CH$_3$)$_3$ | CDCl$_3$: 1.53 (9H, s), 2.70 (2H, t, J = 6.8 Hz), 2.98 (2H, t, J = 6.8 Hz), 4.46 (2H, s), 5.47 (2H, s), 6.69 (1H, d, J = 8.5 Hz), 7.1-7.6 (10H, m), 7.96 (1H, s), 8.48 (1H, br s) |
| 84 | ![biphenylmethyl] | —H | 2.56 (2H, t, J = 6.9 Hz), 2.93 (2H, t, J = 6.9 Hz), 5.36 (2H, s), 6.8-7.65 (11H, m), 7.83 (1H, s), 10.79 (1H, s), 12.6 (1H, br s) |
| 85 | ![biphenylmethyl] | —CH$_2$OCH$_3$ | CDCl$_3$: 2.6-2.8 (m, 2H), 2.9-3.1 (m, 2H), 3.40 (2, 3H), 3.44 (2, 3H), 5.02 (s, 2H), 5.13 (s, 2H), 5.32 (s, 2H), 6.05-7.6 (11H, m), 8.06 (s, 1H) |
| 86 | ![4-chlorobenzyl] | —CH$_3$ | 7.45-7.65 (2H, m), 2.85-3.04 (2H, m), 3.72 (3H, s), 5.12 (2H, s), 7.03 (1H, d, J = 8.7 Hz), 7.06-7.31 (5H, m), 7.82 (1H, s), 12.53 (1H, brs). |
DMSO-d$_6$ is used for measuring NMR, unless otherwise specified.

TABLE 41

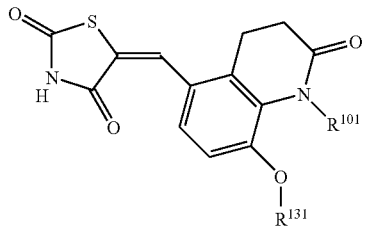

| Ex. | R[101] | R[131] | $^1$H NMR (DMSO-d₆) dppm |
|---|---|---|---|
| 87 | ![5-ethyl-2-(thiophen-3-yl)pyridine] | —CH₃ | 2.48-2.51 (2H, m), 2.96-2.99 (2H, m), 3.75 (3H, s), 5.18 (2H, s), 6.88 (1H, d, J = 10.3 Hz), 7.06 (1H, d, J = 10.3 Hz), 7.53-7.74 (4H, m), 7.84 (1H, s), 8.09-8.10 (1H, m), 8.35 (1H, d, J = 2.0 Hz), 12.57 (1H, brs) |
| 88 | ![5-ethyl-2-phenylpyridine] | —CH₃ | 2.48-2.51 (2H, m), 2.98-3.01 (2H, m), 3.75 (3H, s), 5.19 (2H, s), 7.07 (1H, d, J = 10.5 Hz), 7.20 (1H, d, J = 10.5 Hz), 7.43-7.66 (4H, m), 7.82-7.84 (2H, m), 8.01-8.04 (2H, m), 8.43-8.45 (1H, m), 12.56 (1H, brs) |
| 89 | ![5-ethyl-2-morpholinopyridine] | —CH₃ | DMSO overlap (2H), 2.80-2.85 (2H, m), 3.40-3.47 (4H, m), 3.61-3.68 (4H, m), 3.84 (3H, s), 5.11 (2H, s), 6.65 (1H, d, J = 9.0 Hz), 6.98-7.24 (3H, m), 7.77 (1H, s), 7.87 (1H, d, J = 2.1 Hz), 12.18 (1H, brs) |
| 90 | ![5-ethyl-2-(4-phenylpiperazin-1-yl)pyridine] | —CH₃ | 2.84-2.89 (2H, m), 3.15-3.19 (4H, m), 3.25-3.30 (2H, m), 3.50-3.54 (4H, m), 3.86 (3H, s), 5.12 (2H, s), 6.69-6.90 (2H, m), 6.96 (2H, d, J = 8.0 Hz), 7.07 (1H, d, J = 8.9 Hz), 7.16-7.30 (4H, m), 7.81 (1H, s), 7.88 (1H, d, J = 2.2 Hz), 12.53 (1H, brs) |
| 91 | ![5-ethyl-2-(4-methylpiperazin-1-yl)pyridine] | —CH₃ | 2.35 (3H, s), 2.55-2.59 (4H, m), 2.83-2.89 (2H, m), 3.34-3.44 (6H, m), 3.84 (3H, s), 5.11 (2H, s), 6.68 (1H, d, J = 8.6 Hz), 7.04 (1H, d, J = 8.8 Hz), 7.20 (1H, d, J = 8.8 Hz), 7.26 (1H, dd, J1 = 2.2 Hz, J2 = 8.8 Hz), 7.68 (1H, s), 7.86 (1H, d, J = 2.2 Hz) |

TABLE 42

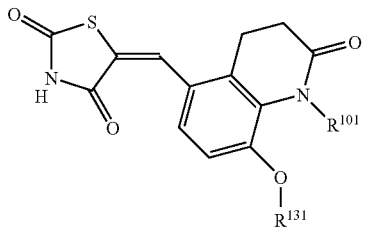

| Ex. | R¹⁰¹ | R¹³¹ | ¹H NMR (DMSO-d₆) dppm |
|---|---|---|---|
| 92 | 5-ethyl-2,2'-bipyridinyl | —CH₃ | 2.50-2.58 (2H, m), 2.95-3.03 (2H, m), 3.71 (3H, s), 5.20 (2H, s), 7.04 (1H, d, J = 8.7 Hz), 7.21 (1H, d, 8.7 Hz), 7.39-7.44 (1H, m), 7.61-7.70 (2H, m), 7.87-7.94 (1H, m), 8.25 (1H, d, J = 8.2 Hz), 8.32 (1H, d, J = 8.0 Hz), 8.45-8.46 (1H, m), 8.64 (1H, d, J = 4.1 Hz), NH n.d. (1H, brs) |
| 93 | 2-ethylquinolinyl | —CH₃ | 2.82-2.87 (2H, m), 3.05-3.10 (2H, m), 3.62 (3H, s), 5.32 (2H, s), 7.06 (1H, d, J = 8.8 Hz), 7.30 (1H, d, J = 8.8 Hz), 7.38 (1H, d, J = 8.6 Hz), 7.50-7.56 (1H, m), 7.67-7.73 (1H, m), 7.87-7.93 (1H, m), 8.24 (1H, d, J = 8.5 Hz), 12.56 (1H, brs) |

TABLE 43

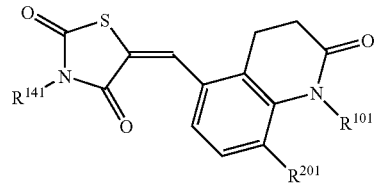

| Ex. | R¹⁰¹ | R¹⁴¹ | R²⁰¹ | ¹H NMR (DMSO-d₆) dppm |
|---|---|---|---|---|
| 94 | 2-ethylnaphthyl | —H | —H | 2.70-2.83 (2H, m), 2.98-3.15 (2H, m), 5.32 (2H, s), 6.99-7.10 (2H, m), 7.18-7.30 (1H, m), 7.35-7.54 (3H, m), 7.70 (1H, s), 7.75-7.90 (3H, m), 7.94 (1H, s), 12.63 (1H, s). |
| 95 | —C₆H₅ | —H | —H | 2.71-2.76 (2H, m), 3.10-3.33 (2H, m), 6.30 (1H, d, J = 7.7 Hz), 7.10-7.28 (4H, m), 7.40-7.57 (3H, m), 7.98 (1H, s), 12.66 (1H, s). |
| 96 | 5-ethyl-2-chloropyridinyl | —H | —H | 2.69-2.75 (2H, m), 3.01-3.06 (2H, m), 5.21 (2H, s), 7.05-7.14 (2H, m), 7.31 (1H, t, J = 8.0 Hz), 7.45 (1H, d, J = 8.3 Hz), 7.69 (1H, dd, J1 = 2.4 Hz, J2 = 8.3 Hz), 7.92 (1H, s), 8.36 (1H, d, J = 2.4 Hz), 12.60 (1H, brs) |

TABLE 44

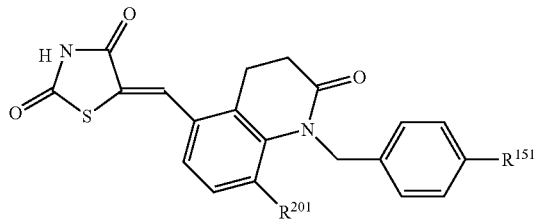

| Ex. | R151 | R201 | 1H NMR (DMSO-d6) dppm |
|---|---|---|---|
| 97 | —C6H5 | —H | 2.68-2.81 (2H, m), 3.04 (2H, t, J = 6.6 Hz), 5.21 (2H, s), 7.01-7.15 (2H, m), 7.21-7.39 (4H, m), 7.39-7.50 (2H, m), 7.5-7.65 (4H, m), 7.93 (1H, s), 12.62 (1H, s). |
| 98 | —Br | —H | 2.60-2.80 (2H, m), 2.95-3.10 (2H, m), 5.13 (2H, s), 6.99 (1H, d, J = 8.2 Hz), 7.09 (1H, d, J = 7.7 Hz), 7.11-7.32 (3H, m), 7.49 (2H, d, J = 8.4 Hz), 7.92 (1H, s), 12.64 (1H, s). |
| 99 | —Cl | —H | 7.63-7.80 (2H, m), 2.92-3.10 (2H, m), 5.16 (2H, s), 7.01 (1H, d, J = 8.1 Hz), 7.10 (1H, d, J = 7.7 Hz), 7.20-7.31 (3H, m), 7.31-7.45 (2H, m), 7.93 (1H, s), 12.65 (1H, brs). |
| 100 | —CH3 | —H | 2.25 (3H, s), 2.49-2.51 (2H, m), 2.68-2.73 (2H, m), 5.12 (2H, s), 7.02 (1H, d, J = 8.2 Hz), 7.07-7.29 (6H, m), 7.93 (1H, s), 12.64 (1H, brs). |
| 101 | —C6H5 | —C6H5 | 2.62-2.77 (2H, m), 2.89-3.07 (2H, m), 4.36 (2H, brs), 6.85 (2H, d, J = 8.2 Hz), 7.20-7.61 (14H, m), 7.93 (1H, s), 12.66 (1H, brs). |
| 102 | —CO2CH3 | —H | 2.71-2.77 (2H, m), 3.02-3.08 (2H, m), 3.83 (3H, s), 5.24 (2H, s), 6.96 (1H, d, J = 7.9 Hz), 7.11 (1H, d, J = 7.9 Hz), 7.27 (1H, t, J = 7.9 Hz), 7.38 (2H, d, J = 8.3 Hz), 7.90 (2H, d, J = 8.3 Hz), 7.94 (1H, s), 12.64 (1H, brs) |
| 103 | —NO2 | —H | 2.72-2.78 (2H, m), 3.04-3.10 (2H, m), 5.31 (2H, s), 6.98 (1H, d, J = 8.0 Hz), 7.12 (1H, d, J = 8.0 Hz), 7.28 (1H, t, J = 8.0 Hz), 7.51 (2H, d, J = 8.7 Hz), 7.94 (1H, s), 8.18 (2H, d, J = 8.7 Hz), 12.66 (1H, brs) |

TABLE 45

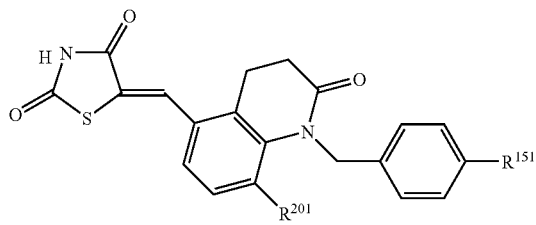

| Ex. | R151 | R201 | 1H NMR (CDCl3) dppm |
|---|---|---|---|
| 104 | —C6H5 | —CH3 | 2.43 (3H, s), 2.57-2.63 (2H, m), 2.84-2.91 (2H, m), 5.12 (2H, s), 7.06-7.22 (4H, m), 7.22-7.60 (7H, m), 7.98 (1H, s), 8.42 (1H, m). |
| 105 | —C6H5 | —Cl | 2.60-2.66 (2H, m), 2.85-2.92 (2H, m), 5.44 (2H, s), 7.11 (1H, d, J = 8.5 Hz), 7.18 (2H, d, J = 8.2 Hz), 7.23-7.48 (6H, m), 7.48-7.59 (2H, m), 7.91 (1H, s), 7.23 (1H, brs). |

TABLE 46

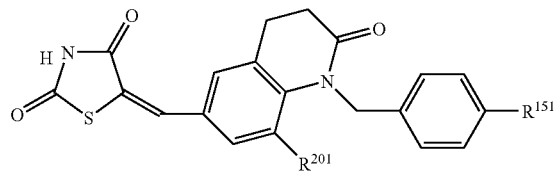

| Ex. | R151 | R201 | 1H NMR (DMSO-d6) dppm |
|---|---|---|---|
| 106 | —C6H5 | —H | 2.70-2.84 (2H, m), 2.97-3.10 (2H, m), 5.22 (2H, s), 7.04-7.20 (2H, m), 7.20-7.49 (6H, m), 7.49-7.65 (4H, m), 7.68 (1H, s), 12.53 (1H, s). |
| 107 | —Br | —H | 2.66-2.81 (2H, m), 2.91-3.09 (2H, m), 5.13 (2H, s), 7.03 (1H, d, J = 8.6 Hz), 7.19 (2H, d, J = 8.4 Hz), 7.36 (1H, dd, J = 2.0, 8.6 Hz), 7.40-7.55 (3H, m), 7.67 (1H, s), 12.54 (1H, brs). |
| 108 | —NO2 | —H | 2.71-2.87 (2H, m), 2.97-3.15 (2H, m), 5.31 (2H, s), 7.02 (1H, d, J = 8.6 Hz), 7.38 (1H, dd, J = 1.9, 8.6 Hz), 7.45-7.60 (3H, m), 7.69 (1H, s), 8.18 (2H, m), 12.55 (1H, brs). |
| 109 | —C6H5 | —OCH3 | 2.55-2.70 (2H, m), 2.85-3.01 (2H, m), 3.78 (3H, s), 5.31 (2H, s), 7.07 (1H, s), 7.12 (1H, s), 7.21 (2H, d, J = 8.2 Hz), 7.25-7.35 (2H, m), 7.35-7.47 (2H, m), 7.54 (2H, d, J = 8.2 Hz), 7.60 (2H, d, J = 7.3 Hz), 7.68 (1H, s), 12.57 (1H, brs). |
| 110 | —C6H5 | —CH3 | 2.36 (3H, s), 2.53-2.68 (2H, m), 2.79-3.04 (2H, m), 5.15 (2H, s), 7.22 (2H, d, J = 8.2 Hz), 7.25-7.36 (3H, m), 7.36-7.49 (2H, m), 7.50-7.70 (5H, m), 12.57 (1H, brs). |

TABLE 47

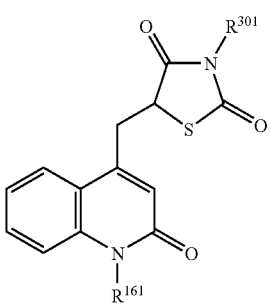

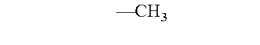

| Ex. | R161 | R301 | M.p. (° C.) |
|---|---|---|---|
| 111 | —H | —H | 290-291 |
| 112 | —CH3 | —H | 246-248 |
| 113 | —CH3 | —CH3 | 143-145 |
| 114 | —CH2-C6H4-C6H5 | —H | 244.7-246.7 |

TABLE 48

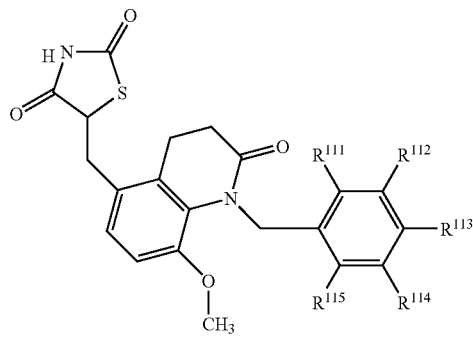

| Ex. | $R^{111}$ | $R^{112}$ | $R^{113}$ | $R^{114}$ | $R^{115}$ | M.p.(° C.) |
|---|---|---|---|---|---|---|
| 115 | —H | —H | —H | —H | —H | 178-180 |
| 116 | —H | —H | —$C_6H_5$ | —H | —H | 211-213 |
| 117 | —H | —H | —H | —H | —H | 210-215 |
| 118 | —H | —H | —$C(CH_3)_3$ | —H | —H | 215-217 |
| 119 | —H | —H | —$NO_2$ | —H | —H | 246.5-246.6 |
| 120 | —H | —H | —$NH_2$ | —H | —H | 174.1-174.8 |
| 121 | —H | —H | —$OCH_3$ | —H | —H | 177.5-179.0 |
| 122 | —H | —H | —Cl | —H | —H | 190.5-191.8 |

TABLE 48-continued

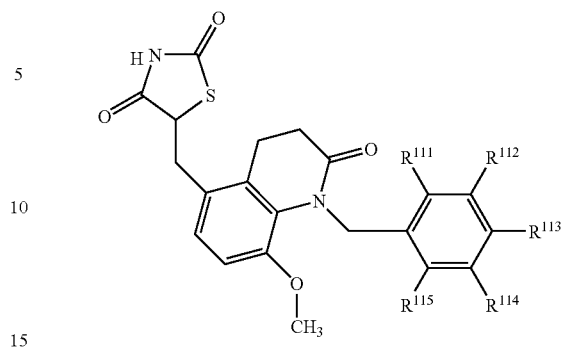

| Ex. | $R^{111}$ | $R^{112}$ | $R^{113}$ | $R^{114}$ | $R^{115}$ | M.p.(° C.) |
|---|---|---|---|---|---|---|
| 123 | —H | —H | —Br | —H | —H | 178.1-179.0 |
| 124 | —H | —H | —F | —H | —H | 177.7-179.2 |
| 125 | —H | —H | —CN | —H | —H | 206.4-208.0 |
| 126 | —H | —H | —$CH_3$ | —H | —H | 165.2-167.0 |
| 127 | —H | —H | —$OCH_2C_6H_5$ | —H | —H | 106.4-109.1 |
| 128 | —H | —H | —$OC_6H_5$ | —H | —H | 213.9-214.7 |

TABLE 49

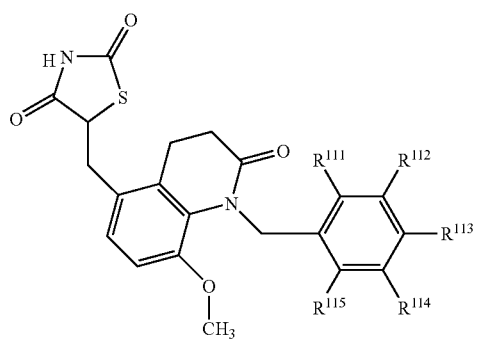

| Ex. | $R^{111}$ | $R^{112}$ | $R^{113}$ | $R^{114}$ | $R^{115}$ | $^1$H NMR (DMSO-$d_6$) dppm |
|---|---|---|---|---|---|---|
| 129 | —H | —H | —H | —H | —$C_6H_5$ | 2.39-2.52 (m, 2H), 2.63-2.80 (m, 2H), 3.06 (dd; J = 9.9, 14.4 Hz, 1H), 3.33 (S, 3H), 3.39 (dd; J = 4.2, 14.4 Hz, 1H), 4.76 (dd; J = 4.2, 9.9 Hz, 1H), 5.18 (s, 2H), 6.69 (d, J = 8.6 Hz, 1H), 6.86 (d, J = 8.6 Hz, 1H), 7.04-7.47 (m, 9H), 12.08 (brs, 1H) |
| 130 | —H | —H | —H | —$C_6H_5$ | —H | 2.45-2.57 (m, 2H), 2.79-2.90 (m, 2H), 3.09 (dd; J = 10.1, 14.4 Hz, 1H), 3.41 (dd; J = 4.3, 14.4 Hz, 1H), 3.68 (S, 3H), 4.77 (dd; J = 4.3, 10.1 Hz, 1H), 5.26 (s, 2H), 6.84 (d, J = 8.6 Hz, 1H), 6.92 (d, J = 8.6 Hz, 1H), 7.03 (d, J = 7.6 Hz, 1H), 7.25-7.55 (m, 8H), 12.09 (brs, 1H) |
| 131 | —H | —H | —$NHSO_2CH_3$ | —H | —H | 2.39-2.54 (2H, m), 2.72-2.87 (2H, m), 2.88 (3H, s), 3.05 (1H, dd, J = 10.0, 14.4 Hz), 3.39 (1H, dd, J = 4.0, 14.4 Hz), 3.67 (3H, s), 4.76 (1H, dd, J = 4.0, 10.0 Hz), 5.13 (2H, s), 6.80 (1H, d, J = 8.6 Hz), 6.89 (1H, d, J = 8.6 Hz), 6.93-7.06 (4H, m), 9.57 (1H, s), 12.05 (1H, s). |

TABLE 50

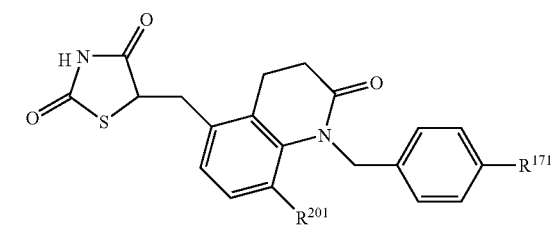

| Ex. | R¹⁷¹ | R²⁰¹ | M.p.(° C.) |
|---|---|---|---|
| 132 | —C₆H₅ | —OCH₂CO₂H | 128-133 |
| 133 | —C₆H₅ | —H | 198.1-199.2 |
| 134 | —Br | —H | 224.3-225.8 |
| 135 | —Cl | —H | 212.1-212.9 |

TABLE 50-continued

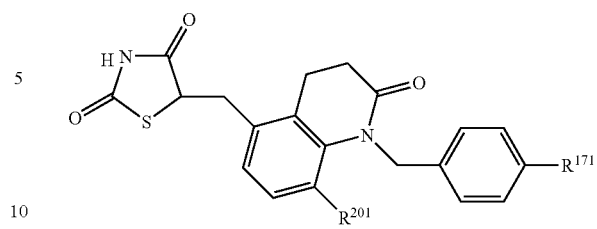

| Ex. | R¹⁷¹ | R²⁰¹ | M.p.(° C.) |
|---|---|---|---|
| 136 | —CH₃ | —H | 209.3-210.3 |
| 137 | —CO₂CH₃ | —H | 247-249 |
| 138 | —NO₂ | —H | 243-250 |

TABLE 51

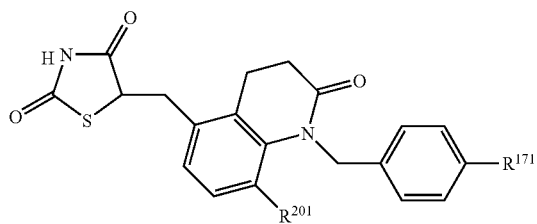

| Ex. | R¹⁷¹ | R²⁰¹ | ¹H NMR δppm |
|---|---|---|---|
| 139 | —C₆H₅ | —OC₄H₉ | 0.82 (t, J = 7.4 Hz, 3H), 1.25-1.33 (m, 2H). 1.46-1.55 (m, 2H), 2.45-2.56 (m, 2H), 2.80-2.91 (m, 2H). 3.11 (dd; J = 9.6, 14.4 Hz, 1H), 3.41 (dd; J = 4.4, 14.4 Hz, 1H), 3.84-3.92 (m, 2H). 4.80 (dd; J = 4.4, 9.6 Hz. 1H), 5.21 (s, 2H), 6.87d, J = 8.6 Hz, 1H), 6.90 (d, J = 8.6 Hz, 1H), 7.14 (d, J = 8.1 Hz, 2H). 7.27-7.62 (m, 7H), 12.08 (brs, 1H) |
| 140 | —C₆H₅ | —CH₃ | 2.28 (3H, s), 2.37-2.57 (2H, m). 2.67-2.94 (2H, m). 3.16 (1H, dd, J = 9.3. 14.3 Hz). 3.44 (1H, d, J = 4.4, 14.3 Hz). 4.83 (1H, dd, J = 4.4, 9.3 Hz), 4.95-5.20 (2H, m), 6.87 (1H, d, J = 7.9 Hz), 7.00 (1H, d, J = 7.9 Hz), 7.15 (2H, d, J = 8.1 Hz), 7.25-7.48 (3H, m), 7.51 (2H, d, J = 8.2 Hz), 7.60 (2H, d, J = 7.4 Hz), 12.07 (1H, brs). |
| 141 | —C₆H₅ | —Cl | 2.43-2.62 (2H, m), 2.80-2.98 (2H, m), 3.21 (1H, dd, J = 9.3, 14.3 Hz), 3.45 (1H, dd, J = 4.7, 14.3 Hz), 4.84 (1H, dd, J = 4.7, 9.3 Hz). 5.31 (2H, s), 6.97 (1H, d, J = 8.4 Hz), 7.15 (2H, d, J = 8.2 Hz), 7.25 (1H, d, J = 8.4 Hz), 7.27-7.45 (3H, m), 7.50 (2H, d, J = 8.2 Hz). 7.59 (2H, d, J = 7.2. Hz), 12.10 (1H, brs). |
| 142 | —C₆H₅ | —C₆H₅ | 2.56-2.75 (2H, m), 2.80-3.00 (2H, m), 3.13-3.30 (1H, m), 3.45-3.60 (1H, m), 4.18-4.50 (2H, m), 4.90 (1H, dd, J = 4.5, 9.4 Hz), 6.80 (2H, d, J = 8.2 Hz), 7.04 (1H, d, J = 8.0 Hz), 7.12 (1H, d, J = 8.0 Hz), 7.21-7.64 (12H, m), 12.12 (1H, brs). |
| 143 | —CO₂H | —H | 2.67-2.72 (2H, m), 2.97-3.02 (2H, m), 3.11-3.60 (2H, m), 4.85 (1H, dd, J1 = 4.6 Hz, J2 = 10.7 Hz), 5.21 (2H, s), 6.79 (1H, d, J = 7.8 Hz), 6.90 (1H, d, J = 7.8 Hz), 7.09 (1H, t, J = 7.8 Hz), 7.32 (2H, d, J = 8.2 Hz), 7.88 (2H, d, J = 8.2 Hz), 12.19 (1H, brs), 12.88 (1H, brs) |
| 144 | —C₆H₅ | —OCH₂CO₂C(CH₃)₃ | CDCl₃: 1.57 (9H, s), 2.55-2.8 (2H, m), 2.75-2.95 (2H, m), 3.05-3.2 (1H, m), 3.5-3.6 (1H, m), 4.38 (3H, s), 4.35-4.5 (1H, m), 5.4-5.55 (2H, m), 6.57 (1H, d, J = 8.6 Hz), 6.87 (1H, d, J = 8.6 Hz), 7.15-7.6 (9H, m), 7.96 (1H, br s) |

DMSO-d₆ is used for measuring NMR, unless otherwise specified.

TABLE 52
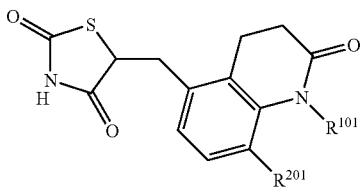
| Ex. | R[101] | R[201] | M.p.(° C.) |
|---|---|---|---|
| 145 | —CH₃ | —OCH₃ | 204-208 |
| 146 | —H | —OCH₃ | 253-256 |
| 147 | —C₂H₅ | —OCH₃ | 179-181 |
| 148 | —CH₂CH₂CN | —OCH₃ | 197.9-199.9 |
| 149 | —(CH₂)₃CO₂H | —OCH₃ | 164.7-165.5 |
| 150 | —C₆H₅ | —H | 225.5-2272 |
| 151 | —(CH₂)₃CO₂C₂H₅ | —OCH₃ | 154.7-156.0 |
| 152 | —CH₂CH=CH₂ | —OCH₃ | 160.0-161.5 |
| 153 | —C₈H₁₇ | —OCH₃ | 102.0-103.0 |
| 154 | (1-naphthylmethyl) | —OCH₃ | 117-121 |
| 155 | (2-naphthylmethyl) | —OCH₃ | 97-99 |
| 156 | (2-chloro-5-pyridylmethyl) | —OCH₃ | 183-185 |
| 157 | (5-(piperidin-1-yl)pyridin-2-ylmethyl) | —OCH₃ | 107-114 |
| 158 | (2-naphthylmethyl) | —H | 228.1-230.0 |
| 159 | (4-(N-Boc-piperidinyl)propyl) | —H | 76-94 |
| 160 | (2-(piperidin-4-yl)ethyl) | —H | 261.5-263 |

TABLE 53
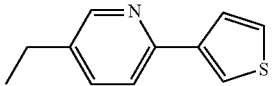
| Ex. | R¹⁰¹ | R²⁰¹ | M.p.(° C.) |
|---|---|---|---|
| 161 | 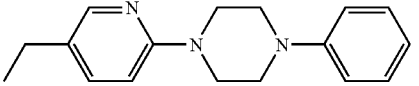 | —OCH₃ | 121-126 |
| 162 | 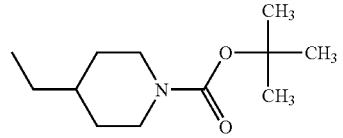 | —OCH₃ | 135-137 |
| 163 | 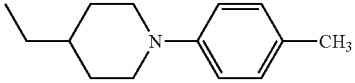 | —OCH₃ | 215(dec.) |
| 164 | 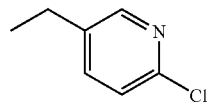 | —OCH₃ | 104-109 |
| 165 |  | —H | 225-226 |
TABLE 54
| Ex. | R¹⁰¹ | R²⁰¹ | ¹H NMR (DMSO-d₆) dppm |
|---|---|---|---|
| 166 | —(CH₂)₃C₆H₅ | —OCH₃ | 1.62-1.73 (m, 2H), 2.32-2.45 (m, 4H), 2.75-2.85 (m, 2H), 3.10 (dd; J = 10.1, 14.4 Hz, 1H), 3.44 (dd; J = 4.3, 14.4 Hz, 1H), 3.70 (S, 3H), 3.85-3.95 (m, 2H), 4.81 (dd; J = 4.3, 10.1 Hz, 1H), 6.93 (d, J = 8.6 Hz, 1H), 6.98 (d, J = 8.6 Hz, 1H), 7.04 (d, J = 7.5 Hz, 2H), 7.14 (t, J = 7.5 Hz, 1H), 7.22 (t, J = 7.5 Hz, 2H), 12.10 (brs, 1H) |
| 167 | —(CH₂)₂C₆H₅ | —OCH₃ | 2.22-2.31 (m, 2H), 2.32-2.55 (m, 2H), 2.63-2.75 (m, 2H). 3.05 (dd; J = 10.4, 14.5 Hz, 1H), 3.41 (dd; J = 4.2, 14.5 Hz, 1H), 3.87 (S, 3H), 4.10-4.30 (m, 2H). 4.69 (dd; J = 4.2, 10.4 Hz, 1H), 6.90-7.05 (m, 4H), 7.12-7.25 (m, 3H), 12.12 (brs, 1H) |
| 168 | —C₄H₉ | —OCH₃ | 0.79 (t; J = 7.2 Hz, 3H), 1.13 (tt; J = 7.2, 7.2 Hz, 2H), 1.36 (tt; J = 7.2, 7.2 Hz, 2H), 2.30-2.42 (m, 2H), 2.70-2.80 (m, 2H), 3.11 (dd; J = 9.8, 14.5 Hz, 1H), 3.42 (dd; J = 4.4, 14.5 Hz, 1H), 3.80 (S, 3H), 3.92 (t; J = 7.2 Hz, 2H), 4.80 (dd; J = 4.4, 9.8 Hz, 1H), 6.80 (d; J = 8.6 Hz, 1H), 6.97 (d; J = 8.6 Hz, 1H), 12.09 (brs, 1H) |

TABLE 54-continued

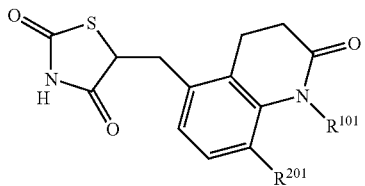

| Ex. | $R^{101}$ | $R^{201}$ | $^{1}$H NMR (DMSO-$d_6$) dppm |
|---|---|---|---|
| 169 | —CH$_2$-cyclo-C$_3$H$_5$ | —OCH$_3$ | 0-0.05 (m, 2H), 0.20-0.26 (m, 2H), 0.73-0.84 (m, 1H), 2.30-2.42 (m, 2H), 2.70-2.85 (m, 2H), 3.14 (dd; J = 9.6, 14.5 Hz, 1H), 3.42 (dd; J = 4.4, 14.5 Hz, 1H), 3.81 (S, 3H), 3.84-3.90 (m, 2H), 4.82 (dd; J = 4.4, 9.6 Hz, 1H), 6.94 (d; J = 8.6 Hz, 1H), 6.98 (d; J = 8.6 Hz, 1H), 12.07 (brs, 1H) |
| 170 | —(CH$_2$)$_2$OC$_6$H$_5$ | —OCH$_3$ | 2.35-2.47 (m, 2H), 2.70-2.83 (m, 2H), 3.07 (dd; J = 10.2, 14.5 Hz, 1H), 3.42 (dd; J = 4.2, 14.5 Hz, 1H), 3.79 (S, 3H), 4.00-4.07 (m, 2H), 4.21-4.30 (m, 2H), 4.73 (dd; J = 4.2, 10.2 Hz, 1H), 6.79 (d, J = 7.7 Hz, 2H), 6.88 (t, J = 7.7 Hz, 1H), 6.95 (d, J = 8.7 Hz, 1H), 6.98 (d, J = 8.7 Hz, 1H), 7.21 (t, J = 7.7 Hz, 2H), 12.11 (brs, 1H) |

TABLE 55

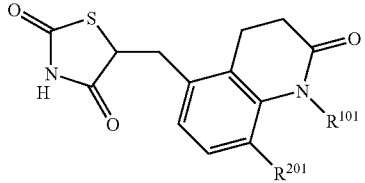

| Ex. | $R^{101}$ | $R^{201}$ | $^{1}$H NMR (DMSO-$d_6$) dppm |
|---|---|---|---|
| 171 | —CH$_2$-cyclo-C$_6$H$_{11}$ | —OCH$_3$ | 0.71-0.80 (m, 2H), 0.94-1.07 (m, 3H), 1.20-1.27 (m, 1H), 1.37-1.45 (m, 2H), 1.45-1.59 (m, 3H), 2.34-2.44 (m, 2H), 2.71-2.82 (m, 2H), 3.13 (dd; J = 9.4, 14.4 Hz, 1H), 3.42 (dd; J = 4.4, 14.4 Hz, 1H), 3.80 (S, 3H), 3.89-3.99 (m, 2H), 4.82 (dd; J = 4.4, 9.4 Hz, 1H), 6.94 (d, J = 8.6 Hz, 1H), 6.97 (d, J = 8.6 Hz, 1H), 12.06 (brs, 1H) |
| 172 | —CH$_2$CH$_2$OCH$_3$ | —OCH$_3$ | 2.35-2.44 (m, 2H), 2.71-2.80 (m, 2H), 3.08 (S, 3H), 3.11 (dd; J = 9.8, 14.5 Hz, 1H), 3.25-3.36 (m, 2H), 3.42 (dd; J = 4.3, 14.5 Hz, 1H), 3.80 (S, 3H), 4.03-4.12 (m, 2H), 4.80 (dd; J = 4.3, 9.8 Hz, 1H), 6.95 (d, J = 8.6 Hz, 1H), 6.98 (d, J = 8.6 Hz, 1H), 12.09 (brs, 1H) |
| 173 | —(CH$_2$)$_2$CH(CH$_3$)$_2$ | —OCH$_3$ | 0.75-0.85 (6H, m), 1.2-1.5 (3H, m), 2.3-2.5 (2H, m), 2.6-2.9 (2H, m), 3.0-3.15 (1H, m), 3.35-3.5 (1H, m), 3.80 (3H, s), 3.94 (2H, t, J = 7.1 Hz), 4.75-4.85 (1H, m), 6.9-7.1 (2H, m), 12.05 (1H, br s) |
| 174 | —(CH$_2$)$_4$C$_6$H$_5$ | —OCH$_3$ | 1.38-1.45 (m, 4H), 2.33-2.42 (m, 2H), 2.44-2.50 (m, 2H). 2.70-2.81 (m, 2H), 3.10 (dd; J = 10.0, 14.5 Hz, 1H), 3.42 (dd; J = 4.3, 14.5 Hz, 1H), 3.74 (S, 3H), 3.88-3.96 (m, 2H), 4.80 (dd; J = 4.3, 10.0 Hz, 1H), 6.93 (d, J = 8.6 Hz, 1H), 6.97 (d, J = 8.6 Hz, 1H), 7.10 (d, J = 7.3 Hz, 2H), 7.14 (t, J = 7.3 Hz, 1H), 7.23 (t, J = 7.3 Hz, 2H), 12.10 (brs, 1H) |
| 175 | —(CH$_2$)$_5$C$_6$H$_5$ | —OCH$_3$ | 1.04-1.15 (m, 2H), 1.35-1.50 (m, 4H), 2.32-2.41 (m, 2H), 2.42-2.53 (m, 2H), 2.65-2.73 (m, 2H), 3.09 (dd; J = 10.0, 14.5 Hz, 1H), 3.42 (dd; J = 4.3, 14.5 Hz, 1H), 3.78 (S, 3H), 3.86-3.96 (m, 2H), 4.78 (dd; J = 4.3, 10.0 Hz, 1H), 6.94 (d, J = 8.6 Hz, 1H), 6.97 (d, J = 8.6 Hz, 1H), 7.11 (d, J = 7.5 Hz, 2H), 7.15 (t, J = 7.5 Hz, 1H), 7.24 (t, J = 7.5 Hz, 2H), 12.10 (brs, 1H) |

TABLE 56

| Ex. | R[101] | R[311] | R[201] | $^1$H NMR (DMSO-d$_6$) dppm |
|---|---|---|---|---|
| 176 | (piperidinyl-butanoyl group) | —H | —OCH$_3$ | 1.25-1.45 (4H, m), 1.45-1.70 (4H, m), 2.09 (2H, t, J = 7.7 Hz), 2.31-2.48 (2H, m), 2.65-2.88 (2H, m), 3.00-3.21 (3H, m), 3.21-3.50 (3H, m), 3.79 (3H, s), 3.85-4.00 (2H, m), 4.78 (1H, dd, J = 4.2, 10.0 Hz), 6.86-8.09 (2H, m), 12.08 (1H, brs). |
| 177 | (5-ethyl-2-phenylpyridin-yl) | —H | —OCH$_3$ | DMSO overlap (2H), 2.82-2.88 (2H, m), 3.06-3.14 (1H, m), 3.37-3.45 (1H, m), 3.66 (3H, s), 4.79 (1H, dd, J1 = 4.4 Hz, J2 = 9.5 Hz), 5.18 (2H, s), 6.85 (1H, d, J = 8.6 Hz), 6.91 (1H, d, J = 8.6 Hz), 7.39-7.66 (4H, m), 7.78-7.81 (2H, m), 8.43 (1H, d, J = 2.0 Hz), 12.56 (1H, brs) |
| 178 | (5-ethyl-2-morpholinopyridin-yl) | —H | —OCH$_3$ | DMSO overlap (2H), 2.67-2.73 (2H, m), 2.98-3.18 (2H, m), DMSO overlap (4H, m), 3.32-3.64 (4H, m), 3.75 (3H, s), 4.68-4.72 (1H, m), 5.09 (2H, s), 6.63 (1H, d, J = 8.9 Hz), 6.82-6.98 (2H, m), 7.18-7.22 (1H, m), 7.85 (1H, d, J = 2.1 Hz), 12.02 (1H, brs) |

TABLE 57

| Ex. | R[101] | R[311] | R[201] | $^1$H NMR (DMSO-d$_6$) dppm |
|---|---|---|---|---|
| 179 | (5-ethyl-2-(4-methylpiperazin-1-yl)pyridin-yl) | —H | —OCH$_3$ | 2.20 (3H, s), 2.34-2.38 (4H, m), DMSO overlap (2H, 4H), 2.71-2.76 (2H, m), 2.97-3.05 (2H, m), 3.75 (3H, s), 4.65-4.70 (1H, m), 5.08 (2H, s), 6.62 (1H, d, J = 8.7 Hz), 6.83 (1H, d, J = 8.6 Hz), 6.90 (1H, d, J = 8.6 Hz), 7.17 (1H, dd, J1 = 3.4 Hz, J2 = 8.7 Hz), 7.83 (1H, d, J = 2.4 Hz), NH n. d. (1H) |
| 180 | (5-ethyl-2,2'-bipyridin-yl) | —H | —OCH$_3$ | 2.55-2.57 (2H, m), 2.87-2.89 (2H, m), 3.07-3.14 (1H, m), 3.39-3.46 (1H, m), 3.64 (3H, s), 4.76-4.82 (1H, m), 5.19 (2H, s), 6.85 (1H, d, J = 8.5 Hz), 6.93 (1H, d, J = 8.5 Hz), 7.38-7.43 (1H, m), 7.61 (1H, dd, J1 = 2 Hz, J2 = 8.2 Hz), 7.90 (1H, ddd, J1 = 1.5 Hz, J2 = 7.8 Hz, J3 = 7.9 Hz), 8.24 (1H, d, J = 8.2 Hz), 8.32 (1H, d, J = 7.9 Hz), 8.45 (1H, d, J = 1.5 Hz), 8.64 (1H, d, J = 4.6 Hz), 12.06 (1H, brs) |

TABLE 57-continued

[Structure: thiazolidine-2,4-dione with R311 on N, connected via CH2 to a 3,4-dihydroquinolin-2(1H)-one with R101 on N and R201 on position 8]

| Ex. | R101 | R311 | R201 | $^1$H NMR (DMSO-$d_6$) dppm |
|---|---|---|---|---|
| 181 | 2-ethylquinolin-yl (CH2 linked) | —H | —OCH$_3$ | 2.55-2.60 (2H, m), 3.02-3.07 (2H, m), 3.11-3.16 (1H, m), 3.41-3.46 (1H, m), 3.52 (3H, s), 4.80-4.86 (1H, m), 5.30 (2H, s), 6.84 (1H, d, J = 8.5 Hz), 6.93 (1H, d, J = 8.5 Hz), 7.33 (1H, d, J = 8.6 Hz), 7.50-7.56 (1H, m), 7.66-7.72 (1H, m), 7.88-7.91 (1H, m), 8.21 (1H, d, J = 8.6 Hz), 12.12 (1H, brs) |

TABLE 58

[Structure: thiazolidine-2,4-dione with R311 on N, connected via CH2 to a 3,4-dihydroquinolin-2(1H)-one with R101 on N and R201 on position 8]

| Ex. | R101 | R311 | R201 | $^1$H NMR dppm |
|---|---|---|---|---|
| 182 | 4-ethylbiphenyl | —CH$_2$OCH$_3$ | —OCH$_2$OCH$_3$ | CDCl$_3$: 2.55-2.75 (2H, m), 2.75-3.0 (2H, m), 3.05-3.15 (1H, m), 3.28 (3H, s), 3.38 (3H, s), 3.55-3.65 (2H, m), 4.35-4.45 (1H, m), 4.9-5.1 (4H, m), 5.25-5.4 (2H, m), 4.35-4.45 (1H, m), 4.9-5.1 (4H, m), 5.25-5.4 (2H, m), 6.88 (1H, d, J = 8.6 Hz), 6.97 (1H, d, J = 8.6 Hz), 7.1-7.6 (11H, m) |
| 183 | 4-ethylbiphenyl | —CH$_2$OCH$_3$ | —OH | 2.45-2.55 (2H, m), 2.75-2.9 (2H, m), 3.05-3.2 (4H, m), 3.35-3.45 (1H, m), 4.7-5.0 (3H, m), 5.34 (2H, s), 6.65 (1H, d, J = 8.4 Hz), 6.76 (1H, d, J = 8.4 Hz), 7.1-7.7 (9H, m), 9.94 (1H, br s) |

DMSO-$d_6$ is used for measuring NMR, unless otherwise specified.

TABLE 59

[Structure: thiazolidine-2,4-dione (NH) linked via CH2 to a 3,4-dihydroquinolin-2(1H)-one bearing R201 and N-benzyl with R151 on the para position]

| Ex. | R151 | R201 | M.p. (° C.) |
|---|---|---|---|
| 184 | —Br | —H | 193.4-195.0 |
| 185 | —NO$_2$ | —H | 215.5-216.1 |

TABLE 60

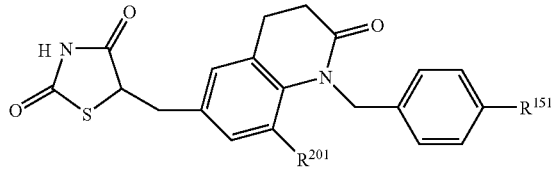

| Ex. | $R^{151}$ | $R^{201}$ | $^1$H NMR (DMSO-$d_6$) dppm |
|---|---|---|---|
| 186 | —C$_6$H$_5$ | —H | 2.62-2.76 (2H, m), 2.85-3.07 (3H, m), 3.20-3.40 (1H, m), 4.85 (1H, dd, J = 4.2, 9.7 Hz). 5.16 (2H, s), 6.89 (1H, d, J = 8.3 Hz), 6.96-7.06 (1H, m), 7.11 (1H, 2), 7.24-7.38 (3H, m), 7.38-7.50 (2H, m), 7.50-7.68 (4H, m), 12.02 (1H, s). |
| 187 | —C$_6$H$_5$ | —OCH$_3$ | 2.4.8-2.60 (2H, m), 2.60-2.88 (2H, m), 2.90-3.06 (1H, m), 3.26-3.40 (1H, m), 3.70 (3H, s), 4.82-4.95 (1H, m), 5.24 (2H, s), 6.73 (1H, d, J = 1.5 Hz), 6.80 (1H, d, J = 1.5 Hz), 7.18 (2H, d, J = 8.2 Hz), 7.25-7.37 (1H, m), 7.37-7.46 (2H, m), 7.46-7.55 (2H, m), 7.55-7.68 (2H, m), 12.06 (1H, brs). |
| 188 | —C$_6$H$_5$ | —CH$_3$ | 2.26 (3H, s), 2.45-2.60 (2H, m), 2.70-2.85 (2H, m), 2.87-3.05 (1H, m), 3.18-3.40 (1H, m), 4.87 (1H, dd, J = 4.3. 9.8 Hz), 5.07 (2H, s), 6.93 (1H, s), 6.98 (1H, s), 7.18 (2H, m), 7.27-7.38 (2H, m), 7.38-7.48 (2H, m), 7.48-7.56 (2H, m), 7.56-7.66 (2H, m), 12.06 (1H, s). |

TABLE 61

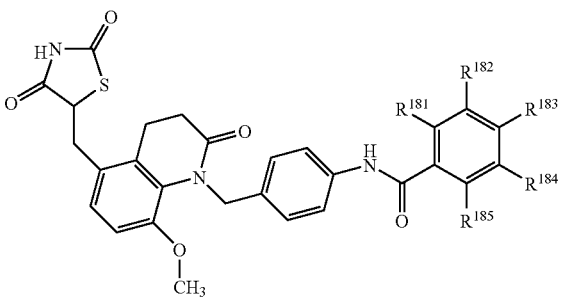

| Ex. | $R^{181}$ | $R^{182}$ | $R^{183}$ | $R^{184}$ | $R^{185}$ | M.p. (° C.) |
|---|---|---|---|---|---|---|
| 189 | —H | —H | —H | —H | —H | 231.1-232.2 |
| 190 | —H | —H | —H | —OC$_6$H$_5$ | —H | 208-209 |
| 191 | —H | —H | —OCH$_3$ | —H | —H | 199-200 |

TABLE 61-continued

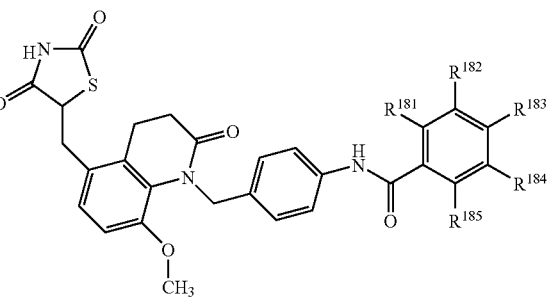

| Ex. | $R^{181}$ | $R^{182}$ | $R^{183}$ | $R^{184}$ | $R^{185}$ | M.p. (° C.) |
|---|---|---|---|---|---|---|
| 192 | —H | —H | —H | —H | —OCH$_3$ | 209 |
| 193 | —H | —H | —Cl | —H | —H | 223-225 |

TABLE 62

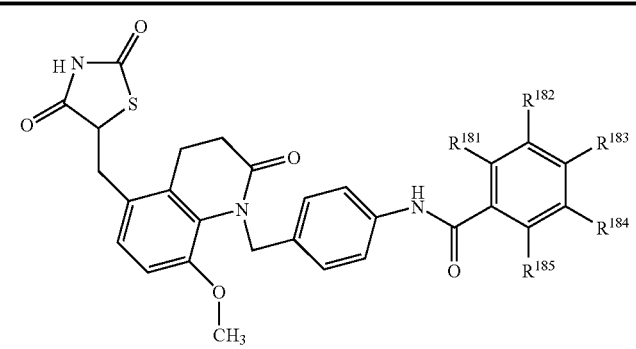

| Ex. | $R^{181}$ | $R^{182}$ | $R^{183}$ | $R^{184}$ | $R^{185}$ | $^1$H NMR (DMSO-$d_6$) dppm |
|---|---|---|---|---|---|---|
| 194 | —H | —H | —H | —OCH$_3$ | —H | 2.81-2.87 (2H, m), 3.01-3.11 (1H, m), DMSO overlap (2H, 1H), 3.71 (3H, s), 3.82 (3H, s), 4.58-4.61 (1H, m), 5.18 (2H, s). 6.82 (1H, d, J = 8.6 Hz), 6.90 (1H, d, J = 8.6 Hz), 7.03 (2H, d, J = 8.5 Hz), 7.11-7.15 (1H, m), |

TABLE 62-continued

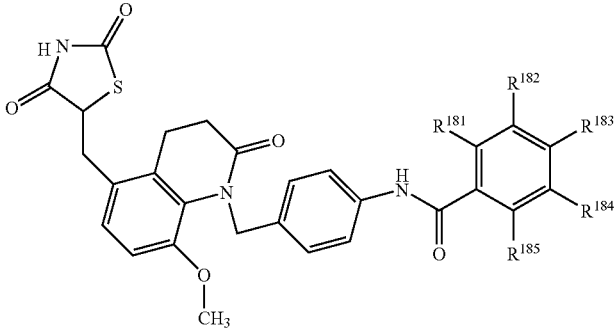

| Ex. | $R^{181}$ | $R^{182}$ | $R^{183}$ | $R^{184}$ | $R^{185}$ | $^1$H NMR (DMSO-$d_6$) dppm |
|---|---|---|---|---|---|---|
| 195 | —H | —H | —OC$_6$H$_5$ | —H | —H | 7.38-7.50 (3H, m), 7.57 (2H, d, J = 8.5 Hz), 10.10 (1H, s), 12.07 (1H, s) 2.80-2.86 (2H, m), 3.01-3.11 (1H, m), DMSO overlap (2H, 1H), 3.72 (3H, s), 4.78 (1H, dd, J1 = 4.4 Hz, J2 = 9.9 Hz), 5.18 (2H, s), 6.82 (1H, d, J = 8.6 Hz), 6.90 (1H, d, J = 8.6 Hz), 7.00-7.12 (6H, m), 7.19-7.25 (1H, m), 7.42-7.48 (2H, m), 7.57 (2H, d, J = 8.5 Hz), 7.94 (2H, d, J = 8.7 Hz), 10.08 (1H, s), 12.07 (1H, s) |
| 196 | —H | —H | —H | —H | —Cl | 2.80-2.86 (2H, m), 3.06 (1H, dd, J1 = 9.9 Hz, J2 = 14.5 Hz), DMSO overlap (2H, 1H), 3.73 (3H, s), 4.78 (1H, dd, J1 = 4.2 Hz, J2 = 9.9 Hz), 5.19 (2H, s), 6.82 (1H, d, J = 8.7 Hz), 6.90 (1H, d, J = 8.7 Hz), 7.02 (2H, d, J = 8.5 Hz), 7.37-7.54 (6H, m), 10.37 (1H, s), 12.05 (1H, 2) |
| 197 | —Cl | —H | —H | —H | —Cl | 2.82-2.88 (2H, m), 3.02-3.12 (1H, m), DMSO overlap (2H, 1H), 3.74 (3H, s), 4.76-4.79 (1H, m), 5.15 (2H, s), 6.78 (1H, d, J = 8.4 Hz), 6.91 (1H, d, J = 8.4 Hz), 7.04 (2H, d, J = 8.2 Hz), 7.48-7.56 (5H, m), 10.63 (1H, s), 12.07 (1H, s) |

TABLE 63

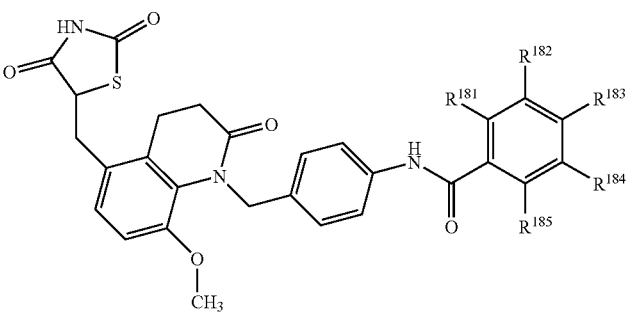

| Ex. | $R^{181}$ | $R^{182}$ | $R^{183}$ | $R^{184}$ | $R^{185}$ | MS (M + 1) |
|---|---|---|---|---|---|---|
| 198 | —H | —H | —NHCOCH$_3$ | —H | —H | 573 |
| 199 | —H | —H | —H | —NHCOCH$_3$ | —H | 573 |
| 200 | —H | —H | —CF$_3$ | —H | —H | 584 |
| 201 | —H | —H | —H | —H | —NO$_2$ | 561 |
| 202 | —H | —H | —H | —H | —C$_6$H$_5$ | 592 |
| 203 | —H | —H | —H | —H | —N(CH$_3$)$_2$ | 559 |
| 204 | —H | —H | —H | —H | —NHC$_6$H$_5$ | 607 |
| 205 | —Cl | —H | —H | —H | —Cl | 584 |
| 206 | —H | —H | —H | —CN | —H | 541 |
| 207 | —H | —H | —H | —NO$_2$ | —H | 561 |
| 208 | —H | —H | —H | —OC$_6$H$_5$ | —H | 608 |
| 209 | —H | —H | —H | —F | —CH$_3$ | 548 |
| 210 | —H | —H | —COCH$_3$ | —H | —H | 558 |
| 211 | —H | —H | —H | —H | —CF$_3$ | 584 |
| 212 | —H | —H | —H | —CF$_3$ | —H | 584 |

TABLE 63-continued
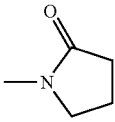
| Ex. | R181 | R182 | R183 | R184 | R185 | MS (M + 1) |
|---|---|---|---|---|---|---|
| 213 | —H | —H | —H | —H | —OC$_6$H$_5$ | 608 |
| 214 | —H | —H | —OC$_6$H$_5$ | —H | —H | 608 |
| 215 | —H | —H | —F | —H | —Cl | 568 |
| 216 | —H | —H | 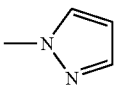 | —H | —H | 599 |
| 217 | —H | —H | -1-PYRRYL | —H | —H | 581 |
| 218 | —H | —H | 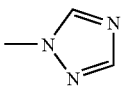 | —H | —H | 582 |
| 219 | —H | —H | 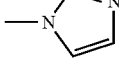 | —H | —H | 583 |
TABLE 64
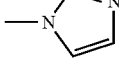
| Ex. | R181 | R182 | R183 | R184 | R185 | MS (M + 1) |
|---|---|---|---|---|---|---|
| 220 | —H | —H | 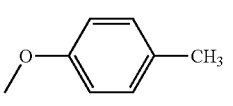 | —H | —H | 582 |
| 221 | —H | —H | —H | —H | —OCH$_3$ | 546 |
| 222 | —H | —Cl | —H | —H | —OCH$_3$ | 580 |
| 223 | —H | —H | —Cl | —H | —H | 550 |
| 224 | —H | —H | —H | —H | —H | 516 |
TABLE 65
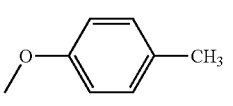
| Ex. | R191 | M.p. (° C.) |
|---|---|---|
| 225 | -cyclo-C$_6$H$_{11}$ | 124.7-126.4 |
| 226 | —NHC$_6$H$_5$ | 233.0-234.6 |
| 227 | —NHC$_2$H$_5$ | 195.7-196.9 |
| 228 | —C$_2$H$_5$ | 198.3-200.3 |
| 229 | —CH$_3$ | 215.2-217.8 |
| 230 | —OCH$_3$ | 136.3-138.6 |
| 231 | -3-PYRIDYL | 233.0-234.2 |
| 232 | —OC$_5$H$_{11}$ | 98-102 |
| 233 | (4-methoxyphenyl-CH$_3$) | 166-168 |
| 234 | —OCH$_2$C$_6$H$_5$ | 186-189 |

TABLE 66

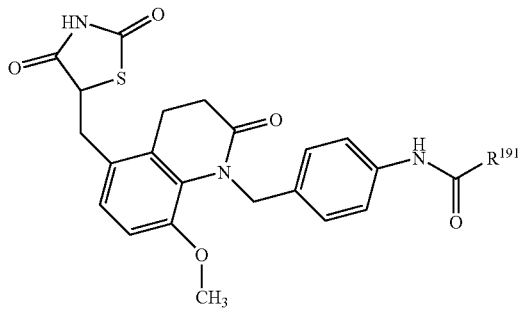

| Ex. | R191 | 1H NMR (DMSO-d6) dppm |
|---|---|---|
| 235 | -2-FURYL | 2.76-2.81 (2H, m), 3.01-3.11 (1H, m), DMSO overlap (2H), 3.32-3.42 (1H, m), 3.71 (3H, s), 4.76-4.79 (1H, m), 5.17 (2H, s), 6.67 (1H, dd, J1 = 1.7 Hz, J2 = 3.5 Hz), 6.82 (1H, d, J = 8.6 Hz), 6.90 (1H, d, J = 8.5 Hz), 7.01 (2H, d, J = 8.5 Hz), 7.28 (1H, dd, J1 = 0.7 Hz, J2 = 3.5 Hz), 7.55 (2H, d, J = 8.6 Hz), 7.90 (1H, dd, J1 = 0.7 Hz, J2 = 1.7 Hz), 10.06 (1H, s), 12.06 (1H, s) |
| 236 | 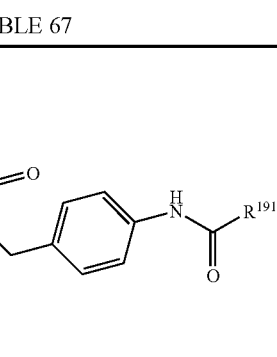 | 2.82-2.88 (2H, m), 3.03-3.13 (1H, m), DMSO overlap (2H, 1H), 3.73 (3H, s), 4.79 (1H, dd, J1 = 4.1 Hz, J2 = 9.9 Hz), 5.20 (2H, s), 6.83 (1H, d, J = 8.6 Hz), 6.91 (1H, d, J = 8.6 Hz), 7.05 (2H, d, J = 8.4 Hz), 7.58-7.66 (4H, m), 7.95-8.08 (4H, m), 8.52 (1H, s), 10.33 (1H, s), 12.06 (1H, s) |
| 237 | 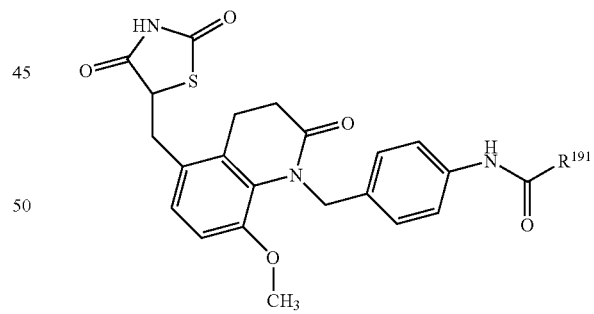 | 2.79-2.85 (2H, m), 3.00-3.10 (1H, m), DMSO overlap (2H, 1H), 3.70 (3H, s), 3.74 (3H, s), 4.74-4.78 (1H, m), 5.15 (2H, s), 6.80 (1H, d, J = 8.7 Hz), 6.91-7.00 (5H, m), 7.06-7.11 (2H, m), 7.30 (2H, d, J = 8.5 Hz), 10.01 (1H, s), 12.05 (1H, s) |

TABLE 67

| Ex. | R191 | MS (M + 1) |
|---|---|---|
| 238 | —(CH2)2OC6H5 | 560 |
| 239 | -3-PYRIDYL | 517 |
| 240 | -4-PYRIDYL | 517 |
| 241 | -2-FURYL | 506 |
| 242 | -2-THIENYL | 522 |
| 243 | -3-FURYL | 506 |
| 244 | -3-THIENYL | 522 |
| 245 | -cyclo-C5H9 | 508 |
| 246 | -cyclo-C6H11 | 522 |
| 247 | —CH2-cyclo-C6H11 | 536 |
| 248 | —CH2OC6H5 | 546 |
| 249 | —(CH2)2C6H5 | 544 |
| 250 | -2-PYRIDYL | 517 |
| 251 | —CH=CHC6H5 (trans) | 542 |
| 252 | —OC6H5 | 532 |
| 253 | —OC3H7 | 498 |
| 254 | —OC5H11 | 526 |
| 255 | —OCH2C6H5 | 546 |
| 256 | —OCH3 | 470 |
| 257 | —OC4H9 | 512 |

TABLE 68

| Ex. | R191 | MS (M + 1) |
| --- | --- | --- |
| 258 | 3-(propyl)pyridine | 545 |
| 259 | 2-ethylpyridine | 531 |
| 260 | 3-ethylpyridine | 531 |
| 261 | 2-ethylthiophene | 536 |
| 262 | 5-methyl-2-(1H-pyrrol-1-yl)pyridine | 582 |
| 263 | 3-ethylthiophene | 536 |
| 264 | ethylcyclopentane | 522 |
| 265 | (4-methylpiperidin-1-yl)(phenyl)methanone | 627 |
| 266 | 1-(4-methylpiperidin-1-yl)ethanone | 565 |

TABLE 69

| Ex. | R191 | MS (M + 1) |
| --- | --- | --- |
| 267 | 2-methylchroman | 572 |
| 268 | 2-methylnaphthalene | 566 |
| 269 | 1-methylnaphthalene | 566 |
| 270 | 5-methylbenzo[d][1,3]dioxole | 560 |
| 271 | 2-ethylisoindoline-1,3-dione | 599 |
| 272 | 3-ethyl-2-thioxothiazolidin-4-one | 585 |
| 273 | 1-propylpiperidine | 551 |
| 274 | 1-chloro-2-ethylbenzene | 564 |
| 275 | 1-chloro-2-(prop-1-enyl)benzene | 576 |

TABLE 70
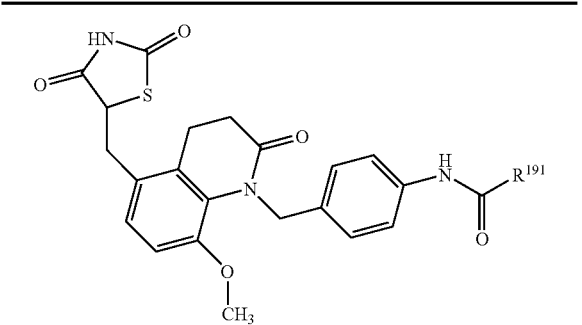
| Ex. | R191 | MS (M + 1) |
|---|---|---|
| 276 | 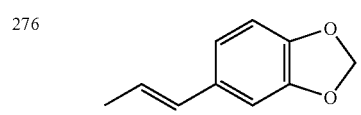 | 586 |
| 277 | 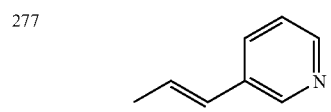 | 543 |
| 278 | 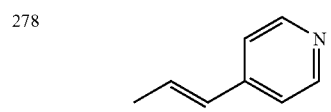 | 543 |
| 279 | 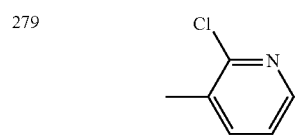 | 551 |
| 280 | 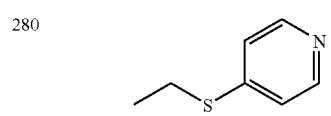 | 563 |
| 281 | 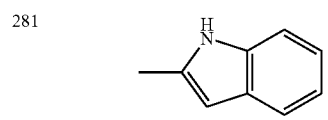 | 555 |
| 282 | 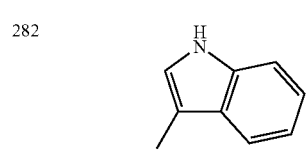 | 555 |
| 283 | 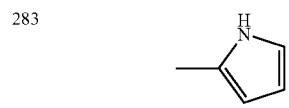 | 505 |
| 284 | 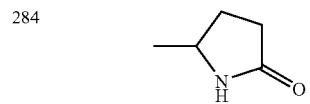 | 523 |
TABLE 71
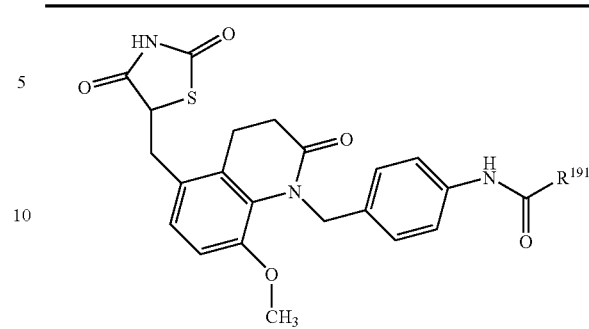
| Ex. | R191 | MS (M + 1) |
|---|---|---|
| 285 |  | 556 |
| 286 | 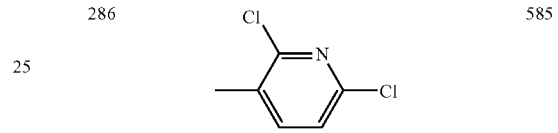 | 585 |
| 287 | 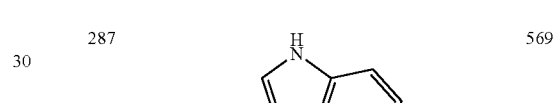 | 569 |
| 288 | 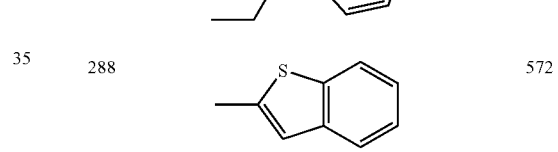 | 572 |
| 289 | 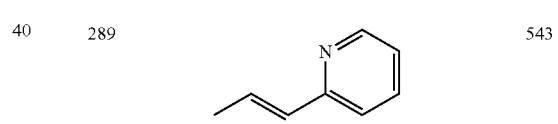 | 543 |
| 290 | 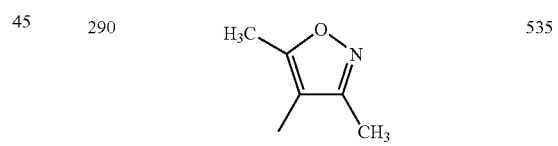 | 535 |
| 291 | 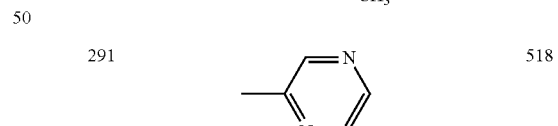 | 518 |
| 292 | 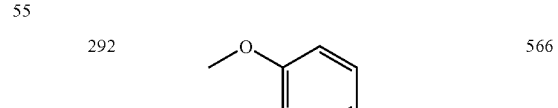 | 566 |
| 293 | 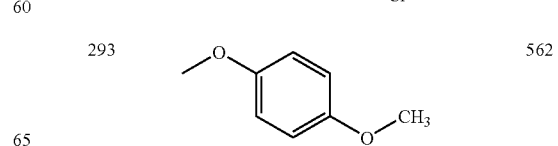 | 562 |

TABLE 72
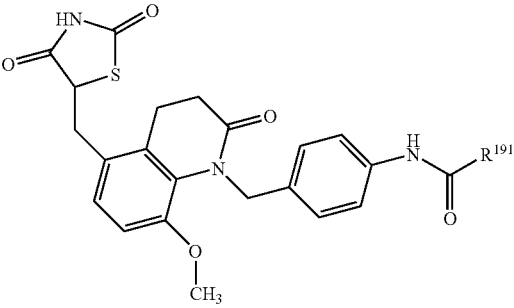
| Ex. | R¹⁹¹ | MS (M + 1) |
|---|---|---|
| 294 | 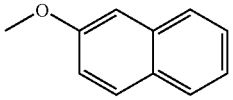 | 582 |
| 295 | 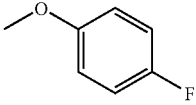 | 550 |
| 296 | 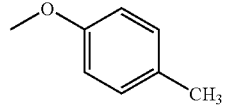 | 546 |
| 297 | 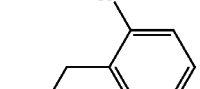 | 580 |
| 298 | 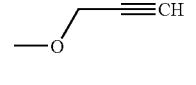 | 494 |
| 299 | 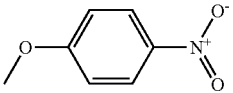 | 577 |
| 300 | 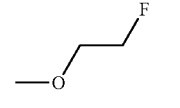 | 502 |
| 301 |  | 510 |
| 302 | 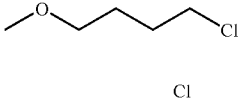 | 546 |
| 303 | 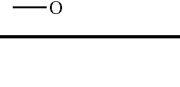 | 518 |
TABLE 73
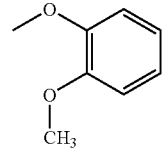
| Ex. | R¹⁹¹ | MS (M + 1) |
|---|---|---|
| 304 | 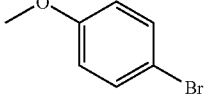 | 562 |
| 305 | 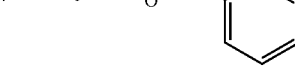 | 612 |
| 306 | 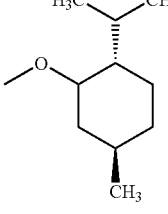 | 590 |
| 307 | 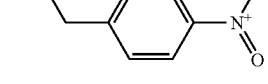 | 594 |
| 308 | 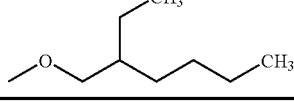 | 591 |
| 309 | | 568 |
TABLE 74
| Ex. | $R^{211}$ | $R^{212}$ | $R^{213}$ | $R^{214}$ | $R^{215}$ | M.p. (° C.) |
|---|---|---|---|---|---|---|
| 310 | —H | —H | —CH(CH₃)₂ | —H | —H | 226 |
| 311 | —H | —H | —H | —OC₆H₅ | —H | 139-142 |
| 312 | —H | —H | —Cl | —H | —H | 154-158 |
| 313 | —H | —H | —OCH₃ | —H | —H | 225-230 |

TABLE 75

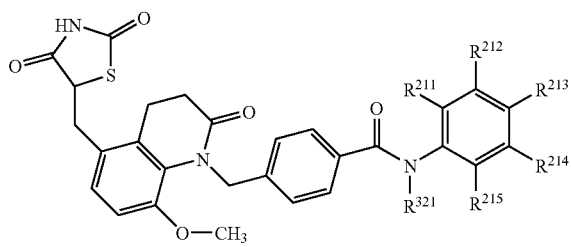

| Ex. | R321 | R211 | R212 | R213 | R214 | R215 | M.p. (° C.) |
|---|---|---|---|---|---|---|---|
| 314 | —H | —H | —H | —H | —H | —H | 242.7-243.5 |
| 315 | —H | —H | —H | —Cl | —H | —H | 240-241 |
| 316 | —H | —H | —H | —CH(CH₃)₂ | —H | —H | 243-244 |

TABLE 75-continued

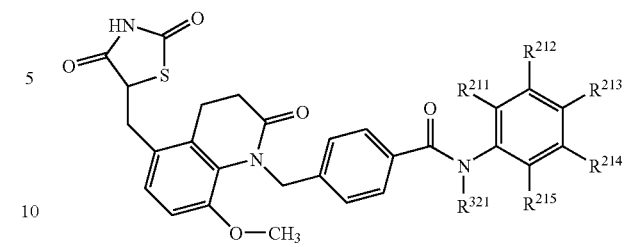

| Ex. | R321 | R211 | R212 | R213 | R214 | R215 | M.p. (° C.) |
|---|---|---|---|---|---|---|---|
| 317 | —H | —H | —H | —OC₆H₅ | —H | —H | 152-156 |
| 318 | —H | —H | —H | —OCH₃ | —H | —H | 215-216 |
| 319 | —H | —H | —H | —H | —OC₆H₅ | —H | 203-204 |

TABLE 76

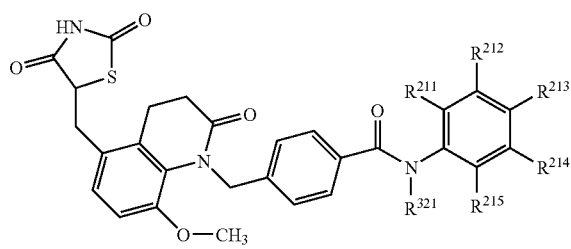

| Ex. | R321 | R211 | R212 | R213 | R214 | R215 | MS (M + 1) |
|---|---|---|---|---|---|---|---|
| 320 | —H | —H | —H | —H | —H | —OCH₃ | 546 |
| 321 | —CH₃ | —H | —H | —H | —H | —OCH₃ | 560 |
| 322 | —H | —H | —H | —H | —SCH₃ | —H | 562 |
| 323 | —H | —H | —H | —H | —H | —SCH₃ | 562 |
| 324 | —H | —H | —H | —Cl | —Cl | —H | 584 |
| 325 | —H | —H | —H | —OCF₃ | —H | —H | 600 |
| 326 | —H | —H | —H | —H | —H | —H | 516 |
| 327 | —H | —H | —H | —Cl | —H | —H | 550 |
| 328 | —H | —H | —H | —OCH₃ | —H | —H | 546 |
| 329 | —H | —H | —H | —H | —OCH₃ | —H | 546 |
| 330 | —H | —H | —H | —H | —Cl | —H | 550 |
| 331 | —H | —H | —H | —CH₃ | —H | —H | 530 |
| 332 | —H | —H | —H | —OCH₃ | —H | —OCH₃ | 576 |
| 333 | —H | —OCH₃ | —H | —H | —Cl | —H | 580 |
| 334 | —H | —OCH₃ | —H | —H | —NHCOCH₃ | —H | 603 |
| 335 | —H | —H | —H | —OCH₃ | —OCH₃ | —H | 576 |
| 336 | —H | —H | —H | —H | —H | —C(CH₃)=CH₂ | 556 |
| 337 | —H | —H | —H | —H | —OCF₃ | —H | 600 |
| 338 | —H | —H | —H | —H | —H | —CH₃ | 530 |
| 339 | —H | —H | —H | —H | —H | —F | 534 |
| 340 | —H | —H | —H | —H | —F | —H | 534 |
| 341 | —H | —H | —H | —F | —H | —H | 534 |
| 342 | —H | —H | —H | —H | —N(CH₃)₂ | —H | 559 |
| 343 | —H | —H | —H | —OC₂H₅ | —H | —H | 560 |
| 344 | —H | —H | —H | —H | —CF₃ | —H | 584 |
| 345 | —H | —H | —H | —H | —NHCOCH₃ | —H | 573 |
| 346 | —H | —H | —H | —NHCOCH₃ | —H | —H | 573 |
| 347 | —CH₃ | —H | —H | —H | —CH₃ | —H | 544 |
| 348 | —H | —H | —H | —H | —H | —OC₆H₅ | 608 |
| 349 | —H | —H | —H | —H | —OC₆H₅ | —H | 608 |
| 350 | —H | —H | —H | —OC₆H₅ | —H | —H | 608 |

TABLE 77

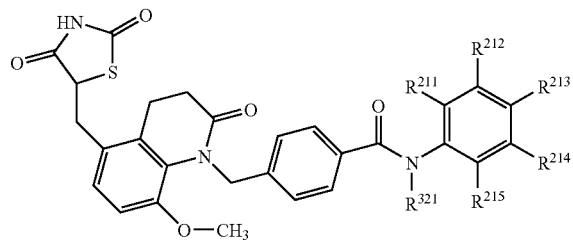

| Ex. | $R^{321}$ | $R^{211}$ | $R^{212}$ | $R^{213}$ | $R^{214}$ | $R^{215}$ | MS (M + 1) |
|---|---|---|---|---|---|---|---|
| 351 | —H | —H | —H | —CF$_3$ | —H | —H | 584 |
| 352 | —H | —H | —Cl | —H | —Cl | —H | 584 |
| 353 | —H | —H | —H | —H | —CH$_3$ | —CH$_3$ | 544 |
| 354 | —H | —H | —H | —CH$_3$ | —H | —CH$_3$ | 544 |
| 355 | —H | —H | —CH$_3$ | —H | —CH$_3$ | —H | 544 |
| 356 | —H | —H | —F | —H | —F | —H | 552 |
| 357 | —H | —H | —H | —OCH$_3$ | —F | —H | 564 |
| 358 | —H | —H | —H | —SO$_2$NH$_2$ | —H | —H | 595 |
| 359 | —H | —H | —H | —CH$_3$ | —OCH$_3$ | —H | 560 |
| 360 | —H | —H | —H | —OCH$_3$ | —Cl | —H | 580 |
| 361 | —H | —H | —H | —CH$_3$ | —Cl | —H | 564 |
| 362 | —H | —H | —OCH$_3$ | —H | —CF$_3$ | —H | 614 |
| 363 | —H | —H | —H | —F | —Cl | —H | 568 |
| 364 | —H | —H | —H | —OH | —Cl | —H | 566 |
| 365 | —H | —Cl | —H | —H | —NHCOCH$_3$ | —H | 607 |
| 366 | —H | —H | —H | —SCH$_3$ | —H | —H | 562 |
| 367 | —H | —H | —H | —CH(CH$_3$)$_2$ | —H | —H | 558 |
| 368 | —H | —H | —H | —C(CH$_3$)$_3$ | —H | —H | 572 |
| 369 | —H | —H | —H | —NHSO$_2$CH$_3$ | —H | —H | 609 |
| 370 | —H | —H | —H | —CONHCH$_3$ | —H | —H | 573 |
| 371 | —H | —H | —H | —H | —H | —OCH$_2$C$_6$H$_5$ | 622 |
| 372 | —H | —H | —H | —CH=CH$_2$ | —H | —H | 544 |
| 373 | —CH$_3$ | —H | —H | —Cl | —H | —H | 564 |
| 374 | —H | —H | —H | —H | —H | —Cl | 550 |
| 375 | —H | —H | —CN | —H | —H | —H | 541 |
| 376 | —H | —H | —H | —F | —H | —Cl | 568 |
| 377 | —H | —H | —H | —CN | —H | —H | 541 |

TABLE 78

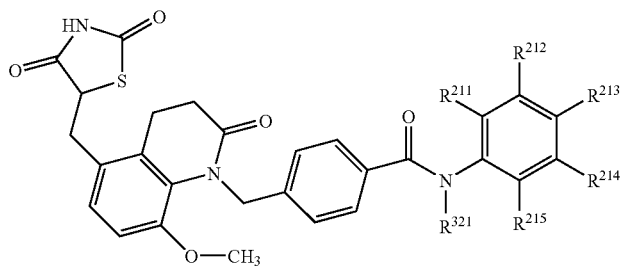

| Ex. | $R^{321}$ | $R^{211}$ | $R^{212}$ | $R^{213}$ | $R^{214}$ | $R^{215}$ | MS(M + 1) |
|---|---|---|---|---|---|---|---|
| 378 | —H | —H | —H | 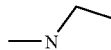 | —H | —H | 599 |
| 379 | —H | —H | —H |  | —H | —H | 614 |

TABLE 79
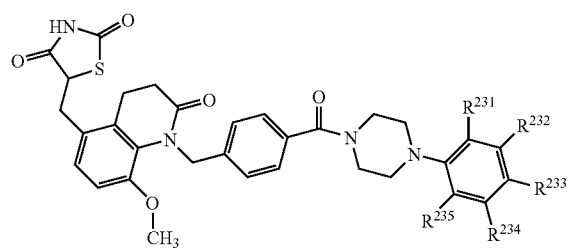
| Ex. | $R^{231}$ | $R^{232}$ | $R^{233}$ | $R^{234}$ | $R^{235}$ | MS (M + 1) |
|---|---|---|---|---|---|---|
| 380 | —H | —H | —H | —Cl | —H | 619 |
| 381 | —H | —H | —H | —H | —F | 603 |
| 382 | —H | —H | —H | —H | —OCH$_3$ | 615 |
| 383 | —H | —H | —F | —H | —H | 603 |
| 384 | —H | —H | —CF$_3$ | —H | —H | 653 |
| 385 | —H | —H | —CN | —H | —H | 610 |
| 386 | —H | —H | —H | —H | —H | 585 |
TABLE 80
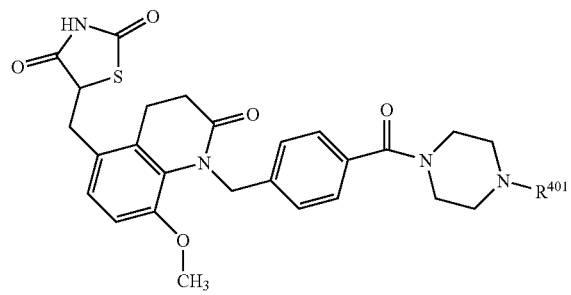
| Ex. | $R^{401}$ | MS (M + 1) |
|---|---|---|
| 387 | -2-PYRIDYL | 586 |
| 388 | -Cyclo-C$_5$H$_5$ | 577 |
| 389 | -4-PYRIDYL | 586 |
| 390 | —(CH$_2$)$_2$C$_6$H$_5$ | 613 |
| 391 | —CH$_3$ | 613 |
| 392 | —C(CH$_3$)$_3$ | 579 |
| 393 | -3-PYRIDYL | 586 |
| 394 | —H | 508 |
TABLE 81
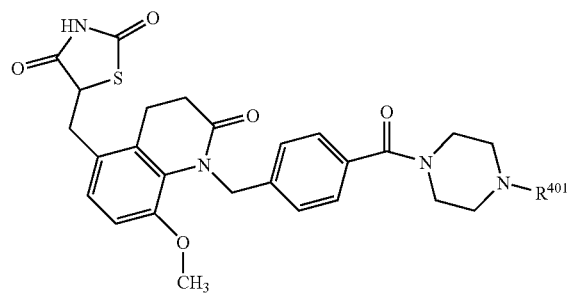
| Ex. | $R^{401}$ | MS (M + 1) |
|---|---|---|
| 395 | 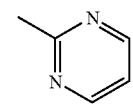 | 600 |
TABLE 81-continued
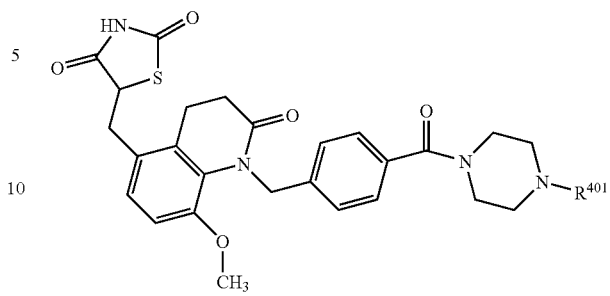
| Ex. | $R^{401}$ | MS (M + 1) |
|---|---|---|
| 396 | 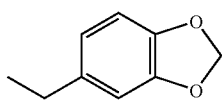 | 600 |
| 397 | 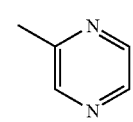 | 587 |
| 398 | 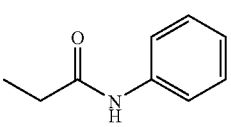 | 643 |
| 399 | 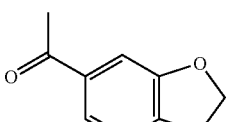 | 587 |
| 400 | 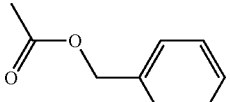 | 626 |
| 401 | 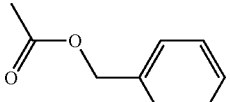 | 642 |
| 402 | 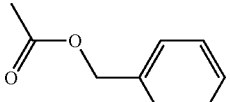 | 657 |
| 403 | 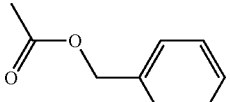 | 643 |

TABLE 82

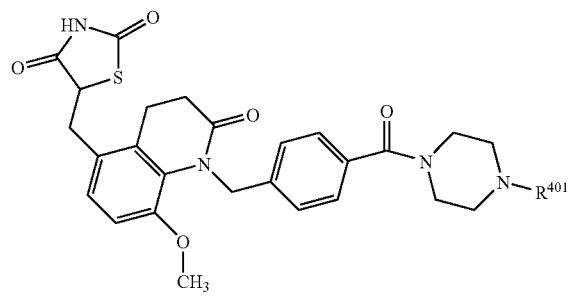

| Ex. | R401 | MS (M + 1) |
|---|---|---|
| 404 | 2-methyl-3-cyanopyridin-yl | 611 |
| 405 | 3-ethylfuran-yl | 589 |
| 406 | tetrahydropyran-4-yl-methyl | 593 |
| 407 | 2-propyl-1,3-dioxolan-2-yl | 609 |
| 408 | 1-propylimidazol-yl | 603 |
| 409 | 2,3-dimethylpyridin-yl | 600 |
| 410 | 2,4-dimethylpyridin-yl | 600 |
| 411 | 2-(pyridin-4-yl)ethyl | 614 |
| 412 | 8-methylnaphthalen-yl | 635 |
| 413 | N-methyl-4-(trifluoromethyl)anilino | 668 |

TABLE 83

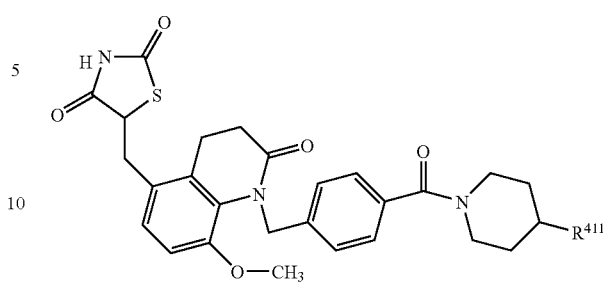

| Ex. | R411 | MS (M + 1) |
|---|---|---|
| 414 | —OCH₃ | 538 |
| 415 | -cyclo-C₆H₁₁ | 590 |
| 416 | —CH₂C₆H₅ | 598 |
| 417 | —C₆H₅ | 584 |

TABLE 84

| Ex. | R411 | MS (M + 1) |
|---|---|---|
| 418 | 1-methylpiperidin-yl | 591 |
| 419 | 2-fluoro-methoxymethylphenyl | 632 |
| 420 | N,N-dimethyl-2-phenylacetamido | 655 |
| 421 | 3,4-dimethylpiperazin-yl | 620 |
| 422 | 1-(4-chlorophenyl)ethanon-yl | 646 |
| 423 | 4-chlorobenzyl | 632 |

TABLE 84-continued
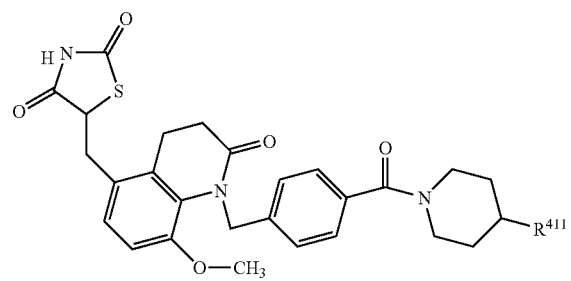
| Ex. | R411 | MS (M + 1) |
|---|---|---|
| 424 | -C(=O)NH-CH₃ (N-ethyl propanamide shown) | 593 |
| 425 | 4-methoxyphenyl | 614 |
| 426 | 1-methyl-3-phenylpyrrolidinyl | 653 |
| 427 | N,N-dimethyl-4-chloroanilino | 647 |
TABLE 85
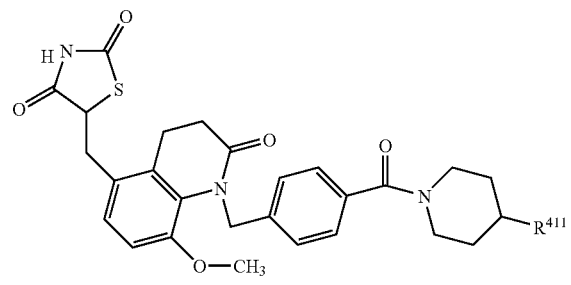
| Ex. | R411 | MS (M + 1) |
|---|---|---|
| 428 | 2-chloro-(ethyl)phenyl | 632 |
| 429 | 3-chloro-(ethyl)phenyl | 632 |
| 430 | 2-chloro-(vinyl)phenyl | 630 |
TABLE 85-continued
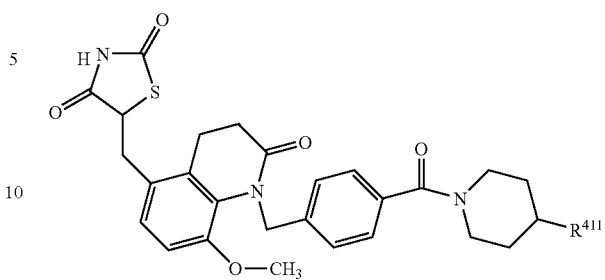
| Ex. | R411 | MS (M + 1) |
|---|---|---|
| 431 | 2-fluoro-(ethyl)phenyl | 616 |
| 432 | morpholinyl | 593 |
| 433 | 3-hydroxy-(methyl)phenyl | 600 |
| 434 | methyl-indanyl | 624 |
TABLE 86
| Ex. | R421 | R422 | M.p.(° C.) |
|---|---|---|---|
| 435 | —C₂H₅ | —H | 277.7-279.1 |
| 436 | —CH(CH₃)₂ | —H | 256.5-257.4 |
| 437 | —CH₂CH₂OH | —H | 248.1-249.9 |
| 438 | -3-PYRIDYL | —H | 251.9-254.1 |

TABLE 87

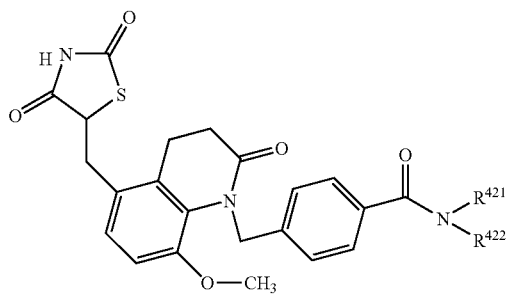

| Ex. | R⁴²¹ | R⁴²² | MS (M + 1) |
|---|---|---|---|
| 439 | -3-PYRIDYL | —H | 517 |
| 440 | -cyclo-C₆H₁₁ | —CH₃ | 536 |
| 441 | —C₄H₉ | —C₄H₉ | 552 |
| 442 | —CH₂CH(CH₃)₂ | —CH₂CH(CH₃)₂ | 552 |
| 443 | —CH₂-cyclo-C₃H₅ | —C₃H₇ | 536 |
| 444 | -cyclo-C₅H₉ | —CH₂CH=CH₂ | 548 |
| 445 | —C₄H₉ | —H | 496 |
| 446 | -cyclo-C₃H₅ | —H | 480 |
| 447 | —CH₂C₆H₅ | —H | 530 |
| 448 | —CH₂C₆H₅ | -cyclo-C₆H₁₁ | 612 |
| 449 | —CH₂C₆H₅ | —CH(CH₃)₂ | 572 |
| 450 | -cyclo-C₆H₁₁ | —C₂H₅ | 550 |
| 451 | —C₃H₇ | —H | 482 |
| 452 | —CH₂-cyclo-C₆H₁₁ | —C₂H₅ | 564 |
| 453 | —CH₂CH₂OC₂H₅ | —H | 512 |
| 454 | -1-CH₃-CYCLOHEXYL | —H | 536 |
| 455 | —CH₂-cyclo-C₆H₁₁ | —H | 536 |
| 456 | —CH(CH₃)C₆H₅ | —H | 544 |
| 457 | —(CH₂)₃C₆H₅ | —H | 558 |
| 458 | —(CH₂)₂C₆H₅ | —H | 544 |
| 459 | —CH₂CONH₂ | —H | 497 |
| 460 | —CH₂CO₂CH₃ | —CH₃ | 526 |
| 461 | —C₅H₁₁ | —CH₃ | 524 |
| 462 | -2-PYRIDYL | —H | 517 |

TABLE 88

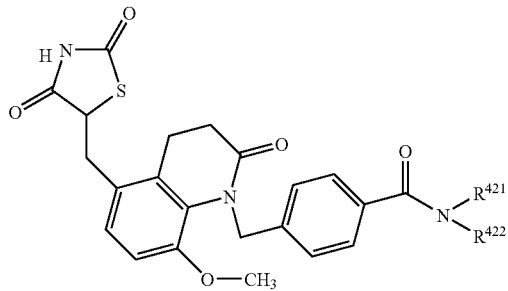

| Ex. | R⁴²¹ | R⁴²² | MS (M + 1) |
|---|---|---|---|
| 463 |  | —CH₃ | 559 |
| 464 | 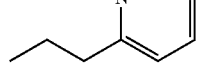 | —CH₃ | 551 |

TABLE 88-continued

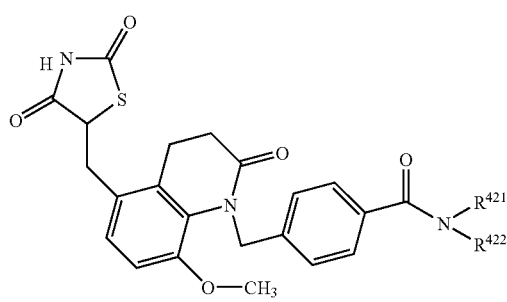

| Ex. | R⁴²¹ | R⁴²² | MS (M + 1) |
|---|---|---|---|
| 465 | 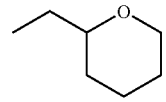 | —C₂H₅ | 566 |
| 466 | 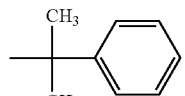 | —H | 558 |
| 467 | 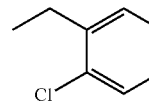 | —H | 564 |
| 468 | 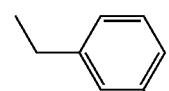 | —H | 564 |
| 469 | 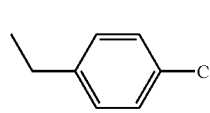 | —H | 564 |
| 470 | 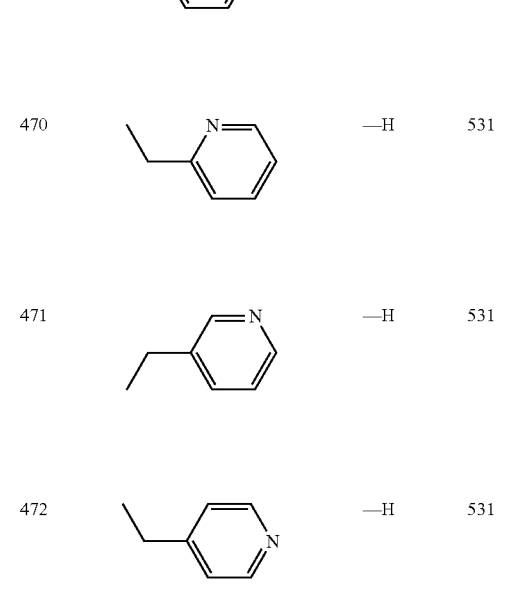 | —H | 531 |
| 471 | | —H | 531 |
| 472 | | —H | 531 |

TABLE 89

| Ex. | R⁴²¹ | R⁴²² | MS (M + 1) |
|---|---|---|---|
| 473 | 2-ethylfuran | —H | 520 |
| 474 | 4-methyl-1-benzoylpiperidine | —CH₃ | 641 |
| 475 | 1-acetyl-4-methylpiperidine | —CH₃ | 579 |
| 476 | N-methylpropanamide | —CH₂C₆H₅ | 601 |
| 477 | N-methyl-N-phenylbutanamide | —CH₃ | 615 |
| 478 | 4-methylbenzyl (ethyl) | —CH₃ | 558 |
| 479 | 6-ethyl-1,3-benzodioxole | —CH₃ | 588 |
| 480 | 2-methoxy-methylbenzene | —CH₃ | 574 |
| 481 | 4-ethylpyridine | —C₂H₅ | 559 |

TABLE 90

| Ex. | R⁴²¹ | R⁴²² | MS (M + 1) |
|---|---|---|---|
| 482 | 4-ethoxyphenethyl | —C₂H₅ | 602 |
| 483 | 2,2-dimethyl-3-phenylpropyl | —H | 572 |
| 484 | 1-(4-chlorophenyl)-4-methylpiperidine | —CH₃ | 647 |
| 485 | 1-methylcyclopropylmethyl | —H | 494 |
| 486 | 1-methylcyclopentyl | —H | 522 |
| 487 | 3-methoxypropylbenzene | —H | 574 |
| 488 | 4-(trifluoromethoxy)phenethyl | —H | 614 |
| 489 | 1-chloro-4-propylbenzene | —H | 578 |
| 490 | 5-ethyl-1,3-benzodioxole | —H | 574 |
| 491 | 4-fluorophenethyl | —H | 548 |

TABLE 91

Core structure: thiazolidine-2,4-dione-CH₂-(8-methoxy-2-oxo-1,2,3,4-tetrahydroquinolin-5-yl) with N-benzyl-4-carboxamide bearing NR⁴²¹R⁴²²

| Ex. | R⁴²¹ | R⁴²² | MS (M + 1) |
|---|---|---|---|
| 492 | (1H-imidazol-1-yl)butyl | —H | 548 |
| 493 | 3-(diisopropylamino)propyl | —H | 567 |
| 494 | methyl 2-methyl-3-(4-hydroxyphenyl)propanoate | —H | 618 |
| 495 | 2-methyl-3-(1H-imidazol-4-yl)propanamide | —H | 577 |
| 496 | methyl 2-methyl-3-(1H-imidazol-4-yl)propanoate | —H | 592 |
| 497 | 3-methyl-2-oxotetrahydrofuran-3-yl | —H | 524 |
| 498 | 2,6-dichloro-phenylethyl | —C₂H₅ | 626 |
| 499 | N-(4-methylphenyl)propanamide | —CH₃ | 601 |

TABLE 92

Core structure: thiazolidine-2,4-dione-CH₂-(8-methoxy-2-oxo-1,2,3,4-tetrahydroquinolin-5-yl) with N-benzyl-4-carboxamide bearing NR⁴²¹R⁴²²

| Ex. | R⁴²¹ | R⁴²² | MS (M + 1) |
|---|---|---|---|
| 500 | 4-chlorophenethyl | —C₂H₅ | 592 |
| 501 | 4-(trifluoromethyl)phenethyl | —C₂H₅ | 626 |
| 502 | 3-bromophenethyl | —C₂H₅ | 638 |
| 503 | 2-methoxyphenethyl | —H | 560 |
| 504 | 3-(2-fluorophenyl)propyl | —H | 562 |
| 505 | 3-(3-fluorophenyl)propyl | —H | 562 |
| 506 | 2-(1-ethylpyrrolidin-2-yl)ethyl | —H | 551 |
| 507 | 3-(pyrrolidin-1-yl)propyl | —H | 537 |
| 508 | 3-morpholinopropyl | —H | 553 |
| 509 | 4-morpholinobutyl | —H | 567 |

TABLE 93

| Ex. | R⁴²¹ | R⁴²² | MS (M+1) |
|---|---|---|---|
| 510 | 2,3-dimethylcyclohexyl | —H | 536 |
| 511 | 1-(4-fluorobenzoyl)-4-methylpiperidin-4-yl | —CH₃ | 659 |
| 512 | 2,3-dimethylpyridin-4-yl | —H | 531 |
| 513 | 3-methoxy-2-methylpyridin-4-yl | —H | 547 |
| 514 | 5-methyl-1H-indol-3-yl | —H | 555 |
| 515 | 2,5-dimethylpyridin-3-yl | —H | 531 |
| 516 | 2-methylthiazol-4-yl | —H | 523 |
| 517 | 3-methyl-1H-1,2,4-triazol-5-yl | —H | 507 |
| 518 | 5-methyl-1H-tetrazol-2-yl | —H | 508 |
| 519 | 3,5-dimethylisoxazol-4-yl | —H | 521 |

TABLE 94

| Ex. | R⁴³¹ | MS (M+1) |
|---|---|---|
| 520 | 1-methylazepan-1-yl | 522 |
| 521 | 2-ethyl-1-methyl-4,5-dihydroimidazol-1-yl | 539 |
| 522 | 4-methylthiomorpholin-4-yl | 526 |
| 523 | 1,2,5-trimethyl-2,5-dihydropyrrol-1-yl | 520 |
| 524 | 3-methylthiazolidin-3-yl | 512 |
| 525 | 3-methyl-3-azabicyclo[3.3.1]nonan-3-yl | 548 |
| 526 | 1,3,5-trimethylpiperidin-1-yl | 536 |
| 527 | 4-methyl-2-oxo-1-phenylpiperazin-4-yl | 599 |
| 528 | 2-methyl-1,2,3,4-tetrahydroisoquinolin-2-yl | 556 |

TABLE 95
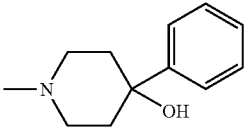
| Ex. | R431 | MS (M + 1) |
|---|---|---|
| 529 | 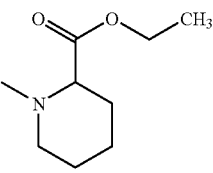 | 600 |
| 530 | 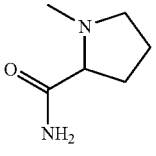 | 580 |
| 531 | 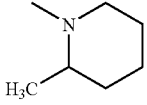 | 537 |
| 532 | 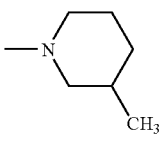 | 522 |
| 533 | 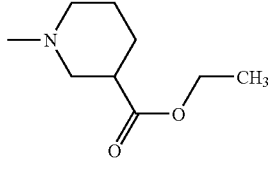 | 522 |
| 534 | 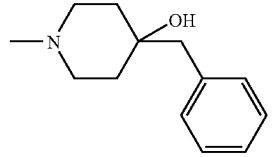 | 580 |
| 535 | 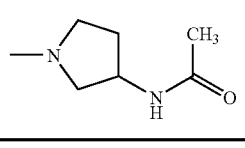 | 614 |
| 536 | 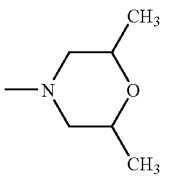 | 551 |
TABLE 96
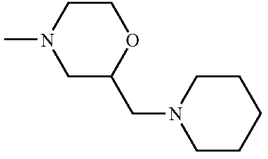
| Ex. | R431 | MS (M + 1) |
|---|---|---|
| 537 | 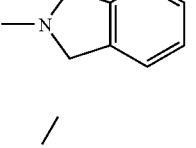 | 538 |
| 538 | 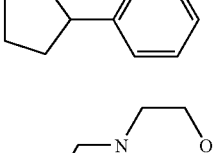 | 607 |
| 539 | 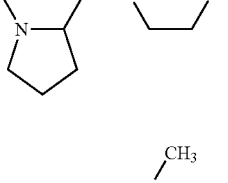 | 542 |
| 540 | 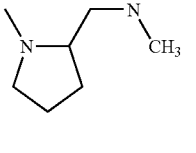 | 570 |
| 541 | 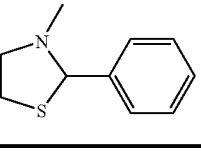 | 593 |
| 542 | | 551 |
| 543 | | 588 |

TABLE 97

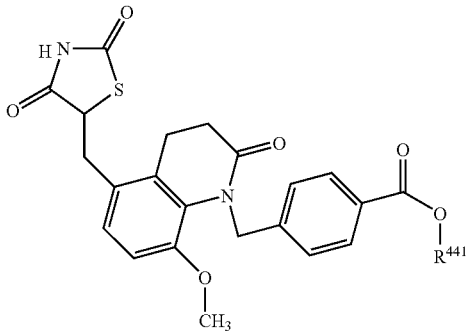

| Ex. | R441 | MS (M + 1) |
|---|---|---|
| 544 | 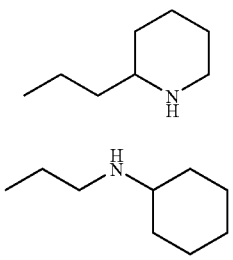 | 552 |
| 545 | 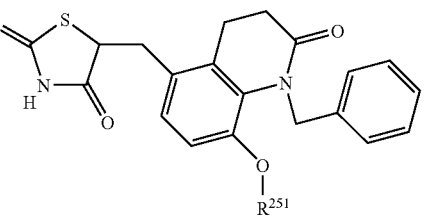 | 566 |

TABLE 98

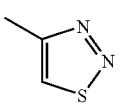

| Ex. | R241 | R242 | R243 | R244 | R245 | MS (M + 1) |
|---|---|---|---|---|---|---|
| 546 | —H | —H | —Cl | —H | —H | 507 |
| 547 | —Cl | —H | —H | —H | —H | 507 |
| 548 | —H | —CF3 | —H | —H | —H | 541 |
| 549 | —H | —H | —CF3 | —H | —H | 541 |
| 550 | —H | —H | —CH3 | —H | —H | 487 |
| 551 | —H | —F | —H | —H | —H | 491 |
| 552 | —H | —CH3 | —H | —H | —H | 487 |
| 553 | —H | —H | —CO2CH3 | —H | —H | 529 |
| 554 | —H | —Cl | —H | —H | —H | 507 |
| 555 | —H | —OCH3 | —H | —H | —H | 503 |
| 556 | —H | —H | —H | —NO2 | —H | 518 |
| 557 | —H | —H | —SO2CH3 | —H | —H | 551 |
| 558 | —OCH3 | —H | —H | —H | —H | 503 |
| 559 | —H | —H | —CH=CHC6H5(trans) | —H | —H | 575 |
| 560 | —H | —H | —OCOCH3 | —H | —H | 531 |
| 561 | —H | —H | —F | —H | —H | 491 |
| 562 | —H | —H | —OCH3 | —H | —H | 503 |
| 563 | —H | —H | 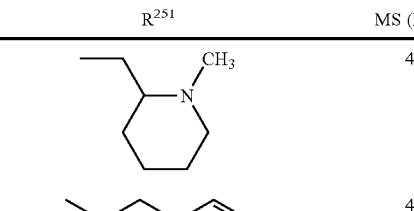 | —H | —H | 557 |
| 564 | —H | —H | —SCF3 | —H | —H | 573 |

TABLE 99

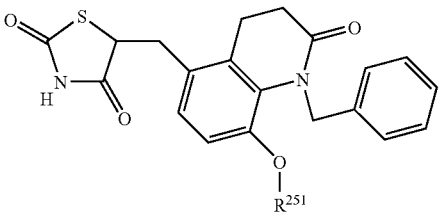

| Ex. | R251 | MS (M + 1) |
|---|---|---|
| 565 | —CH2CH2N(CH3)2 | 454 |
| 566 | —CH2CH=CHCH3(trans) | 437 |
| 567 | —(CH2)3CH=CH2 | 451 |
| 568 | —(CH2)2C6H5 | 487 |
| 569 | —CH2CCCH3 | 435 |
| 570 | —CH2CCC6H5 | 497 |
| 571 | —CH2CH(CH3)2 | 439 |
| 572 | —CH2COCH3 | 439 |
| 573 | —(CH2)3N(CH3)2 | 468 |
| 574 | —(CH2)2SC6H5 | 519 |
| 575 | —CH2CCH | 421 |
| 576 | —CH2CH=CHC6H5 | 499 |
| 577 | —CH2CON(CH3)2 | 468 |
| 578 | —CH2COC6H5 | 501 |
| 579 | —CH2CO2C2H5 | 469 |
| 580 | —(CH2)2OC6H5 | 503 |
| 581 | —(CH2)2OCH2C6H5 | 517 |
| 582 | —(CH2)4COC6H5 | 543 |
| 583 | —(CH2)3OCH2C6H5 | 531 |

TABLE 100

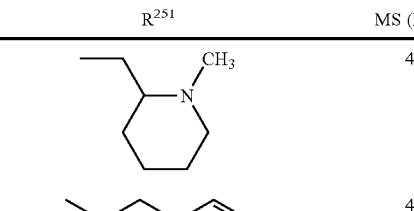

| Ex. | R251 | MS (M + 1) |
|---|---|---|
| 584 | 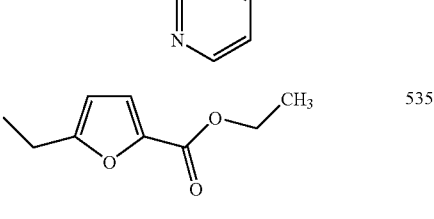 | 494 |
| 585 | 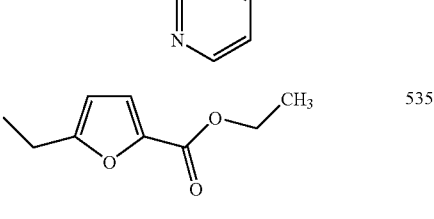 | 488 |
| 586 |  | 535 |

TABLE 100-continued

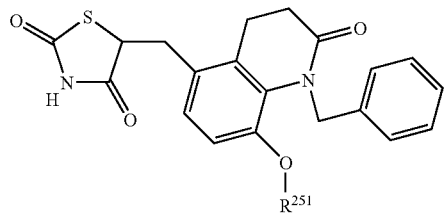

| Ex. | R251 | MS (M + 1) |
|---|---|---|
| 587 | 1-benzyl-5-ethyl-tetrazole | 555 |
| 588 | 5-ethyl-3-(4-tert-butylphenyl)-1,2,4-oxadiazole | 597 |
| 589 | 4-ethyl-3,5-dimethyl-isoxazole | 492 |
| 590 | 5-ethyl-2-(4-methylphenyl)-1,3,4-oxadiazole | 555 |
| 591 | 3-ethyl-pyridine | 474 |
| 592 | 4-ethyl-2-phenyl-thiazole | 556 |
| 593 | 2-ethyl-pyridine | 474 |

TABLE 101

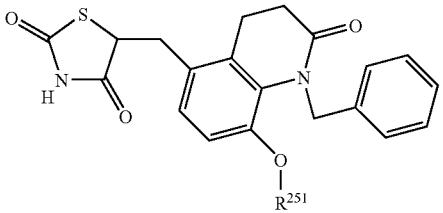

| Ex. | R251 | MS (M + 1) |
|---|---|---|
| 594 | 1-propyl-piperidine | 494 |
| 595 | 5-ethyl-4-methyl-2-(4-chlorophenyl)-thiazole | 604 |
| 596 | 5-ethyl-1-phenyl-tetrazole | 541 |
| 597 | 1-(4-chlorobenzoyl)-4-methyl-piperidine | 604 |
| 598 | 2-propyl-thiophene | 493 |
| 599 | 1-(cyclohexylmethyl)-5-ethyl-tetrazole | 561 |
| 600 | 5-ethyl-2-(trifluoromethyl)-pyridine | 542 |
| 601 | 1-(2-pyridyl)-propan-1-one | 502 |

TABLE 101-continued
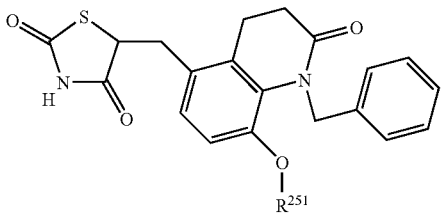
| Ex. | R251 | MS (M + 1) |
|---|---|---|
| 502 | (2-ethyl-1-benzyl-imidazole) | 553 |
TABLE 102
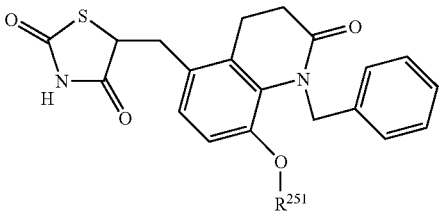
| Ex. | R251 | MS (M + 1) |
|---|---|---|
| 603 | (3-ethylthiophene) | 479 |
| 604 | (3-ethylfuran) | 463 |
| 605 | (2-methylindane) | 499 |
| 606 | (N-butylphthalimide) | 570 |
TABLE 103
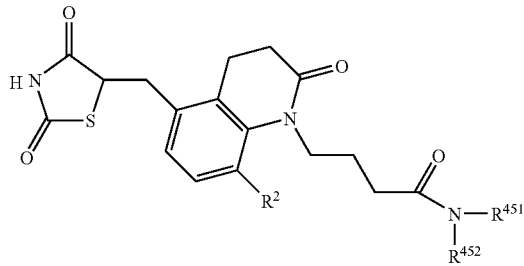
| Ex. | R451 | R452 | R2 | 1H NMR (DMSO-d6) dppm |
|---|---|---|---|---|
| 607 | —C2H5 | —C2H5 | —OCH3 | 0.94 (3H, t, J = 7.1 Hz), 0.99 (3H, t, J = 7.1 Hz), 1.50-1.69 (2H, m), 2.08 (2H, t, J = 7.7 Hz), 2.26-2.45 (2H, m), 2.63-2.85 (2H, m), 2.99-3.22 (5H, m), 3.31-3.49 (1H, m), 3.79 (3H, s), 3.82-4.03 (2H, m), 4.78 (1H, dd, J = 4.2, 10.0 Hz), 6.83-7.06 (2H, m), 12.08 (1H, brs). |
| 608 | —H | —C6H5 | —OCH3 | 1.64-1.81 (2H, m), 2.20 (2H, t, J = 7.4 Hz), 2.30-2.46 (2H, m), 2.63-2.92 (2H, m), 2.99-2.16 (1H, m), 2.35-2.50 (1H, m), 3.78 (3H, s), 3.86-4.02 (2H, m), 4.69-4.85 (1H, m), 6.87-7.07 (3H, m), 7.18-7.32 (2H, m), 7.54 (2H, d, J = 7.6 Hz), 9.80 (1H, s), 12.07 (1H, s). |
| 609 | —H | -cyclo-C6H11 | —OCH3 | 0.95-1.32 (5H, m), 1.42-1.75 (7H, m), 1.83-2.00 (2H, m), 2.25-2.45 (2H, m), 2.64-2.89 (2H, m), 3.00-3.15 (1H, m), 3.35-3.52 (2H, m), 3.79 (3H, s), 3.80-3.95 (2H, m), 4.77 (1H, dd, J = 4.2, 10.0 Hz), 6.81-7.05 (2H, m), 7.56 (1H, d, J = 7.8 Hz), 12.07 (1H, brs). |

TABLE 104
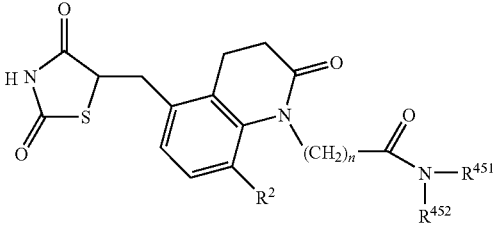
| Ex. | n | R451 | R452 | R2 | M.p. (° C.) |
|---|---|---|---|---|---|
| 610 | 1 | —H | -cyclo-$C_6H_{11}$ | —$OCH_3$ | 105-114 |
| 611 | 1 | —H | —$C_6H_5$ | —$OCH_3$ | 135-138.5 |
| 612 | 1 | —H | 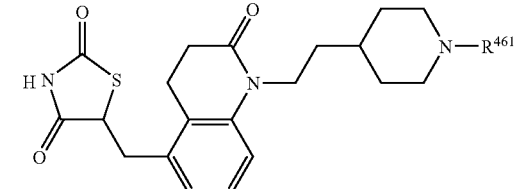 | —$OCH_3$ | 128-132.5 |
| 613 | 3 | —H | —$C_2H_5$ | —$OCH_3$ | 174.2-175.2 |
TABLE 105
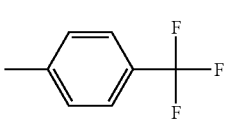
| Ex. | R461 | M.p. (° C.) |
|---|---|---|
| 614 | —$COCH_3$ | 209.5-211 |
| 615 | 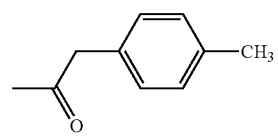 | 120-122 |
| 616 | 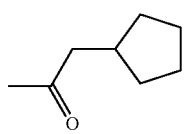 | 182-184.5 |
| 617 | —$COC_3H_7$ | 52-67 |
| 618 | 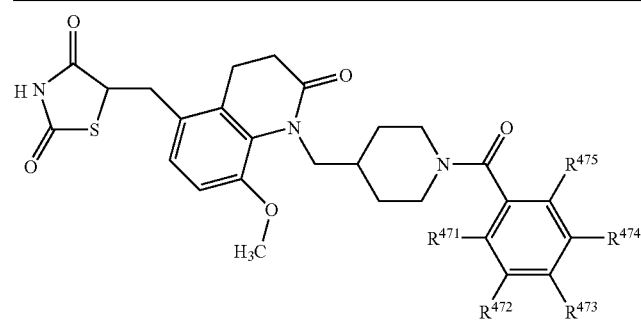 | 53-69 |
TABLE 106
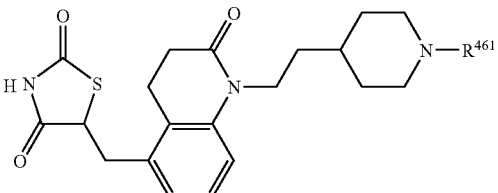
| Ex. | R471 | R472 | R473 | R474 | R475 | MS (M + 1) |
|---|---|---|---|---|---|---|
| 619 | —H | —H | —H | —H | —H | 508 |
| 620 | —H | —H | —$CH_3$ | —H | —H | 522 |
| 621 | —H | —H | —Cl | —H | —H | 542 |
| 622 | —H | —H | —F | —H | —H | 526 |
| 623 | —H | —H | —$OCH_3$ | —H | —H | 538 |
| 624 | —H | —Cl | —Cl | —H | —H | 576 |
| 625 | —Cl | —H | —H | —H | —H | 542 |
| 626 | —$CH_3$ | —H | —H | —H | —H | 522 |

TABLE 106-continued

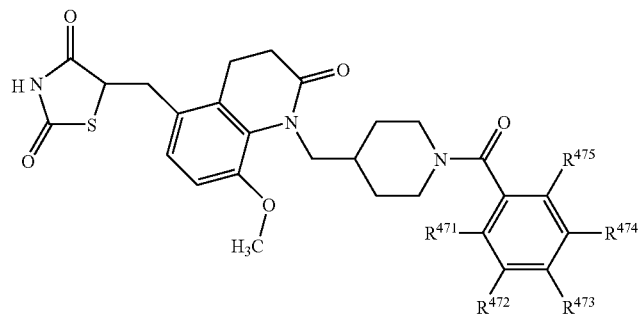

| | | | | | | MS |
|---|---|---|---|---|---|---|
| 627 | —H | —OCH₃ | —H | —H | —H | 538 |
| 628 | —H | —Cl | —H | —H | —H | 542 |
| 629 | —H | —CN | —H | —H | —H | 533 |
| 630 | —Cl | —Cl | —H | —H | —H | 576 |
| 631 | —H | —CF₃ | —H | —H | —H | 576 |
| 632 | —Cl | —H | —F | —H | —H | 560 |
| 633 | —H | —OC₆H₅ | —H | —H | —H | 600 |
| 634 | —OCH₃ | —H | —H | —Cl | —H | 572 |
| 635 | —H | —H | —CF₃ | —H | —H | 576 |
| 636 | —H | —OCF₃ | —H | —H | —H | 592 |
| 637 | —Br | —H | —H | —H | —H | 588 |
| 638 | —H | —H | —OCF₃ | —H | —H | 592 |
| 639 | —OCF₃ | —H | —H | —H | —H | 592 |
| 640 | —H | —H | —CN | —H | —H | 533 |
| 641 | —H | —H | —C(CH₃)₃ | —H | —H | 564 |
| 642 | —H | —H | —CO₂CH₃ | —H | —H | 566 |
| 643 | —H | —Br | —H | —H | —H | 586 |
| 644 | —CF₃ | —H | —H | —H | —H | 576 |
| 645 | —H | —H | -(1-methylpyrazol-3-yl) | —H | | 574 |

TABLE 107

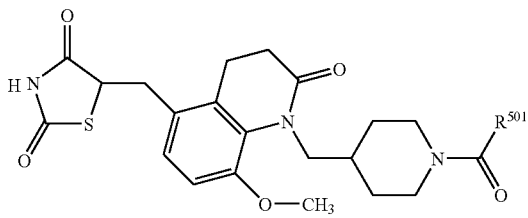

| Ex. | R⁵⁰¹ | MS (M + 1) |
|---|---|---|
| 646 | —CH=CHC₆H₅(trans) | 534 |
| 647 | -2-PYRIDYL | 509 |
| 648 | -3-PYRIDYL | 509 |
| 649 | -4-PYRIDYL | 509 |
| 650 | -2-FURYL | 498 |
| 651 | -2-THIENYL | 514 |
| 652 | -3-FURYL | 498 |
| 653 | -3-THIENYL | 514 |
| 654 | —CH₂-cyclo-C₆H₁₁ | 528 |
| 655 | —(CH₂)₂C₆H₅ | 536 |
| 656 | —OC₆H₅ | 524 |
| 657 | —OCH₂C₆H₅ | 538 |
| 658 | —OC₄H₉ | 504 |

TABLE 107-continued

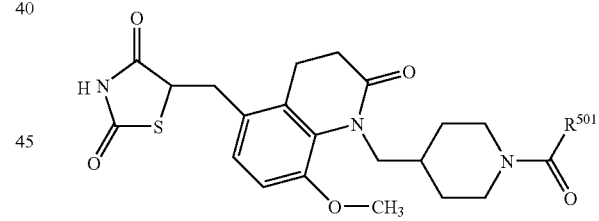

| Ex. | R⁵⁰¹ | MS (M + 1) |
|---|---|---|
| 659 | -cyclo-C₆H₁₁ | 514 |
| 660 | -cyclo-C₃H₅ | 472 |
| 661 | -cyclo-C₄H₇ | 486 |
| 662 | —CH₂OC₆H₅ | 538 |
| 663 | —CH(C₂H₅)C₄H₉ | 530 |
| 664 | —N(C₂H₅)₂ | 503 |
| 665 | —(CH₂)₂SCH₃ | 506 |
| 666 | —OCH₂CCH | 486 |
| 667 | —O(CH₂)₄Cl | 538 |

TABLE 108

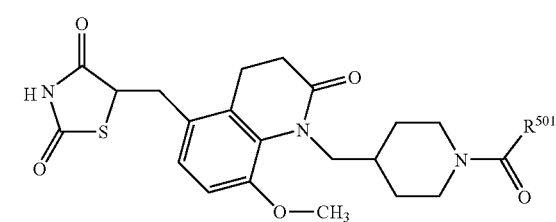

| Ex. | R⁵⁰¹ | MS (M + 1) |
|---|---|---|
| 668 | (4-chlorobenzyl, ethyl linker) | 556 |
| 669 | (4-chlorophenyl ethoxy) | 572 |
| 670 | (4-methyl-1-acetylpiperidine) | 557 |
| 671 | (2-chloro-3-methylpyridine) | 543 |
| 672 | (2,3-dichloro-5-methylpyridine) | 577 |
| 673 | (2-chloro-4-methylpyridine) | 543 |
| 674 | (5-methylpyrrolidin-2-one) | 515 |
| 675 | (5-methyl-2-trifluoromethylpyridine) | 577 |
| 676 | (4-methyltetrahydropyran) | 516 |
| 677 | (6-methylnaphthalene) | 558 |

TABLE 109

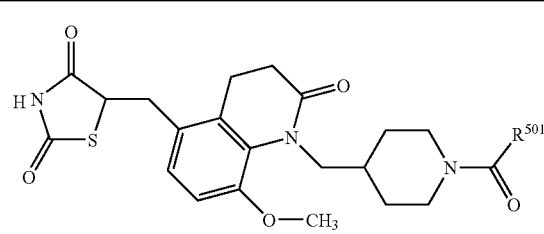

| Ex. | R⁵⁰¹ | MS (M + 1) |
|---|---|---|
| 678 | (2-methylindole) | 547 |
| 679 | (2-methylbenzofuran) | 548 |
| 680 | (2-methylbenzothiophene) | 564 |
| 681 | (4-chloro-2-methoxyphenyl) | 558 |
| 682 | (2,5-dimethoxyphenyl) | 554 |
| 683 | (6-methoxynaphthalene) | 574 |
| 684 | (4-fluoro-2-methoxyphenyl) | 542 |
| 685 | (2-methoxy-4-methylphenyl) | 538 |
| 686 | (2-chloro-6-methoxymethylphenyl) | 572 |
| 687 | (isopropoxyphenyl) | 552 |

TABLE 110
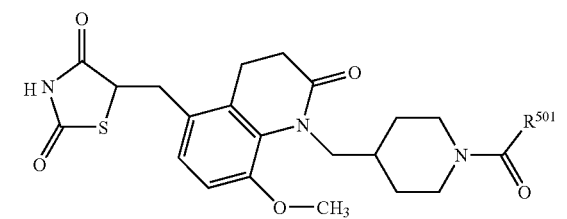
| Ex. | R⁵⁰¹ | MS (M + 1) |
|---|---|---|
| 688 | 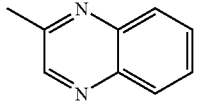 | 560 |
| 689 | 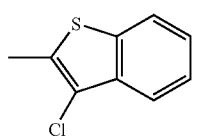 | 598 |
| 690 | 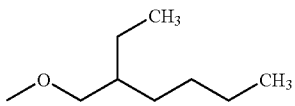 | 560 |
| 691 | 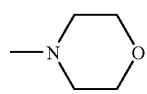 | 517 |
TABLE 110-continued
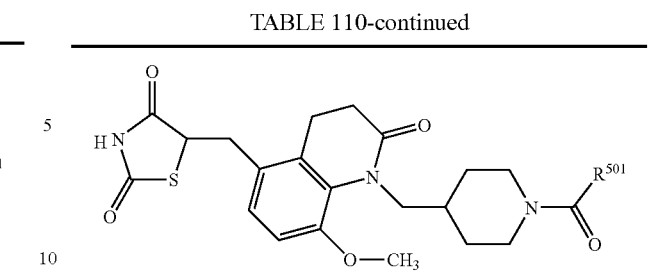
| Ex. | R⁵⁰¹ | MS (M + 1) |
|---|---|---|
| 692 | 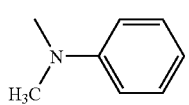 | 537 |
| 693 | 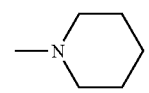 | 515 |
| 694 | 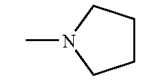 | 501 |
TABLE 111
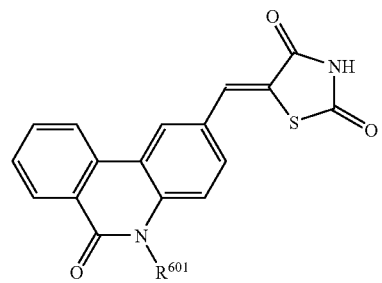
| Ex. | $R^{601}$ | ¹H NMR (DMSO-d₆) dppm |
|---|---|---|
| 695 | —CH₂C₆H₅ | 5.67 (2H, s), 7.0-8.0 (10H, m), 8.45 (1H, dd, J = 8.0 Hz, 1.3 Hz), 8.60 (1H, d, J = 8.0 Hz), 8.80 (1H, d, J = 1.8 Hz), 12.6 (1H, br s) |
| 696 | —C₂H₅ | 1.29 (3H, t, J = 7.1 Hz), 4.41 (2H, t, J = 7.1 Hz), 7.6-8.0 (6H, m), 8.38 (1H, dd, J = 8.0 Hz, 1.2 Hz), 8.56 (1H, d, J = 8.1 Hz), 8.74 (1H, s), 12.6 (1H, br s) |

TABLE 112

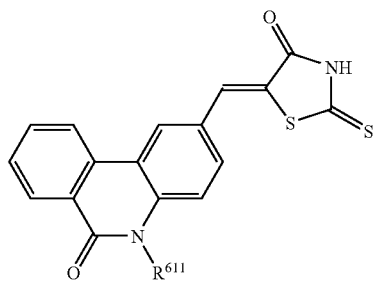

| Ex. | $R^{611}$ | $^1$H NMR (DMSO-$d_6$) dppm |
|---|---|---|
| 697 | —CH$_2$C$_6$H$_5$ | 5.67 (2H, s), 7.1-8.1 (10H, m), 8.55 (1H, dd, J = 8.0 Hz, 1.3 Hz), 8.65 (1H, d, J = 8.0 Hz), 8.81 (1H, d, J = 1.8 Hz), 13.8 (1H, br s) |
| 698 | —C$_2$H$_5$ | 1.30 (3H, t, J = 7.1 Hz), 4.41 (2H, t, J = 7.1 Hz), 7.5-8.0 (6H, m), 8.38 (1H, dd, J = 8.0 Hz, 1.2 Hz), 8.55 (1H, d, J = 8.1 Hz), 8.79 (1H, s), 13.9 (1H, br s) |
| 699 | —CH$_2$-C$_6$H$_4$-C$_6$H$_5$ | 5.72 (2H, s), 7.1-8.0 (14H, m), 8.46 (1H, dd, J = 8.0 Hz, 1.3 Hz), 8.62 (1H, d, J = 8.0 Hz), 8.82 (1H, d, J = 1.8 Hz), 13.5 (1H, br s) |

TABLE 113

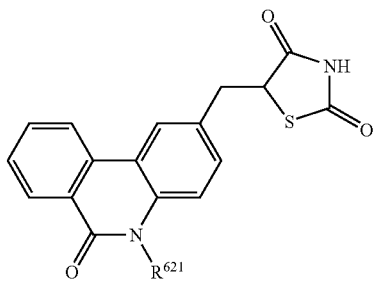

| Ex. | $R^{621}$ | $^1$H NMR (DMSO-$d_6$) dppm |
|---|---|---|
| 700 | —CH$_2$C$_6$H$_5$ | 3.1-3.7 (2H, m), 5.04 (1H, dd, J = 13.8 Hz, 4.8 Hz), 5.76 (2H, s), 7.1-7.45 (5H, m), 7.6-8.0 (2H, m), 8.3-8.6 (3H, m), 12.0 (1H, br s) |
| 701 | —C$_2$H$_5$ | 1.27 (3H, t, J = 7.1 Hz), 3.2-3.7 (2H, m), 4.39 (2H, t, J = 7.1 Hz), 5.09 (1H, dd, J = 13.8 Hz, 4.8 Hz), 7.4-7.9 (4H, m), 8.25-8.6 (3H, m), 12.2 (1H, br s) |

TABLE 114

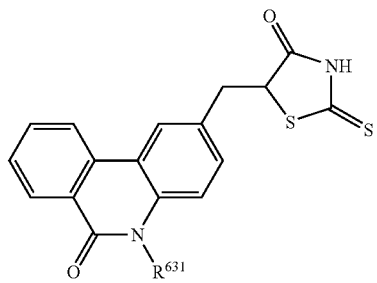

| Ex. | $R^{631}$ | $^1$H NMR (DMSO-$d_6$) dppm |
|---|---|---|
| 702 | —CH$_2$C$_6$H$_5$ | 3.1-3.7 (2H, m), 5.16 (1H, dd, J = 13.8 Hz, 4.8 Hz), 5.63 (2H, s), 7.0-7.45 (5H, m), 7.6-8.0 (2H, m), 8.3-8.6 (3H, m), 13.2 (1H, br s) |

TABLE 114-continued

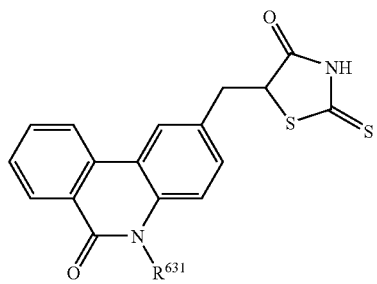

| Ex. | R$^{631}$ | $^1$H NMR (DMSO-d$_6$) dppm |
|---|---|---|
| 703 | 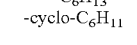 | 3.1-3.7 (2H, m), 5.16 (1H, dd, J = 13.8 Hz, 4.8 Hz), 5.69 (2H, s), 7.1-8.0 (13H, m), 8.4-8.7 (3H, m), 13.2 (1H, br s) |
| 704 | —C$_2$H$_5$ | 1.27 (3H, t, J = 7.1 Hz), 3.2-3.7 (2H, m), 4.39 (2H, t, J = 7.1 Hz), 5.20 (1H, dd, J = 13.8 Hz, 4.8 Hz), 7.4-7.9 (4H, m), 8.35-8.6 (3H, m), 13.2 (1H, br s) |

TABLE 115

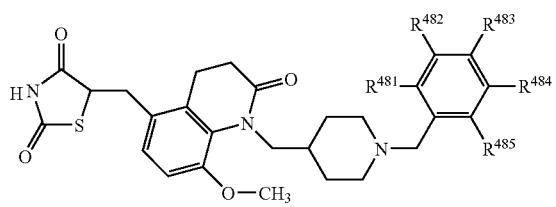

| Ex. | R$^{481}$ | R$^{482}$ | R$^{483}$ | R$^{484}$ | R$^{485}$ | MS (M + 1) |
|---|---|---|---|---|---|---|
| 705 | —H | —H | —H | —H | —H | 494 |
| 706 | —H | —H | —OCH$_3$ | —H | —H | 524 |
| 707 | —H | —OCH$_3$ | —H | —H | —H | 524 |
| 708 | —H | —H | —CN | —H | —H | 519 |
| 709 | —H | —H | —N(C$_2$H$_5$)$_2$ | —H | —H | 565 |
| 710 | —H | —H | —NHCOCH$_3$ | —H | —H | 551 |
| 711 | —Cl | —H | —H | —H | —H | 528 |
| 712 | —H | —Cl | —H | —H | —H | 528 |
| 713 | —H | —H | —Cl | —H | —H | 528 |
| 714 | —F | —H | —H | —H | —H | 512 |
| 715 | —CN | —H | —H | —H | —H | 519 |
| 716 | —CF$_3$ | —H | —H | —H | —H | 562 |
| 717 | —H | —CF$_3$ | —H | —H | —H | 562 |
| 718 | —H | —CH$_3$ | —H | —H | —H | 508 |
| 719 | —H | —H | —CF$_3$ | —H | —H | 562 |
| 720 | —H | —H | —Br | —H | —H | 574 |
| 721 | —H | —H | —F | —H | —H | 512 |
| 722 | —CH$_3$ | —H | —H | —H | —H | 508 |
| 723 | —H | —H | —OC$_4$H$_9$ | —H | —H | 566 |
| 724 | —H | —H | —CO$_2$CH$_3$ | —H | —H | 552 |
| 725 | —H | —F | —H | —H | —H | 512 |
| 726 | —H | —H | —N(CH$_3$)$_2$ | —H | —H | 537 |
| 727 | —H | —H | —OCOCH$_3$ | —H | —H | 552 |
| 728 | —H | —H | —C$_4$H$_9$ | —H | —H | 550 |
| 729 | —H | —H | —SO$_2$CH$_3$ | —H | —H | 572 |
| 730 | —H | —H | —SC$_2$H$_5$ | —H | —H | 554 |
| 731 | —H | —H | —OCHF$_2$ | —H | —H | 560 |
| 732 | —H | —H |  | —H | —H | 563 |

TABLE 116

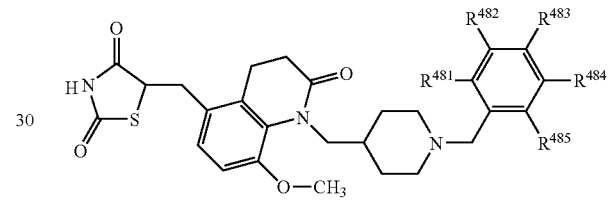

| Ex. | R$^{481}$ | R$^{482}$ | R$^{483}$ | R$^{484}$ | R$^{485}$ | MS (M + 1) |
|---|---|---|---|---|---|---|
| 733 | —H | —H | —OC(CH$_3$)$_3$ | —H | —H | 566 |
| 734 | —H | —H | —H | —H | —H | 508 |
| 735 | —H | —H | —H | —H | —OCH$_3$ | 538 |
| 736 | —H | —H | —H | —OCH$_3$ | —H | 538 |
| 737 | —H | —H | —OCH$_3$ | —H | —H | 538 |
| 738 | —H | —H | —H | —H | —Cl | 542 |
| 739 | —H | —H | —OC$_4$H$_9$ | —H | —H | 580 |

TABLE 117

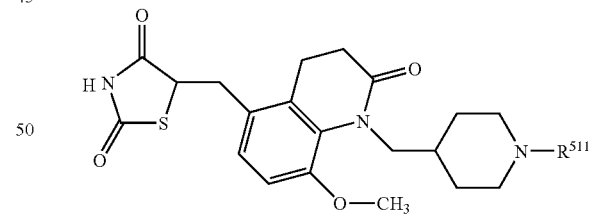

| Ex. | R$^{511}$ | MS (M + 1) |
|---|---|---|
| 740 | —CH$_2$-cyclo-C$_6$H$_{11}$ | 500 |
| 741 | —C$_6$H$_{13}$ | 488 |
| 742 | -cyclo-C$_6$H$_{11}$ | 486 |
| 743 |  | 484 |
| 744 | | 495 |

TABLE 117-continued

[Structure: thiazolidinedione-methyl-dihydroquinolinone with 8-methoxy and N-CH2-piperidine-R511]

| Ex. | R511 | MS (M + 1) |
|---|---|---|
| 745 | 3-pyridyl | 495 |
| 746 | 4-pyridyl | 495 |
| 747 | 2-thienyl | 500 |
| 748 | 3-thienyl | 500 |
| 749 | 2-thiazolyl | 501 |
| 750 | 5-chloro-2-thienyl | 534 |
| 751 | 1-methyl-2-imidazolyl | 498 |

TABLE 118

[Structure: thiazolidinedione-methyl-dihydroquinolinone with 8-methoxy and N-CH2-piperidine-R511]

| Ex. | R511 | MS (M + 1) |
|---|---|---|
| 752 | 1-methyl-2-pyrrolyl | 497 |

TABLE 118-continued

| Ex. | R511 | MS (M + 1) |
|---|---|---|
| 753 | 2-furyl | 484 |
| 754 | 6-bromo-3-pyridyl | 573 |
| 755 | 6-trifluoromethyl-3-pyridyl | 563 |
| 756 | 1-isopropyl-4-methylpiperidinyl | 529 |
| 757 | 4-methyltetrahydropyranyl | 488 |
| 758 | isobutoxy-isopentyl ether | 532 |
| 759 | 4-methyltetrahydrothiopyranyl | 504 |

TABLE 119

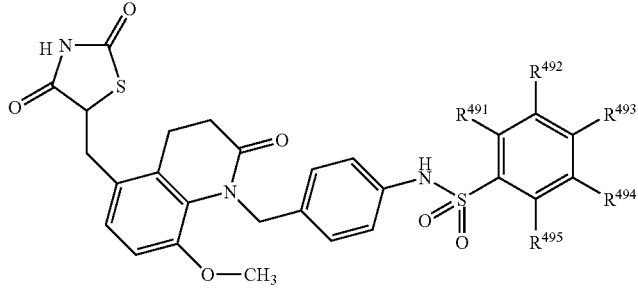

| Ex. | R491 | R492 | R493 | R494 | R495 | MS (M + 1) |
|---|---|---|---|---|---|---|
| 760 | —H | —H | —OCH3 | —H | —H | 582 |
| 761 | —H | —H | —Cl | —H | —H | 586 |
| 762 | —H | —H | —H | —H | —CH3 | 566 |
| 763 | —H | —H | —F | —H | —H | 570 |
| 764 | —OCH3 | —H | —H | —Cl | —H | 616 |
| 765 | —H | —H | —H | —H | —CF3 | 620 |
| 766 | —H | —H | —H | —H | —Cl | 586 |
| 767 | —H | —H | —H | —H | —OCF3 | 636 |
| 768 | —H | —H | —H | —H | —CO2CH3 | 610 |
| 769 | —CN | —H | —H | —H | —H | 577 |
| 770 | —H | —H | —H | —OCH3 | —H | 582 |
| 771 | —H | —H | —H | —F | —H | 570 |
| 772 | —H | —H | —H | —H | —F | 570 |
| 773 | —H | —H | —CF3 | —H | —H | 620 |
| 774 | —H | —H | —H | —CF3 | —H | 620 |
| 775 | —H | —H | —OCF3 | —H | —H | 636 |
| 776 | —H | —H | —OCH3 | —OCH3 | —H | 612 |
| 777 | —OCH3 | —H | —H | —OCH3 | —H | 612 |
| 778 | —H | —H | —H | —CH3 | —H | 566 |
| 779 | —H | —H | —H | —H | —NO2 | 597 |
| 780 | —H | —H | —H | —NO2 | —H | 597 |
| 781 | —H | —H | —Br | —H | —H | 632 |
| 782 | —H | —H | —H | —Cl | —H | 586 |
| 783 | —H | —CH3 | —H | —H | —OCH3 | 596 |
| 784 | —Cl | —H | —H | —H | —Cl | 620 |
| 785 | —H | —H | —H | —OCF3 | —H | 636 |
| 786 | —H | —H | —H | —Cl | —Cl | 620 |
| 787 | —Cl | —H | —H | —Cl | —H | 620 |
| 788 | —H | —H | —Cl | —H | —Cl | 620 |
| 789 | —H | —H | —CH3 | —NO2 | —H | 611 |
| 790 | —H | —H | —F | —H | —Cl | 604 |
| 791 | —H | —CH3 | —Cl | —H | —Cl | 634 |

TABLE 120

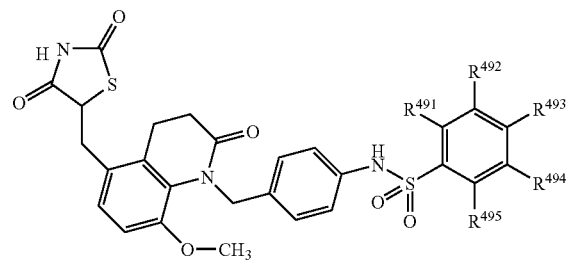

| Ex. | R491 | R492 | R493 | R494 | R495 | MS (M + 1) |
|---|---|---|---|---|---|---|
| 792 | —CH3 | —H | —H | —NO2 | —H | 611 |
| 793 | —Cl | —H | —H | —NO2 | —H | 631 |
| 794 | —H | —H | —CN | —H | —Cl | 611 |
| 795 | —CH3 | —H | —CH3 | —H | —CH3 | 594 |
| 796 | —H | —H | —NHCOCH3 | —H | —H | 609 |
| 797 | —H | —H | —NO2 | —H | —H | 597 |
| 798 | —H | —Cl | —H | —Cl | —OH | 636 |
| 799 | —H | —H | —CH3 | —H | —H | 566 |

TABLE 120-continued

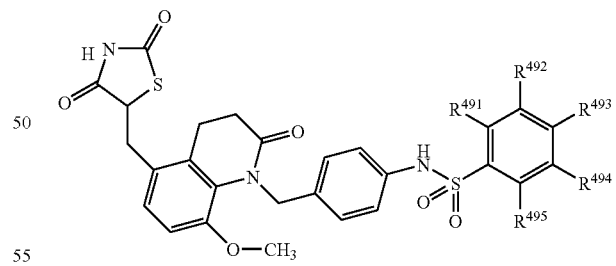

| Ex. | R491 | R492 | R493 | R494 | R495 | MS (M + 1) |
|---|---|---|---|---|---|---|
| 800 | —H | —H | —OCH3 | —H | —NO2 | 627 |
| 801 | —H | —H | —Cl | —Cl | —H | 620 |
| 802 | —H | —H | —C(CH3)3 | —H | —H | 608 |
| 803 | —H | —H | —H | —CO2H | —H | 596 |
| 804 | —Br | —H | —H | —Cl | —H | 666 |
| 805 | —H | —H | —C2H5 | —H | —H | 580 |
| 806 | —H | —CH3 | —H | —H | —CH3 | 580 |
| 807 | —H | —H | —OC4H9 | —H | —H | 624 |

TABLE 120-continued
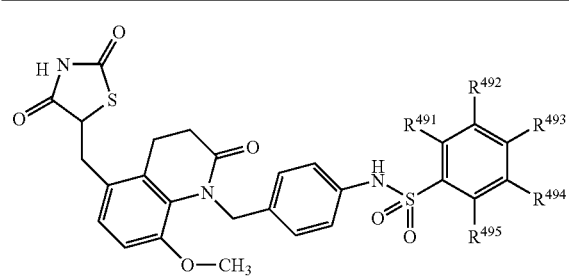
| Ex. | R491 | R492 | R493 | R494 | R495 | MS (M + 1) |
|---|---|---|---|---|---|---|
| 808 | —F | —H | —H | —F | —H | 588 |
| 809 | —H | —H | —H | —CN | —H | 577 |
| 810 | —CH3 | —H | —Cl | —H | —Cl | 634 |
| 811 | —H | —F | —H | —Cl | —CH3 | 618 |
| 812 | —H | —H | —Br | —H | —CH3 | 646 |
| 813 | —H | —H | —H | —Br | —H | 632 |
| 814 | —H | —H | —CN | —H | —H | 577 |
| 815 | —H | —H | —NHCOCH3 | —Cl | —H | 643 |
| 816 | —H | —H | —F | —H | —F | 588 |
| 817 | —H | —H | —CH3 | —H | —OCH3 | 596 |
| 818 | —H | —H | —H | —Cl | —CH3 | 600 |
| 819 | —F | —H | —H | —H | —F | 588 |
| 820 | —CH3 | —H | —H | —F | —H | 584 |
| 821 | —CH3 | —H | —Cl | —CH3 | —H | 614 |
| 822 | —CH3 | —H | —H | —H | —Cl | 600 |
| 823 | —H | —H | —CH(CH3)2 | —H | —H | 594 |
TABLE 121
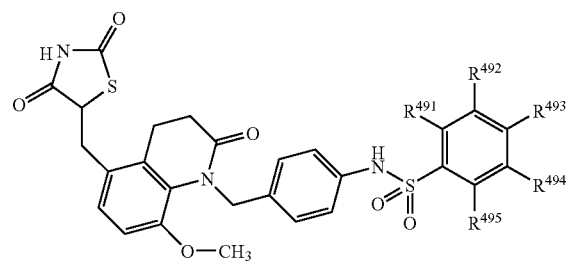
| Ex. | R491 | R492 | R493 | R494 | R495 | MS (M + 1) |
|---|---|---|---|---|---|---|
| 824 | —H | —H | —F | —Cl | —H | 604 |
| 825 | —H | —H | —Br | —H | —F | 650 |
| 826 | —H | —H | —CH3 | —Cl | —H | 600 |
| 827 | —H | —H | —F | —F | —H | 588 |
| 828 | —H | —H | —H | —H | —Br | 632 |
| 829 | —H | —Cl | —H | —Cl | —H | 620 |
| 830 | —H | —H | —(CH2)2CO2CH3 | —H | —H | 638 |
| 831 | —CH3 | —H | —OCH3 | —CH3 | —CH3 | 624 |
| 832 | —H | —H | —OH | —CO2H | —H | 612 |
| 833 | —H | —H | —CO2H | —H | —H | 596 |
| 834 | —F | —H | —F | —F | —H | 606 |
| 835 | —H | —H | —H | —H | —H | 552 |
TABLE 122
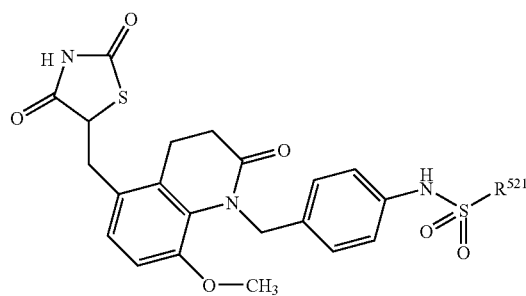
| Ex. | R521 | MS (M + 1) |
|---|---|---|
| 836 | -2-THIENYL | 558 |
| 837 | —C4H9 | 532 |
| 838 | —CH=CH2 | 502 |
| 839 | —(CH2)3Cl | 552 |
| 840 | —CH2-cyclo-C6H11 | 572 |
| 841 | —CH2CF3 | 558 |
| 842 | —CH2C6H5 | 566 |
| 843 | —CH=CHC6H5(trans) | 578 |
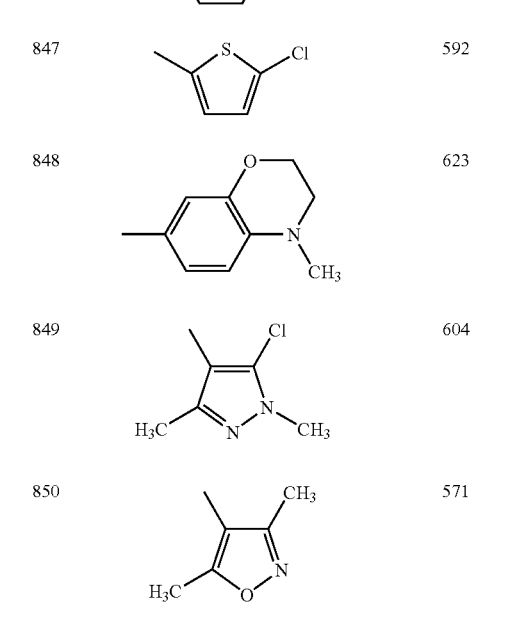

TABLE 123

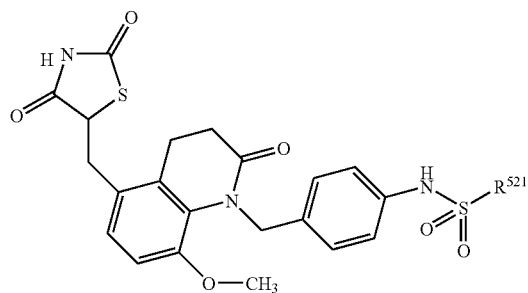

| Ex. | R521 | MS (M + 1) |
|---|---|---|
| 851 | 2,3-dichloro-5-methylthiophene | 626 |
| 852 | 2,5-dichloro-3-methylthiophene | 626 |
| 853 | 5-bromo-2-methylthiophene | 638 |
| 854 | N-(4,5-dimethylthiazol-2-yl)acetamide | 630 |
| 855 | methyl 3-methylthiophene-2-carboxylate | 616 |

TABLE 124

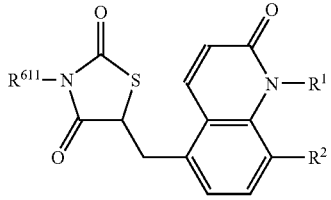

| Ex. | $R^1$ | $R^2$ | $R^{411}$ | M.p. (° C.) |
|---|---|---|---|---|
| 856 | —CH$_3$ | —OCH$_3$ | —H | 254-255 |
| 857 | —CH$_3$ | —OCH$_3$ | —CH$_2$CO$_2$CH$_3$ | 182-184 |
| 858 | —CH$_3$ | —OCH$_3$ | —CH$_2$CO$_2$H | 207-210 |
| 859 | —CH$_3$ | —OCH$_3$ | —H | 141-145 |
| 860 | 4-bromophenethyl | —OCH$_3$ | —H | 247.9-251.8 |

TABLE 125

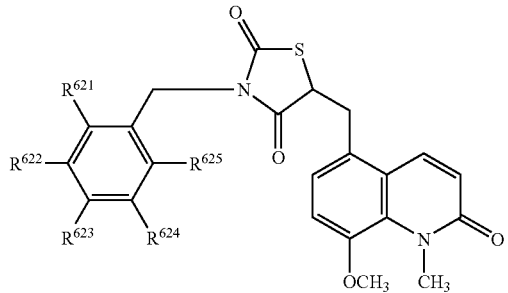

| Ex. | $R^{621}$ | $R^{622}$ | $R^{623}$ | $R^{624}$ | $R^{625}$ | MS (M + 1) |
|---|---|---|---|---|---|---|
| 861 | —H | —H | —Cl | —H | —H | 443 |
| 862 | —H | —H | —H | —H | —Cl | 443 |
| 863 | —H | —H | —H | —CF$_3$ | —H | 477 |
| 864 | —H | —H | —H | —H | —CH$_3$ | 423 |
| 865 | —H | —H | —H | —H | —C$_6$H$_5$ | 485 |
| 866 | —H | —H | —C(CH$_3$)$_3$ | —H | —H | 465 |
| 867 | —H | —H | —CF$_3$ | —H | —H | 477 |
| 868 | —H | —H | —CH$_3$ | —H | —H | 423 |
| 869 | —H | —H | —C$_6$H$_5$ | —H | —H | 485 |
| 870 | —H | —H | —H | —H | —OCH$_3$ | 493 |
| 871 | —H | —H | —H | —F | —H | 427 |
| 872 | —H | —H | —H | —CH$_3$ | —H | 423 |
| 873 | —H | —H | —OCF$_3$ | —H | —H | 493 |
| 874 | —H | —H | —H | —Cl | —H | 443 |
| 875 | —H | —H | —F | —H | —H | 427 |
| 876 | —H | —H | —H | —OCH$_3$ | —H | 439 |
| 877 | —H | —H | —OCH$_3$ | —H | —H | 439 |
| 878 | —H | —H | —CO$_2$CH$_3$ | —H | —H | 467 |
| 879 | —H | —H | —H | —OC$_6$H$_5$ | —H | 501 |
| 880 | —H | —H | —SCH$_3$ | —H | —H | 465 |
| 881 | —H | —H | —H | —H | —H | 409 |
| 882 | —H | —H | —SO$_2$CH$_3$ | —H | —H | 487 |
| 883 | —H | —H | —H | —OCF$_3$ | —H | 493 |
| 884 | —H | —H | —OCH$_2$C$_6$H$_5$ | —H | —H | 515 |
| 885 | —H | —H | —OCH$_3$ | —Cl | —H | 473 |
| 886 | —H | —H | —H | —H | —OCH$_3$ | 439 |
| 887 | —H | —H | —NHCOCH$_3$ | —H | —H | 466 |

TABLE 126

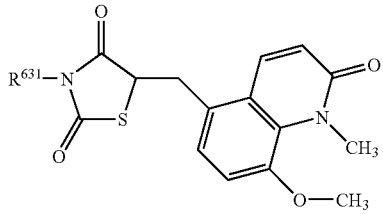

| Ex. | $R^{631}$ | MS (M + 1) |
|---|---|---|
| 888 | —CH$_2$C≡CH | 357 |
| 889 | —CH$_2$CH=CH$_2$ | 359 |
| 890 | —CH$_2$CH=CHC$_6$H$_5$ | 435 |
| 891 | —(CH$_2$)$_2$C$_6$H$_5$ | 423 |
| 892 | —(CH$_2$)$_3$C$_6$H$_5$ | 437 |
| 893 | —CH$_3$ | 333 |
| 894 | —C$_2$H$_5$ | 347 |
| 895 | —CH(CH$_3$)$_2$ | 361 |
| 896 | —C$_4$H$_9$ | 375 |
| 897 | —CH$_2$CH$_2$OH | 363 |
| 898 | —C$_6$H$_{13}$ | 403 |
| 899 | —CH$_3$-cyclo-C$_6$H$_{11}$ | 415 |
| 900 | —CH$_2$CO$_2$C$_2$H$_5$ | 405 |

TABLE 126-continued

Structure: R631-substituted thiazolidinedione linked via methylene to 1-methyl-8-methoxy-2-oxo-quinoline

| Ex. | R631 | MS (M + 1) |
|---|---|---|
| 901 | 2-ethylnaphthalene | 459 |
| 902 | 2-ethylquinoline | 460 |
| 903 | ethyl 5-ethylfuran-2-carboxylate | 471 |
| 904 | 4-ethyl-2-methylthiazole | 430 |
| 905 | 1-ethyl-5-ethyltetrazole | 429 |
| 906 | 3-ethyl-5-chlorobenzothiophene | 499 |

TABLE 127

Structure: R631-substituted thiazolidinedione linked via methylene to 1-methyl-8-methoxy-2-oxo-quinoline

| Ex. | R631 | MS (M + 1) |
|---|---|---|
| 907 | 1-ethylnaphthalene | 459 |
| 908 | 2-ethylbenzimidazole | 449 |

TABLE 127-continued

| Ex. | R631 | MS (M + 1) |
|---|---|---|
| 909 | N-(4-ethylphenyl)acetamide | 466 |
| 910 | 2-ethylpyridine | 410 |
| 911 | 4-ethyl-2-(4-trifluoromethylphenyl)thiazole | 560 |
| 912 | 2-ethyl-1-benzylimidazole | 489 |

TABLE 128

Structure: 2-thioxothiazolidin-4-one linked via methylene to 8-methoxy-2-oxo-tetrahydroquinoline with N-benzyl bearing R531–R535 substituents

| Ex. | R531 | R532 | R533 | R534 | R535 | M.p. (° C.) |
|---|---|---|---|---|---|---|
| 913 | —H | —H | —C6H5 | —H | —H | 164-168 |
| 914 | —H | —H | —C(CH3)3 | —H | —H | 222-224 |
| 915 | —H | —H | —H | —H | —C6H5 | 193-199 |
| 916 | —H | —H | —Cl | —H | —H | 179.8-183.8 |
| 917 | —H | —H | —Br | —H | —H | 191.3-192.1 |
| 918 | —H | —H | —OC6H5 | —H | —H | 156.5-158.5 |

TABLE 129

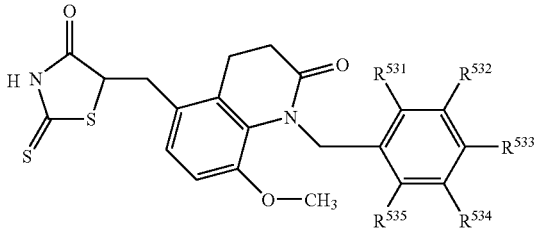

| Ex. | R531 | R532 | R533 | R534 | R535 | 1H NMR (DMSO-d6) δppm |
|---|---|---|---|---|---|---|
| 919 | —H | —H | —H | —H | —H | 2.45-2.54 (m, 2H), 2.75-2.85 (m, 2H), 3.13 (dd; J = 9.5, 14.4 Hz, 1H), 3.38 (dd; J = 4.7, 14.4 Hz, 1H), 3.67 (S, 3H), 4.92 (dd; J = 4.7, 9.5 Hz, 1H), 5.19 (S, 2H), 6.81 (d, J = 8.6 Hz, 1H), 6.89 (d, J = 8.6 Hz, 1H), 7.04 (d, J = 7.5 Hz, 2H), 7.11 (t, J = 7.5 Hz, 1H), 7.19 (t, J = 7.5 Hz, 2H), 13.19 (brs, 1H) |
| 920 | —H | —H | —H | —C$_6$H$_5$ | —H | 2.47-2.57.(m, 2H), 2.80-2.88 (m, 2H), 3.15 (dd; J = 9.9, 14.5 Hz, 1H), 3.40 (dd; J = 4.5, 14.5 Hz, 1H), 3.69 (S, 3H), 4.91 (dd; J = 4.5, 9.9 Hz, 1H), 5.26 (s, 2H), 6.84 (d, J = 8.6 Hz, 1H), 6.91 (d, J = 8.6 Hz, 1H), 7.02 (d, J = 7.7 Hz, 1H), 7.24-7.57 (m, 8H), 13.22 (brs, 1H) |

TABLE 130

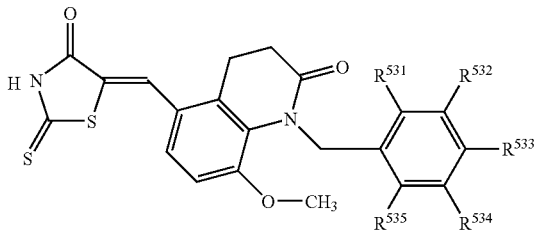

| Ex. | R$^{531}$ | R$^{532}$ | R$^{533}$ | R$^{534}$ | R$^{535}$ | $^1$H NMR (DHSO-d6) dppm |
|---|---|---|---|---|---|---|
| 921 | —H | —H | —H | —H | —H | 2.56 (2H, t, J = 6.9 Hz), 2.97 (2H, t, J = 6.9 Hz), 3.78 (3H, s), 5.21 (2H, s), 7.0-7.55 (7H, m), 7.69 (1H, s), 13.80 (1H, br s) |
| 922 | —H | —H | —C$_6$H$_5$ | —H | —H | 2.58 (2H, t, J = 6.9 Hz), 3.00 (2H, t, J = 6.9 Hz), 3.81 (3H, s), 5.24 (2H, s), 7.0-7.6 (11H, m), 7.80 (1H, s), 13.85 (1H, br s) |
| 923 | —H | —H | —C(CH$_3$)$_3$ | —H | —H | 1.20 (9H, s), 2.54 (2H, t, J = 6.9 Hz), 2.96 (2H, t, J = 6.9 Hz), 3.81 (3H, s), 5.20 (2H, s), 7.00 (2H, d, J = 8.2 Hz), 7.07 (1H, d, J = 8.8 Hz), 7.15 (1H, d, J = 8.8 Hz), 7.22 (2H, d, J = 8.2 Hz), 769 (1H, s), 13.8 (1H, br s) |

TABLE 131

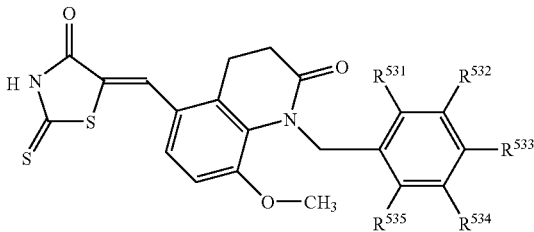

| Ex. | $R^{531}$ | $R^{532}$ | $R^{533}$ | $R^{534}$ | $R^{535}$ | $^1$H NMR (DMSO-d6) dppm |
|---|---|---|---|---|---|---|
| 924 | —H | —H | —H | —$C_6H_5$ | —H | 2.57 (2H, t, J = 6.9 Hz), 3.00 (2H, t, J = 6.9 Hz), 3.79 (3H, s), 5.27 (2H, s), 7.0-7.55 (11H, m), 7.71 (1H, s), 13.7 (1H, br s) |
| 925 | —H | —H | —H | —H | —$C_6H_5$ | 2.49 (2H, t, J = 6.9 Hz), 2.80 (2H, t, J = 6.9 Hz), 3.44 (3H, s), 5.20 (2H, s), 6.91 (1H, d, J = 8.6 Hz), 7.05-7.5 (10H, m), 7.66 (1H, s), 13.8 (1H, br s) |
| 926 | —H | —H | —Cl | —H | —H | 2.49-2.56 (2H, m), 2.84-3.08 (2H, m), 3.74 (3H, s), 5.14 (2H, s), 6.95-7.20 (4H, m), 7.20-7.33 (2H, m), 7.69 (1H, s), 13.79 (1H, brs). |
| 927 | —H | —H | —Br | —H | —H | 2.51-2.62 (2H, m), 2.86-3.05 (2H, m), 3.74 (3H, s), 5.11 (2H, s), 6.98-7.10 (3H, m), 7.16 (1H, d, J = 8.8 Hz), 7.40 (2H, d, J = 8.3 Hz), 7.69 (1H, s), 13.79 (1H, s). |
| 928 | —H | —H | —$OC_6H_5$ | —H | —H | 2.42-2.61 (2H, m), 2.85-2.05 (2H, m), 3.80 (3H, s), 5.17 (2H, s), 6.84 (2H, d, J = 8.6 Hz), 6.91 (2H, d, J = 7.8 Hz), 7.05-7.17 (5H, m), 7.32-7.37 (2H, m), 7.69 (1H, s), 13.76 (1H, brs). |

TABLE 132

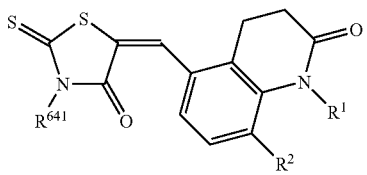

| Ex. | $R^1$ | $R^{641}$ | $R^2$ | $^1$H NMR dppm |
|---|---|---|---|---|
| 929 | —$CH_3$ | —H | —$OCH_3$ | 2.43 (2H, t, J = 6.9 Hz), 2.91 (2H, t, J =6.9 Hz), 3.20 (3H, s), 3.89 (3H, s), 7.17 (1H, d, J = 8.8 Hz), 7.20 (1H, d, J = 8.8 Hz), 7.68 (1H, s) |
| 930 | —H | —H | —$OCH_3$ | 2.48 (2H, t, J = 6.9 Hz), 3.00 (2H, t, J = 6.9 Hz), 3.85 (3H, s), 6.95-7.2 (2H, m), 9.22 (1H, s), 13.77 (1H, br s) |
| 931 | —$CH_3$ | —$CH_3$ | —$OCH_3$ | $CDCl_3$: 2.5-2.6 (2H, m), 2.95-3.0 (2H, m), 3.37 (3H, s), 3.53 (3H, s), 3.93 (3H, s), 6.95 (1H, d, J = 8.8 Hz), 7.24 (1H, d, J = 8.8 Hz), 7.89 (1H, s) |
| 932 | —$C_4H_9$ | —H | —$OCH_3$ | 0.81 (3H, t, J = 7.3 Hz), 1.1-1.2 (2H, m), 1.3-1.4 (2H, m), 2.44 (1H, t, J = 6.9 Hz), 2.90 (2H, t, J = 6.9 Hz), 3.90 (3H, s), 3.92 (2H, t, J = 7.3 Hz), 7.18 (1H, d, J = 8.8 Hz), 7.22 (1H, d, J = 8.8 Hz), 7.71 (1H,s), 13.81 (1H, br s) |
| 933 | —$(CH_2)_3C_6H_5$ | —H | —$OCH_3$ | 1.65-1.8 (2H, m), 2.35-2.5 (4H, m), 2.92 (2H, t, J = 6.9 Hz), 7.0-7.3 (7H, m), 7.72 (1H, s), 13.8 (1H, br s) |
| 934 | —$(CH_2)_2C_6H_5$ | —H | —$OCH_3$ | 2.36 (2H, t, J = 6.9 Hz), 2.59 (2H, t, J = 4.5 Hz), 2.73 (2H, t, J = 6.9 Hz), 3.96 (3H, s), 4.17 (2H, t, J = 4.5 Hz), 7.00 (1H, d, J = 8.8 Hz), 7.1-7.2 (5H, m), 7.64 (1H, s), 13.82 (1H, br s) |
| 935 | —$C_2H_5$ | —H | —$OCH_3$ | 1.07 (3H, t, J = 7.0 Hz), 2.42 (2H, t, J = 6.9 Hz), 2.92 (2H, t, J = 6.9 Hz), 3.86 (2H, q, J = 7.0 Hz), 3.91 (3H, s), 7.19 (1H, d, J = 8.8 Hz), 7.22 (1H, d, J = 8.8 Hz), 7.71 (1H, s), 12.82 (1H, br s) |
| 936 | —$(CH_2)_2OC_6H_5$ | —H | —$OCH_3$ | 2.47 (2H, t, J = 6.9 Hz), 2.88 (2H, t, J = 6.9 Hz), 3.88 (3H, s), 4.06 (2H, t, J = 5.9 Hz), 4.29 (2H, t, J = 5.9 Hz), 6.77 (2H, d, J = 8.6 Hz), 6.88 (1H, t, J = 8.6 Hz), 7.1-7.3 (4H, m), 7.68 (1H, s), 13.8 (1H, br s) |

TABLE 132-continued

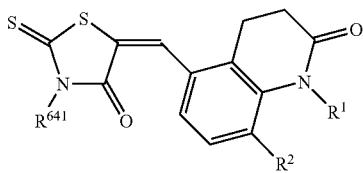

| Ex. | R¹ | R⁶⁴¹ | R² | ¹H NMR dppm |
|---|---|---|---|---|
| 937 | —CH₂-cyclo-C₆H₁₁ | —H | —OCH₃ | 0.75-1.57 (11H, m), 2.45 (2H, t, J = 6.9 Hz), 2.92 (2H, t, J = 6.9 Hz), 3.91 (3H, s), 3.95-4.00 (2H, m), 7.18 (1H, d, J = 8.8 Hz),7.23 (1H, d, J = 8.8 Hz), 7.73 (1H, s), 13.8 (1H, br s) |

TABLE 133

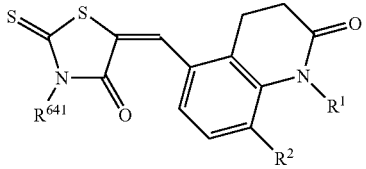

| Ex. | R¹ | R⁶⁴¹ | R² | ¹H NMR (DMSO-d₆) dppm |
|---|---|---|---|---|
| 938 | —CH₂CH₂OCH₃ | —H | —OCH₃ | 2.50 (2H, t, J = 6.9 Hz), 2.89 (2H, t, J = 6.9 Hz), 3.10 (3H, s), 3.35 (2H, t, J = 6.0 Hz), 3.90 (3H, s), 4.10 (2H, t, J = 6.0 Hz), 7.17 (2H, d, J = 8.6 Hz), 7.24 (1H, t, J = 8.6 Hz), 7.71 (1H, s), 13.8 (1H, br s) |
| 939 | —CH(C₆H₅)₂ | —H | —OCH₃ | 2.4-2.5 (2H, m), 2.8-2.95 (2H, m), 3.41 (3H, s), 6.29 (2H, s), 6.95-7.35 (12H, m), 7.73 (1H, s), 13.8 (1H, br s) |
| 940 | —CH₂-cyclo-C₃H₅ | —H | —OCH₃ | 0.05-0.10 (2H, m), 0.25-0.30 (2H, m), 0.75-0.80 (1H, m), 2.46 (2H, t, J = 6.9 Hz), 2.93 (2H, t, J = 6.9 Hz), 3.85-3.950 (5H, m), 7.1-7.3 (2H, m), 7.73 (1H, s), 13.82 (1H, br s) |
| 941 | —C₆H₅ | —H | —H | 2.71-2.76 (2H, m), 3.13-3.18 (2H, m), 6.32 (1H, d, J = 8.1 Hz), 7.10 (1H, d, J = 7.7 Hz), 7.19-7.27 (3H, m), 7.43-7.56 (3H, m), 7.83 (1H, s), 13.85 (1H, brs). |
| 942 | —(CH₂)₄C₆H₅ | —H | —OCH₃ | 1.35-1.50 (4H, m), 2.40-2.70 (4H, m), 2.89 (2H, t, J = 6.9 Hz), 3.83 (3H, s), 3.85-3.95 (2H, m), 7.05-7.3 (7H, m), 7.71 (1H, s), 13.8 (1H, br s) |
| 943 | —(CH₂)₅C₆H₅ | —H | —OCH₃ | 1.05-1.15 (2H, m), 1.35-1.5 (4H, m), 2.35-2.70 (4H, m), 2.80 (2H, t, J = 6.9 Hz), 3.85-4.0 (5H, m), 7.05-7.3 (7H, m), 7.69 (1H, s), 13.82 (1H, br s) |

DMSO-d6 is used for measuring NMR, unless otherwise specified.

TABLE 134

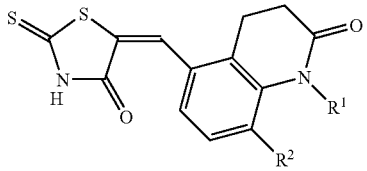

| Ex. | R¹ | R² | ¹H NMR dppm |
|---|---|---|---|
| 944 | ![1-naphthyl-CH₂CH₂-] | —OCH₃ | 2.61 (2H, t, J = 6.9 Hz), 2.87 (2H, t, J = 6.9 Hz), 3.71 (3H, s), 5.64 (2H, s), 7.0-8.05 (9H, m), 13.8 (1H, br s) |
| 945 | ![2-naphthyl-CH₂CH₂-] | —OCH₃ | 2.60 (2H, t, J = 6.9 Hz), 3.02 (2H, t, J = 6.9 Hz), 3.77 (3H, s), 5.37 (2H, s), 6.95-7.85 (9H, m), 13.8 (1H, br s) |

TABLE 134-continued

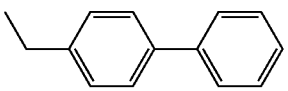

| Ex. | R¹ | R² | ¹H NMR dppm |
|---|---|---|---|
| 946 | 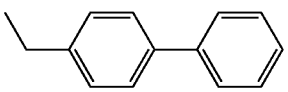 | —OC₄H₉ | 0.82 (3H, t, J = 7.4 Hz), 1.2-1.35 (2H, m), 1.45-1.6 (2H, m), 2.59 (2H, t, J = 6.9 Hz), 3.01 (2H, t, J = 6.9 Hz), 4.01 (2H, t, J = 6.4 Hz), 5.21 (2H, s), 7.0-7.65 (11H, m), 7.71 (1H, s), 13.8 (1H, br s) |
| 947 | 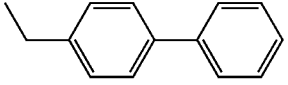 | —OCH₂CO₂C(CH₃)₃ | CDCl₃: 1.54 (9H, s), 2.68 (2H, t, J = 6.8 Hz), 2.98 (2H, t, J = 6.8 Hz), 4.46 (2H, s), 5.47 (2H, s), 6.69 (1H, d, J = 8.5 Hz), 7.1-7.6 (10H, m), 7.78 (1H, s), 9.25 (1H, br s) |
| 948 | 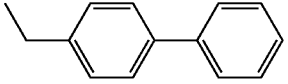 | —OH | 2.57 (2H, t, J = 6.9 Hz), 2.97 (2H, t, J = 6.9 Hz), 5.35 (2H, s), 6.8-7.65 (11H, m), 7.69 (1H, s), 10.92 (1H, s), 13.8 (1H, br s) |
| 949 | 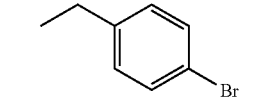 | —H | 2.64-2.82 (2H, m), 3.07 (2H, t, J = 7.8 Hz), 5.21 (2H, brs), 7.00-7.13 (2H, m), 7.24-7.49 (6H, m), 7.54-7.70 (4H, m), 7.79 (1H, s), 13.82 (1H, s). |
| 950 | 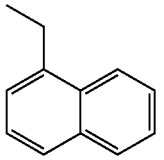 | —H | 2.64-2.80 (2H, m), 2.97-3.12 (2H, m), 5.13 (2H, s), 7.01 (1H, d, J = 8.1. Hz), 7.08 (1H, d, J = 7.7 Hz), 7.11-7.35 (3H, m), 7.44-7.55 (2H, m), 7.78 (1H, s), 13.84 (1H, s). |

DMSO-d₆ is used for measuring NMR, unless otherwise specified.

TABLE 135

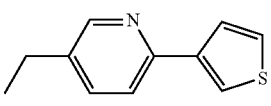

| Ex. | R1 | R2 | 1H NMR (DMSO-d6) dppm |
|---|---|---|---|
| 951 | 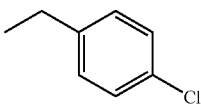 | —H | 2.20-2.37 (2H, m), 2.49-2.69 (2H, m), 4.83 (2H, s), 6.49-6.62 (2H, m), 6.68-6.82 (1H, m), 6.87-7.05 (3H, m), 7.21 (1H, s), 7.25-7.49 (4H, m), 13.36 (1H, s). |
| 952 | | —OCH₃ | 2.58-2.61 (2H, m), 2.98-3.01 (2H, m), 3.77 (3H, s), 5.17 (2H, s), 7.07 (1H, d, J = 8.9 Hz), 7.16 (1H, d, J = 8.9 Hz), 7.53-7.74 (5H, m), 8.09-8.10 (1H, m), 8.35 (1H, d, J = 2.0 Hz), 13.79 (1H, brs) |
| 953 | | —H | 2.65-2.80 (2H, m), 2.99-3.12 (2H, m), 5.16 (2H, s), 7.03 (1H, d, J = 8.1 Hz), 7.09 (1H, d, J = 7.7 Hz), 7.20-7.40 (5H, m), 7.79 (1H, s), 13.87 (1H, brs). |

TABLE 135-continued

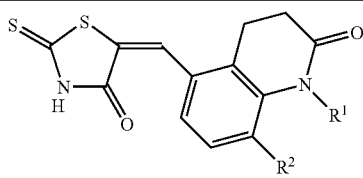

| Ex. | R1 | R2 | 1H NMR (DMSO-d6) dppm |
|---|---|---|---|
| 954 | (4-methylbenzyl with ethyl linker, 4-CH3-C6H4-CH2CH2-) | —H | 2.24 (3H, s), 2.68-2.73 (2H, m), 3.01-3.07 (2H, m), 5.12 (2H, s), 7.02-7.18 (6H, m), 7.26 (1H, t, J = 8.0 Hz), 7.78 (1H, s), 13.86 (1H, brs). |
| 955 | (2-quinolinyl-ethyl) | —OCH3 | 2.61-2.66 (2H, m), 3.16-3.21 (2H, m), 3.64 (3H, s), 5.33 (2H, s), 7.07 (1H, d, J = 8.8 Hz), 7.17 (1H, d, J = 8.8 Hz), 7.39 (1H, d, J = 8.6 Hz), 7.50-7.561 (1H, m), 7.67-7.73 (1H, m), 7.78 (1H, s), 7.87-7.93 (2H, m), 8.24 (1H, d, J = 8.5 Hz), 13.80 (1H, brs) |
| 956 | (N-methyl-N-phenyl-2-aminopyridinyl) | —OCH3 | 2.47-2.52 (2H, m), 2.88-2.93 (2H, m), 3.30 (3H, s), 3.86 (3H, s), 5.11 (2H, s), 6.38 (1H, d, J = 8.7 Hz), 7.06-7.22 (6H, m), 7.35-7.41 (2H, m), 7.67 (1H, s), 7.89 (1H, d, J = 2.1 Hz), 13.75 (1H, brs) |
| 957 | (6-chloro-pyridin-3-yl-ethyl) | —H | 2.70-2.76 (2H, m), 3.03-3.09 (2H, m), 5.21 (2H, s), 7.07-7.12 (2H, m), 7.32 (1H, t, J = 8.0 Hz), 7.45 (1H, d, J = 8.3 Hz), 7.69 (1H, dd, J1 = 2.4 Hz, J2 = 8.3 Hz), 7.78 (1H, s), 8.36 (1H, d, J = 2.4 Hz), 13.81 (1H, brs) |

TABLE 136

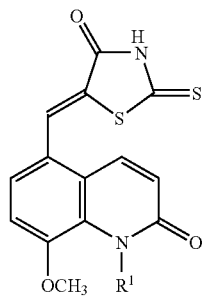

| Ex. | R¹ | ¹H NMR (DMSO-d6) dppm |
|---|---|---|
| 958 | —CH3 | 4.02 (3H, s), 4.07 (3H, s), 6.77 (1H, d, J = 9.8 Hz), 7.35-7.65 (2H, m), 8.07 (1H, s), 8.17 (1H, d, J = 9.8 Hz), |
| 959 | (4-bromobenzyl with ethyl linker, 4-Br-C6H4-CH2CH2-) | 3.66 (3H, s), 5.67 (2H, s), 6.82 (1H, d, J = 9.8 Hz), 7.04 (2H, d, J = 8.5 Hz), 7.28-7.38 (2H, m), 7.40-7.52 (2H, m), 8.05 (1H, s). 8.22 (1H, d, J = 10.0 Hz),13.86 (1H, brs). |

TABLE 137

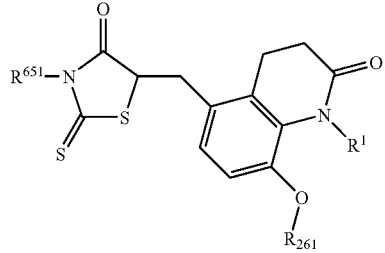

| Ex. | R1 | R651 | R261 | M.p. (° C.) |
|---|---|---|---|---|
| 960 | —CH3 | —H | —CH3 | 204-209 |
| 961 | —H | —H | —CH3 | 266(dec.) |
| 962 | —CH3 | —CH3 | —CH3 | 196-198 |
| 963 | —C2H5 | —H | —CH3 | 200.5-201.5 |
| 964 | —CH(C6H5)2 | —H | —CH3 | 233(dec.) |
| 965 | —(CH2)2CH(CH3)2 | —H | —CH3 | 139.5-141 |
| 966 | —C3H7 | —H | —CH3 | 59-83 |
| 967 | —C5H11 | —H | —CH3 | 143-145.5 |
| 968 | —CH(CH3)2 | —H | —CH3 | 182-184 |
| 969 | —CH2CH(CH3)2 | —H | —CH3 | 208-211 |

TABLE 138

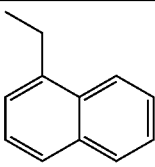

| Ex. | R¹ | R⁶⁵¹ | R²⁶¹ | M.p. (°C.) |
|---|---|---|---|---|
| 970 | (1-ethylnaphthalene) | —H | —H | 238 (dec.) |
| 971 | (2-ethylnaphthalene) | —H | —CH₃ | 133-136 |
| 972 | (4-ethylbiphenyl) | —H | —C₄H₉ | 156-161 |
| 973 | (4-ethylbiphenyl) | —H | —CH₂CO₂H | 128-135 |
| 974 | (5-ethyl-2-chloropyridine) | —H | —CH₃ | 177-181 |

TABLE 139

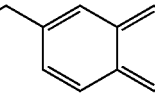

| Ex. | R¹ | R⁶⁵¹ | ¹H NMR dppm |
|---|---|---|---|
| 975 | CH₃OCH₂O(CH₂)₃— | —H | CDCl₃: 1.9-2.0 (2H, m), 2.63 (2H, t, J = 7.1 Hz), 2.75-3.05 (2H, m), 3.16 (1H, dd, J = 13.3 Hz, J = 4.0 Hz), 3.37 (3H, s), 3.60 (2H, t, J = 6.2 Hz), 3.6-3.75 (1H, m), 4.0-4.2 (2H, m), 4.48 (1H, dd, J = 10.3 Hz, J = 4.0 Hz), 4.69 (3H, s), 6.94 (1H, d, J = 7.6 Hz), 7.08 (1H, d, J = 8.2 Hz), 7.5-9.0 (1H, m) |
| 976 | HO(CH₂)₃— | —H | DMSO-d₆: 1.6-1.9 (2H, m), 2.7-3.0 (2H, m), 3.13 (1H, dd, J = 14.4 Hz, J = 4.0 Hz), 3.3-3.8 (5H, m), 3.91 (2H, t, J = 8.4 Hz), 4.55 (1H, t, J = 5.0 Hz), 4.83 (1H, dd, J = 14.4 Hz, J = 4.0 Hz), 6.92 (1H, d, J = 7.5 Hz), 7.0-7.5 (2H, m), 12.13 (1H, br s) |

TABLE 140

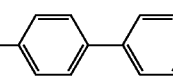

| Ex. | R¹ | R⁶⁵¹ | R²⁶¹ | ¹H NMR (DMSO-d₆) dppm |
|---|---|---|---|---|
| 977 | —(CH₂)₃C₆H₅ | —H | —CH₃ | 1.64-1.73 (m, 2H), 2.32-2.42 (m, 4H), 2.74-2.85 (m, 2H), 3.10 (dd; J = 9.8, 14.4 Hz, 1H), 3.14 (dd; J = 4.6, 14.4 Hz, 1H), 3.69 (S, 3H), 3.85-3.95 (m, 2H), 4.93 (dd; J = 4.6, 9.8 Hz, 1H), 6.93 (d, J = 8.6 Hz, 1H), 6.98 (d, J = 8.6 Hz, 1H), 7.04 (d, J = 7.5 Hz, 2H), 7.14 (t, J = 7.5 Hz, 1H), 7.23 (t, J = 7.5 Hz, 2H), 13.22 (brs, 1H) |
| 978 | —(CH₂)₂C₆H₅ | —H | —CH₃ | 2.22-2.31 (m, 2H), 2.32-2.55 (m, 2H), 2.63-2.75 (m, 2H), 3.12 (dd; J = 10.0, 14.4 Hz, 1H), 3.68 (dd; J = 4.5, 14.4 Hz, 1H), 3.87 (S, 3H), 4.10-4.30 (m, 2H), 4.83 (dd; J = 4.5, 10.0 Hz, 1H), 6.90-7.05 (m, 4H), 7.12-7.25 (m, 3H), 13.25 (brs, 1H) |
| 979 | —C₄H₉ | —H | —CH₃ | 0.79 (t; J = 7.2 Hz, 3H), 1.13 (tt; J = 7.2, 7.2 Hz, 2H), 1.35 (tt; J = 7.2, 7.2 Hz, 2H), 2.34-2.43 (m, 2H), 2.70-2.80 (m, 2H), 3.21 (dd; J = 9.5, 14.5 Hz, 1H), 3.41 (dd; J = 4.7, 14.5 Hz, |

TABLE 140-continued

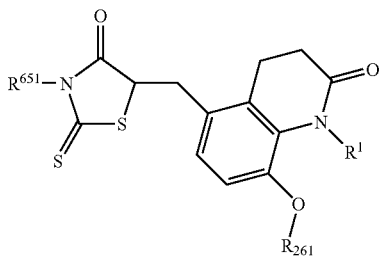

| Ex. | $R^1$ | $R^{651}$ | $R^{261}$ | $^1$H NMR (DMSO-$d_6$) dppm |
|---|---|---|---|---|
| | | | | 1H), 3.80 (S, 3H), 3.93 (t; J = 7.2 Hz, 2H), 4.94 (dd; J = 4.7, 9.5 Hz, 1H), 6.95 (d; J = 8.8 Hz, 1H), 6.97 (d; J = 8.8 Hz, 1H), 13.20 (brs, 1H) |
| 980 | —CH$_2$-cyclo-C$_3$H$_5$ | —H | —CH$_3$ | 0-0.07 (m, 2H), 0.20-0.26 (m, 2H), 0.73-0.84 (m, 1H), 2.30-2.42 (m, 2H), 2.70-2.85 (m, 2H), 3.18 (dd; J = 9.1, 14.5 Hz, 1H), 3.42 (dd; J = 4.7, 14.5 Hz, 1H), 3.81 (S, 3H), 3.84-3.90 (m, 2H), 4.95 (dd; J = 4.7, 9.1 Hz, 1H), 6.94 (d; J = 8.6 Hz, 1H), 6.97 (d; J = 8.6 Hz, 1H), 13.19 (brs, 1H) |
| 981 | —(CH$_2$)$_2$OC$_6$H$_5$ | —H | —CH$_3$ | 2.39-2.47 (m, 2H), 2.70-2.83 (m, 2H), 3.14 (dd; J = 10.0, 14.5 Hz, 1H), 3.40 (dd; J = 4.5, 14.5 Hz, 1H), 3.79 (S, 3H), 4.00-4.07 (m, 2H), 4.20-4.30 (m, 2H), 4.88 (dd; J = 4.5, 10.0 Hz, 1H), 6.79 (d, J = 7.7 Hz, 2H), 6.88 (t, J = 7.7 Hz, 1H), 6.95 (d, J = 8.7 Hz, 1H), 6.98 (d, J = 8.7 Hz, 1H), 7.22 (t, J = 7.7 Hz, 2H), 13.23 (brs, 1H) |

TABLE 141

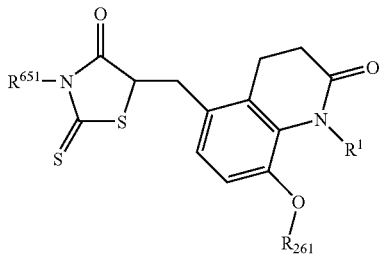

| Ex. | $R^1$ | $R^{651}$ | $R^{261}$ | $^1$H NMR (DMSO-$d_6$) dppm |
|---|---|---|---|---|
| 982 | —CH$_2$-cyclo-C$_6$H$_{11}$ | —H | —CH$_3$ | 0.71-0.80 (m, 2H), 0.94-1.07 (m, 3H), 1.20-1.27 (m, 1H), 1.37-1.45 (m, 2H), 1.45-1.59 (m, 3H), 2.34-2.43 (m, 2H), 2.70-2.80 (m, 2H), 3.19 (dd; J = 9.2, 14.5 Hz, 1H), 3.41 (dd; J = 4.9, 14.5 Hz, 1H), 3.80 (S, 3H), 3.88-3.99 (m, 2H), 4.95 (dd; J = 4.9, 9.2 Hz, 1H), 6.94 (d, J = 8.6 Hz, 1H), 6.97 (d, J = 8.6 Hz, 1H), 13.18 (brs, 1H) |
| 983 | —CH$_2$CH$_2$OCH$_3$ | —H | —CH$_3$ | 2.34-2.43 (m, 2H), 2.69-2.79 (m, 2H), 3.08 (S, 3H), 3.17 (dd; J = 9.6, 14.5 Hz, 1H), 3.25-3.36 (m, 2H), 3.41 (dd; J = 4.6, 14.5 Hz, 1H), 3.80 (S, 3H), 4.03-4.12 (m, 2H), 4.93 (dd; J = 4.6, 9.6 Hz, 1H), 6.95 (d, J = 8.6 Hz, 1H), 6.98 (d, J = 8.6 Hz, 1H), 13.21 (brs, 1H) |
| 984 | —(CH$_2$)$_4$C$_6$H$_5$ | —H | —CH$_3$ | 1.38-1.45 (m, 4H), 2.33-2.42 (m, 2H), 2.43-2.53 (m, 2H), 2.69-2.80 (m, 2H), 3.16 (dd; J = 9.7, 14.6 Hz, 1H), 3.40 (dd; J = 4.6, 14.6 Hz, 1H), 3.74 (S, 3H), 3.88-3.96 (m, 2H), 4.93 (dd; J = 4.6, 9.7 Hz, 1H), 6.93 (d, J = 8.6 Hz, 1H), 6.97 (d, J = 8.6 Hz, 1H), 7.10 (d, J = 7.3 Hz, 2H), 7.14 (t, J = 7.3 Hz, 1H), 7.24 (t, J = 7.3 Hz, 2H), 13.20 (brs, 1H) |

TABLE 141-continued

[Structure: thiazolidinedione-thione substituted with R651-N, linked via CH2 to a tetrahydroquinolin-2-one bearing N-R1 and O-R261]

| Ex. | R¹ | R⁶⁵¹ | R²⁶¹ | ¹H NMR (DMSO-d₆) dppm |
|---|---|---|---|---|
| 985 | —(CH₂)₅C₆H₅ | —H | —CH₃ | 1.05-1.16 (m, 2H), 1.34-1.51 (m, 4H), 2.31-2.41 (m, 2H), 2.43-2.53 (m, 2H), 2.64-2.72 (m, 2H), 3.14 (dd; J = 9.7, 14.5 Hz, 1H), 3.40 (dd; J = 4.6, 14.5 Hz, 1H), 3.78 (S, 3H), 3.87-3.96 (m, 2H), 4.91 (dd; J = 4.6, 9.7 Hz, 1H), 6.94 (d, J = 8.6 Hz, 1H), 6.97 (d, J = 8.6 Hz, 1H), 7.12 (d, J = 7.4 Hz, 2H), 7.15 (t, J = 7.4 Hz, 1H), 7.24 (t, J = 7.5 Hz, 2H), 13.22 (brs, 1H) |

TABLE 142

[Structure: 2-thioxo-thiazolidin-4-one (HN) linked via CH2 to tetrahydroquinolin-2-one bearing N-R1 and O-R261]

| Ex. | R¹ | R²⁶¹ | ¹H NMR dppm |
|---|---|---|---|
| 986 | 5-(thiophen-3-yl)pyridin-2-yl | —CH₃ | 2.83-2.89 (2H, m), 3.20-3.10 (1H, m), 3.36-3.42 (2H, m), DMSO overlap (1H), 3.66 (3H, s), 4.93 (1H, dd, J1 = 4.5 Hz, J2 = 9.5 Hz), 5.15 (2H, s), 6.84 (1H, d, J = 8.6 Hz), 6.92 (1H, d, J = 8.6 Hz), 7.54-7.57 (1H, m), 7.61-7.77 (3H, m), 8.11-8.13 (1H, m), 8.36 (1H, d, J = 1.8 Hz), 13.19 (1H, brs) |
| 987 | 5-ethyl-6-(N-methyl-N-phenylamino)pyridin-2-yl | —CH₃ | 2.84-2.78 (2H, m), 3.15-3.21 (2H, m), DMSO overlap (3H, s), 3.72 (3H, s), 4.90-4.94 (1H, m), 5.01 (2H, s), 6.65 (1H, d, J = 9.0 Hz), 6.88-6.93 (2H, m), 7.36-7.39 (3H, m), 7.50-7.53 (3H, m), 7.85 (1H, s), 13.20 (1H, brs) |

TABLE 142-continued
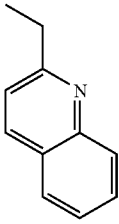
| Ex. | R¹ | R²⁶¹ | ¹H NMR δppm |
|---|---|---|---|
| 988 | (2-ethylquinolin-yl) | —CH₃ | 2.55-2.60 (2H, m), 3.05-3.10 (2H, m), 3.13-3.48 (2H, m), 3.53 (3H, s), 4.93-4.99 (1H, m), 5.31 (2H, s), 6.84 (1H, d, J = 8.5 Hz), 6.93 (1H, d, J = 8.5 Hz), 7.34 (1H, d, J = 8.6 Hz), 7.50-7.56 (1H, m), 7.66-7.72 (1H, m), 7.88-7.95 (2H, m), 8.22 (1H, d, J = 8.6 Hz), 12.77 (1H, brs) |
| 989 | (4-biphenyl)ethyl | —CH₂CO₂C(CH₃)₃ | CDCl₃: 1.52 (s, 9H), 2.6-2.7 (m, 2H), 2.7-2.95 (m, 2H), 3.1-3.2 (m, 1H), 3.35-3.5 (m, 1H), 4.39 (s, 2H), 4.45-4.55 (m, 1H), 5.4-5.55 (m, 1H), 6.57 (d, 1H, J = 8.6 Hz), 6.86 (d, 1H, J = 8.6 Hz), 7.1-7.6 (m, 9H), 8.96 (br s) |
DMSO-d₆ is used for measuring NMR, unless otherwise specified.
TABLE 143
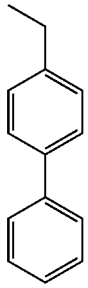
| Ex. | R⁵⁴⁰ | M.p. (° C.) |
|---|---|---|
| 990 | —C₆H₅ | 186.8-188.0 |
| 991 | —Br | 229.6-230.4 |
| 992 | —Cl | 214.6-215.7 |
| 993 | —CH₃ | 188.7-189.5 |
TABLE 144
| Ex. | R⁵⁴⁰ | M.p. (° C.) |
|---|---|---|
| 994 | —Br | 204.5-205.7 |
| 995 | —C₆H₅ | 186.3-187.1 |

TABLE 145

| Ex. | R¹ | R² | M.p. (° C.) |
|---|---|---|---|
| 996 | 2-ethylnaphthyl | —H | 204.1-205.9 |
| 997 | —C₆H₅ | —H | 223.6-225.4 |
| 998 | —CH₂CH=CH₂ | —OCH₃ | 156.5-158.5 |
| 999 | —C₈H₁₇ | —OCH₃ | 114.0-114.5 |

TABLE 146

| Ex. | R¹ | M.p. (° C.) |
|---|---|---|
| 1000 | 4-bromophenethyl | 249.5-250.2 |
| 1001 | —(CH₂)₂CH(CH₃)₂ | 198.5-200.5 |

TABLE 147

| Ex. | R¹ | R² | $^1$H NMR (DMSO-d$_6$) dppm |
|---|---|---|---|
| 1002 | 4-(piperidin-1-ylmethyl)phenethyl | —H | 1.40-1.48 (2H, m), 1.52-1.60 (4H, m), 2.64-2.74 (6H, m), 2.99-3.05 (2H, m), 3.76 (2H, s), 5.16 (2H, s), 6.92 (1H, d, J = 7.0 Hz), 7.14-7.33 (6H, m), 7.66 (1H, s) |
| 1003 | 3-(piperidin-1-ylmethyl)phenethyl | —H | 1.23-1.29 (2H, m), 1.51-1.57 (4H, m), 2.57-2.61 (4H, m), 2.68-2.74 (2H, m), 3.00-3.06 (2H, m), 3.79 (2H, s), 5.19 (2H, s), 6.93 (1H, d, J = 7.6 Hz), 7.12-7.23 (5H, m), 7.30-7.33 (1H, m), 7.69 (1H, s) |
| 1004 | 6-(piperidin-1-ylmethyl)pyridin-2-ylethyl | —H | 1.36-1.44 (2H, m), 1.49-1.57 (4H, m), 2.57-2.64 (4H, m), 2.67-2.73 (2H, m), 3.00-3.06 (2H, m), 3.84 (2H, s), 5.21 (2H, s), 6.90 (1H, d, J = 7.4 Hz), 7.14-7.21 (3H, m), 7.32 (1H, d, J = 7.7 Hz), 7.68 (1H, s), 7.74 (1H, t, J = 7.7 Hz) |
| 1005 | 6-(phenylthiomethyl)pyridin-2-ylethyl | —H | 2.60-2.77 (2H, m), 2.97-3.07 (2H, m), 4.30 (2H, s), 5.16 (2H, s), 6.85 (1H, d, J = 8.0 Hz), 6.90 (1H, d, J = 8.0 Hz), 7.04-7.36 (8H, m), 7.65 (1H, t, J = 7.7 Hz), 7.92 (1H, s), 12.19 (1H, brs) |
| 1006 | 5-(biphenyl-4-yl)pyridin-2-ylethyl | —OCH₃ | 2.57-2.62 (2H, m), 2.98-3.02 (2H, m), 3.76 (3H, s), 5.20 (2H, s), 7.08 (1H, d, J = 8.8 Hz), 7.20 (1H, d, J = 8.8 Hz), 7.40 (1H, d, J = 7.3 Hz), 7.49 (2H, t, J = 7.3 Hz), 7.77 (1H, dd, J1 = 2.0 Hz, J2 = 8.3 Hz), 7.71-7.78 (4H, m), 7.86 (1H, s), 7.89 (1H, d, J = 8.3 Hz), 8.13 (2H, d, J = 8.3 Hz), 8.46-8.47 (1H, m), 12.58 (1H, brs) |

TABLE 147-continued

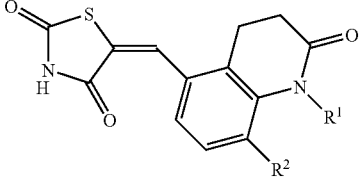

| Ex. | R¹ | R² | ¹H NMR (DMSO-d₆) dppm |
|---|---|---|---|
| 1007 | 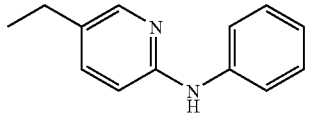 | —OCH₃ | 2.47-2.52 (2H, m), 2.88-2.93 (2H, m), 3.85 (3H, s), 5.13 (2H, s), 6.66 (1H, d, J = 8.8 Hz), 6.84 (1H, t, J = 7.3 Hz), 7.06 (1H, d, J = 8.8 Hz), 7.15-7.29 (4H, m), 7.57-7.61 (2H, m), 7.83 (1H, s), 7.89 (1H, d, J = 2.1 Hz), 8.91 (1H, s), 12.55 (1H, brs) |
| 1008 | 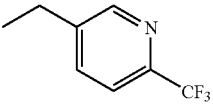 | —OCH₃ | 2.58-2.63 (2H, m), 2.98-3.04 (2H, m), 3.61 (3H, s), 5.13 (2H, s), 7.08 (1H, d, J = 8.8 Hz), 7.22 (1H, d, J = 8.8 Hz), 7.78-7.84 (2H, m), 7.86 (1H, s), 8.60 (1H, s), 12.54 (1H, brs) |
| 1009 | 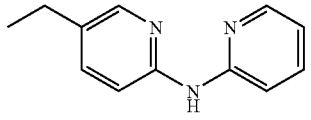 | —OCH₃ | 2.53-2.57 (2H, m), 2.92-2.96 (2H, m), 3.84 (3H, s), 5.15 (2H, s), 6.83 (1H, dd, J1 = 4.1 Hz, J2 = 8.5 Hz), 7.05 (1H, d, J = 8.8 Hz), 7.17 (1H, d, J = 8.8 Hz), 7.36 (1H, dd, J1 = 2.2 Hz, J2 = 8.5 Hz), 7.56-7.63 (3H, m), 7.83 (1H, s), 7.98 (1H, d, J = 1.8 Hz), 8.16-8.18 (1H, m), 9.59 (1H, s), 12.58 (1H, brs) |

TABLE 148

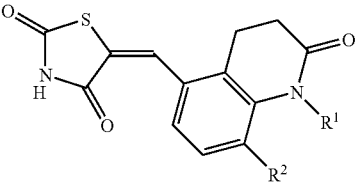

| Ex. | R¹ | R² | ¹H NMR (DMSO-d₆) dppm |
|---|---|---|---|
| 1010 | 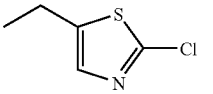 | —OCH₃ | 2.50-2.55 (2H, m), 2.88-2.93 (2H, m), 3.89 (3H, s), 5.11 (2H, s), 7.19 (1H, d, J = 8.8 Hz), 7.26 (1H, d, J = 8.8 Hz), 7.55 (1H, s), 7.84 (1H, s), 12.51 (1H, brs) |
| 1011 | 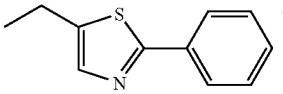 | —OCH₃ | 2.51-2.56 (2H, m), 2.87-2.92 (2H, m), ), 3.93 (3H, s), 5.36 (2H, s), 7.17 (1H, d, J = 8.8 Hz), 7.25 (1H, d, J = 8.8 Hz), 7.44-7.47 (3H, m), 7.69 (1H, s), 7.75 (1H, s), 7.83-7.87 (2H, m) |
| 1012 | 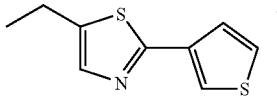 | —OCH₃ | 2.48-2.53 (2H, m), 2.86-2.91 (2H, m), 3.93 (3H, s), 5.33 (2H, s), 7.17 (1H, d, J = 8.8 Hz), 7.24 (1H, d, J = 8.8 Hz), 7.49 (1H, dd, J1 = 1.2 Hz, J2 = 5.0 Hz), 7.61 (1H, s), 7.66 (1H, dd, J1 = 2.9 Hz, J2 = 5.0 Hz), 7.81 (1H, s), 8.04 (1H, dd, J1 = 1.2 Hz, J2 = 2.9 Hz), 12.54 (1H, brs) |
| 1013 | 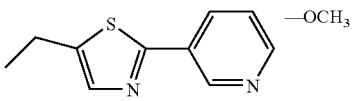 | —OCH₃ | 2.52-2.57 (2H, m), 2.89-2.94 (2H, m), 3.93 (3H, s), 5.34 (2H, s), 7.18 (1H, d, J = 8.8 Hz), 7.25 (1H, d, J = 8.8 Hz), 7.50 (1H, dd, J1 = 4.8 Hz, J2 = 8.0 Hz), 7.79 (1H, s), 7.80 (1H, s), 8.19-8.23 (1H, m), 8.62 (1H, dd, J1 = 1.3 Hz, J2 = 4.8 Hz), 9.05 (1H, d, J = 2.2 Hz), 12.54 (1H, brs) |

TABLE 149

| Ex. | R¹ | R² | ¹H-NMR (CDCl₃) dppm |
|---|---|---|---|
| 1014 | 4-ethylbenzyl-N(CH₃)-phenyl | —H | 2.75-2.81 (2H, m), 2.99 (3H, s), 3.04-3.10 (2H, m), 4.49 (2H, s), 5.16 (2H, s), 6.67-6.74 (3H, m), 6.95 (1H, dd, J1 = 1.5 Hz, J2 = 7.5 Hz), 7.12-7.21 (8H, m), 7.96 (1H, s) |
| 1015 | 3-ethylbenzyl-S-phenyl | —H | 2.74-2.80 (2H, m), 3.03-3.09 (2H, m), 4.07 (2H, s), 5.14 (2H, s), 6.87 (1H, dd, J1 = 2.3 Hz, J2 = 6.9 Hz), 7.04-7.10 (2H, m), 7.13-7.25 (9H, m), , 7.98 (1H, s) |
| 1016 | 4-ethylbenzyl-indoline | —H | 2.77-2.83 (2H, m), 2.92-2.99 (2H, m), 3.05-3.12 (2H, m), 3.25-3.32 (2H, m), 4.21 (2H, s), 5.18 (2H, s), 6.48 (1H, d, J = 7.7 Hz), 6.66 (1H, t, J = 7.1 Hz), 6.94-7.01 (1H, m), 7.07 (1H, t, J = 7.7 Hz), 7.15-7.33 (7H, m), 7.97 (1H, s) |

TABLE 150

| Ex. | R¹ | R² | ¹H NMR (DMSO-d₆) dppm |
|---|---|---|---|
| 1917 | 4-ethylbenzyl-piperidine | —H | 1.44-1.52 (2H, m), 1.61-1.69 (4H, m), 2.69-2.75 (2H, m), 2.90-2.96 (4H, m), 3.02-3.08 (2H, m), 4.07 (2H, s), 5.19 (2H, s), 6.91 (1H, d, J = 8.0 Hz), 7.10 (1H, d, J = 7.6 Hz), 7.14-7.31 (4H, m), 7.37-7.40 (2H, m) |
| 1018 | 3-ethylbenzyl-piperidine | —H | 1.41-1.47 (2H, m), 1.57-1.63 (4H, m), 2.28-2.32 (4H, m), 2.70-2.74 (2H, m), 3.03-3.09 (2H, m), 4.08 (2H, s), 5.21 (2H, s), 6.89 (1H, d, J = 8.1 Hz), 7.08 (1H, d, J = 7.6 Hz), 7.14-7.25 (3H, m), 7.28-7.43 (3H, m) |
| 1019 | 4-ethylbenzyl-S-phenyl | —H | 2.68-2.74 (2H, m), 3.02-3.08 (2H, m), 4.19 (2H, s), 5.13 (2H, s), 7.00 (1H, d, J = 8.0 Hz), 7.07 (1H, d, J = 8.0 Hz), 7.13-7.19 (3H, m), 7.24-7.29 (7H, m), , 7.78 (1H, s), 13.89 (1H, brs) |
| 1020 | 5-ethylpyridin-2-yl-NH-C(O)-pyridin-3-yl | —OCH₃ | 2.48-2.52 (2H, m), 3.29-3.03 (2H, m), 3.79 (3H, s), 5.17 (2H, s), 7.07 (1H, d, J = 8.8 Hz), 7.17 (1H, d, J = 8.8 Hz), 7.50-7.55 (1H, m), 7.59 (1H, dd, J1 = 2.2 Hz, J2 = 8.5 Hz), 7.69 (1H, s), 8.04 (1H, d, J = 8.5 Hz), 8.17 (1H, d, J = 2.0 Hz), 8.30 (1H, dt, J1 = 2.0 Hz, J2 = 8.0 Hz), 8.73 (1H, dd, J1 = 1.6 Hz, J2 = 4.8 Hz), 9.08 (1H, d, J = 1.6 Hz), 10.98 (1H, s), 13.69 (1H, brs) |

TABLE 150-continued

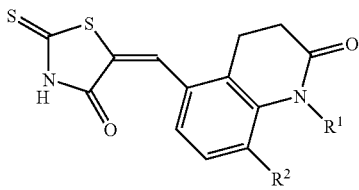

| Ex. | R¹ | R² | ¹H NMR (DMSO-d₆) dppm |
|---|---|---|---|
| 1021 | 5-ethyl-2-(trifluoromethyl)pyridin-yl | —OCH₃ | 2.57-2.63 (2H, m), 3.00-3.05 (2H, m), 3.60 (3H, s), 5.12 (2H, s), 7.06 (1H, d, J = 8.8 Hz), 7.19 (1H, d, J = 8.8 Hz), 7.48 (1H, s), 7.77-7.85 (2H, m), 8.60 (1H, s), 11.98 (1H, brs) |
| 1022 | 5-ethyl-2-(phenylamino)pyridin-yl | —OCH₃ | 2.47-2.52 (2H, m), 2.92-3.07 (2H, m), 3.86 (3H, s), 5.12 (2H, s), 6.66 (1H, d, J = 8.5 Hz), 6.84 (1H, t, J = 7.5 Hz), 7.05-7.29 (5H, m), 7.58 (2H, d, J = 7.5 Hz), 7.66 (1H, s), 7.89 (1H, d, J = 2.2 Hz), 8.92 (1H, s), 13.76 (1H, brs) |
| 1023 | 5-ethyl-2-(biphenyl-4-yl)pyridin-yl | —OCH₃ | 2.57-2.61 (2H, m), 2.99-3.05 (2H, m), 3.77 (3H, s), 5.20 (2H, s), 7.09 (1H, d, J = 8.9 Hz), 7.18 (1H, d, J = 8.9 Hz), 7.40 (1H, d, J = 7.2 Hz), 7.46-7.52 (2H, m), 7.61-7.65 (1H, m), 7.71-7.79 (5H, m), 7.90 (1H, d, J = 8.3 Hz), 8.13 (2H, d, J = 8.3 Hz), 8.46-8.47 (1H, m), 13.81 (1H, brs) |

TABLE 151

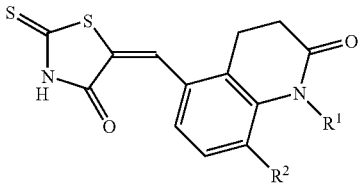

| Ex. | R¹ | R² | ¹H NMR (DMSO-d₆) dppm |
|---|---|---|---|
| 1024 | 6-ethyl-2-(piperidin-1-ylmethyl)pyridin-yl | —H | 1.40-1.48 (2H, m), 1.56-1.64 (4H, m), 2.68-2.74 (2H, m), 2.90-2.98 (4H, m), 3.04-3.09 (2H, m), 4.21 (2H, s), 5.27 (2H, s), 6.89 (1H, d, J = 7.8 Hz), 7.09-7.39 (4H, m), 7.42 (1H, s), 7.83 (1H, t, J = 7.7 Hz) |
| 1025 | 5-ethyl-2-chlorothiazol-yl | —OCH₃ | 2.46-2.52 (2H, m), 2.91-97 (2H, m), 3.90 (3H, s), 5.11 (2H, s), 7.20 (1H, d, J = 8.8 Hz), 7.25 (1H, d, J = 8.8 Hz), 7.56 (1H, s), 7.69 (1H, s), 13.76 (1H, brs) |
| 1026 | 5-ethyl-2-(pyridin-2-yl)thiazol-yl | —OCH₃ | 2.51-2.57 (2H, m), 2.90-2.96 (2H, m), 3.95 (3H, s), 5.36 (2H, s), 7.19 (1H, d, J = 9.1 Hz), 7.23 (1H, d, J = 9.1 Hz), 7.44-7.47 (3H, m), 7.68 (1H, s), 7.70 (1H, s), 7.83-7.86 (2H, m), 13.81 (1H, brs) |
| 1027 | 5-ethyl-2-(thiophen-3-yl)thiazol-yl | —OCH₃ | 2.45-2.50 (2H, m), 2.89-2.94 (2H, m), 3.95 (3H, s), 5.33 (2H, s), 7.16-7.24 (2H, m), 7.49 (1H, dd, J1 = 1.0 Hz, J2 = 5.0 Hz), 7.61 (1H, s), 7.64-7.66 (1H, m), 7.67 (1H, s), 8.03-8.04 (1H, m), 13.80 (1H, brs) |

TABLE 151-continued

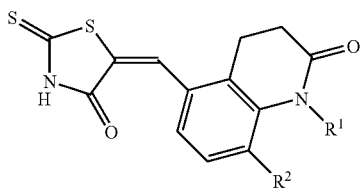

| Ex. | R¹ | R² | ¹H NMR (DMSO-d$_6$) dppm |
|---|---|---|---|
| 1028 | (5-ethyl-thiazol-2-yl)(pyridin-3-yl) | —OCH$_3$ | 2.47-2.52 (2H, m), 2.89-2.94 (2H, m), 3.94 (3H, s), 5.34 (2H, s), 7.17-7.25 (2H, m), 7.49 (1H, dd, J1 = 4.9 Hz, J2 = 8.0 Hz), 7.65 (1H, s), 7.79 (1H, s), 8.19-8.23 (1H, m), 8.61-8.63 (1H, m), 9.04-9.05 (1H, m), 13.80 (1H, brs) |

TABLE 152

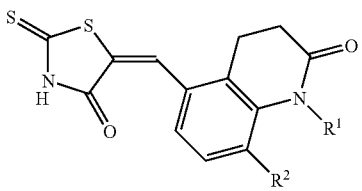

| Ex. | R¹ | R² | ¹H-NMR (CDCl$_3$) dppm |
|---|---|---|---|
| 1029 | 4-ethylbenzyl-N-methyl-N-phenylamine | —H | 2.77-2.83 (2H, m), 2.94 (3H, s), 3.07-3.13 (2H, m), 4.49 (2H, s), 5.17 (2H, s), 6.50-6.74 (3H, m), 6.98 (1H, d, J = 8.2 Hz), 7.08-7.68 (8H, m), 7.86 (1H, s), 9.65 (1H, brs) |
| 1030 | 3-ethylbenzyl phenyl sulfide | —H | 2.75-2.81 (2H, m), 3.05-3.11 (2H, m), 4.07 (2H, s), 5.14 (2H, s), 6.90 (1H, d, J = 7.3 Hz), 7.04-7.13 (3H, m), 7.14-7.33 (8H, m), 7.85 (1H, s), 9.41 (1H, brs) |
| 1031 | 2-ethyl-4-methoxy-3,5-dimethylpyridine | —H | 2.21 (3H, s), 2.33 (3H, s), 2.75-2.81 (2H, m), 3.07-3.13 (2H, m), 3.78 (3H, s), 5.18 (2H, s), 6.97 (1H, d, J = 8.1 Hz), 7.08 (1H, d J = 7.8 Hz), 7.16-7.28 (1H, m), 7.81 (1H, s), 8.10 (1H, s) |

TABLE 153

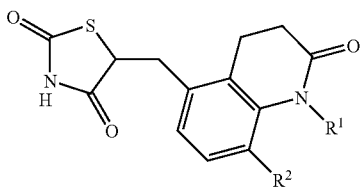

| Ex. | R¹ | R² | M.p.(° C.) |
|---|---|---|---|
| 1032 | —(CH$_2$)$_3$CF$_3$ | —OCH$_3$ | 169-170 |
| 1033 | —(CH$_2$)$_4$F | —OCH$_3$ | 136-138 |

TABLE 153-continued
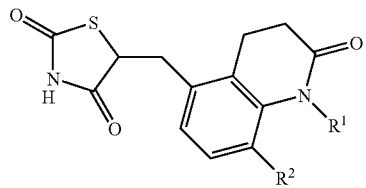
| Ex. | R¹ | R² | M.p.(° C.) |
|---|---|---|---|
| 1034 | 4-ethyl-N-(4-phenoxyphenyl)benzamide group | —H | 153-157 |
| 1035 | 1-(4-ethylbenzyl)indoline group | —H | 114-115 |
| 1036 | 5-ethyl-2-(trifluoromethyl)pyridine group | —OCH₃ | 170-171 |
| 1037 | 5-ethyl-N-phenylpyridin-2-amine group | —OCH₃ | 227-229 |
| 1038 | 5-ethyl-2-(biphenyl-4-yl)pyridine group | —OCH₃ | 269-272 |
| 1039 | 2-ethyl-6-((phenylthio)methyl)pyridine group | —H | 113-114 |
| 1040 | 5-ethyl-2-phenylthiazole group | —OCH₃ | 185-188 |

TABLE 154

[Structure: thiazolidine-2,4-dione-CH2-linked to 5-position of 1-R¹-8-R²-3,4-dihydroquinolin-2(1H)-one]

| Ex. | R¹ | R² | M.p. (° C.) |
|---|---|---|---|
| 1041 | 1-(4-ethylpiperidin-1-yl) attached to naphthalen-1-yl | —H | 221-227 |
| 1042 | 4-ethylpiperidin-1-yl attached to biphenyl-4-yl | —H | 220 (dec.) |
| 1043 | 4-ethylpiperidin-1-yl attached to naphthalen-2-yl | —H | 177 (dec.) |
| 1044 | 4-ethylpiperidin-1-yl attached to 4-methylphenyl | —H | 103-112 |

TABLE 155

[Structure: thiazolidine-2,4-dione-CH2-linked to 5-position of 1-R¹-8-R²-3,4-dihydroquinolin-2(1H)-one]

| Ex. | R¹ | R² | ¹H-NMR (CDCl₃) δppm |
|---|---|---|---|
| 1045 | —(CH₂)₃OSi(CH₃)₂C(CH₃)₃ | —H | 0.08 (6H, s), 0.91 (9H, s), 1.85-2.0 (2H, m), 2.55-2.75 (2H, m), 2.75-3.05 (2H, m), 3.13 (1H, dd, J = 10.6 Hz, J2 = 12.2 Hz), 3.6-3.8 (3H, m), 3.95-4.1 (2H, m), 4.47 (1H, dd, J = 3.8 Hz, J2 = 12.2 Hz), 6.9-7.0 (1H, m), 7.1-7.3 (2H, m) |
| 1046 | —(CH₂)₃OH | —H | 1.5-2.0 (4H, m), 2.6-2.7 (2H, m), 2.8-3.1 (2H, m), 3.16 (1H, dd, J = 10.5 Hz, J2 = 14.5 Hz), 3.6-3.7 (2H, m), 3.67 (1H, dd, J = 3.9 Hz, J2 = 14.5 Hz), 4.05-4.15 (2H, m), 4.47 (1H, dd, J = 3.9 Hz, J2 = 10.5 Hz), 6.96 (1H, d, J = 7.4 Hz), 7.06 (1H, d, J = 7.6 Hz), 7.1-7.2 (1H, m) |
| 1047 | —CH₂CO₂C(CH₃)₃ | —OCH₃ | 1.43 (9H, s), 2.5-2.65 (2H, m), 2.8-3.05 (2H, m), 3.10 (1H, dd, J1 = 10.3 Hz, J2 = 14.5 Hz), 3.61 (1H, dd, J1 = 4.0 Hz, J2 = 14.5 Hz), 3.82 (3H, s), 4.44 (1H, dd, J1 = 4.0 Hz, J2 = 10.3 Hz), 4.55-4.65 (2H, m), 6.80 (1H, d, J = 8.5 Hz), 6.94 (1H, d, J = 8.5 Hz) |
| 1048 | 4-ethylbenzyl-N-methyl-N-phenylamino group | —H | 2.74-2.79 (2H, m), 2.88-3.04 (5H, m), 3.15 (1H, dd, J1 = 10.4 Hz, J2 = 14.5 Hz), 3.68 (1H, dd, J1 = 3.9 Hz, J2 = 14.5 Hz), 4.42-4.51 (3H, m), 5.06-5.22 (2H, m), 6.70-6.74 (3H, m), 6.84-6.91 (2H, m), 7.06-7.23 (7H, m), 8.05 (1H, brs) |

TABLE 156

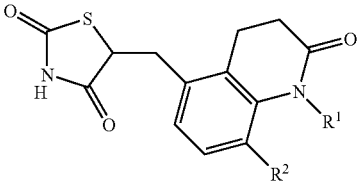

| Ex. | R¹ | R² | ¹H NMR (DMSO-d₆) dppm |
|---|---|---|---|
| 1049 | 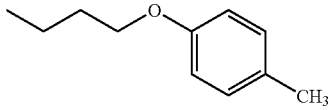 | —H | 2.0-2.2 (2H, m), 2.28 (3H, s), 2.55-3.25 (5H, m), 3.68 (1H, dd, J1 = 3.7 Hz, J2 = 14.4 Hz), 4.02 (2H, t, J = 5.9 Hz), 4.14 (2H, t, J = 7.0 Hz), 4.46 (1H, dd, J1 = 3.7 Hz, J2 = 10.5 Hz). 6.92 (2H, d, J = 7.5 Hz), 7.08 (1H, d, J = 8.0 Hz), 7.05-7.4 (4H, m) |
| 1050 | 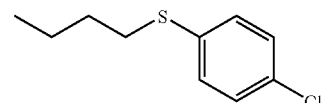 | —H | 1.6-1.9 (2H, m), 2.4-2.6 (2H, m), 2.75-3.25 (5H, m), 3.50 (1H, dd, J = 4.0 Hz, J2 = 14.3 Hz), 3.9-4.1 (2H, m), 4.82 (1H, dd, J = 4.0 Hz, J2 = 10.8 Hz), 6.9-7.05 (2H, m), 7.1-7.3 (1H, m), 7.35-7.5 (4H, m), 12.13 (1H, br s) |
| 1051 | 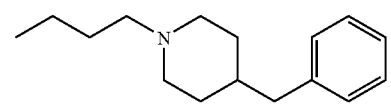 | —H | 1.1-1.3 (2H, m), 1.85-2.1 (2H, m), 2.4-2.6 (2H, m), 2.75-4.1 (2H, m), 4.64 (1H, dd, J = 3.1 Hz, J2 = 10.3 Hz), 6.91(1H, d, J = 7.4 Hz), 7.0-7.35 (7H, m) |
| 1052 | 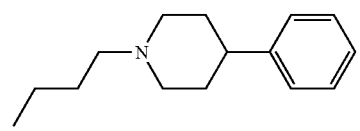 | —H | 1.75-2.1 (3H, m), 2.4-3.6 (16H, m), 3.9-4.05 (2H, m), 4.83 (1H, dd, J1 = 4.0 Hz, J2 = 9.9 Hz), 6.94 (1H, d, J = 7.4 Hz), 7.1-7.3 (7H, m), 9.79 (1H, br s), 12.13 (1H, br s) |
| 1053 | 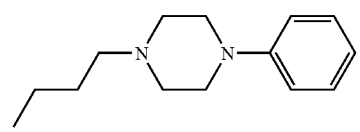 | —H | 1.9-2.1 (2H, m), 2.4-4.0 (18H, m), 4.85 (1H, dd, J1 = 3.9 Hz, J2 = 9.8 Hz), 6.8-7.4 (8H, m), 0.3 (1H, br s), 12.15 (1H, s) |
| 1054 | 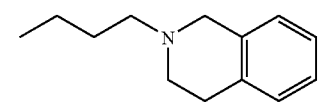 | —H | 1.9-5.2 (19H, m), 6.9-7.8 (7H, m), 10.6-11.0 (1H, m), 12.1-12.6 (1H, m) |
| 1055 | 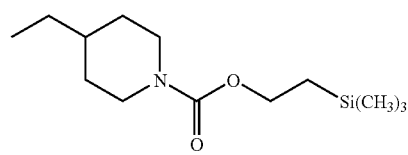 | —H | 0.03 (9H, s), 0.98 (2H, t, J = 8.4 Hz), 1.1-1.4 (3H, m), 1.7-2.0 (3H, m), 2.6-3.3 (7H, m), 3.65 (1H, dd, J1 = 3.8 Hz, J2 = 14.4 Hz), 3.8-4.3 (6H, m), 4.49 (1H, dd, J1 = 3.8 Hz, J2 = 10.2 Hz), 6.9-7.05 (2H, m), 7.21 (1H, d, J = 7.9 Hz) |
| 1056 | 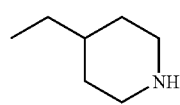 | —H | 1.2-1.45 (2H, m), 1.6-2.0 (3H, m), 2.6-4.2 (13H, m), 6.91 (1H, d, J = 7.6 Hz), 7.08 (1H, d, J = 7.6 Hz), 7.17 (1H, d, J = 7.6 Hz) |
| 1057 | 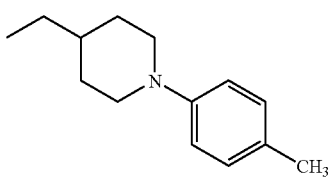 | —H | 0.75-0.95 (1H, m), 1.15-1.4 (3H, m), 1.5-1.85 (3H, m), 2.17 (3H, s), 2.3-3.65 (8H, m), 3.8-4.0 (2H, m), 4.75-4.95 (1H, m), 6.78 (2H, d, J = 8.7 Hz), 6.8-7.0 (3H, m), 6.8-7.0 (3H, m), 7.1-7.3 (2H, m), 12.11 (1H, br s) |
| 1058 | 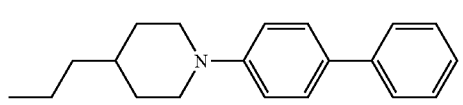 | —H | 0.8-0.95 (1H, m), 1.1-1.7 (6H, m), 1.7-1.9 (2H, m), 2.3-4.1 (10H, m), 4.75-4.95 (1H, m),78 (2H, d, J = 8.7 Hz), 6.8-7.7 (1H, m), 12.11 (1H, br s) |

TABLE 157

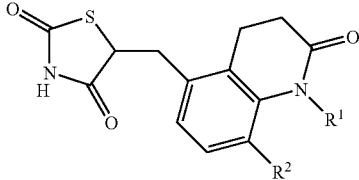

| Ex. | R¹ | R² | ¹H NMR (DMSO-d₆) δppm |
|---|---|---|---|
| 1059 | 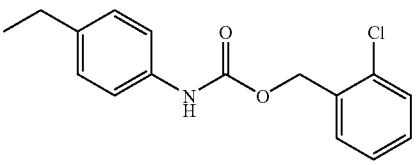 | —OCH₃ | 2.46-2.51 (2H, m), 2.80-2.84 (2H, m), 3.00-3.10 (1H, m), 3.39-3.49 (1H, m), 3.70 (3H, s), 4.77 (1H, dd, J1 = 4.2 Hz, J2 = 10.0 Hz), 5.14 (2H, s), 5.19 (2H, s), 6.80 (1H, d, J = 8.6 Hz), 6.84 (1H, d, J = 8.6 Hz), 6.96 (2H, d, J = 8.4 Hz), 7.28 (2H, d, J = 8.4 Hz), 7.36-7.42 (2H, m), 7.47-7.56 (2H, m), 9.73 (1H, s), 12.07 (1H, s) |
| 1060 | 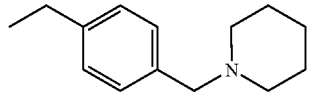 | —H | 1.28-1.58 (6H, m), 2.26-2.46 (4H, m), 2.64-2.70 (2H, m), 2.96-3.03 (2H, m), 3.04-3.13 (1H, m), 3.31-3.40 (1H, m), 3.46 (2H, s), 4.74 (1H, dd, J1 = 3.8 Hz, J2 = 10.2 Hz), 5.11 (2H, d, J = 4.5 Hz), 6.83 (1H, d, J = 7.9 Hz), 6.88 (1H, d, J = 7.9 Hz), 7.08 (1H, t, J = 7.9 Hz), 7.15 (2H, d, J = 7.8 Hz), 7.23 (2H, d, J = 7.8 Hz) |
| 1061 | 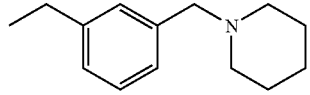 | —H | 1.35-1.71 (6H, m), 2.40-2.44 (4H, m), 2.65-2.73 (2H, m), 2.92-3.00 (2H, m), 3.07-3.17 (1H, m), 3.39-3.49 (1H, m), 3.57 (2H, s), 4.77-4.83 (1H, m), 5.07-5.22 (2H, m), 6.81-6.89 (2H, m), 7.03-7.30 (5H, m) |
| 1062 | 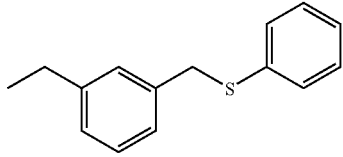 | —H | 2.64-2.70 (2H, m), 2.93-2.99 (2H, m), 3.10-3.20 (1H, m), 3.53 (1H, dd, J1 = 3.7 Hz, J2 = 14.3 Hz), 4.18 (2H, s), 4.84 (1H, dd, J1 = 3.7 Hz, J2 = 10.0 Hz), 5.01-5.16 (2H, m), 6.77 (1H, d, J = 7.8 Hz), 6.89 (1H, d, J = 7.8 Hz), 7.03-7.43 (10H, m), 12.16 (1H, brs) |
| 1063 | 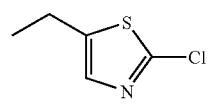 | —OCH₃ | 2.47-2.51 (2H, m), 2.77-2.81 (2H, m), 3.03-3.10 (1H, m), 3.39-3.46 (1H, m), 3.81 (3H, s), 4.79 (1H, dd, J1 = 4.3 Hz, J2 = 10.0 Hz), 5.12 (2H, s), 6.99 (2H, s), 7.52 (1H, s), 12.10 (1H, brs) |
| 1064 | 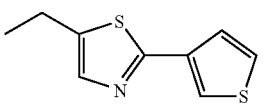 | —OCH₃ | 2.36-2.57 (2H, m), 2.71-2.86 (2H, m), 3.01-3.17 (1H, m), 3.45-3.51 (1H, m), 3.84 (3H, s), 4.77 (1H, dd, J1 = 4.1 Hz, J2 = 10.0 Hz), 5.32 (2H, s), 6.97 (2H, s), 7.48 (1H, d, J = 4.9 Hz), 7.58 (1H, s), 7.63-7.67 (1H, m), 8.02 (1H, d, J = 2.1 Hz), 12.09 (1H, brs) |
| 1065 | 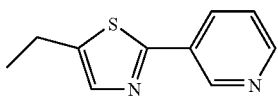 | —OCH₃ | 2.50-2.66 (2H, m), 2.73-2.89 (2H, m), 3.01-3.17 (1H, m), 3.35-3.51 (1H, m), 3.85 (3H, s), 4.78 (1H, dd, J1 = 4.2 Hz, J2 = 9.9 Hz), 5.34 (2H, s), 6.98 (2H, s), 7.48 (1H, dd, J1 = 4.1 Hz, J2 = 7.8 Hz), 7.76 (1H, s), 8.20 (1H, d, J = 7.8 Hz), 8.62 (1H, d, J = 4.1 Hz), 9.04 (1H, s), 12.06 (1H, brs) |

TABLE 158

| Ex. | R¹ | R² | ¹H NMR (DMSO-d₆) dppm |
|---|---|---|---|
| 1066 | 5-ethyl-pyridin-2-yl-NH-pyridin-2-yl | —OCH₃ | 2.48-2.52 (2H, m), 2.79-2.83 (2H, m), 3.00-3.10 (1H, m), 3.34-3.44 (1H, m), 3.74 (3H, s), 4.77 (1H, dd, J1 = 4.1 Hz, J2 = 10.2 Hz), 5.12 (2H, s), 6.79-6.85 (2H, m), 6.91 (1H, d, J = 8.6 Hz), 7.31 (1H, dd, J1 = 2.1 Hz, J2 = 8.6 Hz), 7.54-7.62 (3H, m), 7.95 (1H, d, J = 2.1 Hz), 8.14-8.18 (1H, m), 9.55 (1H, s), 12.09 (1H, brs) |
| 1067 | 6-ethyl-pyridin-2-yl-CH₂-piperidin-1-yl | —H | 1.37-1.52 (6H, m), 2.42-2.46 (4H, m), 2.64-2.71 (2H, m), 2.81-2.95 (2H, m), 3.17 (2H, s), 3.34-3.42 (1H, m), 3.50-3.56 (1H, m), 4.75-4.80 (1H, m), 5.07-5.23 (2H, m), 6.81 (1H, d, J = 7.9 Hz), 6.89 (1H, d, J = 7.9 Hz), 7.01-7.10 (2H, m), 7.29 (1H, d, J = 7.6 Hz), 7.69 (1H, t, J = 7.6 Hz) |
| 1068 | 6-ethyl-pyridin-2-yl-CH₂-N(CH₃)-phenyl | —H | 2.64 (2H, t, J = 6.5 Hz), 2.98 (2H, t, J = 6.5 Hz), 3.04 (3H, s), 3.15 (1H, dd, J1 = 10.3 Hz, J2 = 14.3 Hz), 3.53 (1H, dd, J1 = 4.0 Hz, J2 = 14.3 Hz), 4.59 (2H, s), 4.84 (1H, dd, J1 = 4.0 Hz, J2 = 10.3 Hz), 5.08-5.23 (2H, m), 6.59 (1H, t, J = 7.6 Hz), 6.66 (2H, d, J = 8.2 Hz), 6.83 (1H, d, J = 7.6 Hz), 6.90 (1H, d, J = 7.6 Hz), 6.99-7.14 (5H, m), 7.61 (1H, t, J = 7.7 Hz), 12.15 (1H, brs) |

TABLE 159

| Ex. | R¹ | R² | M.p.(° C.) |
|---|---|---|---|
| 1069 | —(CH₂)₃CF₃ | —OCH₃ | 186-193 |
| 1070 | —(CH₂)₄F | —OCH₃ | 181-183 |
| 1071 | 3-ethyl-benzyl-S-phenyl | —H | 91-96 |
| 1072 | 5-ethyl-pyridin-2-yl-NH-phenyl | —OCH₃ | 241-245 |
| 1073 | 2-ethyl-3,5-dimethyl-4-methoxy-pyridinyl | —H | 146-149 |
| 1074 | 5-ethyl-2-chloro-thiazolyl | —OCH₃ | 206-208 |
| 1075 | 5-ethyl-2-(thiophen-3-yl)-thiazolyl | —OCH₃ | 108-113 |

TABLE 160

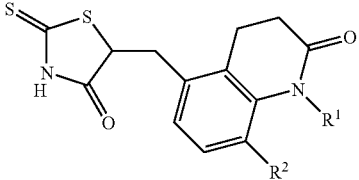

| Ex. | R¹ | R² | ¹H NMR (DMSO-d₆) dppm |
|---|---|---|---|
| 1076 | 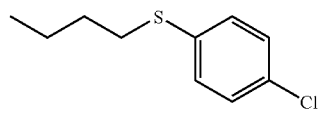 | —H | 1.7-1.95 (2H, m), 2.3-3.6 (8H, m), 3.95-4.1 (2H, m), 4.9-5.1 (1H, m), 6.8-7.5 (7H, m), 13.25 (1H, br s) |
| 1077 | 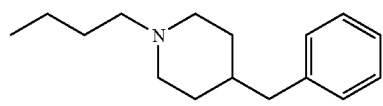 | —H | 1.15-1.45 (2H, m), 1.5-2.0 (5H, m), 2.75-3.05 (5H, m), 3.9-4.05 (2H, m), 4.4-4.5 (1H, m), .91 (1H, d, J = 7.2 Hz), 7.06 (1H, d, J = 7.8 Hz), 7.1-7.4 (6H, m) |
| 1078 | 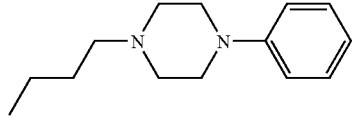 | —H | 1.9-2.1 (2H, m), 2.4-4.1 (18H, m). 4.98 (1H, dd, J1 = 4.3 Hz, J2 = 9.8 Hz), 6.75-7.3 (8H, m), 10.12 1H, br s), 13.28 (1H, br s) |
| 1079 | 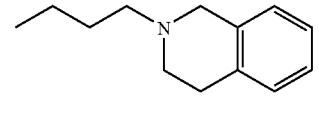 | —H | 1.1-1.7 (3H, m), 2.0-2.2 (2H, m), 2.4-4.6 (13H, m), 4.95-5.05 (1H, m), 6.96 (1H, d, J = 7.2 Hz), 7.0-7.3 (6H, m), 10.75 (1H, br s), 13.28 (1H, br s) |
| 1080 | 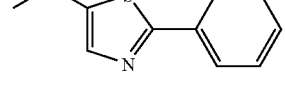 | —OCH₃ | 2.47-2.51 (2H, m), 2.76-2.80 (2H, m), 3.04-3.14 (1H, m), 3.45-3.55 (1H, m), 3.85 (3H, s), 4.85 (1H, dd, J1 = 4.5 Hz, J2 = 10.0 Hz), 5.12 (2H, s), 6.97 (2H, s), 7.43-7.46 (3H, m), 7.67 (1H, s), 7.82-7.86 (2H, m), 13.16 (1H, brs) |
| 1081 | 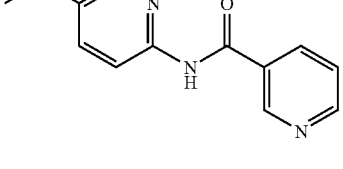 | —OCH₃ | 2.44-2.48 (2H, m), 2.82-2.86 (2H, m), 3.08-3.18 (1H, m), 3.33-3.43 (1H, m), 3.69 (3H, s), 4.90 (1H, dd, J1 = 4.5 Hz, J2 = 9.5 Hz), 5.14 (2H, s), 6.85 (1H, d, J = 8.6 Hz), 6.92 (1H, d, J = 8.6 Hz), 7.50-5.55 (2H, m), 8.04 (1H, d, J = 8.5 Hz), 8.15 (1H, d, J = 1.9 Hz), 8.28-8.33 (1H, m), 8.73 (1H, dd, J1 = 1.5 Hz, J2 = 4.5 Hz), 9.09 (1H, d, J = 1.9 Hz), 10.98 (1H, s), 13.20 (1H, s) |
| 1082 | 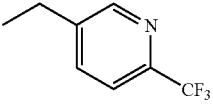 | —OCH₃ | 2.69-2.73 (2H, m), 2.91-2.87 (2H, m), 3.07-3.22 (1H, m), 3.39-3.50 (1H, m), 3.53 (3H, s), 4.94 (1H, dd, J1 = 4.5 Hz, J2 = 9.5 Hz), 5.12 (2H, s), 6.87 (1H, d, J = 8.5 Hz), 6.95 (1H, d, J = 8.5 Hz), 7.78 (2H, dd, J1 = 1.0 Hz, J2 = 3.8 Hz), 8.58 (1H, s), 13.22 (1H, brs) |
| 1083 | 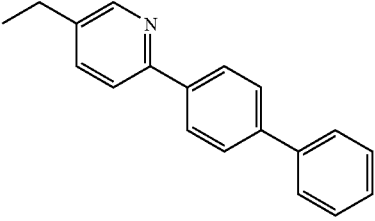 | —OCH₃ | 2.52-2.56 (2H, mn), 2.86-2.90 (2H, in), 3.12-3.22 (1H, m), 3.35-3.44 (1H, m). 3.66 (3H, s), 4.94 (1H, dd, J1 = 4.5 Hz, J2 = 9.4 Hz), 5.18 (2H, s), 6.87 (1H, d, J = 8.6 Hz), 6.94 (1H, d, J = 8.6 Hz), 7.36-7.52 (3H, m), 7.65 (1H, dd, J1 = 2.4 Hz, J2 = 8.0 Hz), 7.73-7.81 (4H, m), 7.93 (1H, d, J = 8.3 Hz), 8.13 (2H, d, J = 8.3 Hz), 8.48 (1H, d, J = 2.4 Hz), 13.21 (1H, brs) |

TABLE 161

| Ex. | R¹ | R² | ¹H NMR (DMSO-d₆) δppm |
|---|---|---|---|
| 1084 | (6-ethylpyridin-2-yl)methyl-piperidine | —H | 1.38-1.52 (6H, m), 2.65-2.75 (6H, m), 2.96-3.04 (3H, m), 3.46-3.51 (1H, m), 3.93 (2H, s), 4.61-4.67 (1H, m), 5.10-5.26 (2H, m), 6.78 (1H, d, J = 7.6 Hz), 6.87 (1H, d, J = 7.6 Hz), 7.05 (1H, t, J = 7.6 Hz), 7.14 (1H, d, J = 7.3 Hz), 7.34 (1H, d, J = 7.3 Hz), 7.75 (1H, t, J = 7.3 Hz) |
| 1085 | (3-ethylphenyl)methyl-piperidine | —H | 1.30-1.66 (6H, m), 2.57-2.61 (4H, m), 2.64-2.70 (2H, m), 2.93-2.99 (2H, m), 3.03-3.48 (2H, m), 3.77 (2H, s), 4.58-4.62 (1H, m), 5.07-5.23 (2H, m), 6.80 (1H, d, J = 7.8 Hz), 6.86 (1H, d, J = 7.8 Hz), 7.05 (1H, t, J = 7.8 Hz), 7.16-7.35 (4H, m) |
| 1086 | (4-ethylphenyl)methyl-piperidine | —H | 1.32-1.42 (2H, m), 1.43-1.47 (4H, m), 2.24-2.35 (4H, m), 2.63-2.70 (2H, m), J1 = 10.4 Hz, J2 = 14.4 Hz), 3.43 (2H, s), 3.51 (1H, dd, J1 = 4.0 Hz, J2 = 14.4 Hz), 4.71 (1H, dd, J1 = 4.0 Hz, J2 = 10.4 Hz), 5.08-5.19 (2H, m), 6.82 (1H, d, J = 8.2 Hz), 6.87 (1H, d, J = 7.5 Hz), 7.04-7.14 (4H, m), 7.24 (1H, t) |
| 1087 | (3-ethylphenyl)methyl-N(CH₃)-phenyl | —H | 2.54-2.60 (2H, m), 2.85-2.92 (5H, m), 3.19 (1H, dd, J1 = 9.9 Hz, J2 = 14.5 Hz), 3.44-3.52 (1H, m), 4.50 (2H, s), 4.95 (1H, dd, J1 = 4.3 Hz, J2 = 9.9 Hz), 5.08-5.23 (2H, m), 6.58-6.64 (3H, m), 6.78 (1H, d, J = 8.2 Hz), 6.86 (1H, d, J = 7.6 Hz), 6.95-7.26 (7H, m), 13.30 (1H, brs) |

TABLE 162

| Ex. | R¹ | R² | ¹H-NMR (CDCl₃) δppm |
|---|---|---|---|
| 1088 | (5-ethylthiazol-2-yl)-pyridin-3-yl | —OCH₃ | 2.57-2.67 (2H, m), 2.77-2.87 (2H, m), 3.13 (1H, dd, J1 = 10.0 Hz, J2 = 14.7 Hz), 3.44-3.56 (1H, m), 3.90 (3H, s), 4.49 (1H, dd, J1 = 4.1 Hz, J2 = 10.0 Hz), 5.47 (2H, s), 6.82 (7.36 (1H, dd, J1 = 4.8 Hz, J2 = 8.0 Hz), 7.66 (1H, s), 8.18 (1H, ddd, J1 = 1.7 Hz, J2 = 4.8 Hz), 8.62 (1H, dd, J1 = 1.7 Hz, J2 = 4.8 Hz), 9.09 (1H, d, J = 1.7 Hz) |
| 1089 | (4-ethylphenyl)methyl-S-phenyl | —H | 2.74-2.80 (2H, m), 2.94-3.09 (2H, m), 3.18 (1H, dd, J1 = 10.6 Hz, J2 = 14.5 Hz), 3.67 (1H, dd, J1 = 3.9 Hz, J2 = 14.5 Hz), 4.08 (2H, s), 4.55 (1H, dd, J1 = 3.9 Hz, J2 = 10.6 Hz), 5.06-5.22 (2H, m), 6.81-6.90 (2H, m), 7.06-7.30 (10H, m), 9.09 (1H, brs) |

TABLE 162-continued

| Ex. | R¹ | R² | ¹H-NMR (CDCl₃) δppm |
|---|---|---|---|
| 1090 | (4-ethylbenzyl)-N-methyl-N-phenylamine group | —H | 2.75-2.80 (2H, m), 2.87-3.09 (5H, m), 3.16 (1H, dd, J1 = 10.7 Hz, J2 = 14.4 Hz), 3.65 (1H, dd, J1 = 3.8 Hz, J2 = 14.4 Hz), 4.46-4.57 (3H, m), 5.07-5.23 (2H, m), 6.67-6.73 (3H, m), 6.84-6.90 (2H, m), 7.05-7.26 (7H, m), 9.73 (1H, brs) |

TABLE 163

| Ex. | R⁹¹¹ | R⁹¹² | R⁹¹³ | R⁹¹⁴ | R⁹¹⁵ | MS (M + 1) |
|---|---|---|---|---|---|---|
| 1091 | —H | —H | —OCH₃ | —H | —H | 441 |
| 1092 | —H | —H | —H | —H | —H | 411 |
| 1093 | —Cl | —H | —H | —H | —H | 445 |
| 1094 | —H | —Cl | —H | —H | —H | 445 |
| 1095 | —H | —H | —Cl | —H | —H | 445 |
| 1096 | —Cl | —Cl | —H | —H | —H | 479 |
| 1097 | —H | —Cl | —Cl | —H | —H | 479 |
| 1098 | —H | —F | —F | —H | —H | 447 |
| 1099 | —H | —H | —CF₃ | —H | —H | 479 |
| 1100 | —H | —H | —C₃H₇ | —H | —H | 453 |
| 1101 | —H | —F | —Cl | —H | —H | 463 |
| 1102 | —OCH₃ | —H | —CH₂CH=CH₂ | —H | —H | 481 |
| 1103 | —Cl | —H | —OCH₃ | —H | —H | 475 |
| 1104 | —H | —H | -cyclo-C₅H₉ | —H | —H | 479 |
| 1105 | —H | —H | —NO₂ | —H | —H | 456 |
| 1106 | —CH₃ | —CH₃ | —H | —H | —H | 439 |
| 1107 | —H | —H | —C₆H₅ | —H | —H | 487 |

TABLE 164

| Ex. | R⁹²¹ | MS(M + 1) |
|---|---|---|
| 1108 | 1-naphthyl | 461 |
| 1109 | 2-naphthyl | 461 |
| 1110 | 2-methylbenzothiazol-5-yl | 482 |
| 1111 | isoquinolin-5-yl | 462 |
| 1112 | 6-methylpyridin-3-yl | 426 |
| 1113 | quinolin-5-yl | 462 |
| 1114 | pyridin-3-yl | 412 |

TABLE 165

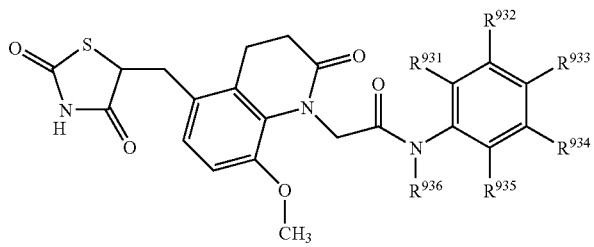

| Ex. | $R^{936}$ | $R^{931}$ | $R^{932}$ | $R^{933}$ | $R^{934}$ | $R^{935}$ | MS(M + 1) |
|---|---|---|---|---|---|---|---|
| 1115 | —H | —H | —H | —H | —SCH$_3$ | —H | 486 |
| 1116 | —H | —H | —H | —OCF$_3$ | —H | —H | 524 |
| 1117 | —H | —H | —H | —C$_4$H$_9$ | —H | —H | 496 |
| 1118 | —H | —H | —H | —Cl | —H | —H | 474 |
| 1119 | —H | —H | —H | —H | —Cl | —Cl | 474 |
| 1120 | —H | —H | —H | —H | —Cl | —H | 474 |
| 1121 | —H | —H | —H | —H | —H | —C$_6$H$_5$ | 516 |
| 1122 | —H | —H | —H | —H | —H | —F | 458 |
| 1123 | —H | —H | —H | —H | —F | —H | 458 |
| 1124 | —H | —H | —H | —F | —H | —H | 458 |
| 1125 | —H | —H | —H | —H | —N(CH$_3$)$_2$ | —H | 483 |
| 1126 | —H | —CN | —H | —H | —H | —H | 465 |
| 1127 | —CH$_3$ | —H | —H | —H | —CH$_3$ | —H | 468 |
| 1128 | —H | —H | —H | —H | —H | —OC$_6$H$_5$ | 532 |
| 1129 | —H | —H | —H | —H | —OC$_6$H$_5$ | —H | 532 |
| 1130 | —H | —H | —H | —OC$_6$H$_5$ | —H | —H | 532 |
| 1131 | —H | —H | —H | —CF$_3$ | —H | —H | 508 |
| 1132 | —H | —H | —H | —CH$_3$ | —CH$_3$ | —H | 468 |
| 1133 | —H | —H | —CH$_3$ | —H | —CH$_3$ | —H | 468 |
| 1134 | —H | —CH$_3$ | —H | —CH$_3$ | —H | —CH$_3$ | 482 |
| 1135 | —H | —H | —H | —F | —H | —F | 476 |
| 1136 | —H | —H | —H | —F | —F | —H | 476 |
| 1137 | —H | —H | —H | —CH$_3$ | —H | —Cl | 488 |
| 1138 | —H | —H | —H | —CN | —H | —H | 465 |
| 1139 | —H | —H | —H | —SCH$_3$ | —H | —H | 486 |
| 1140 | —H | —H | —H | —H | —H | —CH(CH$_3$)$_2$ | 482 |
| 1141 | —H | —H | —H | —CH(CH$_3$)$_2$ | —H | —H | 482 |
| 1142 | —H | —H | —H | —C$_6$H$_{13}$ | —H | —H | 524 |
| 1143 | —H | —H | —H | -cyclo-C$_6$H$_{11}$ | —H | —H | 522 |
| 1144 | —H | —H | —H | —H | —OCH$_2$C$_6$H$_5$ | —H | 546 |
| 1145 | —H | —H | —H | —OCH$_2$C$_6$H$_5$ | —H | —H | 546 |
| 1146 | —H | —H | —H | —NHSO$_2$CH$_3$ | —H | —H | 533 |
| 1147 | —H | —H | —H | —H | —H | —OCH$_2$C$_6$H$_5$ | 546 |
| 1148 | —H | —H | —H | —NHC$_6$H$_5$ | —H | —H | 531 |
| 1149 | —CH$_2$C$_6$H$_5$ | —H | —H | —H | —H | —H | 530 |
| 1150 | —CH$_2$CH$_2$OH | —H | —H | —H | —H | —H | 484 |

TABLE 166

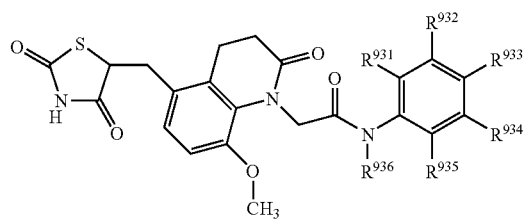

| Ex. | $R^{936}$ | $R^{931}$ | $R^{932}$ | $R^{933}$ | $R^{934}$ | $R^{935}$ | MS (M + 1) |
|---|---|---|---|---|---|---|---|
| 1151 | —H | —H | —H | —H | —OCH$_3$ | —H | 470 |
| 1152 | —H | —H | —H | —CH$_3$ | —H | —H | 454 |
| 1153 | —H | —H | —OCH$_3$ | —H | —OCH$_3$ | —H | 500 |
| 1154 | —H | —H | —H | —H | —C$_2$H$_5$ | —H | 468 |
| 1155 | —H | —H | —H | —N(CH$_3$)$_2$ | —H | —H | 483 |
| 1156 | —H | —H | —H | —C$_2$H$_5$ | —H | —H | 468 |
| 1157 | —H | —H | —H | —H | —H | —CF$_3$ | 508 |
| 1158 | —H | —H | —CN | —H | —H | —H | 465 |
| 1159 | —CH$_3$ | —H | —H | —H | —Cl | —H | 488 |

TABLE 166-continued

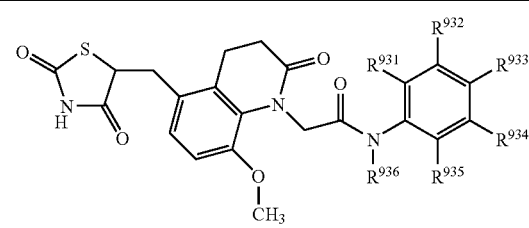

| Ex. | $R^{936}$ | $R^{931}$ | $R^{932}$ | $R^{933}$ | $R^{934}$ | $R^{935}$ | MS (M + 1) |
|---|---|---|---|---|---|---|---|
| 1160 | —C$_2$H$_5$ | —H | —H | —H | —H | —OCH$_3$ | 498 |
| 1161 | —H | —H | —H | —H | —F | —F | 476 |
| 1162 | —H | —H | —H | —OCH$_3$ | —Cl | —H | 504 |
| 1163 | —H | —H | —H | —CH$_3$ | —Cl | —H | 488 |
| 1164 | —H | —H | —OCH$_3$ | —H | —CF$_3$ | —H | 538 |
| 1165 | —H | —Cl | —H | —H | —CF$_3$ | —H | 542 |
| 1166 | —H | —H | —H | —F | —H | —Cl | 492 |

TABLE 166-continued

| Ex. | R^936 | R^931 | R^932 | R^933 | R^934 | R^935 | MS (M + 1) |
|---|---|---|---|---|---|---|---|
| 1167 | —H | —H | —CN | —H | —H | —Cl | 499 |
| 1168 | —H | —Cl | —H | —H | —CONH$_2$ | —H | 517 |
| 1169 | —H | —H | —H | —C$_5$H$_{11}$ | —H | —H | 510 |
| 1170 | —H | —H | —H | —CH$_2$C$_6$H$_5$ | —H | —H | 530 |

TABLE 167

| Ex. | R^936 | R^931 | R^932 | R^933 | R^934 | R^935 | MS(M + 1) |
|---|---|---|---|---|---|---|---|
| 1171 | —H | —H | —H | *1-methyl-pyrrolidin-2-one* | —H | —H | 523 |
| 1172 | —H | —H | —H | *2-acetyl-1,2,3,4-tetrahydroisoquinoline* | —H | —H | 599 |
| 1173 | —H | —H | —H | *1-acetyl-6-methyl-1,2,3,4-tetrahydroquinoline* | —H | —H | 613 |
| 1174 | —H | —H | —F | —H | —H | *N-methyl-4-fluoroaniline* | 567 |
| 1175 | —H | —H | —H | *1-acetyl-4-methyl-1,2,3,4-tetrahydroquinoxaline* | —H | —H | 614 |
| 1176 | —H | —H | —H | *2-methyl-4-phenylthiazole* | —H | —H | 599 |

TABLE 168
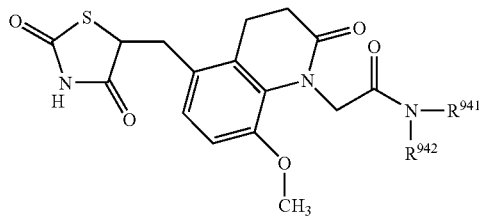
| Ex. | R941 | R942 | MS(M + 1) |
|---|---|---|---|
| 1177 | -cyclo-C6H11 | —CH3 | 460 |
| 1178 | -cyclo-C6H11 | —H | 446 |
| 1179 | —C4H9 | —C4H9 | 476 |
| 1180 | —CH2CH(CH3)2 | —CH2CH(CH3)2 | 476 |
| 1181 | -cyclo-C7H13 | —H | 460 |
| 1182 | -cyclo-C5H9 | —H | 432 |
| 1183 | —CH2-cyclo-C6H11 | —H | 460 |
| 1184 | —CH2CONH2 | —H | 421 |
| 1185 | —(CH2)2C6H5 | —H | 468 |
| 1186 | —(CH2)3C6H5 | —C5H11 | 552 |
| 1187 | —C6H5 | —C2H5 | 468 |
| 1188 | —CH(CH3)C6H5 | —H | 468 |
| 1189 | —CH2C6H5 | -cyclo-C6H11 | 536 |
| 1190 | —CH2C6H5 | —CH3 | 468 |
| 1191 | —CH2C6H5 | —C5H11 | 524 |
| 1192 | —CH2C6H5 | —CH2C6H5 | 544 |
| 1193 | -cyclo-C6H11 | —C2H5 | 474 |
TABLE 169
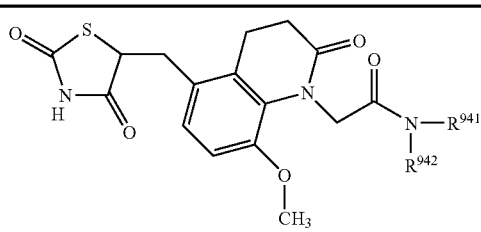
| Ex. | R941 | R942 | MS(M + 1) |
|---|---|---|---|
| 1194 | ![H3C-CH(C2H5)-CH2-] | —H | 448 |
| 1195 | ![propyl-N(iPr)2] | —H | 491 |
| 1196 | ![4-MeO-C6H4-CH2-] | —H | 484 |
| 1197 | ![4-F-C6H4-CH2-] | —H | 472 |
TABLE 169-continued
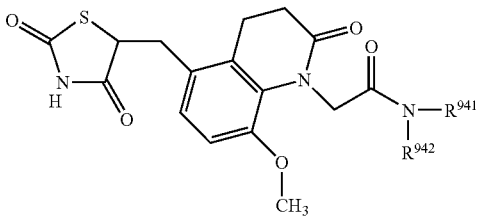
| Ex. | R941 | R942 | MS(M + 1) |
|---|---|---|---|
| 1198 | ![3-Cl-4-F-C6H3-CH2-] | —H | 506 |
| 1199 | ![4-Me-C6H4-CH2-] | —CH3 | 482 |
| 1200 | ![4-Br-C6H4-CH2-] | —C2H5 | 560 |
| 1201 | ![4-CF3-C6H4-CH2-] | —CH3 | 536 |
| 1202 | ![2,4-diCl-C6H3-CH2-] | —C2H5 | 550 |
TABLE 170
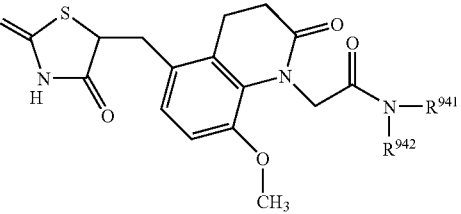
| Ex. | R941 | R942 | MS(M + 1) |
|---|---|---|---|
| 1203 |  | —C2H5 | 558 |

TABLE 170-continued

Structure: thiazolidine-2,4-dione-CH2-tetrahydroquinolin-2-one with 8-OCH3 and N-CH2-C(=O)-N(R941)(R942)

| Ex. | R941 | R942 | MS(M + 1) |
|---|---|---|---|
| 1204 | 3-phenylphenyl-ethyl (biphenyl-3-yl-ethyl) | —C2H5 | 558 |
| 1205 | 2-bromophenyl-ethyl | —C2H5 | 560 |
| 1206 | 3-chloro-4-(difluoromethoxy)phenyl-ethyl | —H | 554 |
| 1207 | 4-chloro-3-(trifluoromethyl)phenyl-ethyl | —H | 556 |
| 1208 | 4-chlorophenyl-ethyl | —H | 488 |
| 1209 | 4-methoxyphenyl-propyl | —H | 498 |
| 1210 | 4-chlorophenyl-propyl | —C2H5 | 530 |
| 1211 | 4-methoxyphenyl-propyl | —CH2C6H5 | 588 |
| 1212 | 2-methoxyphenyl-propyl | —CH2C6H5 | 588 |

TABLE 171

Structure: thiazolidine-2,4-dione-CH2-tetrahydroquinolin-2-one with 8-OCH3 and N-CH2-C(=O)-N(R941)(R942)

| Ex. | R941 | R942 | MS(M + 1) |
|---|---|---|---|
| 1213 | 4-chlorophenyl-propyl | —H | 502 |
| 1214 | 2-chlorophenyl-propyl | —H | 502 |
| 1215 | 3-methylphenyl-propyl | —H | 482 |
| 1216 | 3-chlorophenyl-propyl | —H | 502 |
| 1217 | 1,2,3,4-tetrahydronaphthalen-1-yl-ethyl | —C2H5 | 536 |
| 1218 | naphthalen-2-yl-ethyl | —H | 504 |
| 1219 | 4-chlorophenyl-methyl | —CH3 | 488 |
| 1220 | naphthalen-1-yl-methyl | —H | 490 |
| 1221 | fluoren-2-yl-methyl | —H | 528 |

TABLE 172

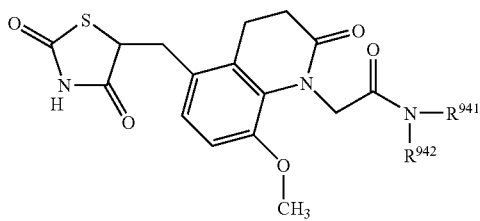

| Ex. | R⁹⁴¹ | R⁹⁴² | MS(M+1) |
|---|---|---|---|
| 1222 | -4-PYRIDYL | —H | 441 |
| 1223 | 2-ethylpyridine | —H | 455 |
| 1224 | 3-ethylpyridine | —H | 455 |
| 1225 | 4-ethylpyridine | —H | 455 |
| 1226 | 2-propylpyridine | —H | 469 |
| 1227 | 3-propylpyridine | —H | 469 |
| 1228 | 4-propylpyridine | —H | 469 |
| 1229 | 2-methylpyrimidine | —H | 442 |
| 1230 | ethyl-dimethylpyrazine | —H | 470 |
| 1231 | 2-methylthiazole | —H | 447 |
| 1232 | ethyl-dimethylpyrazole | —H | 472 |
| 1233 | 3-ethylthiophene | —H | 460 |

TABLE 173

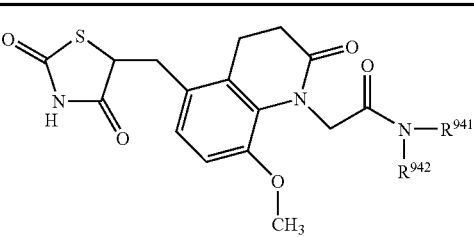

| Ex. | R⁹⁴¹ | R⁹⁴² | MS(M+1) |
|---|---|---|---|
| 1234 | 4-methyl-1-benzylpiperidine | —H | 537 |
| 1235 | 4-methyl-1-benzylpiperidine | —CH₃ | 551 |
| 1236 | 4-methyl-1-(4-chlorobenzyl)piperidine | —C₂H₅ | 599 |
| 1237 | 4-methyl-1-(3-methylbenzyl)piperidine | —C₂H₅ | 579 |
| 1238 | 4-methyl-1-phenethylpiperidine | —C₂H₅ | 579 |
| 1239 | 1,4-dimethylpiperidine | —CH₃ | 475 |
| 1240 | 4-methyl-1-benzoylpiperidine | —CH₃ | 565 |
| 1241 | 5-methylindole | —H | 479 |
| 1242 | 6-methylindazole | —H | 480 |

TABLE 174
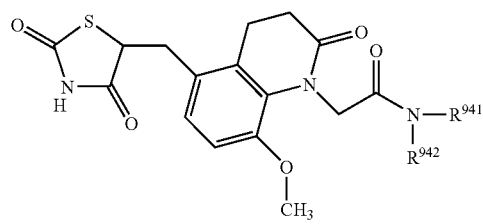
| Ex. | R⁹⁴¹ | R⁹⁴² | MS(M + 1) |
|---|---|---|---|
| 1243 | 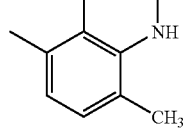 | —H | 523 |
| 1244 | 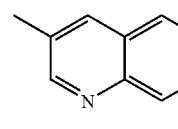 | —H | 491 |
| 1245 | 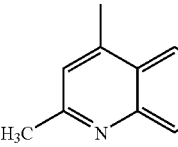 | —H | 505 |
| 1246 | 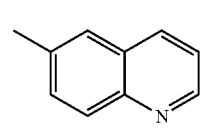 | —H | 491 |
| 1247 | 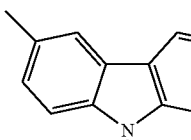 | —H | 557 |
TABLE 175
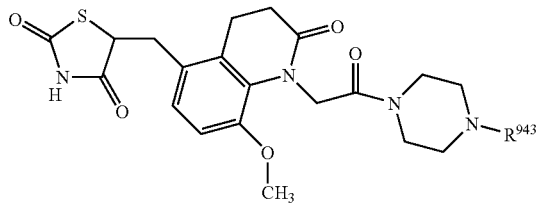
| Ex. | R⁹⁴³ | MS(M + 1) |
|---|---|---|
| 1248 | —C₂H₅ | 461 |
| 1249 | —C₃H₇ | 475 |
| 1250 |  | 551 |
TABLE 175-continued
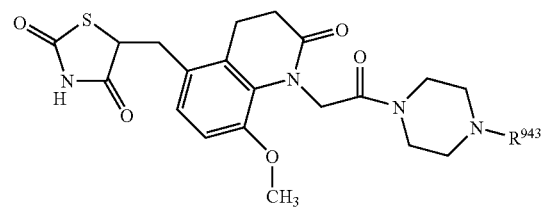
| Ex. | R⁹⁴³ | MS(M + 1) |
|---|---|---|
| 1251 | 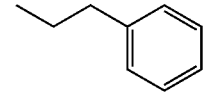 | 537 |
| 1252 | 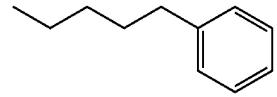 | 565 |
| 1253 |  | 629 |
| 1254 | 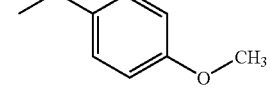 | 667 |
| 1255 | 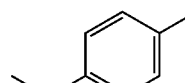 | 573 |
| 1256 |  | 594 |
| 1257 | 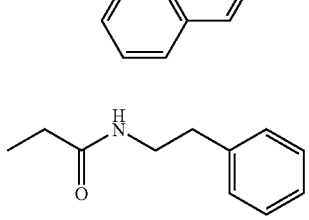 | 566 |

TABLE 176

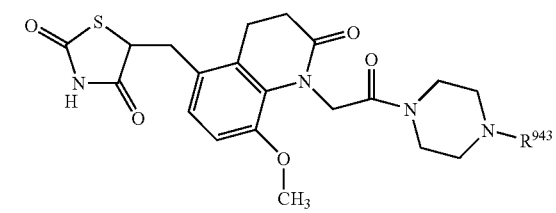

| Ex. | R943 | MS(M + 1) |
|---|---|---|
| 1258 | (benzyl acetate) | 567 |
| 1259 | (4-chlorophenyl butyl ether) | 601 |
| 1260 | (2-methylbiphenyl) | 585 |
| 1261 | (phenyl) | 509 |
| 1262 | (3,4-dichlorophenyl) | 577 |
| 1263 | (4-chlorophenyl) | 543 |
| 1264 | (2-chlorophenyl) | 543 |
| 1265 | (2,3-difluorophenyl) | 545 |
| 1266 | (6-chloroindanyl) | 583 |

TABLE 177

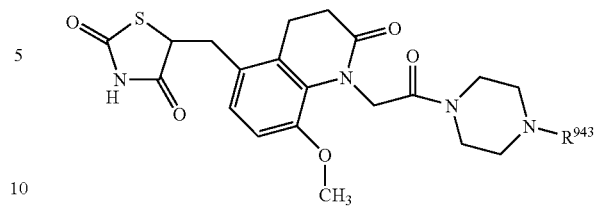

| Ex. | R943 | MS(M + 1) |
|---|---|---|
| 1267 | -2-BENZTHIAZOLYL | 566 |
| 1268 | -3-PYRIDYL | 510 |
| 1269 | (2-methylpyridyl) | 510 |
| 1270 | (3,5-dichloro-4-methylpyridyl) | 578 |
| 1271 | (4-methylbenzothiophene) | 565 |
| 1272 | (7-methylbenzothiophene) | 565 |
| 1273 | (3-methylisothiazolopyridine) | 566 |
| 1274 | (methylthienopyridine) | 566 |
| 1275 | (2-methyl-6-chlorobenzothiazole) | 600 |

TABLE 178

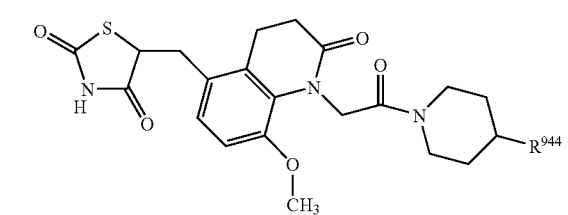

| Ex. | R⁹⁴⁴ | MS(M + 1) |
|---|---|---|
| 1276 | —CONH₂ | 475 |
| 1277 | 3,4-dichlorophenyl-ethyl | 590 |
| 1278 | phenyl-ethyl | 522 |
| 1279 | 2-fluorophenyl-ethyl | 540 |
| 1280 | 3-fluorophenyl-ethyl | 540 |
| 1281 | 3-trifluoromethoxyphenyl-ethyl | 606 |
| 1282 | 4-trifluoromethoxyphenyl-ethyl | 606 |
| 1283 | 2-chlorophenyl-ethyl | 556 |
| 1284 | 4-chlorophenyl-methyl | 542 |
| 1285 | phenyl-methyl | 508 |

TABLE 179

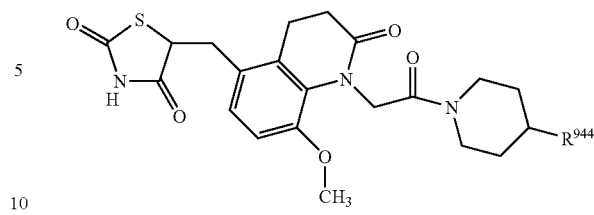

| Ex. | R⁹⁴⁴ | MS(M + 1) |
|---|---|---|
| 1286 | benzyloxymethyl | 538 |
| 1287 | 2,3-dichlorophenyl-methoxymethyl | 606 |
| 1288 | 2-methoxyphenyl | 524 |
| 1289 | 2-methoxy-3-chlorophenyl | 558 |
| 1290 | 4-methoxy-...chlorophenyl | 558 |
| 1291 | 4-trifluoromethylphenyl propoxy | 620 |
| 1292 | 4-methoxyphenyl acetyl | 566 |
| 1293 | 4-chlorophenyl acetyl | 570 |
| 1294 | 4-trifluoromethoxyphenyl methylamino | 607 |

TABLE 179-continued

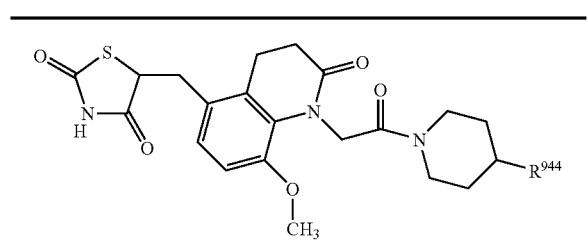

| Ex. | R⁹⁴⁴ | MS(M + 1) |
|---|---|---|
| 1295 | H₃C–N(CH₃)–C₆H₄–Cl (4-chloro-N-methyl-N-ethylaniline) | 585 |

TABLE 180

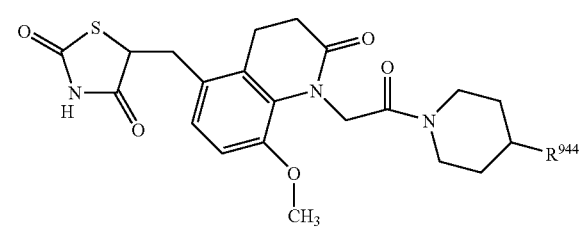

| Ex. | R⁹⁴⁴ | MS(M + 1) |
|---|---|---|
| 1296 | 4-indanyl | 548 |
| 1297 | 4-benzofuranyl | 548 |
| 1298 | 1-naphthyl | 558 |

TABLE 181

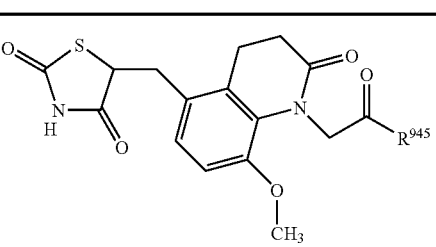

| Ex. | R⁹⁴⁵ | MS(M + 1) |
|---|---|---|
| 1299 | 4-methyl-3-oxo-1-phenylpiperazin-1-yl | 523 |
| 1300 | 4-methyl-1-(4-chlorophenyl)-2,5-dioxopiperazinyl | 557 |
| 1301 | 1-methyl-4-phenyl-1,2,3,6-tetrahydropyridin-4-yl | 506 |
| 1302 | 1-methyl-4-(4-fluorophenyl)-1,2,3,6-tetrahydropyridin-4-yl | 524 |
| 1303 | 1-methyl-4-(2,3-dihydro-1H-indol-4-yl)-1,2,3,6-tetrahydropyridine | 546 |
| 1304 | 1-methyl-4-(benzothiophen-4-yl)-1,2,3,6-tetrahydropyridine | 562 |
| 1305 | 1-methyl-2-phenylpyrrolidin-2-yl | 494 |

TABLE 181-continued

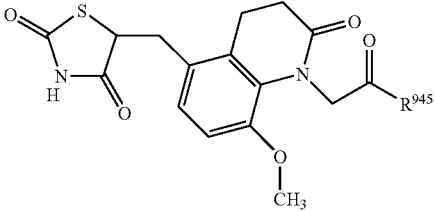

| Ex. | R⁹⁴⁵ | MS(M + 1) |
|---|---|---|
| 1306 | 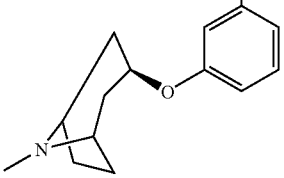 | 568 |

TABLE 182

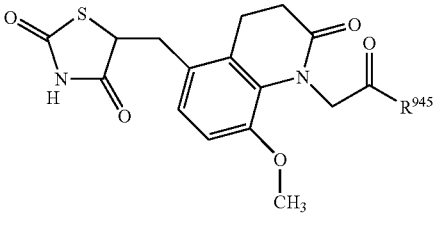

| Ex. | R⁹⁴⁵ | MS(M + 1) |
|---|---|---|
| 1307 | 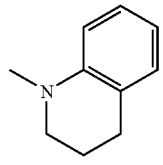 | 480 |
| 1308 | 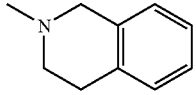 | 480 |
| 1309 | 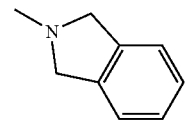 | 466 |
| 1310 | 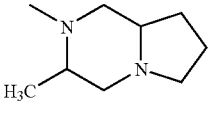 | 487 |
| 1311 | 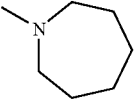 | 446 |

TABLE 182-continued

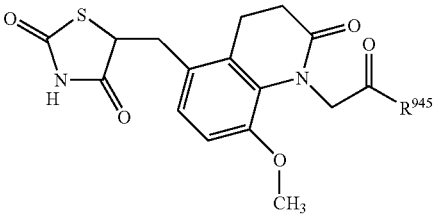

| Ex. | R⁹⁴⁵ | MS(M + 1) |
|---|---|---|
| 1312 | 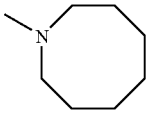 | 460 |
| 1313 | 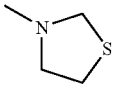 | 436 |
| 1314 | 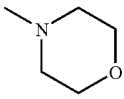 | 434 |

Example 1315

Synthesis of 8-methoxy-1-(3-methylbutyl)-5-(4-oxo-2-thioxothiazolidin-5-ylmethyl)-3,4-dihydro-1H-quinolin-2-one 3.0 g of 8-methoxy-1-(3-methylbutyl)-4-ylmethyl-2-oxo-1,2,3,4-tetrahydroquinoline-5-carboxaldehyde and 1.53 g of 2-thioxo-1,3-thiazolidin-4-one were suspended in 30 ml of toluene. Five drops of piperidine and five drops of acetic acid were added, followed by heating and refluxing for overnight. After allowing to cool, the solid thus precipitated was collected by filtration, and dried, and then suspended in 16 ml of toluene. 2.29 g of diethyl 1,4-dihydro-2,6-dimethyl-3,5-pyridine dicarboxylate and 4.0 g of silica gel were added to the suspension, followed by heating and refluxing overnight. The solvent was distilled off from the reaction mixture, and the residue was purified by silica gel column chromatography (n-hexane:ethyl acetate=3:1→1:1). The purified product was recrystallized from an ethyl acetate-n-hexane mixed solvent, giving 2.11 g (55.2% yield) of 8-methoxy-1-(3-methylbutyl)-5-(4-oxo-2-thioxothiazolidin-5-ylmethyl)-3,4-dihydro-1H-quinolin-2-one as a yellow powder.

Melting point: 139.5° C. to 141° C.

Example 1316

Synthesis of 5-[1-(3-hydroxypropyl)-2-oxo-1,2,3,4-tetrahydroquinolin-5-ylmethyl]-3-tritylthiazolidine-2,4-dione A DMF solution (10 ml) of 1.0 g (2.99 mmol) of 5-[1-(3-hydroxypropyl)-2-oxo-1,2,3,4-tetrahydroquinolin-5-ylmethyl]thiazolidine-2,4-dione and 0.455 g (3.29 mmol) of potassium carbonate was cooled with ice, and 0.876 g (3.04 mmol) of triphenylmethylchloride was added thereto, followed by stirring at room temperature overnight. Water was added to the reaction liquid and the mixture was extracted with ethyl acetate. The organic layer was washed twice with water and once with saturated sodium chloride solution, and concentrated under reduced pressure. The residue was purified by silica gel column chromatography (n-hexane:ethyl acetate=2:1→ethyl acetate). The purified product was concentrated under reduced pressure and evaporated to dryness, giving 700 mg (40.6% yield) of 5-[1-(3-hydroxypropyl)-2-oxo-1,2,3,4-tetrahydroquinolin-5-ylmethyl]-3-tritylthiazolidine-2,4-dione as a colorless amorphous solid.

Example 1317

Synthesis of 5-{1-[3-(4-methylphenoxy)propyl]-2-oxo-1,2,3,4-tetrahydroquinolin-5-ylmethyl}thiazolidine-2,4-dione A THF solution (2 ml) of 100 mg (0.18 mmol) of 5-[1-(3-hydroxypropyl)-2-oxo-1,2,3,4-tetrahydroquinolin-5-ylmethyl]-3-trityl thiazolidine-2,4-dione, 0.0363 ml (0.347 mmol) of p-cresol, and 91.1 mg (0.35 mmol) of triphenylphosphine was cooled with ice. 0.158 ml of azodicarboxylic acid diethyl (2.2 M toluene solution) was added to the solution in an argon atmosphere. The mixture was stirred at room temperature for two hours, and ethyl acetate was added to the reaction liquid. After washing with water, the organic layer was concentrated under reduced pressure, and the residue was purified by preparative silica gel thin layer chromatography (n-hexane:ethyl acetate=1:1). The purified product was concentrated under reduced pressure, and 2 ml of a solution of 4N-hydrogen chloride/ethyl acetate was added to the residue. The mixture was stirred at room temperature overnight, and further stirred at 70° C. for 1.5 hours. The mixture was concentrated under reduced pressure, and the residue was purified by preparative silica gel thin layer chromatography (n-hexane:ethyl acetate=1:1). The purified product was concentrated under reduced pressure and evaporated to dryness, giving 27.1 mg (34.4% yield) of 5-{1-[3-(4-methylphenoxy)propyl]-2-oxo-1,2,3,4-tetrahydroquinolin-5-ylmethyl}thiazolidine-2,4-dione as a colorless amorphous solid.

$^1$H-NMR(DMSO-$d_6$) dppm: 2.0-2.2 (2H, m), 2.28 (3H, s), 2.55-3.25 (5H, m), 3.68 (1H, dd, $J_1$=3.7 Hz, $J_2$=14.4 Hz), 4.02 (2H, t, J=5.9 Hz), 4.14 (2H, t, J=7.0 Hz), 4.46 (1H, dd, $J_1$=3.7 Hz, $J_2$=10.5 Hz), 6.92 (2H, d, J=7.5 Hz), 7.08 (1H, d, J=8.0 Hz), 7.05-7.4 (4H, m)

Preparation Example 1

| | |
|---|---|
| 1-Methyl-8-methoxy-5-(4-oxo-2-thioxo-5-thiazolidinyl)methyl-3,4-dihydro-1H-quinolin-2-one | 5 mg |
| Starch | 132 mg |
| Magnesium stearate | 18 mg |
| Lactose | 45 mg |
| Total | 200 mg |

Tablets containing the above composition per tablet are prepared in the conventional manner.

Preparation Example 2

| | |
|---|---|
| 1-(2-Phenylethyl)-8-methoxy-5-(4-oxo-2-thioxo-5-thiazolidinyl)methyl-3,4-dihydro-1H-quinolin-2-one | 5 g |
| Polyethyleneglycol (molecular weight: 4000) | 0.3 g |
| Sodium chloride | 0.9 g |
| Polyoxyethylenesorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved into distilled water at 80° C. with agitation. The obtained solution is cooled to 40° C., and the compound of the invention, polyethyleneglycol and polyoxyethylenesorbitan monooleate are dissolved into the above solution. Further distilled water for injection is then added to the solution to adjust the solution to the final amount. The resultant solution is subjected to filter sterilization using an appropriate filter paper, and 1 ml of the filtered solution is dispensed into ampules to prepare injectable solutions.

Test Example 1

Transcription promoting activity on human Trefoil Factor 2 (hTFF2) gene of test compounds was evaluated by means of an hTFF2 gene reporter assay.

(1) Preparation of hTFF2 Gene Reporter Vector pGL3-hTFF2pro

DNA was extracted from HeLa cells (CCL-2, DAINIPPON PHARMACEUTICAL CO., LTD.) using a deoxyribonucleic acid (DNA) extraction kit (DNeasy™ Tissue Kit, manufactured by QIAGEN). The hTFF2 promoter region was amplified using the extracted DNA as a template by means of the polymerase chain reaction (PCR). The oligomers 5'-CACGCGTCAGACTGGCAACCCCCTGTC-3' and 5'-GAAGCTTCTAGCTCAGCTGCACCCCAG-3' were selected as PCR primers to be amplified, based on the report by Beck et al. (Beck S., Sommer P., Blin N., Gott P., 5'-flanking motifs control cell-specific expression of trefoil factor genes (TFF), Int. J. Mol. Med. 2(3), 353-361 (1998)). Platinum® Pfx DNA polymerase was used as DNA polymerase. The PCR was performed under the conditions of denaturing for 30 seconds at 95° C., annealing for 30 seconds at 55° C. and extending for 75 seconds at 68° C., and the procedures were repeated for 32 cycles.

The PCR products were separated and purified by 1% agarose gel electrophoresis, and cloned to a pCR-BluntII-TOPO vector attached to a cloning kit (Zero Blunt® TOPO® PCR Cloning Kit, manufactured by Invitrogen Corporation). The produced plasmid pCR-Blunt-TFF2pro was introduced into E. coli for transformation (TOP 10 Ultracomp™ Cells, manufactured by Invitrogen Corporation), and transformant strain pCR-Blunt-TFF2pro/TOP10 was selectively cultured in LB agar medium containing 30 µg/ml of Zeocin (Zeocin, manufactured by Invitrogen Corporation). The pCR-Blunt-TFF2pro/TOP10 was subjected to shaking culture in 50 ml of LB medium containing 30 µg/ml of Zeocin at 37° C. over night, and a plasmid was prepared using a plasmid preparation kit (Concert™ High Purity Midiprep System, manufactured by GIBCO BRL).

The nucleotide sequence of the PCR product cloned to the plasmid pCR-Blunt-TFF2pro was determined. The determined nucleotide sequence was compared with the counterpart of hTFF2 promoter region reported in a gene bank (GenBank accession AB038162). The nucleotide sequence of the MluI-HindIII region cloned in pCR-Blunt-TFF2pro was identical to GenBank accession AB038162 (FIG. 1).

FIG. 1 shows in the upper register the nucleotide sequence and nucleotide numbering of the hTFF2 promoter region reported in GenBank (accession AB038162). The lower register shows the nucleotide sequence (see appended Sequence Number 1 shown in Sequence Listing) of the PCR product cloned in the plasmid pCR-Blunt-TFF2pro. The underlined portions indicate the recognition sequence (ACGCGT) of the restriction enzyme MluI and the recognition sequence (AAGCTT) of the restriction enzyme HindIII. The nucleotide sequences of the MluI-HindIII region are identical between the hTFF2 promoter region reported in GenBank and the PCR product cloned to the plasmid pCR-Blunt-TFF2pro. ATG enclosed in the box is the translation start codon and the arrow shows the transcription initiation site.

The plasmid pCR-Blunt-hTFF2pro was cleaved by the restriction enzymes MluI and HindIII, fractionated by 1% agarose gel electrophoresis, and the hTFF2 promoter region was purified using a nucleic acid purification kit (Concert™ Matrix Gel Extraction System, manufactured by GIBCO BRL). The hTFF2 promoter region was inserted into the MluI-HindIII region of a commercial plasmid pGL-Basic (manufactured by Promega Corporation) using a ligation kit (Ligation high, manufactured by TOYOBO CO., LTD.) to produce pGL3-hTFF2pro. The plasmid pGL3-hTFF2pro was introduced into *E. coli* for transformation (DH5α Competent Cell, manufactured by TOYOBO CO., LTD.) and transformant strain pGL3-hTFF2pro/DH5α was selectively cultured in LB agar medium containing 100 μg/ml of ampicillin.

The pGL3-hTFF2pro/DH5α was inoculated into a 2-liter Erlenmeyer flask containing 400 ml of LB medium containing 100 μg/ml ampicillin, and subjected to 200 rpm shaking culture at 37° C. in a rotary shaker overnight. The plasmid pGL3-hTFF2pro was extracted and purified from the cultured cells using a plasmid preparation kit (EndoFree Plasmid Maxi Kit, manufactured by QIAGEN).

A commercial vector, pWLneo (manufactured by Stratagene), containing a drug-selection marker was introduced into *E. coli* for transformation (DH5α Competent Cell, manufactured by TOYOBO CO., LTD.) and transformant strain pWLneo/DH5α was selectively cultured in LB agar medium containing 100 μg/ml of ampicillin. The pWLneo/DH5α was inoculated into a 1-liter Erlenmeyer flask containing 150 ml of LB medium containing 100 μg/ml of ampicillin, and subjected to 200 rpm shaking culture at 37° C. in a rotary shaker overnight. The plasmid pWLneo was extracted and purified from the cultured cells using a plasmid preparation kit (EndoFree Plasmid Maxi Kit, manufactured by QIAGEN).

(2) Preparation of Cell Line pGL3-hTFF2pro•pWL-neo/MKN-45 #6-2 for hTFF2 Gene Reporter Assay Human gastric cancer cell line MKN-45 (JCRB0254, Health Science Research Resources Bank) was cultured in medium (IMDM medium) composed of 500 ml of medium (Iscove's Modified Dulbecco's Medium, manufactured by SIGMA), 50 ml of fetal bovine serum (manufactured by SIGMA) immobilized by heating at 56° C. for 30 minutes, 5 ml of Penicillin-Streptomycin liquid (manufactured by SIGMA) and 20 ml of 200 mM L-glutamin (manufactured by SIGMA), using a culture dish having a diameter of 10 cm (CORNING Incorporated) placed in a 5% $CO_2$ incubator at 37° C. The cells were washed with buffer (Dulbecco's Phosphate Buffered Saline, manufactured by SIGMA) and subjected to trypsin (0.25% Tripsin-1 mM EDTA•4Na, manufactured by SIGMA) treatment for suspension. The cells were suspended in the IMDM medium, stained using Trypan Blue Stain, 0.4% (tradename, Invitrogen Corporation) and the number of cells which did not stain was counted as live cells using a hemocytometer. The cells were washed once with buffer (Dulbecco's Phosphate Buffered Saline, manufactured by SIGMA) and $10^6$ live cells were suspended in a solution for gene transfer (0.25 M Mannitol/0.1 mM $CaCl_2$/0.1 mM $MgCl_2$/0.2 mM Tris-HCl, pH7.2 to 7.4) to which 10 μg of the prepared plasmid pGL3-hTFF2pro and 2 μg of the plasmid pWLneo were added. The plasmid-added cell suspension was transferred to a 1 mm cuvette (manufactured by Bio-Rad Laboratories, Inc.) and gene introduction into cells was performed by means of electroporation using an SSH-1 cell fusion apparatus (Shimadzu Corporation). The cells were suspended in the IMDM medium, inoculated in a culture dish having a diameter of 10 cm (CORNING Incorporated) and cultured in a 5% $CO_2$ incubator at 37° C. for 2 days. Selective culturing was then carried out using IMDM medium containing 400 μg/ml of Geneticin (manufactured by Invitrogen Corporation). 100 μl of the culture medium was then first inoculated into each well of a 96-well plate (manufactured by BD Falcon), and proliferated cells were sequentially subjected to passaged culturing in a 24-well plate (manufactured by BD Falcon) and further in a 6-well plate (manufactured by BD Falcon) to prepare pGL3-hTFF2pro•pWL-neo/MKN-45 #6 cells. The obtained pGL3-hTFF2pro•pWL-neo/MKN-45 #6 cells were suspended in IMDM medium containing 400 μg/ml of Geneticin, inoculated into a 96-well plate by means of limiting dilution for cloning to obtain single clone pGL3-hTFF2pro•pWL-neo/MKN-45 #6-2 cells. The pGL3-hTFF2prod•pWL-neo/MKN-45 #6-2 cells were proliferated in a 10 cm culture dish, harvested and cryopreserved.

(3) The hTFF2 Genetic Reporter Assay Using pGL3-hTFF2pro•pWL-neo/MKN-45 #6-2 Cell Line pGL3-hTFF2pro•pWL-neo/MKN-45 #6-2 was thawed from the frozen state for use. The cells were inoculated into IMDM medium containing 400 μg/ml of Geneticin in a 10 cm culture dish and sequentially passaged every 3 to 5 days. During the passage culturing, the cells were washed with buffer (Dulbecco's Phosphate Buffered Saline, manufactured by SIGMA), and tripsin (0.25% Tripsin-1 mM EDTA•4Na, manufactured by SIGMA) was added to separate the cells by treatment for 5 minutes at 37° C. The cell suspension was collected by adding IMDM medium, and the cells were stained using Trypan Blue Stain, 0.4% (tradename, Invitrogen Corporation) and the number of cells which did not stain was counted as live cells using a hemocytometer. A cell survival rate of 90% or higher was confirmed prior to the live cells being used for the hTFF2 genetic reporter assay.

A day before test compounds were added, 100 μl of the cell suspension containing about $7.5 \times 10^4$ cells was inoculated into each well of 96-well plates (manufactured by COSTAR) and cultured in a 5% $CO_2$ incubator at 37° C. The test compounds were prepared to have a concentration 200 times the final measurement concentration with dimethylsulfoxide (Wako Pure Chemical Industries, Ltd.). The test compounds having a predetermined concentration were respectively diluted 100 times with IMDM medium, and 100 μl of the diluted compounds was dispensed into wells of the 96-well plates. Demethylsulfoxide was diluted 100 times with IMDM medium and added to those wells to which test compounds were not added. After the test compounds were added, the cells were cultured in a 5% $CO_2$ incubator at 37° C. for 24 hours. When the culturing was completed, the culture supernatant was removed and the 96-well plates were frozen in a deep freezer (manufactured by SANYO Electric Co., Ltd.). The 96-well plates were thawed at room temperature when the luciferase activity was measured, and 100 μl of PicaGene LT2.0 (Wako Pure Chemical Industries, Ltd.) diluted two times with buffer (Dulbecco's Phosphate Buffered Saline, manufactured by SIGMA) was added to each well. The plates were allowed to stand at room temperature for at least 30 minutes and the luciferase activity was measured using a Labsystems Luminoskan (manufactured by ICN Biomedicals Inc.).

Taking the average measurement of the dimethylsulfoxide-added well groups in each plate as 100%, a percentage for each test compound to the demethylsulfoxide-added well groups (control %) was calculated.

The results are shown in the table below.

TABLE 183

| Test Compound | TFF2 Production Promoting Activity |
|---|---|
| Compound of Example 22 | ++ |
| Compound of Example 25 | ++ |
| Compound of Example 32 | + |
| Compound of Example 116 | ++ |

TABLE 183-continued

| Test Compound | TFF2 Production Promoting Activity |
|---|---|
| Compound of Example 122 | ++ |
| Compound of Example 127 | ++ |
| Compound of Example 133 | ++ |
| Compound of Example 154 | ++ |
| Compound of Example 157 | ++ |
| Compound of Example 158 | ++ |
| Compound of Example 164 | ++ |
| Compound of Example 166 | ++ |
| Compound of Example 171 | ++ |
| Compound of Example 176 | ++ |
| Compound of Example 184 | ++ |
| Compound of Example 226 | ++ |
| Compound of Example 233 | ++ |
| Compound of Example 316 | ++ |
| Compound of Example 349 | ++ |
| Compound of Example 438 | + |
| Compound of Example 607 | + |
| Compound of Example 662 | + |
| Compound of Example 685 | ++ |
| Compound of Example 700 | ++ |
| Compound of Example 740 | + |
| Compound of Example 963 | ++ |
| Compound of Example 965 | ++ |
| Compound of Example 974 | ++ |
| Compound of Example 981 | ++ |
| Compound of Example 986 | ++ |
| Compound of Example 992 | ++ |
| Compound of Example 1032 | ++ |
| Compound of Example 1034 | ++ |
| Compound of Example 1040 | ++ |
| Compound of Example 1042 | ++ |
| Compound of Example 1050 | ++ |
| Compound of Example 1052 | ++ |
| Compound of Example 1057 | ++ |
| Compound of Example 1076 | ++ |
| Compound of Example 1315 | ++ |

In the above table, a TFF2 production promoting activity of 1000% or higher at a test compound concentration of $10^{-6}$ M is indicated as "++" and a TFF2 production promoting activity of 300% or higher at a test compound concentration of $10^{-6}$ M as "+".

The above results show that the concentration of compound of the present invention for showing 300% or higher TFF2 production promoting activity is less than $10^{-5}$ M, and more preferably less than $10^{-6}$ M.

Test Example 2

Healing Effects on Rat Models with Acetic Acid-Induced Gastric Ulcers (1) Production of Gastric Ulcer by Acetic Acid Rats were fasted from the previous day. A celiotomy was done in each rat under ether anesthesia, and the stomach was exteriorized. Subsequently, 20 μL of a 30% acetic acid solution was injected into the submucosa at the junction of the body of the glandular stomach and the pyloric antrum using a disposable syringe to produce a gastric ulcer.

(2) Test Compound Administration

Each test compound was suspended in a 0.5% carboxymethylcelullose (CMC) solution at concentrations of 0.75 or 2.5 mg/ml. The rats were orally administrated once a day for 8 days starting with the forth day from operation at doses of 3 or 10 mg/kg. A gastric tube and a syringe were used for the oral administration. The volumes of each test compound and vehicle (0.5% CMC) were 4 ml/kg.

(3) Dissection

On the next day the vehicle and the test compound were finally administrated to the rats, the rats were sacrificed by exsanguination under anesthesia with ether, and each stomach was removed. The removed stomachs were fixed in 1% formalin for 15 minutes, dissected along the greater curvature of stomach to expose the ulcer, and the ulcerated area was measured.

(4) Measurement of the Ulcerated Area

The ulcerated area was measured under a stereo microscope (10×) with an ocular micrometer (1 mm$^2$/grid), and the percentage healing ratio was calculated. The test results were shown in the Table 184. The percentage healing ratio was calculated by the following formula.

$$\text{Healing ratio}(\%) = \frac{\text{average ulcerated area of control group} - \text{average ulcerated area of test compound group}}{\text{average ulcerated area of control group}} \times 100$$

TABLE 184

| Test Compound | Dose (mg/kg) | Healing Ratio (%) |
|---|---|---|
| Example 1 | 10 | >20 |
| Example 115 | 3 | >20 |
| Example 122 | 3 | >20 |
| Example 123 | 3 | >20 |
| Example 155 | 10 | >20 |
| Example 913 | 3 | >20 |
| Example 919 | 3 | >20 |
| Example 960 | 10 | >20 |
| Example 961 | 10 | >20 |
| Example 965 | 3 | >20 |
| Example 966 | 3 | >20 |
| Example 968 | 3 | >20 |
| Example 969 | 3 | >20 |
| Example 978 | 10 | >20 |

The Table 184 demonstrates that the compounds of the present invention are effective in preventing and/or treating mucosal injury.

---

The invention claimed is:

1. A therapeutic composition for a disorder in which TFF up-regulation has a therapeutic effect, comprising as an active ingredient a carbostyril compound or salt thereof, wherein the carbostyril compound is represented by General Formula (1)

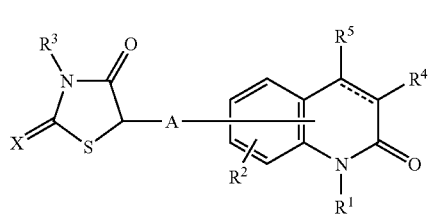

(1)

or a salt thereof,
wherein A is a direct bond, a lower alkylene group, or a lower alkylidene group;
X is an oxygen atom or a sulfur atom;
the bond between the 3 and 4 positions of the carbostyril skeleton is a single bond or a double bond;
$R^4$ and $R^5$ each represent a hydrogen atom, with the proviso that when the bond between the 3 and 4 positions of the carbostyril skeleton is a double bond, $R^4$ and $R^5$ instead may be linked together in the form of a —CH=CH—CH=CH— group;
$R^1$ is one of the following (1-1) to (1-29):
(1-1) a hydrogen atom,
(1-2) a lower alkyl group,
(1-3) a phenyl lower alkyl group optionally substituted on the phenyl ring with one or more members selected from the group consisting of a phenyl group, lower alkyl groups, lower alkoxy groups, halogen atoms, —(B)$_j$NR$^6$R$^7$ groups, a nitro group, a carboxy group, lower alkoxycarbonyl groups, a cyano group, phenyl lower alkoxy groups, a phenoxy group, a piperidinyl lower alkoxycarbonyl groups, amino lower alkoxycarbonyl groups optionally substituted with one or more cycloalkyl groups, 2-imidazolinylcarbonyl groups optionally substituted on the 2-imidazoline ring with one or more lower alkylthio groups, 3-pyrrolinylcarbonyl groups optionally substituted on the 3-pyrroline ring with one or more lower alkyl groups, thiazolidinylcarbonyl groups optionally substituted on the thiazolidine ring with a phenyl group, 3-azabicyclo[3.2.2]nonylcarbonyl groups, piperidinyl lower alkyl groups, anilino lower alkyl groups optionally substituted on the amino group with one or more lower alkyl groups, phenylthio lower alkyl groups, indolinyl lower alkyl groups, and piperidinylcarbonyl groups optionally substituted on the piperidine ring with one or more lower alkyl groups,
(1-4) a cycloalkyl lower alkyl group,
(1-5) a phenoxy lower alkyl group,
(1-6) a naphthyl lower alkyl group,
(1-7) a lower alkoxy lower alkyl group,
(1-8) a carboxy lower alkyl group,
(1-9) a lower alkoxycarbonyl lower alkyl group,
(1-10) a pyridyl lower alkyl group optionally substituted on the pyridine ring with one or more members selected from the group consisting of halogen atoms; piperidinyl groups; a morpholino group; piperazinyl groups optionally substituted on the piperazine ring with one or more members selected from the group consisting of a phenyl group and lower alkyl group; thienyl groups; a phenyl group; pyridyl groups; piperidinyl lower alkyl groups; phenylthio lower alkyl groups; biphenyl groups; lower alkyl groups optionally substituted with one or more halogen atoms; pyridylamino groups; pyridylcarbonylamino groups; lower alkoxy groups; anilino lower alkyl groups optionally substituted on the amino group with one or more lower alkyl groups; and anilino groups optionally substituted on the amino group with one or more lower alkyl groups,
(1-11) a cyano lower alkyl group,
(1-12) an -A$_1$-CONR$^8$R$^9$ group,
(1-13) a group of the following formula

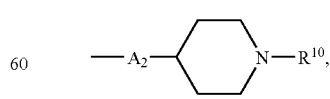

(1-14) a phenyl group,
(1-15) a quinolyl lower alkyl group,
(1-16) a lower alkoxy lower alkoxy-substituted lower alkyl group,
(1-17) a hydroxy-substituted lower alkyl group, (1-18) a thiazolyl lower alkyl group optionally substituted on the thiazole ring with one or more members selected from the group consisting of halogen atoms, a phenyl group, thienyl groups, and pyridyl groups,
(1-19) a lower alkyl group optionally substituted with one or more halogen atoms,
(1-20) a lower alkylsilyloxy lower alkyl group,
(1-21) a phenoxy lower alkyl group optionally substituted on the phenyl ring with one or more members selected from the group consisting of lower alkyl groups optionally substituted with one or more halogen atoms; lower alkoxy groups; halogen atoms; lower alkenyl groups; cycloalkyl groups; a nitro group; and a phenyl group,
(1-22) a phenylthio lower alkyl group optionally substituted on the phenyl ring with one or more halogen atoms,
(1-23) a piperidinyl lower alkyl groups optionally substituted on the piperidine ring with one or more members selected from the group consisting of phenyl lower alkyl groups and a phenyl group,
(1-24) a piperazinyl lower alkyl group optionally substituted on the piperazine ring with one or more phenyl groups,
(1-25) a 1,2,3,4-tetrahydroisoquinolyl lower alkyl group,
(1-26) a naphthyloxy lower alkyl group,
(1-27) a benzothiazolyloxy lower alkyl group optionally substituted on the benzothiazole ring with one or more alkyl groups,
(1-28) a lower alkyl group substituted with one or more members selected from the group consisting of quinolyloxy groups and isoquinolyloxy groups,
(1-29) a pyridyloxy lower alkyl group optionally substituted on the pyridine ring with one or more lower alkyl groups;
$R^2$ is one of the following (2-1) to (2-33):
(2-1) a hydrogen atom,
(2-2) a lower alkoxy group,
(2-3) a lower alkyl group,
(2-4) a carboxy lower alkoxy group,
(2-5) a lower alkoxycarbonyl lower alkoxy group,
(2-6) a hydroxy group,
(2-7) a phenyl lower alkoxy group optionally substituted on the phenyl ring with one or more members selected from the group consisting of halogen atoms; lower alkyl groups optionally substituted with one or more halogen atoms; lower alkylthio groups optionally substituted with one or more halogen atoms; lower alkoxy groups; a nitro group; lower alkylsulfonyl groups; lower alkoxycarbonyl groups; phenyl lower alkenyl groups; lower alkanoyloxy groups; and 1,2,3-thiadiazolyl groups,
(2-8) a piperidinyl lower alkoxy group optionally substituted on the piperidine ring with one or more lower alkyl groups,
(2-9) an amino-substituted lower alkoxy group optionally substituted with one or more lower alkyl groups,
(2-10) a lower alkenyloxy group,
(2-11) a pyridyl lower alkoxy group optionally substituted on the pyridine ring with one or more lower alkyl groups, each lower alkyl substituent optionally being substituted with one or more halogen atoms,
(2-12) a lower alkynyloxy group,
(2-13) a phenyl lower alkynyloxy group,
(2-14) a phenyl lower alkenyloxy group,
(2-15) a furyl lower alkoxy group optionally substituted on the furan ring with one or more lower alkoxycarbonyl groups,
(2-16) a tetrazolyl lower alkoxy group optionally substituted on the tetrazole ring with one member selected from the group consisting of a phenyl group, phenyl lower alkyl groups, and cycloalkyl lower alkyl groups,
(2-17) a 1,2,4-oxadiazolyl lower alkoxy group optionally substituted on the 1,2,4-oxadiazole ring with a phenyl group, the phenyl substituent optionally being substituted on the phenyl ring with one or more lower alkyl groups,
(2-18) an isoxazolyl lower alkoxy group optionally substituted on the isoxazole ring with one or more lower alkyl groups,
(2-19) a 1,3,4-oxadiazolyl lower alkoxy group optionally substituted on the 1,3,4-oxadiazole ring with a phenyl group, the phenyl substituent optionally being substituted on the phenyl ring with one or more lower alkyl groups,
(2-20) a lower alkanoyl lower alkoxy group,
(2-21) a thiazolyl lower alkoxy group optionally substituted on the thiazole ring with one or more members selected from the group consisting of lower alkyl groups and a phenyl group, each phenyl substituent optionally being substituted on the phenyl ring with one or more halogen atoms,
(2-22) a piperidinyloxy group optionally substituted on the piperidine ring with one or more benzoyl groups, each benzoyl substituent optionally being substituted on the phenyl ring with one or more halogen atoms,
(2-23) a thienyl lower alkoxy group,
(2-24) a phenylthio lower alkoxy group,
(2-25) a carbamoyl-substituted lower alkoxy group optionally substituted with one or more lower alkyl groups,
(2-26) a benzoyl lower alkoxy group,
(2-27) a pyridylcarbonyl lower alkoxy group,
(2-28) an imidazolyl lower alkoxy group optionally substituted on the imidazole ring with one or more phenyl lower alkyl groups,
(2-29) a phenoxy lower alkoxy group,
(2-30) a phenyl lower alkoxy-substituted lower alkoxy group,
(2-31) a 2,3-dihydro-1H-indenyloxy group,
(2-32) an isoindolinyl lower alkoxy group optionally substituted on the isoindoline ring with one or more oxo groups,
(2-33) a phenyl group;
$R^3$ is one of the following (3-1) to (3-19):
(3-1) a hydrogen atom,
(3-2) a lower alkyl group,
(3-3) a hydroxy-substituted lower alkyl group,
(3-4) a cycloalkyl lower alkyl group,
(3-5) a carboxy lower alkyl group,
(3-6) a lower alkoxycarbonyl lower alkyl group,
(3-7) a phenyl lower alkyl group optionally substituted on the phenyl ring with one or more members selected from the group consisting of halogen atoms; lower alkyl groups optionally substituted with one or more halogen atoms; lower alkoxy groups optionally substituted with one or more halogen atoms; a phenyl group; lower alkoxycarbonyl groups; a phenoxy group; lower alkylthio groups; lower alkylsulfonyl groups; phenyl lower alkoxy groups; and amino groups optionally substituted with one or more lower alkanoyl groups,
(3-8) a naphthyl lower alkyl group,
(3-9) a furyl lower alkyl group optionally substituted on the furan ring with one or more lower alkoxycarbonyl groups,
(3-10) a thiazolyl lower alkyl group optionally substituted on the thiazole ring with one or more members selected from the group consisting of lower alkyl groups and a phenyl group, each phenyl substituent optionally being substituted on the phenyl ring with one or more optionally halogen-substituted lower alkyl groups,
(3-11) a tetrazolyl lower alkyl group optionally substituted on the tetrazole ring with one or more lower alkyl groups,
(3-12) a benzothienyl lower alkyl group optionally substituted on the benzothiophene ring with one or more halogen atoms,
(3-13) a lower alkynyl group,
(3-14) a lower alkenyl group,
(3-15) a phenyl lower alkenyl group,
(3-16) a benzoimidazolyl lower alkyl group,
(3-17) a pyridyl lower alkyl group,
(3-18) an imidazolyl lower alkyl group optionally substituted on the imidazole ring with one or more phenyl lower alkyl groups,
(3-19) a quinolyl lower alkyl group;
B is a carbonyl group or an —NHCO— group;
l is 0 or 1;

$R^6$ and $R^7$ each independently represent one of the following (4-1) to (4-79):
(4-1) a hydrogen atom,
(4-2) a lower alkyl group,
(4-3) a lower alkanoyl group,
(4-4) a lower alkylsulfonyl group optionally substituted with one or more halogen atoms,
(4-5) an alkoxycarbonyl group optionally substituted with one or more halogen atoms,
(4-6) a hydroxy-substituted lower alkyl group,
(4-7) a pyridylcarbonyl group optionally substituted on the pyridine ring with one or more members selected from the group consisting of pyrrolyl groups and halogen atoms,
(4-8) a pyridyl group optionally substituted on the pyridine ring with one or more members selected from the group consisting of lower alkyl groups and lower alkoxy groups,
(4-9) a pyridyl lower alkyl group,
(4-10) a phenyl group optionally substituted on the phenyl ring with one or more members selected from the group consisting of halogen atoms; lower alkyl groups optionally substituted with one or more halogen atoms; a phenoxy group; lower alkoxy groups optionally substituted with one or more halogen atoms; lower alkylthio groups; lower alkylsulfonyl groups; amino groups optionally substituted with one or more members selected from the group consisting of lower alkyl groups and lower alkanoyl groups; pyrrolidinyl groups optionally substituted on the pyrrolidine ring with one or more oxo groups; piperidinyl groups optionally substituted on the piperidine ring with one or more lower alkyl groups; lower alkenyl groups; an aminosulfonyl group; a hydroxy group; carbamoyl groups optionally substituted with one or more lower alkyl groups; phenyl lower alkoxy groups; and a cyano group,
(4-11) a cycloalkyl group optionally substituted on the cycloalkyl ring with one or more lower alkyl groups,
(4-12) a benzoyl group optionally substituted on the phenyl ring with one or more members selected from the group consisting of halogen atoms; a phenoxy group; a phenyl group; lower alkyl groups optionally substituted with one or more halogen atoms; lower alkoxy groups; lower alkanoyl groups; a nitro group; a cyano group; amino groups optionally substituted with one or more members selected from the group consisting of a phenyl group and lower alkyl groups; pyrrolidinyl groups optionally substituted on the pyrrolidine ring with one or more oxo groups; pyrrolyl groups; pyrazolyl groups; 1,2,4-triazolyl groups; and imidazolyl groups,
(4-13) a benzoyl group substituted on the phenyl ring with one or more lower alkylenedioxy groups,
(4-14) a cycloalkylcarbonyl group,
(4-15) a furylcarbonyl group,
(4-16) a naphthylcarbonyl group,
(4-17) a phenoxycarbonyl group optionally substituted on the phenyl ring with one or more members selected from the group consisting of lower alkoxy groups, lower alkyl groups, halogen atoms, and a nitro group,
(4-18) a phenyl lower alkoxycarbonyl group optionally substituted on the phenyl ring with one or more members selected from the group consisting of halogen atoms and a nitro group,
(4-19) a piperidinyl group optionally substituted on the piperidine ring with one or more members selected from the group consisting of lower alkyl groups; lower alkanoyl groups; benzoyl groups optionally substituted on the phenyl ring with one or more halogen atoms; and phenyl groups optionally substituted on the phenyl ring with one or more halogen atoms,
(4-20) a tetrahydropyranyl lower alkyl group,
(4-21) a cycloalkyl lower alkyl group,
(4-22) a lower alkenyl group,
(4-23) a phenyl lower alkyl group optionally substituted on the alkyl group with one or more lower alkoxycarbonyl groups; and optionally substituted on the phenyl ring with one or more members selected from the group consisting of halogen atoms, lower alkyl groups optionally substituted with one or more halogen atoms, lower alkoxy groups optionally substituted with one or more halogen atoms, and a hydroxy group,
(4-24) a lower alkylenedioxy-substituted phenyl lower alkyl group,
(4-25) a furyl lower alkyl group,
(4-26) a carbamoyl lower alkyl group optionally substituted with one or more members selected from lower alkyl groups and a phenyl group, each phenyl substituent optionally being substituted on the phenyl ring with one or more lower alkyl groups,
(4-27) a lower alkoxy lower alkyl group,
(4-28) an imidazolyl lower alkyl group optionally substituted on the lower alkyl group with one or more members selected from the group consisting of a carbamoyl group and lower alkoxycarbonyl groups,
(4-29) an amino-substituted lower alkyl group optionally substituted with one or more lower alkyl groups,
(4-30) a 2,3,4,5-tetrahydrofuryl group optionally substituted on the 2,3,4,5-tetrahydrofuran ring with one or more oxo groups,
(4-31) a lower alkoxycarbonyl lower alkyl group,
(4-32) a pyrrolidinyl lower alkyl group optionally substituted on the pyrrolidine ring with one or more lower alkyl groups,
(4-33) a phenoxy lower alkanoyl group,
(4-34) a morpholino lower alkyl group,
(4-35) a indolyl group,
(4-36) a thiazolyl group,
(4-37) a 1,2,4-triazolyl group,
(4-38) a pyridyl lower alkanoyl group,
(4-39) a thienylcarbonyl group,
(4-40) a thienyl lower alkanoyl group,
(4-41) a cycloalkyl lower alkanoyl group,
(4-42) an isoxazolylcarbonyl group optionally substituted on the isoxazole ring with one or more lower alkyl groups,
(4-43) a pyrazylcarbonyl group,
(4-44) a piperidinylcarbonyl group optionally substituted on the piperidine ring with one or more members selected from a benzoyl group and lower alkanoyl groups,
(4-45) a chromanylcarbonyl group,
(4-46) an isoindolinyl lower alkanoyl group optionally substituted on the isoindoline ring with one or more oxo groups,
(4-47) a thiazolidinyl lower alkanoyl group optionally substituted on the thiazolidine ring with one or more members selected from an oxo group and a thioxo group,
(4-48) a piperidinyl lower alkanoyl group,
(4-49) a phenyl lower alkenylcarbonyl group optionally substituted on the phenyl ring with one or more halogen atoms,
(4-50) a phenyl lower alkenylcarbonyl group substituted on the phenyl ring with one or more alkylenedioxy groups,
(4-51) a pyridyl lower alkenyl carbonyl group,
(4-52) a pyridylthio lower alkanoyl group,
(4-53) an indolylcarbonyl group,
(4-54) a pyrrolylcarbonyl group,
(4-55) a pyrrolidinylcarbonyl group optionally substituted on the pyrrolidine ring with one or more oxo groups,
(4-56) a benzofurylcarbonyl group,
(4-57) an indolyl lower alkanoyl group,
(4-58) a benzothienylcarbonyl group,
(4-59) a phenyl lower alkanoyl group optionally substituted on the phenyl ring with one or more halogen atoms,
(4-60) a phenylsulfonyl group optionally substituted on the phenyl ring with one or more members selected from the group consisting of lower alkoxycarbonyl groups; a cyano group; a nitro group; amino groups optionally substituted with one or more alkanoyl groups; a hydroxy group; a carboxyl group; lower alkoxycarbonyl lower alkyl groups; halogen atoms; lower alkyl groups optionally substituted with one or more halogen atoms; and lower alkoxy groups optionally substituted with one or more halogen atoms, (4-61) a thienylsulfonyl group optionally substituted on the thiophene ring with one or more members selected from the group consisting of halogen atoms and lower alkoxycarbonyl groups,
(4-62) a quinolylsulfonyl group,
(4-63) an imidazolylsulfonyl group optionally substituted on the imidazole ring with one or more lower alkyl groups,
(4-64) a phenylsulfonyl group optionally substituted on the phenyl ring with one or more lower alkylenedioxy groups,
(4-65) a lower alkenylsulfonyl group,
(4-66) a cycloalkyl lower alkylsulfonyl group,
(4-67) a 3,4-dihydro-2H-1,4-benzoxazinylsulfonyl group optionally substituted on the 3,4-dihydro-2H-1,4-benzoxazine ring with one or more lower alkyl groups,
(4-68) a pyrazolylsulfonyl group optionally substituted on the pyrazole ring with one or more members selected from halogen atoms and lower alkyl groups,
(4-69) an isoxazolylsulfonyl group optionally substituted on the isoxazole ring with one or more lower alkyl groups,
(4-70) a thiazolylsulfonyl group optionally substituted on the thiazole ring with one or more members selected from the group consisting of lower alkyl groups and an amino group, each amino substituent optionally being substituted with one or more alkanoyl groups,
(4-71) a phenyl lower alkylsulfonyl group,
(4-72) a phenyl lower alkenylsulfonyl group,
(4-73) a naphthyloxycarbonyl group,
(4-74) a lower alkynyloxycarbonyl group,
(4-75) a lower alkenyloxycarbonyl group,
(4-76) a phenyl lower alkoxy-substituted lower alkoxycarbonyl group,
(4-77) a cycloalkyloxycarbonyl group optionally substituted on the cycloalkyl ring with one or more lower alkyl groups,
(4-78) a tetrazolyl group,
(4-79) an isoxazolyl group optionally substituted on the isoxazole ring with one or more lower alkyl groups; or instead, $R^6$ and $R^7$ may be linked together to form, together with the nitrogen atom to which they are bound, a 1,2,3,4-tetrahydroisoquinolyl group, an isoindolinyl group, or a 5- to 7-membered saturated heterocyclic group, the heterocyclic group optionally containing one or more additional heteroatoms and optionally being substituted with one to three members from the following (5-1) to (5-28):

(5-1) lower alkyl groups,
(5-2) lower alkoxy groups,
(5-3) an oxo group,
(5-4) a hydroxy group,
(5-5) pyridyl lower alkyl groups,
(5-6) phenyl groups optionally substituted on the phenyl ring with one or more members selected from the group consisting of halogen atoms; lower alkoxy groups optionally substituted with one or more halogen atoms; lower alkyl groups optionally substituted with one or more halogen atoms; a cyano group; and a hydroxy group,
(5-7) lower alkylenedioxy-substituted phenyl lower alkyl groups,
(5-8) phenyl lower alkyl groups optionally substituted on the phenyl ring with one or more halogen atoms,
(5-9) pyrimidyl groups,
(5-10) pyrazyl groups,
(5-11) cycloalkyl groups,
(5-12) phenyl lower alkoxy groups optionally substituted on the phenyl ring with one or more halogen atoms,
(5-13) benzoyl groups optionally substituted on the phenyl ring with one or more halogen atoms,
(5-14) benzoyl groups substituted on the phenyl ring with one or more lower alkylenedioxy groups,
(5-15) carbamoyl lower alkyl groups optionally substituted with one or more members selected from the group consisting of a phenyl group and lower alkyl groups,
(5-16) benzoxazolyl groups,
(5-17) lower alkoxycarbonyl groups,
(5-18) a carbamoyl group,
(5-19) phenyl lower alkylidene groups optionally substituted on the phenyl ring with one or more halogen atoms,
(5-20) phenyl lower alkoxycarbonyl groups,
(5-21) pyridyl groups optionally substituted on the pyridine ring with one or more members selected from the group consisting of a cyano group and lower alkyl groups,
(5-22) furyl lower alkyl groups,
(5-23) tetrahydropyranyl groups,
(5-24) imidazolyl lower alkyl groups,
(5-25) naphthyl groups,
(5-26) 2,3-dihydro-1H-indenyl groups,
(5-27) 1,3-dioxolanyl lower alkyl groups,
(5-28) -$(A_3)_m NR^{11}R^{12}$ groups;

$A_1$ is a lower alkylene group;
$R^8$ and $R^9$ each independently represent one of the following (6-1) to (6-25):
(6-1) a hydrogen atom,
(6-2) a lower alkyl group,
(6-3) a phenyl group optionally substituted on the phenyl ring with one or more members selected from the group consisting of lower alkyl groups optionally substituted with one or more halogen atoms; lower alkylthio groups; lower alkoxy groups optionally substituted with one or more halogen atoms; halogen atoms; a phenyl group; lower alkylamino groups; a cyano group; a phenoxy group; cycloalkyl groups; pyrrolidinyl groups optionally substituted with one or more oxo groups; 1,2,3,4-tetrahydroisoquinolylcarbonyl groups; 1,2,3,4-tetrahydroquinolylcarbonyl groups optionally substituted with one or more lower alkyl groups; 1,2,3,4-tetrahydroquinoxalinylcarbonyl groups optionally substituted with one or more lower alkyl groups; thiazolyl groups optionally substituted with one or more phenyl groups; a carbamoyl group; phenyl lower alkoxy groups; lower alkylsulfonylamino groups; anilino groups optionally substituted with one or more halogen atoms; phenyl lower alkyl groups; and hydroxy-substituted lower alkyl groups,
(6-4) a cycloalkyl group,
(6-5) a cycloakyl lower alkyl group,
(6-6) a carbamoyl lower alkyl group,
(6-7) a phenyl lower alkyl group optionally substituted on the phenyl ring with one or more members selected from the group consisting of lower alkyl groups optionally substituted with one or more halogen atoms; lower alkoxy groups optionally substituted with one or more halogen atoms; halogen atoms; and a phenyl group,
(6-8) lower alkyl-substituted amino lower alkyl group,
(6-9) a naphthyl group,
(6-10) a naphthyl lower alkyl group,
(6-11) a tetrahydronaphthyl lower alkyl group,
(6-12) a fluorenyl group,
(6-13) a pyridyl group,
(6-14) a pyridyl lower alkyl group,
(6-15) a pyrimidinyl group,
(6-16) a pyrazinyl lower alkyl group optionally substituted on the pyrazine ring with one or more lower alkyl groups,
(6-17) a thiazolyl group,
(6-18) a pyrazolyl lower alkyl group optionally substituted on the pyrazole ring with one or more lower alkyl groups,
(6-19) a thienyl lower alkyl group
(6-20) a piperidinyl group optionally substituted on the piperidine ring with one or more members selected from the group consisting of lower alkyl groups; a benzoyl group; and phenyl lower alkyl groups optionally substituted on the phenyl ring with one or more members selected from the group consisting of halogen atoms and lower alkyl groups,
(6-21) an indolyl group,
(6-22) an indazolyl group,
(6-23) a 3,4-dihydrocarbostyril optionally substituted with one or more lower alkyl groups,
(6-24) a quinolyl group optionally substituted with one or more lower alkyl groups, (6-25) a carbazolyl group optionally substituted with one or more lower alkyl groups; or $R^8$ and $R^9$ may be linked together to form, together with the nitrogen atom to which they are bound, a 5- to 8-membered saturated heterocyclic group optionally containing one or more additional heteroatoms and optionally substituted on the heterocyclic ring with one or more members selected from the group consisting of the following (6-28-1) to (6-28-24):

(6-28-1) lower alkyl groups,
(6-28-2) phenyl lower alkyl groups optionally substituted on the phenyl ring with one or more members selected from halogen atoms and lower alkoxy groups optionally substituted with one or more halogen atoms,
(6-28-3) naphthyl lower alkyl groups,
(6-28-4) phenyl lower alkylcarbamoyl lower alkyl groups,
(6-28-5) phenylcarbamoyl lower alkyl groups,
(6-28-6) phenyl lower alkoxycarbonyl groups,
(6-28-7) phenoxy lower alkyl groups optionally substituted on the phenyl ring with one or more members selected from the group consisting of halogen atoms and lower alkyl groups optionally substituted with one or more halogen atoms,
(6-28-8) biphenyl groups,
(6-28-9) phenyl groups optionally substituted on the phenyl ring with one or more halogen atoms,
(6-28-10) 2,3-dihydroindenyl groups optionally substituted with one or more halogen atoms,
(6-28-11) benzothiazolyl groups optionally substituted with one or more halogen atoms,
(6-28-12) pyridyl groups optionally substituted with one or more halogen atoms,
(6-28-13) benzothienyl groups,
(6-28-14) benzoisothiazolyl groups,
(6-28-15) thienopyridyl groups,
(6-28-16) a carbamoyl group,
(6-28-17) phenyl lower alkoxy groups optionally substituted on the phenyl ring with one or more halogen atoms,
(6-28-18) phenoxy groups optionally substituted with one or more halogen atoms,
(6-28-19) benzoyl groups optionally substituted on the phenyl ring with one or more members selected from halogen atoms and lower alkoxy groups,
(6-28-20) anilino groups optionally substituted on the phenyl ring with one or more lower alkyl groups, each lower alkyl substituent optionally being substituted with one or more halogen atoms,
(6-28-21) anilino groups substituted on the amino group with one or more lower alkyl groups, and optionally further substituted on the phenyl ring with one or more halogen atoms,
(6-28-22) benzofuryl groups,
(6-28-23) naphthyl groups,
(6-28-24) an oxo group; or $R^8$ and $R^9$ may be linked together to form, together with the nitrogen atom to which they are bound, a 5- or 6-membered unsaturated heterocyclic group, the unsaturated heterocyclic group optionally being substituted on the heterocyclic ring with one or more members selected from the group consisting of the following (6-29-1) to (6-29-3):

(6-29-1) phenyl groups optionally substituted with one or more halogen atoms,
(6-29-2) 2,3-dihydroindenyl groups,
(6-29-3) benzothienyl groups; or instead, $R^8$ and $R^9$ may be linked together to form, together with the nitrogen atom to which they are bound, a 1,2,3,4-tetrahydroquinolyl group; a 1,2,3,4-tetrahydroisoquinolyl group, a 1,3-dihydroisoindolyl group; an octahydropyrrolo[1,2-a]pyrazinyl group optionally substituted on the pyrazine ring with one or more lower alkyl groups; or an 8-azabicyclo[3.2.1]octyl group optionally substituted on the 8-azabicyclo[3.2.1]octyl group with one or more phenoxy groups, each phenoxy substituent optionally being substituted on the phenyl ring with one or more halogen atoms;

$A_2$ is a lower alkylene group;

$R^{10}$ is one of the following (7-1) to (7-44):

(7-1) a hydrogen atom,
(7-2) a lower alkyl group,
(7-3) an alkoxycarbonyl group optionally substituted with one or more halogen atoms,
(7-4) a benzoyl group optionally substituted on the phenyl ring with one or more members selected from the group consisting of lower alkyl groups optionally substituted with one or more halogen atoms; a phenyl group; halogen atoms; a cyano group; a phenoxy group; lower alkoxycarbonyl groups; pyrazolyl groups; and lower alkoxy groups optionally substituted with one or more halogen atoms,
(7-5) an alkanoyl group,
(7-6) a phenyl lower alkanoyl group optionally substituted on the phenyl ring with one or more members selected from the group consisting of halogen atoms and lower alkyl groups,
(7-7) a cycloalkyl lower alkanoyl group,
(7-8) a phenyl group optionally substituted on the phenyl ring with one or more lower alkyl groups,
(7-9) a phenoxy lower alkanoyl group optionally substituted on the phenyl ring with one or more halogen atoms,
(7-10) a phenyl lower alkenylcarbonyl group,
(7-11) a pyridylcarbonyl group optionally substituted on the pyridine ring with one or more members selected from the group consisting of halogen atoms and lower alkyl groups, each lower alkyl substituent optionally being substituted with one or more halogen atoms,
(7-12) a furylcarbonyl group,
(7-13) a thienylcarbonyl group,
(7-14) a piperidinylcarbonyl group optionally substituted on the piperidine ring with one or more lower alkanoyl groups,
(7-15) a pyrrolidinylcarbonyl group optionally substituted on the pyrrolidine ring with one or more oxo groups,
(7-16) a tetrahydropyranylcarbonyl group,
(7-17) a naphthylcarbonyl group,
(7-18) an indolylcarbonyl group,
(7-19) a benzofurylcarbonyl group,
(7-20) a benzothienylcarbonyl group optionally substituted on the benzothiophene ring with one or more halogen atoms,
(7-21) a furyl lower alkyl group,
(7-22) a pyridyl lower alkyl group optionally substituted on the pyridine ring with one or more members selected from the group consisting of halogen atoms and lower alkyl groups, each lower alkyl substituent optionally being substituted with one or more halogen atoms,
(7-23) a thienyl lower alkyl group optionally substituted on the thiophene ring with one or more halogen atoms,
(7-24) a phenyl lower alkyl group optionally substituted on the phenyl ring with one or more members selected from the group consisting of lower alkoxy groups optionally substituted with one or more halogen atoms; a cyano group; lower alkyl groups optionally substituted with one or more halogen atoms; amino groups optionally substituted with one or more members selected from the group consisting of lower alkyl groups and lower alkanoyl groups; halogen atoms; lower alkoxycarbonyl groups; lower alkanoyloxy groups; lower alkylsulfonyl groups; lower alkylthio groups; and pyrrolidinyl groups,
(7-25) a thiazolyl lower alkyl group,
(7-26) an imidazolyl lower alkyl group optionally substituted on the imidazole ring with one or more lower alkyl groups,
(7-27) a pyrrolyl lower alkyl group optionally substituted on the pyrrole ring with one or more lower alkyl groups,
(7-28) a cycloalkyl lower alkyl group,
(7-29) a lower alkylthio lower alkyl group, (7-30) a phenoxycarbonyl group optionally substituted on the phenyl ring with one or more members selected from the group consisting of halogen atoms, lower alkyl groups, and lower alkoxy groups,
(7-31) a phenyl lower alkoxycarbonyl group optionally substituted on the phenyl ring with one or more halogen atoms,
(7-32) a naphthyloxycarbonyl group,
(7-33) a lower alkynyloxycarbonyl group,
(7-34) a cycloalkylcarbonyl group,
(7-35) a quinoxalinylcarbonyl group,
(7-36) a —CO—NR$^{13}$R$^{14}$ group,
(7-37) a piperidinyl group optionally substituted on the piperidine ring with one or more lower alkyl groups,
(7-38) a cycloalkyl group,
(7-39) a tetrahydropyranyl group,
(7-40) a lower alkoxy lower alkyl group,
(7-41) a tetrahydro-2H-thiopyranyl group,
(7-42) a naphthyl group,
(7-43) a biphenyl group,
(7-44) a lower alkylsilyl lower alkoxycarbonyl group;
A$^3$ is a lower alkylene group;
m is 0 or 1;
R$^{11}$ and R$^{12}$ each independently represent one of the following (8-1) to (8-5):
(8-1) a hydrogen atom,
(8-2) a lower alkyl group,
(8-3) a lower alkanoyl group,
(8-4) a phenyl lower alkanoyl group,
(8-5) a phenyl group optionally substituted on the phenyl ring with one or more halogen atoms; or instead,
R$^{11}$ and R$^{12}$ may be linked together to form, together with the nitrogen atom to which they are bound, a 5- or 6-membered saturated heterocyclic group which optionally contains one or more additional heteroatoms, the heterocyclic group optionally being substituted with one to three members selected from the group consisting of the following (9-1) and (9-2):
(9-1) lower alkyl groups,
(9-2) a phenyl group; and
R$^{13}$ and R$^{14}$ each independently represent one of the following (10-1) to (10-3):
(10-1) a hydrogen atom,
(10-2) a lower alkyl group,
(10-3) a phenyl group, or instead
R$^{13}$ and R$^{14}$ may be linked together to form, together with the nitrogen atom to which they are bound, a 5- or 6-membered saturated heterocyclic group which optionally contains one or more additional heteroatoms.

2. A therapeutic composition according to claim 1, wherein the disorder in which TFF up-regulation has a therapeutic effect is an alimentary tract disease, oral disease, upper respiratory tract disease, respiratory tract disease, eye disease, cancer, or wound.

3. A therapeutic composition according to claim 1, wherein the disorder in which TFF up-regulation has a therapeutic effect is a drug-induced ulcer, peptic gastric ulcer, ulcerative colitis, Crohn's disease, drug-induced enteritis, ischemic colitis, irritable bowel syndrome, ulcer developed after endoscopic demucosation, acute gastritis, chronic gastritis, reflux esophagitis, esophageal ulcer, Barrett esophagus, gastrointestinal mucositis, hemorrhoidal diseases, stomatitis, Sjögren syndrome, xerostomia, rhinitis, pharyngitis, bronchial asthma, chronic obstructive lung disease, dry eye, or keratoconjunctivitis.

4. A therapeutic composition according to claim 1, wherein the TFF is TFF2.

5. A method for treating a disorder in which TFF up-regulation has a therapeutic effect, comprising administering to a patient an effective amount of a carbostyril compound or salt thereof, wherein the carbostyril compound is represented by General Formula (1)

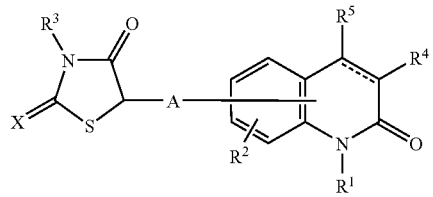

or a salt thereof,
wherein A is a direct bond, a lower alkylene group, or a lower alkylidene group;
X is an oxygen atom or a sulfur atom;
the bond between the 3 and 4 positions of the carbostyril skeleton is a single bond or a double bond;
R$^4$ and R$^5$ each represent a hydrogen atom, with the proviso that when the bond between the 3 and 4 positions of the carbostyril skeleton is a double bond, R$^4$ and R$^5$ instead may be linked together in the form of a —CH═CH—CH═CH— group;
R$^1$ is one of the following (1-1) to (1-29):
(1-1) a hydrogen atom,
(1-2) a lower alkyl group,
(1-3) a phenyl lower alkyl group optionally substituted on the phenyl ring with one or more members selected from the group consisting of a phenyl group, lower alkyl groups, lower alkoxy groups, halogen atoms, —(B)$_i$NR$^6$R$^7$ groups, a nitro group, a carboxy group, lower alkoxycarbonyl groups, a cyano group, phenyl lower alkoxy groups, a phenoxy group, a piperidinyl lower alkoxycarbonyl groups, amino lower alkoxycarbonyl groups optionally substituted with one or more cycloalkyl groups, 2-imidazolinylcarbonyl groups optionally substituted on the 2-imidazoline ring with one or more lower alkylthio groups, 3-pyrrolinylcarbonyl groups optionally substituted on the 3-pyrroline ring with one or more lower alkyl groups, thiazolidinylcarbonyl groups optionally substituted on the thiazolidine ring with a phenyl group, 3-azabicyclo[3.2.2]nonylcarbonyl groups, piperidinyl lower alkyl groups, anilino lower alkyl groups optionally substituted on the amino group with one or more lower alkyl groups, phenylthio lower alkyl groups, indolinyl lower alkyl groups, and piperidinylcarbonyl groups optionally substituted on the piperidine ring with one or more lower alkyl groups,
(1-4) a cycloalkyl lower alkyl group,
(1-5) a phenoxy lower alkyl group,
(1-6) a naphthyl lower alkyl group,
(1-7) a lower alkoxy lower alkyl group,
(1-8) a carboxy lower alkyl group,
(1-9) a lower alkoxycarbonyl lower alkyl group,
(1-10) a pyridyl lower alkyl group optionally substituted on the pyridine ring with one or more members selected from the group consisting of halogen atoms; piperidinyl groups; a morpholino group; piperazinyl groups optionally substituted on the piperazine ring with one or more members selected from the group consisting of a phenyl group and lower alkyl group; thienyl groups; a phenyl group; pyridyl groups; piperidinyl lower alkyl groups; phenylthio lower alkyl groups; biphenyl groups; lower alkyl groups optionally substituted with one or more halogen atoms; pyridylamino groups; pyridylcarbonylamino groups; lower alkoxy groups; anilino lower alkyl groups optionally substituted on the amino group with one or more lower alkyl groups; and anilino groups optionally substituted on the amino group with one or more lower alkyl groups,
(1-11) a cyano lower alkyl group,
(1-12) an -A$_1$-CONR$^8$R$^9$ group,
(1-13) a group of the following formula

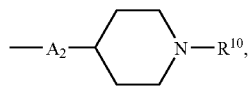

(1-14) a phenyl group,
(1-15) a quinolyl lower alkyl group,
(1-16) a lower alkoxy lower alkoxy-substituted lower alkyl group,
(1-17) a hydroxy-substituted lower alkyl group,
(1-18) a thiazolyl lower alkyl group optionally substituted on the thiazole ring with one or more members selected from the group consisting of halogen atoms, a phenyl group, thienyl groups, and pyridyl groups,
(1-19) a lower alkyl group optionally substituted with one or more halogen atoms,
(1-20) a lower alkylsilyloxy lower alkyl group,
(1-21) a phenoxy lower alkyl group optionally substituted on the phenyl ring with one or more members selected from the group consisting of lower alkyl groups optionally substituted with one or more halogen atoms; lower alkoxy groups; halogen atoms; lower alkenyl groups; cycloalkyl groups; a nitro group; and a phenyl group,
(1-22) a phenylthio lower alkyl group optionally substituted on the phenyl ring with one or more halogen atoms,
(1-23) a piperidinyl lower alkyl groups optionally substituted on the piperidine ring with one or more members selected from the group consisting of phenyl lower alkyl groups and a phenyl group,
(1-24) a piperazinyl lower alkyl group optionally substituted on the piperazine ring with one or more phenyl groups,
(1-25) a 1,2,3,4-tetrahydroisoquinolyl lower alkyl group,
(1-26) a naphthyloxy lower alkyl group,
(1-27) a benzothiazolyloxy lower alkyl group optionally substituted on the benzothiazole ring with one or more alkyl groups,
(1-28) a lower alkyl group substituted with one or more members selected from the group consisting of quinolyloxy groups and isoquinolyloxy groups,
(1-29) a pyridyloxy lower alkyl group optionally substituted on the pyridine ring with one or more lower alkyl groups;
R$^2$ is one of the following (2-1) to (2-33):
(2-1) a hydrogen atom,
(2-2) a lower alkoxy group,
(2-3) a lower alkyl group,
(2-4) a carboxy lower alkoxy group,
(2-5) a lower alkoxycarbonyl lower alkoxy group,
(2-6) a hydroxy group,
(2-7) a phenyl lower alkoxy group optionally substituted on the phenyl ring with one or more members selected from the group consisting of halogen atoms; lower alkyl groups optionally substituted with one or more halogen atoms; lower alkylthio groups optionally substituted with one or more halogen atoms; lower alkoxy groups; a nitro group; lower alkylsulfonyl groups; lower alkoxycarbonyl groups; phenyl lower alkenyl groups; lower alkanoyloxy groups; and 1,2,3-thiadiazolyl groups,
(2-8) a piperidinyl lower alkoxy group optionally substituted on the piperidine ring with one or more lower alkyl groups,
(2-9) an amino-substituted lower alkoxy group optionally substituted with one or more lower alkyl groups,
(2-10) a lower alkenyloxy group,
(2-11) a pyridyl lower alkoxy group optionally substituted on the pyridine ring with one or more lower alkyl groups, each lower alkyl substituent optionally being substituted with one or more halogen atoms,
(2-12) a lower alkynyloxy group,
(2-13) a phenyl lower alkynyloxy group,
(2-14) a phenyl lower alkenyloxy group,
(2-15) a furyl lower alkoxy group optionally substituted on the furan ring with one or more lower alkoxycarbonyl groups,
(2-16) a tetrazolyl lower alkoxy group optionally substituted on the tetrazole ring with one member selected from the group consisting of a phenyl group, phenyl lower alkyl groups, and cycloalkyl lower alkyl groups,
(2-17) a 1,2,4-oxadiazolyl lower alkoxy group optionally substituted on the 1,2,4-oxadiazole ring with a phenyl group, the phenyl substituent optionally being substituted on the phenyl ring with one or more lower alkyl groups,
(2-18) an isoxazolyl lower alkoxy group optionally substituted on the isoxazole ring with one or more lower alkyl groups,
(2-19) a 1,3,4-oxadiazolyl lower alkoxy group optionally substituted on the 1,3,4-oxadiazole ring with a phenyl group, the phenyl substituent optionally being substituted on the phenyl ring with one or more lower alkyl groups,
(2-20) a lower alkanoyl lower alkoxy group,
(2-21) a thiazolyl lower alkoxy group optionally substituted on the thiazole ring with one or more members selected from the group consisting of lower alkyl groups and a phenyl group, each phenyl substituent optionally being substituted on the phenyl ring with one or more halogen atoms,
(2-22) a piperidinyloxy group optionally substituted on the piperidine ring with one or more benzoyl groups, each benzoyl substituent optionally being substituted on the phenyl ring with one or more halogen atoms,
(2-23) a thienyl lower alkoxy group,
(2-24) a phenylthio lower alkoxy group,
(2-25) a carbamoyl-substituted lower alkoxy group optionally substituted with one or more lower alkyl groups,
(2-26) a benzoyl lower alkoxy group,
(2-27) a pyridylcarbonyl lower alkoxy group,
(2-28) an imidazolyl lower alkoxy group optionally substituted on the imidazole ring with one or more phenyl lower alkyl groups,
(2-29) a phenoxy lower alkoxy group,
(2-30) a phenyl lower alkoxy-substituted lower alkoxy group,
(2-31) a 2,3-dihydro-1H-indenyloxy group,
(2-32) an isoindolinyl lower alkoxy group optionally substituted on the isoindoline ring with one or more oxo groups,
(2-33) a phenyl group;
R$^3$ is one of the following (3-1) to (3-19):
(3-1) a hydrogen atom,
(3-2) a lower alkyl group,
(3-3) a hydroxy-substituted lower alkyl group,
(3-4) a cycloalkyl lower alkyl group,
(3-5) a carboxy lower alkyl group,
(3-6) a lower alkoxycarbonyl lower alkyl group,
(3-7) a phenyl lower alkyl group optionally substituted on the phenyl ring with one or more members selected from the group consisting of halogen atoms; lower alkyl groups optionally substituted with one or more halogen atoms; lower alkoxy groups optionally substituted with one or more halogen atoms; a phenyl group; lower alkoxycarbonyl groups; a phenoxy group; lower alkylthio groups; lower alkylsulfonyl groups; phenyl lower alkoxy groups; and amino groups optionally substituted with one or more lower alkanoyl groups,
(3-8) a naphthyl lower alkyl group,
(3-9) a furyl lower alkyl group optionally substituted on the furan ring with one or more lower alkoxycarbonyl groups,
(3-10) a thiazolyl lower alkyl group optionally substituted on the thiazole ring with one or more members selected from the group consisting of lower alkyl groups and a phenyl group, each phenyl substituent optionally being substituted on the phenyl ring with one or more optionally halogen-substituted lower alkyl groups,
(3-11) a tetrazolyl lower alkyl group optionally substituted on the tetrazole ring with one or more lower alkyl groups,
(3-12) a benzothienyl lower alkyl group optionally substituted on the benzothiophene ring with one or more halogen atoms,
(3-13) a lower alkynyl group,
(3-14) a lower alkenyl group,
(3-15) a phenyl lower alkenyl group,
(3-16) a benzoimidazolyl lower alkyl group,
(3-17) a pyridyl lower alkyl group,
(3-18) an imidazolyl lower alkyl group optionally substituted on the imidazole ring with one or more phenyl lower alkyl groups,
(3-19) a quinolyl lower alkyl group;
B is a carbonyl group or an —NHCO— group;
l is 0 or 1;
$R^6$ and $R^7$ each independently represent one of the following (4-1) to (4-79):
(4-1) a hydrogen atom,
(4-2) a lower alkyl group,
(4-3) a lower alkanoyl group,
(4-4) a lower alkylsulfonyl group optionally substituted with one or more halogen atoms,
(4-5) an alkoxycarbonyl group optionally substituted with one or more halogen atoms,
(4-6) a hydroxy-substituted lower alkyl group,
(4-7) a pyridylcarbonyl group optionally substituted on the pyridine ring with one or more members selected from the group consisting of pyrrolyl groups and halogen atoms,
(4-8) a pyridyl group optionally substituted on the pyridine ring with one or more members selected from the group consisting of lower alkyl groups and lower alkoxy groups,
(4-9) a pyridyl lower alkyl group,
(4-10) a phenyl group optionally substituted on the phenyl ring with one or more members selected from the group consisting of halogen atoms; lower alkyl groups optionally substituted with one or more halogen atoms; a phenoxy group; lower alkoxy groups optionally substituted with one or more halogen atoms; lower alkylthio groups; lower alkylsulfonyl groups; amino groups optionally substituted with one or more members selected from the group consisting of lower alkyl groups and lower alkanoyl groups; pyrrolidinyl groups optionally substituted on the pyrrolidine ring with one or more oxo groups; piperidinyl groups optionally substituted on the piperidine ring with one or more lower alkyl groups; lower alkenyl groups; an aminosulfonyl group; a hydroxy group; carbamoyl groups optionally substituted with one or more lower alkyl groups; phenyl lower alkoxy groups; and a cyano group,
(4-11) a cycloalkyl group optionally substituted on the cycloalkyl ring with one or more lower alkyl groups,
(4-12) a benzoyl group optionally substituted on the phenyl ring with one or more members selected from the group consisting of halogen atoms; a phenoxy group; a phenyl group; lower alkyl groups optionally substituted with one or more halogen atoms; lower alkoxy groups; lower alkanoyl groups; a nitro group; a cyano group; amino groups optionally substituted with one or more members selected from the group consisting of a phenyl group and lower alkyl groups; pyrrolidinyl groups optionally substituted on the pyrrolidine ring with one or more oxo groups; pyrrolyl groups; pyrazolyl groups; 1,2,4-triazolyl groups; and imidazolyl groups,
(4-13) a benzoyl group substituted on the phenyl ring with one or more lower alkylenedioxy groups,
(4-14) a cycloalkylcarbonyl group,
(4-15) a furylcarbonyl group,
(4-16) a naphthylcarbonyl group,
(4-17) a phenoxycarbonyl group optionally substituted on the phenyl ring with one or more members selected from the group consisting of lower alkoxy groups, lower alkyl groups, halogen atoms, and a nitro group,
(4-18) a phenyl lower alkoxycarbonyl group optionally substituted on the phenyl ring with one or more members selected from the group consisting of halogen atoms and a nitro group,
(4-19) a piperidinyl group optionally substituted on the piperidine ring with one or more members selected from the group consisting of lower alkyl groups; lower alkanoyl groups; benzoyl groups optionally substituted on the phenyl ring with one or more halogen atoms; and phenyl groups optionally substituted on the phenyl ring with one or more halogen atoms,
(4-20) a tetrahydropyranyl lower alkyl group,
(4-21) a cycloalkyl lower alkyl group,
(4-22) a lower alkenyl group,
(4-23) a phenyl lower alkyl group optionally substituted on the alkyl group with one or more lower alkoxycarbonyl groups; and optionally substituted on the phenyl ring with one or more members selected from the group consisting of halogen atoms, lower alkyl groups optionally substituted with one or more halogen atoms, lower alkoxy groups optionally substituted with one or more halogen atoms, and a hydroxy group,
(4-24) a lower alkylenedioxy-substituted phenyl lower alkyl group,
(4-25) a furyl lower alkyl group,
(4-26) a carbamoyl lower alkyl group optionally substituted with one or more members selected from lower alkyl groups and a phenyl group, each phenyl substituent optionally being substituted on the phenyl ring with one or more lower alkyl groups,
(4-27) a lower alkoxy lower alkyl group,
(4-28) an imidazolyl lower alkyl group optionally substituted on the lower alkyl group with one or more members selected from the group consisting of a carbamoyl group and lower alkoxycarbonyl groups,
(4-29) an amino-substituted lower alkyl group optionally substituted with one or more lower alkyl groups,
(4-30) a 2,3,4,5-tetrahydrofuryl group optionally substituted on the 2,3,4,5-tetrahydrofuran ring with one or more oxo groups,
(4-31) a lower alkoxycarbonyl lower alkyl group,
(4-32) a pyrrolidinyl lower alkyl group optionally substituted on the pyrrolidine ring with one or more lower alkyl groups,
(4-33) a phenoxy lower alkanoyl group,
(4-34) a morpholino lower alkyl group,
(4-35) a indolyl group,
(4-36) a thiazolyl group,
(4-37) a 1,2,4-triazolyl group,
(4-38) a pyridyl lower alkanoyl group,
(4-39) a thienylcarbonyl group,
(4-40) a thienyl lower alkanoyl group,
(4-41) a cycloalkyl lower alkanoyl group,
(4-42) an isoxazolylcarbonyl group optionally substituted on the isoxazole ring with one or more lower alkyl groups,
(4-43) a pyrazylcarbonyl group,
(4-44) a piperidinylcarbonyl group optionally substituted on the piperidine ring with one or more members selected from a benzoyl group and lower alkanoyl groups,
(4-45) a chromanylcarbonyl group,
(4-46) an isoindolinyl lower alkanoyl group optionally substituted on the isoindoline ring with one or more oxo groups,
(4-47) a thiazolidinyl lower alkanoyl group optionally substituted on the thiazolidine ring with one or more members selected from an oxo group and a thioxo group,
(4-48) a piperidinyl lower alkanoyl group,
(4-49) a phenyl lower alkenylcarbonyl group optionally substituted on the phenyl ring with one or more halogen atoms,
(4-50) a phenyl lower alkenylcarbonyl group substituted on the phenyl ring with one or more alkylenedioxy groups,
(4-51) a pyridyl lower alkenyl carbonyl group,
(4-52) a pyridylthio lower alkanoyl group, (4-53) an indolylcarbonyl group,
(4-54) a pyrrolylcarbonyl group,
(4-55) a pyrrolidinylcarbonyl group optionally substituted on the pyrrolidine ring with one or more oxo groups,
(4-56) a benzofurylcarbonyl group,
(4-57) an indolyl lower alkanoyl group,
(4-58) a benzothienylcarbonyl group,
(4-59) a phenyl lower alkanoyl group optionally substituted on the phenyl ring with one or more halogen atoms,
(4-60) a phenylsulfonyl group optionally substituted on the phenyl ring with one or more members selected from the group consisting of lower alkoxycarbonyl groups; a cyano group; a nitro group; amino groups optionally substituted with one or more alkanoyl groups; a hydroxy group; a carboxyl group; lower alkoxycarbonyl lower alkyl groups; halogen atoms; lower alkyl groups optionally substituted with one or more halogen atoms; and lower alkoxy groups optionally substituted with one or more halogen atoms,
(4-61) a thienylsulfonyl group optionally substituted on the thiophene ring with one or more members selected from the group consisting of halogen atoms and lower alkoxycarbonyl groups,
(4-62) a quinolylsulfonyl group,
(4-63) an imidazolylsulfonyl group optionally substituted on the imidazole ring with one or more lower alkyl groups,
(4-64) a phenylsulfonyl group optionally substituted on the phenyl ring with one or more lower alkylenedioxy groups,
(4-65) a lower alkenylsulfonyl group,
(4-66) a cycloalkyl lower alkylsulfonyl group,
(4-67) a 3,4-dihydro-2H-1,4-benzoxazinylsulfonyl group optionally substituted on the 3,4-dihydro-2H-1,4-benzoxazine ring with one or more lower alkyl groups,
(4-68) a pyrazolylsulfonyl group optionally substituted on the pyrazole ring with one or more members selected from halogen atoms and lower alkyl groups,
(4-69) an isoxazolylsulfonyl group optionally substituted on the isoxazole ring with one or more lower alkyl groups,
(4-70) a thiazolylsulfonyl group optionally substituted on the thiazole ring with one or more members selected from the group consisting of lower alkyl groups and an amino group, each amino substituent optionally being substituted with one or more alkanoyl groups,
(4-71) a phenyl lower alkylsulfonyl group,
(4-72) a phenyl lower alkenylsulfonyl group,
(4-73) a naphthyloxycarbonyl group,
(4-74) a lower alkynyloxycarbonyl group,
(4-75) a lower alkenyloxycarbonyl group,
(4-76) a phenyl lower alkoxy-substituted lower alkoxycarbonyl group,
(4-77) a cycloalkyloxycarbonyl group optionally substituted on the cycloalkyl ring with one or more lower alkyl groups,
(4-78) a tetrazolyl group,
(4-79) an isoxazolyl group optionally substituted on the isoxazole ring with one or more lower alkyl groups; or instead, $R^6$ and $R^7$ may be linked together to form, together with the nitrogen atom to which they are bound, a 1,2,3,4-tetrahydroisoquinolyl group, an isoindolinyl group, or a 5- to 7-membered saturated heterocyclic group, the heterocyclic group optionally containing one or more additional heteroatoms and optionally being substituted with one to three members from the following (5-1) to (5-28):
(5-1) lower alkyl groups,
(5-2) lower alkoxy groups,
(5-3) an oxo group,
(5-4) a hydroxy group,
(5-5) pyridyl lower alkyl groups,
(5-6) phenyl groups optionally substituted on the phenyl ring with one or more members selected from the group consisting of halogen atoms; lower alkoxy groups optionally substituted with one or more halogen atoms; lower alkyl groups optionally substituted with one or more halogen atoms; a cyano group; and a hydroxy group,
(5-7) lower alkylenedioxy-substituted phenyl lower alkyl groups,
(5-8) phenyl lower alkyl groups optionally substituted on the phenyl ring with one or more halogen atoms,
(5-9) pyrimidyl groups,
(5-10) pyrazyl groups,
(5-11) cycloalkyl groups,
(5-12) phenyl lower alkoxy groups optionally substituted on the phenyl ring with one or more halogen atoms,
(5-13) benzoyl groups optionally substituted on the phenyl ring with one or more halogen atoms,
(5-14) benzoyl groups substituted on the phenyl ring with one or more lower alkylenedioxy groups,
(5-15) carbamoyl lower alkyl groups optionally substituted with one or more members selected from the group consisting of a phenyl group and lower alkyl groups,
(5-16) benzoxazolyl groups,
(5-17) lower alkoxycarbonyl groups,
(5-18) a carbamoyl group,
(5-19) phenyl lower alkylidene groups optionally substituted on the phenyl ring with one or more halogen atoms,
(5-20) phenyl lower alkoxycarbonyl groups,
(5-21) pyridyl groups optionally substituted on the pyridine ring with one or more members selected from the group consisting of a cyano group and lower alkyl groups,
(5-22) furyl lower alkyl groups,
(5-23) tetrahydropyranyl groups,
(5-24) imidazolyl lower alkyl groups,
(5-25) naphthyl groups,
(5-26) 2,3-dihydro-1H-indenyl groups,
(5-27) 1,3-dioxolanyl lower alkyl groups,
(5-28) -$(A_3)_m NR^{11}R^{12}$ groups;
$A_3$ is a lower alkylene group;
$R^8$ and $R^9$ each independently represent one of the following (6-1) to (6-25):
(6-1) a hydrogen atom,
(6-2) a lower alkyl group,
(6-3) a phenyl group optionally substituted on the phenyl ring with one or more members selected from the group consisting of lower alkyl groups optionally substituted with one or more halogen atoms; lower alkylthio groups; lower alkoxy groups optionally substituted with one or more halogen atoms; halogen atoms; a phenyl group; lower alkylamino groups; a cyano group; a phenoxy group; cycloalkyl groups; pyrrolidinyl groups optionally substituted with one or more oxo groups; 1,2,3,4-tetrahydroisoquinolylcarbonyl groups; 1,2,3,4-tetrahydroquinolylcarbonyl groups optionally substituted with one or more lower alkyl groups; 1,2,3,4-tetrahydroquinoxalinylcarbonyl groups optionally substituted with one or more lower alkyl groups; thiazolyl groups optionally substituted with one or more phenyl groups; a carbamoyl group; phenyl lower alkoxy groups; lower alkylsulfonylamino groups; anilino groups optionally substituted with one or more halogen atoms; phenyl lower alkyl groups; and hydroxy-substituted lower alkyl groups,
(6-4) a cycloalkyl group,
(6-5) a cycloakyl lower alkyl group,
(6-6) a carbamoyl lower alkyl group,
(6-7) a phenyl lower alkyl group optionally substituted on the phenyl ring with one or more members selected from the group consisting of lower alkyl groups optionally substituted with one or more halogen atoms; lower alkoxy groups optionally substituted with one or more halogen atoms; halogen atoms; and a phenyl group,
(6-8) lower alkyl-substituted amino lower alkyl group,
(6-9) a naphthyl group,
(6-10) a naphthyl lower alkyl group,
(6-11) a tetrahydronaphthyl lower alkyl group,
(6-12) a fluorenyl group,
(6-13) a pyridyl group,
(6-14) a pyridyl lower alkyl group,
(6-15) a pyrimidinyl group, (6-16) a pyrazinyl lower alkyl group optionally substituted on the pyrazine ring with one or more lower alkyl groups,
(6-17) a thiazolyl group,
(6-18) a pyrazolyl lower alkyl group optionally substituted on the pyrazole ring with one or more lower alkyl groups,
(6-19) a thienyl lower alkyl group
(6-20) a piperidinyl group optionally substituted on the piperidine ring with one or more members selected from the group consisting of lower alkyl groups; a benzoyl group; and phenyl lower alkyl groups optionally substituted on the phenyl ring with one or more members selected from the group consisting of halogen atoms and lower alkyl groups,
(6-21) an indolyl group,
(6-22) an indazolyl group,
(6-23) a 3,4-dihydrocarbostyril optionally substituted with one or more lower alkyl groups,
(6-24) a quinolyl group optionally substituted with one or more lower alkyl groups,
(6-25) a carbazolyl group optionally substituted with one or more lower alkyl groups; or
   $R^8$ and $R^9$ may be linked together to form, together with the nitrogen atom to which they are bound, a 5- to 8-membered saturated heterocyclic group optionally containing one or more additional heteroatoms and optionally substituted on the heterocyclic ring with one or more members selected from the group consisting of the following (6-28-1) to (6-28-24):
(6-28-1) lower alkyl groups,
(6-28-2) phenyl lower alkyl groups optionally substituted on the phenyl ring with one or more members selected from halogen atoms and lower alkoxy groups optionally substituted with one or more halogen atoms,
(6-28-3) naphthyl lower alkyl groups,
(6-28-4) phenyl lower alkylcarbamoyl lower alkyl groups,
(6-28-5) phenylcarbamoyl lower alkyl groups,
(6-28-6) phenyl lower alkoxycarbonyl groups,
(6-28-7) phenoxy lower alkyl groups optionally substituted on the phenyl ring with one or more members selected from the group consisting of halogen atoms and lower alkyl groups optionally substituted with one or more halogen atoms,
(6-28-8) biphenyl groups,
(6-28-9) phenyl groups optionally substituted on the phenyl ring with one or more halogen atoms,
(6-28-10) 2,3-dihydroindenyl groups optionally substituted with one or more halogen atoms,
(6-28-11) benzothiazolyl groups optionally substituted with one or more halogen atoms,
(6-28-12) pyridyl groups optionally substituted with one or more halogen atoms,
(6-28-13) benzothienyl groups,
(6-28-14) benzoisothiazolyl groups,
(6-28-15) thienopyridyl groups,
(6-28-16) a carbamoyl group,
(6-28-17) phenyl lower alkoxy groups optionally substituted on the phenyl ring with one or more halogen atoms,
(6-28-18) phenoxy groups optionally substituted with one or more halogen atoms,
(6-28-19) benzoyl groups optionally substituted on the phenyl ring with one or more members selected from halogen atoms and lower alkoxy groups,
(6-28-20) anilino groups optionally substituted on the phenyl ring with one or more lower alkyl groups, each lower alkyl substituent optionally being substituted with one or more halogen atoms,
(6-28-21) anilino groups substituted on the amino group with one or more lower alkyl groups, and optionally further substituted on the phenyl ring with one or more halogen atoms,
(6-28-22) benzofuryl groups,
(6-28-23) naphthyl groups,
(6-28-24) an oxo group; or
   $R^8$ and $R^9$ may be linked together to form, together with the nitrogen atom to which they are bound, a 5- or 6-membered unsaturated heterocyclic group, the unsaturated heterocyclic group optionally being substituted on the heterocyclic ring with one or more members selected from the group consisting of the following (6-29-1) to (6-29-3):
(6-29-1) phenyl groups optionally substituted with one or more halogen atoms,
(6-29-2) 2,3-dihydroindenyl groups,
(6-29-3) benzothienyl groups; or instead,
   $R^8$ and $R^9$ may be linked together to form, together with the nitrogen atom to which they are bound, a 1,2,3,4-tetrahydroquinolyl group; a 1,2,3,4-tetrahydroisoquinolyl group, a 1,3-dihydroisoindolyl group; an octahydropyrrolo[1,2-a]pyrazinyl group optionally substituted on the pyrazine ring with one or more lower alkyl groups; or an 8-azabicyclo[3.2.1]octyl group optionally substituted on the 8-azabicyclo[3.2.1]octyl group with one or more phenoxy groups, each phenoxy substituent optionally being substituted on the phenyl ring with one or more halogen atoms;
$A_2$ is a lower alkylene group;
$R^{10}$ is one of the following (7-1) to (7-44):
(7-1) a hydrogen atom,
(7-2) a lower alkyl group,
(7-3) an alkoxycarbonyl group optionally substituted with one or more halogen atoms,
(7-4) a benzoyl group optionally substituted on the phenyl ring with one or more members selected from the group consisting of lower alkyl groups optionally substituted with one or more halogen atoms; a phenyl group; halogen atoms; a cyano group; a phenoxy group; lower alkoxycarbonyl groups; pyrazolyl groups; and lower alkoxy groups optionally substituted with one or more halogen atoms,
(7-5) an alkanoyl group,
(7-6) a phenyl lower alkanoyl group optionally substituted on the phenyl ring with one or more members selected from the group consisting of halogen atoms and lower alkyl groups,
(7-7) a cycloalkyl lower alkanoyl group,
(7-8) a phenyl group optionally substituted on the phenyl ring with one or more lower alkyl groups,
(7-9) a phenoxy lower alkanoyl group optionally substituted on the phenyl ring with one or more halogen atoms,
(7-10) a phenyl lower alkenylcarbonyl group,
(7-11) a pyridylcarbonyl group optionally substituted on the pyridine ring with one or more members selected from the group consisting of halogen atoms and lower alkyl groups, each lower alkyl substituent optionally being substituted with one or more halogen atoms,
(7-12) a furylcarbonyl group,
(7-13) a thienylcarbonyl group,
(7-14) a piperidinylcarbonyl group optionally substituted on the piperidine ring with one or more lower alkanoyl groups,
(7-15) a pyrrolidinylcarbonyl group optionally substituted on the pyrrolidine ring with one or more oxo groups,
(7-16) a tetrahydropyranylcarbonyl group,
(7-17) a naphthylcarbonyl group,
(7-18) an indolylcarbonyl group,
(7-19) a benzofurylcarbonyl group,
(7-20) a benzothienylcarbonyl group optionally substituted on the benzothiophene ring with one or more halogen atoms,
(7-21) a furyl lower alkyl group,
(7-22) a pyridyl lower alkyl group optionally substituted on the pyridine ring with one or more members selected from the group consisting of halogen atoms and lower alkyl groups, each lower alkyl substituent optionally being substituted with one or more halogen atoms,
(7-23) a thienyl lower alkyl group optionally substituted on the thiophene ring with one or more halogen atoms,
(7-24) a phenyl lower alkyl group optionally substituted on the phenyl ring with one or more members selected from the group consisting of lower alkoxy groups optionally substituted with one or more halogen atoms; a cyano group; lower alkyl groups optionally substituted with one or more halogen atoms; amino groups optionally substituted with one or more members selected from the group consisting of lower alkyl groups and lower alkanoyl groups; halogen atoms; lower alkoxycarbonyl groups; lower alkanoyloxy groups; lower alkylsulfonyl groups; lower alkylthio groups; and pyrrolidinyl groups, (7-25) a thiazolyl lower alkyl group,
(7-26) an imidazolyl lower alkyl group optionally substituted on the imidazole ring with one or more lower alkyl groups,
(7-27) a pyrrolyl lower alkyl group optionally substituted on the pyrrole ring with one or more lower alkyl groups,
(7-28) a cycloalkyl lower alkyl group,
(7-29) a lower alkylthio lower alkyl group,
(7-30) a phenoxycarbonyl group optionally substituted on the phenyl ring with one or more members selected from the group consisting of halogen atoms, lower alkyl groups, and lower alkoxy groups,
(7-31) a phenyl lower alkoxycarbonyl group optionally substituted on the phenyl ring with one or more halogen atoms,
(7-32) a naphthyloxycarbonyl group,
(7-33) a lower alkynyloxycarbonyl group,
(7-34) a cycloalkylcarbonyl group,
(7-35) a quinoxalinylcarbonyl group,
(7-36) a —CO—NR$^{13}$R$^{14}$ group,
(7-37) a piperidinyl group optionally substituted on the piperidine ring with one or more lower alkyl groups,
(7-38) a cycloalkyl group,
(7-39) a tetrahydropyranyl group,
(7-40) a lower alkoxy lower alkyl group,
(7-41) a tetrahydro-2H-thiopyranyl group,
(7-42) a naphthyl group,
(7-43) a biphenyl group,
(7-44) a lower alkylsilyl lower alkoxycarbonyl group;
A$^3$ is a lower alkylene group;
m is 0 or 1;

R$^{11}$ and R$^{12}$ each independently represent one of the following (8-1) to (8-5):
(8-1) a hydrogen atom,
(8-2) a lower alkyl group,
(8-3) a lower alkanoyl group,
(8-4) a phenyl lower alkanoyl group,
(8-5) a phenyl group optionally substituted on the phenyl ring with one or more halogen atoms; or instead,
R$^{11}$ and R$^{12}$ may be linked together to form, together with the nitrogen atom to which they are bound, a 5- or 6-membered saturated heterocyclic group which optionally contains one or more additional heteroatoms, the heterocyclic group optionally being substituted with one to three members selected from the group consisting of the following (9-1) and (9-2):
(9-1) lower alkyl groups,
(9-2) a phenyl group; and
R$^{13}$ and R$^{14}$ each independently represent one of the following (10-1) to (10-3):
(10-1) a hydrogen atom,
(10-2) a lower alkyl group,
(10-3) a phenyl group, or instead
R$^{13}$ and R$^{14}$ may be linked together to form, together with the nitrogen atom to which they are bound, a 5- or 6-membered saturated heterocyclic group which optionally contains one or more additional heteroatoms.

6. A therapeutic composition for alimentary tract diseases, oral diseases, upper respiratory tract diseases, respiratory tract diseases, eye diseases, cancers, or wounds, the composition comprising a compound that induces the production of TFF.

7. A therapeutic composition according to claim 6, wherein the TFF is TFF2.

* * * * *

SEQUENCE LISTING

<160> NUMBER OF SEQ ID NOS: 1

<210> SEQ ID NO 1
<211> LENGTH: 898
<212> TYPE: DNA
<213> ORGANISM: HeLa cell

<400> SEQUENCE: 1
acgcgtcaga ctggcaaccc cctgtcattt ccctggcgtg gggaacttcg ggtcccctct    60

-continued

```
gtccttccca ccacactttt ccctctttct ttccgggtgt ctactctctg gcttctgtct      120
tctctgtcag gtccacagaa tccttctcca gcacatccta ccccaggaag gccatgggct      180
gggtcccagg tgccatcttt cagaagatgt agagcattcc catggaacaa aaataaccca      240
tttcaggggt tggctgaaaa tgaacttatt aaaacctgcc tgtcacaggc tactccgctg      300
accctgtcag cctcatctcc atggagagca gcccctcctg ctgaagatgg gacaaagggc      360
atcgtgctgc ggttggggag gctctaacca cagccctggg agcagtctct tacctcctct      420
gagatgcttc ccttcctcag ggaggggact tttccatgct atctgctggc ctgtacattt      480
tccccagtaa acttggccct aatattttct aaattcctgt ggtccctgcc cactctatca      540
atagaaatgc atagcttatc ccttcctggg tgtgaccctg tgtgtgccca gccccagacc      600
tgcacgtggc cggttttcca cgctggcagc ctggcatgac ccaactctct gtccagggca      660
ggaagaggta tcaccgagca gggagagagt caccctggcc cggaagcctc gcctgcacag      720
ggcacagctg cctcttgcct cctcttcgcc tccacggtgg aagggctggg gccacggggc      780
agagaagaaa ggttatctct gcttgttgga caaacagagg ggagattata aaacataccc      840
ggcagtggac accatgcatt ctgcaagcca ccctggggtg cagctgagct agaagctt        898
```